(12) United States Patent
Tang et al.

(10) Patent No.: US 12,084,672 B2
(45) Date of Patent: Sep. 10, 2024

(54) GENETICALLY ENGINEERED LAND PLANTS THAT EXPRESS AN INCREASED SEED YIELD PROTEIN AND/OR AN INCREASED SEED YIELD RNA

(71) Applicant: YIELD10 BIOSCIENCE, INC., Woburn, MA (US)

(72) Inventors: Jihong Tang, West Roxbury, MA (US); Meghna Malik, Saskatoon (CA); Nirmala Sharma, Saskatoon (CA); Claire Burkitt, Saskatoon (CA); Yuanyuan Ji, Saskatoon (CA); Madana M. R. Ambavaram, Andover, MA (US); Kieran Ryan, Sharon, MA (US); Oliver P. Peoples, Arlington, MA (US); Kristi D. Snell, Belmont, MA (US); Frank Anthony Skraly, Watertown, MA (US); Venkatesh Bollina, Saskatoon (CA)

(73) Assignee: Yield10 Bioscience, Inc., Woburn, MA (US)

( * ) Notice: Subject to any disclaimer, the term of this patent is extended or adjusted under 35 U.S.C. 154(b) by 446 days.

(21) Appl. No.: 17/273,159

(22) PCT Filed: Sep. 3, 2019

(86) PCT No.: PCT/US2019/049281
§ 371 (c)(1),
(2) Date: Mar. 3, 2021

(87) PCT Pub. No.: WO2020/051108
PCT Pub. Date: Mar. 12, 2020

(65) Prior Publication Data
US 2021/0348182 A1    Nov. 11, 2021

Related U.S. Application Data

(60) Provisional application No. 62/834,766, filed on Apr. 16, 2019, provisional application No. 62/744,932, filed on Oct. 12, 2018, provisional application No. 62/726,653, filed on Sep. 4, 2018.

(51) Int. Cl.
*C12N 15/82* (2006.01)
*C07K 14/415* (2006.01)

(52) U.S. Cl.
CPC ........ *C12N 15/8262* (2013.01); *C07K 14/415* (2013.01); *C12N 15/8249* (2013.01)

(58) Field of Classification Search
None
See application file for complete search history.

(56) References Cited

U.S. PATENT DOCUMENTS

| 6,713,666 B2* | 3/2004 | Helentjaris | C12N 15/8245 800/278 |
| 2004/0250312 A1 | 12/2004 | Rausch | |
| 2009/0293142 A1* | 11/2009 | Thomas | C12N 15/8261 800/278 |
| 2016/0138038 A1* | 5/2016 | Sederoff | C12N 15/8227 426/615 |

FOREIGN PATENT DOCUMENTS

| WO | 2007038566 A2 | 4/2007 |
| WO | 2014209792 A1 | 12/2014 |
| WO | 2015103074 A1 | 7/2015 |
| WO | 2017136668 A1 | 8/2017 |
| WO | 2018156686 A1 | 8/2018 |
| WO | 2018232232 A1 | 12/2018 |
| WO | 2019104278 A1 | 5/2019 |

OTHER PUBLICATIONS

Joshua Zuber masters thesis entitled "RNAi Mediated Silencing of Cell Wall Invertase Inhibitors to Increase Sucrose Allocation to Sink Tissues in Transgenic Camelina Saliva Engineered with a Carbon Concentrating Mechanism" by Zuber (University of Massachusetts Amherst, May 2015).*
Zuber, 2015, RNAi Mediated Silencing of Cell Wall Invertase Inhibitors to Increase Sucrose Allocation to Sink Tissues in Transgenic Camelina Sativa Engineered with a Carbon Concentrating Mechanism, Thesis, University of Massachusetts Amherst, pp. 1-50 ( Year: 2015).*
Cocula et al, The Plant Invertase/Pectin Methylesterase Inhibitor Superfamily, 2022, Frontiers in Plant Science 13: 863892 (Year: 2022).*
International Search Report and Written Opinion for International Application No. PCT/US2019/049281 mailed Jan. 13, 2020.
(Continued)

*Primary Examiner* — Anne Kubelik
*Assistant Examiner* — Aleksandar Radosavljevic
(74) *Attorney, Agent, or Firm* — Pearne & Gordon LLP

(57) ABSTRACT

A genetically engineered land plant that expresses a protein that has homology to a plant invertase inhibitor and/or a pectin methylesterase inhibitor and that increases seed yield with increased expression ("an ISY protein") is disclosed. The plant comprises a modified gene for the ISY protein. The ISY protein comprises one or more of an ISY protein of *Camelina sativa* comprising SEQ ID NO: 2 or a fragment, *Camelina sativa* homolog, or ortholog thereof. The modified gene comprises a promoter and a nucleic acid sequence encoding the ISY protein. The promoter is non-cognate with respect to the nucleic acid sequence encoding the ISY protein. The modified gene is configured such that transcription of the nucleic acid sequence is initiated from the promoter and results in expression of the ISY protein. A genetically engineered land plant that expresses an RNA that increases seed yield with increased expression also is disclosed.

8 Claims, 49 Drawing Sheets

Specification includes a Sequence Listing.

(56) References Cited

OTHER PUBLICATIONS

Zuber, "RNAi Mediated Silencing of Cell Wall Invertase Inhibitors to Increase Sucrose Allocation to Sink Tissues in Transgenic Camelina Sativa Engineered with a Carbon Concentrating Mechanism" Thesis, University of Massachusetts Amherst, May 2015 [online] [Retrieved on Oct. 18, 2019] Retrieved from the internet <URL: https://scholarworks.umass.edu/masters_theses_2/218/ > especially, p. 19, para 2; p. 19, Table 2.

Ammens et al., "Crystal Structures of *Arabidopsis thaliana* cell-wall invertase mutants in complex with sucrose," Journal of Molecular Biology, vol. 377, pp. 378-385 (2008), Abstract Only.

Wang et al., "Control of rice grain-filling and yield by a gene with a potential signature of domestication," Nature Genetics, vol. 40, pp. 1370-1374 (2008).

Fridman et al., "Zooming In on a Quantitative Trait for Tomato Yield Using Interspecific Introgressions," Science, vol. 305, pp. 1786-1789 (2004).

Cheng et al., "The Miniature1 Seed Locus of Maize Encodes a Cell Wall Invertase Required for Normal Development of Endosperm and Maternal Cells in the Pedicel," The Plant Cell, vol. 8, pp. 971-983 (1996).

Jin et al., "Posttranslational Elevation of Cell Wall Invertase Activity by Silencing Its Inhibitor in Tomato Delays Leaf Senescence and Increases Seed Weight and Fruit Hexose Level," The Plant Cell, vol. 21, pp. 2072-2089 (2009).

Mcdougall, "The cost and time involved in the discovery, development and authorisation of a new plant biotechnology derived trait," Crop Life International, Sep. 2011, pp. 1-24, available at https://croplife.org/wp-content/uploads/pdf_files/Getting-a-Biotech-Crop-to-Market-Phillips-McDougall-Study.pdf, last accessed Apr. 29, 2020.

Belhaj et al., "Plant genome editing made easy: targeted mutagenesis in model and crop plants using the CRISPR/Cas system," Plant Methods (2013); 9:39, pp. 1-10.

Khandagale et al., "Genome editing for targeted improvement of plants," Plant Biotechnol. Rep. (Nov. 2016); vol. 10, pp. 327-343.

Kang et al., "CPC2: a fast and accurate coding potential calculator based on sequence intrinsic features," Nucleic Acids Research, vol. 45, Web server issue, W12-W16, doi: 10.1093/nar/gkx428 (2017).

Kagale et al., "The developmental transcriptome atlas of the biofuel crop Camelina sativa," The Plant Journal, vol. 88, pp. 879-894 and Supporting Information Legends, Supplemental Figures S1-S5, and Supplemental Tables S1-S3 (2016) (Supplemental Data S1-S7 Not Included).

Zhang et al., "Plant Long ncRNAs: A New Frontier for Gene Regulatory Control," American Journal of Plant Sciences, vol. 4, pp. 1038-1045 (2013).

Hube et al., "Coding and Non-coding RNAs, the Frontier Has Never Been So Blurred", Frontiers in Genetics, vol. 9, article 140, pp. 1-5, doi: 10.3389/fgene.2018.00140 (2018).

Huang et al., "Long noncoding miRNA gene represses wheat B-diketone waxes," Proceedings of the National Academy of Sciences, U.S.A., www.pnas.org/cgi/doi/10.1073/pnas.1617483114, pp. E3149-E3158 (2017).

Wan et al., "Evolution of Sucrose Metabolism: The Dichotomy of Invertases and Beyond," Trends Plant Sci., vol. 23, pp. 163-177 (2018), Abstract Only.

Tang et al., "Suppression of extracellular invertase inhibitor gene expression improves seed weight in soybean (Glycine max)," Journal of Experimental Botany, vol. 68, pp. 469-482 (2017).

Malik, et al., "Production of high levels of poly-3-hydroxybutyrate in plastids of Camelina sativa seeds," Plant Biotechnology Journal, vol. 13, pp. 675-688 (2015).

Qu, et al., "Evaluation of tissue specificity and expression strength of rice seed component gene promoters in transgenic rice," Plant Biotechnology Journal, vol. 2, pp. 113-125 (2004).

Qu, et al., "Expression pattern and activity of six glutelin gene promoters in transgenic rice," Journal of Experimental Botany, vol. 59, pp. 2417-2424 (2008).

Malik et al., "Camelina sativa, an oilseed at the nexus between model system and commercial crop," Plant Cell Reports, vol. 37, pp. 1367-1381 (2018).

Extended European Search Report for European Patent Application No. 19858165.4 dated Apr. 26, 2022, pp. 1-8.

* cited by examiner

FIG. 1A

```
CSA15G017550_190AA   CVKYYWI------SPFFAKESY---IIFEKILIPMTLTKML*-------------------------------  190
CSA15G017550_134AA   CVKYYWI------SPFFAKESY---IIFEKILIPMTLTKML*-------------------------------  134
CSA15G017550_168AA   CVKYYWI------SPFFAKESY---IIFEKILIPMTLTKML*-------------------------------  168
XP_010685378.1       CRMAFPEGKV-PGRIVGRTR--MLHGVSNVAASMIEKSLE---------------------------------  184
AEE32232.1           CQGGFNGS-----SPLTSLTK---SMQKISNVTRAIFYSNSIVKEEACGSSWPSLALNIDSK-----------  187
Y12805.1             CEEYFKGSK----SPFSALNI---AVHELSDVGRAIVRNLL-------------------------------  166
SOLYC12G099200       CEEYFKATTIKYSPLSKLNI--DVHELSDVGRAIVRNLL*--------------------------------  171
AY145781.1           CEEFSFKY-NGLVSPVSDMNK--EIIELSSVAKSIIRMLL--------------------------------  172
GU321341.1           CEYSFNYYNKLDFPISNLSR--EIIELSKVAKSIIRMLL*--------------------------------  181
SOLYC12G099190       CEFSFNYYNKSDFPISNMSK--DIVELSKVAKSIIRMLL*--------------------------------  175
AT5G64620            CRNIFRRVKGLAYPVEIRRREASLRRICGVVSGILDRIVE--------------------------------  180
XP_008668976.1       CEQGFQDLG-VRSPL--ASEDAGFRKDASIALSVTAAL----------------------------------  176
                     *  .       .       .             .   :

CSA15G017550_190AA   ------------------------------------------ 190 (SEQ ID NO: 4)
CSA15G017550_134AA   ------------------------------------------ 134 (SEQ ID NO: 2)
CSA15G017550_168AA   ------------------------------------------ 168 (SEQ ID NO: 5)
XP_010685378.1       ACVVSLQNIQFNRGRTCW------------------------ 205 (SEQ ID NO: 13)
AEE32232.1           ------------------------------------------ 166 (SEQ ID NO: 10)
Y12805.1             ------------------------------------------ 171 (SEQ ID NO: 15)
SOLYC12G099200       ------------------------------------------ 172 (SEQ ID NO: 12)
AY145781.1           ------------------------------------------ 181 (SEQ ID NO: 14)
GU321341.1           ------------------------------------------ 175 (SEQ ID NO: 16)
SOLYC12G099190       ------------------------------------------ 180 (SEQ ID NO: 11)
AT5G64620            ------------------------------------------ 180 (SEQ ID NO: 9)
XP_008668976.1       ------------------------------------------ 176 (SEQ ID NO: 8)
```

FIG. 1B

CLUSTAL O(1.2.4) multiple sequence alignment

```
Csa15g017550_134aa   ------------------------------------------------MKYDFCVNSLTQDFQ    15
Csa15g017550_168aa   ----------------LVSLVVFSLLLIGFASAQTLIVDSCKKAAAKEFMKYDFCVNSLTQDFQ    49
Csa17g075360         ---MKMIVM---------------------VMMMMMSEGSMIDQTCKQT-------PDFNLCVSLLNSDPR    41
Csa03g051630         ---MKLIVM---------------------VMTMMMISEGSMIDQTCKQT-------PDFKLCVSLLNSDPR    41
Csa14g051860         ---MKLIVM---------------------VMTMMMISEGSMIDQTCKQT-------PDFKLCVSLLNSDPR    41
Csa02g074171         MASSLIF-LLIEFTLSFPSSTLISAKSNATIIESTCKTT-------NNYKFCVSALKSDPR    53
Csa11g101740         MASSLIFLLFLIFTLSFSSPTLISAKSNATIIESTCKTT-------NNYKFCVSALKSDPR    54
Csa18g038260         MASSLIFLLFLIFTLSFSSSTLVSAKSNATIIESTCKTT-------NNYKFCVSALKSDPR    54
                                                                    .: **. *..***:

Csa15g017550_134aa   SKTATTLEGL---VLASTKNAAAETLNVKGLAEQILKGKGYGPGMEAAGLHKCVKIYGGAYD    73
Csa15g017550_168aa   SKTATTLEGL---VLASTKNAAAETLNVKGLAEQILKGKGYGPGMEAAGLHKCVKIYGGAYD   107
Csa17g075360         GSSADISGLALILIDKIKVLATKTLN----EINGLYK----KRPELKQALDQCSRRYKTILN    95
Csa03g051630         GSSADISGLALILIDKIKVLATKTLT----EINGLYK----KRPELKQALDQCSRRYKTILN    95
Csa14g051860         GSSADTSGLALILIDKIKVLATKTLT----EINGLYK----KRPELKQALDQCSRRYKTILN    95
Csa02g074171         SPTADTKGLAAIMIGVGMTNATSTAT----YIAGNLTSAANDVVLKKVLQDCSEKYALAAD   110
Csa11g101740         SPTADTKGLAAIMIGVGMTNATSTAT----YIAGNLTSAANDVVLKKVLQDCSEKYALAVD   111
Csa18g038260         SPTADTKGLAAIMIGVGMTNATSTAT----YIAGNLTSAANDVVLKKVLKDCSEKYALAAD   111
                      .* :                              .    *.* .*       :

Csa15g017550_134aa   F-LNTALANVQSHHYSTAVEEFLYASFAPFDCVKYYWIS-PFAKESYII-FEKIL------   125
Csa15g017550_168aa   F-LNTALANVQSHHYSTAVEEFLYASFAPFDCVKYYWIS-PFAKESYII-FEKIL------   159
Csa17g075360         ADVPEAIEAISKGVPKFGEDGVIDAGVEASVCEEGFQGKSPLITSL-------TKSMQNISS   149
Csa03g051630         ADVPEAIEAISKGVPKFGEDGVIDAGVEASVCEEGFQGKSPLITSL-------TKSMQNISS   149
Csa14g051860         ADVPEAIEAISKGVPKFGEDGVMDAGVEASACEEGFQGKSPLITSL-------TKSMQNISS   149
Csa02g074171         S-LRQTIQDIDDEAYDYASMHVLAAEDYPNVCRNIFRRAKGLSYPVGIRRREQSLRRICG   169
Csa11g101740         S-LRQTIQDLDSEAYDYASMHVLAAEDYPNVCRNIFRRAKGLSYPVEIRRREQSLRRICG   170
Csa18g038260         S-LRQTIQDLDDEAYDYASMHVLAAEDYPNVCRNIFRRAKGLSYPVEIHRREQSLRRICG   170
                       .*  :                  :

Csa15g017550_134aa   IPMTLTKML--   134    (SEQ ID NO: 2)
Csa15g017550_168aa   IPMTLTKML--   168    (SEQ ID NO: 5)
Csa17g075360         VTRAVVRMLL-   159    (SEQ ID NO: 81)
Csa03g051630         VTRAVVRMLL-   159    (SEQ ID NO: 77)
Csa14g051860         VTRAVV-----   155    (SEQ ID NO: 79)
Csa02g074171         VVSGILDRLVE   180    (SEQ ID NO: 83)
Csa11g101740         VVSGILDRLVE   181    (SEQ ID NO: 85)
Csa18g038260         VVSGILDRLVE   181    (SEQ ID NO: 87)
                     ::
```

FIG. 2

Analysis of multiple open reading frames of the Csa15g017550 putative plant invertase inhibitor/pectin methylesterase inhibitor.

```
          *  T  C  S  S  S  I  N  S  Y  F  I  Y  F  P  Q  K  ·
  1   TGAACATGTT CTTCATCAAT CAATTCTTAT TTTATATACT TTCCCCAAAA

· K  N  K  I  K  L  L  V  S  L  V  V  F  S  L  L  L  ·
 51   GAAAAACAAA ATAAAGTTAT TGGTTTCCTT GGTTGTGTTC TCTCTTCTCT
                                        P675

· I  G  F  A  S  A  Q  T  L  I  V  D  S  C  K  K
101   TGATCGGTTT TGCATCTGCG CAAACTCTCA TAGTAGATTC TTGCAAGAAA

A  A  A  K  E  P  F  M  K  Y  D  F  C  V  N  S  L  ·
151   GCAGCCGCAA AAGAGCCGTT TATGAAATAT GATTTCTGCG TCAATTCTCT

· T  Q  D  P  Q  S  K  T  A  T  T  L  E  G  L  V  L  ·
201   TACACAAGAT CCACAAAGCA AAACGGCGAC CACCCTCGAA GGTTTAGTCC
                                                      P677

· A  S  T  K  N  A  A  A  E  T  L  N  V  K  G  L
251   TAGCATCGAC GAAGAATGCT GCGGCGGAAA CACTGAACGT AAAAGGACTC
           P677                                    P676

A  E  Q  I  L  K  G  K  G  Y  G  P  G  M  E  A  G  ·
301   GCTGAACAGA TCCTCAAGGG GAAGGGATAT GGGCCAGGTA TGGAGGCAGG
           P676

· L  H  K  C  V  K  I  Y  G  G  A  Y  D  F  L  N  T  ·
351   GCTACACAAG TGCGTCAAGA TTTATGGAGG TGCTTATGAT TTTTTAAACA

· A  L  A  N  V  Q  S  H  H  Y  S  T  A  V  E  E
401   CTGCTTTAGC GAACGTTCAA TCACACCATT ATAGTACTGC TGTAGAGGAA

F  L  Y  A  S  F  A  P  F  D  C  V  K  Y  Y  W  I  ·
451   TTTCTTTATG CTTCATTTGC ACCGTTCGAC TGCGTGAAAT ATTATTGGAT
                                                       P678

· S  P  F  A  K  E  S  Y  I  I  F  E  K  I  L  I  P  ·
501   TTCTCCCTTC GCTAAGGAGA GCTATATTAT CTTTGAGAAG ATTTTGATTC
           P678

· M  T  L  T  K  M  L  *
551   CTATGACTTT AACTAAAATG TTGTGA  (SEQ ID NO: 4)
```

FIG. 5

```
CLUSTAL O(1.2.4) multiple sequence alignment

Csa15g017550_134aa      ------------------------------------------MKYDFCVNSLTQDPQSKTATTLE     23
Csa15g017550_168aa      ---LVSLVVFSLLLIGFASAQTLIVDSCKKAAAKEPFMKYDFCVNSLTQDPQSKTATTLE       57
XP_013675048            MKFFVSVALFFLFLNCFATAQTLIRDSCKTAAAKDPTLKYDFCVQSLEQDPQSKTATSLK       60
XP_013675049            MKFFVSVVMFFLLLNCFAAAQTLIRDSCKTAAAKDPNLKYDFCIQSLEQDPQSKTATSLS       60
XP_013714182            MKFFVSVVMFFLLLNCFAAAQTLIRDSCKTAAAKDPNLKYDFCVQSLEQDPQSKTATSLS       60
XP_013718725            MKFFVSVVMFFLLLNCFAAAQTLIRDSCKTAAAKDPNLKYDFCVQSLEQDPQSKTATSLS       60
                                                                  :******:** *********:*.

Csa15g017550_134aa      GLVLASTKNAAAETLNVKGLAEQIILKGKGYGPGMEAGLHKCVKIYGGAYDFLNTALANVQ     83
Csa15g017550_168aa      GLVLASTKNAAAETLNVKGLAEQIILKGKGYGPGMEAGLHKCVKIYGGAYDFLNTALANVQ    117
XP_013675048            GLVLASTTNAESKTTNVKGIVETILKSKTYPPGTEPALSTCVELYDDANNSLNEALMNVK     120
XP_013675049            GLVLAATNNAASKTINVKGIVETILKSKKYAPSTEPALRTCVKLYDDAYGSLKEALMNVK     120
XP_013714182            GLVLASTNNAASKTINVKGIVETILKSKKYAPSTEPALRTCVKLYDNAYGSLKEALMNVK     120
XP_013718725            GLVLASTNNAASKIINVKGIVEIILKSKKYQPGTEPALRTCVELYDDANDSLKEALMNVK     120
                        *****:*..**   :  ****:** :** .  .   ..  *. .  **..  ** **:

Csa15g017550_134aa      SHHYSTAVEEFLYASFAPFDCVKYY------WISPFAKESYIIFEKILIPMTLTKML*         134 (SEQ ID NO: 2)
Csa15g017550_168aa      SHHYSTAVEEFLYASFAPFDCVKYY------WISPFAKESYIIFEKILIPMTLTKML*         168 (SEQ ID NO: 5)
XP_013675048            SGDYKSANVDLSAALDEPGTCEDGFKEKHAKSPVTNENNVLFQKILIPLAFTNML--          175 (SEQ ID NO: 75)
XP_013675049            SSDYKSANMHLSAALDEPVTCEDGFKEKHAKSPVTNENNVLFQKILIPLAFTNML--          175 (SEQ ID NO: 71)
XP_013714182            SDDYRSANVHLSAALDEPNTCEDGFKEKHTKSPVTNENNILFQKILIPLAFTNML--          175 (SEQ ID NO: 69)
XP_013718725            SDDYRSANVHLSAALDEPNTCEDGFKEKHTKSPVTNENNILFQKILIPLAFTNML--          175 (SEQ ID NO: 73)
                        * *  :.   .::  * :.*:: ****:. :*********:*
```

FIG. 14

CLUSTAL O(1.2.4) multiple sequence alignment

```
XP_006604724         --MERSTKLFSAALVLCVVMAHQTAAQELKGXNLINKVCTIT-------PSRDLCVGILS  52
Csa15g017550_134aa   ------------------------------------------------MKYDFCVNSLIT 11
Csa15g017550_168aa   --------LVSLVVFSLLL----------IGFASAQTLIVDSCKKAAAKEPTMKYDFCVNSLIT 45
NP_001235997         MILPSSSLLFTLTILLCSF----------LSFVCANRLIQQTCKNCSKNDPNISYKFCVTSFQ 53
XP_003550932         MKFAYNL-----VMIFFIFL---------FQXSNGSNLILQSCKEASKNDPNLSYDFCVASLE 49
XP_006579665         MKFAS-Y-----LVIFLIFL---------FHCSNGSNLIPQSCKEASKHDPNLSYDFCVASLE 48
                                                                         . :**  .

XP_006604724         SDPIRS--PDADLKDLAVISLRVAARNASGILSE-AKMLIDDNLDPDVQQGLSDCKETI 109
Csa15g017550_134aa   QDPQSK--TATTLEGIVLASTKNAAAETLNV-KGLAEQILKGKGYGPGMEAGLHKCVKIY  68
Csa15g017550_168aa   QDPQSK--TATTLEGIVLASTKNAAAETLNY-KGLAEQILKGKGYGPGMEAGLHKCVKIY 102
NP_001235997         SDHRSH--YAKNLQELGLISIKITRHNVTDTNAHINELLKKNKSLDPFIKECLDDCVEVY 111
XP_003550932         EALSKCHFPPTNLEDLVGMSINLSKSNVTNMVSIISN-LLKNKTFDQYTKACLKDCFDLY 108
XP_006579665         EASSKCHFPPTNFEDLVGMSIQLTESNVTNMVSIISN-LLEMKSFDQVTKACLKDCFDLY 107
                             . .    *                              *     *    .

XP_006604724         LDAESQLEDTIASLLVDSDTDTQIWLKAALAAIDTCDASIPGDDDV----LSVKSAMFRR 165
Csa15g017550_134aa   GGAYDFLNTALANVQSHHYSTAVEEFLYASFAPFDC------VKYYWISPFAKESYIIFE 122
Csa15g017550_168aa   GGAYDFLNTALANVQSHHYSTAVEEFLYASFAPFDC------VKYYWISPFAKESYIIFE 156
NP_001235997         SDTISTFREAIRDYKAKRYADCNVKLSSIIDASTTCEDGFKQKND-AISPLTKRNKDTFQ 170
XP_003550932         SDSLSALDDAVVAFKSKDLDTAGINLSASLDNSVTCEDQFKDKKGET-SPITKENNVYFQ 167
XP_006579665         SDSLSALDDAVVAFKSKDLDTAAINLSATFDMSVTCEDQFKDKKGETSSPLTMENRVYFQ 167
                              :             .                                  *

XP_006604724         LCNIAIAITKRLNKPLKF 183 (SEQ ID NO: 95)
Csa15g017550_134aa   KILIPMTLITKML----- 134 (SEQ ID NO: 2)
Csa15g017550_168aa   KILIEMTLTKML------ 168 (SEQ ID NO: 5)
NP_001235997         LSAIALSIVNMLINTDK- 187 (SEQ ID NO: 93)
XP_003550932         LNVISLAFIQMFRQHY-- 183 (SEQ ID NO: 89)
XP_006579665         LNVISLAFIQMFRQHY-- 183 (SEQ ID NO: 91)
                     * :::  :
```

FIG. 15

```
CLUSTAL O(1.2.4) multiple sequence alignment

NP_001143588         MLAATMYYHNKTKMPPPCSCFSAVSVPFSSFKTITMLLLLLILQQLSAAA------------   52
XP_008668976         ------------------------------MKLLQALCPLVI------------------   12
XP_008655849         ---------------------------SGTP--------YTAVGVIF-------------   21
Csa15g017550_134aa   ------------------------------------------------------------    0
Csa15g017550_168aa   ---------------------------------LVSLVVFSLLLIGFASAQ---------   18
NP_001148423         ------------------MTRA----------SSSSSSRAVTLVLLGLRLLLLVGVAQAV----VELVP   37
NP_001149041         ------------------MAMRSLALLVLLSLLVVGVAQAVELEMELVP-----------   31

NP_001143588         ------VAGMATTKLGLSDVVTDTCDRCSKSNPQVNYTLCVSSLSSDPESRQ   98
XP_008668976         ------LLACSTSNASVLQDACKSFAAKIPDTGYAYCIKFFQADRGSAG   55
XP_008655849         A-----ASAGRTAAPAAAPSSKYSLEEEACEQT------AGHEDLCVETLSADPSSKT   67
Csa15g017550_134aa   ------------------------------MKYDFCVNSLTQDFQSKT   18
Csa15g017550_168aa   -------------TLIVDSCKKAAAKEPTMKYDFCVNSLTQDFQSKT   52
NP_001148423         ADDNIAAAAGTAVDDGEPPQQCATPVSVEEACRGASETHAGVAYDHCMASLGADPRSKE   97
NP_001149041         AD--------AIAMTMDREFPQECATPVSVEEACRSASETHAGVAYDHCMASLGADFRSKE   84
                                                    *:  :    *    *

NP_001143588         ADL---HGLAIISAKLLRSGAVAMEAKMADLSREE------RPWSPRRSCLDACVGVYRNSL   151
XP_008668976         ADK---RGLAAIAVRIMGAAAKSTASHIAALRAS------EKDKERLACLSDCSEVYAQAV   107
XP_008655849         ADTTGLARLAIQAAQRNASETATYLSSIYDDD---SLE--NKTAQLQQCLEMCGERIESAV   123
Csa15g017550_134aa   ATTL--EGLVLASTKNAAA-----ETLNVKGLAEQILKGKGYGPGMEAGLHKCVKIYGGAY   72
Csa15g017550_168aa   ATTL--EGLVLASTKNAAA-----ETLNVKGLAEQILKGKGYGPGMEAGLHKCVKIYGGAY   106
NP_001148423         AGNKNMHGLAVLATRMAIDHAASTESKIDDLA--ELRAASSDFQARARFNHCLEQYGGAA   155
NP_001149041         AGNKNMHALAVLATRMAIDHAASTESKIDDLA--ELERAASSDFQARARFNHCLEQYGGAA   142
                      *         :  :                            *         *  :

NP_001143588         YDLGSSIVAI----QERRYADAKTSMSAAVDAPVTCEDEFKE-QGLEPPMRAETKRLFQQA   207
XP_008668976         DQTGVAAKGIASGTPRGRADAVMALSTVEDAPGTCEQGFQD-LGVRSPLASEDAGFRKDA   166
XP_008655849         EQLSDATSAL---DTGAYSESEELVVASQAEVRLCQRGCQAVPNHRNILSARNRNVDQLC   180
Csa15g017550_134aa   DFLNTALANV----QSHHYSTAVEEFLYASFAPFDCVKYYWISPFAKES---------YIIFE   122
Csa15g017550_168aa   DFLNTALANV----QSHHYSTAVEEFLYASFAPFDCVKYYWISPFAKES---------YIIFE   156
NP_001148423         DLLRDALDNL----KAKIYGKAMEQLTAAMGASESCED-AWKGEEEDVPVAAHDREYGRMA   211
NP_001149041         DLLRDALDNL----KAKIYGKAMEQLTAAMGASESCED-AWKGE-EDVFVAAHDREYGRMA   197
                                                        *

FIG. 16A
```

```
NP_0011435688         VISLAIISLL--------  217 (SEQ ID NO: 99)
XP_008668976          SIALSVTAAL--------  176 (SEQ ID NO: 107)
XP_008655849          SIALAIYKLIH--GPFS   195 (SEQ ID NO: 105)
Csa15g017550_134aa    KILIPMTLTKML------  134 (SEQ ID NO: 2)
Csa15g017550_168aa    KILIPMTLTKML------  168 (SEQ ID NO: 5)
NP_0011448423         HIAFGFTHHAAVAAAAA   228 (SEQ ID NO: 101)
NP_0011149041         HIAFGFTHHAAAAAA--   211 (SEQ ID NO: 103)
                      * :
```

FIG. 16B

```
CLUSTAL O(1.2.4) multiple sequence alignment

NP_001148423_corn      ------------------------------MTRA----SSSSSSRRV----TLVLLGLRLLLLVGVAQAV----VELVP    37
NP_001149041_corn      ------------------------------------------MAMR----SLALLVLLSLLVVGVAQAVELEMELVP    31
XP_008668976_corn      --------------------------------------------------MKLLQALCPLVILLACS---------    17
NP_001143588_corn      MLAATMYYHNKIKMPPPCSCFSAVSVPFSSFKTITMLLLLLLLLLLQQLSAAAV---------------------    53
NP_001235997_soybean   --------------------------------MILPSSSLLFTLTILLCSFLSF---------------------    22
XP_003550932_soybean   --------------------------------MKFAYN----LVMIFFIFLFQY---------------------    18
XP_006579665_soybean   --------------------------------MKFAS-----YLIVIFLIFLFHC--------------------    17
Csa15g017550_134aa     ---------------------------------------------------------------------------    0
Csa15g017550_168aa     ---------------------------------LV------SIVVFSLLLIGF---------------------    14
XP_013675048_canola    --------------------------------MKFFV-----SVALFFLFLNCF---------------------    17
XP_013675049_canola    --------------------------------MKFFV-----SVVMFFLLLNCF---------------------    17
XP_013714182_canola    --------------------------------MKFFV-----SVVMFFLLLNCF---------------------    17
XP_013718725_canola    --------------------------------MKFTV-----SVVMFFLLLNCF---------------------    17
XP_006604724_soybean   --------------------------------MERSTKLFSAALV-LCVVVMAHQ-------------------    22
XP_008655849_corn      --------------------------------MASGTPYTAVGVIFLSVFLVAAAS------------------    24

NP_001148423_corn      ADDNIAAAAAGTAVDDGEPPQQCATPVSVEEACRGASETHAGVAYDHCMASLGADPRSKE                 97
NP_001149041_corn      AD----------AIAMTMDREPPQECATPVSVEEACRSASETHAGVAYDHCMASLGADPRSKE              84
XP_008668976_corn      --------------TSNASVLQDACKSFAAKIPDTGYAYCIKFFQADRGS---                        53
NP_001143588_corn      --AGMATTKLGLSDVVTDTCDRCSKSNFQVNYTLCVSSLSSDPHS---                             96
NP_001235997_soybean   ------------VCAMRLIQQTCKNCSKNDPNISYKFCVTSFQSDHRS---                          58
XP_003550932_soybean   ------------SNGSNLIQSCKEASKNDPNLSYDFCVASLEEALSKCH                            56
XP_006579665_soybean   ------------SNGSNLIPQSCKEASKHDPNLSYDFCVASLEEASSKCH                           55
Csa15g017550_134aa     ---------------MKYDFCVNSLTQDPQS---                                           16
Csa15g017550_168aa     ------------ASAQTLIVDSCKKAAAKEPFMKYDFCVNSLTQDPQS---                          50
XP_013675048_canola    ------------ATAQTLIRDSCKTAAAKDPTLKYDFCVQSLEQDPQS---                          53
XP_013675049_canola    ------------AAAQTLIRDSCKTAAAKDPNLKYDFCIQSLEQDPQS---                          53
XP_013714182_canola    ------------AAAQTLIRDSCKTAAAKDPNLKYDFCVQSLEQDPQS---                          53
XP_013718725_canola    ------------AAAQTLIRDSCKTAAAKDPNLKYDFCVQSLEQDPQS---                          53
XP_006604724_soybean   ----------T-AAQELKGKNLINKVCTI-T----PSRDLCVGILSSDPIR---                       57
XP_008655849_corn      ------AGRTAAPAAAPSSKYSLEEACEQTA------GHEDLCVETLSADPSS                        65
                                                                        *:    :
```

FIG. 17A

| | | |
|---|---|---|
| NP_001148423_corn | AGNKNMHGLAVLATRMAIDHAASTESKIDDLAE----LEAASSDPQARAREFNHCLEQYGGA | 154 |
| NP_001149041_corn | AGNKREMEHALAVLATRMAIDHAASTESKIDDLAE----LEAASSDPQARAREFNHCLEQYGGA | 141 |
| XP_008668976_corn | -AGADKRGLAAIAVRIMGAAAKSTASHIAALR-------ASEKDKERLACLSDCSEVYAQA | 106 |
| NP_001143588_corn | -RQADLHGLAIISAKLLRSGAVAMEAKMADLS-----RKKERPWSP-RRSCLDACVGVYRNS | 150 |
| NP_001235997_soybean | HYAKNLQELGLISIKITRHNVTDTNAHINELL----KKNKSLDPFIKECLDDCVEVYSDT | 114 |
| XP_003550932_soybean | PPPTNLEDLVGMSINLSKSNVTNMVSII-SNL-----LKNKTFDQYTKACLKDCFDLYSDS | 111 |
| XP_006579665_soybean | PPPTNFEDLVGMSIQLTESNVTNMVSII-SNL-----LENKSFDQYTKACLKDCFDLYSDS | 110 |
| Csa15g017550_134aa | KTATTLEGLVLASTRNAAAAETINVKGLA-EQI-----LKGKGYGPGMEAGLHKCVKIYGGA | 71 |
| Csa15g017550_168aa | KTATTLEGLVLASTRNAAAAETINVKGLA-EQI-----LKGKGYGPGMEAGLHKCVKIYGGA | 105 |
| XP_013675048_canola | KTATSLKGLVLASTTNAESKTTNVKGIV-ETI-----LKSKTYFPGTEPALSTCVELYDDA | 108 |
| XP_013675049_canola | KTATSLSGLVLAATNNAASKTINVKGIV-ETI-----LKSKKYAPSTEPALRTCVKLYDDA | 108 |
| XP_013714182_canola | KTATSLSGLVLASTNNAASKIINVKGIV-ETI-----LKSKKYAPSTEPALRTCVKLYDNA | 108 |
| XP_013718725_canola | KTATSLSGLVLASTNNAASKIINVKGIV-EII-----LKSKKYQPGTEPALRTCVELYDDA | 108 |
| XP_006604724_soybean | SPDADLKDLAVISLRVAARNASGILSEARMLIDDDNLD------PDVQQGLSDCKETILDA | 112 |
| XP_008655849_corn | K-TADTTGLARLATQAAQRNASETATYLSSIYDDDSLEN---KTAQLQQCLENCGERYESA | 122 |
| | : * :: * | |
| NP_001148423_corn | ADLLRDALDNLK----AKIYGKAMEQLTAAMGASESCEDAWKGEEE--DVPVAAHDREYGR | 209 |
| NP_001149041_corn | ADLLRDALDNLK----AKIYGKAMEQLTAAMGASESCEDAWKGE-E--DVPVAAHDREYGR | 195 |
| XP_008668976_corn | VDQTGVAAKGIASGTPRGRADAVMALSTVEDAPGTCEQGFQDLGV--RSPLASEDAGFRK | 164 |
| NP_001143588_corn | LYDLGSSIVAIQ----ERRYADAKTSMSAAVDAPVTCEDEFKEQGL--EPPMRAETKRLFQ | 205 |
| NP_001235997_soybean | ISTFREAIRDYK----AKRYADCNVKLSSIIDASTTCEDGFKQKND-AISPLIKRNKDTFQ | 170 |
| XP_003550932_soybean | LSALDDAVVAFK----SKDLDTAGINLSASLDNSVTCEDQFKDKKGET-SPITKENNVYFQ | 167 |
| XP_006579665_soybean | LSALDDAVVAFK----SKDLDTAAINLSATFDNSVTCEDQFKDKKGETSSPLTMENRVYFQ | 167 |
| Csa15g017550_134aa | YDFLNTALANVQ----SHHYSTAVEEFLYASFAPFDCVKYY-----W--ISPFAKESYIIFE | 122 |
| Csa15g017550_168aa | YDFLNTALANVQ----SHHYSTAVEEFLYASFAPFDCVKYY-----W--ISPFAKESYIIFE | 156 |
| XP_013675048_canola | NNSLNEALMNVK----SGDYKSANVDLSAALDEPGTCEDGFKEKHA--KSPVTNENNVLFQ | 163 |
| XP_013675049_canola | YGSLKEALMNVK----SSDYKSANMHLSAALDEPVTCEDGFKEKHA--KSPVTNENNVLFQ | 163 |
| XP_013714182_canola | YGSLKEALMNVK----SDDYRSANVHLSAALDEPNTCEDGFKEKHT--KSFVTNENNILFQ | 163 |
| XP_013718725_canola | NDSLKEALMNVK----SDDYRSANVHLSAALDEPNTCEDGFKEKHT--KSPVTNENNILFQ | 163 |
| XP_006604724_soybean | ESQLEDTIASLL----TQSDTDTQIWLKAALAAIDTCD--ASIPG-DDDVLSVKSAMFRR | 165 |
| XP_008655849_corn | VEQLSDATSALD---TGAYSESEELVVASQAEVRLCQRGCQAVFN-HRNILSARNRNVDQ | 178 |
| | * | |

FIG. 17B

| | | |
|---|---|---|
| NP_001148423_corn | MAHIAFGFTHHAAVAAAAA | 228 (SEQ ID NO: 101) |
| NP_001149041_corn | MAHIAFGFTHHAAAAA------ | 211 (SEQ ID NO: 103) |
| XP_008668976_corn | DASIALSVTAAL---------- | 176 (SEQ ID NO: 107) |
| NP_001143588_corn | QAVISLAIISLL---------- | 217 (SEQ ID NO: 99) |
| NP_001235997_soybean | LSAIALSIVNMLINTDK----- | 187 (SEQ ID NO: 93) |
| XP_003550932_soybean | LNVISLAFIQMFRQHY------ | 183 (SEQ ID NO: 89) |
| XP_006579665_soybean | LNVISLAFIQMFRQHY------ | 183 (SEQ ID NO: 91) |
| Csa15g017550_134aa | KILIPMTLITKML--------- | 134 (SEQ ID NO: 2) |
| Csa15g017550_168aa | KILIPMTLITKML--------- | 168 (SEQ ID NO: 5) |
| XP_013675048_canola | KILIPLAFTNML---------- | 175 (SEQ ID NO: 75) |
| XP_013675049_canola | KILIPLAFTNML---------- | 175 (SEQ ID NO: 71) |
| XP_013714182_canola | KILIPLAFTNML---------- | 175 (SEQ ID NO: 69) |
| XP_013718725_canola | KILIPLAFTNML---------- | 175 (SEQ ID NO: 73) |
| XP_006604724_soybean | LCNIAIAITKRLNKPLKF---- | 183 (SEQ ID NO: 95) |
| XP_008655849_corn | LCSIALAITKLIHGPPS----- | 195 (SEQ ID NO: 105) |
| | *  : | |

FIG. 17C

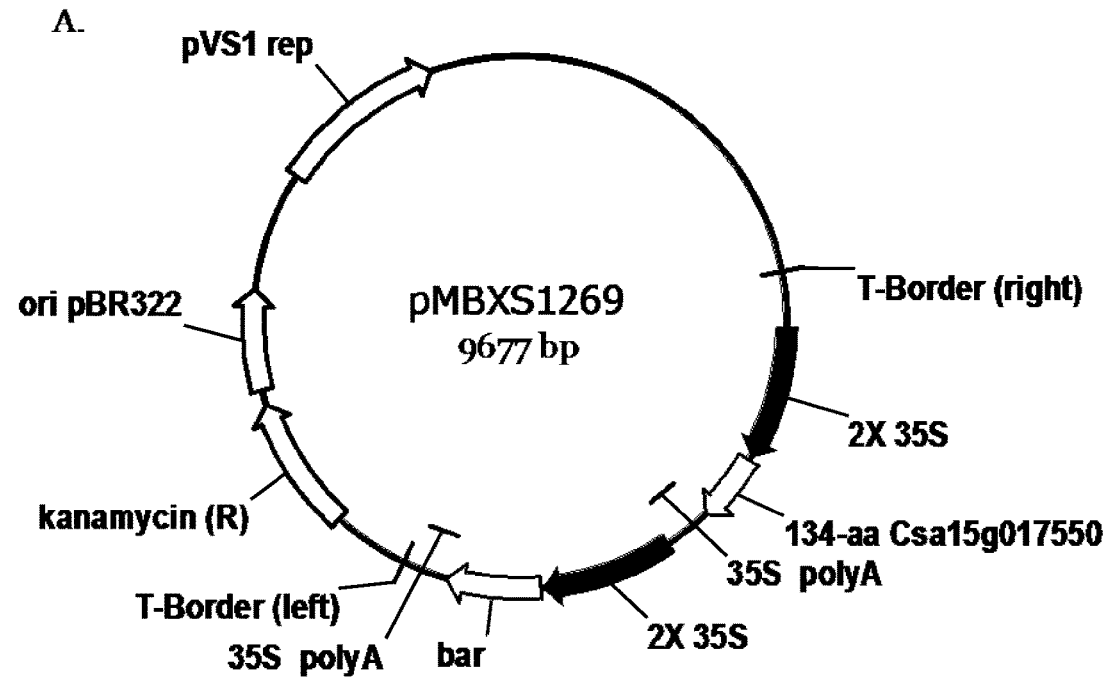
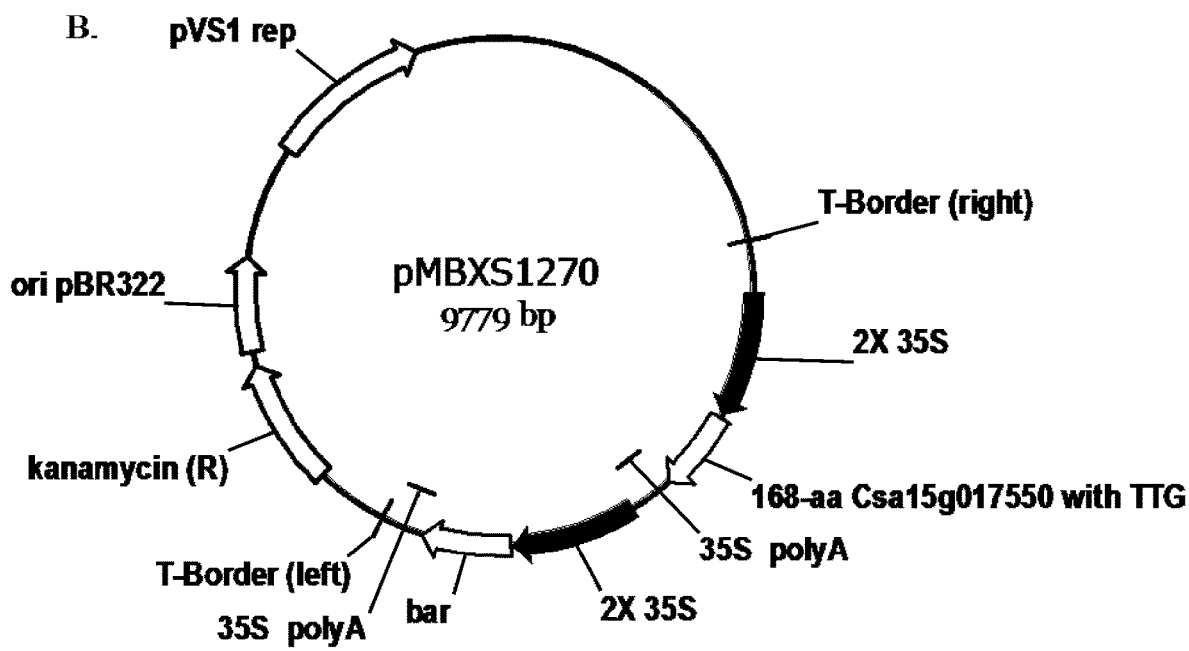
FIG. 19

CLUSTAL O(1.2.4) multiple sequence alignment

```
XP_006589707.1      ------------------------------------------------MLPITCILFMC    11
XP_003526981.1      ------------------------------------------------MTSTLLSLLFLLFSL    15
XP_003535958.1      ------------------------------------------------MAVSSSATKWVLFLLLAL   18
XP_003555714.4      MLEPSESTFPNSLSLLFLSSTFSLTKATTHTLRARGIQLSAMAVSSSSATKWVELLLAL   60
                                                                     :  *:

XP_006589707.1      LL----------SSFSPPINALLNLN---------------------LTLPHQIPHEESVVQ   42
XP_003526981.1      LIP-----------------------------------------------------------   34
XP_003535958.1      LIREEAMAMATTPQISDLRNVEVERHRLPSLTNSSMVERAKEADKLNEQAAVANPEEVVS   78
XP_003555714.4      LIREEAMA----TPQISDLRNLEVERHRLPSLTNSSMAERAKEAEKLNEQAAVANPEEVVS  117
                     *:                                              : **.**.

XP_006589707.1      DIQRKVNASLRRREMLSKDEQQGMSSCLITGNPIDDCWRCFPNWAAERQKLAECGLGFGKY   102
XP_003526981.1      EVNRKINGSIA------RPRRNLGYIWCGSGNPIDDCWRCDPNWEQNRQRLADCAIGFGKN    89
XP_003535958.1      MVEMSIQN---S-----TERRKLGYFSCGTGNPIDDCWRCDPNWQRNRKRLADCGIGFGRN   131
XP_003555714.4      MVEMSIQN---S-----TERRKLGFFSCGTGNPIDDCWRCDPNWQRNRKRLADCGIGFGRN   170
                     . .:         . :  * .********** ***::.*:* ***.  *****:

XP_006589707.1      AMGGKGGQIYIVTDSSDRDPANPIPGTLRHAVIQDEALMTVFAADMTINLKHELIFNSYK   162
XP_003526981.1      AIGGRDGKIYIVVDDDGDDDAVNPKPGSLRHAVIQDEPLWIIFARDMVIQIKEELLMNSFK   149
XP_003535958.1      AIGGRDGKFYVVTDFRDDDPVNPKPGTLRHAVIQDRPLMIVFKRDMVIQLKQELIMNSFK   191
XP_003555714.4      AIGGRDGKFYVVTDPRDDDPVNPKPGTLRHAVIQDKPLMIVFKRDMVIQLKQELIMNSFK   230
                    *:**::.: :*:.**  ****:**.**********.** ::*  **.*::*:**::**:*

XP_006589707.1      TLDGRGANVHVTGHGCITLQYVSNIIIHNIHHCTESGNTNIRASPTHVGWRGKSDGDG   222
XP_003526981.1      TIDGRGASVHVAGGPCITIQYVTNVIINGIHNIHIHDCKQGGNAMVRDSPRHYGWRTVSDGDG   209
XP_003535958.1      TIDAARGVNVHIANGACITIQFVTNVIIHGLHIHGLHIHDCKPTGNAMVRSSPTHFGWRTMADGDA   251
XP_003555714.4      TIDGRGVNVHIANGACITIQFVTNVIIHGLHIHGLHIHDCKPTGNAMVRSSPTHFGWRTMADGDA   290
                    *:*  *.*** .* ***:*:*:*:*:  :* :* .** * **: *:** *:* ** :.***.

XP_006589707.1      ISIFGSRKIWIDHCSLSYCTDGLIDAIMGSTGITISNSHFAKHDEVMLLGHDDKYLVDRG   282
XP_003526981.1      VSIFGGSHVWIDHCSLSNCMDGLIDAIHGSTAITISNNYMTHHDKVMLLGHSDAYTQDKA   269
XP_003535958.1      ISIFGSSHIWVDHNSLSHCADGLVDAVMGSTAITI SNNHFTHRNEVILLGHSDSYTRDKL   311
XP_003555714.4      ISIFGSSHIWVDHNSLSHCADGLVDAVLGSTAITI SNNHFTHRNEVILLGHSDSYTRDKQ   350
                    :****.  :*:**.***.* ***:**::***.:***:     :::*:::**.*.*  .:
```

FIG. 24A

```
XP_006589707.1      MQVTIAFNHFGEGLVQRMPRCRLGYIHVNNDFTQWRMYAIGGSANPTINSQGNRYTAPG    342
XP_003526981.1      MQVTIAFNHFGEGLVQRMPRCRLGYIHVNNDYTHWRMYAIGGSANPTINCQGNRFVAPD    329
XP_003535958.1      MQVTIAINHFGEGLIQRMPRCRHGYFHVNNDYTHWRMYAIGGSANPTINSQGNRYNAPT    371
XP_003555714.4      MQVTIAYNHFGEGLIQRMPRCRHGYFHVNNDYTHWRMYAIGGSANPTINSQGNRYNAPT    410
                    ******:*******:*******:**:*.***********.****:**

XP_006589707.1      DPDAKEVTKRVDTDDREWSGWNWRTEGDIMVNGAFFVPSGAAGQSGQYQEATSVQAKSAV    402
XP_003526981.1      DRFSKEVTKREDAPESEWQDWNWRSEGDLLVNGAFFTSSGAG-ASSSYARASSLSARPSS    388
XP_003535958.1      NPFAKEVTKRVETAETQWKGWNWRSEGDLLINGAYFTPSGAG-ASASYARASSLGAKSSS    430
XP_003555714.4      NRFAKEVTKRVETAESQWKGWNWRSEGDLLINGAYFTPSGAG-ASASYARASSLGAKSSS    469
                      :*******  :  .  :* **** ***::***:*:.:*.*  :*: ***:*. ...

XP_006589707.1      QIDQLTMYSGVLGDFRDNGDLYPGFNGGGTVTGATSKGNTDGSSSDDGGDFFGMIFRGGS    462
XP_003526981.1      LVGSITTGAAGALSCKKGSPC---------------------------------------    408
XP_003535958.1      MVDSMTSNAGALGCKKRGRQC---------------------------------------    450
XP_003555714.4      MVGSMTSNAGALGCKKRGSQC---------------------------------------    489
                     : .:*   ..**   *:.  :

XP_006589707.1      SSSSSSQAAPPSSVLFVSIFLSLLIIFVLDTTMHAFLLSLL                       504   (SEQ ID NO: 142)
XP_003526981.1      -----------------------------------------                       408   (SEQ ID NO: 141)
XP_003535958.1      -----------------------------------------                       450   (SEQ ID NO: 143)
XP_003555714.4      -----------------------------------------                       489   (SEQ ID NO: 144)
```

FIG. 24B

CLUSTAL O(1.2.4) multiple sequence alignment

```
XP_006587735.1      ------------------------------------------------------------MAACIF      6
XP_003543834.1      ------------------------------------------------------------MAALVI      6
ISY                 ---LVS--LVVFSLLLIGFASAQTLIVDSCKEAAKEPFMKYDFCVN                           42
NP_001237215.2      MTNLKPLILFFYLLAIVVMISIPSSHCSRTLLFENEKLIENTCKKT-------PNYNVCLE            54
NP_001235420.1      MKIMESLALIFYSTLVLATISVPATNSRIIHQKMNANLIEETCKQT-------PHHDLCIQ            54
                                                                         :

XP_006587735.1      TVAQDGTADFQTVQEAIDAVPLGNIRRTVIRVSFGIYRQPVYVFKTKNFITLAALSPEDT             66
XP_003543834.1      TVSQDGTGQYRTVQEAIDAVPLGNTRRTVIRVSPGTYRQPLYVAKTKNFITLVGLRPEDT             66
ISY                 SLTQDPQSKTATTLEGIVLA---------------------------------STKNA               67
NP_001237215.2      SIKASPGSSSADV-TGLAQI---------------------------------MVKEM               78
NP_001235420.1      YLSSDPRSTEADV-TGLALI---------------------------------MVNVI               78
                     :   .             :                                 :

XP_006587735.1      VLTWNNTATGIDHHQPARVIGTGTFGCGSTIVEGEDFIAENITFENSAPEGSGQAVAIRV            126
XP_003543834.1      VLTWNNTATSIHHHQDARVIGTGTGTFGCGTIIVEGGDFIAENITFENSSPQGAGQAVAVRV          126
ISY                 AAETLNVKGLAEQILKGK--------------------------------GYGPGMEA               93
NP_001237215.2      KAKANDALKRIQELQRVG--------------------------------ASGPKQRR-             104
NP_001235420.1      KIKANNALDKIHQLLQK---------------------------------NPEPSQKE-             103
                     :  :    :: :                                    .

XP_006587735.1      TADRCAFYNCREFLGWQDTLYLHYGKQYLKDCYIEGSSVDEIFGNSTALLEHCHIHCKSAGF          186
XP_003543834.1      TVDRCAFYNCREFLGWQDTLYLHYGIQYLKDCYIEGSVDEIFGNSTALLEHCHIHCKSAGF           186
ISY                 GLHKCVKI-------------------Y-----GGAYDFLN-TALANVQSHHYSTAVEEF            128
NP_001237215.2      ALSSCADK-------------------Y-----KAVLIADYPQATEALQKGDPKFAEDGA            140
NP_001235420.1      PLSSCAAR-------------------Y-----KAIVEADVAQAVASLQKGDPKFAEDGA            139
                     *  *                      *

XP_006587735.1      ITAQSRKSSQETTGYVFLRCVITGNGGNSYAYLGRFWGPFGRKVVFAYTYMDQCIRHVGWD           246
XP_003543834.1      ITAQSRNSPQEKTGYVFLRCVTGNGGTSYAYLGRPWRFARVVFAFTYMDQCIKPAGWN             246
ISY                 LY----------------------------------------------------------            130
NP_001237215.2      ND----------------------------------------------------------            142
NP_001235420.1      ND----------------------------------------------------------            141
```

FIG. 25A

```
XP_006587735.1    NWGKMENERSACFYEYRCFGPGCCPSKRVTWCRELLDEEAEQFLTHPFIDPELEKPWLAQ    306
XP_003543834.1    NWGKIENEKTACFYEYRCFGPGWCPSQRVKWARELQAEAAEQFLMHSFIDPESERPWLAQ    306
ISY               ----ASFAPFDCVKYY--------------WISPFAKE----SYIIFEKIL----IPMTLT    165
NP_001237215.2    ----AANEATYCETDFS-------------AAGNSPLHKQ------MNAMHDVAA----VTAAIV    180
NP_001235420.1    ----AAIEATTCENSFS-------------AGKSPLTNH------MNAMHDVAT----ITAAIV    178
                      :                              *   :

XP_006587735.1    RMALRIPYSA    316  (SEQ ID NO: 146)
XP_003543834.1    RMALKIPYSA    316  (SEQ ID NO: 145)
ISY               KML*------    168  (SEQ ID NO: 5)
NP_001237215.2    RLLL------    184  (SEQ ID NO: 147)
NP_001235420.1    RQLL------    182  (SEQ ID NO: 148)
                   :
```

FIG. 25B

CLUSTAL O(1.2.4) multiple sequence alignment

```
ISY              ----LVS--LVVFSLL----------------LIGFASAQTLIVDSCKKAAAKEFMKYDFCVN     42
NP_001237215.2   MTNLKPLILFFYLLAIVVMISIPSSHCSRTLLPENEKLIENTCKKT-------PNYNVCLE     54
NP_001235420.1   MKIMESLALIFYSTLVLATISVRPATMSRIIHQKMNANLIEETCKQT-------PHHDLCIQ     54
                     :  * :* :                    :  ** ::**:       :::*:

ISY              SLTQDPQSKTATTLEGIVLASTKNAAAETLNVKGLAEQILKGKGYGPGMEAGLHKCVKIY       102
NP_001237215.2   SIKASPGSSSADV-TGLAQIMVKEMKAKANDALKRIQELQRVGASGPKQRRALSSCADKY      113
NP_001235420.1   YLSSDPRSTEADV-TGLALIMVNVIKIKANNALDKIHQLLQK-NPEFSQKEFLSSCAARY      112
                  : .. .*   ::  ***. : *::::*.:*: .**:*::*   .. .::* :. :

ISY              GGAYDFLN-TALANVQSHHYSTAVEEFLYASFAPFDCVKYY----WISPFAKESYIIFEKI    158
NP_001237215.2   KAVLIADVPQATEALQKGDPKFAEDGANDAANEATYCETDFSAAGNSPLTKQMNAMHDVA    173
NP_001235420.1   KAIVEADVAQAVASLQKGDPKFAEDGANDAAIEATTCENSFS--AGKSPLTNHNNAMHDVA    171
                  *  .  .  **  *  .  :  **    *.     . :.    **:.*: :..: .
```

```
ISY              LIPMTLITKML*      168 (SEQ ID NO: 5)
NP_001237215.2   AVTAAIVRLLL       184 (SEQ ID NO: 147)
NP_001235420.1   TITAAIVRQLL       182 (SEQ ID NO: 148)
                  : :::  :
```

FIG. 26

```
XP_003517432.1      MATTTLMKLAF---MLLMNLVICSAESSIGRK-------SNPNPEEFVKSSCRATRYPVLC    51
XP_003530773.1      MRTQRLNHLLLSLFLFAAAFSSLHPTATAGDEGAPSPGDGDGDADFIRTSCNTTLYPDVC    60
XP_003525240.1      MRTQRLNHLLLSLFLFAAAFSSLHPTATAGDEGAPSAGDGDRDADFIRTSCNTTLYPEVC    60
                    *   *   *:*: :       .       . :            :*:***:.** **.:*

XP_003517432.1      VKSLLAYASVIRRSDRQLAFTALSVSISRSRSSAWLVKKMLKARGM--KPREYRAVQDCV   109
XP_003530773.1      FTSLSRYASAVQQNPGQLARVAISVSLSKVHRAASYVSNLTRDADYDGTTRAALALHDCF   120
XP_003525240.1      FTSLSRYANAVQQNPGHLARVAIAVSLSKVHRAASYVSNLTRDADYGGGSTRAALALHDCF  120
                    .**  **:. *:.:  **  *:*** *: .:::*  *   : *.     .   *  *:**

XP_003517432.1      ENIGDSVDRLRQSVTEL------GRTGEDFVWHMSNVQTWVSAALTDDSTCLDGFAGSAM   163
XP_003530773.1      SNLGDAVDEIRGSLKQMRQIGAAGAGASSFLFQMSNVQTWMSAALTDEETCTDGFQDVA-   179
XP_003525240.1      SNLGDAVDEIRGSLKQMRQIGSAGAGASSFLFQMSNVQTWLSAALTDEETCTDGFQDVA-   179
                    .*:***:** :* *: ::    * ...:.:* :******:.********:.** ***.*

XP_003517432.1      NGNVKALIKDRIVHVAQVTSNALALVNRFASRHPSATQTP            203  (SEQ ID NO: 149)
XP_003530773.1      DCPVKHDVCDRVTNVKKFTSNALALVNSYANKGMP-----            214  (SEQ ID NO: 150)
XP_003525240.1      DCPMKTGVCDRVSNVKKFTSNALALVNSYANKGMP-----            214  (SEQ ID NO: 151)
                     :*: : . ***: ::.:::***********   :  
```

FIG. 27

```
CLUSTAL O(1.2.4) multiple sequence alignment

XP_003531408.1      ------------------------------------------------------------       0
XP_003526711.1      ------------------------------MEYGRLGPSDPGGSS---------------RLNNV      20
XP_003553658.2      MPATNHPIYPLQTSHSTKSQYHLPSSSSSSSSSSSSSSSSSIYIYIYTMYSPISRKK      60

XP_003531408.1      --------MMASSSLFYLSLILTLTSAARHKPHPSPAKPEAKPAVTTATSPAIQQACA      52
XP_003526711.1      PPTSSGRKKIVLLSLFSVLLIAASAVTAVVV--RSRIQQNTRAHETRLGKPTQAISRTCS      78
XP_003553658.2      PFMESH-VDTILSAIFVLLLSSLTHF--------SITANATRTFQENSLHFQVANSTCE     110

XP_003531408.1      ATRFPQQCEASLSQSQNLPPNPNPTPLQLLQSAIALSSDMLATAQTMVKSLHD-ASADSR     111
XP_003526711.1      KIRFKTLCVKSLLDFPGSEEASEKD----LVHISFNVTLQHF--SKALYSSAAMSYTAMDP    133
XP_003553658.2      GTLYSDLCVSTLASFPDLTSKTLPQ----MIRSVVNHTIYEVTLSASNCSGLRRNLPKLDK    167
                         *   .  :  *

XP_003531408.1      NRTVAAATCIEILANSHYRIS------LASDALPRGRTKDARAWLGAALAYQYDCWNSLKY    166
XP_003526711.1      RVPAAYDDCLELLDDSVDALARSLNTVSVGAVGSA-NDDVLTWLSAALTNQDTCAEGFTD    192
XP_003553658.2      LEQRALDDCINLFDDTVSELETTIADLSQSTIGPKRYHDAQTLLSGAMTNLYTCLDGFAY    227
                         *  *::::  ::            .   ::  .    *. *..*:    *  :::

XP_003531408.1      ANDTEMVGKTMLFIDNLETLSSNALSMAFSFDAFGNDTASWKPFVTERDGFWEAVGSGGP    226
XP_003526711.1      AVGTVKDHMSSN--LRDLSELVSNCLAIFSGA----GAGDDFAGVFIQNRRRLMEMREDNFP    248
XP_003553658.2      SKGHVRDRFEEG--LLEISHHVSNSLAMLKKL---PAGVKKLASKNE--VFPGYGKIKDGFP    282
                         .          **.*:.     :                                *

XP_003531408.1      A------SAGGVPENMLTPDVTVCNNGGDGCYKTVQEAVNAAPANGTKRFVIYIKEGVIE    279
XP_003526711.1      TWLSREDRKLLILPLSQIQADIVVSKDGNGTVKTIAEAIKKVPEYSSRIIIYVRAGRYE    308
XP_003553658.2      TWLSTKDRKLLQAAVNETNFNLLVAKDGTGNFTTIAEAVAVAPNSSATRFVIHIKAGAYF    342
                                    :    : ::.  :   *.  .::*    . :   .*::.:::  * *

XP_003531408.1      E--TVRIPLEKRNVVFLGDGIGKTVITGNGNVGQQGMTTYNSATVAVLGDGFMAKELTVEN    338
XP_003526711.1      EENLKILGRKKTNVMFIGDGKGKTVITGGRNY--YQNLITFHTASFAASGSGFIAKDMTFEN    367
XP_003553658.2      E--NVEVIRKKTNLMFVGDGIGKTVVKASRNV--VDGWTTFQSATVAVVGDGFIAKGITFEN    400
                    *   :   : :*:  *:***  ***:           : ::*::::.**: .** :* ::*

XP_003531408.1      TAGPDAHQAVAFRLDSDLSVIENCEFLGNQDTLYAHSLRQFYKSCRIEGSVDFIFGNAAA    398
XP_003526711.1      YAGPGRHQAVALRVGADHAVVYRCNIIGYQDTMYVHSNRQFYRECDIYGTVDFIFGNAAV    427
XP_003553658.2      SAGPSKHQAVALRSGSDFSAFYKCSFVAYQDTLYVHSLRQFYRDCDVYGTVDFIFGNAAT    460
                     ***  ****:* :: * :.  :*    ::***:*.** ****::*  *.:******** .

FIG. 28A
```

```
XP_003531408.1    VFQDCQILYRPQVKPEKGENNAITAHGRTDPAEPTGFVFQNCLINGTEEYIALYLSKPQ       458
XP_003526711.1    VFQNCILWAR-----KPMAQQKNTITAQNRKDPNQNTGISIHNCRIMATPDLEAS-----KG    479
XP_003553658.2    VLQNCNLYAR-----KPNENQRNLFTAQGREDPNQNTGISILNCKVAAAADLIPV-----KS    512
                  *:*:*  . *     **    :****..* **.  *** ; **  :  :    :

XP_003531408.1    VHKNYLGRPWKEYSRTVFINSILEALVTPQGWMPWSG-DFALKTLYYGEFENKGTGSDLS    517
XP_003526711.1    SYPTYLGRPWKLYARTVYMLSYIGDHVHPRGWLEWNTSSFALDTCIYGEYMNYGPGSGLG    539
XP_003553658.2    QFKNYLGRPWKKYSRTVYLNSYMEDLIDPKGWLEWNG-TFALDTLYYGEYNNRGPGSNTS    571
                   .******* * : :*** :.*    ::   ** : .  :***.* :***: * **.

XP_003531408.1    QRVFWSSKIPA----EHVLTYSVQNFIQGNDWIPSSVGSPSS------    555  (SEQ ID NO: 152)
XP_003526711.1    QRVNWAGIRVINSTVEASRFTVGQFISGSSWLFSTGVAFIAGLST          584  (SEQ ID NO: 153)
XP_003553658.2    ARVTWPGIRVIKNATEANQFTVRNFIQGNEWLSSTDIPFFSDFS--        615  (SEQ ID NO: 154)
                  .**  .  :       :  :*  .*: *. *:  *.

FIG. 28B
```

```
CLUSTAL O(1.2.4) multiple sequence alignment

XP_025981966.1      MTNPKLGYAGISDSEEHIPSSKKNHKKLLLSLLATLLVAASVVAIVAGVERKTKNSDNSD    60
XP_003528739.1      MTNPKLGYAGISDSGNHIPSSKKNHKKLLLSLLATLLVAASLVAIVVGVKNKNSDNSAT-    59
                    **************.:***********************:****.**.**:******

XP_025981966.1      TNSTSLSXXXXXXXXXXXXXXXXXXXXXXXXXXXXXXNQRKVLTMTRDVIQLSLSI       120
XP_003528739.1      --STPLSLSHHSHTIVKSACS----STFYPELCYSAIASEPNVTHKITTNRDVIQLSLKI   113
                      ** ***                  :           *   ::**********.*

XP_025981966.1      TFRAVERNYFTVKKLLTKH-DLITKRETTALHDCLETIDETLDELREAQHDLELYPNKKTL   179
XP_003528739.1      TFRAVEQNIFTVKKLFTEHDDLITKREKTALHDCLETIDETLDELREAQHMLELYPNKKTL  173
                    ******:* ******:*:* *******:********************* **********

XP_025981966.1      YQHADDLKTLISAAITNQVTCLDGFSHDDADKHVRKELRKGQVTHVEHMCSNALAMTKNMT  239
XP_003528739.1      YQHADDLKTLISAAITNQVTCLDGFSHDDADKHVRKALRKGQVTHVEHMCSNALAMTKNMT  233
                    ************************************.***********************

XP_025981966.1      DGDIANYEYKMKVEN-----TNSNRKLLVENGVEWPEWISAADRRLLQAATVKADVTVAAD  295
XP_003528739.1      DSDIANYEYNMRVENNGQNGNSNRKLLVENDVEWPEWISAADRRLLQASTVKADVTVAAD   293
                    *.*******:*:***     .********:**************** :***********

XP_025981966.1      GSGDFKTVTEAVKAAPLKSSKRYVIRIKGGVTRENVEVDKKKTNIMFLGDGRTNTIITAS   355
XP_003528739.1      GSGDFKTVTEAVDAAPLKSSKRFVIRIKAGVYRENVEVPKKKNNIMFLGDGRTNTIITAS   353
                    ************.*********:*****.** ****** ***.*****************

XP_025981966.1      RNVVDGSTTFHSATVAVVGANFLARDITFQNTAGPSKHQAVALRVGGDLSAFFNCDFLAF   415
XP_003528739.1      RNVVDGSTTFHSATVAVVGSNFLARDLTFQNTAGPSKHQAVALRVGGDLSAFFNCDILAF   413
                    *******************:******:****************************:***

XP_025981966.1      QDTLYVHNNRQFFVKCLIITGTVDFIFGNSAVVFQDCDIHARLPDSGQKNMVTAQGRVDPN  475
XP_003528739.1      QDTLYVHNNRQFFVKCLIAGTVDFIFGNSAVVFQDCDIHARLPSSGQKNMVTAQGRVDPN   473
                    ******************..********************** ***************

XP_025981966.1      QNTGIVIQKCRIGATKDLESVKKNFKTYLGRPWKEYSRTTVIMQSSISDVIDPIGWHEWSG  535
XP_003528739.1      QNTGIVIQKCRIGAINDLESVKKNFKTYLGRPWKEYSRTTVIMQSSISDVIDPIGWHEWSG  533
                    **************::********************************************

FIG. 29A
```

```
XP_025981966.1   NFALSTLVYREYQNTGPGAGTSNRVTWKGYKVITDAAEARDYTPGSFIGGSSWLGSTGFP   595
XP_003528739.1   NFGLSTLVYREYQNTGPGAGTSNRVTWKGYKVITDTAEAREYTPGSFIGGSSWLGSTGFP   593
                 **.**********************************:**********************

XP_025981966.1   FSLGL 600  (SEQ ID NO: 155)
XP_003528739.1   FSLGL 598  (SEQ ID NO: 156)
                 *****
```

FIG. 29B

GENETICALLY ENGINEERED LAND PLANTS THAT EXPRESS AN INCREASED SEED YIELD PROTEIN AND/OR AN INCREASED SEED YIELD RNA

FIELD OF THE INVENTION

The present invention relates to genetically engineered land plants, and more particularly to genetically engineered land plants that express a protein that has homology to a plant invertase inhibitor and/or a pectin methylesterase inhibitor and that increases seed yield with increased expression ("an ISY protein") and/or an RNA that increases seed yield with increased expression ("an ISY RNA").

BACKGROUND OF THE INVENTION

The world faces a major challenge in the next 30 years to meet the increased demands for food production to feed a growing global population, which is expected to reach 9 billion by the year 2050. Food output will need to be increased by up to 70% in view of the growing population. Increased demand for improved diet, concomitant land use changes for new living space and infrastructure, alternative uses for crops and changing weather patterns will add to the challenge.

Major agricultural crops include food crops, such as maize, wheat, oats, barley, soybean, millet, sorghum, pulses, bean, tomato, corn, rice, cassava, sugar beets, and potatoes, forage crop plants, such as hay, alfalfa, and silage corn, and oilseed crops, such as *Camelina, Brassica* species (e.g. *B. napus* (canola), *B. rapa, B. juncea*, and *B. carinata*), *crambe*, soybean, sunflower, safflower, oil palm, flax, and cotton, among others. Productivity of these crops, and others, is limited by numerous factors, including for example relative inefficiency of photochemical conversion of light energy to fixed carbon during photosynthesis, as well as loss of fixed carbon by photorespiration and/or other essential metabolic pathways having enzymes catalyzing decarboxylation reactions. For seed (grain), tuber or fruit crops, the ratio of seed, tubers or fruit produced per unit plant biomass is also a major determinant of crop productivity. Crop productivity is also limited by the availability of water. Achieving step changes in crop yield requires new approaches.

Increasing seed yield in major crops can be viewed as a two-step carbon optimization problem, the first is improving photosynthetic carbon fixation and the second is optimizing the flow of fixed carbon to seed production versus vegetative biomass (roots, stems, leaves etc.). The ratio of harvested seed to vegetative plant biomass is also described as the harvest index. Increasing the harvest index of seed, fruit and tuber crops is an objective of this invention.

There are a number of examples of using genetic engineering to increase carbon capture in crops including the use of genes from other photosynthetic species such as algae. It has recently been shown by Schnell et al., WO2015/103074, that *Camelina* plants transformed to express CCP1 of the eukaryotic algal species *Chlamydomonas reinhardtii* have reduced transpiration rates, increased $CO_2$ assimilation rates and higher yield than control plants which do not express the CCP1 gene. Although these engineered plants had higher seed yield, the inventors also disclosed that the size of individual seeds from these plants was significantly reduced. A reasonable interpretation of these results is that the CCP1 protein increases carbon capture efficiency, resulting in increased availability of carbon for seed production. This in turn results in an increased number of seed bearing structures and seeds being produced, but the plant is either unable to provide sufficient fixed carbon to produce the large number of seeds at full size or the increased availability of fixed carbon in green tissue is signaling the plant to shut off the flow of carbon to seeds.

In WO2017/136668, to Yield10 Bioscience, a number of orthologs of CCP1 from algal species that share common protein sequence domains including mitochondrial membrane domains and transporter protein domains were shown to increase seed yield when expressed constitutively in *Camelina* plants.

In WO2018/156686, to Yield10 Bioscience, CCP1 and its orthologs from other algae are referred to as mitochondrial transporter proteins. The inventors tested the impact of expressing CCP1 or its algal orthologs using seed-specific promoters with the unexpected outcome that both seed yield and seed size increased. Again this implies that in the original CCP1 plants where CCP1 was constitutively expressed the plant was shutting off flow of carbon to seeds. These inventors also recognized the benefits of combining constitutive expression and seed-specific expression of CCP1 or any of its orthologs in the same plant as a means to further increase seed yield.

In WO2018/232232, to Yield10 Bioscience, genetically engineered plants that express a plant CCP1-like mitochondrial transporter protein are disclosed. The genetically engineered plants include a modified gene for the plant CCP1-like mitochondrial transporter protein. The modified gene includes a promoter and a nucleic acid sequence encoding the plant CCP1-like mitochondrial transporter protein. The promoter is non-cognate with respect to the nucleic acid sequence.

In WO2019/104278, to Yield10 Bioscience, genetically engineered plants that express a plant CCP1-like mitochondrial transporter protein and a LCID/E gene are disclosed.

The primary product of photosynthesis is sucrose (sugar), which is then transported throughout the plant and used in plants cells and tissues as a source of both fixed carbon and energy. Sucrose partitioning to seeds and other carbon sink tissues such as fruits or tubers is a key factor in determining yield. Plant invertases and their respective inhibitors have been shown to have a significant role in regulating the partitioning of sugar in plants. Invertases accomplish this through regulating phloem loading, unloading, and sucrose transport (Lammens et al. (2008), J Mol Biol, 377(2):378-385). Plant invertases are a class of proteins that hydrolyze sucrose into fructose and glucose. Plant invertases include cell wall invertases (CWIs) and vacuolar invertases. Cell wall invertases, located within the cell wall, play key roles in the unloading of sucrose from the apoplast to the sink tissues. Cell wall and vacuolar invertases are highly stable proteins due to the presence of glycans. As a result, their activity may be highly dependent on posttranslational regulation by their inhibitory proteins, termed plant invertase inhibitors, which include cell wall invertase inhibitors (CWIIs) and vacuolar invertase inhibitors. Thus, for example, cell wall invertases interact with cell wall invertase inhibitors, which post-transcriptionally regulate their activity.

The plant invertase inhibitors, including cell wall invertase inhibitors, are small peptides, with molecular masses (MW) ranging from 15 to 23 kDa, and may be localized to either the cell wall or vacuole. The cell wall invertase inhibitors are expressed in pollen development, early developing seeds, and senescing leaves, indicative of assimilate allocation being a limiting factor at these stages of development.

Quantitative trait loci analysis for fruit size in tomato (Lin5), and grain size in rice (GIF1) and maize (MN1) identified mutations in cell wall invertases that led to reduction in their activity in pedicel/fruit tissues (Wang et al. (2008), Nature Genetics, 40(11):1370-1374; Fridman et al. (2004), Science, 305(5691):1786-1789; Cheng et al. (1996), Plant Cell, 8(6):971-983). Fruit-specific suppression of the cell wall invertase inhibitor (CWII) in tomato or rice led to increases in net seed/grain weight of 22% and 10%, respectively (Wang et al. (2008), Nature Genetics, 40(11):1370-1374; Jin et al. (2009), Plant Cell, 21(7):2072-2089).

Thus, based on the teachings in the literature, two general approaches can be used to enhance assimilate flux into sink tissues to increase the yield of seeds, fruits or tubers: overexpression of CWI or repression of its inhibitor protein CWII. Methods using one or both of these general approaches for producing plants having an increased number of seeds and methods for producing plants having increased assimilate partitioning directed into fruits, seeds and/or other plant part (e.g., roots and/or tubers), and/or increased seed, root and/or tuber size, or any combination thereof and transgenic plants made by these methods were disclosed in Sederoff et al., WO2014209792.

"Transgenic plants," "GMO crops," and/or "biotech traits" are not widely accepted in some regions and countries and are subject to regulatory approval processes that are very time consuming and prohibitively expensive. The current regulatory framework for transgenic plants results in significant costs (~$136 million per trait; McDougall, P. 2011, "The cost and time involved in the discovery, development, and authorization of a new plant biotechnology derived trait." Crop Life International) and lengthy product development timelines that limit the number of technologies that are brought to market. This has severely impaired private investment and the adoption of innovation in this crucial sector. Recent advances in genome editing technologies provide an opportunity to precisely remove genes or edit control sequences to significantly improve plant productivity (Belhaj (2013), Plant Methods, 9:39; Khandagale & Nadaf (2016), Plant Biotechnol Rep, 10:327-343) and open the way to produce plants that may benefit from an expedited regulatory path, or possibly unregulated status.

These risks have severely impaired private investment and the adoption of innovation in this crucial sector. Recent changes in the regulations governing genetically modified crops by USDA-APHIS in the United States and new technologies such as genome editing have begun to change this situation. For example, a corn plant which has been genetically engineered to modify the activity of a corn gene using only DNA sequences from corn, technically described as cis-genic, not transgenic, may be classified as non-regulated provided the engineered corn plant contains no foreign DNA sequences. Advances in genome editing technologies provide an opportunity to precisely remove or insert DNA sequences in the plant genome of interest to inactivate specific plant genes or to alter their expression by modifying their promoter sequences to improve plant performance (Belhaj (2013), Plant Methods, 9:39; Khandagale & Nadaf (2016), Plant Biotechnol Rep, 10:327-343). Genetically engineered plants made using this approach contain no foreign DNA sequences and may also be categorized as non-regulated by USDA-APHIS. In both cases however, the regulatory status of the engineered plants are appropriately subject to the usual criteria for approval of any new plant variety.

Given the costs and challenges associated with obtaining regulatory approval and societal acceptance of transgenic crops there is a need to identify, where possible, plant genes, that can be genetically engineered to increase seed, fruit or tuber yield, particularly without relying on genes, control sequences, or proteins derived from non-plants to the extent possible. Herein we disclose novel plant genes and methods for identifying those novel plant genes which can be used to increase the yield of seed, fruits and tubers in major food crops. We also disclose methods of use of those novel plant genes, and fragments thereof, to increase the yield of seed, fruits, and/or tubers. We also disclose plants engineered to have higher expression of those genes having higher seed, fruit, and/or tuber yield.

BRIEF SUMMARY OF THE INVENTION

A genetically engineered land plant that expresses a protein that has homology to a plant invertase inhibitor and/or a pectin methylesterase inhibitor and that increases seed yield with increased expression ("an ISY protein") is disclosed. The genetically engineered land plant comprises a modified gene for the ISY protein. The ISY protein comprises one or more of (i) an ISY protein of *Camelina sativa* comprising SEQ ID NO: 2; (ii) a fragment of an ISY protein of *Camelina sativa* comprising SEQ ID NO: 2; (iii) a *Camelina sativa* homolog of an ISY protein of *Camelina sativa* comprising SEQ ID NO: 2; or (iv) an ortholog of an ISY protein of *Camelina sativa* comprising SEQ ID NO: 2. The modified gene comprises (i) a promoter and (ii) a nucleic acid sequence encoding the ISY protein. The promoter is non-cognate with respect to the nucleic acid sequence encoding the ISY protein. The modified gene is configured such that transcription of the nucleic acid sequence is initiated from the promoter and results in expression of the ISY protein.

In some examples, the ISY protein comprises the ISY protein of *Camelina sativa* comprising SEQ ID NO: 2. In some of these examples, the ISY protein of *Camelina sativa* comprising SEQ ID NO: 2 corresponds to one or more of ISY protein of *Camelina sativa* of SEQ ID NO: 2, ISY protein of *Camelina sativa* of SEQ ID NO: 5, modified ISY protein of *Camelina sativa* of SEQ ID NO: 138, or modified ISY protein of *Camelina sativa* of SEQ ID NO: 140.

In some examples, the ISY protein comprises the fragment of an ISY protein of *Camelina sativa* comprising SEQ ID NO: 2. In some of these examples, the fragment corresponds to 114 to 133 contiguous amino acids of SEQ ID NO: 2.

In some examples, the ISY protein comprises the *Camelina sativa* homolog of an ISY protein of *Camelina sativa* comprising SEQ ID NO: 2. In some of these examples, the *Camelina sativa* homolog corresponds to one or more *Camelina sativa* proteins of SEQ ID NOS: 21-40.

In some examples, the ISY protein comprises the ortholog of an ISY protein of *Camelina sativa* comprising SEQ ID NO: 2. In some of these examples, the ortholog corresponds to one or more (i) canola proteins of SEQ ID NOS: 69, 71, 73, and/or 75; (ii) soybean proteins of SEQ ID NOS: 89, 91, 93, and/or 95; or (iii) corn proteins of SEQ ID NOS: 99, 101, 103, 105, and/or 107.

In some examples, the ISY protein comprises (i) (a) a cysteine residue at position 40, (b) a leucine residue at position 59, (c) a cysteine residue at position 98, and (d) a cysteine residue at position 138, with numbering of positions relative to ISY protein of *Camelina sativa* of SEQ ID NO: 5, and (ii) an overall identity of at least 10% with ISY protein of *Camelina sativa* of SEQ ID NO: 2. In some of these examples, the ISY protein further comprises only between 1 to 14 amino acid residues N-terminal to the cysteine residue at position 40, with numbering of positions relative to ISY protein of *Camelina sativa* of SEQ ID NO: 5. Also in some of these examples, the ISY protein lacks an N-terminal signal peptide. Also in some of these examples, the ISY protein lacks a PKF motif.

In some examples, the ISY protein comprises (i) (a) a cysteine residue at position 25, (b) a cysteine residue at position 40, (c) a leucine residue at position 59, (d) a cysteine residue at position 98, and (e) a cysteine residue at position 138, with numbering of positions relative to ISY protein of *Camelina sativa* of SEQ ID NO: 5, and (ii) an overall identity of at least 10% with ISY protein of *Camelina sativa* of SEQ ID NO: 5. In some of these examples, the ISY protein lacks a PKF motif.

In some examples, the ISY protein is heterologous with respect to the genetically engineered land plant. In some examples, the ISY protein is homologous with respect to the genetically engineered land plant.

In some examples, the promoter is a constitutive promoter. In some examples, the promoter is a seed-specific promoter.

In some examples, the modified gene is integrated into genomic DNA of the genetically engineered land plant.

In some examples, the modified gene is stably expressed in the genetically engineered land plant.

In some examples, the genetically engineered land plant exhibits increased expression of the ISY protein in comparison to a reference land plant that does not include the modified gene.

In some examples, the genetically engineered land plant exhibits increased seed yield, fruit yield, and/or tuber yield in comparison to a reference land plant that does not include the modified gene.

In some examples, the genetically engineered land plant is a C3 plant. In some examples, the genetically engineered land plant is a C4 plant.

In some examples, the genetically engineered land plant is a food crop plant selected from the group consisting of maize, wheat, oat, barley, soybean, millet, sorghum, potato, sugar beet, pulse, chickpea, green pea, yellow pea, lentils, bean, tomato, and rice. In some examples, the genetically engineered land plant is an oilseed crop plant selected from the group consisting of *Camelina*, *Brassica* species (e.g. *B. napus* (canola), *B. rapa, B. juncea*, and *B. carinata*), *crambe*, soybean, sunflower, safflower, oil palm, flax, and cotton.

A genetically engineered land plant that expresses an RNA that increases seed yield with increased expression ("an ISY RNA") also is disclosed. The genetically engineered land plant comprises a modified gene for the ISY RNA. The ISY RNA comprises a contiguous sequence of codons encoding a protein that has homology to a plant invertase inhibitor and/or a pectin methylesterase inhibitor ("an encoded protein"). The encoded protein comprises one or more of (i) a protein of *Camelina sativa* comprising SEQ ID NO: 2; (ii) a fragment of a protein of *Camelina sativa* comprising SEQ ID NO: 2; (iii) a *Camelina sativa* homolog of a protein of *Camelina sativa* comprising SEQ ID NO: 2; or (iv) an ortholog of a protein of *Camelina sativa* comprising SEQ ID NO: 2. The modified gene comprises (i) a promoter and (ii) a nucleic acid sequence encoding the ISY RNA. The promoter is non-cognate with respect to the nucleic acid sequence encoding the ISY RNA. The modified gene is configured such that transcription of the nucleic acid sequence is initiated from the promoter and results in expression of the ISY RNA.

In some examples, the encoded protein comprises the protein of *Camelina sativa* comprising SEQ ID NO: 2.

In some examples, the encoded protein comprises the fragment of a protein of *Camelina sativa* comprising SEQ ID NO: 2, wherein the fragment corresponds to 114 to 133 contiguous amino acids of SEQ ID NO: 2.

In some examples, the encoded protein comprises the *Camelina sativa* homolog of a protein of *Camelina sativa* comprising SEQ ID NO: 2, wherein the *Camelina sativa* homolog corresponds to one or more *Camelina sativa* proteins of SEQ ID NOS: 21-40.

In some examples, the encoded protein comprises the ortholog of a protein of *Camelina sativa* comprising SEQ ID NO: 2, wherein the ortholog corresponds to one or more (i) canola proteins of SEQ ID NOS: 69, 71, 73, and/or 75; (ii) soybean proteins of SEQ ID NOS: 89, 91, 93, and/or 95; or (iii) corn proteins of SEQ ID NOS: 99, 101, 103, 105, and/or 107.

In some examples, the encoded protein comprises (i) (a) a cysteine residue at position 40, (b) a leucine residue at position 59, (c) a cysteine residue at position 98, and (d) a cysteine residue at position 138, with numbering of positions relative to the protein of *Camelina sativa* of SEQ ID NO: 5, and (ii) an overall identity of at least 10% with the protein of *Camelina sativa* of SEQ ID NO: 2.

In some examples, the encoded protein comprises (i) (a) a cysteine residue at position 25, (b) a cysteine residue at position 40, (c) a leucine residue at position 59, (d) a cysteine residue at position 98, and (e) a cysteine residue at position 138, with numbering of positions relative to the protein of *Camelina sativa* of SEQ ID NO: 5, and (ii) an overall identity of at least 10% with the protein of *Camelina sativa* of SEQ ID NO: 5.

In some examples, the encoded protein is heterologous with respect to the genetically engineered land plant.

In some examples, the encoded protein is homologous with respect to the genetically engineered land plant.

In some examples, the promoter is a constitutive promoter. In some examples, the promoter is a seed-specific promoter.

In some examples, the modified gene is integrated into genomic DNA of the genetically engineered land plant.

In some examples, the modified gene is stably expressed in the genetically engineered land plant.

In some examples, the genetically engineered land plant exhibits increased expression of the ISY RNA in comparison to a reference land plant that does not include the modified gene.

In some examples, the genetically engineered land plant exhibits increased seed yield, fruit yield, and/or tuber yield in comparison to a reference land plant that does not include the modified gene.

In some examples, the genetically engineered land plant is a food crop plant selected from the group consisting of maize, wheat, oat, barley, soybean, millet, sorghum, potato, sugar beet, pulse, chickpea, green pea, yellow pea, lentils, bean, tomato, and rice. In some examples, the genetically engineered land plant is an oilseed crop plant selected from the group consisting of *Camelina*, *Brassica* species (e.g. *B. napus* (canola), *B. rapa, B. juncea*, and *B. carinata*), *crambe*, soybean, sunflower, safflower, oil palm, flax, and cotton.

In some examples, the nucleic acid sequence encoding the ISY RNA is at least 80% identical to SEQ ID NO: 1. In some of these examples, the nucleic acid sequence encoding the ISY RNA comprises SEQ ID NO: 1.

In some examples, expression of the ISY RNA results in expression of the encoded protein. In some examples, expression of the ISY RNA does not result in expression of the encoded protein.

BRIEF DESCRIPTION OF THE DRAWINGS

FIG. 1A-B shows a multiple sequence alignment of three putative *Camelina* plant invertase inhibitor/pectin methylesterase inhibitor proteins, or increased seed yield (ISY) proteins, that incorporate CSA15G017550.1, with nine proteins identified as known plant invertase inhibitors according to CLUSTAL O(1.2.4). The three ISY proteins differ in size with respect to the total number of amino acids due to different start codons. Sequences are as follows: Csa15g017550 protein with 134 amino acids (Csa15g017550_134aa; SEQ ID NO: 2); a 168 amino acid protein containing a different start codon using sequence upstream of Csa15g017550 (Csa15g017550_168aa; SEQ ID NO: 5); a 190 amino acid fragment containing sequence upstream of Csa15g017550 (Csa15g017550_190aa; SEQ ID NO: 4); *Zea mays* (XP_008668976.1) (SEQ ID NO: 8); *Arabidopsis thaliana* (AT5G64620) (SEQ ID NO: 9); *Arabidopsis thaliana* (AEE32232.1) (SEQ ID NO: 10); *Solanum lycopersicum* (Solyc12g099190) (SEQ ID NO: 11); *Solanum lycopersicum* (Solyc12g099200) (SEQ ID NO: 12); *Beta vulgaris* subsp. vulgaris (XP_010685378.1) (SEQ ID NO: 13); *Nicotiana tabacum* (AY145781.1) (SEQ ID NO: 14); *Nicotiana tabacum* (Y12805.1) (SEQ ID NO: 15); *Solanum tuberosum* cultivar Shepody (GU321341.1) (SEQ ID NO: 16). Csa15g017550.1 has been annotated as a putative plant invertase inhibitor/pectin methylesterase inhibitor. Sequences identified as known plant invertase inhibitors were described by Wan et al. (2018), Trends Plant Sci, 23:163-177, and Tang et al. (2017), J Exp Bot, 68:469-482, and are further described in TABLE 3.

FIG. 2 shows a multiple sequence alignment of two ISY proteins that incorporate Csa15g017550.1, with two cell wall invertase inhibitors from *Camelina* previously described in Sederoff et al., U.S. Pub. No. 2016/0138038, according to CLUSTAL O(1.2.4). The three homeologs to each of the two cell wall invertase inhibitors (CWII1 and CWII2) are shown in the alignment. Sequences are as follows: the Csa15g017550 protein with 134 amino acids (Csa15g017550_134aa; SEQ ID NO: 2); a 168 amino acid protein containing a different start codon using sequence upstream of Csa15g017550 (Csa15g017550_168aa: SEQ ID NO: 5); Csa03g051630, cell wall invertase inhibitor protein 1 (CWII1) with 159 amino acids (SEQ ID NO: 77); CWII1 homeolog Csa14g051860, CWII1 with 155 amino acids (SEQ ID NO: 79); CWII1 homeolog Csa17g075360, CWII1 with 159 amino acids (SEQ ID NO: 81); CWII2 Csa02g074171, CWII2 with 180 amino acids (SEQ ID NO: 83); CWII2 homeolog Csa11g101740, CWII2 with 181 amino acids (SEQ ID NO: 85); CWII2 homeolog Csa18g038260, CWII2 with 181 amino acids (SEQ ID NO: 87). The PKF amino acid signature sequence for cell wall invertase inhibitors can be found in the CWII1 sequences (Csa03g051630, Csa14g051860, and Csa17g075360) from residues 110-112.

FIG. 5 shows analysis of multiple open reading frames of the gene fragment in SEQ ID NO: 7 producing different size ISY proteins. "M" Predicted start codon according to *Camelina Sativa* Genome Browser Csa15g017550.1 that produces a 134 amino acid protein (SEQ ID NO: 2). "L," Alternative start codon, encoded by TTG, that produces a 168 amino acid protein (SEQ ID NO: 5). This start codon was chosen based on alignments with other cell wall invertase inhibitors (FIG. 1). "T" first amino acid of 190 amino acid large amino acid sequence encompassing Csa15g017550. The binding sites of primers P675, P676, P677, and P678 used for PCR and RT-PCR (FIG. 7) experiments are shown.

FIG. 4), expressing the CCP1 gene from the seed-specific oleosin promoter (lines ND79, ND 11, ND04, and ND78), compared to the wild-type control line WT43. Control experiments to probe the presence of transcripts of the actin gene were also performed

FIG. 14 shows a multiple sequence alignment of the Camelina ISY proteins with four orthologs from the Brassica napus ZS11 cultivar according to CLUSTAL O(1.2.4). Sequences are as follows: Csa15g017550_134aa, ISY protein with 134 amino acids (SEQ ID NO: 2); Csa15g017550_168aa, ISY protein with 168 amino acids (SEQ ID NO: 5); XP_013675048, B. napus ortholog with 175 amino acids (SEQ ID NO: 75); XP_013675049, B. napus ortholog with 175 amino acids (SEQ ID NO: 71); XP_013714182, B. napus ortholog with 175 amino acids (SEQ ID NO: 69); and XP_013718725, B. napus ortholog with 175 amino acids (SEQ ID NO: 73).

FIG. 15 shows a multiple sequence alignment of the Camelina ISY proteins with four orthologs from the Glycine max "Williams 82" cultivar according to CLUSTAL O(1.2.4). Sequences are as follows: Csa15g017550_134aa, ISY protein with 134 amino acids (SEQ ID NO: 2); Csa15g017550_168aa, ISY protein with 168 amino acids (SEQ ID NO: 5); XP_003550932.1, Glycine max ortholog with 183 amino acids (SEQ ID NO: 89); XP_006579665.1, Glycine max ortholog with 183 amino acids (SEQ ID NO: 91); NP_001235997, Glycine max ortholog with 187 amino acids (SEQ ID NO: 93); and XP_006604724, Glycine max ortholog with 183 amino acids (SEQ ID NO: 95).

FIG. 16A-B shows a multiple sequence alignment of the Camelina ISY proteins with five orthologs identified from the maize reference genome Zea mays B73 according to CLUSTAL O(1.2.4). Sequences are as follows: Csa15g017550_134aa, ISY protein with 134 amino acids (SEQ ID NO: 2); Csa15g017550_168aa, ISY protein with 168 amino acids (SEQ ID NO: 5); NP_001143588, maize ortholog with 217 amino acids (SEQ ID NO: 99); NP_001148423, maize ortholog with 228 amino acids (SEQ ID NO: 101); NP_001149041, maize ortholog with 211 amino acids (SEQ ID NO: 103); XP_008655849, maize ortholog with 195 amino acids (SEQ ID NO: 105); XP_008668976, maize ortholog with 176 amino acids (SEQ ID NO: 107).

FIG. 17A-C shows a multiple sequence alignment of the Camelina ISY proteins with the crop orthologs from canola, soybean, and corn listed in TABLE 12. Sequences are as follows: Csa15g017550_134aa, ISY protein with 134 amino acids (SEQ ID NO: 2) from Camelina sativa; Csa15g017550_168aa, ISY protein with 168 amino acids (SEQ ID NO: 5) from *Camelina sativa*; XP_013675048, *B. napus* ortholog with 175 amino acids (SEQ ID NO: 75); XP_013675049, *B. napus* ortholog with 175 amino acids (SEQ ID NO: 71); XP_013714182, *B. napus* ortholog with 175 amino acids (SEQ ID NO: 69); XP_013718725, *B. napus* ortholog with 175 amino acids (SEQ ID NO: 73); XP_003550932.1, *Glycine max* ortholog with 183 amino acids (SEQ ID NO: 89); XP_006579665.1, *Glycine max* ortholog with 183 amino acids (SEQ ID NO: 91); NP_001235997, *Glycine max* ortholog with 187 amino acids (SEQ ID NO: 93); XP_006604724, *Glycine max* ortholog with 183 amino acids (SEQ ID NO: 95); NP_001143588, maize ortholog with 217 amino acids (SEQ ID NO: 99); NP_001148423, maize ortholog with 228 amino acids (SEQ ID NO: 101); NP_001149041, maize ortholog with 211 amino acids (SEQ ID NO: 103); XP_008655849, maize ortholog with 195 amino acids (SEQ ID NO: 105); and XP_008668976, maize ortholog with 176 amino acids (SEQ ID NO: 107).

FIG. 19 shows plasmid maps for 1) pMBXS1269 (SEQ ID NO: 197) and B) pMBXS1270 (SEQ ID NO: 198), vectors designed for *Agrobacterium*-mediated transformation of Canola with the 134 amino acid and 168 amino acid *Camelina* ISY genes, respectively. A) Transformation vector pMBXS1269 contains the double enhanced CaMV35S constitutive promoter (2× 35S) operably linked to a gene (SEQ ID NO: 1) encoding the 134 amino acid protein for Csa15g017550 (SEQ ID NO: 2) operably linked to a 35S polyadenylation sequence. B) Transformation vector pMBXS1270 contains the double enhanced CaMV35S constitutive promoter (2× 35S) operably linked to a gene (SEQ ID NO: 6) encoding the 168 amino acid *Camelina* ISY protein (SEQ ID NO: 5) operably linked to a 35S polyadenylation sequence. An expression cassette for the bar gene, driven by the double enhanced CaMV35S constitutive promoter (2× 35S), imparts transgenic plants resistance to the herbicide bialaphos in both vectors.

FIG. 24A-B shows a multiple sequence alignment of the Group 1 proteins of the phylogenetic tree (cladogram) in FIG. 23 according to CLUSTAL O(1.2.4). Group 1 proteins have GO terms of probable pectate lyases. Sequences are as follows: XP_003526981.1 (SEQ ID NO: 141), XP_006589707.1 (SEQ ID NO: 142), XP_003535958.1 (SEQ ID NO: 143), and XP_003555714.4 (SEQ ID NO: 144).

FIG. 25A-B shows a multiple sequence alignment of the Group 2 proteins of the phylogenetic tree in FIG. 23 according to CLUSTAL O(1.2.4). Group 2 proteins include the *Camelina* ISY protein, and proteins that have GO terms of pectinesterases or cell wall/vacuolar inhibitors of fructosidase 1. Sequences are as follows: *Camelina* ISY protein (SEQ ID NO: 5), XP_003543834.1 (SEQ ID NO: 145), XP_006587735.1 (SEQ ID NO: 146), NP_001237215.2 (SEQ ID NO: 147), and NP_001235420.1 (SEQ ID NO: 148).

FIG. 26 shows a multiple sequence alignment of the Camelina ISY protein with the two cell wall/vacuolar inhibitor of fructosidase 1 proteins in Group 2 of the phylogenetic tree in FIG. 23 according to CLUSTAL O(1.2.4). Sequences are as follows: Camelina ISY protein (SEQ ID NO: 5), NP_001237215.2 (SEQ ID NO: 147), and NP_001235420.1 (SEQ ID NO: 148).

FIG. 27 shows a multiple sequence alignment of the Group 3 proteins of the phylogenetic tree in FIG. 23 according to CLUSTAL O(1.2.4). Group 3 proteins have GO terms of pectinesterase inhibitor or plant invertase/pectin methylesterase inhibitor superfamily protein. Sequences are as follows: XP 003517432.1 (SEQ ID NO: 149), XP_003530773.1 (SEQ ID NO: 150), XP_003525240.1 (SEQ ID NO: 151).

FIG. 28A-B shows a multiple sequence alignment of the Group 4 proteins of the phylogenetic tree in FIG. 23 according to CLUSTAL O(1.2.4). Group 4 proteins have GO terms of probable pectinesterase/pectinesterase inhibitors. Sequences are as follows: XP_003531408.1 (SEQ ID NO: 152), XP_003526711.1 (SEQ ID NO: 153), XP_003553658.2 (SEQ ID NO: 154).

FIG. 29A-B shows a multiple sequence alignment of the Group 5 proteins of the phylogenetic tree in FIG. 23 according to CLUSTAL O(1.2.4). Group 5 proteins have GO terms of pectinesterase/pectinesterase inhibitors. Sequences are as follows: XP_025981966.1 (SEQ ID NO: 155) and XP_003528739.1 (SEQ ID NO: 156).

DETAILED DESCRIPTION OF THE INVENTION

Figure 3:
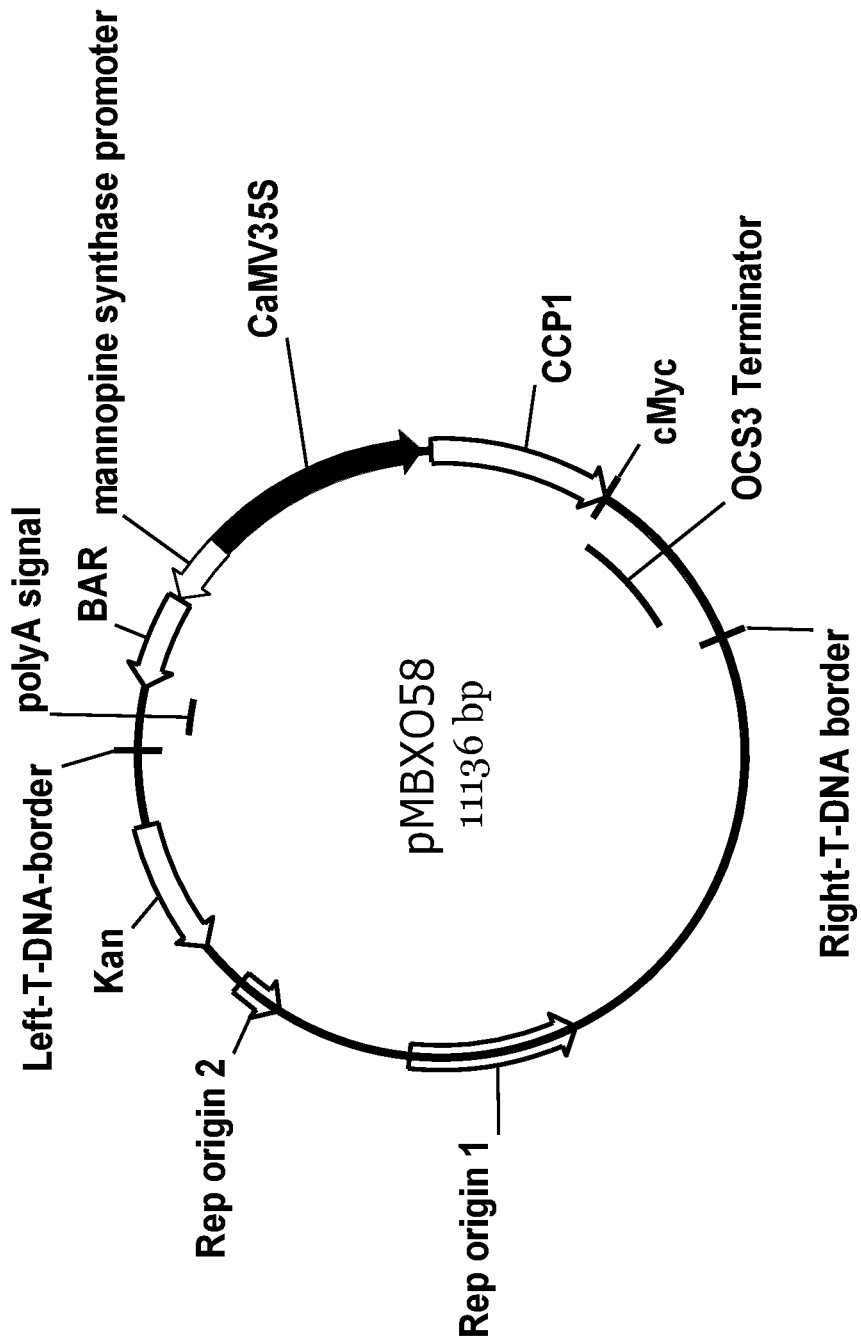
FIG. 3 shows a plasmid map of transformation vector pMBXO58 (SEQ ID NO: 19) expressing the CCP1 gene from the 35S constitutive promoter. Plasmid pMBXO58 contains a CaMV35S constitutive promoter operably linked to CCP1 from *Chlamydomonas reinhardtii* fused to a C-terminal myc tag operably linked to an OCS3 termination sequence. An expression cassette for the bar gene, driven by the mannopine synthase promoter, imparts transgenic plants resistance to the herbicide bialaphos.

A genetically engineered land plant that expresses a protein that has homology to a plant invertase inhibitor and/or a pectin methylesterase inhibitor and that increases seed yield with increased expression ("an ISY protein") is disclosed. The genetically engineered land plant comprises a modified gene for the ISY protein. The ISY protein comprises one or more of (i) an ISY protein of Camelina sativa comprising SEQ ID NO: 2; (ii) a fragment of an ISY protein of Camelina sativa comprising SEQ ID NO: 2; (iii) a Camelina sativa homolog of an ISY protein of Camelina sativa comprising SEQ ID NO: 2; or (iv) an ortholog of an ISY protein of Camelina sativa comprising SEQ ID NO: 2. The modified gene comprises (i) a promoter and (ii) a nucleic acid sequence encoding the ISY protein. The promoter is non-cognate with respect to the nucleic acid sequence encoding the ISY protein. The modified gene is configured such that transcription of the nucleic acid sequence is initiated from the promoter and results in expression of the ISY protein.

Figure 1A:
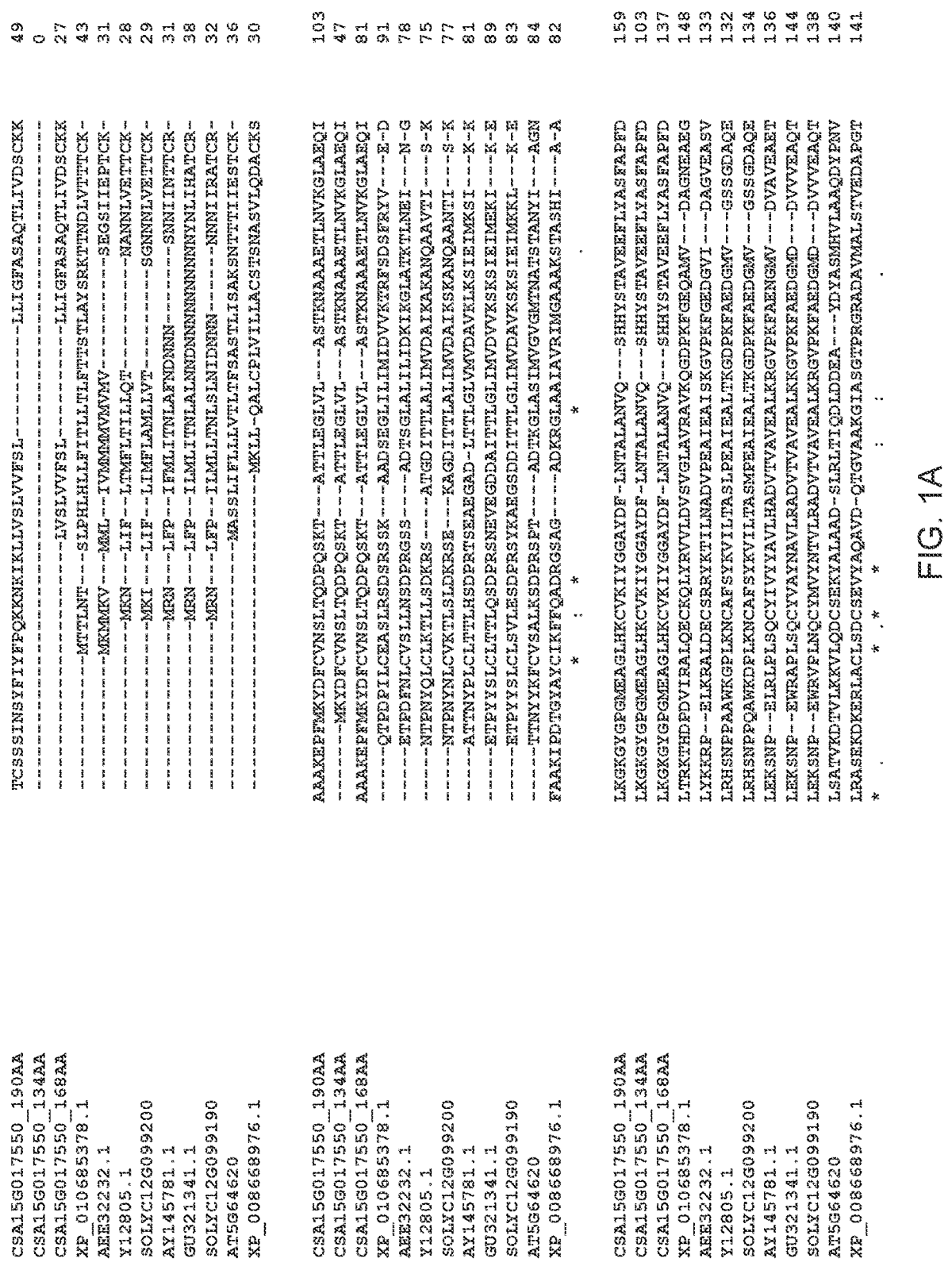

Constitutive expression of a mitochondrial metabolite transporter encoded by the algal gene CCP1 in Camelina was noted to not only increase carbon fixation and seed yield but also to result in smaller seed size (WO2015/103074, to the University of Massachusetts). Independently we have shown that similar changes in seed yield and seed size are obtained when CCP1 is expressed in canola and soybean. Gene expression analysis of the CCP1 high yield Camelina lines was performed using the RNASeq technology to determine the impacts of over-expressing the CCP1 gene on the expression of native Camelina genes. One gene in particular, Csa15g017550 (SEQ ID NO: 1) that encodes a 134 amino acid protein (SEQ ID NO: 2) was found to be highly up-regulated and is a putative plant invertase inhibitor and/or pectin methylesterase inhibitor (also termed "plant invertase inhibitor/pectin methylesterase inhibitor"). Analysis of the upstream region of the Csa15g017550 gene shows that there are several alternative start sites (FIG. 5). Using the methionine predicted start codon according to Camelina Sativa Genome Browser, Csa15g017550.1 produces a 134 amino acid protein (SEQ ID NO: 2). An alternative leucine start codon upstream, encoded by TTG, produces a 168 amino acid protein (SEQ ID NO: 5). This alternative start codon was chosen based on alignments with other cell wall invertase inhibitors (FIG. 1). The plant invertase inhibitor/pectin methylesterase inhibitor family of genes is very large and diverse with the majority of genes being assigned to this family based on regions of in most cases limited sequence homology. Very few individual genes have been characterized at the molecular level and so it is reasonable to conclude that for the vast majority of genes listed in this family their actual activity and function is unknown. Cell wall invertase inhibitor (CWII) genes for increasing seed yield have been studied in *Camelina*. PCT/US2014/043407 to North Carolina State University demonstrated that reduced expression of CWII genes in *Camelina* results in increased seed yield.

We hypothesized that expression of CCP1 in the high yielding plants had increased the level of fixed carbon and had increased seed numbers albeit with a smaller seed size. We hypothesized that the putative up-regulated plant invertase inhibitor/pectin methylesterase inhibitor gene homolog may be responsible for reducing the flow of carbon to the increased number of seeds resulting in smaller seed size. In order to test this hypothesis we overexpressed both the 134 amino acid (SEQ ID NO: 2) and 168 amino acid (SEQ ID NO: 5) plant invertase inhibitor/pectin methylesterase ortholog proteins in *Camelina* using a constitutive promoter with the expectation that this would result in plants with reduced seed size and lower seed yield.

Surprisingly, we found that increased expression of this putative plant invertase inhibitor/pectin methylesterase inhibitor ortholog gene resulted in a large increase in branching, seed yield, and, in some plants, an increase in the average size of individual seeds.

Based on these results we re-investigated the homology with characterized plant invertase inhibitor and/or pectin methylesterase inhibitor genes and concluded that this gene is a novel gene with an as yet unknown function in *Camelina*. Furthermore, although *Camelina* is an allohexaploid with 3 copies of each chromosome, we found that Csa15g017550.1 is only present in a single copy. Examination of the region of the chromosome where Csa15g017550.1 is located on the other two chromosomes indicated that the Csa15g017550.1 is not present on the other two chromosomes. tBLASTn (search excludes *Camelina sativa*) and FASTA searches of other crop species to identify homologs of the *Camelina* Csa15g017550 did not reveal any genes encoding proteins with greater than 58% identity over the length of the whole protein. For these reasons we believe that the *Camelina* Csa15g017550 gene is very rare and of unknown function. To distinguish it from characterized plant invertase inhibitor and pectin methylesterase inhibitor genes we refer to this gene and similar genes with weak homology to plant invertase inhibitor and pectin methylesterase inhibitor genes in other crop species whose expression is increased by expression of CCP1 as the increased seed yield gene ("ISY gene").

Accordingly, disclosed herein are genetically engineered land plants having increased expression of the ISY gene (SEQ ID NO: 1) encoding a 134 amino acid protein (SEQ ID NO: 2), and genetic constructs, materials and methods for making such plants. Such plants may have increased branching and/or higher seed, tuber or fruit yield and optionally increased seed, tuber or fruit size as compared to reference land plants that do not have increased expression of the ISY gene.

Also disclosed herein are genetic constructs such that the ISY gene is expressed from different translation start sites, such as the ISY gene with an alternative start codon (SEQ ID NO: 6) encoding a 168 amino acid protein (SEQ ID NO: 5), and plants expressing them which have increased branching and/or higher seed, tuber or fruit yield and optionally increased seed, tuber or fruit size as compared to the same plants which do not have increased expression of the ISY gene Also disclosed herein are methods for identifying ISY genes in any land plant. The methods comprise genetically engineering land plants to have increased expression of one or more mitochondrial metabolite transporter genes to produce plants having higher seed yield and optionally smaller seed size, then carrying out gene expression studies to identify native plant ISY genes whose expression is significantly increased in the plants having increased expression of the one or more mitochondrial metabolite transporter genes wherein the ISY genes are native plant genes whose expression is significantly increased and which have sequence homology to invertase inhibitor/pectin methylesterase inhibitor genes. We refer to these genes herein as ISY genes. An ISY gene can be, for example, a gene encoding a protein having 10-65% sequence identity to at least one protein encoded by a gene of the plant invertase inhibitor/pectin methylesterase inhibitor family of genes and whose expression is significantly increased, e.g. by at least 5%, 10%, 20%, or more, in plants engineered to have higher expression of one or more mitochondrial metabolite transporter genes.

Also disclosed herein are land plants genetically engineered to have increased expression of the ISY genes identified by the aforementioned genetic constructs, materials and methods having increased branching and/or higher seed, tuber or fruit yield and optionally increased seed, tuber or fruit size.

Also disclosed herein are genetically engineered land plants made using the materials and methods having increased expression of the ISY genes and increased expression of mitochondrial metabolite transporter genes which have higher seed, tuber or fruit yield and possibly increased seed, tuber or fruit size. Plants are engineered to have higher levels of expression of the identified ISY genes such that they have higher seed, fruit or tuber yield. Preferably the plants engineered to have higher expression of the ISY genes are the same species of plant as the ISY genes used to increase the expression of the ISY genes. For example the *Camelina* ISY gene preferably is expressed in *Camelina*, the canola ISY gene preferably is expressed in canola, the soy ISY gene preferably is expressed in soy, rice ISY preferably is expressed in rice, wheat ISY gene preferably is expressed in wheat, potato ISY gene preferably is expressed in potato, sugar beet ISY gene preferably is increased in sugar beet, tomato ISY gene preferably is increased in tomato, and so on. When the ISY gene expression is increased then the degree of branching, yield of seeds, fruit or tubers and optionally seed, fruit or tuber size is also increased.

The term "land plant" includes mature plants, seeds, shoots and seedlings, and parts, propagation material, plant organ tissue, protoplasts, callus and other cultures, for example cell cultures, derived from plants belonging to the plant subkingdom Embryophyta, and all other species of groups of plant cells giving functional or structural units, also belonging to the plant subkingdom Embryophyta. The term "mature plants" refers to plants at any developmental stage beyond the seedling. The term "seedlings" refers to young, immature plants at an early developmental stage.

Land plants encompass all annual and perennial monocotyledonous or dicotyledonous plants and includes by way of example, but not by limitation, those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Cichorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus,*

*Lolium, Oryza, Zea, Elaeis, Saccharum, Avena, Hordeum, Secale, Triticum, Sorghum, Picea, Populus, Camelina, Beta, Solanum,* and *Carthamus*. Preferred plants are those from the following plant families: Amaranthaceae, Asteraceae, Brassicaceae, Carophyllaceae, Chenopodiaceae, Compositae, Cruciferae, Cucurbitaceae, Euphorbiaceae, Fabaceae, Labiatae, Leguminosae, Papilionoideae, Liliaceae, Linaceae, Malvaceae, Poaceae, Rosaceae, Rubiaceae, Saxifragaceae, Scrophulariaceae, Solanaceae, Sterculiaceae, Tetragoniaceae, Theaceae, and Umbelliferae.

The land plant can be a monocotyledonous plant or a dicotyledonous plant. Preferred dicotyledonous plants are selected in particular from the dicotyledonous crop plants such as, for example, Asteraceae such as sunflower, tagetes or calendula and others; Compositae, especially the genus *Lactuca*, very particularly the species *sativa* (lettuce) and others; Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli) and other cabbages; and the genus *Arabidopsis*, very particularly the species *thaliana*, and cress or canola and others; Cucurbitaceae such as melon, pumpkin/squash or zucchini and others; Leguminosae, particularly the genus *Glycine*, very particularly the species max (soybean), soya, and alfalfa, pea, beans or peanut and others; Rubiaceae, preferably the subclass Lamiidae such as, for example *Coffea arabica* or *Coffea liberica* (coffee bush) and others; Solanaceae, particularly the genus *Lycopersicon*, very particularly the species *esculentum* (tomato), the genus *Solanum*, very particularly the species *tuberosum* (potato) and *melongena* (aubergine) and the genus *Capsicum*, very particularly the genus *annuum* (pepper) and tobacco or paprika and others; Sterculiaceae, preferably the subclass Dilleniidae such as, for example, *Theobroma cacao* (cacao bush) and others; Theaceae, preferably the subclass Dilleniidae such as, for example, *Camellia sinensis* or *Thea sinensis* (tea shrub) and others; Umbelliferae, particularly the genus *Daucus* (very particularly the species *carota* (carrot)) and *Apium* (very particularly the species *graveolens dulce* (celery)) and others; and linseed, cotton, hemp, flax, cucumber, spinach, carrot, sugar beet and the various tree, nut and grapevine species, in particular banana and kiwi fruit. Preferred monocotyledonous plants include maize, rice, wheat, sugarcane, sorghum, oats and barley.

Of particular interest are oilseed plants. In oilseed plants of interest the oil is accumulated in the seed and can account for greater than 10%, greater than 15%, greater than 18%, greater than 25%, greater than 35%, greater than 50% by weight of the weight of dry seed. Oil crops encompass by way of example: *Borago officinalis* (borage); *Camelina* (false flax); *Brassica* species such as *B. campestris, B. napus, B. rapa, B. carinata* (mustard, oilseed rape or turnip rape); *Cannabis sativa* (hemp); *Carthamus tinctorius* (safflower); *Cocos nucifera* (coconut); *Crambe abyssinica* (*crambe*); *Cuphea* species (*Cuphea* species yield fatty acids of medium chain length, in particular for industrial applications); *Elaeis guinensis* (African oil palm); *Elaeis oleifera* (American oil palm); *Glycine max* (soybean); *Gossypium hirsutum* (American cotton); *Gossypium barbadense* (Egyptian cotton); *Gossypium herbaceum* (Asian cotton); *Helianthus annuus* (sunflower); *Jatropha curcas* (*Jatropha*); *Linum usitatissimum* (linseed or flax); *Oenothera biennis* (evening primrose); *Olea europaea* (olive); *Oryza sativa* (rice); *Ricinus communis* (castor); *Sesamum indicum* (sesame); *Thlaspi caerulescens* (pennycress); *Triticum* species (wheat); *Zea mays* (maize), and various nut species such as, for example, walnut or almond.

*Camelina* species, commonly known as false flax, are native to Mediterranean regions of Europe and Asia and seem to be particularly adapted to cold semiarid climate zones (steppes and prairies). The species *Camelina sativa* was historically cultivated as an oilseed crop to produce vegetable oil and animal feed. In addition to being useful as an industrial oilseed crop, *Camelina* is a very useful model system for developing new tools and genetically engineered approaches to enhancing the yield of crops in general and for enhancing the yield of seed and seed oil in particular. Demonstrated transgene improvements in *Camelina* obtained through genetic engineering of specific genes can then be deployed in other major food and feed crops including oilseed crops including *Brassica* species including *B. napus* (canola), *B. rapa, B. juncea, B. carinata*, crambe, soybean, sunflower, safflower, oil palm, flax, and cotton and starch crops including maize, grain sorghum, wheat, rice, oats, barley, potatoes and sucrose producing crops such as sugar beet. Sugarcane and pulses including peas, chickpeas, lentils and the like.

As will be apparent, the land plant can be a C3 photosynthesis plant, i.e. a plant in which RubisCO catalyzes carboxylation of ribulose-1,5-bisphosphate by use of $CO_2$ drawn directly from the atmosphere, such as for example, *Camelina*, canola, soybean, wheat, rice, oat, barley, sweet potato, potato, sugar beet among others. The land plant also can be a C4 plant, i.e. a plant in which RubisCO catalyzes carboxylation of ribulose-1,5-bisphosphate by use of $CO_2$ shuttled via malate or aspartate from mesophyll cells to bundle sheath cells, such as for example maize, millet, sorghum, sugarcane among others.

Accordingly, in some examples the genetically engineered land plant is a C3 plant. Also, in some examples the genetically engineered land plant is a C4 plant. Also, in some examples the genetically engineered land plant is a major food crop plant selected from the group consisting of maize, wheat, oat, barley, soybean, millet, sorghum, potato, sugar beet, pulse, chickpea, green pea, yellow pea, lentils, bean, tomato, and rice. In some of these examples, the genetically engineered land plant is maize. Also, in some examples the genetically engineered land plant is an oilseed crop plant selected from the group consisting of *Camelina*, *Brassica* species (e.g. *B. napus* (canola), *B. rapa, B. juncea*, and *B. carinata*), crambe, soybean, sunflower, safflower, oil palm, flax, and cotton.

As noted, the genetically engineered land plant comprises a modified gene for the ISY protein. The ISY protein comprises one or more of (i) an ISY protein of *Camelina sativa* comprising SEQ ID NO: 2; (ii) a fragment of an ISY protein of *Camelina sativa* comprising SEQ ID NO: 2; (iii) a *Camelina sativa* homolog of an ISY protein of *Camelina sativa* comprising SEQ ID NO: 2; or (iv) an ortholog of an ISY protein of *Camelina sativa* comprising SEQ ID NO: 2.

The term "fragment," as used herein in reference to a polynucleotide sequence or polypeptide sequence, means a contiguous part of the polynucleotide sequence or polypeptide sequence that is less than the entire polynucleotide sequence or polypeptide sequence.

The phrases "fragment of an ISY protein of *Camelina sativa* comprising SEQ ID NO: 2" and "fragment of a protein of *Camelina sativa* comprising SEQ ID NO: 2," as used herein, means at least 30 contiguous amino acids of SEQ ID NO: 2. Such a fragment can be, for example, 30 or more contiguous amino acids of SEQ ID NO: 2. Such a fragment also can be, for example, 40 or more, 50 or more, 60 or more, 70 or more, 80 or more, 90 or more, or 100 or more contiguous amino acids of SEQ ID NO: 2. Such a fragment also can be, for example, 114 to 133 contiguous amino acids of SEQ ID NO: 2.

The term "ortholog," as used herein, means a polynucleotide sequence or polypeptide sequence possessing a high degree of homology, i.e. sequence relatedness, to a subject sequence and being a functional equivalent of the subject sequence, wherein the sequence that is orthologous is from a species that is different than that of the subject sequence. Homology may be quantified by determining the degree of identity and/or similarity between the sequences being compared.

As used herein, "percent homology" of two polynucleotide sequences or of two polypeptide sequences is the percent identity over the length of the entire sequence determined using the ALIGNX alignment function of the Vector NTI software package (Vector NTI Advance, Version 11.5.3, ThermoFisher), which uses the Clustal W algorithm. Default parameters of the program were used.

The percentage of sequence identity between two polypeptides can also be determined by making a pairwise sequence alignment. This can be done using EMBOSS Needle Pairwise Sequence Alignment (PROTEIN) tool using default settings (matrix: BLOSUM62; gap open: 10; gap extend: 0.5; output format: pair; end gap penalty: false; end gap open: 10; end gap extend: 0.5) (website:ebi.ac.uk/Tools/psa/emboss_needle/). This also can be done using other pairwise sequence alignment tools that are analogous.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Many other polypeptides will meet the same criteria.

For reference, ISY genes as defined herein can have some homology to classical plant invertase inhibitor and/or pectin methylesterase inhibitor genes. Plant invertase inhibitor and pectin methylesterase inhibitor genes are well known in the art and comprise a large family of genes in most crop species. For example, BLAST searches using the *Camelina* genome database (website://www.camelinadb.ca/prairiegold/cgi-bin/blast.cgi) yielded 49 hits when using the 168 amino acid protein (SEQ ID NO: 5) and an additional 17 hits when using the 507-bp coding sequence (SEQ ID NO: 6) (TABLE 6). Keyword searches of the NCBI Entrez Gene database (website://www.ncbi.nlm.nih.gov/search/?ga suggest=a&utm_expid=.fAeHyO5JTBGxnObh2WlrCA.1&utm_referrer=https%3A%2F%2Fwww.ncbi.nlm.nih.gov%2FClass%2FMLACourse%2FOriginal8Hour%2FEntrez%2F), found a total of 324 genes in the *Camelina* genome. This included 51 annotated as invertase inhibitors, 200 annotated as pectinesterase/pectinesterase inhibitors, as well as 73 sequences that belong to an uncharacterized subfamily of plant invertase inhibitor/pectin methylesterase inhibitor domains. For the most part systematic studies on the expression and function of individual genes within the family are very limited with only a few genes having been studied in any detail. Examples of CWII genes in *Camelina* that have been studied include two cell wall invertase inhibitor genes described in Sederoff et al., U.S. Pub. No. 2016/0138038. Sederoff used RNAi gene silencing to reduce expression of these genes in *Camelina* and demonstrated an increase in seed yield. Three copies of each of these genes are present in the *Camelina* genome (*Camelina* is an allohexaploid). These include homeologs of cell wall invertase inhibitor 1 (CWII1) (SEQ ID NO: 76 (Csa03g051630), SEQ ID NO: 78 (Csa14g051860), and SEQ ID NO: 80 (Csa17g075360)) and homeologs of CWII2 (SEQ ID NO: 82 (Csa02g074171), SEQ ID NO: 84 (Csa11g101740), and SEQ ID NO: 86 (Csa18g038260)). A CLUSTAL alignment of the proteins encoded by these genes to the ISY protein is shown in FIG. 2 and their percent homology to the 168 (SEQ ID NO: 5) and 134 (SEQ ID NO: 2) amino acid *Camelina* ISY protein is shown in TABLE 7.

Accordingly, the ISY gene is derived from a plant or is a synthetic version of a plant ISY gene.

In some examples the source plant is a different type of plant than the genetically engineered land plant. In accordance with these examples, the ISY protein can be heterologous with respect to the genetically engineered land plant. By this it is meant that the particular ISY protein derived from the source plant is not normally encoded, expressed, or otherwise present in plants of the type from which the genetically engineered land plant is derived. This can be because plants of the type from which the genetically engineered land plant is derived do not normally encode, express, or otherwise include the particular ISY protein, and this can be so whether or not the plants normally express a different, endogenous ISY protein. The genetically engineered land plant expresses the particular ISY protein based on expressing the modified gene for the ISY protein. Accordingly, the modified gene can be used to accomplish modified expression of the ISY protein, and particularly increased expression of any endogenous ISY proteins.

Also in some examples the source plant is the same type of plant as the genetically engineered land plant. In accordance with these examples, the ISY protein can be homologous with respect to the genetically engineered land plant. By this it is meant that the particular ISY protein is normally encoded, and may normally be expressed, in plants of the type from which the genetically engineered land plant is derived. In accordance with these examples, the plant can be genetically engineered to include additional copies of a gene for the ISY protein and/or to express an endogenous copy of a gene for the ISY protein at higher levels and/or in a tissue-preferred manner based on modification and/or replacement of a promoter for the endogenous copy of the gene. Again, the genetically engineered land plant expresses the particular ISY protein based on comprising the modified gene for the ISY protein, resulting in modified expression of the ISY protein, and particularly increased expression of the ISY gene.

As discussed above, it is believed that increased expression of an ISY protein may enhance the flow of carbon from source tissue to sink tissue. The sink tissue may be seed, fruit or tuber.

Suitable ISY proteins are disclosed herein or can be identified using the materials and methods disclosed herein for example by increasing the expression of mitochondrial transporters in a plant and carrying out gene expression analysis followed by sequence homology searches of genes whose expression is increased. Such searches can be carried out, for example, by use of BLAST, e.g. tblastn, and databases including translated polynucleotides, whole genome shotgun sequences, and/or transcriptome assembly sequences, among other sequences and databases. Potential orthologs of ISY may be identified, for example, based on percentage of identity and/or percentage of similarity, with respect to polypeptide sequence, of individual sequences in the databases in comparison to *Camelina sativa* ISY proteins of SEQ ID NO: 2 and/or SEQ ID NO: 5. For example, potential orthologs of ISY may be identified based on percentage of identity of an individual sequence in a database of at least 25%, e.g. at least 30%, at least 35%, at least 40%, at least 45%, at least 50%, at least 55%, at least 60%, at least 65%, at least 70%, at least 75%, at least 80%, at least 90%, or at least 95%, wherein the individual sequence is derived from a land plant or a eukaryotic alga.

Following identification of an ISY gene, genetic engineering of a plant to express the ISY gene or a truncated version of it can be carried out by methods that are known in the art, as discussed in detail below.

The genetically engineered land plant can be a genetically engineered land plant that includes no heterologous proteins, e.g. wherein the ISY protein is homologous with respect to the genetically engineered land plant, or only one heterologous protein, e.g. wherein the only heterologous plant protein that the genetically engineered land plant comprises is the ISY protein.

Considering the ISY protein in more detail, again as noted the ISY protein comprises one or more of (i) an ISY protein of *Camelina sativa* comprising SEQ ID NO: 2; (ii) a fragment of an ISY protein of *Camelina sativa* comprising SEQ ID NO: 2; (iii) a *Camelina sativa* homolog of an ISY protein of *Camelina sativa* comprising SEQ ID NO: 2; or (iv) an ortholog of an ISY protein of *Camelina sativa* comprising SEQ ID NO: 2.

In some examples, the ISY protein comprises an ISY protein of *Camelina sativa* comprising SEQ ID NO: 2. In some of these examples, the ISY protein of *Camelina sativa* comprising SEQ ID NO: 2 corresponds to one or more of ISY protein of *Camelina sativa* of SEQ ID NO: 2, ISY protein of *Camelina sativa* of SEQ ID NO: 5, modified ISY protein of *Camelina sativa* of SEQ ID NO: 138, or modified ISY protein of *Camelina sativa* of SEQ ID NO: 140. The ISY protein of *Camelina sativa* of SEQ ID NO: 2 is the *Camelina sativa* ISY protein having 134 amino acids as described herein. Likewise, ISY protein of *Camelina sativa* of SEQ ID NO: 5 is the *Camelina sativa* ISY protein having 168 amino acids as described herein. The modified ISY protein of *Camelina sativa* of SEQ ID NO: 138 is a modified version of the ISY protein of SEQ ID NO: 5 in which the N-terminal leucine has been replaced with an N-terminal methionine. This modified ISY protein can be encoded, for example, by the nucleotide sequence of SEQ ID NO: 137, which is identical to SEQ ID NO: 6 except that the TTG alternative start codon has been replaced by an ATG start codon. The modified ISY protein of *Camelina sativa* of SEQ ID NO: 140 is a modified version of the ISY protein of SEQ ID NO: 5 in which the N-terminal leucine has been preceded with an N-terminal methionine. This modified ISY protein can be encoded, for example, by the nucleotide sequence of SEQ ID NO: 139, which is identical to SEQ ID NO: 6 except that the TTG alternative start codon has been preceded by an ATG start codon. The ISY protein of *Camelina sativa* comprising SEQ ID NO: 2 also can correspond to additional modified ISY proteins, for example additional modified ISY proteins similar to SEQ ID NO: 2, SEQ ID NO: 5, SEQ ID NO: 138, or SEQ ID NO: 140, but including one or more additional amino acid residues at the N-terminus and/or C-terminus.

In some examples, the ISY protein comprises a fragment of an ISY protein of *Camelina sativa* comprising SEQ ID NO: 2. In some of these examples, the fragment corresponds to 30 or more contiguous amino acids of SEQ ID NO: 2. In some of these examples, the fragment corresponds to 40 or more, 50 or more, 60 or more, 70 or more, 80 or more, 90 or more, or 100 or more contiguous amino acids of SEQ ID NO: 2. In some of these examples, the fragment corresponds to 114 to 133 contiguous amino acids of SEQ ID NO: 2. Thus, in some of these examples the fragment corresponds a protein that is identical to ISY protein of *Camelina sativa* of SEQ ID NO: 2, except that the fragment lacks 1 to 20 amino acids at the N-terminus of the fragment relative to SEQ ID NO: 2. Also in some examples, the fragment corresponds a protein that is identical to ISY protein of *Camelina sativa* of SEQ ID NO: 2, except that the fragment lacks 1 to 20 amino acids at the C-terminus of the fragment relative to SEQ ID NO: 2. Also in some examples, the fragment corresponds a protein that is identical to ISY protein of *Camelina sativa* of SEQ ID NO: 2, except that the fragment lacks 1 to 10 amino acids at the N-terminus of the fragment, and 1 to 10 amino acids at the C-terminus of the fragment, relative to SEQ ID NO: 2. In some examples, the fragment is as described, except that the fragment also includes a methionine residue at the N-terminus of the fragment. Based on results obtained for the 134 amino acid ISY protein of SEQ ID NO: 2, which lacks a signal peptide and a stretch of N-terminal amino acids relative to characterized invertase inhibitors, it is believed that increased expression of fragments of ISY proteins would be sufficient for increased seed yield, fruit yield, and/or tuber yield.

In some examples, the ISY protein comprises a *Camelina sativa* homolog of an ISY protein of *Camelina sativa* comprising SEQ ID NO: 2. In some of these examples, the *Camelina sativa* homolog corresponds to one or more *Camelina sativa* proteins of SEQ ID NOS: 21-40. These homologs are described below.

In some examples, the ISY protein comprises the ortholog of an ISY protein of *Camelina sativa* comprising SEQ ID NO: 2. In some of these examples, the ortholog corresponds to one or more (i) canola proteins of SEQ ID NOS: 69, 71, 73, and/or 75; (ii) soybean proteins of SEQ ID NOS: 89, 91, 93, and/or 95; or (iii) corn proteins of SEQ ID NOS: 99, 101, 103, 105, and/or 107. These orthologs are described below.

In some examples, the ISY protein comprises (i) (a) a cysteine residue at position 40, (b) a leucine residue at position 59, (c) a cysteine residue at position 98, and (d) a cysteine residue at position 138, with numbering of positions relative to ISY protein of *Camelina sativa* of SEQ ID NO: 5, and (ii) an overall identity of at least 10% with ISY protein of *Camelina sativa* of SEQ ID NO: 2. In some of these examples, the ISY protein further comprises only between 1 to 14 amino acid residues N-terminal to the cysteine residue at position 40, with numbering of positions relative to ISY protein of *Camelina sativa* of SEQ ID NO: 5. Also in some of these examples, the ISY protein lacks an N-terminal signal peptide. Also in some of these examples, the ISY protein lacks a PKF motif. Based on results obtained for the 134 amino acid ISY protein of SEQ ID NO: 2, which includes a cysteine residue at position 40, a leucine residue at position 59, a cysteine residue at position 98, and a cysteine residue at position 138, with numbering of positions relative to ISY protein of *Camelina sativa* of SEQ ID NO: 5, and which includes only between 1 to 14 amino acid residues N-terminal to the cysteine residue at position 40, namely 5 amino acid residues N-terminal to the cysteine residue at position 40, also with numbering of positions relative to ISY protein of *Camelina sativa* of SEQ ID NO: 5, and which also lacks an N-terminal signal peptide and a PKF motif, it is believed that increased expression of an ISY protein having these characteristics would be sufficient for increased seed yield, fruit yield, and/or tuber yield.

In some examples, the ISY protein comprises (i) (a) a cysteine residue at position 25, (b) a cysteine residue at position 40, (c) a leucine residue at position 59, (d) a cysteine residue at position 98, and (e) a cysteine residue at position 138, with numbering of positions relative to ISY protein of *Camelina sativa* of SEQ ID NO: 5, and (ii) an overall identity of at least 10% with ISY protein of *Camelina sativa* of SEQ ID NO: 5. In some of these examples, the ISY protein lacks a PKF motif. Based on results obtained for the 168 amino acid ISY protein of SEQ ID NO: 5, which includes a cysteine residue at position 25, a cysteine residue at position 40, a leucine residue at position 59, a cysteine residue at position 98, and a cysteine residue at position 138, with numbering of positions relative to ISY protein of *Camelina sativa* of SEQ ID NO: 5, and which lacks a PKF motif, it is believed that increased expression of an ISY protein having these characteristics also would be sufficient for increased seed yield, fruit yield, and/or tuber yield.

The modified gene for the ISY gene comprises (i) a promoter and (ii) a nucleic acid sequence encoding the ISY gene.

The promoter is non-cognate with respect to the nucleic acid sequence encoding the ISY gene. A promoter that is non-cognate with respect to a nucleic acid sequence means that the promoter is not naturally paired with the nucleic acid sequence in organisms from which the promoter and/or the nucleic acid sequence are derived. Instead, the promoter has been paired with the nucleic acid sequence based on use of recombinant DNA techniques to create a modified gene.

The modified gene for the ISY gene is configured such that transcription of the nucleic acid sequence encoding the ISY gene is initiated from the promoter and results in expression of the ISY gene. Accordingly, in the context of the modified gene, the promoter functions as a promoter of transcription of the nucleic acid sequence, and thus of expression of the ISY gene. In a preferred example, the expression of the ISY gene is higher in the genetically engineered land plant than in a corresponding plant that does not include the modified gene.

In some examples, the promoter is a constitutive promoter. In some examples, the promoter is a seed-specific promoter. In some examples, the modified gene is integrated into genomic DNA of the genetically engineered land plant. In some examples, the modified gene is stably expressed in the genetically engineered land plant. In some examples the nucleic acid sequence encodes a wild-type ISY gene. In some examples, the nucleic acid sequence encodes a variant, modified, mutant, or otherwise non-wild-type ISY gene. These exemplary characteristics, and others, of the promoter, the nucleic acid sequence, and the modified gene are discussed in detail below.

The genetically engineered land plant also can be a genetically engineered land plant that expresses nucleic acid sequences encoding ISY genes in both a seed-specific and/or a constitutive manner, wherein the nucleic acid sequences encoding the ISY genes may be the same or different nucleic acid sequences, e.g. from the same source plant or from different source plants. In some examples the genetically engineered land plant (i) expresses the ISY gene in a seed-specific manner, and (ii) expresses another ISY gene constitutively, the other ISY gene also corresponding to an ortholog of ISY derived from a source plant.

The genetically engineered land plant can exhibit increased expression of the ISY protein in comparison to a reference land plant that does not include the modified gene. The genetically engineered land plant also can exhibit increased seed yield, fruit yield, and/or tuber yield in comparison to a reference land plant that does not include the modified gene. For example, the genetically engineered land plant can have a seed yield that is at least 5% higher, at least 10% higher, at least 20% higher, at least 40% higher, at least 60% higher, or at least 80% higher, than for a corresponding reference land plant that does not comprise the modified gene. Also for example, the genetically engineered land plant can have a fruit yield that is at least 5% higher, at least 10% higher, at least 20% higher, at least 40% higher, at least 60% higher, or at least 80% higher, than for a corresponding reference land plant that does not comprise the modified gene. Also for example, the genetically engineered land plant can have a tuber yield that is at least 5% higher, at least 10% higher, at least 20% higher, at least 40% higher, at least 60% higher, or at least 80% higher, than for a corresponding reference land plant that does not comprise the modified gene.

As noted above, following identification of an ISY gene of a source plant, genetic engineering of a land plant to express the ISY gene can be carried out by methods that are known in the art, for example as follows.

DNA constructs useful in the methods described herein include transformation vectors capable of introducing transgenes or other modified nucleic acid sequences into plants. As used herein, "genetically engineered" refers to an organism in which a nucleic acid fragment containing a heterologous nucleotide sequence has been introduced, or in which the expression of a homologous gene has been modified, for example by genome editing. Transgenes in the genetically engineered organism are preferably stable and inheritable. Heterologous nucleic acid fragments may or may not be integrated into the host genome.

Several plant transformation vector options are available, including those described in *Gene Transfer to Plants,* 1995, Potrykus et al., eds., Springer-Verlag Berlin Heidelberg N.Y., *Genetically engineered Plants: A Production System for Industrial and Pharmaceutical Proteins,* 1996, Owen et al., eds., John Wiley & Sons Ltd. England, and *Methods in Plant Molecular Biology: A Laboratory Course Manual,* 1995, Maliga et al., eds., Cold Spring Laboratory Press, New York. Plant transformation vectors generally include one or more coding sequences of interest under the transcriptional control of 5' and 3' regulatory sequences, including a promoter, a transcription termination and/or polyadenylation signal, and a selectable or screenable marker gene.

Many vectors are available for transformation using *Agrobacterium tumefaciens.* These typically carry at least one T-DNA sequence and include vectors such as pBIN19. Typical vectors suitable for *Agrobacterium* transformation include the binary vectors pCIB200 and pCIB2001, as well as the binary vector pCIB10 and hygromycin selection derivatives thereof. See, for example, U.S. Pat. No. 5,639, 949.

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. The choice of vector for transformation techniques that do not rely on *Agrobacterium* depends largely on the preferred selection for the species being transformed. Typical vectors suitable for non-*Agrobacterium* transformation include pCIB3064, pSOG 19, and pSOG35. See, for example, U.S. Pat. No. 5,639,949. Alternatively, DNA fragments containing the transgene and the necessary regulatory elements for expression of the transgene can be excised from a plasmid and delivered to the plant cell using microprojectile bombardment-mediated methods.

Zinc-finger nucleases (ZFNs) are also useful in that they allow double strand DNA cleavage at specific sites in plant chromosomes such that targeted gene insertion or deletion can be performed (Shukla et al., 2009, *Nature* 459: 437-441; Townsend et al., 2009, Nature 459: 442-445).

The CRISPR/Cas9 system (Sander, J. D. and Joung, J. K., Nature Biotechnology, published online Mar. 2, 2014; doi; 10.1038/nbt.2842) is particularly useful for editing plant genomes to modulate the expression of homologous genes encoding enzymes. All that is required to achieve a CRISPR/Cas edit is a Cas enzyme, or other CRISPR nuclease (Murugan et al. (2017), Mol Cell, 68:15), and a single guide RNA (sgRNA) as reviewed extensively by others (Belhag et al. (2015), Curr Opin Biotech, 32: 76; Khandagale & Nadaf (2016), Plant Biotechnol Rep, 10:327-343). Several examples of the use of this technology to edit the genomes of plants have now been reported (Belhaj et al. (2013), Plant Methods, 9:39; Zhang et al. (2016), Journal of Genetics and Genomics, 43: 251).

TALENs (transcriptional activator-like effector nucleases) or meganucleases can also be used for plant genome editing (Malzahn et al., Cell Biosci, 2017, 7:21).

Transformation protocols as well as protocols for introducing nucleotide sequences into plants may vary depending on the type of plant or plant cell targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606), *Agrobacterium*-mediated transformation (Townsend et al., U.S. Pat. No. 5,563,055; Zhao et al. WO US98/01268), direct gene transfer (Paszkowski et al. (1984) EMBO J. 3:2717-2722), and ballistic particle acceleration (see, for example, Sanford et al., U.S. Pat. No. 4,945,050; Tomes et al. (1995) *Plant Cell, Tissue, and Organ Culture: Fundamental Methods*, ed. Gamborg and Phillips (Springer-Verlag, Berlin); and McCabe et al. *Biotechnology* 6:923-926 (1988)). Also see Weissinger et al. *Ann. Rev. Genet.* 22:421-477 (1988); Sanford et al. Particulate Science and Technology 5:27-37 (1987) (onion); Christou et al. *Plant Physiol.* 87:671-674 (1988) (soybean); McCabe et al. (1988) BioTechnology 6:923-926 (soybean); Finer and McMullen *In Vitro Cell Dev. Biol.* 27P:175-182 (1991) (soybean); Singh et al. *Theor. Appl. Genet.* 96:319-324 (1998)(soybean); Dafta et al. (1990) *Biotechnology* 8:736-740 (rice); Klein et al. *Proc. Natl. Acad. Sci. USA* 85:4305-4309 (1988) (maize); Klein et al. *Biotechnology* 6:559-563 (1988) (maize); Tomes, U.S. Pat. No. 5,240,855; Buising et al., U.S. Pat. Nos. 5,322,783 and 5,324,646; Tomes et al. (1995) in Plant Cell, Tissue, and Organ Culture: Fundamental Methods, ed. Gamborg (Springer-Verlag, Berlin) (maize); Klein et al. Plant Physiol. 91:440-444 (1988) (maize); Fromm et al. *Biotechnology* 8:833-839 (1990) (maize); Hooykaas-Van Slogteren et al. *Nature* 311:763-764 (1984); Bowen et al., U.S. Pat. No. 5,736,369 (cereals); Bytebier et al. *Proc. Natl. Acad. Sci. USA* 84:5345-5349 (1987) (Liliaceae); De Wet et al. in The Experimental Manipulation of Ovule Tissues, ed. Chapman et al. (Longman, N.Y.), pp. 197-209 (1985) (pollen); Kaeppler et al. *Plant Cell Reports* 9:415-418 (1990) and Kaeppler et al. *Theor. Appl. Genet.* 84:560-566 (1992) (whisker-mediated transformation); D'Halluin et al. *Plant Cell* 4:1495-1505 (1992) (electroporation); Li et al. *Plant Cell Reports* 12:250-255 (1993) and Christou and Ford Annals of Botany 75:407-413 (1995) (rice); Osjoda et al. *Nature Biotechnology* 14:745-750 (1996) (maize via *Agrobacterium tumefaciens*). References for protoplast transformation and/or gene gun for Agrisoma technology are described in WO 2010/037209. Methods for transforming plant protoplasts are available including transformation using polyethylene glycol (PEG), electroporation, and calcium phosphate precipitation (see for example Potrykus et al., 1985, Mol. Gen. Genet., 199, 183-188; Potrykus et al., 1985, Plant Molecular Biology Reporter, 3, 117-128), Methods for plant regeneration from protoplasts have also been described (Evans et al., in Handbook of Plant Cell Culture, Vol 1, (Macmillan Publishing Co., New York, 1983); Vasil, IK in Cell Culture and Somatic Cell Genetics (Academic, Orlando, 1984)).

Recombinase technologies which are useful for producing the disclosed genetically engineered land plants include the cre-lox, FLP/FRT and Gin systems. Methods by which these technologies can be used for the purpose described herein are described for example in (U.S. Pat. No. 5,527,695; Dale and Ow, 1991, *Proc. Natl. Acad. Sci. USA* 88: 10558-10562; Medberry et al., 1995, *Nucleic Acids Res.* 23: 485-490).

Transformation protocols as well as protocols for introducing nucleotide sequences into plants may vary depending on the type of plant or plant cell, i.e., monocot or dicot, targeted for transformation.

Suitable methods of introducing nucleotide sequences into plant cells and subsequent insertion into the plant genome are described in US 2010/0229256 A1 to Somleva & Ali and US 2012/0060413 to Somleva et al.

The transformed cells are grown into plants in accordance with conventional techniques. See, for example, McCormick et al., 1986, *Plant Cell Rep.* 5: 81-84. These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

Procedures for in planta transformation can be simple. Tissue culture manipulations and possible somaclonal variations are avoided and only a short time is required to obtain genetically engineered land plants. However, the frequency of transformants in the progeny of such inoculated plants is relatively low and variable. At present, there are very few species that can be routinely transformed in the absence of a tissue culture-based regeneration system. Stable *Arabidopsis* transformants can be obtained by several in planta methods including vacuum infiltration (Clough & Bent, 1998, *The Plant J.* 16: 735-743), transformation of germinating seeds (Feldmann & Marks, 1987, *Mol. Gen. Genet.* 208: 1-9), floral dip (Clough and Bent, 1998, *Plant J.* 16: 735-743), and floral spray (Chung et al., 2000, *Genetically engineered Res.* 9: 471-476). Other plants that have successfully been transformed by in planta methods include rapeseed and radish (vacuum infiltration, Ian and Hong, 2001, *Genetically engineered Res.*, 10: 363-371; Desfeux et al., 2000, *Plant Physiol.* 123: 895-904), *Medicago trunca-*

*tula* (vacuum infiltration, Trieu et al., 2000, *Plant J.* 22: 531-541), *Camelina* (floral dip, WO/2009/117555 to Nguyen et al.), and wheat (floral dip, Zale et al., 2009, *Plant Cell Rep.* 28: 903-913). In planta methods have also been used for transformation of germ cells in maize (pollen, Wang et al. 2001, *Acta Botanica Sin.*, 43, 275-279; Zhang et al., 2005, *Euphytica*, 144, 11-22; pistils, Chumakov et al. 2006, *Russian J. Genetics*, 42, 893-897; Mamontova et al. 2010, *Russian J. Genetics*, 46, 501-504) and Sorghum (pollen, Wang et al. 2007, *Biotechnol. Appl. Biochem.*, 48, 79-83).

Following transformation by any one of the methods described above, the following procedures can be used to obtain a transformed plant expressing the transgenes: select the plant cells that have been transformed on a selective medium; regenerate the plant cells that have been transformed to produce differentiated plants; select transformed plants expressing the transgene producing the desired level of desired polypeptide(s) in the desired tissue and cellular location.

The cells that have been transformed may be grown into plants in accordance with conventional techniques. See, for example, McCormick et al. *Plant Cell Reports* 5:81-84 (1986). These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

Genetically engineered land plants can be produced using conventional techniques to express any genes of interest in plants or plant cells (*Methods in Molecular Biology*, 2005, vol. 286, Genetically engineered Plants: Methods and Protocols, Pena L., ed., Humana Press, Inc. Totowa, N.J.; Shyamkumar Barampuram and Zhanyuan J. Zhang, Recent Advances in Plant Transformation, in James A. Birchler (ed.), *Plant Chromosome Engineering: Methods and Protocols*, Methods in Molecular Biology, vol. 701, Springer Science+Business Media). Typically, gene transfer, or transformation, is carried out using explants capable of regeneration to produce complete, fertile plants. Generally, a DNA or an RNA molecule to be introduced into the organism is part of a transformation vector. A large number of such vector systems known in the art may be used, such as plasmids. The components of the expression system can be modified, e.g., to increase expression of the introduced nucleic acids. For example, truncated sequences, nucleotide substitutions or other modifications may be employed. Expression systems known in the art may be used to transform virtually any plant cell under suitable conditions. A transgene comprising a DNA molecule encoding a gene of interest is preferably stably transformed and integrated into the genome of the host cells. Transformed cells are preferably regenerated into whole fertile plants. Detailed description of transformation techniques are within the knowledge of those skilled in the art.

Plant promoters can be selected to control the expression of the transgene in different plant tissues or organelles for all of which methods are known to those skilled in the art (Gasser & Fraley, 1989, *Science* 244: 1293-1299). In one embodiment, promoters are selected from those of eukaryotic or synthetic origin that are known to yield high levels of expression in plants and algae. In a preferred embodiment, promoters are selected from those that are known to provide high levels of expression in monocots.

Constitutive promoters include, for example, the core promoter of the Rsyn7 promoter and other constitutive promoters disclosed in WO 99/43838 and U.S. Pat. No. 6,072,050, the core CaMV 35S promoter (Odell et al., 1985, *Nature* 313: 810-812), rice actin (McElroy et al., 1990, *Plant Cell* 2: 163-171), ubiquitin (Christensen et al., 1989, *Plant Mol. Biol.* 12: 619-632; Christensen et al., 1992, *Plant Mol. Biol.* 18: 675-689), pEMU (Last et al., 1991, *Theor. Appl. Genet.* 81: 581-588), MAS (Velten et al., 1984, *EMBO J.* 3: 2723-2730), and ALS promoter (U.S. Pat. No. 5,659,026). Other constitutive promoters are described in U.S. Pat. Nos. 5,608,149; 5,608,144; 5,604,121; 5,569,597; 5,466,785; 5,399,680; 5,268,463; and 5,608,142.

"Tissue-preferred" promoters can be used to target gene expression within a particular tissue. Tissue-preferred promoters include those described by Van Ex et al., 2009, *Plant Cell Rep.* 28: 1509-1520; Yamamoto et al., 1997, *Plant J.* 12: 255-265; Kawamata et al., 1997, *Plant Cell Physiol.* 38: 792-803; Hansen et al., 1997, *Mol. Gen. Genet.* 254: 337-343; Russell et al., 1997, *Transgenic Res.* 6: 157-168; Rinehart et al., 1996, *Plant Physiol.* 112: 1331-1341; Van Camp et al., 1996, *Plant Physiol.* 112: 525-535; Canevascini et al., 1996, *Plant Physiol.* 112: 513-524; Yamamoto et al., 1994, *Plant Cell Physiol.* 35: 773-778; Lam, 1994, *Results Probl. Cell Differ.* 20: 181-196, Orozco et al., 1993, *Plant Mol. Biol.* 23: 1129-1138; Matsuoka et al., 1993, *Proc. Natl. Acad. Sci. USA* 90: 9586-9590, and Guevara-Garcia et al., 1993, *Plant J.* 4: 495-505. Such promoters can be modified, if necessary, for weak expression.

Seed-specific promoters can be used to target gene expression to seeds in particular. Seed-specific promoters include promoters that are expressed in various tissues within seeds and at various stages of development of seeds. Seed-specific promoters can be absolutely specific to seeds, such that the promoters are only expressed in seeds, or can be expressed preferentially in seeds, e.g. at rates that are higher by 2-fold, 5-fold, 10-fold, or more, in seeds relative to one or more other tissues of a plant, e.g. stems, leaves, and/or roots, among other tissues. Seed-specific promoters include, for example, seed-specific promoters of dicots and seed-specific promoters of monocots, among others. For dicots, seed-specific promoters include, but are not limited to, bean β-phaseolin, napin, β-conglycinin, soybean oleosin 1, *Arabidopsis thaliana* sucrose synthase, flax conlinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, and globulin 1.

Chemical-regulated promoters can be used to modulate the expression of a gene in a plant through the application of an exogenous chemical regulator.

Specific exemplary promoters useful for expression of genes in dicots and monocots are provided in TABLE 1 and TABLE 2, respectively.

TABLE 1

Promoters useful for expression of genes in dicots.

| Gene/Promoter | Expression | Native organism of promoter | Gene ID* (SEQ ID NO) |
|---|---|---|---|
| CaMV 35S | Constitutive | Cauliflower mosaic virus | (SEQ ID NO: 108) |
| Hsp70 | Constitutive | *Glycine max* | Glyma.02G093200 (SEQ ID NO: 41) |
| Chlorophyll A/B Binding Protein (Cab5) | Constitutive | *Glycine max* | Glyma.08G082900 (SEQ ID NO: 42) |
| Pyruvate phosphate dikinase (PPDK) | Constitutive | *Glycine max* | Glyma.06G252400 (SEQ ID NO: 43) |
| Actin | Constitutive | *Glycine max* | Glyma.19G147900 (SEQ ID NO: 44) |
| ADP-glucose pyrophosphorylase (AGPase) | Seed-specific | *Glycine max* | Glyma.04G011900 (SEQ ID NO: 45) |
| Glutelin C (GluC) | Seed-specific | *Glycine max* | Glyma.03G163500 (SEQ ID NO: 46) |
| β-fructofuranosidase insoluble isoenzyme 1 (CIN1) | Seed-specific | *Glycine max* | Glyma.17G227800 (SEQ ID NO: 47) |
| MADS-Box | Cob-specific | *Glycine max* | Glyma.04G257100 (SEQ ID NO: 48) |
| Glycinin (subunit G1) | Seed-specific | *Glycine max* | Glyma.03G163500 (SEQ ID NO: 49) |
| oleosin isoform A | Seed-specific | *Glycine max* | Glyma.16G071800 (SEQ ID NO: 50) |
| Hsp70 | Constitutive | *Brassica napus* | BnaA09g05860D |
| Chlorophyll A/B Binding Protein (Cab5) | Constitutive | *Brassica napus* | BnaA04g20150D |
| Pyruvate phosphate dikinase (PPDK) | Constitutive | *Brassica napus* | BnaA01g18440D |
| Actin | Constitutive | *Brassica napus* | BnaA03g34950D |
| ADP-glucose pyrophosphorylase (AGPase) | Seed-specific | *Brassica napus* | BnaA06g40730D |
| Glutelin C (GluC) | Seed-specific | *Brassica napus* | BnaA09g50780D |
| β-fructofuranosidase insoluble isoenzyme 1 (CIN1) | Seed-specific | *Brassica napus* | BnaA04g05320D |
| MADS-Box | Cob-specific | *Brassica napus* | BnaA05g02990D |
| Glycinin (subunit G1) | Seed-specific | *Brassica napus* | BnaA01g08350D |
| oleosin isoform A | Seed-specific | *Brassica napus* | BnaC06g12930D |
| 1.7S napin (napA) | Seed-specific | *Brassica napus* | BnaA01g17200D |

*Gene ID includes sequence information for coding regions as well as associated promoters, 5' UTRs, and 3' UTRs and are available at Phytozome (see JGI website phytozome.jgi.doe.gov/pz/portal.html).

TABLE 2

Promoters useful for expression of genes in monocots, including maize and rice.

| Gene/Promoter | Expression | Rice* | Maize* | Other |
|---|---|---|---|---|
| Hsp70 | Constitutive | LOC_Os05g38530 (SEQ ID NO: 51) | GRMZM2G310431 (SEQ ID NO: 59) | |
| Chlorophyll A/B Binding Protein (Cab5) | Constitutive | LOC_Os01g41710 (SEQ ID NO: 52) | AC207722.2_FG009 (SEQ ID NO: 60) GRMZM2G351977 (SEQ ID NO: 61) | |
| maize ubiquitin promoter/maize ubiquitin intron (sequence listed in Genbank KT962835) | Constitutive | | (SEQ ID NO: 109) | |
| maize ubiquitin promoter/maize ubiquitin intron (maize promoter and intron sequence with 99% identity to sequence in Genbank KT985051.1) | Constitutive | | (SEQ ID NO: 110) | |
| CaMV 35S | Constitutive | — | — | Cauliflower mosaic virus (SEQ ID NO: 108) |
| Pyruvate phosphate dikinase (PPDK) | Constitutive | LOC_Os05g33570 (SEQ ID NO: 53) | GRMZM2G306345 (SEQ ID NO: 62) | |
| Actin | Constitutive | LOC_Os03g50885 (SEQ ID NO: 54) | GRMZM2G047055 (SEQ ID NO: 63) | |

TABLE 2-continued

Promoters useful for expression of genes in monocots, including maize and rice.

| Gene/Promoter | Expression | Rice* | Maize* | Other |
|---|---|---|---|---|
| Hybrid cab5/hsp70 intron promoter | Constitutive | N/A | SEQ ID NO: 64 | |
| ADP-glucose pyrophos-phorylase (AGPase) | Seed-specific | LOC_Os01g44220 (SEQ ID NO: 55) | GRMZM2G429899 (SEQ ID NO: 65) | |
| Glutelin C (GluC) | Seed-specific | LOC_Os02g25640 (SEQ ID NO: 56) | N/A | |
| β-fructofuranosidase insoluble isoenzyme 1 (CIN1) | Seed-specific | LOC_Os02g33110 (SEQ ID NO: 57) | GRMZM2G139300 (SEQ ID NO: 66) | |
| MADS-Box | Cob-specific | LOC_Os12g10540 (SEQ ID NO: 58) | GRMZM2G160687 (SEQ ID NO: 67) | |
| Maize TrpA promoter | Seed-specific | | GRMZM5G841619 (SEQ ID NO: 111) | |

*Gene ID includes sequence information for coding regions as well as associated promoters. 5' UTRs, and 3' UTRs and are available at Phytozome (see JGI website phytozome.jgi.doe.gov/pz/portal.html).

Certain embodiments use genetically engineered land plants or plant cells having multi-gene expression constructs harboring more than one transgene and promoter. The promoters can be the same or different.

Any of the described promoters can be used to control the expression of one or more of genes, their homologs and/or orthologs as well as any other genes of interest in a defined spatiotemporal manner.

Nucleic acid sequences intended for expression in genetically engineered land plants are first assembled in expression cassettes behind a suitable promoter active in plants. The expression cassettes may also include any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be transferred to the plant transformation vectors described infra. The following is a description of various components of typical expression cassettes.

A variety of transcriptional terminators are available for use in expression cassettes. These are responsible for the termination of transcription beyond the transgene and the correct polyadenylation of the transcripts. Appropriate transcriptional terminators are those that are known to function in plants and include the CaMV 35S terminator, the tm1 terminator, the nopaline synthase terminator and the pea rbcS E9 terminator. These are used in both monocotyledonous and dicotyledonous plants.

The coding sequence of the selected gene may be genetically engineered by altering the coding sequence for optimal expression in the crop species of interest. Methods for modifying coding sequences to achieve optimal expression in a particular crop species are well known (Perlak et al., 1991, *Proc. Natl. Acad. Sci. USA* 88: 3324 and Koziel et al., 1993, *Biotechnology* 11: 194-200).

Individual plants within a population of genetically engineered land plants that express a recombinant gene(s) may have different levels of gene expression. The variable gene expression is due to multiple factors including multiple copies of the recombinant gene, chromatin effects, and gene suppression. Accordingly, a phenotype of the genetically engineered land plant may be measured as a percentage of individual plants within a population. The yield of a plant can be measured simply by weighing. The yield of seed from a plant can also be determined by weighing. The increase in seed weight from a plant can be due to a number of factors, including an increase in the number or size of the seed pods, an increase in the number of seed and/or an increase in the number of seed per plant. In the laboratory or greenhouse seed yield is usually reported as the weight of seed produced per plant and in a commercial crop production setting yield is usually expressed as weight per acre or weight per hectare.

A recombinant DNA construct including a plant-expressible gene or other DNA of interest is inserted into the genome of a plant by a suitable method. Suitable methods include, for example, *Agrobacterium tumefaciens*-mediated DNA transfer, direct DNA transfer, liposome-mediated DNA transfer, electroporation, co-cultivation, diffusion, particle bombardment, microinjection, gene gun, calcium phosphate coprecipitation, viral vectors, and other techniques. Suitable plant transformation vectors include those derived from a Ti plasmid of *Agrobacterium tumefaciens*. In addition to plant transformation vectors derived from the Ti or root-inducing (Ri) plasmids of *Agrobacterium*, alternative methods can be used to insert DNA constructs into plant cells. A genetically engineered land plant can be produced by selection of transformed seeds or by selection of transformed plant cells and subsequent regeneration.

In some embodiments, the genetically engineered land plants are grown (e.g., on soil) and harvested. In some embodiments, above ground tissue is harvested separately from below ground tissue. Suitable above ground tissues include shoots, stems, leaves, flowers, grain, and seed. Exemplary below ground tissues include roots and root hairs. In some embodiments, whole plants are harvested and the above ground tissue is subsequently separated from the below ground tissue.

Genetic constructs may encode a selectable marker to enable selection of transformation events. There are many methods that have been described for the selection of transformed plants (for review see (Miki et al., *Journal of Biotechnology*, 2004, 107, 193-232) and references incorporated within). Selectable marker genes that have been used extensively in plants include the neomycin phosphotransferase gene nptII (U.S. Pat. Nos. 5,034,322, 5,530,196), hygromycin resistance gene (U.S. Pat. No. 5,668,298, Waldron et al., (1985), *Plant Mol Biol*, 5:103-108; Zhijian et al., (1995), *Plant Sci*, 108:219-227), the bar gene encoding resistance to phosphinothricin (U.S. Pat. No. 5,276,268), the expression of aminoglycoside 3"-adenyltransferase (aadA) to confer spectinomycin resistance (U.S. Pat. No. 5,073,675), the use of inhibition resistant 5-enolpyruvyl-3-phosphoshikimate synthetase (U.S. Pat. No. 4,535,060) and methods for producing glyphosate tolerant plants (U.S. Pat. Nos. 5,463,175; 7,045,684). Other suitable selectable markers include, but are not limited to, genes encoding resistance to chloramphenicol (Herrera Estrella et al., (1983), *EMBO J,* 2:987-992), methotrexate (Herrera Estrella et al., (1983), *Nature,* 303:209-213; Meijer et al, (1991), *Plant Mol Biol,* 16:807-820); streptomycin (Jones et al., (1987), *Mol Gen Genet,* 210:86-91); bleomycin (Hille et al., (1990), *Plant Mol Biol,* 7:171-176); sulfonamide (Guerineau et al., (1990), *Plant Mol Biol,* 15:127-136); bromoxynil (Stalker et al., (1988), *Science,* 242:419-423); glyphosate (Shaw et al., (1986), *Science,* 233:478-481); phosphinothricin (DeBlock et al., (1987), *EMBO J,* 6:2513-2518).

Methods of plant selection that do not use antibiotics or herbicides as a selective agent have been previously described and include expression of glucosamine-6-phosphate deaminase to inactive glucosamine in plant selection medium (U.S. Pat. No. 6,444,878) and a positive/negative system that utilizes D-amino acids (Erikson et al., *Nat Biotechnol,* 2004, 22, 455-8). European Patent Publication No. EP 0 530 129 A1 describes a positive selection system which enables the transformed plants to outgrow the nontransformed lines by expressing a transgene encoding an enzyme that activates an inactive compound added to the growth media. U.S. Pat. No. 5,767,378 describes the use of mannose or xylose for the positive selection of genetically engineered plants.

Methods for positive selection using sorbitol dehydrogenase to convert sorbitol to fructose for plant growth have also been described (WO 2010/102293). Screenable marker genes include the beta-glucuronidase gene (Jefferson et al., 1987, *EMBO J.* 6: 3901-3907; U.S. Pat. No. 5,268,463) and native or modified green fluorescent protein gene (Cubitt et al., 1995, *Trends Biochem. Sci.* 20: 448-455; Pan et al., 1996, *Plant Physiol.* 112: 893-900).

Transformation events can also be selected through visualization of fluorescent proteins such as the fluorescent proteins from the nonbioluminescent Anthozoa species which include DsRed, a red fluorescent protein from the *Discosoma* genus of coral (Matz et al. (1999), Nat Biotechnol 17: 969-73). An improved version of the DsRed protein has been developed (Bevis and Glick (2002), Nat Biotech 20: 83-87) for reducing aggregation of the protein.

Visual selection can also be performed with the yellow fluorescent proteins (YFP) including the variant with accelerated maturation of the signal (Nagai, T. et al. (2002), Nat Biotech 20: 87-90), the blue fluorescent protein, the cyan fluorescent protein, and the green fluorescent protein (Sheen et al. (1995), Plant J 8: 777-84; Davis and Vierstra (1998), Plant Molecular Biology 36: 521-528). A summary of fluorescent proteins can be found in Tzfira et al. (Tzfira et al. (2005), Plant Molecular Biology 57: 503-516) and Verkhusha and Lukyanov (Verkhusha, V. V. and K. A. Lukyanov (2004), Nat Biotech 22: 289-296). Improved versions of many of the fluorescent proteins have been made for various applications. It will be apparent to those skilled in the art how to use the improved versions of these proteins, including combinations, for selection of transformants.

The plants modified for enhanced yield may have stacked input traits that include herbicide resistance and insect tolerance, for example a plant that is tolerant to the herbicide glyphosate and that produces the *Bacillus thuringiensis* (BT) toxin. Glyphosate is a herbicide that prevents the production of aromatic amino acids in plants by inhibiting the enzyme 5-enolpyruvylshikimate-3-phosphate synthase (EPSP synthase). The overexpression of EPSP synthase in a crop of interest allows the application of glyphosate as a weed killer without killing the modified plant (Suh, et al., J. M Plant Mol. Biol. 1993, 22, 195-205). BT toxin is a protein that is lethal to many insects providing the plant that produces it protection against pests (Barton, et al. Plant Physiol. 1987, 85, 1103-1109). Other useful herbicide tolerance traits include but are not limited to tolerance to Dicamba by expression of the dicamba monoxygenase gene (Behrens et al, 2007, Science, 316, 1185), tolerance to 2,4-dichlorophenoxyacetic acid (2,4-D) and 2,4-D choline by expression of a bacterial aad-1 gene that encodes for an aryloxyalkanoate dioxygenase enzyme (Wright et al., Proceedings of the National Academy of Sciences, 2010, 107, 20240), glufosinate tolerance by expression of the bialaphos resistance gene (bar) or the pat gene encoding the enzyme phosphinotricin acetyl transferase (Droge et al., Planta, 1992, 187, 142), as well as genes encoding a modified 4-hydroxyphenylpyruvate dioxygenase (HPPD) that provides tolerance to the herbicides mesotrione, isoxaflutole, and tembotrione (Siehl et al., Plant Physiol, 2014, 166, 1162).

The genetically engineered land plant that expresses an ISY gene, as disclosed, can be further modified for further enhanced yield too.

For example, the genetically engineered land plant can express one or more mitochondrial transporter proteins that are also expressed as members of carbon-concentrating mechanisms of eukaryotic algae, as well as expressing an ISY gene. In some examples, the mitochondrial transporter protein is a CCP1 mitochondrial transporter protein. In some examples the mitochondrial transporter protein is expressed under the control of plant promoters which may be constitutive, tissue-specific, or seed-specific. Such genetically engineered land plants are expected to have further enhanced yield as compared to plants not expressing the mitochondrial transporter protein, the ISY gene, or both. For example, such genetically engineered land plants may have improved performance, such as increased $CO_2$ fixation rates, reduced transpiration, and/or increased biomass and/or seed yield.

Thus, in some examples the genetically engineered land plant expresses a CCP1 mitochondrial transporter protein. In these examples, the genetically engineered land plant comprises a modified gene for the CCP1 mitochondrial transporter protein. The CCP1 mitochondrial transporter protein comprises: (i) CCP1 of *Chlamydomonas reinhardtii* of SEQ ID NO: 112 or (ii) an ortholog of CCP1 as disclosed in PCT/US2018/037740 and PCT/US2017/016421 to Yield10 Bioscience. The ortholog of CCP1 can be, for example, an algal CCP1 ortholog, such as a CCP1 ortholog of *Gonium pectorale* (e.g. SEQ ID NO: 113 or SEQ ID NO: 114), *Volvox carteri* f. *nagariensis* (e.g. SEQ ID NO: 115), *Ettlia oleoabundans* (e.g. SEQ ID NO: 116), *Chlorella sorokiniana* (e.g. SEQ ID NO: 117). The ortholog of CCP1 also can be, for example, a plant CCP1 ortholog, such as a CCP1 ortholog of *Erigeron breviscapus* (e.g. SEQ ID NO: 118), *Zea nicaraguensis* (e.g. SEQ ID NO: 119), *Poa pratensis* (e.g. SEQ ID NO: 120), *Cosmos bipinnatus* (e.g. SEQ ID NO: 121), *Glycine max* (e.g. SEQ ID NO: 122), *Zea mays* (e.g. SEQ ID NO: 123), *Oryza sativa* (e.g. SEQ ID NO: 124), *Triticum aestivum* (e.g. SEQ ID NO: 125), *Sorghum bicolor* (e.g. SEQ ID NO: 126), or *Solanum tuberosum* (e.g. SEQ ID NO: 127).

The CCP1 mitochondrial transporter protein is localized to mitochondria of the genetically engineered land plant based on a mitochondrial targeting signal. The modified gene for the CCP1 mitochondrial transporter protein comprises (i) another promoter and (ii) a nucleic acid sequence encoding the CCP1 mitochondrial transporter protein. The other promoter is non-cognate with respect to the nucleic acid sequence. The modified gene for the CCP1 mitochondrial transporter protein is configured such that transcription of the nucleic acid sequence encoding the CCP1 mitochondrial transporter protein is initiated from the other promoter and results in expression of the CCP1 mitochondrial transporter protein.

A genetically engineered land plant that expresses an RNA that increases seed yield with increased expression ("an ISY RNA") also is disclosed. The genetically engineered land plant comprises a modified gene for the ISY RNA. The ISY RNA comprises a contiguous sequence of codons encoding a protein that has homology to a plant invertase inhibitor and/or a pectin methylesterase inhibitor ("an encoded protein"). The encoded protein comprises one or more of (i) a protein of *Camelina sativa* comprising SEQ ID NO: 2; (ii) a fragment of a protein of *Camelina sativa* comprising SEQ ID NO: 2; (iii) a *Camelina sativa* homolog of a protein of *Camelina sativa* comprising SEQ ID NO: 2; or (iv) an ortholog of a protein of *Camelina sativa* comprising SEQ ID NO: 2. The modified gene comprises (i) a promoter and (ii) a nucleic acid sequence encoding the ISY RNA. The promoter is non-cognate with respect to the nucleic acid sequence encoding the ISY RNA. The modified gene is configured such that transcription of the nucleic acid sequence is initiated from the promoter and results in expression of the ISY RNA.

An ISY RNA expressed from an ISY gene may cause an increase in seed yield independent of ISY protein. In *Camelina*, the ISY gene is a weakly transcribed gene, with a coding potential score of 0.885 (website://cpc.gao-lab.org/programs/cpc.do, Kang Y-J et al, Nucleic Acids Research, 2017, Vol. 45, Web Server issue W12-16), and is only expressed at low levels in senescing leaves and early silique development (Kagale et al, Plant Journal (2016) 88, 879-894 supplementary data). Also, it is not entirely clear which codon or codons correspond to start codons for ISY protein in wild-type *Camelina* plants. These observations may reflect a role for ISY RNA as, for example, a long non-coding RNA (lncRNA) and/or as a bifunctional RNA (bifRNA). An lncRNA is an RNA, generally including more than 200 nucleotides, that can perform regulatory functions in a cell in its form as RNA, without necessarily coding a protein (Zhang et al., Plant Sciences, 2013, 4, 1038-1045; Hube and Francastel, Frontiers in Genetics, 2018, 9, Article 140). A bifRNA is an RNA that can perform regulatory functions in a cell in its form as RNA and that also codes a protein (Hube and Francastel, 2018). For comparison, a messenger RNA (mRNA) is an RNA that codes a protein, without apparently performing regulatory functions in a cell in its form as RNA. Regarding the ISY gene, it is possible, for example, that the ISY gene can be transcribed to produce an lncRNA that can cause an increase in seed yield based on a regulatory function, without translation of ISY protein from the ISY RNA. It also is possible, for example, that the ISY gene can be transcribed to produce a bifRNA that can cause an increase in seed yield based on both a regulatory function and translation of ISY protein from the ISY RNA. Translation of SEQ ID NO: 3, the genomic region that contains the coding regions for the 168 amino acid protein (DNA SEQ ID NO: 6, encoded protein SEQ ID NO: 5) and the 134 amino acid protein (DNA SEQ ID NO: 1, encoded protein SEQ ID NO: 2), shows that there are no apparent additional start codons for the gene upstream of the TTG start codon of the 168 amino acid protein (FIG. 5). The TTG start codon of SEQ ID NO: 6 would also be the expected start codon based on alignment for the best orthologs of the *Camelina* ISY gene in canola, soybean, and corn (FIG. 17A-B) as well as alignments to known plant invertase inhibitors (FIG. 1A-B). A weak start codon may be consistent with a role for the ISY gene in expressing an lncRNA and/or a bifRNA. lncRNAs have important functions in plant growth and development (Huang et al, 2017, Proceedings of the National Academy of Sciences, U.S.A., 2017, 114:E3149-E3158, website:www.pnas.org/cgi/doi/10.1073/pnas.1617483114; Zhang et al., 2013). bifRNAs may too. Thus, for example, ISY RNA may act as a transcript to enhance the pathways related to seed yield or regulate the genes that lead to increased plant seed yield, and this may be so independent of, or in conjunction with, expression of ISY protein.

In some examples, the genetically engineered land plant is a food crop plant selected from the group consisting of maize, wheat, oat, barley, soybean, millet, sorghum, potato, sugar beet, pulse, chickpea, green pea, yellow pea, lentils, bean, tomato, and rice. In some examples, the genetically engineered land plant is an oilseed crop plant selected from the group consisting of *Camelina, Brassica* species (e.g. *B. napus* (canola), *B. rapa, B. juncea*, and *B. carinata*), *crambe*, soybean, sunflower, safflower, oil palm, flax, and cotton.

As noted, the ISY RNA comprises a contiguous sequence of codons encoding a protein that has homology to a plant invertase inhibitor and/or a pectin methylesterase inhibitor ("an encoded protein"). Also as noted, the encoded protein comprises one or more of (i) a protein of *Camelina sativa* comprising SEQ ID NO: 2; (ii) a fragment of a protein of *Camelina sativa* comprising SEQ ID NO: 2; (iii) a *Camelina sativa* homolog of a protein of *Camelina sativa* comprising SEQ ID NO: 2; or (iv) an ortholog of a protein of *Camelina sativa* comprising SEQ ID NO: 2.

In some examples, the protein of *Camelina sativa* comprising SEQ ID NO: 2 corresponds to one or more of ISY protein of *Camelina sativa* of SEQ ID NO: 2, ISY protein of *Camelina sativa* of SEQ ID NO: 5, modified ISY protein of *Camelina sativa* of SEQ ID NO: 138, or modified ISY protein of *Camelina sativa* of SEQ ID NO: 140, each as described above.

In some examples, the fragment of a protein of *Camelina sativa* comprising SEQ ID NO: 2 corresponds to 30 or more contiguous amino acids of SEQ ID NO: 2, as described above. In some of these examples, the fragment corresponds to 40 or more, 50 or more, 60 or more, 70 or more, 80 or more, 90 or more, or 100 or more contiguous amino acids of SEQ ID NO: 2, also as described above. In some of these examples, the fragment corresponds to 114 to 133 contiguous amino acids of SEQ ID NO: 2, also as described above.

In some examples, the *Camelina sativa* homolog of a protein of *Camelina sativa* comprising SEQ ID NO: 2 corresponds to one or more *Camelina sativa* proteins of SEQ ID NOS: 21-40.

In some examples, the ortholog of a protein of *Camelina sativa* comprising SEQ ID NO: 2 corresponds to one or more (i) canola proteins of SEQ ID NOS: 69, 71, 73, and/or 75; (ii) soybean proteins of SEQ ID NOS: 89, 91, 93, and/or 95; or (iii) corn proteins of SEQ ID NOS: 99, 101, 103, 105, and/or 107.

In some examples, the encoded protein comprises (i) (a) a cysteine residue at position 40, (b) a leucine residue at position 59, (c) a cysteine residue at position 98, and (d) a cysteine residue at position 138, with numbering of positions relative to the protein of *Camelina sativa* of SEQ ID NO: 5, and (ii) an overall identity of at least 10% with the protein of *Camelina sativa* of SEQ ID NO: 2.

In some examples, the encoded protein comprises (i) (a) a cysteine residue at position 25, (b) a cysteine residue at position 40, (c) a leucine residue at position 59, (d) a cysteine residue at position 98, and (e) a cysteine residue at position 138, with numbering of positions relative to the protein of *Camelina sativa* of SEQ ID NO: 5, and (ii) an overall identity of at least 10% with the protein of *Camelina sativa* of SEQ ID NO: 5.

In some examples, the encoded protein is heterologous with respect to the genetically engineered land plant. In some examples, the encoded protein is homologous with respect to the genetically engineered land plant.

As noted, the modified gene comprises (i) a promoter and (ii) a nucleic acid sequence encoding the ISY RNA. Also, the promoter is non-cognate with respect to the nucleic acid sequence encoding the ISY RNA. In addition, the modified gene is configured such that transcription of the nucleic acid sequence is initiated from the promoter and results in expression of the ISY RNA.

In some examples, the promoter is a constitutive promoter. In some examples, the promoter is a seed-specific promoter.

In some examples, the modified gene is integrated into genomic DNA of the genetically engineered land plant. In some examples, the modified gene is stably expressed in the genetically engineered land plant.

In some examples, the genetically engineered land plant exhibits increased expression of the ISY RNA in comparison to a reference land plant that does not include the modified gene. In some examples, the genetically engineered land plant exhibits increased seed yield, fruit yield, and/or tuber yield in comparison to a reference land plant that does not include the modified gene.

In some examples, the nucleic acid sequence encoding the ISY RNA is at least 80% identical to SEQ ID NO: 1. The nucleic acid sequence can be, for example, at least 85%, at least 90%, at least 95%, at least 96%, at least 97%, at least 98%, or at least 99% identical to SEQ ID NO: 1. In some examples, the nucleic acid sequence encoding the ISY RNA comprises SEQ ID NO: 1. In some examples, the nucleic acid sequence encoding the ISY RNA comprises SEQ ID NO: 6. In some examples, the nucleic acid sequence encoding the ISY RNA comprises SEQ ID NO: 7.

As noted above, an ISY RNA expressed from an ISY gene may cause an increase in seed yield independent of ISY protein. Thus, in some examples, expression of the ISY RNA results in expression of the encoded protein. In some of these examples, the ISY RNA is a bifRNA that causes an increase in seed yield based on a regulatory function and based on translation of the encoded protein from the ISY RNA. Also, in some examples expression of the ISY RNA does not result in expression of the encoded protein. In some of these examples, the ISY RNA is an lncRNA that causes an increase in seed yield based on a regulatory function, without translation of the encoded protein from the ISY RNA.

EXAMPLES

Example 1. Expression of CCP1 in *Camelina* Using a Constitutive Promoter, Impact on Seed Yield and Seed Size, Identification of Up-Regulated ISY Genes in Lines Having Higher Seed Yield and Optionally Reduced Seed Size Schnell et al., WO 2015/103074, have reported that heterologous expression of CCP1 from *Chlamydomonas reinhardtii* in *Camelina* leads to significant improvements in levels of photosynthesis in the transgenic plants. For these experiments a vector equivalent to pMBXO58 (FIG. 3, SEQ ID NO: 19) was used.

Schnell et al., WO 2015/103074, also disclose that functional data suggest that *Camelina* plants transformed to express CCP1 of *Chlamydomonas reinhardtii* respond to higher $CO_2$ transport capacity by decreasing transpiration and gas exchange (i.e. closing stomata), and that in field studies involving comparison of plants of three transformants versus wild-type plants, two of the three transformants exhibited an increase in overall oil yield (lb/acre) of 43% and 76%, respectively. Schnell et al., WO 2015/103074, also reported a decrease in seed size in higher yielding *Camelina* lines expressing CCP1 constitutively.

The Csa15g017550 gene was identified from transcriptome analysis (RNASeq) of *Camelina* lines engineered to constitutively express the CCP1 gene from the 35S constitutive promoter using greenhouse grown samples (J. Zuber, RNAi Mediated Silencing of Cell Wall Invertase Inhibitors to Increase Sucrose Allocation to Sink Tissues in Transgenic *Camelina sativa* Engineered with a Carbon Concentrating Mechanism, thesis submitted to the Graduate School of The University of Massachusetts, Amherst, Master of Science, May 2015).

Subsequent analysis of the expression of the Csa15g017550 gene by RT-PCR in *Camelina* lines transformed with pMBXO58 (FIG. 3, SEQ ID NO: 19) at Yield10 Bioscience with primers shown in TABLE 4 also showed an increase in Csa15g017550 mRNA (FIG. 7C).

The Csa15g017550 gene has limited sequence homology to genes from the plant invertase inhibitor/pectin methylesterase inhibitor superfamily. Cell wall invertase inhibitor (CWII) genes have previously been shown in *Camelina* to be useful targets for down regulation using RNAi to increase seed yield in *Camelina* (Sederoff et al., U.S. Pub. No. 2016/0138038). Fruit-specific suppression of the cell wall invertase inhibitor (CWII) in tomato or rice led to increases in net seed/grain weight of 22% and 10%, respectively (Wang et al. (2008) *Nat Genet,* 40(11):1370-1374; Jin et al, *Plant Cell*, (2009) 21(7):2072-89).

Example 2. Expression of CCP1 in *Camelina* Using a Seed-Specific Promoter and RT-PCR Analysis of the Impact on Expression of the Csa15g017550 Gene Identified in Example 1

Figure 4:
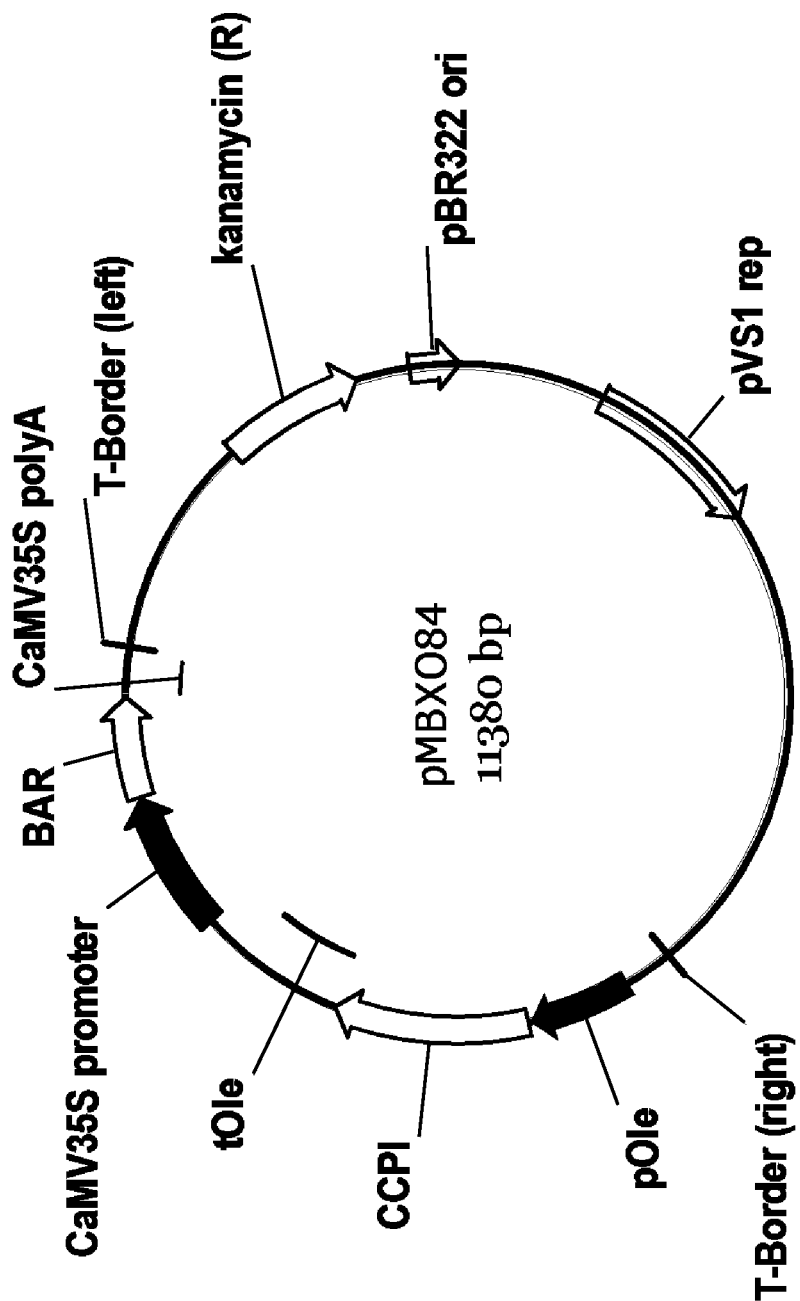
FIG. 4 shows a plasmid map of transformation vector pMBXO84 (SEQ ID NO: 96). Plasmid pMBXO84 contains a seed-specific expression cassette, driven by the promoter from the soya bean oleosin isoform A gene, for expression of CCP1 from *Chlamydomonas reinhardtii*. An expression cassette for the bar gene, driven by the CaMV35S promoter, imparts transgenic plants resistance to the herbicide bialaphos.

In co-pending Patent Application, PCT/US2018/019105 (WO2018/156686) to Yield10 Bioscience, a seed-specific expression construct for CCP1 was described (pMBXO84 (FIG. 4, SEQ ID NO: 96)). Transformation of pMBXO84 into *Camelina* resulted in higher seed yield and a normal seed size. RT-PCR analysis was performed on RNA isolated from these lines to compare the expression of the Csa15g017550 gene in wild-type and transgenic lines and a small amount of overexpression of the Csa15g017550 gene was observed (FIG. 7D) using primers shown in TABLE 4.

Example 3. Novel Gene to Increase Seed Yield (Csa15g017550.1)

On the *Camelina sativa* genome browser (website:// www.camelinadb.ca/), a 612 bp fragment for Csa15g017550.1 is provided that contains a 141 bp 5' UTR, a 405 bp coding sequence (CDS; SEQ ID NO: 1), and a 66 bp 3' UTR, such that the encoded protein is predicted to be 134 amino acids in length (SEQ ID NO: 2). A protein with a longer sequence (SEQ ID NO: 20) was annotated as a "putative invertase inhibitor" in GenBank (LOC104745594) (webiste://www.ncbi.nlm.nih.gov/nucleotide/727584402?report=genbank&log$=nucltop&blast_rank=1&RID=YAF599RN015), however this record was removed from GenBank during standard genome annotation processing.

This protein is predicted to be related to the plant invertase inhibitor/pectin methylesterase inhibitor superfamily. An alignment of the predicted 134 amino acid protein (SEQ ID NO: 2) with other plant invertase inhibitors was performed. This alignment (TABLE 3, FIG. 1) showed that the 134 amino acid protein (SEQ ID NO: 2) was shorter than the other invertase inhibitors, which were 168 to 205 amino acids in length. SEQ ID NO: 2 is missing a stretch of amino acids at the N-terminus, often associated with a signal peptide, and only possesses three of the four conserved cysteine residues that are typically observed in plant invertase inhibitors (Wan et al (2018), Trends Plant Sci, 23:163-177; Tang at al. (2017), J Exp Bot, 68:469-482). In fact the gene was labeled a "partial mRNA" in Genbank under the accession XM_010466881.1 (this accession has recently been removed from Genbank due to standard genome annotation processing). A larger DNA fragment was downloaded from NCBI (LOC104745594; website://www.ncbi.nlm.nih.gov/gene/104745594) that contains additional sequence on the 5' and 3' ends. The record for LOC104745594 was later removed from NCBI because the model on which it was based was not predicted in a later annotation. A 3376 bp portion of this fragment (SEQ ID NO: 3) was searched for an alternative start site to produce a larger protein with a fourth conserved cysteine. A 576 bp DNA fragment (SEQ ID NO: 7) was identified within SEQ ID NO: 3 that encodes for a 190 amino acid open reading frame that contains an internal TTG (base pair 70; FIG. 5). This TTG encodes a Leucine at amino acid 23 (FIG. 5) that if used as an alternative start site would yield a 168 amino acid protein (SEQ ID NO: 5). SEQ ID NO: 5 contains the fourth conserved cysteine (FIG. 1A, FIG. 5).

Figure 6:
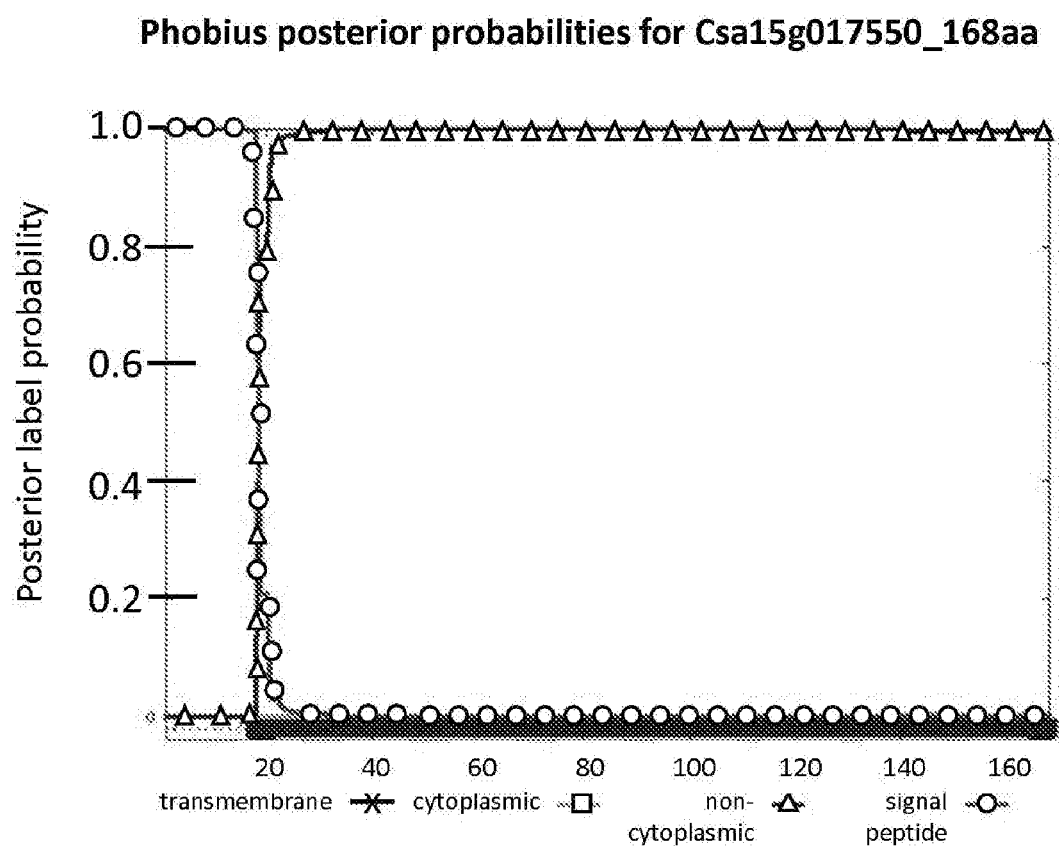
FIG. 6 shows a Phobius-generated plot of a predicted N-terminal signal peptide for the 168 amino acid ISY protein (SEQ ID NO: 5). The Phobius plot shows the probability of predicted transmembrane domain (X), cytoplasmic domain (square), non-cytoplasmic domain (triangle), and signal peptide sequence (circle). Only a signal peptide and a non-cytoplasmic domain were predicted. The Y-axis corresponds to posterior label probability, plotted from 0 to 1 in increments of 0.2. The X-axis corresponds to amino acid residue number of the 168 amino acid ISY protein of SEQ ID NO: 5, plotted from 0 to 168 in increments of 20.

The Phobius transmembrane topology and signal peptide prediction program (website://phobius.sbc.su.se/) was used to probe the 134 amino acid protein (SEQ ID NO: 2) and the 168 amino acid protein (SEQ ID NO: 5) sequences for a signal peptide. A putative 17 amino acid signal peptide was identified on the 168 amino acid protein (SEQ ID NO: 5; FIG. 6) and the protein was predicted to be non-cytoplasmic. No signal peptide was identified on the 134 amino acid sequence (SEQ ID NO: 2).

The 134 amino acid protein (SEQ ID NO: 2) and the 168 amino acid protein (SEQ ID NO: 5) sequences were also analyzed using the TargetP 1.1 Server (website://www.cbs.dtu.dk/cgi-bin/webface2.fcgi?jobid=5B84A216000034F4085302D6&wait=20) which predicts chloroplast, mitochondrial, and signal peptides. This program also predicted the presence of a signal peptide involved in a secretory pathway for the 168 amino acid protein and a transit peptide length of 17 amino acids. For the 134 amino acid protein no signal peptide was predicted.

The 134 amino acid protein (SEQ ID NO: 2) and the 168 amino acid protein (SEQ ID NO: 5) were also analyzed using the Plant-mPloc software (website://www.csbio.sjtu.edu.cn/bioinf/plant-multi/) useful for predicting the subcellular localization of proteins. This program predicted the location of both the 134 and 168 amino acid proteins in the cell membrane.

Based on these analyses the function of this gene is unknown and so we have defined it herein as the increased seed yield gene (ISY).

TABLE 3

Plant invertase inhibitor sequences used for comparison to the novel Camelina plant ISY protein

| Crop | SEQ ID of Protein | Gene ID | Function of protein | Size of encoded protein (amino acids) | Experimentally verified |
|---|---|---|---|---|---|
| Camelina sativa | SEQ ID NO: 2 | Csa15g017550.1 | Putative plant invertase inhibitor/pectin methylesterase inhibitor | 134 | no |
| Camelina sativa | SEQ ID NO: 4 | Csa15g017550.1 with additional upstream region (SEQ ID NO: 7) | Putative plant invertase inhibitor/pectin methylesterase inhibitor | 190 | no |
| Camelina sativa | SEQ ID NO: 5 | Csa15g017550.1 with alternative start codon (SEQ ID NO: 6) | Putative plant invertase inhibitor/pectin methylesterase inhibitor | 168 | no |
| Zea mays | SEQ ID NO: 8 | XP_008668976.1 | Cell wall/vacuolar inhibitor of fructosidase 2 | 176 | yes[2] |
| Arabidopsis thaliana | SEQ ID NO: 9 | AT5G64620 | Cell wall/vacuolar inhibitor of fructosidase | 180 | yes[2] |
| Arabidopsis thaliana | SEQ ID NO: 10 | AEE32232.1 | Cell wall/vacuolar inhibitor of fructosidase 1 | 205 | |

TABLE 3-continued

Plant invertase inhibitor sequences used for comparison to the novel Camelina plant ISY protein

| Crop | SEQ ID of Protein | Gene ID | Function of protein | Size of encoded protein (amino acids) | Experimentally verified |
|---|---|---|---|---|---|
| Solanum lycopersicum[1] | SEQ ID NO: 11 | Solyc12g099190 | Invertase inhibitor | 175 | yes[2] |
| Solanum lycopersicum[1] | SEQ ID NO: 12 | Solyc12g099200 | Invertase inhibitor | 171 | yes[2] |
| Beta vulgaris subsp. vulgaris | SEQ ID NO: 13 | XP_010685378.1 | Predicted cell wall/vacuolar inhibitor of fructosidase 1 | 184 | yes[3] |
| Nicotiana tabacum | SEQ ID NO: 14 | AY145781.1 | Vacuolar invertase inhibitor | 172 | yes[3] |
| Nicotiana tabacum | SEQ ID NO: 15 | Y12805.1 | Invertase inhibitor | 166 | yes[2] |
| Solanum tuberosum cultivar Shepody | SEQ ID NO: 16 | GU321341.1 | Putative invertase inhibitor (INVINH2A) | 181 | yes[2] |

[1]Protein sequence obtained from website://solgenomics.net/search/locus.
[2]Protein listed as experimentally characterized in review by Wan et al. (2018), Trends Plant Sci, 23: 163-177.
[3]Protein listed as experimentally characterized in review by Tang et al. (2017), J ExpBot, 68: 469-482.

Most invertase inhibitors also contain a conserved three amino acid conserved motif of Proline-Lysine-Phenylalanine (PKF; Tang et al. (2017), J Exp Bot, 68:469-482). Neither the 134 amino acid protein (SEQ ID NO: 2) nor the 168 amino acid protein (SEQ ID NO: 5) contain the conserved PKF motif. The presence of the PKF motif can be found at position 132 through 134 of the *Beta vulgaris* predicted cell wall/vacuolar inhibitor of fructosidase 1 (Gene ID XP_010685378.1, SEQ ID NO: 13, FIG. 1).

Figure 7:
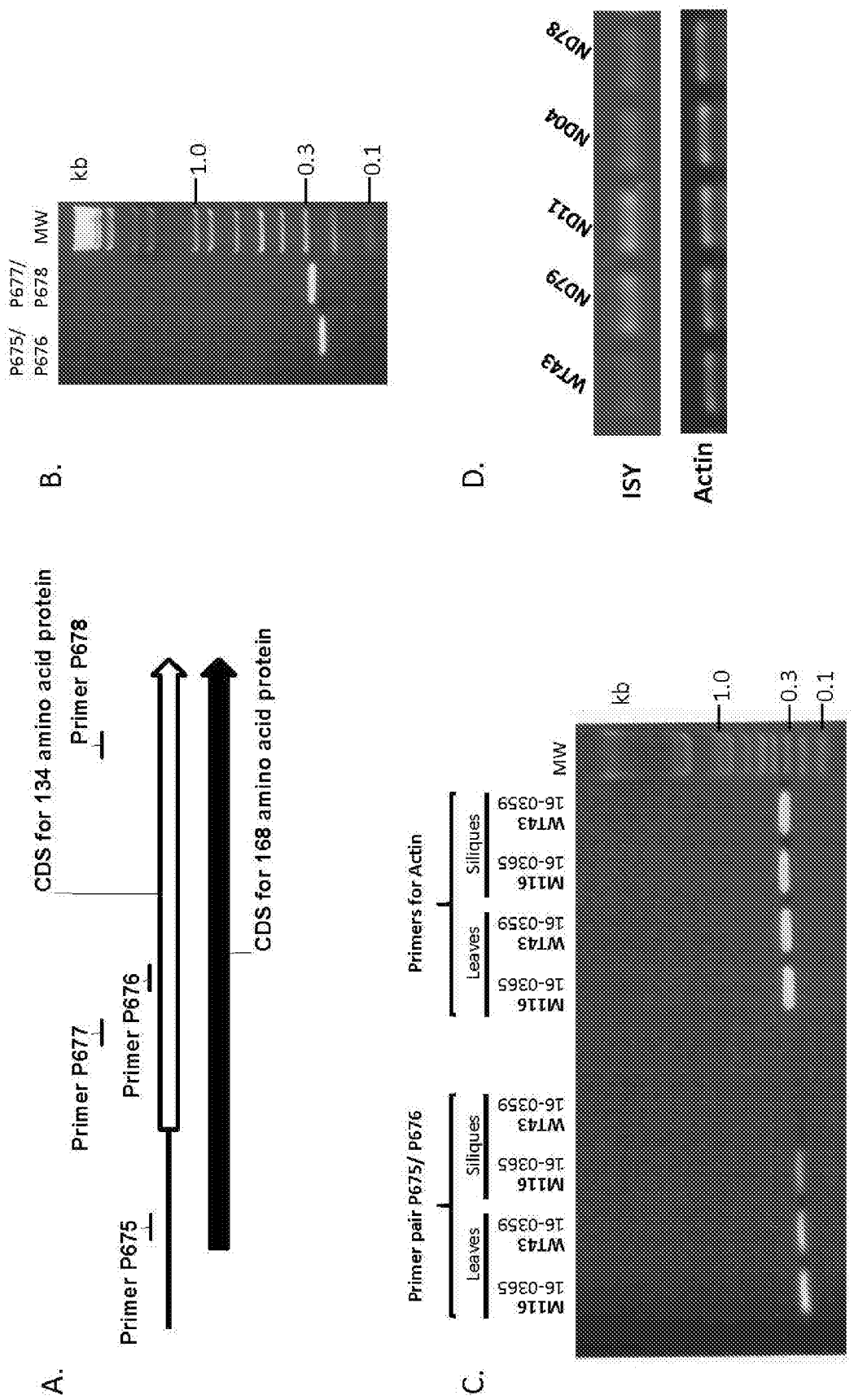
FIG. 7 shows experiments to verify the presence of the Csa150g17550 gene and RNA transcript in *Camelina sativa* germplasm 10CS0043 (abbreviated WT43). A) Map of 576 bp of DNA (SEQ ID NO: 7) in the region of the Csa15g017550 gene. The coding sequences for the 134 amino acid and 168 amino acid ISY proteins are shown. Primer binding sites for primers P675, P676, P677, and P678 for PCR and RT PCR experiments are shown. B) PCR experiments on genomic DNA from wild-type *Camelina* line WT43 showing the presence of the Csa15g017550 gene (SEQ ID NO: 1), as well as sequence upstream of the Csa15g017550 gene, in the genome. A PCR reaction with primer pair P675/P676 produced a band consistent with the expected 0.236 kb fragment. A PCR reaction with primer pair P677/P678 produced a band consistent with the expected 0.269 kb fragment. C) RT-PCR experiments with RNA from transgenic line M116 16-0365, expressing the CCP1 gene from the 35S constitutive promoter in vector pMBXO58 (SEQ ID NO: 19, FIG. 3), and wild-type control line WT43 line 16-0359. Increased expression of the putative plant invertase inhibitor is observed in leaves and siliques of CCP1 lines. Control experiments to probe the presence of transcripts of the actin gene were also performed. D) RT-PCR experiments with RNA from developing seeds transformed with vector pMBXO84 (SEQ ID 96.

Since Genbank removed the record for XM_010466881 (Csa15g017550.1), an effort was made to verify the presence of the gene in the genome. Genomic DNA was extracted from plants of *Camelina sativa* germplasm 10CS0043 (abbreviated WT43; germplasm obtained from Kevin Falk at Agriculture and Agri-Food Canada). PCR experiments were conducted using primer pair P675 and P676, as well as primer pair P677 and P678 (TABLE 4). The binding sites of these primers within SEQ ID NO: 7 (contains 576 bp DNA fragment that encodes for a 190 amino acid open reading frame that contains an internal TTG) is shown in FIG. 5 and FIG. 7. These PCR reactions demonstrated that the two overlapping regions of the gene were present in genomic DNA of WT43. A PCR reaction with primer pair P675/P676 produced a band consistent with the expected 0.236 kb fragment (FIG. 7B). A PCR reaction with primer pair P677/P678 produced a band consistent with the expected 0.269 kb fragment.

RNA transcript levels of the ISY gene were also tested in RNA isolated from the WT43 line (line 16-0359) and a transgenic line expressing CCP1 (MI16 line 16-0365). RNA was isolated from leaves of both lines just prior to bolting and from siliques collected 12 days after flowering. RT-PCR experiments with RNA from both the transgenic and control lines with primer pair P675/P676 (FIG. 5 and FIG. 7) showed that the transgenic line expressing the CCP1 gene contained more transcript for the ISY compared to the wild-type line in both leaves and siliques (FIG. 7).

TABLE 4

Primers used to verify the presence of Csa15g017550.1 in genomic DNA and RNA transcripts.

| Primer | Sequence | Expected PCR or RT-PCR product |
|---|---|---|
| P675 | 5'-CCTTGGTTGTG TTCTCTCTTCT-3' (SEQ ID NO: 131) | 0.236 kb fragment of putative invertase inhibitor |
| P676 | 5'-GATCTGTTCAG CGAGTCCTTT-3' (SEQ ID NO: 132) | |
| P677 | 5'-TAGTCCTAGCA TCGACGAAGA-3' (SEQ ID NO: 133) | 0.269 kb fragment of putative invertase inhibitor |
| P678 | 5'-AGCGAAGGGAG AAATCCAATAA-3' (SEQ ID NO: 134) | |
| P602 | 5'-CGGCCGATTCT GTTTATCTC-3' (SEQ ID NO: 135) | 0.77 kb fragment of actin with genomic DNA and 0.32 kb fragment actin with RNA/cDNA as template |
| P603 | 5'-TCCTTCTGGTT CATCCCAAC-3' (SEQ ID NO: 136) | |

Since *Camelina* is an allohexaploid, there are typically three homeologs of each gene. BLAST searches were performed with the 168 amino acid protein encoded by the Csa15g017550.1 against the *Camelina* genome database (website://www.camelinadb.ca/prairiegold/cgi-bin/blast.cgi) in efforts to identify the two other homeologs to Csa15g017550.1. The results of the protein BLAST search showing gene IDs and E values are shown in TABLE 5 (homeologs 1-38, 41, 57-66). Apparent candidates for two other ISY gene Csa15g017550 homeologs could not be found. An additional BLAST search was performed using the 507 base pair coding sequence (SEQ ID NO: 6) for the 168 amino acid protein (SEQ ID NO: 5) of Csa15g017550. Homeologs 39, 40, and 42-56 were identified and are indicated with a "*k" next to the homeolog number. No apparent candidates for the two other ISY gene Csa15g017550 homeologs could be found. The percent homology of the 168 amino acid protein (SEQ TD NO: 5) to the first twenty best match homeologs, as indicated by E value, were calculated using phe ArGNX alignment function of the Vector NTI software package (ThermoFisher) and are shown in TABLE 5. Their protein sequences are provided as SEQ TD NOS: 21-40. Percent homologies were also calculated for Csa11g10174S (SEQ TD NO: 85) and Csa18g038260 (SEQ ID NO: 87) in TABLE 5, two homeologs of the cell wall invertase inhibitor 2 (CWII2) protein described in Sederoff et al., U.S. Pub. No. 2016/0138038. These proteins are also described in TABLE 6.

TABLE 5

*Camelina* homeologs to novel *Camelina* ISY gene Csa15g017550.1

| Homeolog No. [1] | Gene ID | E Value | Encoded Protein | % homology to protein in SEQ ID NO: 5[2] |
|---|---|---|---|---|
|  | Csa15g017550 |  | SEQ ID NO: 5 (168 amino acid protein) | 100 |
|  | Csa15g017550 | 6.00E−74 | SEQ ID NO: 2 (134 amino acid protein) | 79.8 |
| 1 | Csa18g003060 | .00E−53 | SEQ ID NO: 21 (176 amino acid protein) | 64.8 |
| 2 | Csa11g064960 | 1.00E−51 | SEQ ID NO: 22 (174 amino acid protein) | 63.1 |
| 3 | Csa11g064980 | 3.00E−51 | SEQ ID NO: 23 (168 amino acid protein)23 | 63.0 |
| 4 | Csa20g081200 | 1.00E−50 | SEQ ID NO: 24 (175 amino acid protein) | 63.1 |
| 5 | Csa18g003050 | 1.00E−49 | SEQ ID NO: 25 (175 amino acid protein) | 62.5 |
| 6 | Csa20g077790 | 2.00E−49 | SEQ ID NO: 26 (176 amino acid protein) | 60.5 |
| 7 | Csa11g064950 | 2.00E−46 | SEQ ID NO: 27 (176 amino acid protein) | 59.1 |
| 8 | Csa02g070240 | 7.00E−46 | SEQ ID NO: 28 (175 amino acid protein) | 57.4 |
| 9 | Csa20g081210 | 7.00E−46 | SEQ ID NO: 29 (176 amino acid protein) | 59.1 |
| 10 | Csa18g003030 | 8.00E−45 | SEQ ID NO: 30 (175 amino acid protein) | 56.8 |
| 11 | Csa18g005290 | 9.00E−44 | SEQ ID NO: 31 (176 amino acid protein) | 56.5 |
| 12 | Csa07g013600 | 3.00E−43 | SEQ ID NO: 32 (176 amino acid protein) | 55.4 |
| 13 | Csa17g022200 | 4.00E−43 | SEQ ID NO: 33 (176 amino acid protein) | 55.9 |
| 14 | Csa15g021010 | 1.00E−42 | SEQ ID NO: 34 (176 amino acid protein) | 55.9 |
| 15 | Csa15g020370 | 2.00E−39 | SEQ ID NO: 35 (147 amino acid protein) | 50.0 |
| 16 | Csa20g077190 | 6.00E−39 | SEQ ID NO: 36 (175 amino acid protein) | 52.8 |
| 17 | Csa18g003080 | 2.00E−34 | SEQ ID NO: 37 (183 amino acid sequence) | 44.3 |
| 18 | Csa20g081180 | 3.00E−34 | SEQ ID NO: 38 (175 amino acid sequence) | 42.9 |
| 19 | Csa20g081190 | 4.00E−34 | SEQ ID NO: 39 (179 amino acid sequence) | 45.8 |
| 20 | Csa18g003070 | 2.00E−32 | SEQ ID NO: 40 (178 amino acid sequence) | 44.9 |
| 21 | Csa11g064990 | 3.00E−32 |  |  |
| 22 | Csa11g065000 | 3.00E−29 |  |  |
| 23 | Csa20g081220 | 6.00E−29 |  |  |
| 24 | Csa18g003020 | 8.00E−16 |  |  |
| 25 | Csa20g081240 | 3.00E−13 |  |  |
| 26 | Csa18g003010 | 4.00E−13 |  |  |
| 27 | Csa20g081230 | 1.00E−10 |  |  |
| 28 | Csa11g066240 | 3.00E−10 |  |  |
| 29 | Csa11g064940 | 2.00E−09 |  |  |
| 30 | Csa10g044780 | 7.00E−06 |  |  |
| 31 | Csa11g053620 | 2.00E−05 |  |  |
| 32 | Csa12g083870 | 2.00E−05 |  |  |
| 33 | Csa13g054980 | 0.013 |  |  |
| 34 | Csa08g052220 | 0.013 |  |  |
| 35 | Csa02g005450 | 0.013 |  |  |

TABLE 5-continued

Camelina homeologs to novel Camelina ISY gene Csa15g017550.1

| Homeolog No.[1] | Gene ID | E Value | Encoded Protein | % homology to protein in SEQ ID NO: 5[2] |
|---|---|---|---|---|
| 36 | Csa11g101740 | 0.017 | SEQ ID NO: 85 (181 amino acid sequence) | 19.2 |
| 37 | Csa02g074170 | 0.017 | | |
| 38 | Csa11g064930 | 0.037 | | |
| 39* | Csa15g002570 | 0.72 | | |
| 40* | Csa19g004990 | 0.72 | | |
| 41 | Csa18g038260 | 0.083 | SEQ ID NO: 87 (181 amino acid sequence) | 18.7 |
| 42* | Csa01g001500 | 2.8 | | |
| 43* | Csa01g025990 | 2.8 | | |
| 44* | Csa03g032110 | 2.8 | | |
| 45* | Csa03g059400 | 2.8 | | |
| 46* | Csa03g062690 | 2.8 | | |
| 47* | Csa07g030720 | 2.8 | | |
| 48* | Csa08g002670 | 2.8 | | |
| 49* | Csa08g058620 | 2.8 | | |
| 50* | Csa13g007860 | 2.8 | | |
| 51* | Csa14g036540 | 2.8 | | |
| 52* | Csa15g001530 | 2.8 | | |
| 53* | Csa17g040740 | 2.8 | | |
| 54* | Csa19g002590 | 2.8 | | |
| 55* | Csa19g031990 | 2.8 | | |
| 56* | Csa20g008110 | 2.8 | | |
| 57 | Csa08g034720 | 0.24 | | |
| 58 | Csa01g019830 | 0.31 | | |
| 59 | Csa05g029780 | 0.41 | | |
| 60 | Csa19g024110 | 0.41 | | |
| 61 | Csa12g032200 | 0.7 | | |
| 62 | Csa15g023200 | 0.7 | | |
| 63 | Csa16g012150 | 3.5 | | |
| 64 | Csa07g011430 | 5.9 | | |
| 65 | Csa02g040660 | 5.9 | | |
| 66 | Csa04g024120 | 5.9 | | |

Csa gene IDs are from the *Camelina* genome database found at (website://www.camelinadb.ca/prairiegold/cgi-bin/blast.cgi).
[1] Entries with a "*" were found with BLAST searches using the 507-bp coding sequence. All other entries were found using BLAST searches with the 168 amino acid protein found in SEQ ID NO: 5,
[2] Percent homology over the whole protein of SEQ ID NO: 5 was determined using the ALIGNX alignment function of the Vector NTI software package (ThermoFisher).

Figure 8:
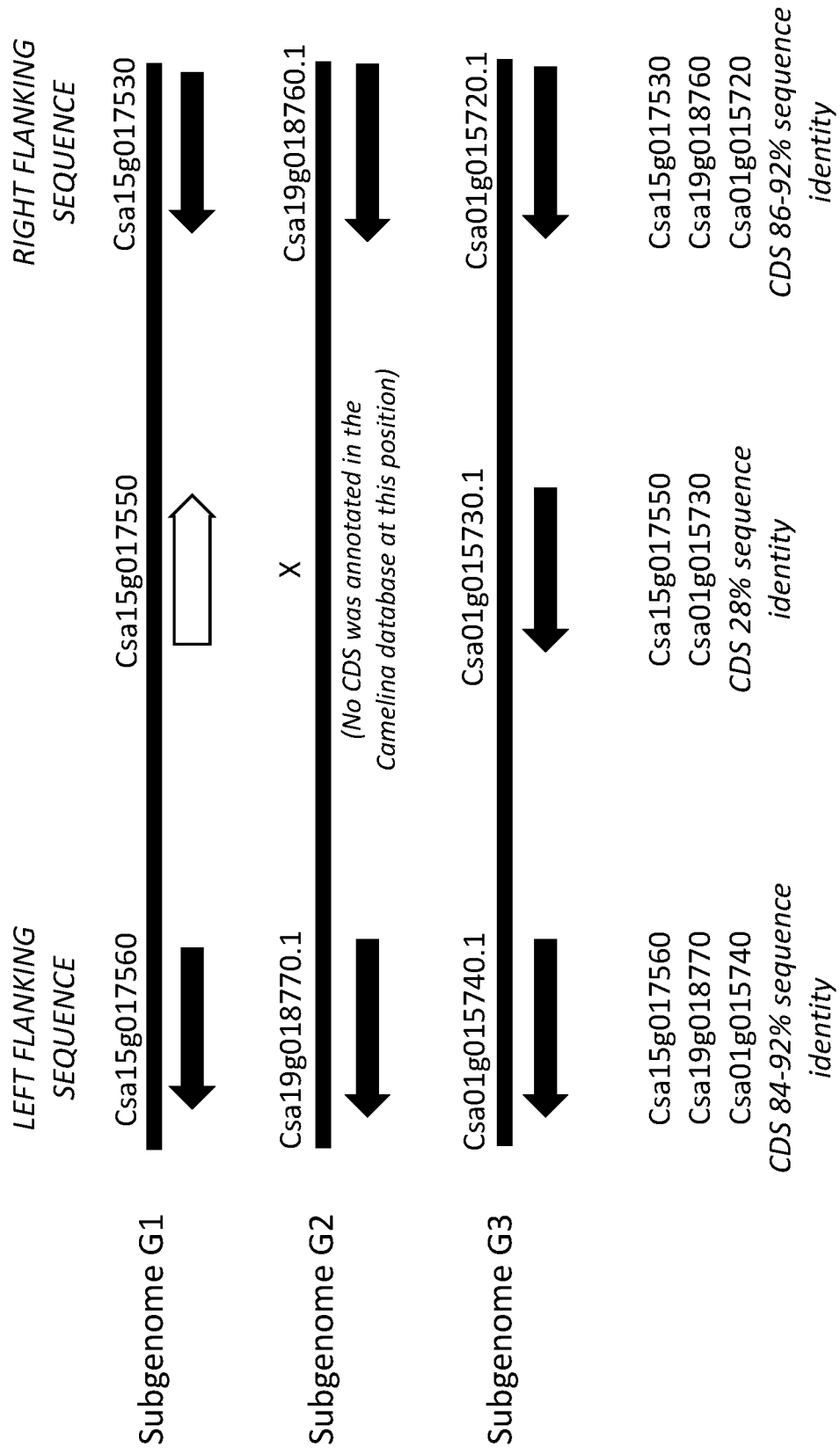
FIG. 8 shows the syntenic analysis of Csa15g017550. The putative plant invertase inhibitor/pectin methylesterase inhibitor (Csa15g017550, white arrow) was found to be on subgenome G1 and is flanked by coding sequences for Csa15g017560 on the left and by Csa15g017530 on the right. The two homeologs of the left flanking gene Csa15g017560 on subgenomes G2 (Csa19g018770) and G3 (Csa01g015740) are shown. The sequence homeolog of the right flanking gene Csa15g017530 on subgenome 2 (Csa19g018760) and on subgenome 3 (Csa01g015720) are shown. No homeologs were identified for the putative plant invertase inhibitor/pectin methylesterase inhibitor Csa15g017550. On subgenome 2, there was no CDS annotated at the expected genomic position in the Camelina genome database. On subgenome G3, the gene Csa01g015730.1 is present with only 28% sequence identity to Csa15g017550. Figure is not drawn to scale.

In other efforts to identify two homeologs to the ISY gene Csa15g017550, a syntenic analysis was performed (FIG. 8). Csa15g017550 was found to be on subgenome G1 and is flanked by coding sequences for Csa15g017560 on the left and by Csa15g017530 on the right. The two homeologs of the left flanking gene Csa15g017560 on subgenomes G2 (Csa19g018770) and G3 (Csa01g015740) have been previously identified by Kagale et al. (2014), Nat Commun, 5:3706). The coding sequence identity of Csa15g017560, Csa19g018770, and Csa01g015740 is between 84-92%. The sequence homolog of the right flanking gene Csa15g017530 on subgenome 2 (Csa19g018760) was also identified by Kagale et al. (2014). Our work has identified Csa01g015720 as the likely other homeolog to Csa15g017530 on subgenome 3 based on its position in the genome and high codon sequence identity (86-92%) to the other two genes. However, no homeologs were identified for Csa15g017550. On subgenome 2, there was no CDS annotated at the expected genomic position in the *Camelina* genome database. Repeated sequences in the genome were observed in this region suggesting possible gene rearrangement or deletion may have occurred. On subgenome G3, the CDS Csa01g015730.1 is present with only 28% sequence identity to Csa15g017550. This was not annotated as a homeolog of Csa15g017550 by Kagale et al. (2014). It thus appears that ISY gene Csa15g017550 is present as a single copy within the allohexaploid *Camelina*.

Csa15g017550 is distinct from the prior two CWII genes in *Camelina* that have been studied (Sederoff et al., U.S. Pub. No. 2016/0138038, at North Carolina State University). Sederoff et al. used RNAi gene silencing to reduce expression of these genes in *Camelina* and demonstrated an increase in seed yield. Three copies of each of these genes is present (*Camelina* is an allohexaploid). These homeologs include homeologs of cell wall invertase inhibitor 1 (CWII1) (SEQ ID NO: 76 (Csa03g051630), SEQ ID NO: 78 (Csa14g051860), and SEQ ID NO: 80 (Csa17g075360)) and homeologs of cell wall invertase inhibitor 2 (CWII2) (SEQ ID NO: 82 (Csa02g074171), SEQ ID NO: 84 (Csa1g101740), and SEQ ID NO: 86 (Csa18g038260)) found in the *Camelina* genome. A CLUSTAL alignment of the proteins encoded by these genes to the 134 and 168 amino acid ISY protein is shown in FIG. 2 and the percent of each homeolog to the ISY protein is shown in TABLE 6. The percent homology to the 168 amino acid ISY protein (SEQ ID NO: 5) ranges from 12.3 to 19.2% over the entire length of the sequence. Because of the low homology, only SEQ ID NO: 84 (Csa11g101740) and SEQ ID NO: 86 (Csa18g038260) showed up in our BLAST searches of Csa15g017550 shown in TABLE 5.

TABLE 6

Homology of novel *Camelina* ISY gene Csa15g017550.1 to previously described *Camelina* cell wall invertase inhibitor proteins

| Gene ID[1] | SEQ ID NO of Protein | Size of encoded protein (amino acids) | % homology to protein in SEQ ID NO: 2[2] | % homology to protein in SEQ ID NO: 5[3] |
|---|---|---|---|---|
| Csa15g017550 | SEQ ID NO: 5 | 168 | 79.8 | 100 |
| Csa15g017550 | SEQ ID NO: 2 | 134 | 100 | 79.8 |
| CWII1 homeolog SEQ ID NO: 76 (Csa03g051630) | SEQ ID NO: 77 | 159 | 11.0 | 12.3 |
| CWII1 homeolog SEQ ID NO: 78 (Csa14g051860) | SEQ ID NO: 79 | 155 | 11.3 | 12.5 |
| CWII1 homeolog SEQ ID NO: 80 (Csa17g075360) | SEQ ID NO: 81 | 159 | 11.0 | 12.9 |
| CWII2 homeolog SEQ ID NO: 82 (Csa02g074171) | SEQ ID NO: 83 | 180 | 14.4 | 18.2 |
| CWII2 homeolog SEQ ID NO: 84 (Csa11g101740) | SEQ ID NO: 85 | 181 | 14.8 | 19.2 |
| CWII2 homeolog SEQ ID NO: 86 (Csa18g038260) | SEQ ID NO: 87 | 181 | 14.3 | 18.7 |

[1]Csa gene IDs are from the *Camelina sativa* genome browser (website://www.camelinadb.ca/prairiegold/cgi-bin/gbrowse/camelina/); CWII1 and CWII2 homeologs are the three copies of the CWII genes that were studied in U.S. Pub No. 2016/0138038.
[2]Percent homology over the whole protein of SEQ ID NO: 2 was determined using the alignment function of the Vector NTI software package (ThermoFisher).
[3]Percent homology over the whole protein of SEQ ID NO: 5 was determined using the ALIGNX alignment function of the Vector NTI software package (ThermoFisher).

Example 4. Overexpressing the Csa15g017550.1 Gene Identified in Example 1 in *Camelina* Alone or in Combination with Expression of CCP1

We have previously observed in *Camelina*, canola, and soybean lines engineered to constitutively express CCP1 that, in addition to increased seed yield, there was a reduction in individual seed weight. This together with the work disclosed by Sederoff et al., U.S. Pub. No. 2016/0138038, on reducing expression of CWII genes to increase seed yield led to the hypothesis that expression of CCP1 results in increased availability of carbon from photosynthesis, increased seed numbers, and increased expression of the Csa15g017550 gene, which may be a CWII or other plant invertase inhibitor that is responsible for reducing the flow of carbon to seed. To test this hypothesis, we overexpressed the Csa15g017550 gene in two different *Camelina* backgrounds. Based on the fact that the Csa15g017550 gene has two possible translation initiation sites (FIG. 5), we made expression constructs for both for transformation of *Camelina* (TABLE 7). The Csa15g017550 gene expression cassette in construct pMBXS 1168 (FIG. 9, SEQ ID NO: 17) starts at an ATG codon and encodes a 134 amino acid protein (SEQ ID NO: 2) whereas the Csa15g017550 gene expression cassette in construct pMBXS 1169 (FIG. 10, SEQ ID NO: 18) starts upstream at a TTG codon and encodes a 168 amino acid protein (SEQ ID NO: 5). Both constructs were transformed into the *Camelina* Suneson wild-type background and into Suneson lines which had previously been engineered with vector pMBXO58 (FIG. 3, SEQ ID NO: 19) to express CCP1.

TABLE 7

Summary of constructs for transformation into *Camelina*

Figure 9:
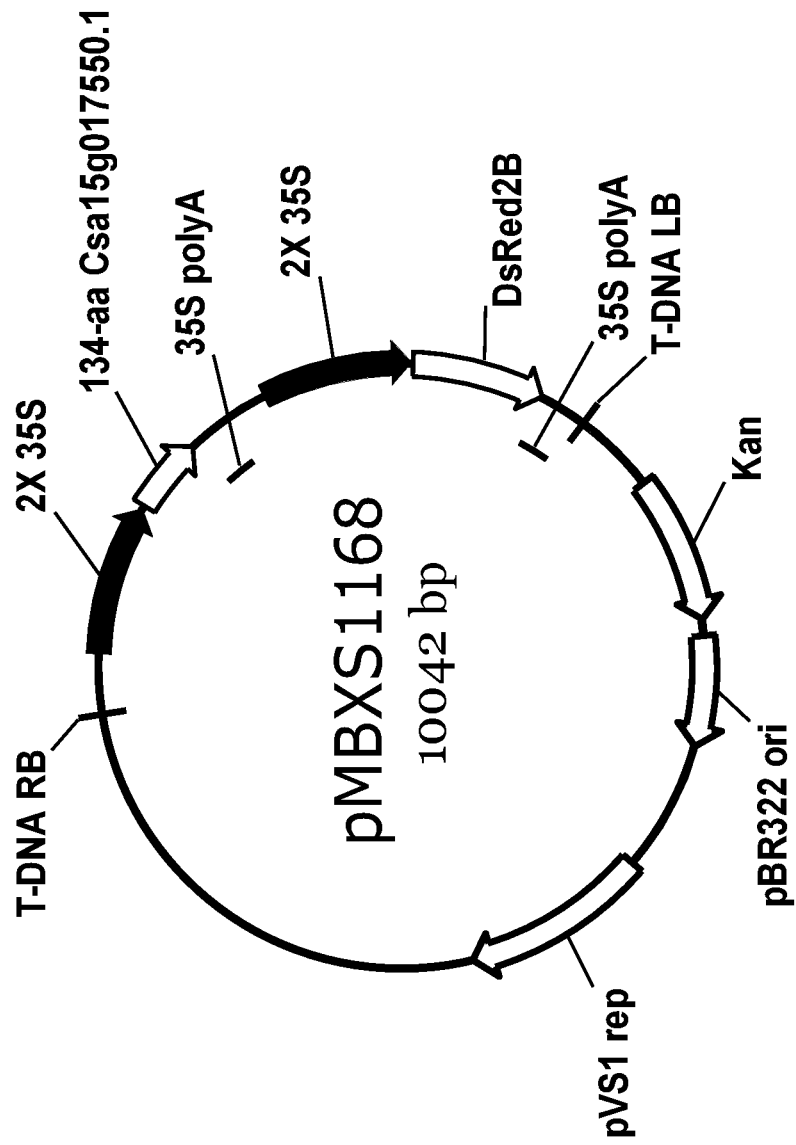
FIG. 9 shows a map for pMBXS 1168 (SEQ ID NO: 17), a transformation vector designed for Agrobacterium-mediated transformation of dicots, including Camelina. The vector contains the double enhanced CaMV35S constitutive promoter (2× 35S) operably linked to a gene (SEQ ID NO: 1) encoding the 134 amino acid protein for Csa15g017550 (SEQ ID NO: 2) operably linked to a 35S polyadenylation sequence. The visual marker DsRed2B is used to identify transgenic seeds.
Figure 10:
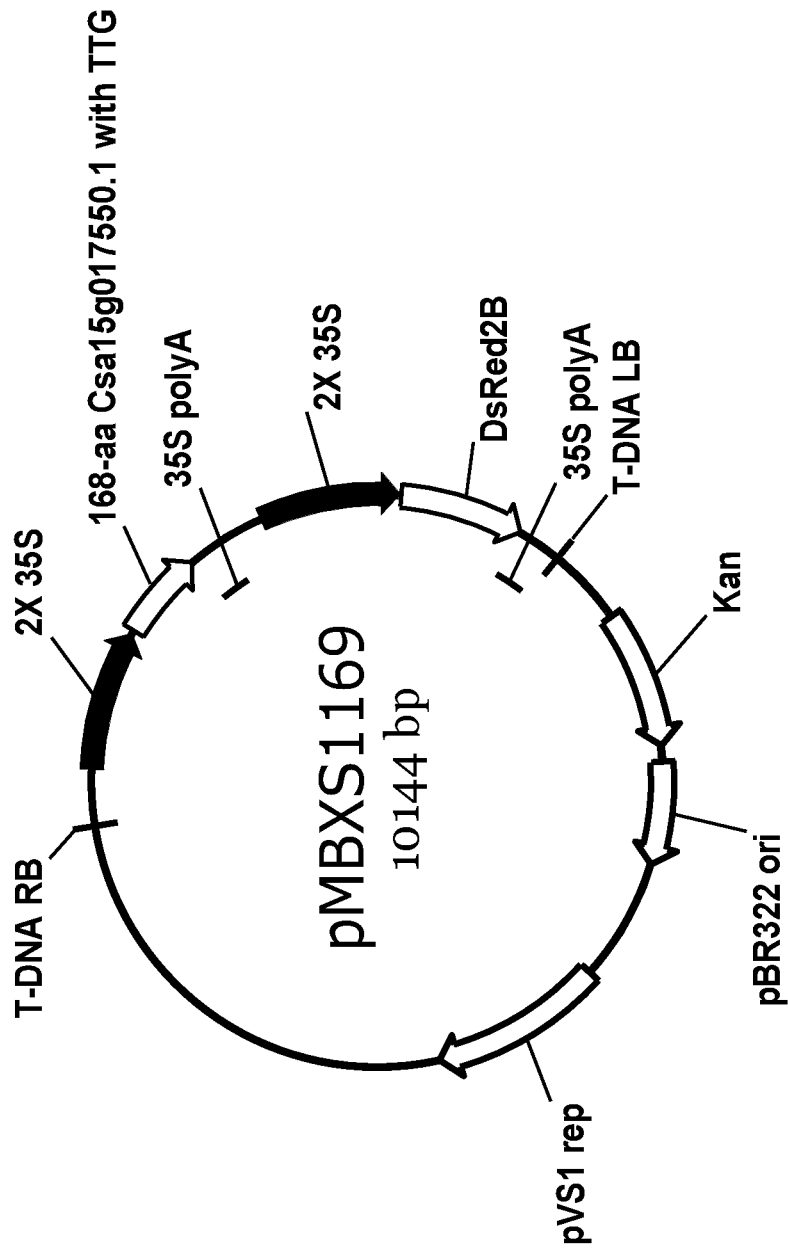
FIG. 10 shows a map for pMBXS 1169 (SEQ ID NO: 18), a transformation vector designed for Agrobacterium-mediated transformation of dicots, including Camelina. The vector contains the double enhanced CaMV35S constitutive promoter (2× 35S) operably linked to a gene (SEQ ID NO: 6) encoding the 168 amino acid ISY protein (SEQ ID NO: 5) operably linked to a 35S polyadenylation sequence. The visual marker DsRed2B is used to identify transgenic seeds.

| Construct | Size of Csa15g017550.1 encoded protein | Promoter |
|---|---|---|
| pMBXS1168 (SEQ ID NO: 17; FIG. 9) | 134 amino acids (SEQ ID NO: 2) | CaMV 35S (constitutive) |
| pMBXS1169 (SEQ ID NO: 18; FIG. 10) | 168 amino acids (SEQ ID NO: 5) | CaMV 35S (constitutive) |

These constructs were transformed into *Camelina* as follows.

In preparation for plant transformation experiments, seeds of *Camelina sativa* germplasm 10CS0043 (abbreviated WT43, obtained from Agriculture and Agri-Food Canada) were sown directly into 4 inch (10 cm) pots filled with soil in the greenhouse. Growth conditions were maintained at 24° C. during the day and 18° C. during the night. Plants were grown until flowering. Plants with a number of unopened flower buds were used in "floral dip" transformations.

*Agrobacterium* strain GV3101 (pMP90) was transformed with either plasmid pMBXS1168 or pMBXS1169 using electroporation. A single colony of GV3101 (pMP90) containing the construct of interest was obtained from a freshly streaked plate and was inoculated into 5 mL LB medium. After overnight growth at 28° C., 2 mL of culture was transferred to a 500-mL flask containing 300 mL of LB and incubated overnight at 28° C. Cells were pelleted by centrifugation (4,000 rpm, 20 min), and diluted to an OD600 of ~0.8-1.0 with infiltration medium containing 5% sucrose and 0.05% (v/v) Silwet-L77 (Lehle Seeds, Round Rock, Tex., USA). Plants of *Camelina sativa* germplasm 10CS0043 (abbreviated WT43; germplasm obtained from Kevin Falk at Agriculture and Agri-Food Canada) were transformed by "floral dip" using pMBXS 1168 or pMBXS 1169 transformation constructs as follows. Pots containing plants at the flowering stage were placed inside a 460 mm height vacuum desiccator (Bel-Art, Pequannock, N.J., USA). Inflorescences were immersed into the *Agrobacterium* inoculum contained in a 500-ml beaker. A vacuum (85 kPa) was applied and held for 5 min. Plants were removed from the desiccator and were covered with plastic bags in the dark for 24 h at room temperature. Plants were removed from the bags and returned to normal growth conditions within the greenhouse for seed formation (T1 generation of seed).

T1 seeds were screened by monitoring the expression of DsRed, a marker on the T-DNA in plasmid vectors pMBXS 1168 or pMBXS 1169 (FIGS. 9 and 10) allowing the identification of transgenic seeds. DsRed expression in the seed was visualized by fluorescent microscopy using a Nikon AZ100 microscope with a TRITC-HQ(RHOD)2 filter module (HQ545/30X, Q570LP, HQ610/75M) as previously described (Malik et al., 2015, Plant Biotechnology Journal, 13, 675). Between 20 and 32 T1 plants were produced from each transformation and progressed through to the T2 generation. T1 seeds were planted in soil and transgenic plants were obtained. Transgenic plant lines were further confirmed using PCR with primers specific to the gene of interest.

Overexpression of the Csa15g017550 gene in 3 independent transgenic lines each of pMBXO58/pMBXS1168 and pMBXO58/pMBXS1169, and two independent transgenic T2 lines each of pMBXS1168 and pMBXS1169 in the wild type Suneson background was determined by semi-quantitative RT-PCR. Overexpression of Csa15g017550 was observed (more transcript of the gene in transgenic lines) in 8 out of 10 lines. Expression of the CCP1 gene was also confirmed in the lines containing pMBXO58 (FIG. 3; SEQ ID NO: 19) along with the overexpression of the Csa15g017550 transcript. Lines were progressed to the T3 generation to generate homozygous Csa15g017550 lines. TABLE 8 shows the constructs and number of lines for each construct used in the subsequent yield testing experiments performed in a plant growth chamber.

limited sterility on tertiary branches may be due to a limitation of resources available to the plant in a 6 inch (15 cm) pot. Overall the phenotype on the side branches of the Csa15g017550 plants looked healthier and more productive for seed yield. On completion of the growth experiment the following parameters were measured: plant heights were noted, the number of tertiary branches were determined, seed weight and 1000 seed weight was determined, and seed samples were prepared for oil content and oil composition analysis.

TABLE 8

Homozygous T3 line grow-out in a plant growth chamber.

| Background Germplasm | Vector construct transformed[1] | Promoter/ gene overexpressed[2] | Generation | # of lines selected for advancement |
|---|---|---|---|---|
| Suneson/pMBXO58 (called NJ02) | pMBXS1168 | 35S/CCP1 35S/Csa15g017550 134 aa | T3 | 4 |
| Suneson/pMBXO58 (called NJ02) | pMBXS1169 | 35S/CCP1 35S/Csa15g017550 168 aa | T3 | 6 |
| Suneson (called WTSU) | pMBXS1168 | 35S/Csa15g017550 134 aa | T3 | 6 |
| Suneson (called WTSU) | pMBXS1169 | 35S/Csa15g017550 168 aa | T3 | 7 |

[1]Sequence ID numbers for constructs are as follows: pMBXO58 (SEQ ID NO: 19); pMBXS1168 (SEQ ID NO: 17); pMBXS1169 (SEQ ID NO: 18).
[2]Csa15g017550 134 aa, Csa15g017550 with an ATG start codon producing a 134 aa peptide (SEQ ID NO: 2); Csa15g017550 168 aa, Csa15g017550 with a TTG start codon producing a 168 aa peptide (SEQ ID NO: 5).

Growth Experiment 1

A yield experiment was carried out to evaluate the T3 homozygous Csa15g017550 lines shown in TABLE 8 under equal watering and an equalized fertilizer (100 ppm NPK 20-20-20) feed applied three times a week in Sunshine 4 potting mix. The plant growth chamber was set at a 16 hour photoperiod, a 22° C./18° C. day/night temperature, and ~350-450 μmol/m2/sec light intensity.

Figure 11:
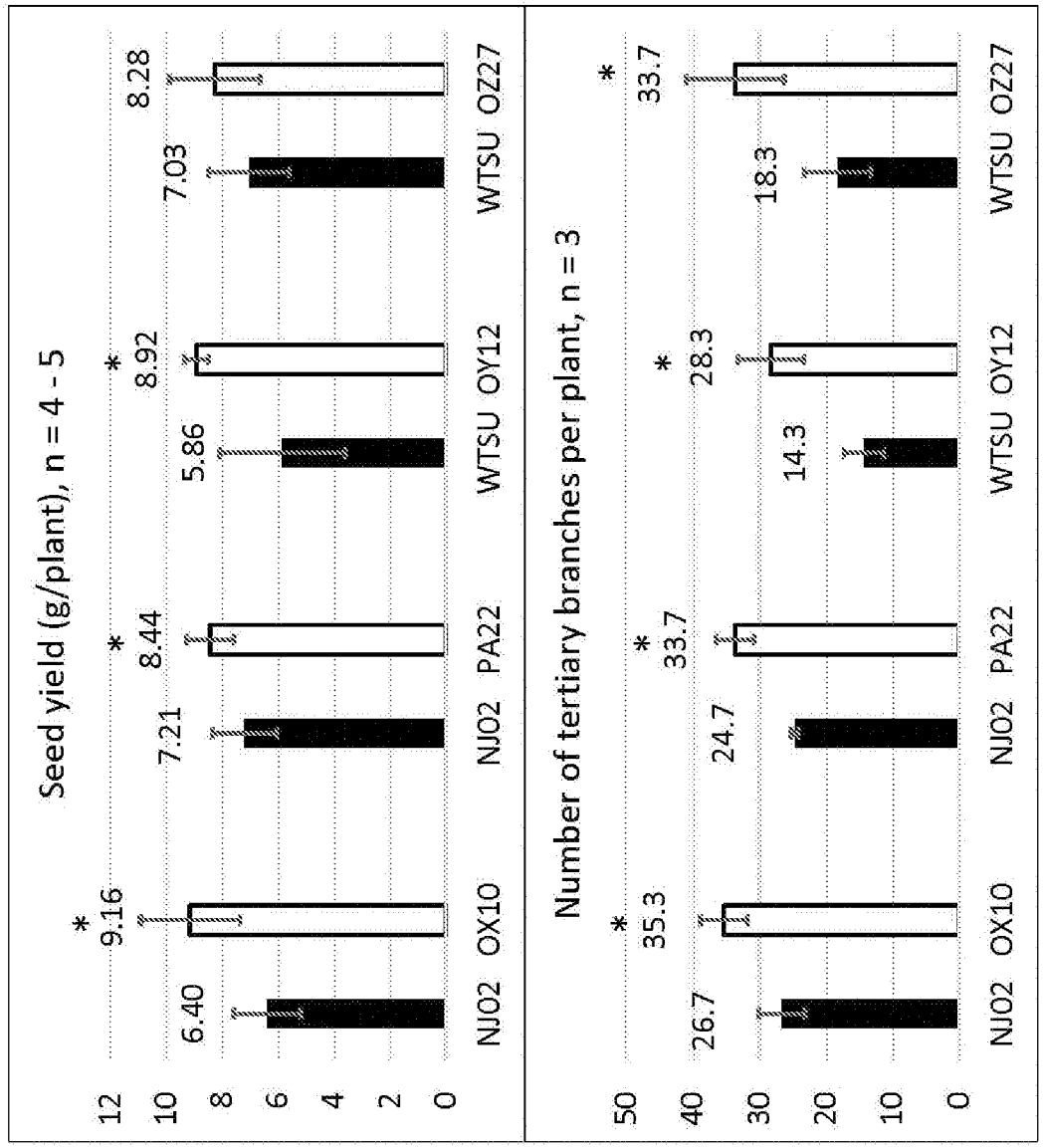
FIG. 11 shows a comparison of seed yield and number of tertiary branches in Camelina lines transformed with transformation vectors pMBXS 1168 and pMBXS1169. Lines are as follows: control line NJ02, wild-type Suneson transformed with pMBXO58 expressing CCP1; OX10, line of NJ02 transformed with pMBXS1168 (SEQ ID NO: 17) expressing the 134 amino acid Csa15g017550 of SEQ ID NO: 2; PA22, line of NJ02 transformed with pMBXS 1169 (SEQ ID NO: 18) expressing the 168 amino acid ISY protein of SEQ ID NO: 5; WTSU, wild-type Suneson; line OY12, wild-type Suneson transformed with pMBXS 1168; line OZ27, wild-type Suneson transformed with pMBXS 1169. *, indicates statistically significant results according to the student's t-test (p<0.05).

No differences were observed in Csa15g017550 and control plants during the first 10 days of plant development. However, as this experiment progressed the Csa15g017550 lines in all backgrounds showed improved vigor and also produced higher numbers of tertiary branches in the majority of Csa15g017550 plants as compared to the controls. As the study progressed further we also noted that Csa15g017550 expressing lines, in addition to having increased vigor and branching, had prolonged flowering. There was evidence of some sterility in several flowers of tertiary branches. The Total seed yield (g/plant) was significantly higher in several Csa15g017550 lines, with or without expression of CCP1, as compared to their background controls (TABLE 9). The highest yielding line was OY15, which expressed pMBXS 1168 in the wild-type Suneson background, which produced 9.65±1.46 g of seed, a 65% increase over the 5.86±2.25 g of seed produced by the wild-type Suneson control. This increase in seed production was statistically significant (Student's t-test, p<0.05). Other seed yield related parameters (1000 seed weight, estimated total number of seeds per plant, and plant height at maturity) were also found to be generally increased in the Csa15g017550 lines. Analysis of total seed yield per line revealed that lines expressing Csa15g017550 with a significantly higher number of tertiary branches (40-100% more branching) compared to the controls also produced significantly higher seed yield (FIG. 11).

TABLE 9

T4 seed yield in lines of Camelina transformed with Csa15g017550 expression constructs.

| Genetic Construct for Csa15g017550 | Line transformed[1] | Line Produced | Number of plants analyzed | Seed Yield (g) | Standard Deviation | % of control[2] | t-test |
|---|---|---|---|---|---|---|---|
| None | — | Wild-type Suneson | 4 | 5.86 | 2.25 | 100% | |
| pMBXS1168 | Wild-type Suneson | OY03 | 4 | 7.40 | 1.36 | 126% | 0.14740 |
| | | OY04 | 4 | 8.23 | 1.32 | 141% | 0.06517 |
| | | OY12 | 4 | 8.92 | 0.44 | 152%* | 0.03503 |
| | | OY15 | 4 | 9.65 | 1.46 | 165%* | 0.01793 |
| | | OY16 | 3 | 8.57 | 2.97 | 146% | 0.13152 |
| | | OY17 | 4 | 8.95 | 1.14 | 153%* | 0.03209 |
| None | — | NJ02 | 3 | 6.40 | 1.20 | 100% | |
| pMBXS1168 | NJ02 | OX10 | 4 | 9.16 | 1.78 | 143%* | 0.02385 |
| | | OX13 | 4 | 8.66 | 0.94 | 135%* | 0.01348 |
| | | OX20 | 4 | 7.83 | 0.80 | 122% | 0.05060 |
| | | OX21 | 3 | 6.61 | 1.67 | 103% | 0.43094 |

TABLE 9-continued

T4 seed yield in lines of Camelina transformed
with Csa15g017550 expression constructs.

| Genetic Construct for Csa15g017550 | Line transformed[1] | Line Produced | Number of plants analyzed | Seed Yield (g) | Standard Deviation | % of control[2] | t-test |
|---|---|---|---|---|---|---|---|
| None | — | Wild-type Suneson | 5 | 7.03 | 1.45 | 100% | |
| MBXS1169 | Wild-type Suneson | OZ05 | 4 | 8.31 | 1.47 | 118% | 0.11822 |
| | | OZ12 | 4 | 9.56 | 0.90 | 136%** | 0.00790 |
| | | OZ15 | 4 | 10.16 | 1.69 | 144%* | 0.01314 |
| | | OZ19 | 4 | 8.30 | 2.52 | 118% | 0.20825 |
| | | OZ21 | 4 | 9.72 | 1.55 | 138%* | 0.01787 |
| | | OZ26 | 4 | 9.20 | 3.13 | 131% | 0.13398 |
| | | OZ27 | 4 | 8.28 | 1.61 | 118% | 0.13666 |
| None | — | NJ02 | 5 | 7.21 | 1.14 | 100% | |
| pMBXS1169 | NJ02 | PA03 | 4 | 6.74 | 1.05 | 93% | 0.27115 |
| | | PA11 | 4 | 7.09 | 1.81 | 98% | 0.45568 |
| | | PA12 | 3 | 6.75 | 0.76 | 94% | 0.25838 |
| | | PA15 | 4 | 6.57 | 0.63 | 91% | 0.16023 |
| | | PA16 | 4 | 6.99 | 1.27 | 97% | 0.39467 |
| | | PA22 | 4 | 8.44 | 0.85 | 117%* | 0.05358 |

[1]Line NJ02 contains pMBXO58 expressing CCP1 from the constitutive 35S promoter transformed into the wild-type Suneson background.
[2]Statistically significant results according to the student's t-test with a p < 0.05 are indicated with*, and P < 0.01 are indicated with**.

Growth Experiment 2

A second growth experiment was performed with the same T3 generation seed lot of select lines ISY lines in the wild-type Suneson background. In the second experiment, growth conditions were different. The plants were grown in Sunshine 4 potting mix in 6" pots with equalized fertilizer (100 ppm NPK 20-20-20) feed three times a week until the end of flowering in a Conviron BDR16 chamber set at 16 hrs photoperiod, 22° C./18° C. day/night temperature and ~450-650 μmol/m²/sec light intensity. The plants received additional water as needed in each pot. Most of the pMBXS1168 lines (OY04, OY12, OY15 and OY17) showed increased seedling vigor and improved overall plant growth compared to the wild type Suneson controls. pMBXS 1169 lines (OZ lines) were generally comparable to the wild type at early vegetative stage.

Figure 12A:
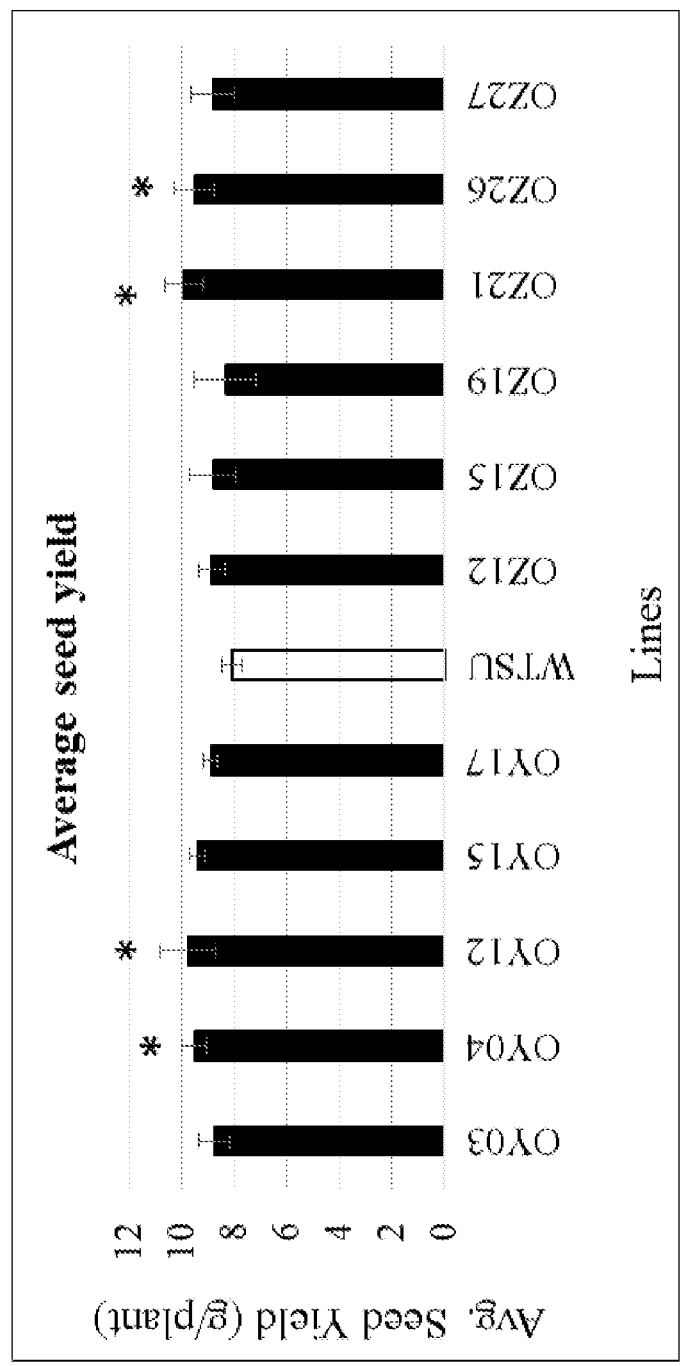
FIG. 12A-E shows the results from a second growth experiment of T3 generation Camelina lines transformed with transformation vectors pMBXS 1168 and pMBXS1169. A) Average T4 seed yield (in grams) of C3004 Camelina lines compared to wild-type controls (WTSU), n=4 plants. B) Average number of tertiary branches per plant of C3004 Camelina lines compared to wild-type controls, n=3-4 plants. C) Average number of siliques per plant of C3004 Camelina lines compared to wild-type controls, n=3-4 plants. D) Average number of seeds per plant of C3004 Camelina lines compared to wild-type controls, n=4 plants. E) Average 1000 seed weight of C3004 Camelina lines compared to wild-type controls, n=4 plants. C3004 Camelina lines of pMBXS1168 (OY02, OY04, OY12, OY15 and OY17) and pMBXS 1169 (OZ12, OZ15, OZ19, OZ21, OZ26 and OZ27) and the corresponding wildtype (WTSU) were grown in a Conviron BDR16 Growth Chamber set at a 16 hour photoperiod and a 22° C./18° C. day/night temperature. With the lights on, a light reading of 450-650 µmol/m²/sec light intensity was recorded 12 inches below the bulbs in the chamber. *=ANOVA & DMRT significant (p=0.05).

The seed yield of each plant was measured and average seed yield for each line (n=4 plants) was calculated (FIG. 12A). The best performing Suneson line transformed with construct pMBXS1168 (line OY12) produced 9.77±1.08 g of seed per plant, a 20.7% increase over the seed yield of the wild-type Suneson control. This increase was statistically significant (ANOVA & DMRT significant (p=0.05)). Line OY04 also had a statistically significant increase in seed yield producing 9.54±0.48 g of seed per plant, a 17.9% increase above the wild-type control. The best performing lines transformed with pMBXS1169 were OZ21 and OZ26 producing statistically significant increases in seed yield of 22.6% and 17.5%, respectively, compared to the wild-type control (ANOVA & DMRT significant (p=0.05)). Line OZ21 produced an average of 9.93±0.74 g of seed per plant whereas line OZ26 produced an average of 9.51±0.76 g of seed per plant.

Figure 12B:
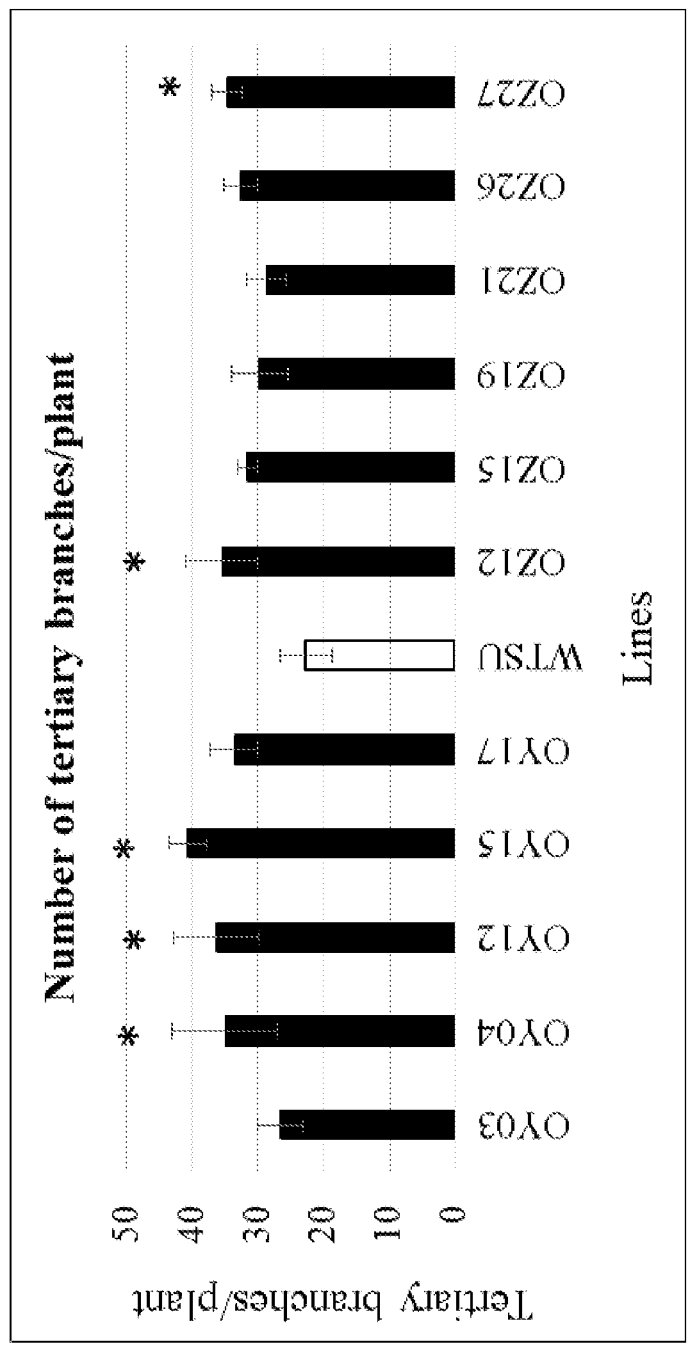

The average number of tertiary branches per plant was determined for each line and increases were observed (FIG. 12B). Of the lines transformed with pMBXS1168, the lines with the most tertiary branches were lines OY04, OY12, and OY15 producing statistically significant increases in the number of tertiary branches of 53.9%, 59.7%, and 78.8% respectively, compared to the wild-type control (ANOVA & DMRT significant (p=0.05)). Line OY04 produced 35.00±8.00 branches, line OY12 produced 36.33±6.43 branches, and the Suneson control line produced 22.80±3.94 branches. The lines of pMBXS 1169 with the highest number of tertiary branches were OZ12 and OZ27 which were statistically significant with 55.7% and 52.0% more tertiary branches, respectively, compared to the wild-type control (ANOVA & DMRT significant (p=0.05)). Line OZ12 produced 35.50±5.45 branches whereas line OZ27 produced 34.67±2.31 branches.

Figure 12C:
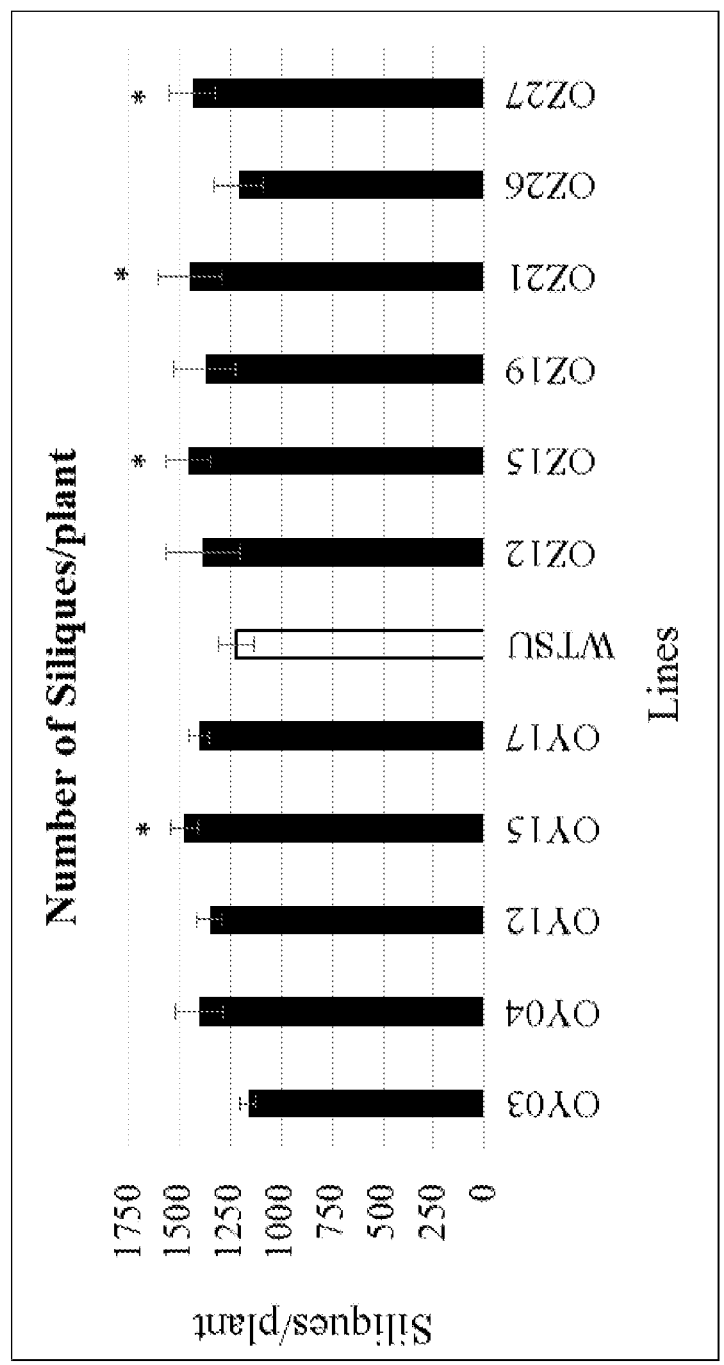

The average number of siliques per plant was determined for each line and increases were observed (FIG. 12C). Of the lines transformed with pMBXS 1168, the line with the most siliques was line OY15 producing 1480.0±68.4 siliques, a statistically significant increase of 21.3% compared to the wild-type control which had 1220.0±86.8 siliques (ANOVA & DMRT significant (p=0.05)). Lines transformed with pMBXS 1169 also had statistically significant numbers of siliques (FIG. 12C).

Figure 12D:
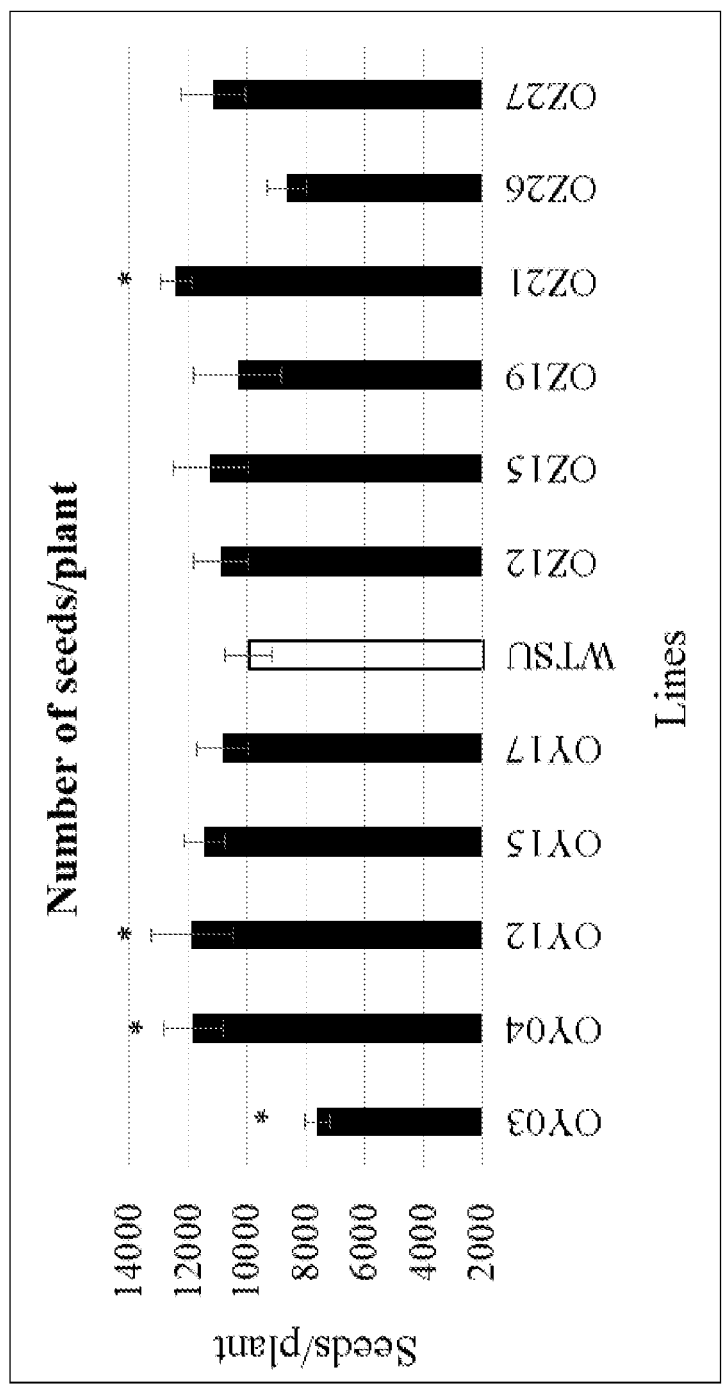

The average number of seeds per plant was also determined (FIG. 12D). The best producing lines transformed with pMBXS 1168 were lines OY04 and OY12 which produced statistically significant increases in seed per plant of 19.0% and 19.4%, respectively. Line OY04 had 11,832±1,007 seed per plant whereas line OY12 had 11,879±1,374 seed per plant. The wild-type Suneson control plant had 9,946±779 seeds per plant.

Figure 12E:
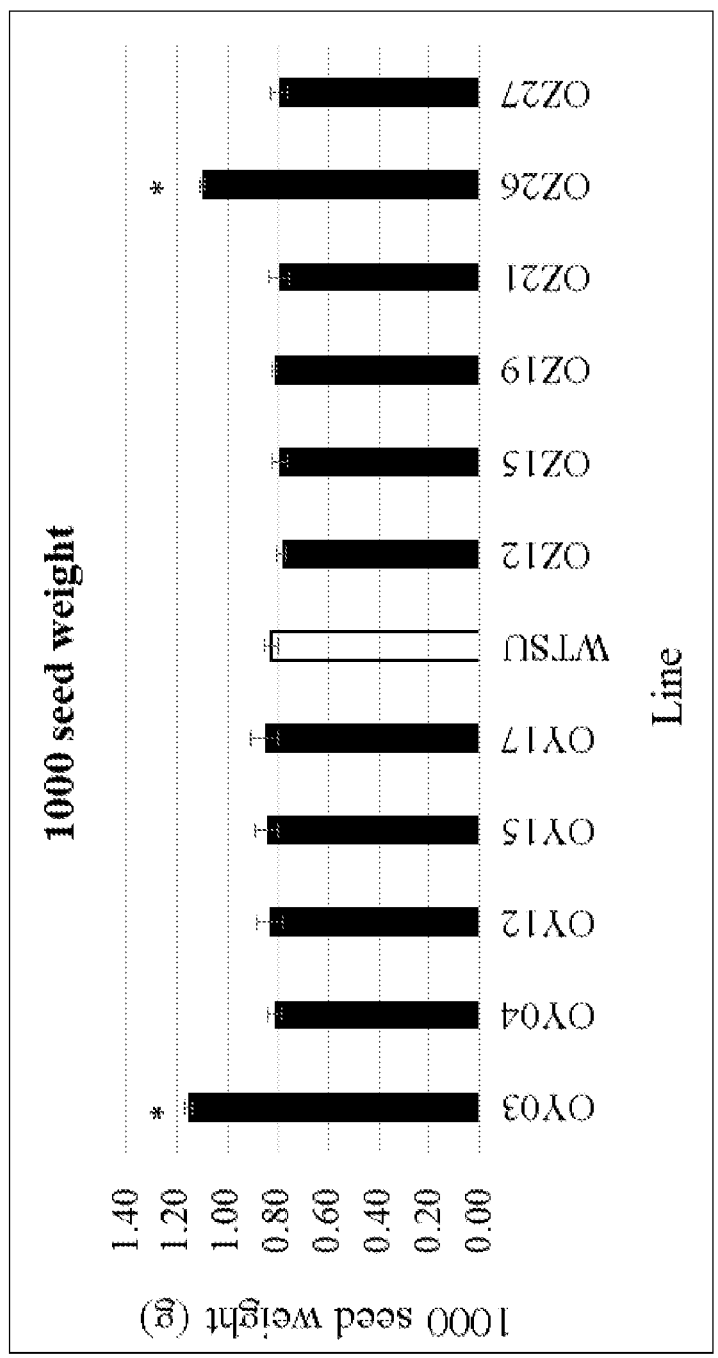

The individual seed weight, as determined by measuring the mass of 1000 seeds which was sampled using a seed counter, was also determined (FIG. 12E). Lines with a 1000 seed weight close to the wild-type control (FIG. 12E) in general had an increase in the number of seeds per plant compared to wild-type (FIG. 12D). There were some lines where there was a tradeoff between the number of seeds per plant and the individual seed weight. Lines OY03 (transformed with pMBXS 1168) and OZ26 (transformed with pMBXS1169) with the highest average 1000 seed weight also possessed the least number of seeds per plant (FIG. 12D, E).

Figure 13A:
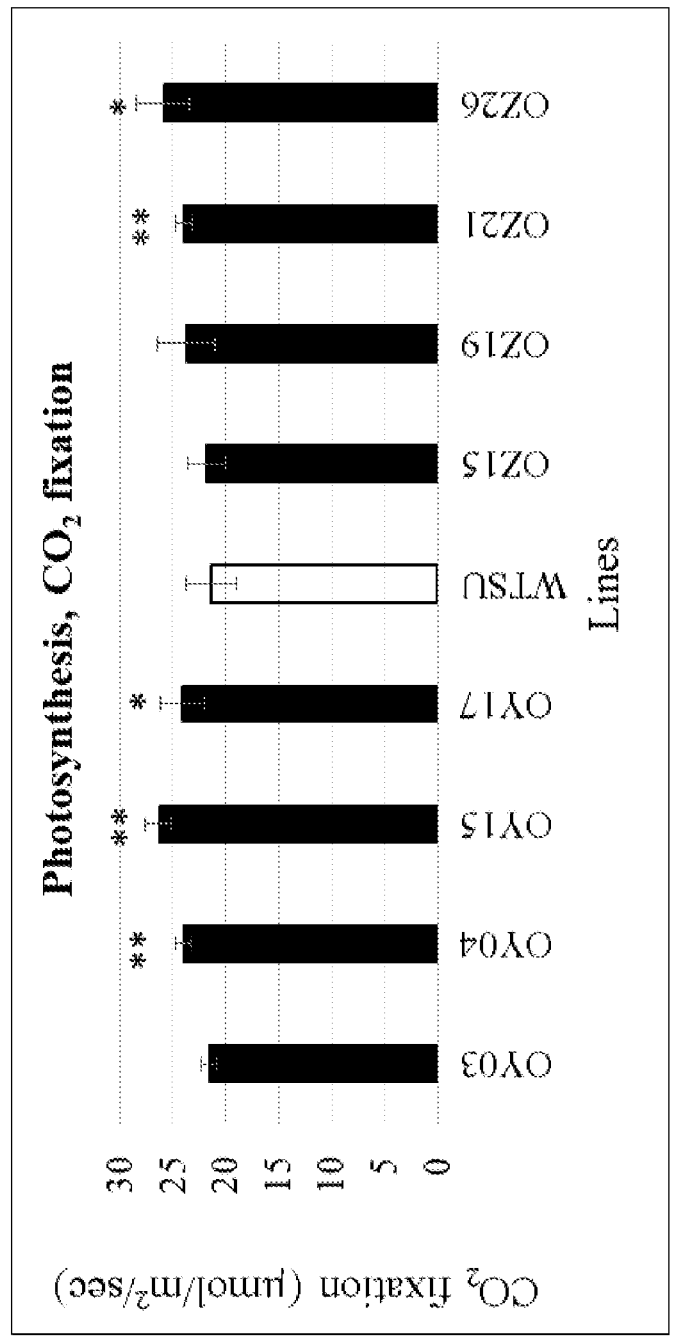
FIG. 13A-C shows the results from photosynthetic measurements of select Camelina sativa cv. Suneson C3004 transformants compared to their wild-type controls under field growth conditions. A) Photosynthesis, $CO_2$ fixation (µmol/m²/sec), n=4-10 plants. B) Effective quantum yield of Photosystem II (PSII), n=4-10 plants. C) Electron transfer rate (ETR) of PSII (µmol/m²/sec), n=4-10 plants. T4 generation seeds of C3004 Camelina sativa cv. Suneson lines transformed with pMBXS 1168 (OY03, OY04, OY15 and OY17) and pMBXS 1169 (OZ15, OZ19, OZ21, and OZ26) and the corresponding wildtype controls (WTSU) were planted in a field trial in Saskatoon, Canada during the 2019 growth season. Photosynthesis measurements were performed on T4 generation plants at a pre-bolting stage about 3.5 weeks after germination. Data analyzed by Student's t-tests. **, *=t-test significant at $p \leq 0.01$ and $p \leq 0.05$, respectively.
Figure 13B:
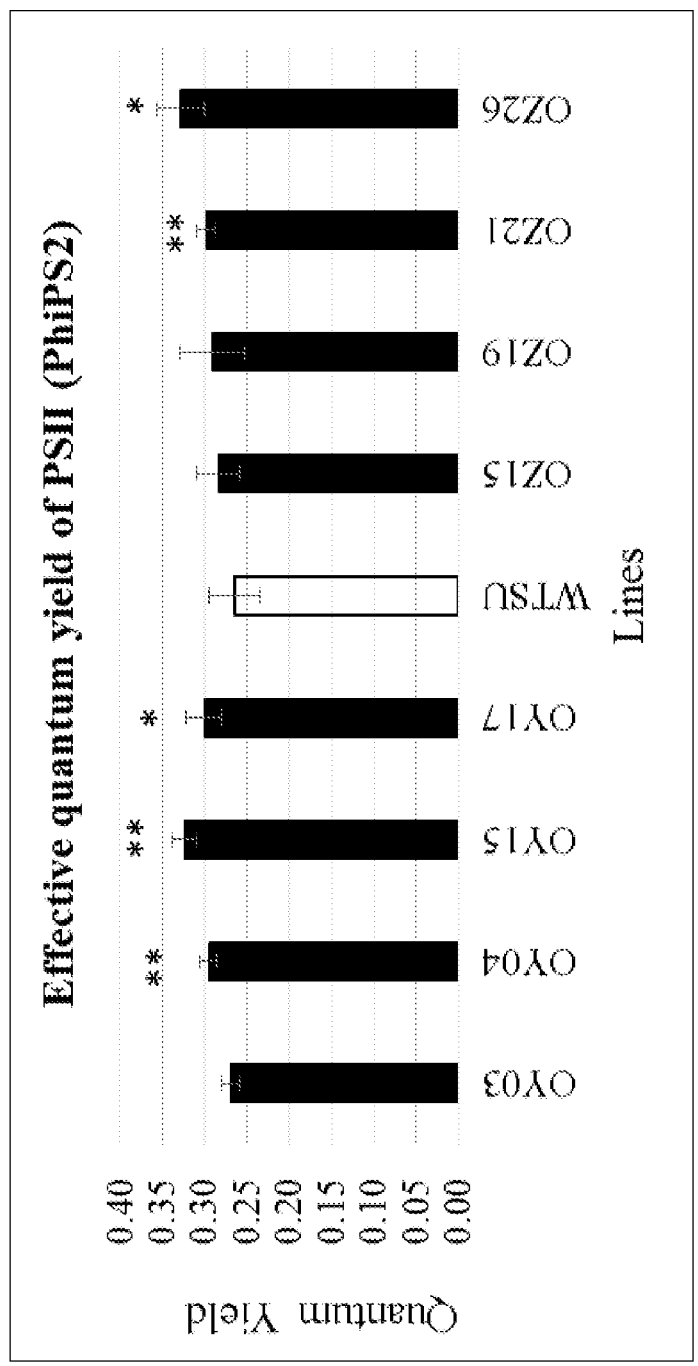
Figure 13C:
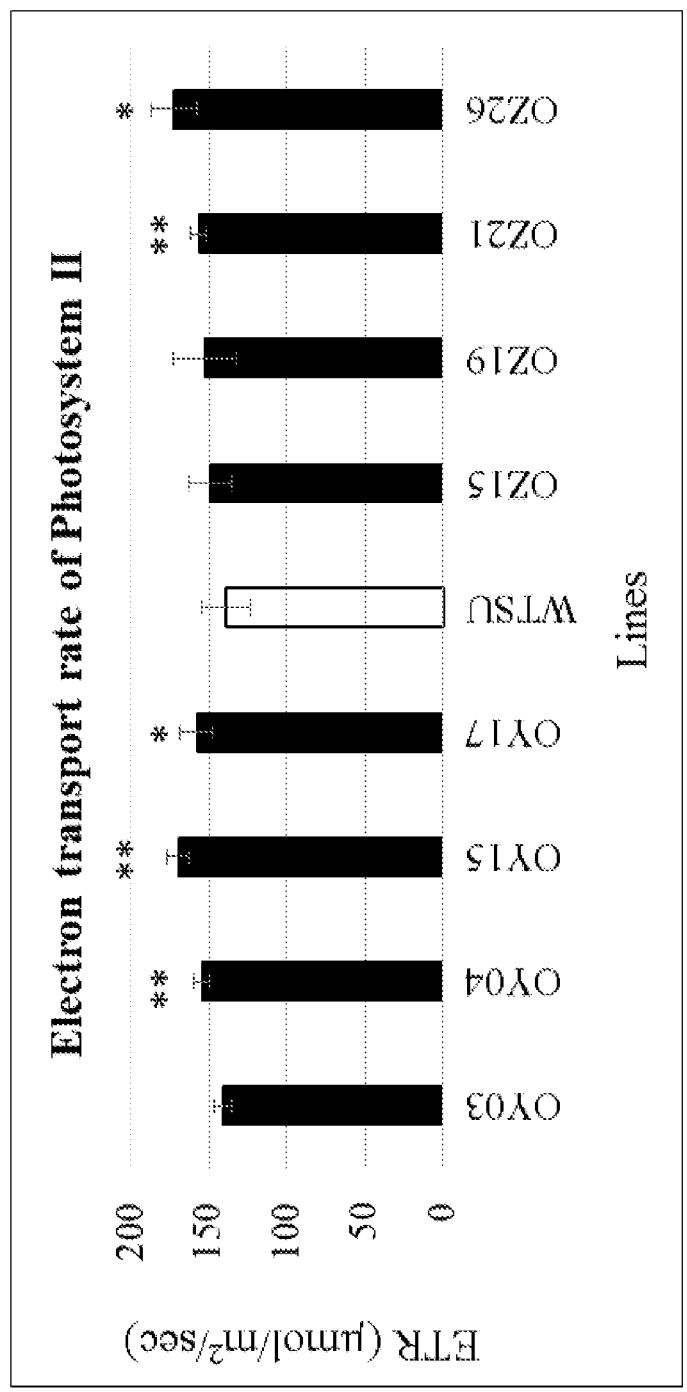

T4 generation seeds of select C3004 plants were planted in a field trial in Saskatoon, Canada, during the 2019 growth season. Photosynthesis measurements were performed on T4 generation plants at a pre-bolting stage about 3.5 weeks after germination using a LI-6400XT Portable Photosynthesis System (LI-COR Inc., Lincoln, Nebr., USA). Combined photosynthesis and light adapted chlorophyll fluorescence measurements were recorded from fully developed young leaves of each line and the corresponding wild type. This allowed the determination of the net photosynthetic assimilation, electron transfer rate (actual flux of photons driving the PSII) and the quantum yield efficiency (PhiPS2) of the photosystem II (PSII).*Camelina sativa* cv. Suneson lines transformed with pMBXS1168 that had statistically significant increases in photosynthetic parameters for $CO_2$ fixation (FIG. 13A), effective quantum yield of Photosystem II (PSII) (FIG. 13B), and electron transport rate (ETR) of PSII (FIG. 13C) included lines OY04, OY15, and OY17 (TABLE 10). Suneson lines transformed with pMBXS 1169 that had statistically significant increases in photosynthetic parameters for $CO_2$ fixation (FIG. 13A), effective quantum yield of Photosystem II (PSII) (FIG. 13B), and electron transport rate (ETR) around PSII (FIG. 13C) included lines OZ21 and OZ26 (TABLE 10). These results indicate a higher proportion of absorbed light used in photochemistry and improved overall photosynthesis. The C3004 lines showing higher photosynthetic efficiencies under field growth condition had higher yields during growth experiments 1 and 2 described above.

TABLE 10

Percent increases in photosynthetic parameters for *Camelina sativa* cv. Suneson transformed with either pMBXS1168 or pMBXS1169.

| Line | Vector | % Increase in Photosynthesis ($CO_2$ fixation) | % Increase in Effective Quantum Yield of PSII | % Increase in Electron Transport Rate of PSII |
|---|---|---|---|---|
| OY04 | pMBXS1168 | 12** | 12** | 12** |
| OY15 | pMBXS1168 | 23** | 23** | 22** |
| OY17 | pMBXS1168 | 12* | 14* | 14* |
| WTSU | — | — | — | — |
| OZ21 | pMBXS1169 | 12** | 13** | 13** |
| OZ26 | pMBXS1169 | 21* | 24* | 24* |

[1]Only lines with statistically significant increases are shown. Data analyzed by Student's t-tests.
**, *= t-test significant at $p \leq 0.01$ and $p \leq 0.05$, respectively Overall, increased expression of Csa15g017550 in *Camelina* results in a significant increase in plant growth vigor, number of branches, number of siliques, seed yield, and some photosynthetic parameters. These results are the opposite of what would be predicted based on the hypothesis that Csa15g017550 may be a plant invertase inhibitor gene. In addition with the limited number of plant lines tested for each vector in each genetic background, there is some evidence that the gene encoding the 134 aa ISY protein may be more effective plus or minus the CCP1 gene and hence may be a preferred embodiment. These results also support the theory that Csa15g017550 does not encode a plant invertase inhibitor.

Example 5. Overexpressing the *Camelina* ISY Gene in Other Crops: Canola, Soybean, Corn, Wheat, Rice, Potato, Tomato Etc.

For dicot plants, vectors pMBXS 1168 and pMBXS 1169 can be modified to include a selectable marker appropriate for selection of transformants for the crop of interest.
Canola Transformation.

For transformation of canola, vectors pMBXS1168 and pMBXS1169 can be modified to include a cassette for expression of the bar gene, providing resistance to the herbicide bialaphos. Construct pMBXS1269 (FIG. 19A, SEQ ID NO: 197) was prepared that contains the *Camelina* ISY gene (SEQ ID NO: 1) encoding the 134 amino acid ISY protein (SEQ ID NO: 2) expressed from the double enhanced CaMV35S constitutive promoter (2× 35S). Construct pMBXS1270 (FIG. 19B, SEQ ID NO: 198) was prepared that contains the *Camelina* ISY gene (SEQ ID NO: 6) encoding the 168 amino acid *Camelina* ISY protein (SEQ ID NO: 5) expressed from the double enhanced CaMV35S constitutive promoter (2× 35S). An expression cassette for the bar gene, driven by the double enhanced CaMV35S constitutive promoter (2× 35S), was included for selection. Both constructs were transformed into canola.

In preparation for plant transformation experiments, seeds of *Brassica napus* cv DH12075 (obtained from Agriculture and Agri-Food Canada) were surface sterilized with sufficient 95% ethanol for 15 seconds, followed by 15 minutes incubation with occasional agitation in full strength Javex (or other commercial bleach, 7.4% sodium hypochlorite) and a drop of wetting agent such as Tween 20. The Javex solution was decanted and 0.025% mercuric chloride with a drop of Tween 20 was added and the seeds were sterilized for another 10 minutes. The seeds were then rinsed three times with sterile distilled water. The sterilized seeds were plated on half strength hormone-free Murashige and Skoog (MS) media (Murashige T, Skoog F (1962). *Physiol Plant* 15:473-498) with 1% sucrose in 15×60 mm petri dishes that were then placed, with the lid removed, into a larger sterile vessel (Majenta GA7 jars). The cultures were kept at 25° C., with 16 h light/8 h dark, under approximately 70-80 μE of light intensity in a tissue culture cabinet. 4-5 days old seedlings were used to excise fully unfolded cotyledons along with a small segment of the hypocotyl. Excisions were made so as to ensure that no part of the apical meristem was included.

Separate *Agrobacterium* strains of GV3101 (pMP90) carrying either pMBXS1269 (FIG. 19A, SEQ ID NO: 197) or pMBXS1270 (FIG. 19B, SEQ ID NO: 198) were prepared and were grown overnight in 5 ml of LB media with 50 mg/L kanamycin, gentamycin, and rifampicin. The culture was centrifuged at 2000 g for 10 min., the supernatant was discarded and the pellet was suspended in 5 ml of inoculation medium (Murashige and Skoog with B5 vitamins (MS/B5; Gamborg O L, Miller R A, Ojima K. *Exp Cell Res* 50:151-158), 3% sucrose, 0.5 mg/L benzyl aminopurine (BA), pH 5.8). Cotyledons were collected in Petri dishes with ~1 ml of sterile water to keep them from wilting. The water was removed prior to inoculation and explants were inoculated in a mixture of 1 part *Agrobacterium* suspension and 9 parts inoculation medium in a final volume sufficient to bathe the explants. After explants were well exposed to the *Agrobacterium* solution and inoculated, a pipet was used to remove any extra liquid from the petri dishes.

The Petri plates containing the explants incubated in the inoculation media were sealed and kept in the dark in a tissue culture cabinet set at 25° C. After 2 days the cultures were transferred to 4° C. and incubated in the dark for 3 days. The cotyledons, in batches of 10, were then transferred to selection medium consisting of Murashige Minimal Organics (Sigma), 3% sucrose, 4.5 mg/L BA, 500 mg/L MES, 27.8 mg/L Iron (II) sulfate heptahydrate, pH 5.8, 0.7% Phytagel with 300 mg/L timentin, and 2 mg/L L-phosphinothricin (L-PPT) added after autoclaving. The cultures were kept in a tissue culture cabinet set at 25° C., 16 h/8 h, with a light intensity of about 125 μmol m$^{-2}$ s$^{-1}$. The cotyledons were transferred to fresh selection every 3 weeks until shoots were obtained. The shoots were excised and transferred to shoot elongation media containing MS/B5 media, 2% sucrose, 0.5 mg/L BA, 0.03 mg/L gibberellic acid (GA$_3$), 500 mg/L 4-morpholineethanesulfonic acid (MES), 150 mg/L phloroglucinol, pH 5.8, 0.9% Phytagar and 300 mg/L timentin and 3 mg/L L-phosphinothricin added after autoclaving. After 3-4 weeks any callus that was formed at the base of shoots with normal morphology was cut off and shoots were transferred to rooting media containing half strength MS/B5 media with 1% sucrose and 0.5 mg/L indole butyric acid, 500 mg/L MES, pH 5.8, 0.8% agar, with 1.5 mg/L L-PPT and 300 mg/L timentin added after autoclaving. The plantlets with healthy shoots were hardened and transferred to 6 inch (15 cm) pots in the greenhouse and T1 transgenic seeds were collected.

For genetic construct pMBXS1269, 22 T0 lines were isolated and grown to maturity to harvest T1 seeds. T1 seeds of 6 single copy lines, 2 double copy lines and 1 multi-copy lines are grown in a greenhouse to identify homozygous transgenic plants of pMBXS1269.

For genetic construct pMBXS1270, 32 T0 lines were isolated and grown to maturity to harvest T1 seeds. T1 seeds of 11 single copy lines are grown in a greenhouse to identify homozygous transgenic plants of pMBXS1270.

Screening of transgenic plants of canola expressing the ISY gene to identify plants with higher yield is performed as follows. T2 generation of seed from each line is harvested. Seed yield from each plant is determined by harvesting all of the mature seeds from a plant and drying them in an oven with mechanical convection set at 22° C. for two days. The weight of the entire harvested seed is recorded. The 100 seed weight is measured to obtain an indication of seed size. The oil content of seeds is measured using published procedures for preparation of fatty acid methyl esters (Malik et al. 2015, *Plant Biotechnology Journal*, 13, 675-688).

Soybean Transformation.

For transformation of soybean, the expression cassettes for the ISY gene can be excised from either vector pMBXS 1168 or pMBXS 1169. Transformation of soybean can be performed with the expression cassette for the ISY gene of choice and an expression cassette for the selectable marker hygromycin resistance as follows. The purified DNA cassettes are co-bombarded using biolistics into embryogenic cultures of soybean *Glycine max* cultivars X5 and Westag97, to obtain transgenic plants. The hygromycin resistance gene is expressed from a plant promoter, such as the soybean actin promoter (TABLE 1; SEQ ID NO: 44) and is flanked by a suitable 3' UTR, such as the 3' UTR from the soybean actin gene (soybean actin Gene ID Glyma.19G147900). The ISY gene can also be expressed from the soybean actin promoter and flanked by the 3' UTR of the soybean actin gene in cases where it is useful to use only DNA sequences from soybean for regulatory approval purposes under USDA-APHIS in the United States.

The transformation, selection, and plant regeneration protocol is adapted from Simmonds (2003) (Simmonds, 2003, Genetic Transformation of Soybean with Biolistics. In: Jackson J F, Linskens H F (eds) *Genetic Transformation of Plants*. Springer Verlag, Berlin, pp 159-174) and is performed as follows.

Induction and Maintenance of Proliferative Embryogenic Cultures: Immature pods, containing 3-5 mm long embryos, are harvested from host plants grown at 28/24° C. (day/night), 15-h photoperiod at a light intensity of 300-400 µmol m$^{-2}$ s$^{-1}$. Pods are sterilized for 30 s in 70% ethanol followed by 15 min in 1% sodium hypochlorite (with 1-2 drops of Tween 20 (Sigma, Oakville, ON, Canada)) and three rinses in sterile water. The embryonic axis is excised and explants are cultured with the abaxial surface in contact with the induction medium (MS salts, B5 vitamins (Gamborg O L, Miller R A, Ojima K. Exp Cell Res 50:151-158), 3% sucrose, 0.5 mg/L BA, pH 5.8), 1.25-3.5% glucose (concentration varies with genotype), 20 mg/l 2,4-D, pH 5.7). The explants, maintained at 20° C. at a 20-h photoperiod under cool white fluorescent lights at 35-75 µmol m$^{-2}$ s$^{-1}$, are sub-cultured four times at 2-week intervals. Embryogenic clusters, observed after 3-8 weeks of culture depending on the genotype, are transferred to 125-ml Erlenmeyer flasks containing 30 ml of embryo proliferation medium containing 5 mM asparagine, 1-2.4% sucrose (concentration is genotype dependent), 10 mg/l 2,4-D, pH 5.0 and cultured as above at 35-60 µmol m$^{-2}$ s$^{-1}$ of light on a rotary shaker at 125 rpm. Embryogenic tissue (30-60 mg) is selected, using an inverted microscope, for subculture every 4-5 weeks.

Transformation: Cultures are bombarded 3 days after subculture. The embryogenic clusters are blotted on sterile Whatman filter paper to remove the liquid medium, placed inside a 10×30-mm Petri dish on a 2×2 cm$^2$ tissue holder (PeCap, 1005 µm pore size, Band SH Thompson and Co. Ltd. Scarborough, ON, Canada) and covered with a second tissue holder that is then gently pressed down to hold the clusters in place. Immediately before the first bombardment, the tissue is air dried in the laminar air flow hood with the Petri dish cover off for no longer than 5 min. The tissue is turned over, dried as before, bombarded on the second side and returned to the culture flask. The bombardment conditions used for the Biolistic PDS-I000/He Particle Delivery System are as follows: 737 mm Hg chamber vacuum pressure, 13 mm distance between rupture disc (Bio-Rad Laboratories Ltd., Mississauga, ON, Canada) and macrocarrier. The first bombardment uses 900 psi rupture discs and a microcarrier flight distance of 8.2 cm, and the second bombardment uses 1100 psi rupture discs and 11.4 cm microcarrier flight distance. DNA precipitation onto 1.0 µm diameter gold particles is carried out as follows: 2.5 µl of 100 ng/µl of DNA containing the expression cassette for the ISY gene from either pMBXS1168 or pMBXS1169, and 2.5 µl of 100 ng/µl selectable marker DNA (cassette for hygromycin selection) are added to 3 mg gold particles suspended in 50 µl sterile dH$_2$O and vortexed for 10 sec; 50 µl of 2.5 M CaCl$_2$ is added, vortexed for 5 sec, followed by the addition of 20 µl of 0.1 M spermidine which is also vortexed for 5 sec. The gold is then allowed to settle to the bottom of the microfuge tube (5-10 min) and the supernatant fluid is removed. The gold/DNA is resuspended in 200 µl of 100% ethanol, allowed to settle and the supernatant fluid is removed. The ethanol wash is repeated and the supernatant fluid is removed. The sediment is resuspended in 120 µl of 100% ethanol and aliquots of 8 µl are added to each macrocarrier. The gold is resuspended before each aliquot is removed. The macrocarriers are placed under vacuum to ensure complete evaporation of ethanol (about 5 min).

Selection: The bombarded tissue is cultured on embryo proliferation medium described above for 12 days prior to subculture to selection medium (embryo proliferation medium contains 55 mg/l hygromycin added to autoclaved media). The tissue is sub-cultured 5 days later and weekly for the following 9 weeks. Green colonies (putative transgenic events) are transferred to a well containing 1 ml of selection media in a 24-well multi-well plate that is maintained on a flask shaker as above. The media in multi-well dishes is replaced with fresh media every 2 weeks until the colonies are approximately 2-4 mm in diameter with proliferative embryos, at which time they are transferred to 125 ml Erlenmeyer flasks containing 30 ml of selection medium. A portion of the proembryos from transgenic events is harvested to examine gene expression by RT-PCR.

Plant regeneration: Maturation of embryos is carried out, without selection, at conditions described for embryo induction. Embryogenic clusters are cultured on Petri dishes containing maturation medium (MS salts, B5 vitamins, 6% maltose, 0.2% gelrite gellan gum (Sigma), 750 mg/l $MgCl_2$, pH 5.7) with 0.5% activated charcoal for 5-7 days and without activated charcoal for the following 3 weeks. Embryos (10-15 per event) with apical meristems are selected under a dissection microscope and cultured on a similar medium containing 0.6% phytagar (Gibco, Burlington, ON, Canada) as the solidifying agent, without the additional $MgCl_2$, for another 2-3 weeks or until the embryos become pale yellow in color. A portion of the embryos from transgenic events after varying times on gelrite are harvested to examine gene expression by RT-PCR.

Mature embryos are desiccated by transferring embryos from each event to empty Petri dish bottoms that are placed inside Magenta boxes (Sigma) containing several layers of sterile Whatman filter paper flooded with sterile water, for 100% relative humidity. The Magenta boxes are covered and maintained in darkness at 20° C. for 5-7 days. The embryos are germinated on solid B5 medium containing 2% sucrose, 0.2% gelrite and 0.075% $MgCl_2$ in Petri plates, in a chamber at 20° C., 20-h photoperiod under cool white fluorescent lights at 35-75 $\mu mol\ m^{-2}\ s^{-1}$. Germinated embryos with unifoliate or trifoliate leaves are planted in artificial soil (Sunshine Mix No. 3, SunGro Horticulture Inc., Bellevue, Wash., USA), and covered with a transparent plastic lid to maintain high humidity. The flats are placed in a controlled growth cabinet at 26/24° C. (day/night), 18 h photoperiod at a light intensity of 150 $\mu mol\ m^{-2}\ s^{-1}$. At the 2-3 trifoliate stage (2-3 weeks), the plantlets with strong roots are transplanted to pots containing a 3:1:1:1 mix of ASB Original Grower Mix (a peat-based mix from Greenworld, ON, Canada):soil:sand:perlite and grown at 18-h photoperiod at a light intensity of 300-400 $\mu molm^{-2}\ s^{-1}$.

T1 seeds are harvested and planted in soil and grown in a controlled growth cabinet at 26/24° C. (day/night), 18 h photoperiod at a light intensity of 300-400 $\mu mol\ m^{-2}\ s^{-1}$. Plants are grown to maturity and T2 seed is harvested. Seed yield per plant and oil content of the seeds is measured.

The selectable marker can be removed by segregation if desired by identifying co-transformed plants that have not integrated the selectable marker expression cassette and the ISY gene cassette into the same locus. Plants are grown, allowed to set seed and germinated. Leaf tissue is harvested from soil grown plants and screened for the presence of the selectable marker cassette. Plants containing only the ISY gene expression cassette are advanced.

Corn Transformation

An expression cassette for the ISY gene can be constructed using a variety of different promoters for expression. Candidate constitutive and seed-specific promoters for use in monocots including corn are listed in TABLE 2, however those skilled in the art will understand that other promoters can be selected for expression.

In some instances, it may be advantageous to create a hybrid promoter containing a promoter sequence and an intron. These promoters can deliver higher levels of stable expression. Examples of such hybrid promoters include the hybrid maize Cab-m5 promoter/maize hsp70 intron (SEQ ID NO: 64, TABLE 2) and the maize ubiquitin promoter/maize ubiquitin intron (SEQ ID NO: 109 and 110, TABLE 2).

An example expression cassette for the ISY gene for maize includes the genetic elements in TABLE 11, in which the promoter is operably linked to the ISY gene which is operably linked to the termination sequence.

TABLE 11

Example transformation cassette for the *Camelina* ISY gene for maize

| Promoter | Gene | Terminator |
| --- | --- | --- |
| hybrid maize Cab-m5 promoter/maize hsp70 intron (SEQ ID NO: 64) | ISY gene encoding the 134 amino acid protein (SEQ ID NO: 1) | Hsp70 3' UTR Glyma.02G093200* |

*GENE ID Glyma.02G093200 includes sequence information for coding regions as well as associated promoters, 5' UTRs, and 3' UTRs (available at Phytozome, see JGI website phytozome.jgi.doe.gov/pz/portal.html).

Methods to transform the expression cassette described in TABLE 11 into maize are routine and well known in the art and have recently been reviewed by Que et al., (2014), Frontiers in Plant Science 5, article 379, pp 1-19.

Protoplast transformation methods useful for practicing the invention are well known to those skilled in the art. Such procedures include for example the transformation of maize protoplasts as described by Rhodes and Gray (Rhodes, C. A. and D. W. Gray, *Transformation and regeneration of maize protoplasts, in Plant Tissue Culture Manual: Supplement 7*, K. Lindsey, Editor. 1997, *Springer Netherlands: Dordrecht*. p. 353-365). For protoplast transformation of maize, the expression cassette described in TABLE 11 can be co-bombarded with an expression cassette for a selectable marker, such as the bar gene imparting transgenic plants resistance to bialaphos.

For *Agrobacterium*-mediated transformation of maize, the expression cassette described in TABLE 11 can be inserted into a binary vector that also contains an expression cassette for a selectable marker, such as the bar gene. The binary vector is transformed into an *Agrobacterium tumefaciens* strain, such as *A. tumefaciens* strain EHA101.

*Agrobacterium*-mediated transformation of maize can be performed following a previously described procedure (Frame et al. (2006), *Agrobacterium* Protocols, Wang K., ed., Vol. 1, pp 185-199, Humana Press) as follows.

Plant Material: Plants grown in a greenhouse are used as an explant source. Ears are harvested 9-13 days after pollination and surface sterilized with 80% ethanol.

Explant Isolation, Infection and Co-Cultivation: Immature zygotic embryos (1.2-2.0 mm) are aseptically dissected from individual kernels and incubated in an *A. tumefaciens* strain EHA101 culture containing the transformation vector of interest for genome editing (grown in 5 ml N6 medium supplemented with 100 μM acetosyringone for stimulation of the bacterial vir genes for 2-5 h prior to transformation) at room temperature for 5 min. The infected embryos are transferred scutellum side up on to a co-cultivation medium (N6 agar-solidified medium containing 300 mg/l cysteine, 5 μM silver nitrate and 100 μM acetosyringone) and incubated at 20° C., in the dark for 3 d. Embryos are transferred to N6 resting medium containing 100 mg/l cefotaxime, 100 mg/l vancomycin and 5 μM silver nitrate and incubated at 28° C., in the dark for 7 d.

Callus Selection: All embryos are transferred on to the first selection medium (the resting medium described above supplemented with 1.5 mg/l bialaphos) and incubated at 28° C. in the dark for 2 weeks followed by subculture on a selection medium containing 3 mg/l bialaphos. Proliferating pieces of callus are propagated and maintained by subculture on the same medium every 2 weeks.

Plant Regeneration and Selection: Bialaphos-resistant embryogenic callus lines are transferred on to regeneration medium I (MS basal medium supplemented with 60 g/l sucrose, 1.5 mg/l bialaphos and 100 mg/l cefotaxime and solidified with 3 g/l Gelrite) and incubated at 25° C. in the dark for 2 to 3 weeks. Mature embryos formed during this period are transferred on to regeneration medium II (the same as regeneration medium I with 3 mg/l bialaphos) for germination in the light (25° C., 80-100 µmol/m$^2$/s light intensity, 16/8-h photoperiod). Regenerated plants are ready for transfer to soil within 10-14 days. Plants are grown in the greenhouse to maturity and T1 seeds are isolated.

The copy number of the transgene insert is determined, through methods such as Southern blotting or digital PCR, and lines are selected to bring forward for further analysis. Overexpression of the ISY gene is determined by RT-PCR and/or Western blotting techniques and plants with the desired level of expression are selected. Homozygous lines are generated. The yield seed of homozygous lines is compared to control lines.

Rice Transformation

Candidate constitutive and seed-specific promoters for use in monocots can be used in the expression cassettes for the ISY gene in rice and are listed in TABLE 2. Those skilled in the art will understand that other promoters can be selected for expression.

The example expression cassette in TABLE 11 can be used to transform the ISY gene into rice. The expression cassette can be inserted into a binary vector that also contains an expression cassette for a selectable marker, such as the hygromycin selectable marker. The binary vector is transformed into an *Agrobacterium tumefaciens* AGL1 strain.

In preparation for rice transformation, callus of the rice cultivar Nipponbare is initiated from mature, dehusked, surface sterilized seeds on N6-basal salt callus induction media (N6-CI; contains per liter 3.9 g CHU (N$_6$) basal salt mix (Sigma Catalog #C1416); 10 ml of 100×N6-vitamins (contains in final volume of 500 mL, 100 mg glycine, 25 mg nicotinic acid, 25 mg pyridoxine hydrochloride and 50 mg thiamine hydrochloride); 0.1 g myo-inositol; 0.3 g casamino acid (casein hydrolysate); 2.88 g proline; 10 ml of 100× 2,4-D, 30 g sucrose, pH 5.8 with 4 g gelrite or phytagel). Approximately 100 seeds are used for each transformation. The frequency of callus induction is scored after 21 days of culture in the dark at 27±1° C. Callus induction from the scutellum with a high frequency (of about 96% total callus induction) is observed.

The rice transformation vector is transformed into *Agrobacterium* strain AGL1. The resulting *Agrobacterium* strain is resuspended in 10 mL of MG/L medium (5 g tryptone, 2.4 g yeast extract, 5 g mannitol, 5 g Mg$_2$SO$_4$, 0.25 g K$_2$HPO$_4$, 1 g glutamic acid and 1 g NaCl) to a final OD600 of 0.3. Approximately twenty-one day old scutellar embryogenic callus are cut to about 2-3 mm in size and are infected with *Agrobacterium* containing the transformation vector for 5 min. After infection, the calli are blotted dry on sterile filter papers and transferred onto co-cultivation media (N6-CC; contains per liter 3.9 g CHU (N$_6$) basal salt mix; 10 ml of 100× N6-vitamins; 0.1 g myo-inositol; 0.3 g casamino acid; 10 ml of 100× 2,4-D, 30 g sucrose, 10 g glucose, pH 5.2 with 4 g gelrite or phytagel and 1 mL of acetosyringone (19.6 mg/mL stock)). Co-cultivated calli are incubated in the dark for 3 days at 25° C. After three days of co-cultivation, the calli are washed thoroughly in sterile distilled water to remove the bacteria. A final wash with a timentin solution (250 mg/L) is performed and calli are blotted dry on sterile filter paper. Callus are transferred to selection media (N6-SH; contains per liter 3.9 g CHU (N$_6$) basal salt mix, 10 ml of 100×N6-vitamins, 0.1 g myo-inositol, 0.3 g casamino acid, 2.88 g proline, 10 ml of 100×, 2,4-D, 30 g sucrose, pH 5.8 with 4 g phytagel and 500 µL of hygromycin (stock concentration: 100 mg/ml) and incubated in the dark for two-weeks at 27±1° C. The transformed calli that survive the selection pressure and that proliferate on N6-SH medium are sub-cultured on the same media for a second round of selection. These calli are maintained under the same growth conditions for another two weeks. The number of plants regenerated after 30 days on N6-SH medium is scored and the frequency calculated. After 30 days, the proliferating calli are transferred to regeneration media (N6-RH medium; contains per liter 4.6 g MS salt mixture, 10 ml of 100×MS-vitamins (MS-vitamins contains in 500 mL final volume 250 mg nicotinic acid, 500 mg pyridoxine hydrochloride, 500 mg thiamine hydrochloride, 100 mg glycine), 0.1 g myo-inositol, 2 g casein hydrolysate, 1 ml of 1,000×1-naphtylacetic acid solution (NAA; contains in 200 mL final volume 40 mg NAA and 3 mL of 0.1 N NaOH), 20 ml of 50× kinetin (contains in 500 mL final volume 50 mg kinetin and 20 mL 0.1 N HCl), 30 g sucrose, 30 g sorbitol, pH 5.8 with 4 g phytagel and 500 µl of a 100 mg/mL hygromycin stock). The regeneration of plantlets from these calli occurs after about 4-6 weeks. Rooted plants are transferred into peat-pellets for one week to allow for hardening of the roots. The plants are then kept in sealable bags for acclimatization. Plants are transferred into pots and grown in a greenhouse to maturity.

Seed is harvested from each panicle (T1 generation) and the seed yield per plant is calculated. T1 seed is grown in a greenhouse to produce T2 seed. The mass of the total seed per plant is collected to compare seed yield of transgenics to wild-type control plants.

Example 6. Identification of Homologs and/or Orthologs of the *Camelina* ISY in Other Crop Species The *Brassica napus* genome of the cultivar ZS11 was searched for orthologs of the *Camelina* ISY gene using BLAST searches. The best four orthologs are listed in TABLE 12 with calculations of their percent homology to the Csa15g017550.1 gene encoding both 134 (SEQ ID NO: 2) and 168 (SEQ ID NO: 5) amino acid proteins. A CLUSTAL alignment is shown in FIG. 14.

The soybean reference genome (*Glycine max* Williams 82) was searched for orthologs of the *Camelina* ISY gene using BLAST searches. The best four orthologs are listed in TABLE 12 with calculations of their percent homology to the Csa15g017550.1 gene encoding both 134 (SEQ ID NO: 2) and 168 (SEQ ID NO: 5) amino acid proteins. A CLUSTAL alignment is shown in FIG. 15.

The corn reference genome (*Zea mays* B73) was searched for orthologs of the *Camelina* ISY gene using BLAST searches. The best 5 orthologs are listed in TABLE 12 with calculations of their percent homology to the Csa15g017550.1 gene encoding both 134 (SEQ TD NO: 2) and 168 (SEQ ID NO: 5) amino acid proteins. A CLUSTAL alignment is shown in FIG. 16.

Figure 18:
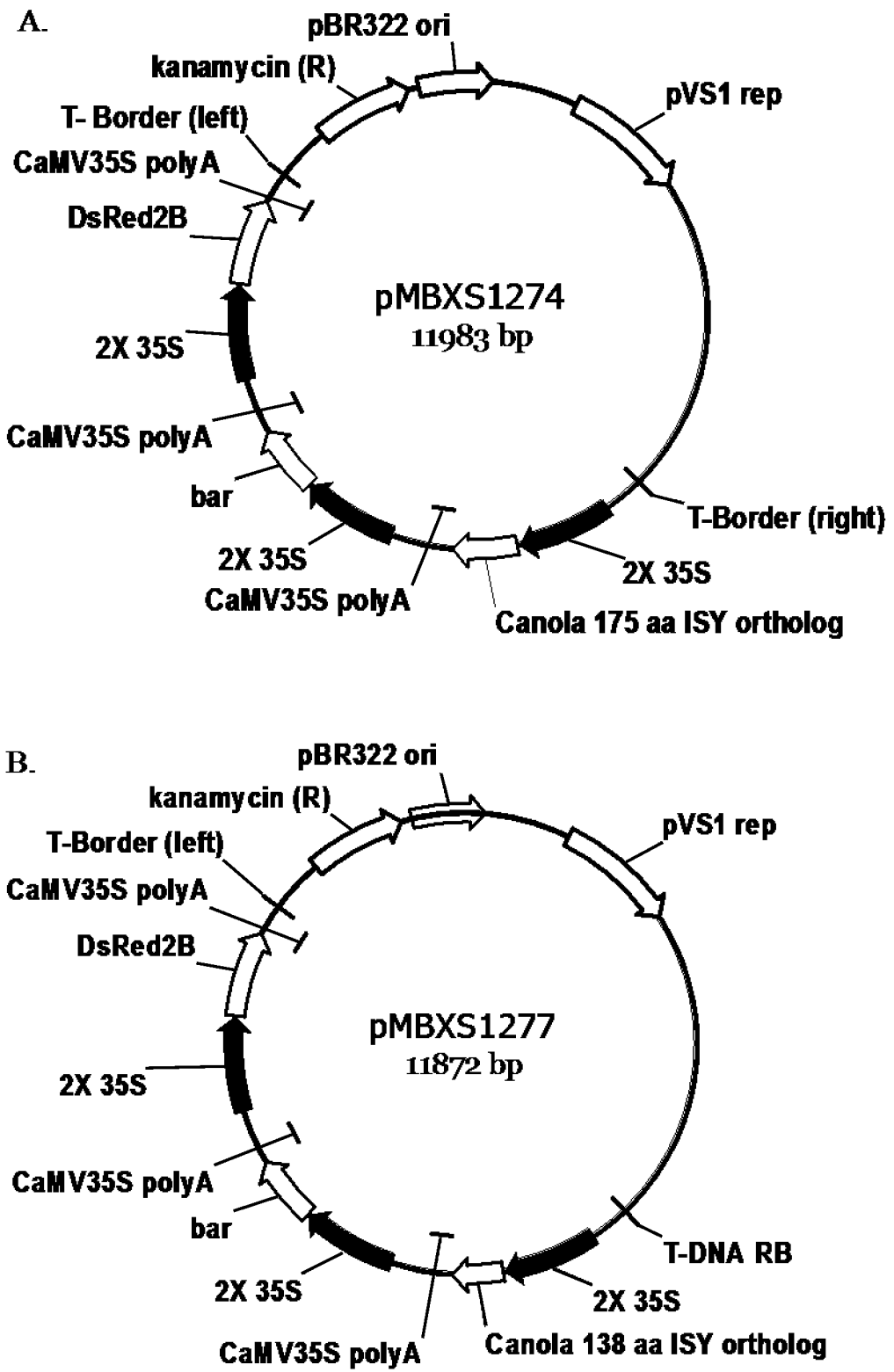
FIG. 18 shows maps of DNA constructs for transformation of a canola ortholog of the *Camelina* ISY gene into canola. A) Transformation construct pMBXS1274 (SEQ ID NO: 193) contains a gene fragment (gene sequence XM_013819595.2, SEQ ID NO: 70), expressed from the double enhanced CaMV35S constitutive promoter (2× 35S), that encodes the 175 amino acid protein in SEQ ID NO: 71. B) Construct pMBXS1277 (SEQ ID NO: 196) contains the SEQ ID NO: 194 DNA fragment, expressed from the double enhanced CaMV35S constitutive promoter (2× 35S), to produce the 138 amino acid protein of SEQ ID NO: 195. The visual marker DsRed2B in both constructs is used to identify transgenic seeds.

A CLUSTAL alignment of the 134 (SEQ ID NO: 2) and 168 (SEQ ID NO: 5) amino acid proteins of Csa5g017550 with the canola, soybean, and corn orthologs listed in TABLE 12 is shown in FIG. 17. Conserved residues in all proteins include a cysteine at residue 40, a leucine at residue 59, a cysteine at residue 98, and a cysteine at residue 138, all based on the numbering of the Csa1g01755 168 amino acid protein (SEQ TD NO: 5). In addition, a cysteine is conserved at residue 25 (based on numbering of Csa15g01750 168 amino acid protein, SEQ TD NO: 5) for all proteins except the truncated Csa15g017550 134 amino acid protein (SEQ TD NO: 2).

first codon of the gene sequence encoding the protein was thus changed so that it would encode a methionine instead of a leucine resulting in SEQ ID NO: 194 (gene sequence) and SEQ ID NO: 195 (protein sequence). Construct pMBXS1277 (FIG. 18B, SEQ ID NO: 196) was prepared that contains the SEQ ID NO: 194 DNA fragment expressed from the double enhanced CaMV35S constitutive promoter

TABLE 12

Orthologs to *Camelina* Csa15g017550 gene in Canola, Soybean and Corn.

| Crop | Gene ID[1] | Protein ID and/or SEQ ID NO of Protein | Size of encoded protein (amino acids) | % homology to protein in SEQ ID NO: 2[2] | % homology to protein in SEQ ID NO: 5[3] |
|---|---|---|---|---|---|
| *Camelina* | Csa15g017550.1 (SEQ ID NO: 1) | SEQ ID NO: 2 | 134 | 100 | 79.8 |
| *Camelina* | Csa15g017550.1 (SEQ ID NO: 6) | SEQ ID NO: 5 | 168 | 79.8 | 100 |
| canola | XM_013858728.2 (SEQ ID NO: 68) | XP_013714182 (SEQ ID NO: 69) | 175 | 41.1 | 54.3 |
| canola | XM_013819595.2 (SEQ ID NO: 70) | XP_013675049 (SEQ ID NO: 71) | 175 | 39.4 | 52.6 |
| canola | XM_013863271 (SEQ ID NO: 72) | XP_013718725 (SEQ ID NO: 73) | 175 | 40.6 | 53.7 |
| canola | XM_013819594.2 (SEQ ID NO: 74) | XP_013675048 (SEQ ID NO: 75) | 188 | 40.0 | 52.0 |
| soybean | XM_003550884 (SEQ ID NO: 88) | XP_003550932.1 (SEQ ID NO: 89) | 183 | 18.0 | 23.0 |
| soybean | XM_006579602 (SEQ ID NO: 90) | XP_006579665.1 (SEQ ID NO: 91) | 183 | 16.4 | 22.4 |
| soybean | NM_001249068.2 (SEQ ID NO: 92) | NP_001235997 (SEQ ID NO: 93) | 187 | 17.6 | 22.5 |
| soybean | XM_006604661 (SEQ ID NO: 94) | XP_006604724 (SEQ ID NO: 95) | 183 | 15.3 | 16.4 |
| corn | NM_001150116 (SEQ ID NO: 98) | NP_001143588 (SEQ ID NO: 99) | 217 | 13.8 | 15.6 |
| corn | NM_001154951 (SEQ ID NO: 100) | NP_001148423 (SEQ ID NO: 101) | 228 | 15.4 | 21.1 |
| corn | NM_001155569 (SEQ ID NO: 102) | NP_001149041 (SEQ ID NO: 103) | 211 | 16.1 | 22.3 |
| corn | XM_008657627 (SEQ ID NO: 104) | XP_008655849 (SEQ ID NO: 105) | 195 | 15.4 | 19.0 |
| corn | XM_008670754 (SEQ ID NO: 106) | XP_008668976 (SEQ ID NO: 107) | 176 | 16.5 | 23.0 |

[1]Csa gene IDs are from the *Camelina sativa* genome browser (website://www.camelinadb.ca/prairiegold/cgi-bin/gbrowse/camelina/);
[2]Percent homology over the whole protein of SEQ ID NO: 2 was determined using the ALIGNX alignment function of the Vector NTI software package (ThermoFisher).
[3]Percent homology over the whole protein of SEQ ID NO: 5 was determined using the ALIGNX alignment function of the Vector NTI software package (ThermoFisher).

A transformation construct was prepared to express one of the canola orthologs to the *Camelina* ISY gene (gene sequence XM_013819595.2, SEQ ID NO: 70 encoding protein sequence XP_013675049, SEQ ID NO: 71) in canola. Transformation construct pMBXS1274 (FIG. 18A, SEQ ID NO: 193) expresses a gene fragment that encodes the 175 amino acid protein in SEQ ID NO: 71 expressed from the double enhanced CaMV35S constitutive promoter (2× 35S). Construct pMBXS1274 was transformed into canola as described above and 93 T0 lines were isolated.

A Clustal Omega multiple sequence alignment was examined to identify a smaller gene fragment for expression that would yield a canola protein of similar length to 134 amino acid *Camelina* ISY sequence (SEQ ID NO: 2). FIG. 17 shows alignments of multiple orthologs to the *Camelina* ISY proteins, including 175 amino acid SEQ ID NO: 71, the chosen Canola ortholog for expression. A 138 amino acid protein fragment of SEQ ID NO: 71 was identified that was similar in length to, and aligned with, the *Camelina* ISY 134 amino acid protein in SEQ ID NO: 2 (FIG. 15). The first amino acid of this protein fragment was a leucine (L). The (2× 35S). Construct pMBXS1277 was transformed into canola as described above and T0 lines were isolated.

Example 7. Expression of CCP1 in Canola Using Constitutive and Seed-Specific Promoters and Identification of Up-Regulated Genes Having Homology to Genes from the Plant Invertase Inhibitor/Pectin Methylesterase Inhibitor Family Having Higher Seed Yield and Optionally Reduced Individual Seed Weight Vector pMBXO58 (FIG. 3), engineered for constitutive expression of CCP1, was transformed into *Agrobacterium* strain GV3101 (pMP90). The resulting strain was used to transform *Brassica napus* cv DH12075 as described above. Transgenic lines that are resistant to the herbicide bialaphos were obtained.

Screening of transgenic plants of canola expressing the CCP1 gene to identify plants with higher yield was performed as follows. The T1 seeds of several independent lines were grown in a randomized complete block design in a greenhouse maintained at 24° C. during the day and 18° C.

during the night. The T2 generation of seed from each line was harvested. Seed yield from each plant was determined by harvesting all of the mature seeds from a plant and drying them in an oven with mechanical convection set at 22° C. for two days. The weight of the entire harvested seed was recorded. The 1000 seed weight was measured to determine individual seed weight. The oil content of seeds can be measured using published procedures for preparation of fatty acid methyl esters (Malik et al. 2015, *Plant Biotechnology Journal*, 13, 675-688). A number of T1 lines were progressed to the T3 generation to generate homozygous lines followed by seed bulk up in the greenhouse to produce sufficient seed for field tests. These field tests were conducted in Saskatchewan in the 2017 growing season. The best canola line developed in these experiments was line MW82 which had showed a statistically significant increase in seed yield of 13% as compared to a control plant. The 1000 seed weight from this line (an indicator of seed size), in common with the other CCP1 lines tested was approximately 20% lower than the 1000 seed weight from the control plants. This reduced seed size was consistent among the CCP1 lines tested in the field trials. These data indicate that the constitutive expression of CCP1 in canola results in similar phenotypes to that observed in *Camelina*, i.e. increased seed yield and smaller seed size.

Tissue from plants with higher seed yield and optionally reduced individual seed weight were harvested as follows. Leaf tissue from plants in the vegetative stage and developing seed tissue from higher yield lines were harvested for RNA Seq analysis to identify up-regulated canola genes that have some sequence homology to genes from the plant invertase inhibitor/pectin methylesterase inhibitor family of genes or the gene ontology categories listed in TABLE 16. RNA Seq analysis was performed through a contract vendor and differential gene expression data was obtained and analyzed for up-regulated and down-regulated genes. Results of the RNA-SEQ experiments are described in Example 18.

Similar transformations were performed with construct pMBXO84 (FIG. 4, SEQ ID NO: 96) engineered for seed-specific expression of CCP1. Transgenic lines were obtained and advanced as described above for lines transformed with pMBXO58. Homozygous lines were grown in a field trial during the 2018 growth season in Elm Creek, Manitoba, Canada. The best lines contained a statistically significant 11% increase in seed yield compared to control plants with no significant difference in seed size. RNA SEQ analysis on tissue harvested from these lines can be performed to identify ISY related genes or genes in the gene ontology categories listed in TABLE 16.

Figure 20A:
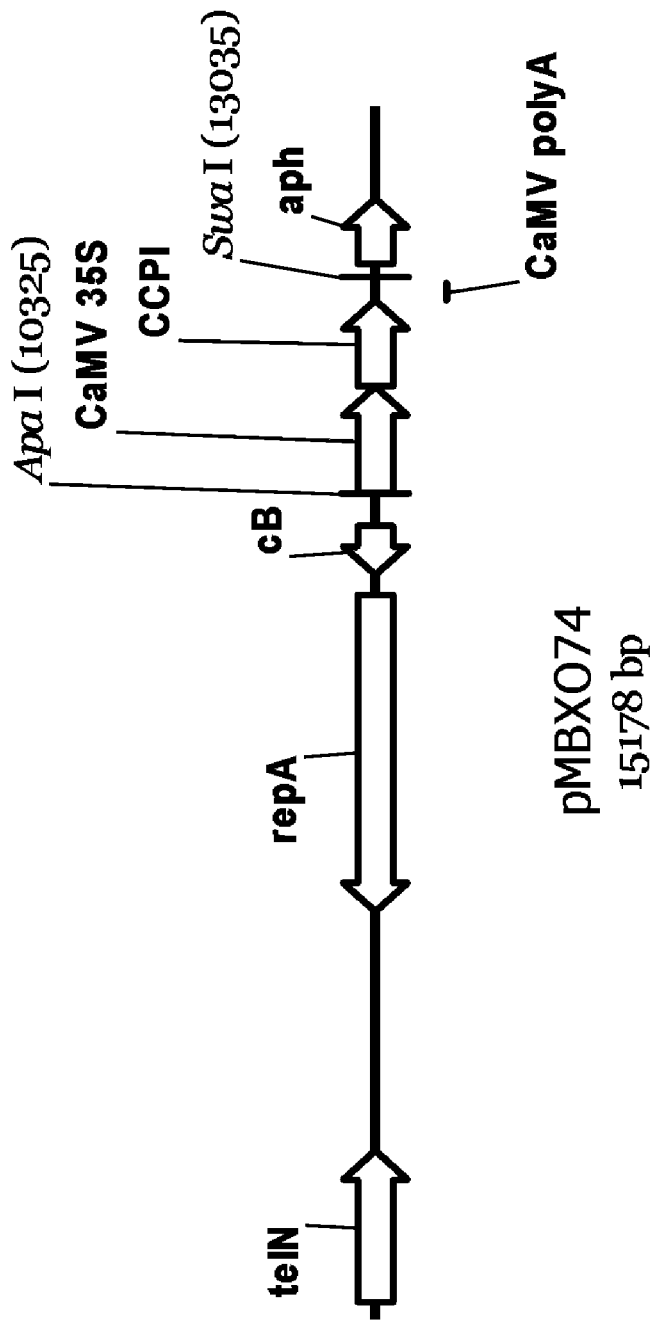
FIG. 20A-C shows maps of DNA for transformation into soybean. A) Plasmid pMBXO74 (SEQ ID NO: 128) contains a constitutive CaMV35S promoter for expression of CCP1 from *Chlamydomonas reinhardtii* in the pJAZZ (Lucigen) linear vector. The codon usage of the CCP1 gene is from the native *Chlamydomonas reinhardtii* gene. The 2.7 kb, Apa I-Swa I CaMV35S-CCP1-terminator fragment was excised and co-bombarded with a hygromycin cassette into soybean embryogenic cultures. B) DNA fragment pMBXO92 (SEQ ID NO: 129) contains a constitutive CaMV35S promoter for expression of CCP1 from *Chlamydomonas reinhardtii*. This CaMV35S promoter has a slightly different sequence than the one in pMBXO74. The CCP1 gene is codon optimized for soybean. The 2.2 kb, Hind III-Eco RI CaMV35S-CCP1-terminator fragment was co-bombarded with a hygromycin cassette into soybean embryogenic cultures. C) Plasmid pMBXO75 (SEQ ID NO: 130) contains a seed-specific expression cassette, driven by the promoter from the soya bean oleosin isoform A gene, for expression of CCP1 from *Chlamydomonas reinhardtii* in the pJAZZ (Lucigen) linear vector. The CCP1 gene is codon optimized for soybean. The 2.2 kb, SmaI Oleosin-CCP1-oleosin terminator fragment was excised and co-bombarded with a hygromycin cassette in soybean embryogenic cultures.

Example 8. Expression of CCP1 in Soybean Using Constitutive and Seed-Specific Promoters and Identification of Up-Regulated Genes Having Homology to Genes from the Plant Invertase Inhibitor/Pectin Methylesterase Inhibitor Family in Lines Having Higher Seed Yield and Optionally Reduced Seed Size To express CCP1 from a constitutive promoter in soybean, the pJAZZ (Lucigen) based linear vector pMBXO74 (FIG. 20A, SEQ ID NO: 128) was used. A DNA fragment containing the CaMV 35S promoter, the CCP1 gene, and the CaMV polyA termination sequence was excised from pMBXO74 by digestion with the Apa I and Swa I restriction enzymes (FIG. 20A) and a 2.7 kb DNA fragment was isolated and co-bombarded with a hygromycin cassette into soybean embryogenic cultures as described above.

Figure 20B:
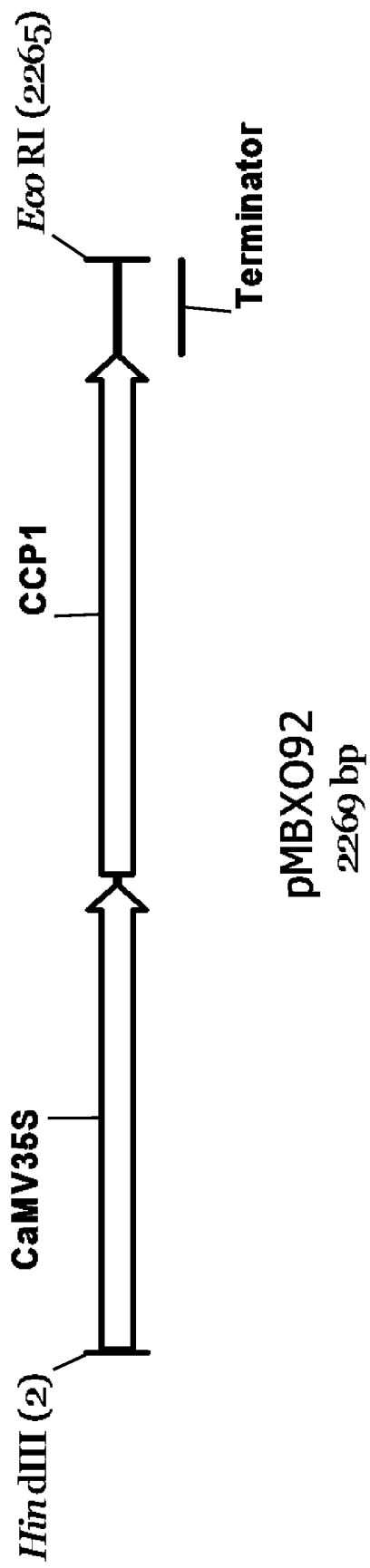

Another constitutive expression cassette for CCP1 was prepared and the Eco RI Hind III excised fragment used for bombardment is shown in FIG. 20B (pMBXO92, SEQ ID NO: 129). This expression cassette contains a CCP1 gene codon optimized for expression in soybean and was co-bombarded with a hygromycin cassette into soybean embryogenic cultures as described above.

Figure 20C:
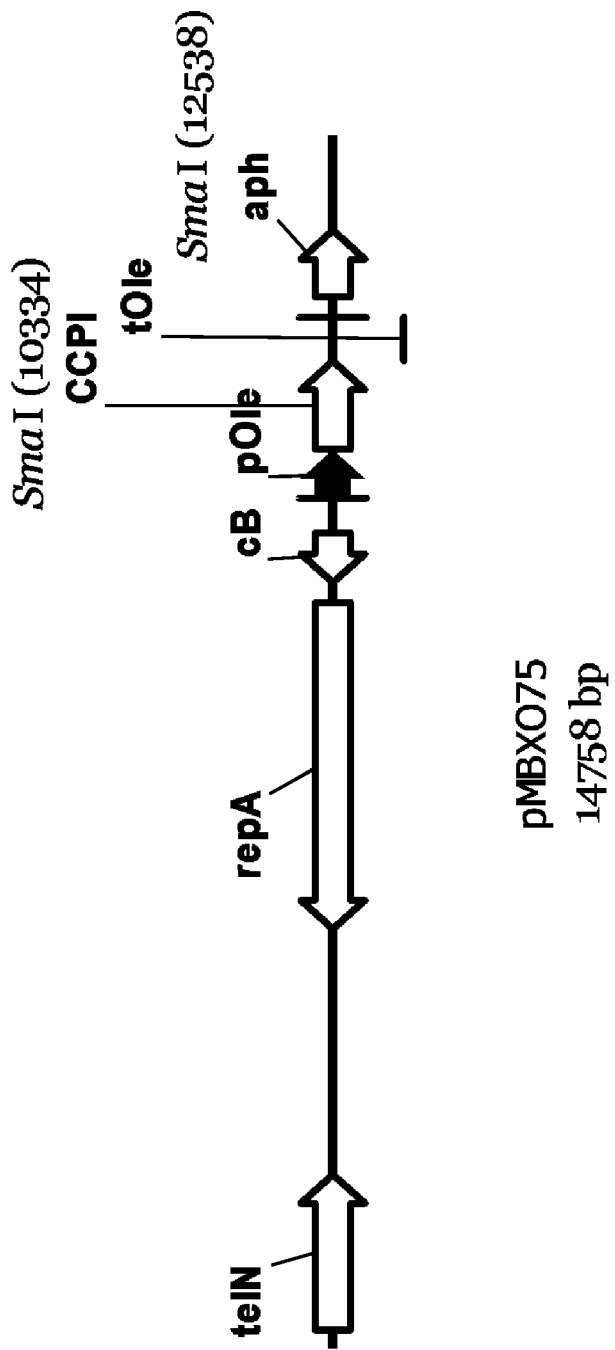

To express CCP1 from a seed-specific promoter in soybean, the pJAZZ (Lucigen) based linear vector pMBXO75 (FIG. 20C, SEQ ID NO: 130) was used. A DNA fragment containing the promoter from the soya bean oleosin isoform A gene, the CCP1 gene, and the soya bean oleosin isoform A termination sequence was excised from pMBXO75 by digestion with the Sma I restriction enzyme (FIG. 20C) and a 2.2 kb, Sma I Oleosin promoter-CCP1-oleosin terminator fragment was excised and co-bombarded with a hygromycin cassette into soybean embryogenic cultures.

Soybean plants from the pMBXO74, pMBXO92, and pMBXO75 transformations were generated as described above and grown for several generations.

Tissue from plants with higher seed yield and/or increased branching and optionally reduced individual seed weight was harvested as follows.

Leaf tissue from plants in the vegetative stage and developing seed tissue from higher yield lines was harvested, RNA was extracted, and RNASeq analysis was performed through a contract vendor. Differential gene expression data was obtained and analyzed for up-regulated and down-regulated genes. Results of these RNA SEQ experiments are described in Example 15.

Example 9. Expression of CCP1 in Rice Using Constitutive and Seed-Specific Promoters and Identification of Up-Regulated Genes Having Homology to Genes from the Plant Invertase Inhibitor/Pectin Methylesterase Inhibitor Family in Lines Having Higher Seed Yield and Optionally Reduced Seed Size Several promoters were chosen for expression of the CCP1 gene in rice based on their experimental or in silico predicted expression profiles in rice seed.

Figure 21:
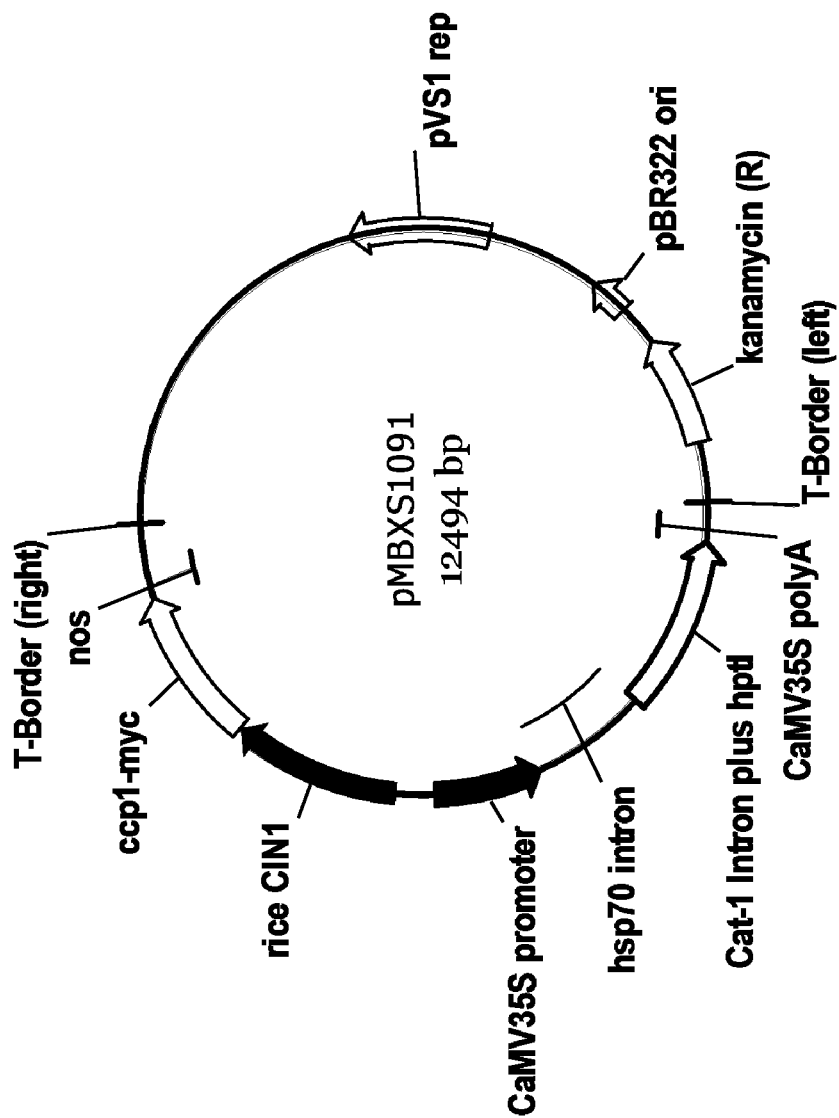
FIG. 21 shows a plasmid map of rice transformation vector pMBXS1091 (SEQ ID NO: 97). Plasmid pMBXS1091 contains an expression cassette for CCP1 from *Chlamydomonas reinhardtii* fused to a C-terminal myc tag. The expression of the ccp1-myc gene is controlled by the promoter from the rice beta-fructofuranosidase insoluble isoenzyme 1 (CIN1) gene (LOC_Os02g33110). An expression cassette for the hptI gene, driven by the CaMV35S promoter and including the hsp70 intron as well as an intron from the bean catalase-1 gene (CAT-1) imparts transgenic plants resistance to the herbicide hygromycin.

A transformation construct pMBXS1091 (FIG. 21) containing the promoter from the rice beta-fructofuranosidase insoluble isoenzyme 1 (CIN1) gene driving the expression of CCP1 fused to a myc tag was prepared. The CIN1 promoter was chosen based on in silico expression data showing expression throughout various developmental stages but with highest expression in the inflorescence and seeds (Rice Genome Annotation Project; website://rice-.plantbiology.msu.edu/cgi-bin/ORF_infopage.cgi?orf=LOC_Os02g33110.1).

Rice was transformed with construct pMBXS1091 as described above using callus of the rice cultivar Nipponbare. Regeneration of plantlets from transformed calli was performed and rooted plants were transferred into peat-pellets to allow for hardening of the roots. The plants were then kept in sealable bags for acclimatization. Plants were transferred into pots and grown in a greenhouse to maturity. The number of tillers and panicles in these primary transformants compared to the wild-type control lines are shown in TABLE 13.

TABLE 13

Comparison of number of tillers and panicles produced in primary transformants of transgenic rice transformed with pMBXS1091 compared with wild-type controls.

| | Tillers | | Panicles | |
|---|---|---|---|---|
| Line | Number | % of highest wild-type control[1] | Number | % of highest wild-type control[2] |
| NB-E (wild-type) | 29 | | 26 | 100 |
| NB-D (wild-type) | 36 | 100 | 22 | |
| NB-C (wild-type) | 24 | | 0 | |
| P1091-8B | 81 | 225 | 48 | 185 |
| P1091-9B | 51 | 142 | 43 | 165 |
| P1091-2C | 61 | 169 | 38 | 146 |
| P1091-8A | 48 | 133 | 35 | 135 |
| P1091-1A | 53 | 147 | 32 | 123 |
| P1091-8C | 51 | 142 | 30 | 115 |
| P1091-11C | 43 | 119 | 29 | 112 |
| P1091-2A | 32 | | 29 | 112 |
| P1091-2B | 35 | | 29 | 112 |
| P1091-6A | 48 | 133 | 28 | 108 |
| P1091-9D | 36 | 100 | 28 | 108 |
| P1091-10F | 57 | 158 | 27 | 104 |
| P1091-11B | 42 | 117 | 27 | 104 |
| P1091-4A | 48 | 133 | 27 | 104 |
| P1091-4B | 34 | | 27 | 104 |
| P1091-3B | 29 | | 26 | 100 |
| P1091-7A | 71 | 197 | 26 | 100 |
| P1091-10E | 30 | | 24 | |
| P1091-12B | 31 | | 24 | |
| P1091-11A | 32 | | 23 | |
| P1091-9A | 43 | 119 | 21 | |
| P1091-10A | 34 | | 20 | |
| P1091-1D | 24 | | 17 | |
| P1091-2E | 39 | 108 | 16 | |
| P1091-2D | 36 | 100 | 10 | |
| P1091-4C | 58 | 161 | 9 | |
| P1091-1B | 23 | | 7 | |
| P1091-1E | 19 | | 7 | |
| P1091-5A | 28 | | 6 | |
| P1091-9C | 45 | 125 | 4 | |
| P1091-10C | 63 | 175 | 0 | |
| P1091-10D | 46 | 128 | 0 | |
| P1091-4D | 33 | | 0 | |
| P1091-5C | 31 | | 0 | |

[1]The % to wild-type control was calculated using the best wild-type plant that produced the most tillers. Only % to control values equal or greater than 100% are shown.
[2]The % to wild-type control was calculated using the best wild-type plant that produced the most panicles. Only % to control values equal or greater than 100% are shown.

Seed is harvested from each panicle (T1 generation) and the seed yield per plant is calculated. T1 seed is grown in a greenhouse to produce T2 seed. The mass of the total seed per plant is collected to compare seed yield of transgenics to wild-type control plants. Samples of plant tissue were collected for RNA extraction, RNA was extracted, and RNASeq analysis was performed through a contract vendor. Differential gene expression data can be analyzed for up-regulated and down-regulated genes, with a focus on identifying genes from the plant invertase inhibitor/pectin methylesterase inhibitor gene family or the gene ontology categories listed in TABLE 16.

Example 10. Increased Expression of CCP1 in Maize Using Constitutive and Seed-Specific Promoters and Identification of Up-Regulated Genes Having Homology to Genes from the Plant Invertase Inhibitor/Pectin Methylesterase Inhibitor Family in Lines Having Higher Seed Yield and Optionally Reduced Seed Size For transformation of maize, a binary vector containing a promoter, the CCP1 gene, and a terminator is constructed. Appropriate constitutive promoters for maize include monocot promoters listed in TABLE 2. For example, an expression cassette containing the hybrid cab5/hsp70 intron promoter (SEQ ID NO: 64) operably linked to the CCP1 gene from *Chlamydomonas reinhardtii*, operably linked to the nos terminator of the nopaline synthase gene can be used. An expression cassette for a selectable marker, such as the bar gene imparting resistance to the herbicide bialaphos, is included.

For seed specific expression, a binary vector containing a promoter, the CCP1 gene, and a terminator is constructed. Appropriate seed-specific promoters include monocot promoters listed in TABLE 2. For example, an expression cassette containing the maize β-fructofuranosidase insoluble isoenzyme 1 (CIN1) promoter (SEQ ID NO: 66) operably linked to the CCP1 gene from *Chlamydomonas reinhardtii*, operably linked to the nos terminator of the nopaline synthase gene can be used. An expression cassette for a selectable marker, such as the bar gene imparting resistance to the herbicide bialaphos, is included.

In preparation for transformation, the binary vector is transformed into an *Agrobacterium tumefaciens* strain, such as *A. tumefaciens* strain EHA101. *Agrobacterium*-mediated transformation of maize can be performed following a previously described procedure (Frame et al. (2006), *Agrobacterium* Protocols, Wang K., ed., Vol. 1, pp 185-199, Humana Press) as described above.

Bialaphos-resistant embryogenic callus lines are regenerated as described above and transferred to soil. Plants are grown in a greenhouse to produce T1 seed. T1 seed is grown in soil in a greenhouse to produce T2 seed. The mass of the total seed per plant is collected to compare seed yield of transgenics to wild-type control plants.

RNA is extracted and RNASeq analysis is performed through a contract vendor. Differential gene expression data can be analyzed for up-regulated and down-regulated genes, with a focus on identifying genes from the plant invertase inhibitor/pectin methylesterase inhibitor gene family or the gene ontology categories listed in TABLE 16.

Example 11. Use of Genome Editing to Alter the Expression of the ISY Gene in *Camelina*, or Orthologs of the *Camelina* ISY Gene in Other Crops The expression of ISY gene can be modified by replacing the native promoter sequences upstream of the coding sequence with a promoter containing a stronger or more optimal tissue-specific expression profile. Example promoters useful for this purpose are listed in TABLE 1 and TABLE 2. To increase the concentration of the gene product, a stronger promoter than the native one is used. The tissue specificity of expression of the promoter can also be modified, to increase or reduce the types of tissues where the gene is expressed.

Figure 22:
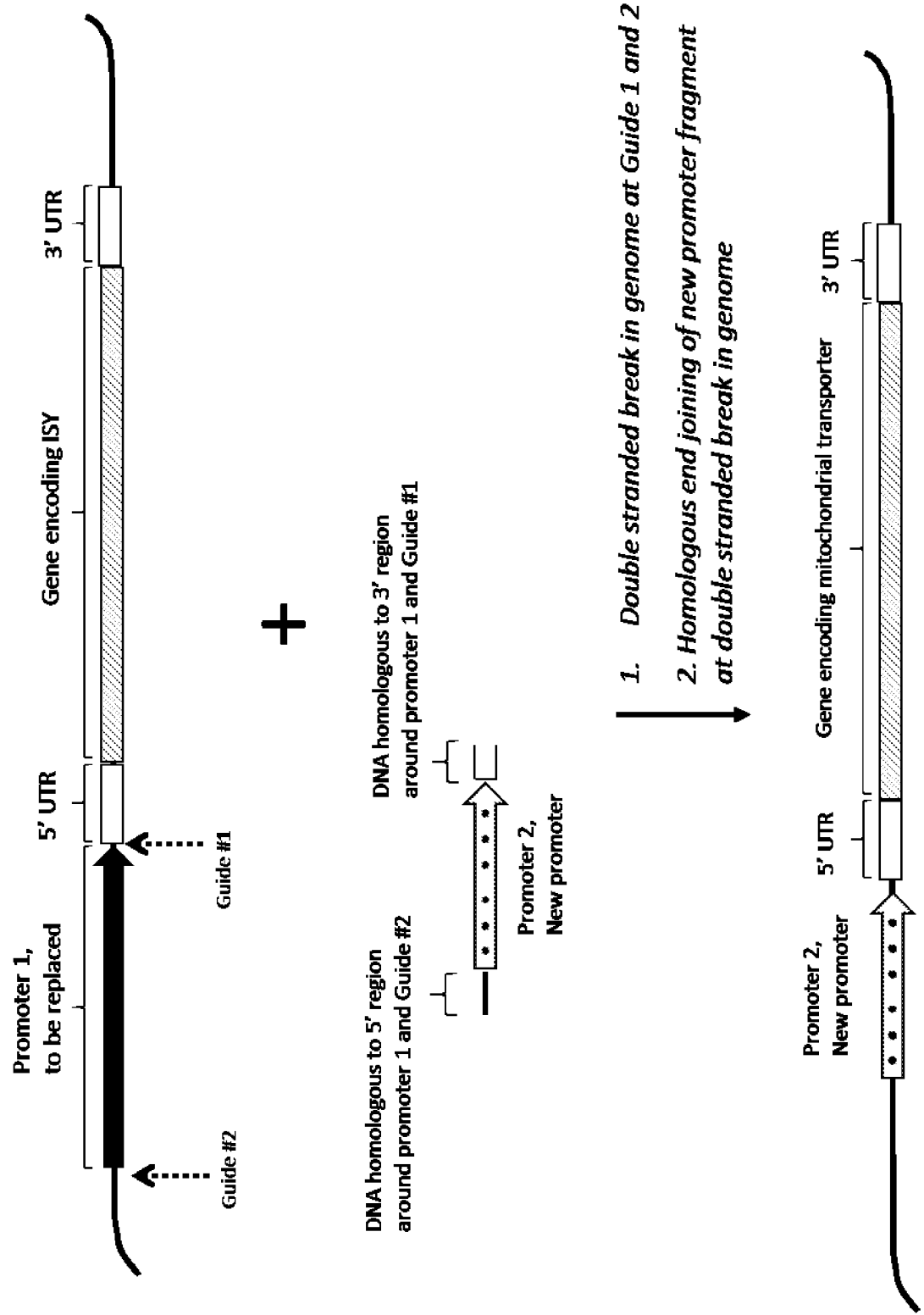
FIG. 22 details a strategy for promoter replacement in front of the native Csa15g017550 sequence using genome editing and a homologous directed repair mechanism. Guide #1 and Guide #2 are used to excise the promoter to be replaced (Promoter 1). A new promoter cassette (Promoter 2), flanked by sequences with homology to the upstream and downstream region of Promoter 1, is introduced and is inserted into the site previously occupied by Promoter 1 using the homologous directed repair mechanism.

Replacement of the native promoter can be achieved using a genome editing enzyme to make the targeted double stranded cuts to remove the native promoter (Promoter 1) (FIG. 22). A new promoter (Promoter 2) is then inserted via a homology-directed repair (HDR) repair mechanism, in which the new promoter is flanked by DNA sequences with homology to regions upstream and downstream of the original native promoter (Promoter 1). In one embodiment, these promoter flanking regions can additionally be flanked by guide target sequences and adjacent PA1 sites to allow release of the promoter by Cas9 from a construct or other DNA.

There are multiple methods to achieve double stranded breaks in genomic DNA, including the use of zinc finger nucleases (ZFN), transcription activator-like effector nucleases (TALENs), engineered meganucleases, and the CRISPR/Cas system (CRISPR is an acronym for clustered, regularly interspaced, short, palindromic repeats and Cas an abbreviation for CRISPR-associated protein) (for review see Khandagale & Nadaf (2016), Plant Biotechnol Rep, 10:327-343). CRISPR/Cas mediated genome editing is the easiest of these methods to implement since all that is needed is the Cas9 enzyme and a single guide RNA (sgRNA) with homology to the modification target to direct the Cas9 enzyme to desired cut site for cleavage. The ZFN, TALENs, and engineered meganucleases methods require more complex design and protein engineering to bind the DNA sequence to enable editing. For this reason, the CRISPR/Cas mediated system has become the method of choice for genome editing.

The sgRNA used in the CRISPR/Cas system is a synthetic RNA chimera created by fusing crRNA with tracrRNA. The guide sequence, located at the 5' end of the sgRNA, confers DNA target specificity. Therefore, by modifying the guide sequence, it is possible to create sgRNAs with different target specificities. The canonical length of the guide sequence is ~20 bp. In plants, sgRNAs have been expressed using plant RNA polymerase III promoters, such as U6 and U3. Cas9 expression plasmids for use in the methods of the invention can be constructed as described in the art.

It will be apparent to those skilled in the art that any of these systems can be used for generating the double stranded breaks necessary for promoter excision in this example.

In this example the CRISPR/Cas system is used. There are many variations of the CRISPR/Cas system that can be used for this technology including the use of wild-type Cas9 from *Streptococcus pyogenes* (Type II Cas) (Barakate & Stephens (2016), Frontiers in Plant Science, 7:765; Bortesi & Fischer (2015), Biotechnology Advances 5:33, 41; Cong et al. (2013), Science, 339:819; Rani et al. (2016), Biotechnology Letters, 1-16; Tsai et al. (2015), Nature Biotechnology, 33:187), the use of a Tru-gRNA/Cas9 in which off-target mutations were significantly decreased (Fu et al. (2014), Nature Biotechnology, 32:279; Osakabe et al. (2016), Scientific Reports, 6:26685; Smith et al. (2016), Genome Biology, 17:1; Zhang et al. (2016), Scientific Reports, 6:28566), a high specificity Cas9 (mutated *S. pyogenes* Cas9) with little to no off target activity (Kleinstiver et al. (2016), Nature 529:490; Slaymaker et al. (2016), Science, 351:84), the Type I and Type III Cas Systems in which multiple Cas protein need to be expressed to achieve editing (Li et al. (2016), Nucleic Acids Research, 44:e34; Luo et al. (2015), Nucleic Acids Research, 43:674), the Type V Cas system using the Cpf1 enzyme (Kim et al. (2016), Nature Biotechnology, 34:863; Toth et al. (2016), Biology Direct, 11:46; Zetsche et al. (2015), Cell, 163:759), DNA-guided editing using the NgAgo Agronaute enzyme from *Natronobacterium gregoryi* that employs guide DNA (Xu et al. (2016), Genome Biology, 17:186), and the use of a two vector system in which Cas9 and gRNA expression cassettes are carried on separate vectors (Cong et al. (2013), Science, 339:819).

It will be apparent to those skilled in the art that any of the CRISPR enzymes can be used for generating the double stranded breaks necessary for promoter excision in this example. There is ongoing work to discover new variants of CRISPR enzymes which, when discovered, can also be used to generate the double stranded breaks around the native promoters of the ISY genes.

In this example, the CRISPR/Cas9 system is used. FIG. 22 details a strategy for promoter replacement in front of a native ISY sequence using CRISPR/Cas9 and a homologous directed repair mechanism. An sgRNA containing Guide #1 and Guide #2 are used to excise the promoter to be replaced (Promoter 1). A new promoter cassette (Promoter 2), flanked by sequences with homology to the upstream and downstream region of Promoter 1, is introduced and is inserted into the site previously occupied by Promoter 1 using the homologous directed repair mechanism.

It will be apparent to those skilled in the art that many different promoters are available for expression in plants. TABLE 1 and TABLE 2 list some of the additional options for use in dicots and monocots that can be used as replacement promoters for the genome editing strategy.

The promoter replacement strategy shown in FIG. 22 can also be performed in other crops containing orthologs of the *Camelina* ISY gene to modify the expression of the ortholog, including soybean, corn, and canola. The native promoter in front of orthologs of the *Camelina* ISY gene in soybean, corn, and canola listed in TABLE 12 can be replaced with a different promoter using genome editing methods such as the CRISPR-Cas method.

Example 12. Expression of Orthologs to the *Camelina* ISY Gene, or Genes with Homology to Plant Invertase Inhibitors/Pectin Methylesterase Inhibitors Identified in CCP1 Lines, in Soybean For transformation of soybean with orthologs to the *Camelina* Csa15g017550 ISY gene described in TABLE 12, or for transformation of genes with homology to plant invertase inhibitors/pectin methylesterase inhibitors or genes within the GO categories of TABLE 16 that were identified using the procedures described in Example 8 and Example 15 for CCP1 overexpressing soybean lines, an expression cassette containing a promoter, the gene of interest, and a polyadenylation sequence is prepared. Suitable promoters for dicots are listed in TABLE 1. For example, an expression cassette can contain the constitutive CaMV 35S promoter (SEQ ID NO: 108), the ISY gene, and the CaMV polyadenylation sequence. A DNA fragment containing the cassette is purified and co-bombarded with a hygromycin cassette into soybean embryogenic cultures.

The purified DNA fragment(s) are introduced into embryogenic cultures of soybean *Glycine max* cultivars X5 and Westag97 via biolistics, to obtain transgenic plants. The transformation, selection, and plant regeneration of soybean is performed as described above.

Germinated transformed embryos are transferred to soil as described above and grown at 18-h photoperiod at a light intensity of 300-400 µmol m$^{-2}$ s$^{-1}$.

T1 seeds are harvested and planted in soil and grown in a controlled growth cabinet at 26/24° C. (day/night), 18 h photoperiod at a light intensity of 300-400 µmol m$^{-2}$ s$^{-1}$. Plants are grown to maturity and T2 seed is harvested. Seed yield per plant and oil content of the seeds is measured.

There are also *Agrobacterium*-mediated transformation methods for soybean that can be used to generate similar transgenic plants expressing the ISY gene.

Example 13. Expression of Orthologs to the *Camelina* ISY Gene, or Genes with Homology to Plant Invertase Inhibitors/Pectin Methylesterase Inhibitors Identified in CCP1 Lines, in Rice and Maize For transformation of rice with genes with homology to plant invertase inhibitors/pectin methylesterase inhibitors identified using the procedures described in Example 9 for CCP1-overexpressing lines, a binary vector containing an expression cassette with a promoter, the gene of interest, and a polyadenylation sequence, as well as an expression cassette for a selectable marker, such as the hygromycin resistance marker, is prepared. The ISY and hygromycin resistance cassette can be co-localized on one binary vector or, alternatively, positioned on two separate binary vectors that can be co-bombarded.

Several promoters are chosen for expression of genes with homology to plant invertase inhibitors/pectin methylesterase inhibitors in rice based on their experimental or in silico predicted expression profiles in rice seed and are shown in TABLE 2, above. It will be apparent to those skilled in the art that TABLE 2 is not an exhaustive list of promoters that can be used for expression in rice and that there are many additional promoters that would work to practice the invention, depending on the tissue specificity desired for expression of the transgene. The promoter from the rice ADP-glucose pyrophosphorylase (AGPase) gene (TABLE 2, SEQ ID NO: 55) was chosen since it has been shown to be expressed in the seed as well as the phloem of vegetative tissues in rice (Qu and Takaiwa (2004), Plant Biotechnology Journal, 2:113-125). The promoter from the rice glutelin C (GluC) gene (TABLE 2, promoter with SEQ ID NO: 56) has been shown to be expressed in the whole endosperm of rice seed (Qu et al. (2008), Journal of Experimental Biology, 59:2417-2424). The promoter from the rice beta-fructofuranosidase insoluble isoenzyme 1 (CIN1) gene (TABLE 2, SEQ ID NO: 57) was chosen based on in silico expression data showing expression throughout various developmental stages but with highest expression in the inflorescence and seeds (Rice Genome Annotation Project; website://rice-.plantbiology.msu.edu/cgi-bin/ORF_infopage.cgi?orf=LOC_Os02g33110.1). The prepared transformation construct is transformed into callus of the rice cultivar Nipponbare using *Agrobacterium* mediated transformation as described above.

Plantlets are regenerated from calli and transferred to peat-pellets and then soil as described above. Plants are grown in a greenhouse to maturity prior to seed harvest (T1 generation). T1 seed is grown in a greenhouse to produce T2 seed. The mass of the total seed per plant is collected to compare seed yield of transgenics to wild-type control plants.

For transformation of maize with orthologs to the *Camelina* Csa15g017550 ISY gene described in TABLE 12, or for transformation of genes with homology to plant invertase inhibitors/pectin methylesterase inhibitors identified using the procedures described in Example 10 for maize CCP1-overexpressing lines, a binary vector containing a promoter, the gene of interest, and a terminator is constructed. Appropriate promoters include the monocot promoters listed in TABLE 2. For example, an expression cassette containing the hybrid cab5/hsp70 intron promoter (SEQ ID NO: 64) operably linked to the ISY gene, operably linked to the nos terminator of the nopaline synthase gene can be used. An expression cassette for a selectable marker, such as the bar gene imparting resistance to the herbicide bialaphos, is included. In preparation for transformation, the binary vector is transformed into an *Agrobacterium tumefaciens* strain, such as *A. tumefaciens* strain EHA101. *Agrobacterium*-mediated transformation of maize can be performed following a previously described procedure (Frame et al. (2006), *Agrobacterium* Protocols, Wang K., ed., Vol. 1, pp 185-199, Humana Press) as described above. Plants are regenerated as described above and are transferred to soil. Plants are grown in a greenhouse to produce T1 seed. T1 seed is grown in soil in a greenhouse to produce T2 seed. The mass of the total seed per plant is collected to compare seed yield of transgenics to wild-type control plants.

Example 14. Expression of the *Camelina* ISY Gene, its Orthologs, or Genes with Homology to Plant Invertase Inhibitors/Pectin Methylesterase Inhibitors, in Plants in Combination with CCP1 Genes The *Camelina* ISY gene, ortholog genes, or genes with homology to plant invertase inhibitors/pectin methylesterase inhibitors can be co-expressed in a plant with a CCP1 gene by placing expression cassettes for the *Camelina* ISY gene, an ortholog gene, or a gene with homology to a plant invertase inhibitor/pectin methylesterase inhibitor and the CCP1 gene on the same transformation vector and transforming the plant. The gene cassettes can contain a variety of different promoters to control expression, including seed-specific promoters, constitutive promoters, leaf-specific promoters, or other tissue-specific promoters which will be apparent to those skilled in the art. An expression cassette for a selectable marker, such as the bar gene, providing resistance to the herbicide bialaphos, is also included. The selectable marker is chosen based on the plant to be transformed.

Four examples given here are constructs in which the expression of both genes is controlled by constitutive CaMV35S promoter and terminators, the expression of both genes is controlled by seed-specific oleosin promoters and matching oleosin terminators, the *Camelina* ISY, ortholog gene, or gene with homology to a plant invertase inhibitor/pectin methylesterase inhibitor expression is controlled by the 35S promoter and the CCP1 gene is controlled by the oleosin promoter, and the *Camelina* ISY gene, ortholog gene, or gene with homology to a plant invertase inhibitor/pectin methylesterase inhibitor expression is controlled by the oleosin promoter and the CCP1 gene is controlled by the constitutive promoter. These vectors (constructs A, B, C, and D in TABLE 14) are designed for transformation into dicots, including *Camelina* and canola, whose transformation procedures are described above. Co-transformation of constructs A and B into the same plant may provide enhanced yield benefits.

TABLE 14

Example expression cassettes for co-expression of an ISY or CWII gene with CCP1.

| | Expression Cassette 1 | | | Expression Cassette 2 | | |
|---|---|---|---|---|---|---|
| Construct | promoter | gene | terminator | promoter | gene | terminator |
| A | constitutive CaMV35S | Camelina ISY gene or gene with homology to plant invertase inhibitor/pectin methylesterase inhibitor | CaMV35S | constitutive CaMV35S | CCP1 | CaMV35S |
| B | seed-specific oleosin | Camelina ISY gene or gene with homology to plant invertase inhibitor/pectin methylesterase inhibitor | oleosin | seed-specific oleosin | CCP1 | oleosin |
| C | constitutive CaMV35S | Camelina ISY gene or gene with homology to plant invertase inhibitor/pectin methylesterase inhibitor | CaMV35S | seed-specific oleosin | CCP1 | oleosin |
| D | seed-specific oleosin | Camelina ISY gene or gene with homology to plant invertase inhibitor/pectin methylesterase inhibitor | oleosin | constitutive CaMV35S | CCP1 | CaMV35S |

It will be apparent to those skilled in the art that co-expression of ISY or CWII and CCP1 genes can also be achieved by co-transformation of separate vectors that contain an ISY or CWII expression cassette on one plasmid and a CCP1 expression cassette on another plasmid and screening the transformants for the presence of both expression cassettes. It will also be apparent to those skilled in the art that co-expression of ISY or CWII and CCP1 genes can be achieved by crossing plants expressing the individual genes to obtain a plant expressing both genes.

Vectors selected from A, B, C and/or D (TABLE 14) can be optimized for transformation into soybean by replacing the bar expression cassette with an expression cassette encoding the hygromycin gene. A DNA fragment(s) containing the CCP1 gene, ISY or CWII gene, and hygromycin resistance gene expression cassettes can be excised and introduced into soybean using the biolistics method described above. In some cases, it may be desirable to optimize the promoter's expression for CCP1 and ISY or the gene with homology to a plant invertase inhibitor/pectin methylesterase inhibitor. Promoters for expression of these transgenes can be selected from those listed in TABLE 1, depending on the desired tissue specificity for expression, or can be selected from any other promoter that provides good expression in dicots.

Vectors selected from A, B, C and/or D (TABLE 14) can be optimized for transformation into rice by replacing the bar expression cassette with an expression cassette encoding the hygromycin gene. In some instances, it may be desirable to optimize the promoters driving the expression of the ISY or the gene with homology to a plant invertase inhibitor/pectin methylesterase inhibitor and CCP1 genes using a monocot specific promoter, such as the ones described in TABLE 2, above, or any other promoter that provides good expression in monocots. The choice of the promoter may be dictated by the desired tissue specificity for expression. The modified binary vectors are introduced into an *Agrobacterium* strain, such as *Agrobacterium* strain AGL1, and the rice transformation procedure described above is followed.

Vectors selected from A, B, C and/or D (TABLE 14) can be optimized for transformation into maize by using a monocot specific promoter, such as the ones described in TABLE 2, or any other promoter that provides good expression in monocots, to drive the expression of the ISY or the gene with homology to a plant invertase inhibitor/pectin methylesterase inhibitor and CCP1 genes. The choice of the promoter may be dictated by the desired tissue specificity for expression. The modified binary vectors are introduced into an *Agrobacterium* strain, such as *A. tumefaciens* strain EHA101, and the maize transformation procedure described above is followed.

Example 15. Identification of Up- and Down-Regulated Genes in Soybean Lines Expressing the CCP1 Gene Using RNA Sequencing Select soybean T2 generation lines, produced as described in Examples 5 and 8, were grown in a growth chamber to generate samples for analysis by RNA Sequencing. TABLE 15 shows lines that were selected for analysis, the tissue type collected, and classifies the lines into groups for analysis purpose. Samples were harvested at the indicated stage and quickly frozen in liquid nitrogen. Samples were stored at −80° C. RNA was extracted using the Omega Bio-Tek E.Z.N.A Plant RNA kit and shipped to a contract service provider that performed RNA Sequencing and data processing.

TABLE 15

Glycine max samples used in the RNA-seq analysis.

| Group | Tissue* | Line** | CCP1 |
|---|---|---|---|
| A | Leaf | Westag wild-type control | − |
| B | Leaf | Null line | − |
| C | Leaf | pMBXO74 (35S-CCP1, heterozygous) | + |
| C-1 | Leaf | pMBXO74 (35S-CCP1, homozygous) | + |
| D | Maturing seed | Westag control | − |
| E | Maturing seed | Null line | − |
| F | Maturing seed | pMBXO74 (35S-CCP1, heterozygous) | + |
| F-1 | Maturing seed | pMBXO74 (35S-CCP1, homozygous) | + |
| L | Maturing seed | Westag control | − |
| M | Maturing seed | Null line | − |
| P | Maturing seed | pMBXO75 (pOle-CCP1, homozygous) | + |
| H | Developing seed | Westag control | − |
| J | Developing seed | Null line | − |
| K | Developing seed | pMBXO75 (pOle-CCP1, homozygous) | + |

*Harvested tissue stages are as follows: Leaf, expanded leaf at V6 stage collected from 5.5 week old plants; Maturing yellow green seed, 1.2-1.3 cm in size collected from 8 week old plants; developing green seed, 1 cm in size collected from 7 week old plants
**Null line generated through segregation.

Due to their possible relationship to the function of the *Camelina* ISY gene, the Gene Ontology (GO) terms listed in TABLE 16 were investigated. The objective of this work was to search the *Glycine max* genome for genes that were differentially expressed in CCP1+ lines that could be associated with one or more of these GO terms. Nearly all genes within the RNA-seq data set had a corresponding best BLAST hit in the *Arabidopsis thaliana* genome, which is very well-annotated with respect to associated GO terms. Therefore, for each of the GO terms in TABLE 16, a list of *Arabidopsis thaliana* genes associated with the GO term was made. All genes within the *Glycine max* genome that had one of those *Arabidopsis thaliana* genes as its best BLAST hit were then identified. Among these *Glycine max* genes, some were up- or down-regulated in CCP1 lines in a statistically significant way; that is, a Tukey test suggested that the probability was greater than 90% that the means of the transcript levels in transgenic vs. wild-type lines were different.

Differentially Expressed Genes in Leaves:

There were a large number of very significant changes in harvested leaf tissue, especially in the homozygous line (C-1) compared to the wild-type control (A) (For line information, see TABLE 15). The up- and down-regulated genes along with the comparison corresponding to the fold changes are shown in TABLE 17. Only comparisons in which the fold difference between the two lines C-1 and A exceeds 2 are shown. It is important to note that genes whose expression was also up- or down-regulated in the null line (B) compared to the control line (A) were excluded from consideration because they may not have been a result of addition of the CCP1 gene to the plant.

TABLE 16

Gene Ontology categories used to investigate RNA Sequencing data.

| GO category | Description |
|---|---|
| GO: 0030570 | pectate lyase activity |
| GO: 0030599 | pectinesterase activity |
| GO: 0046910 | pectinesterase inhibitor activity |
| GO: 0052793 | pectin acetylesterase activity |

Figure 23:
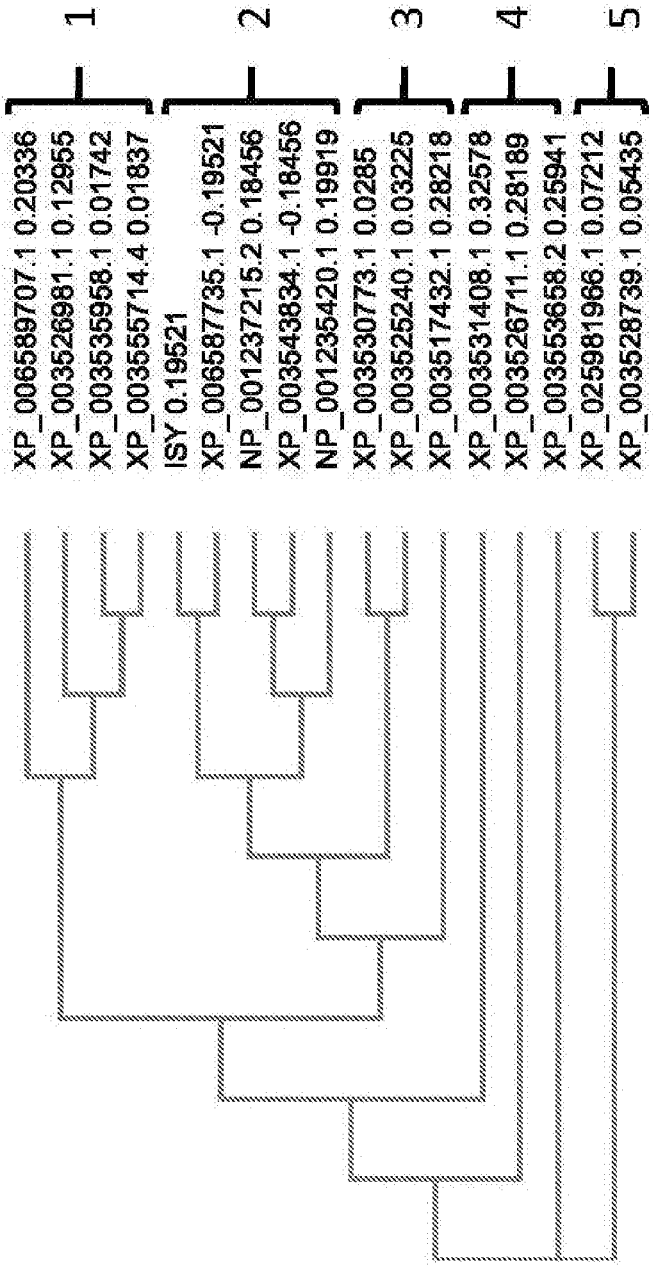
FIG. 23 shows a phylogenetic tree (cladogram) of proteins encoded by differentially expressed genes in select gene ontology (GO) categories that were identified in RNA Sequencing data of leaves of a soybean line expressing the CCP1 gene from a constitutive promoter. The 168 amino acid *Camelina* ISY protein (SEQ ID NO: 5) was included in the alignment. The select GO categories are shown in TABLE 16. The proteins were grouped into five categories for further analysis and include: Group 1, XP_003526981.1 (SEQ ID NO: 141), XP_006589707.1 (SEQ ID NO: 142), XP_003535958.1 (SEQ ID NO: 143), and XP_003555714.4 (SEQ ID NO: 144); Group 2, *Camelina* ISY protein (SEQ ID NO: 5), XP_003543834.1 (SEQ ID NO: 145), XP_006587735.1 (SEQ ID NO: 146), NP_001237215.2 (SEQ ID NO: 147), and NP_001235420.1 (SEQ ID NO: 148); Group 3, XP_003517432.1 (SEQ ID NO: 149), XP_003530773.1 (SEQ ID NO: 150), XP_003525240.1 (SEQ ID NO: 151); Group 4, XP_003531408.1 (SEQ ID NO: 152), XP_003526711.1 (SEQ ID NO: 153), XP_003553658.2 (SEQ ID NO: 154); Group 5, XP_025981966.1 (SEQ ID NO: 155), XP_003528739.1 (SEQ ID NO: 156).

To further sort and examine the relationship of the differentially expressed genes in CCP1+ soybean lines in these Gene Ontology (GO) categories, a phylogenetic tree (cladogram) (FIG. 23) was created using the CLUSTAL Omega program (website://www.ebi.ac.uk/Tools/msa/clustalo/). The *Camelina* ISY gene was also included to determine if any of the differentially expressed soybean genes were similar to the *Camelina* ISY gene. Using the phylogenetic tree (FIG. 23) as well as the CLUSTAL Omega multiple sequence alignments, the proteins encoded by the differentially expressed genes were grouped into five groups (FIG. 23 and TABLE 17). In the phylogenetic tree (FIG. 23), the protein encoded by the *Camelina* ISY gene grouped with the soybean proteins in group 2 which are classified with the GO terms of pectinesterases or cell wall/vacuolar inhibitors of fructosidase 1. The group 2 proteins were investigated more closely with sequence alignments and the *Camelina* ISY gene appeared to be more closely matched to the cell wall/vacuolar inhibitors of fructosidase 1 (Genes NP_001237215.2 and NP_001235420.1; FIGS. 25 and 26).

Alignments of proteins in each of the other phylogenetic groupings in TABLE 17 were performed and show a high degree of similarity (FIGS. 24, 27, 28, and 29).

TABLE 17

Differentially expressed *Glycine max* genes from the plant invertase inhibitor/pectin methylesterase inhibitor superfamily in CCP1+ homozygous line (C-1) and null line (B) vs. wild type (A).

| Glycine max locus | Protein ID | A. thaliana locus | A. thaliana description | Fold (C-1)/A | Fold B/A* | Assigned group in phylogenetic tree |
|---|---|---|---|---|---|---|
| LOC100787082 | XP_003526981.1 (SEQ ID NO: 141) | AT1G67750 | Probable pectate lyase 5 | 3.937 | 0.133 | 1 |
| LOC100789303 | XP_006589707.1 (SEQ ID NO: 142) | AT5G04310 | Pectate lyase | 4.172 | DNP | |
| LOC100781845 | XP_003535958.1 (SEQ ID NO: 143) | AT4G13710 | Probable pectate lyase 15 | 106.093 | DNP | |
| LOC100808253 | XP_003555714.4 (SEQ ID NO: 144) | AT1G04680 | Probable pectate lyase 1 | 16.906 | DNP | |
| LOC100810259 | XP_003543834.1 (SEQ ID NO: 145) | AT3G29090 | Pectinesterase 31 | 0.079 | DNP | 2 |
| LOC100786786 | XP_006587735.1 (SEQ ID NO: 146) | AT3G29090 | Pectinesterase 31 | 4.297 | DNP | |

TABLE 17-continued

Differentially expressed *Glycine max* genes from the plant invertase inhibitor/pectin methylesterase inhibitor superfamily in CCP1+ homozygous line (C-1) and null line (B) vs. wild type (A).

| *Glycine max* locus | Protein ID | *A. thaliana* locus | *A. thaliana* description | Fold (C-1)/A | Fold B/A* | Assigned group in phylogenetic tree |
|---|---|---|---|---|---|---|
| LOC100500640 | NP_001237215.2 (SEQ ID NO: 147) | AT1G47960 | Cell wall/vacuolar inhibitor of fructosidase 1 | 0.003 | DNP | |
| LOC100306719 | NP_001235420.1 (SEQ ID NO: 148) | AT1G47960 | Cell wall/vacuolar inhibitor of fructosidase 1 | 0.016 | DNP | |
| LOC100776636 | XP_003517432.1 (SEQ ID NO: 149) | AT1G62770 | Pectinesterase inhibitor 9 | 0.191 | DNP | 3 |
| LOC100812251 | XP_003530773.1 (SEQ ID NO: 150) | AT1G14890 | Plant invertase/pectin methylesterase inhibitor superfamily protein | 2.328 | DNP | |
| LOC100803842 | XP_003525240.1 (SEQ ID NO: 151) | AT1G14890 | Plant invertase/pectin methylesterase inhibitor superfamily protein | 4.499 | DNP | |
| LOC100801231 | XP_003531408.1 (SEQ ID NO: 152) | AT5G09760 | Probable pectinesterase/ pectinesterase inhibitor 51 | 44.942 | DNP | 4 |
| LOC100776752 | XP_003526711.1 (SEQ ID NO: 153) | AT5G53370 | Probable pectinesterase/ pectinesterase inhibitor 61 | 25.882 | DNP | |
| LOC100813592 | XP_003553658.2 (SEQ ID NO: 154) | AT2G45220 | Probable pectinesterase/ pectinesterase inhibitor 17 | 192.005 | DNP | |
| LOC100776623 | XP_025981966.1 (SEQ ID NO: 155) | AT3G14310 | Pectinesterase/ pectinesterase inhibitor 3 | 14.818 | DNP | 5 |
| LOC100777646 | XP_003528739.1 (SEQ ID NO: 156) | AT3G14310 | Pectinesterase/ pectinesterase inhibitor 3 | 23.049 | DNP | |

*DNP = did not pass Tukey test at P < 0.1 (fold change not significantly different from 1.00). See TABLE 15 for explanation of samples.

An additional analysis was performed with the *Glycine max* RNA-seq data in which the Bioconductor R package DESeq2 was used to determine differential expression. In this analysis, filtering used a different statistical treatment and additional genes of interest were identified. In the alternative filtering method, the Tukey test was not used to filter the data, but rather all comparisons for which σ/μ<0.75 for both lines were retained (is the mean value of the normalized reads for a particular line and a is their standard deviation). Only comparisons where the two mean read counts from RNA-Seq analysis added up to ≥2.00 were retained.

The genes that fulfilled these criteria and that fall within the GO categories listed in TABLE 16 are shown in TABLE 18. In TABLE 18, only comparisons in which the fold difference between the two compared lines exceeds 1.5 are included.

TABLE 18

Differentially expressed *Glycine max* genes from the plant invertase inhibitor/pectin methylesterase inhibitor superfamily in harvested leaves of CCP1+ and null lines vs. wild type control line.*

| *Glycine max* locus | Protein ID | *A. thaliana* locus | *A. thaliana* description | Fold C1/A | Fold B/A |
|---|---|---|---|---|---|
| LOC100808438 | XP_003555884.1 (SEQ ID NO: 159) | AT3G53190 | Probable pectate lyase 12 | 4.25 | 0.24 |
| LOC100815062 | XP_003541430.1 (SEQ ID NO: 160) | AT3G53190 | Probable pectate lyase 12 | 49.89 | |
| LOC100782388 | XP_003551943.1 (SEQ ID NO: 157) | AT1G67750 | Probable pectate lyase 5 | 35.65 | |

TABLE 18-continued

Differentially expressed *Glycine max* genes from the plant invertase inhibitor/pectin methylesterase inhibitor superfamily in harvested leaves of CCP1+ and null lines vs. wild type control line.*

| *Glycine max* locus | Protein ID | *A. thaliana* locus | *A. thaliana* description | Fold C1/A | Fold B/A |
|---|---|---|---|---|---|
| LOC100816256 | XP_006591479.1 (SEQ ID NO: 158) | AT1G67750 | Probable pectate lyase 5 | 34.37 | |
| LOC100789303 | XP_006589707.1 (SEQ ID NO: 142) | AT5G04310 | Pectate lyase | 4.17 | |
| LOC100779940 | NP_001242543.1 (SEQ ID NO: 170) | AT5G63180 | Probable pectate lyase 22 | 2.14 | |
| LOC100802068 | XP_003556544.1 (SEQ ID NO: 171) | AT3G55140 | Pectate lyase | 0.61 | |
| LOC100777128 | XP_003528738.1 (SEQ ID NO: 172) | AT1G53840 | Pectinesterase 1 | 1.51 | 0.58 |
| LOC100814987 | XP_003551027.1 (SEQ ID NO: 173) | AT3G43270 | Probable pectinesterase/pectinesterase inhibitor 32 | 2.17 | |
| LOC100801231 | XP_003531408.1 (SEQ ID NO: 152) | AT5G09760 | Probable pectinesterase/pectinesterase inhibitor 51 | 44.94 | |
| LOC100777500 | XP_003546532.1 (SEQ ID NO: 174) | AT4G33220 | Probable pectinesterase/pectinesterase inhibitor 44 | 0.47 | |
| LOC100816190 | XP_003517421.1 (SEQ ID NO: 168) | AT5G47500 | Probable pectinesterase 68 | 870.46 | |
| LOC100810031 | XP_003538735.1 (SEQ ID NO: 167) | AT5G47500 | Probable pectinesterase 68 | 262.40 | |
| LOC100796327 | XP_003550907.1 (SEQ ID NO: 166) | AT5G47500 | Probable pectinesterase 68 | 245.06 | |
| LOC100793773 | XP_003524409.1 (SEQ ID NO: 162) | AT5G19730 | Probable pectinesterase 53 | 64.24 | |
| LOC100819675 | XP_003524299.2 (SEQ ID NO: 164) | AT5G09760 | Probable pectinesterase/pectinesterase inhibitor 51 | 48.82 | |
| LOC100802832 | XP_006584808.1 (SEQ ID NO: 163) | AT5G19730 | Probable pectinesterase 53 | 47.04 | |
| LOC100808236 | XP_006578909.1 (SEQ ID NO: 165) | AT5G53370 | Probable pectinesterase/pectinesterase inhibitor 61 | 38.78 | |
| LOC100793314 | XP_003516527.2 (SEQ ID NO: 161) | AT5G19730 | Probable pectinesterase 53 | 28.80 | |
| LOC100777646 | XP_003528739.1 (SEQ ID NO: 156) | AT3G14310 | Pectinesterase/pectinesterase inhibitor 3 | 23.05 | |
| LOC100776623 | XP_025981966.1 (SEQ ID NO: 155) | AT3G14310 | Pectinesterase/pectinesterase inhibitor 3 | 14.82 | |
| LOC100786786 | XP_006587735.1 (SEQ ID NO: 146) | AT3G29090 | Pectinesterase 31 | 4.30 | |
| LOC100776222 | XP_003527461.1 (SEQ ID NO: 175) | AT1G41830 | SKU-similar 6 | 2.55 | |
| LOC100789567 | XP_003527069.1 (SEQ ID NO: 176) | AT1G53840 | Pectinesterase 1 | 0.51 | |
| LOC100816686 | XP_003546521.1 (SEQ ID NO: 169) | AT5G20740 | Pectinesterase inhibitor 3 | 173.35 | |
| LOC100305900 | NP_001238450.1 (SEQ ID NO: 177) | AT5G62350 | Replication protein A 32 kDa subunit A | 4.23 | |
| LOC100812251 | XP_003530773.1 (SEQ ID NO: 150) | AT1G14890 | Plant invertase/pectin methylesterase inhibitor superfamily protein | 2.33 | |
| LOC100776636 | XP_003517432.1 (SEQ ID NO: 149) | AT1G62770 | Pectinesterase inhibitor 9 | 0.19 | |
| LOC100306719 | NP_001235420.1 (SEQ ID NO: 148) | AT1G47960 | Cell wall/vacuolar inhibitor of fructosidase 1 | 0.02 | |
| LOC100500640 | NP_001237215.2 (SEQ ID NO: 147) | AT1G47960 | Cell wall/vacuolar inhibitor of fructosidase 1 | 0.00 | 0.53 |
| LOC100776478 | XM_006587593.3 (SEQ ID NO: 178) | AT5G45280 | Pectin acetylesterase 11 | 0.63 | |
| LOC100781246 | XP_014624577.1 (SEQ ID NO: 179) | AT4G19420 | Pectin acetylesterase 8 | 0.61 | |

*Lines are identified in TABLE 15.

Figure 30:
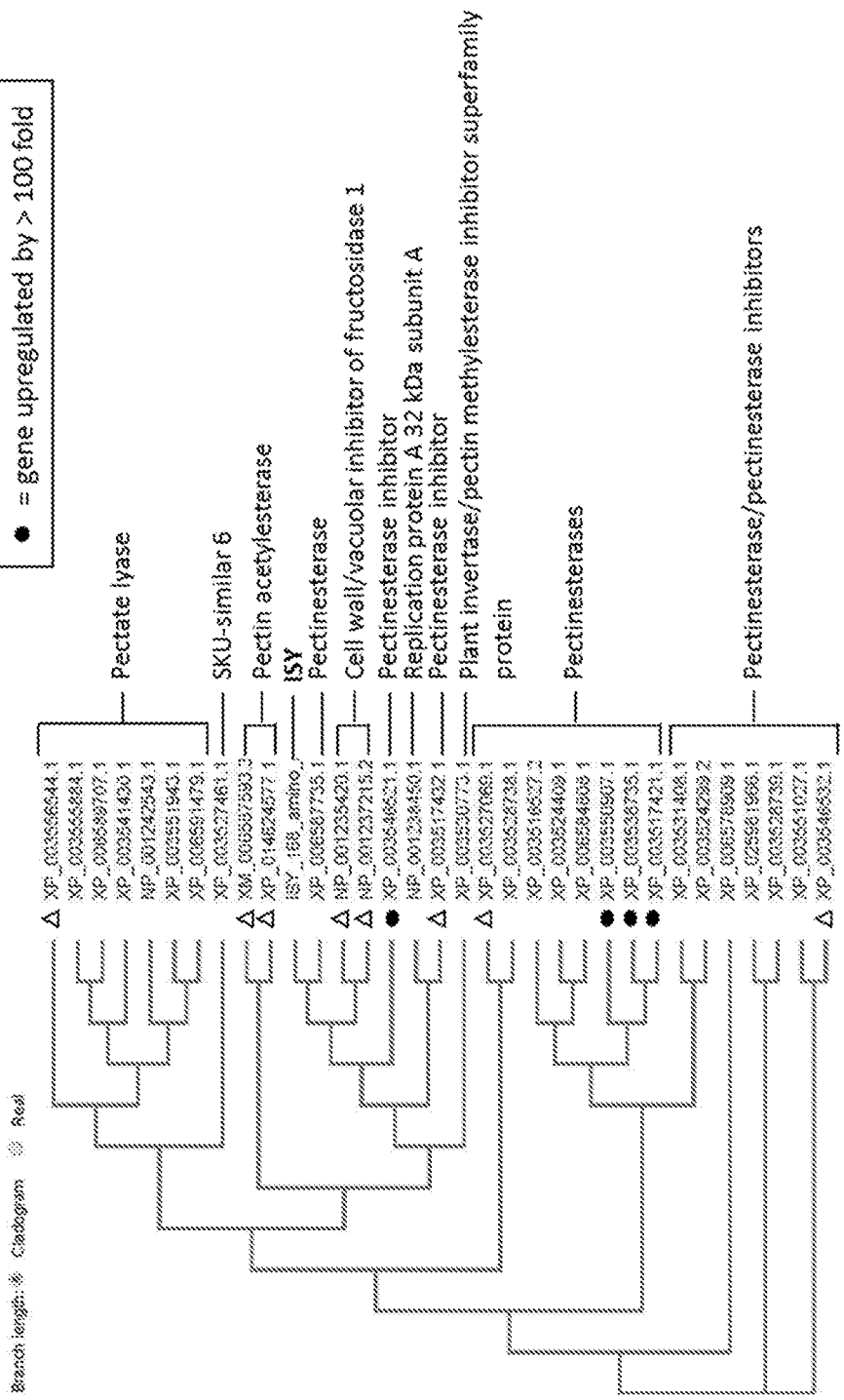
FIG. 30 shows a phylogenetic tree (cladogram) of proteins encoded by differentially expressed genes in select gene ontology (GO) categories that were identified in RNA Sequencing data of leaves of soybean lines transformed with pMBXO74 (FIG. 20A) expressing the CCP1 gene from a 35S constitutive promoter (C1/A comparison in TABLE 18). The 168 amino acid Camelina ISY protein (SEQ ID NO: 5) was included in the alignment. The select GO categories are shown in TABLE 16. Genes that are downregulated are indicated in the figure with a triangle. Genes that are upregulated by more than 100 fold are indicated in the figure with a shaded circle.

The Clustal Omega multiple sequence alignment tool was used to create a phylogenetic tree (cladogram) (FIG. 30) with all the soybean protein sequences listed in TABLE 18 and the 168 amino acid ISY gene (SEQ ID NO: 5). Differentially expressed genes in the CCP1+ soybean lines with upregulated expression greater than 100 fold, as well as all downregulated genes are labeled in FIG. 30. The phylogenetic tree (FIG. 30) and sequence alignments of the *Camelina* ISY protein with the proteins in TABLE 18 showed the closest matches to the ISY protein to be two cell wall/vacuolar inhibitors of fructosidase 1 [NP_001237215.2 (SEQ ID NO: 147) and NP_001235420.1 (SEQ ID NO:

148)] and a pectinesterase [XP_006587735.1 (SEQ ID NO: 146)].

Differentially Expressed Genes in Seeds:

Three different kinds of seed samples were analyzed in the RNA SEQ experiment focusing on seeds: maturing seeds harvested from plants transformed with the 35S constitutive promoter construct (pMBXO74, FIG. 20A, SEQ ID NO: 128) and appropriate controls, as well as developing and maturing seeds from an oleosin seed specific promoter construct (pMBXO75, FIG. 20C, SEQ ID NO: 130) and appropriate controls. Additional information about the samples is described in TABLE 15.

For seed samples, RNA-seq data analysis was performed with the Bioconductor R package DESeq2 to determine differential expression. In this analysis, the Tukey test was not used to filter the data, but rather all comparisons for which σ/μ<0.75 for both lines were retained (is the mean value of the normalized reads for a particular line and a is their standard deviation). Only comparisons where the two mean read counts from RNA-Seq analysis added up to ≥2.00 were retained.

The genes that fulfilled these criteria and that fall within the GO categories listed in TABLE 16 are shown in TABLE 19. In TABLE 19, only comparisons in which the fold difference between the two compared lines exceeds 1.5 are included.

TABLE 19

Differentially expressed *Glycine max* genes from the plant invertase inhibitor/pectin methylesterase inhibitor superfamily in maturing and developing seeds of CCP1+ and null lines vs. the wild type control line.*

| *Glycine max* locus | Protein ID | *A. thaliana* locus | *A. thaliana* description | Fold F1/D | Fold P/L | Fold K/H |
|---|---|---|---|---|---|---|
| LOC100802068 | XP_003556544.1 (SEQ ID NO: 171) | AT3G55140 | Pectate lyase | 0.53 | | |
| LOC100814679 | XP_003523121.1 (SEQ ID NO: 180) | AT5G63180 | Probable pectate lyase 22 | 0.35 | 0.63 | |
| LOC100101868 | XP_003549832.1 (SEQ ID NO: 181) | AT5G63180 | Probable pectate lyase 22 | | | |
| LOC100799009 | XP_014618078.1 (SEQ ID NO: 182) | AT3G55140 | Pectate lyase | | | 1.97 |
| LOC100801813 | XP_003534983.1 (SEQ ID NO: 183) | AT4G33220 | Probable pectinesterase/pectinesterase inhibitor 44 | 3.65 | 1.63 | |
| LOC100784642 | XP_003547912.1 (SEQ ID NO: 184) | AT1G53840 | Pectinesterase 1 | 3.25 | | |
| LOC100808236 | XP_006578909.1 (SEQ ID NO: 165) | AT5G53370 | Probable pectinesterase/pectinesterase inhibitor 61 | 2.83 | | |
| LOC106796002 | XP_014622597.1 (SEQ ID NO: 185) | AT5G53370 | Probable pectinesterase/pectinesterase inhibitor 61 | 2.74 | | 1.99 |
| LOC100776222 | XP_003527461.1 (SEQ ID NO: 175) | AT1G41830 | SKU-similar 6 | 2.33 | | |
| LOC100776752 | XP_003526711.1 (SEQ ID NO: 153) | AT5G53370 | Probable pectinesterase/pectinesterase inhibitor 61 | 2.23 | | 1.66 |
| LOC100777500 | XP_003546532.1 (SEQ ID NO: 174) | AT4G33220 | Probable pectinesterase/pectinesterase inhibitor 44 | 1.92 | | |
| LOC100789567 | XP_003527069.1 (SEQ ID NO: 176) | AT1G53840 | Pectinesterase 1 | 1.87 | | 1.88 |
| LOC102666380 | XP_006593974.1 (SEQ ID NO: 186) | AT2G26440 | Probable pectinesterase/pectinesterase inhibitor 12 | 0.41 | | |
| LOC100819675 | XP_003524299.2 (SEQ ID NO: 164) | AT5G09760 | Probable pectinesterase/pectinesterase inhibitor 51 | | 1.52 | |
| LOC100815836 | XP_006573891.1 (SEQ ID NO: 187) | AT1G11580 | Pectinesterase/pectinesterase inhibitor 18 | | 0.43 | |
| LOC100777646 | XP_003528739.1 (SEQ ID NO: 156) | AT3G14310 | Pectinesterase/pectinesterase inhibitor 3 | | | 1.89 |
| LOC100791264 | XP_003521571.1 (SEQ ID NO: 188) | AT3G62820 | Plant invertase/pectin methylesterase inhibitor superfamily protein | | 0.51 | |
| LOC100797734 | XP_003533952.1 (SEQ ID NO: 189) | AT2G01610 | Pectinesterase inhibitor 7 | | | 1.70 |
| LOC100776636 | XP_003517432.1 (SEQ ID NO: 149) | AT1G62770 | Pectinesterase inhibitor 9 | | | 0.55 |
| LOC100795394 | XP_003529510.2 (SEQ ID NO: 190) | AT1G47960 | Cell wall/vacuolar inhibitor of fructosidase 1 | | | 1.64 |
| LOC100776478 | XM_006587593.3 (SEQ ID NO: 178) | AT5G45280 | Pectin acetylesterase 11 | 6.49 | | |

TABLE 19-continued

Differentially expressed *Glycine max* genes from the plant invertase
inhibitor/pectin methylesterase inhibitor superfamily in maturing and
developing seeds of CCP1+ and null lines vs. the wild type control line.*

| *Glycine max* locus | Protein ID | *A. thaliana* locus | *A. thaliana* description | Fold F1/D | Fold P/L | Fold K/H |
|---|---|---|---|---|---|---|
| LOC100788448 | XP_006604776.1 (SEQ ID NO: 191) | AT3G62060 | Pectin acetylesterase 6 | 1.59 | | |
| LOC100780171 | XP_014623997.1 (SEQ ID NO: 192) | AT4G19420 | Pectin acetylesterase 8 | 0.12 | | |

*Lines are identified in TABLE 15. There were not significant fold changes in the null lines for the genes in TABLE 19 and thus null lines are not shown in the TABLE 19.

Figure 31:
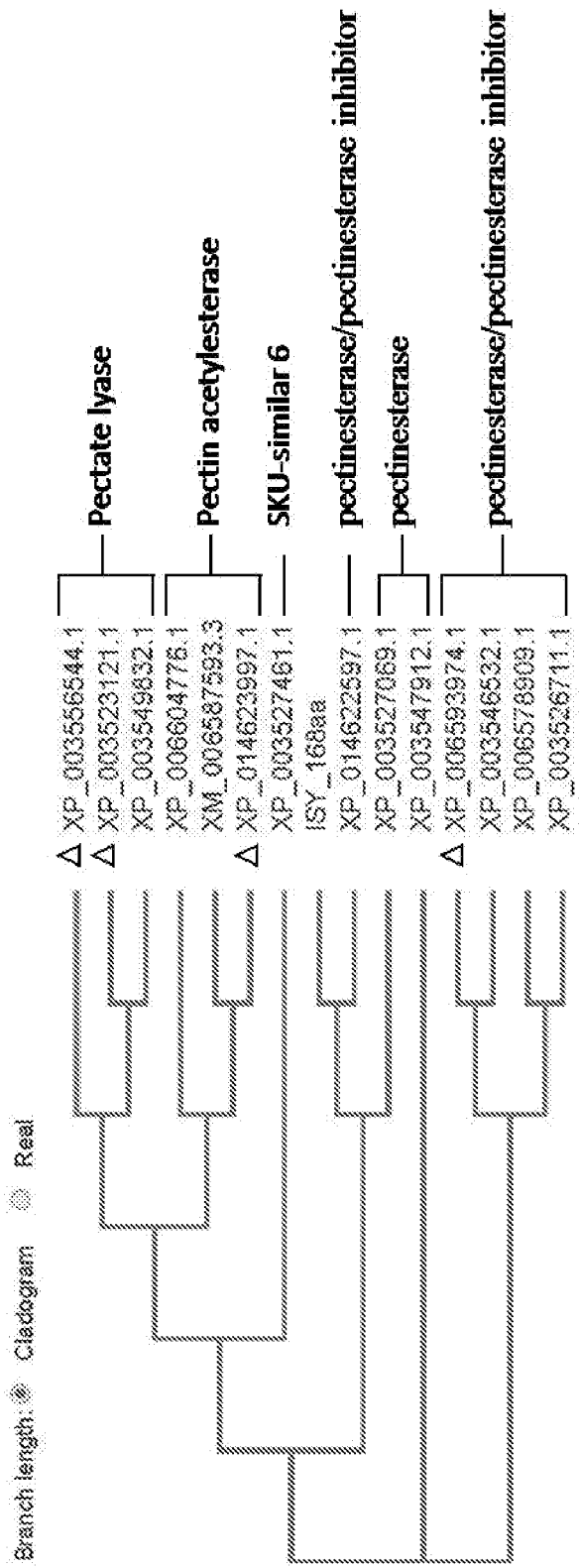
FIG. 31 shows a phylogenetic tree (cladogram) of proteins encoded by differentially expressed genes in select gene ontology (GO) categories that were identified in RNA Sequencing data of maturing seeds of a soybean line transformed with pMBXO74 (FIG. 20A) expressing the CCP1 gene from a 35S constitutive promoter (F1/D comparison in TABLE 19). The 168 amino acid Camelina ISY protein (SEQ ID NO: 5) was included in the alignment. The select GO categories are shown in TABLE 16. Genes that are downregulated are indicated in the figure with a triangle. Genes that are upregulated by more than 100 fold are indicated in the figure with a shaded circle.
Figure 32:
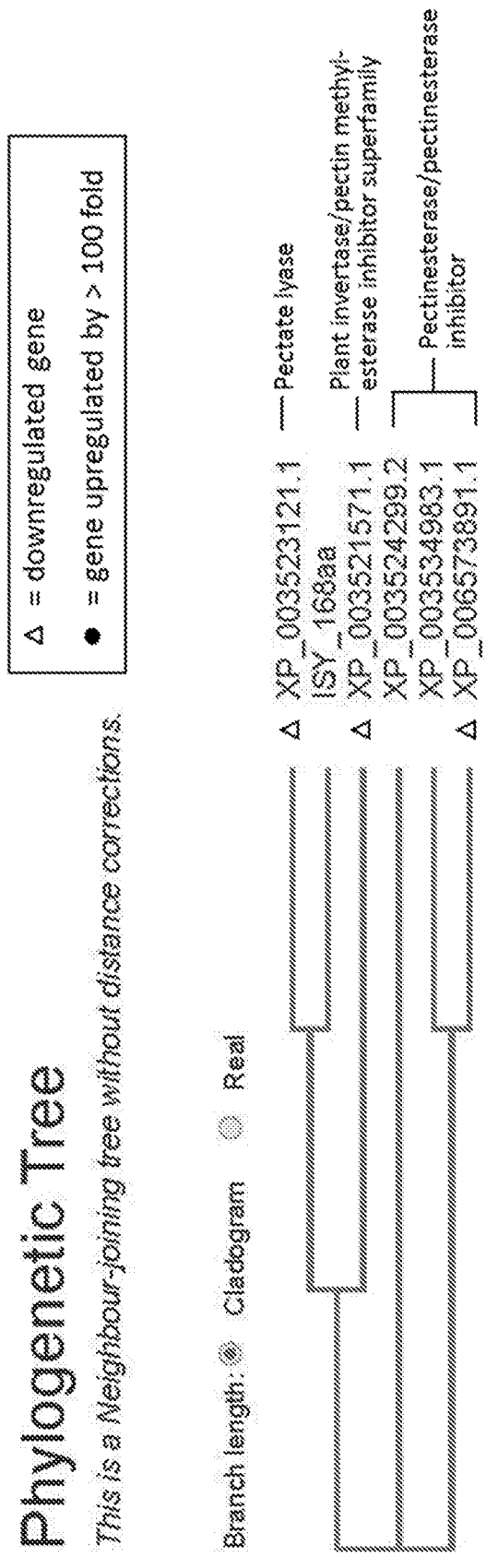
FIG. 32 shows a phylogenetic tree (cladogram) of proteins encoded by differentially expressed genes in select gene ontology (GO) categories that were identified in RNA Sequencing data of developing seeds of a soybean line transformed with pMBXO75 (FIG. 20C) expressing the CCP1 gene from a soybean oleosin seed specific promoter (P/L comparison in TABLE 19). The 168 amino acid Camelina ISY protein (SEQ ID NO: 5) was included in the alignment. The select GO categories are shown in TABLE 16. Genes that are downregulated are indicated in the figure with a triangle. Genes that are upregulated by more than 100 fold are indicated in the figure with a shaded circle.
Figure 33:
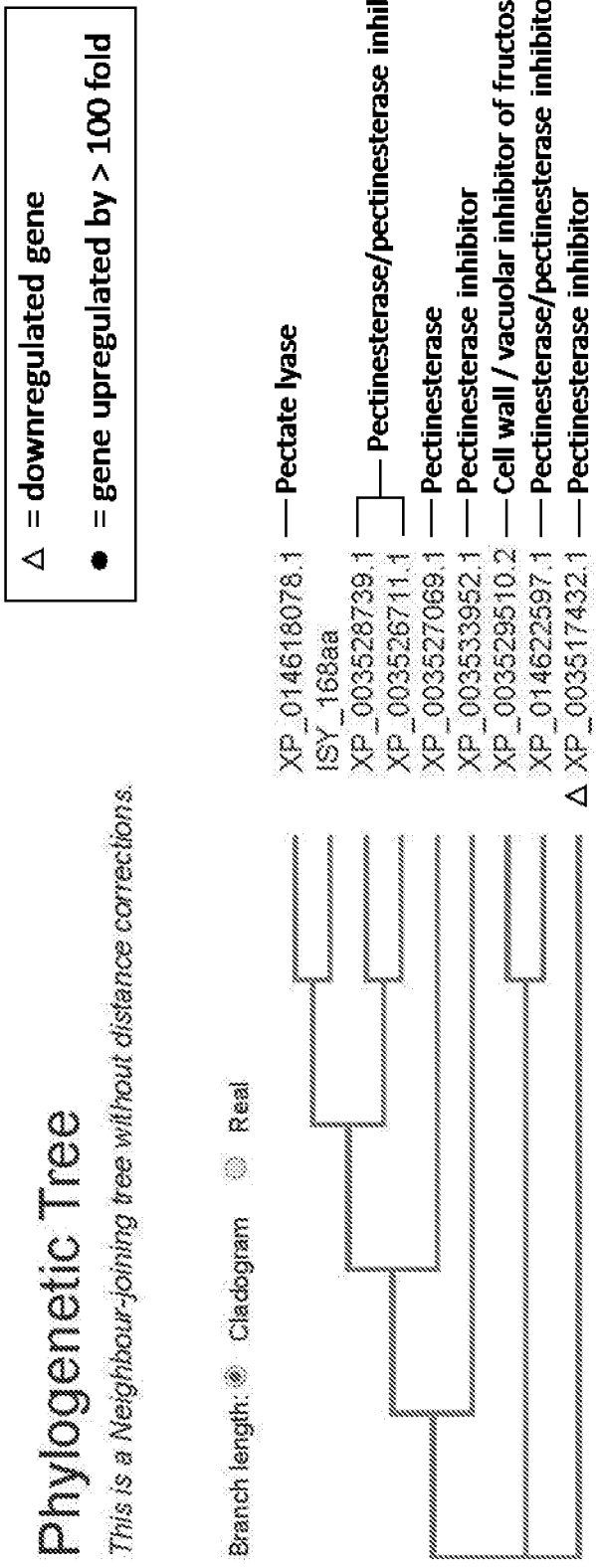
FIG. 33 shows a phylogenetic tree (cladogram) of proteins encoded by differentially expressed genes in select gene ontology (GO) categories that were identified in RNA Sequencing data of maturing seeds of a soybean line transformed with pMBXO75 (FIG. 20C) expressing the CCP1 gene from a soybean oleosin seed specific promoter (K/H comparison in TABLE 19). The 168 amino acid Camelina ISY protein (SEQ ID NO: 5) was included in the alignment. The select GO categories are shown in TABLE 16. Genes that are downregulated are indicated in the figure with a triangle. Genes that are upregulated by more than 100 fold are indicated in the figure with a shaded circle.

The Clustal Omega multiple sequence alignment tool was used to create phylogenetic trees (cladograms) with the soybean sequences listed in TABLE 19 and the 168 amino acid ISY gene (SEQ ID NO: 5) for the maturing seed of lines transformed with pMBXO74 (35S-CCP1 homozygous line) compared to Westag wild-type control (F1/D comparison in TABLE 19, FIG. 31), maturing seed of lines transformed with pMBXO75 (oleosin promoter—CCP1 homozygous line) compared to Westag (P/L comparison in TABLE 19, FIG. 32), and developing seed of lines transformed with pMBXO75 (oleosin promoter—CCP1 homozygous line) compared to Westag (K/H comparison in TABLE 19, FIG. 33). In FIGS. 31-33, differentially expressed genes in the CCP1+ soybean lines with upregulated expression greater than 100 fold, as well as all downregulated genes are labeled.

For the maturing seed of lines transformed with pMBXO74 (F1/D comparison in TABLE 19, FIG. 31), the phylogenetic tree and subsequent sequence alignments of proteins encoded by the differentially expressed genes with the *Camelina* ISY protein were used to find the genes most similar to ISY. XP_014622597.1 (SEQ ID NO: 185, a probable pectinesterase/pectinesterase inhibitor 61) and XP_003527069.1 (SEQ ID NO: 176, a pectinesterase 1) were the closest matching proteins in the phylogenetic tree. Interestingly, the gene encoding XP_003527069.1 (SEQ ID NO: 176) was found to be differentially expressed in both leaf (TABLE 18, C1/A comparison, downregulated) and maturing seed tissue (TABLE 19, F1/D comparison, upregulated) of lines transformed with pMBXO74.

For the maturing seed of lines transformed with pMBXO75 (P/L comparison in TABLE 19, FIG. 32), the phylogenetic tree and subsequent sequence alignments of proteins encoded by the differentially expressed genes with the *Camelina* ISY protein were used to find the genes most similar to ISY. The proteins XP_003523121.1 (SEQ ID NO: 180, a probable pectate lyase) and XP_003521571.1 (SEQ ID NO: 188, a plant invertase/pectin methylesterase inhibitor superfamily protein) were identified, both of which are encoded by downregulated genes in the pMBXO75 transformed lines. Interestingly, the gene encoding XP_003523121.1 (SEQ ID NO: 180) is also downregulated in the maturing seed of lines transformed with pMBXO74 (F1/D comparison in TABLE 19).

For the developing seed of lines transformed with pMBXO75 (K/H comparison in TABLE 19, FIG. 33), the phylogenetic tree and subsequent sequence alignments of proteins encoded by the differentially expressed genes with the *Camelina* ISY protein were used to find the genes most similar to ISY. The proteins XP_014618078.1 (SEQ ID NO: 182, a pectate lyase), XP_003528739.1 (SEQ ID NO: 156, a pectinesterase/pectinesterase inhibitor 3), and XP_003526711.1 (SEQ ID NO: 153, a probable pectinesterase/pectinesterase inhibitor 61) were identified.

Interestingly, the gene encoding XP_003528739.1 (SEQ ID NO: 156), was found to also be upregulated in the harvested leaves of lines transformed with pMBXO74 compared to wild-type controls (C1/A comparison, TABLE 18). The gene encoding XP_003526711.1 (SEQ ID NO: 153) was found to be upregulated in both maturing seed of lines transformed with pMBXO74 (F1/D comparison) and developing seed of lines transformed with pMBXO75 (K/H comparison).

Differentially expressed genes listed in TABLES 18 and 19 that are present in multiple samples and/or tissue types may be particularly interesting as targets for genetic manipulation through genome editing or other methods. TABLE 20 summarizes the *Glycine max* genes and their encoded proteins that are differentially expressed in RNA SEQ samples harvested from more than one sample or tissue type. For example, SEQ ID NO: 174, 176, and 178 are proteins encoded by differentially expressed genes that are downregulated in leaf tissue of lines transformed with pMBXO74 compared to wild-type controls (C1/A comparison) but are upregulated in mature seed tissue (F1/D comparison). This may be indicative of some change in carbon partitioning between leaves and seed tissue. Thus targets listed in TABLE 20 may represent preferred targets for engineering to increase seed yield and/or plant productivity.

TABLE 20

Differentially expressed *Glycine max* genes appearing
in multiple samples from TABLES 18 and 19.

| *Glycine max* locus | Protein ID | *A. thaliana* locus | *A. thaliana* description | FOLD C1/A | Fold F1/D | Fold P/L | Fold K/H |
|---|---|---|---|---|---|---|---|
| Differentially expressed genes in both leaves and mature seeds of lines transformed with pMBXO74 (C1/A and F1/D comparisons) | | | | | | | |
| LOC100802068 | XP_003556544.1 (SEQ ID NO: 171) | AT3G55140 | Pectate lyase | 0.61 | 0.53 | | |

TABLE 20-continued

Differentially expressed *Glycine max* genes appearing
in multiple samples from TABLES 18 and 19.

| *Glycine max* locus | Protein ID | *A. thaliana* locus | *A. thaliana* description | FOLD C1/A | Fold F1/D | Fold P/L | Fold K/H |
|---|---|---|---|---|---|---|---|
| LOC100808236 | XP_006578909.1 (SEQ ID NO: 165) | AT5G53370 | Probable pectinesterase/ pectinesterase inhibitor 61 | 38.78 | 2.83 | | |
| LOC100776222 | XP_003527461.1 (SEQ ID NO: 175) | AT1G41830 | SKU-similar 6 | 2.55 | 2.33 | | |
| LOC100777500 | XP_003546532.1 (SEQ ID NO: 174) | AT4G33220 | Probable pectinesterase/ pectinesterase inhibitor 44 | 0.47 | 1.92 | | |
| LOC100789567 | XP_003527069.1 (SEQ ID NO: 176) | AT1G53840 | Pectinesterase 1 | 0.51 | 1.87 | | 1.88 |
| LOC100776478 | XM_006587593.3 (SEQ ID NO: 178) | AT5G45280 | Pectin acetylesterase 11 | 0.63 | 6.49 | | |
| Differentially expressed genes in mature seeds of lines transformed with pMBXO74 and pMBXO75 (F1/D and P/L comparisons) | | | | | | | |
| LOC100814679 | XP_003523121.1 (SEQ ID NO: 180) | AT5G63180 | Probable pectate lyase 22 | | 0.35 | 0.63 | |
| LOC100801813 | XP_003534983.1 (SEQ ID NO: 183) | AT4G33220 | Probable pectinesterase/ pectinesterase inhibitor 44 | | 3.65 | 1.63 | |
| Differentially expressed genes in both leaves of lines transformed with pMBXO74 (C1/A comparison) and developing seeds of lines transformed with pMBXO75 (K/H comparison) | | | | | | | |
| LOC100789567 | XP_003527069.1 (SEQ ID NO: 176) | AT1G53840 | Pectinesterase 1 | 0.51 | 1.87 | | 1.88 |
| LOC100777646 | XP_003528739.1 (SEQ ID NO: 156) | AT3G14310 | Pectinesterase/ pectinesterase inhibitor 3 | 23.05 | | | 1.89 |
| LOC100776636 | XP_003517432.1 (SEQ ID NO: 149) | AT1G62770 | Pectinesterase inhibitor 9 | 0.19 | | | 0.55 |
| Differentially expressed genes in both mature seeds of lines transformed with pMBXO74 (F1/D comparison) and developing seeds of lines transformed with pMBXO75 (K/H comparison) | | | | | | | |
| LOC106796002 | XP_014622597.1 (SEQ ID NO: 185) | AT5G53370 | Probable pectinesterase/ pectinesterase inhibitor 61 | | 2.74 | | 1.99 |
| LOC100776752 | XP_003526711.1 (SEQ ID NO: 153) | AT5G53370 | Probable pectinesterase/ pectinesterase inhibitor 61 | | 2.23 | | 1.66 |
| LOC100789567 | XP_003527069.1 (SEQ ID NO: 176) | AT1G53840 | Pectinesterase 1 | 0.51 | 1.87 | | 1.88 |

Example 16. Creation of Soybean Lines with Overexpressed Genes Identified in TABLES 17, 18, 19, and 20

Soybean lines can be engineered to overexpress the genes, or combinations of the genes, identified in TABLES 17, 18, 19, and 20 by creating an expression cassette with a promoter operably linked to the gene of interest operably linked to a termination sequence. For constitutive expression, a promoter such as the cauliflower mosaic virus promoter (SEQ ID NO: 108) can be used. For expression primarily in green tissue, a promoter such as the soybean cab5 promoter (TABLE 1, SEQ ID NO: 42) can be used. For seed specific expression, a promoter such as the soybean oleosin promoter (TABLE 1, SEQ ID NO: 50) can be used. Soybean can be transformed with expression cassettes overexpressing the gene sequences identified in TABLES 17, 18, 19, and 20 using the procedures described in Example 5. Gene targets in TABLE 20, that were found to be differentially expressed in more than one harvested sample or tissue type, may be preferred targets for this exercise.

Soybean lines can also be engineered to overexpress the genes identified in TABLES 17, 18, 19, and 20 using a promoter replacement strategy with the CRISPR/Cas system. In this system, the native promoter in front of a gene is replaced with a stronger promoter, or a promoter with a different expression pattern, using a strategy similar to the one described in FIG. 22 and Example 11.

The CRISPR/Cas system can also be used to insert a new expression cassette into the plant genome containing a promoter operably linked to a gene identified in TABLES 17, 18, and 19, operably linked to a termination sequence. For this procedure, one or more sgRNAs are used with the Cas enzyme to generate a double stranded break. The new expression cassette, flanked by sequences with homology to the insertion site of the plant genome, is inserted using the plant's homology directed repair mechanism.

Example 17. Creation of Soybean Lines with Reduced Activity of Genes Identified in TABLES 17, 18, 19, and 20

Soybean lines can be engineered for reduced expression of one or more genes listed in TABLES 17, 18, 19, and 20 using antisense technology or RNAi technology. A preferred method is to use genome editing, such as the CRISPR/CAS genome editing technology.

To reduce expression of a native plant gene, the CRISPR/Cas system can be used to replace the native promoter in front of a gene with a weaker promoter using a strategy similar to the one described in FIG. 22 and Example 11. The expression of the pectinesterase (XP_003543834.1, SEQ ID NO: 145), the cell wall/vacuolar inhibitor of fructosidase 1 (NP_001237215.2, SEQ ID NO: 147 and NP_001235420.1, SEQ ID NO: 148), and/or the pectinesterase inhibitor (XP_003517432.1, SEQ ID NO: 149) genes can be reduced using this strategy. Other useful targets for downregulation or deletion include XP_003556544.1 (SEQ ID NO: 171), XP_003523121.1 (SEQ ID NO: 180), XP_003546532.1 (SEQ ID NO: 174), XP_003527069.1 (SEQ ID NO: 176), XP_006593974.1 (SEQ ID NO: 186), XP_006573891.1 (SEQ ID NO: 187), XP_003521571.1 (SEQ ID NO: 188), XM_006587593.3 (SEQ ID NO: 178), and XP_014623997.1 (SEQ ID NO: 192).

Alternatively, the CRISPR/Cas system can be used to weaken the strength of a promoter by inducing a mutation in an important region of the promoter and allowing non-homologous end joining (NHEJ) to occur.

Alternatively, the activity of a protein can be reduced or eliminated by removing, inserting, or changing one or more base pairs in the sequence of a gene. This can be achieved by designing a sgRNA with its ~20 bp guide sequence targeting the region of the gene to be modified. With the CRISPR/Cas enzyme, the sgRNA can be used to create INDELs (insertion or deletion of a small number of bases). The Cas nuclease makes a double strand break near the binding of the sgRNA and the error prone DNA repair pathway, with non-homologous end joining, corrects the break creating a mutation. Out of frame mutations can lead to elimination of the enzyme's activity. In frame insertion or deletion mutations can reduce the activity of the protein. The activities of the pectinesterase (XP_003543834.1, SEQ ID NO: 145), the cell wall/vacuolar inhibitor of fructosidase 1 (NP_001237215.2, SEQ ID NO: 147 and NP_001235420.1, SEQ ID NO: 148), and/or the pectinesterase inhibitor (XP_003517432.1, SEQ ID NO: 149) genes in TABLE 17 can be reduced or eliminated using this strategy. Other useful targets for downregulation or deletion include XP_003556544.1 (SEQ ID NO: 171), XP_003523121.1 (SEQ ID NO: 180), XP_003546532.1 (SEQ ID NO: 174), XP_003527069.1 (SEQ ID NO: 176), XP_006593974.1 (SEQ ID NO: 186), XP_006573891.1 (SEQ ID NO: 187), XP_003521571.1 (SEQ ID NO: 188), XM_006587593.3 (SEQ ID NO: 178), and XP_014623997.1 (SEQ ID NO: 192).

Gene targets in TABLE 20, expressed in more than one sample or tissue type, may be preferred targets for this exercise.

Example 18. Identification of Up- and Down-Regulated Genes in Canola Lines Expressing the CCP1 Gene Using RNA Sequencing Select canola T4 generation lines expressing the CCP1 gene (TABLE 21), produced as described in Example 5, were chosen for analysis by RNA sequencing. These lines were grown in the field at a site in Canada during the spring/summer of 2017. TABLE 21 shows lines that were selected for analysis, the tissue type collected, and classifies the lines into groups for analysis purposes. Samples were harvested at the indicated stage and quickly frozen in liquid nitrogen. Samples were stored at −80° C. RNA was extracted using the Agilent Plant RNA isolation kit and shipped to a contract service provider that performed RNA Sequencing and data processing. Differentially expressed genes from this analysis are shown in TABLE 22.

TABLE 21

Brassica napus samples used in the RNA-seq analysis.

| Group | Tissue[1] | Line | Nitrogen addition[2] | CCP1 | Increased seed yield relative to control[3] |
|---|---|---|---|---|---|
| Q | Leaf | BN00 wild-type control | 150% | − | — |
| R | Leaf | MW82 (pMBXO58, 35S-CCP1 homozygous) | 150% | + | 13.1%* |
| S | Silique | BN00 wild-type control | 150% | − | — |
| T | Silique | MW82 (pMBXO58, 35S-CCP1 homozygous) | 150% | + | 13.1%* |
| U | Leaf | BN00 wild-type control | 50% | − | — |
| W | Leaf | MW82 (pMBXO58, 35S-CCP1 homozygous) | 50% | + | 8.7%* |
| X | Silique | BN00 wild-type control | 50% | − | — |
| Y | Silique | MW82 (pMBXO58, 35S-CCP1 homozygous) | 50% | + | 8.7%* |

[1]Harvested tissue stages are as follows: Leaf, newly expanded leaf from 39 day old canola plants; silique, developing silique collected 15 days after flowering;
[2]50% or 150% of the nitrogen required to provide a 40 bushel per acre canola yield. AGROTAIN(R) fertilizer used.
[3]Statistically significant, P < 0.1. The map of plasmid pMBXO58 is shown in FIG. 3.

In order to analyze genes in the same family as the ISY gene (Csa15g017550.1; SEQ ID NO: 6), the GO terms listed in TABLE 16 were investigated. The resulting up- and down-regulated genes, along with the comparison corresponding to the fold change, are given in TABLE 22. Only comparisons in which the fold difference between the two lines exceeds 1.5 are included.

TABLE 22

Differentially expressed Brassica napus genes from the plant invertase inhibitor/pectin methylesterase inhibitor superfamily in CCP1+ lines vs. wild type.

| | | GO:0030570 pectate lyase activity | | | |
|---|---|---|---|---|---|
| | | Fold change* | | | |
| B. napus locus | Description | Leaf R/Q | Leaf W/U | Silique T/S | Silique Y/X |
| LOC106367786 | Probable pectate lyase 12 | 3.2 | | | |
| LOC106361318 | Probable pectate lyase 18 | 0.49 | | | |

TABLE 22-continued

Differentially expressed *Brassica napus* genes from the plant invertase inhibitor/pectin methylesterase inhibitor superfamily in CCP1+ lines vs. wild type.

| | | | | | |
|---|---|---|---|---|---|
| LOC106363861 | Probable pectate lyase 1 | 2.9 | | | |
| LOC106452978 | Probable pectate lyase 8 | | | 2.1 | |
| LOC106430113 | Probable pectate lyase 9 | | | | 1.7 |

| | | Fold change | | | |
|---|---|---|---|---|---|
| *B. napus* locus | Description | Leaf R/Q | Leaf W/U | Silique T/S | Silique Y/X |
| GO:0030599 pectinesterase activity | | | | | |
| LOC111205093 | Probable pectinesterase 29 | | | | 0.41 |
| GO:0046910 pectinesterase inhibitor activity | | | | | |
| LOC106447685 | Probable pectinesterase/pectinesterase inhibitor 34 | 2.0 | | | |
| LOC106371735 | Probable pectinesterase/pectinesterase inhibitor 64 | 1.8 | | | |
| LOC106416267 | Pectinesterase/pectinesterase inhibitor 18 | 1.8 | | | |
| LOC106412069 | Pectinesterase/pectinesterase inhibitor 18 | 1.6 | | | |
| LOC106434483 | Probable pectinesterase/pectinesterase inhibitor 16 | | | 0.66 | |
| LOC106347212 | Plant invertase/pectin methylesterase inhibitor superfamily protein | 1.6 | | | |
| LOC106392321 | Pectinesterase inhibitor 6 | 2.9 | | | |
| LOC106436652 | Pectin methylesterase inhibitor 1 | | 1.7 | | |
| LOC106450421 | Pectinesterase inhibitor 6 | | 0.51 | | |
| LOC111205564 | Pectinesterase inhibitor 6 | | 0.48 | | |
| LOC106397464 | Pectinesterase inhibitor 10 | | | | 1.5 |
| GO:0052793 pectin acetylesterase activity | | | | | |
| LOC106368499 | Pectin acetylesterase 6 | | | 0.67 | |
| LOC106450464 | Pectin acetylesterase 3 | | | 1.8 | |
| LOC106450462 | Pectin acetylesterase 3 | | | 1.6 | |
| LOC106377080 | Pectin acetylesterase 7 | | 1.6 | | |

*Groups described in TABLE 21.

An alternative filtering of the genes was performed to see if any new genes appeared. In this case, the Tukey test was not used to filter the data, but rather all comparisons for which $\sigma/\mu<0.75$ for both lines were retained, where is the mean value of the normalized reads for a particular line and a is their standard deviation. The up- and downregulated genes obtained with this filtering method, along with the comparison corresponding to the fold change, are given in TABLE 23. Only comparisons in which the fold difference between the two lines exceeds 2.0 are included.

TABLE 23

Differentially expressed *Brassica napus* genes from the GO categories in TABLE 16 in CCP1+ lines vs. wild type.

GO:0030570 pectate lyase activity

| | | Fold change* | | | |
|---|---|---|---|---|---|
| *B. napus* locus | Description | RQ | W/U | T/S | Y/X |
| LOC106367786 | probable pectate lyase 12 | 3.2 | — | — | — |
| LOC106422643 | probable pectate lyase 22 | 3.2 | — | — | — |
| LOC106363861 | probable pectate lyase 1 | 2.9 | — | — | — |
| LOC106409544 | probable pectate lyase 5 | 2.5 | — | — | — |
| LOC106419852 | probable pectate lyase 1, transcript variant X1 | 2.3 | — | — | — |
| LOC106436935 | probable pectate lyase 18 | 2.2 | — | — | — |
| LOC106381139 | probable pectate lyase 5 | 2.2 | — | — | — |
| LOC106370994 | probable pectate lyase 1 | 2.1 | — | — | — |

TABLE 23-continued

Differentially expressed *Brassica napus* genes from the
GO categories in TABLE 16 in CCP1+ lines vs. wild type.

| LOC106361318 | probable pectate lyase 18 | 0.50 | — | — | — |
| LOC106352880 | probable pectate lyase 13 | — | 2.4 | — | — |
| LOC106452978 | probable pectate lyase 8 | — | — | 2.1 | — |
| LOC111208330 | probable pectate lyase 18 | — | — | 2.1 | — |

| | | Fold change | | | |
|---|---|---|---|---|---|
| *B. napus* locus | Description | R/Q | W/U | T/S | Y/X |
| GO:0030599 pectinesterase activity | | | | | |
| LOC106447685 | probable pectinesterase/ pectinesterase inhibitor 34 | 2.0 | — | — | — |
| LOC106365512 | probable pectinesterase/ pectinesterase inhibitor 41 | 0.43 | — | — | — |
| LOC111205093 | probable pectinesterase 29 | — | — | — | 0.41 |
| GO:0046910 pectinesterase inhibitor activity | | | | | |
| LOC106392321 | pectinesterase inhibitor 6-like | 2.9 | — | — | — |
| LOC106365512 | probable pectinesterase/ pectinesterase inhibitor 41 | 0.43 | — | — | — |
| GO:0052793 pectin acetylesterase activity | | | | | |
| LOC106377080 | pectin acetylesterase 7 | 2.1 | — | — | — |
| LOC106416258 | pectin acetylesterase 6-like | 2.1 | — | — | — |
| LOC106450464 | pectin acetylesterase 3-like | — | 0.44 | — | — |

*Groups described in TABLE 21.

Example 19. Identification of Up- and Down-Regulated Genes in *Camelina sativa* Lines Expressing the CCP1 Gene Using RNA Sequencing Select homozygous *Camelina sativa* lines expressing the CCP1 gene (TABLE 24) were chosen for analysis by RNA sequencing. These lines were grown in the field at a site in Canada during the spring/summer of 2016. TABLE 24 shows lines that were selected for analysis, the tissue type collected, and classifies the lines into groups for analysis purposes. Samples were harvested at the indicated stage and quickly frozen in liquid nitrogen. Samples were stored at −80° C. RNA was extracted from newly expanded leaves (33 days after planting) and developing siliques (15 days after flowering) using the Agilent Plant RNA isolation kit and shipped to a contract service provider that performed RNA Sequencing and data processing.

TABLE 24

*Camelina sativa* samples used in the RNA-seq analysis.

| Group | Tissue* | Line | CCP1 |
|---|---|---|---|
| A | Leaf | MI116 | + |
| B | Leaf | WT43 | − |
| C | Leaf | NJ01 | + |
| D | Leaf | NJ02 | + |
| E | Leaf | WTSU | − |
| F | Silique | MI116 | + |
| G | Silique | WT43 | − |
| H | Silique | NJ01 | + |
| I | Silique | NJ02 | + |
| J | Silique | WTSU | − |

*Leaf, newly expanded leaves 33 days after planting; Silique, siliques harvested 15 days after flowering. WT43, abbreviation for *Camelina sativa* cultivar 10CS0043 that was isolated in a breeding program at Agriculture and Agri-Food Canada (Malik et al., 2018, Plant Cell Reports, 37, 1367). MI116, line obtained upon transformation of *Camelina* cultivar WT43 with plasmid pMBXO58 (FIG. 3). WTSU, abbreviation for *Camelina sativa* cultivar Suneson (Malik et al., 2018, Plant Cell Reports, 37, 1367). NJ01 and NJ02, lines obtained upon transformation of *Camelina* cultivar Suneson with plasmid pMBXO58.

In order to analyze genes in the same family as the ISY gene (Csa15g017550.1; SEQ ID NO: 6), the GO terms listed in TABLE 16 were investigated. The objective was to search the *Camelina sativa* genome for differentially regulated genes that could be associated with one or more of these GO terms. Nearly all genes within the RNA-seq data had a corresponding best BLAST hit in the *Arabidopsis thaliana* genome, which is very well-annotated with respect to associated GO terms. Therefore, for each of the above GO terms, a list of *Arabidopsis thaliana* genes associated with each GO term was made, then all genes within the *Camelina sativa* genome that had one of those *Arabidopsis thaliana* genes as its best BLAST hit were identified. Among these *Camelina sativa* genes, some were up- or down-regulated in CCP1 lines in a statistically significant way; that is, a Tukey test suggested that the probability was greater than 90% that the means of the transcript levels in transgenic vs. wild-type lines were different.

The up- and down-regulated genes, along with the comparison corresponding to the fold change, are given in TABLE 25. Only comparisons in which the fold difference between the two lines exceeds 1.5 are included.

TABLE 25

Differentially expressed *Camelina sativa* genes from the
GO categories in TABLE 16 in CCP1+ lines vs. wild type.

GO: 0030570 pectate lyase activity

| C. sativa locus | Description | Fold change* | | | | | |
|---|---|---|---|---|---|---|---|
| | | Leaf A/B | Leaf C/E | Leaf D/E | Silique F/G | Silique H/J | Silique I/J |
| LOC104734443 | Pectate lyase | 0.55 | | | | | |
| LOC104747027 | Probable pectate lyase 10 | | | 1.7 | | | |
| LOC104701382 | Probable pectate lyase 5 | | | | 2.0 | | |
| LOC104717795 | probable pectate lyase 18 | | | | | 2.4 | 2.3 |
| LOC104722501 | probable pectate lyase 18 | | | | | 2.2 | 2.5 |
| LOC104726924 | Probable pectate lyase 22 | | | | | 0.57 | 0.60 |
| LOC104726926 | Probable pectate lyase 22 | | | | | 0.54 | 0.59 |
| LOC104762495 | probable pectate lyase 1 | | | | | 2.1 | — |
| LOC104754610 | probable pectate lyase 1 | | | | | 2.0 | 1.8 |
| LOC104738994 | probable pectate lyase 1 | | | | | 1.9 | |
| LOC104762495 | Probable pectate lyase 1 | | | | | | 1.7 |

| C. sativa locus | Description | Fold change | | | | | |
|---|---|---|---|---|---|---|---|
| | | Leaf A/B | Leaf C/E | Leaf D/E | Silique F/G | Silique H/J | Silique I/J |

GO: 0030599 pectinesterase activity

| LOC104758734 | Pectinesterase 2 | | | 0.31 | | | |
| LOC104735956 | Probable pectinesterase 29 | | | | 0.66 | | |
| LOC104736702 | Putative pectinesterase 52 | | | | 1.7 | | |
| LOC104726108 | Pectinesterase QRT1 | | | | | 0.56 | |
| LOC104732089 | Pectinesterase QRT1 | | | | | 0.53 | 0.66 |
| LOC104742103 | Putative pectinesterase | | | | | 1.8 | 1.9 |
| LOC104777520 | Putative pectinesterase | | | | | 1.7 | 1.7 |
| LOC104757890 | Putative pectinesterase | | | | | 1.5 | 1.7 |
| LOC104736040 | Probable pectinesterase 53 | | | | | | 1.6 |
| LOC104770344 | Probable pectinesterase 53 | | | | | | 1.6 |

GO: 0046910 pectinesterase inhibitor activity

| LOC104745251 | Probable pectinesterase/ pectinesterase inhibitor 25 | | | | 1.5 | | |
| LOC104707868 | Probable pectinesterase/ pectinesterase inhibitor 41 | | | | | 2.7 | |
| LOC104708142 | Probable pectinesterase/ pectinesterase inhibitor 51 | | | | | 1.5 | |
| LOC104791148 | Probable pectinesterase/ pectinesterase inhibitor 34 | | | | | 1.7 | |
| LOC104760099 | Probable pectinesterase/ pectinesterase inhibitor 7 | | | | | 2.7 | 2.8 |
| LOC104754377 | Probable pectinesterase/ pectinesterase inhibitor 7 | | | | | 2.5 | 2.1 |
| LOC104778832 | Probable pectinesterase/ pectinesterase inhibitor 6 | | | | | 0.66 | |
| LOC104769166 | Probable pectinesterase/ pectinesterase inhibitor 51 | | | | | | 1.7 |
| LOC104708141 | Probable pectinesterase/ pectinesterase inhibitor 51 | | | | | | 1.5 |

TABLE 25-continued

Differentially expressed *Camelina sativa* genes from the
GO categories in TABLE 16 in CCP1+ lines vs. wild type.

| Locus | Description | 1 | 2 | 3 | 4 |
|---|---|---|---|---|---|
| LOC104770309 | Pectinesterase/pectinesterase inhibitor 18 | | | | 1.8 |
| LOC104728508 | Plant invertase/pectin methylesterase inhibitor superfamily protein | 2.0 | | | |
| LOC109132214 | Plant invertase/pectin methylesterase inhibitor superfamily protein | 0.37 | | | |
| LOC104765570 | Plant invertase/pectin methylesterase inhibitor superfamily protein | 0.36 | | | |
| LOC104749039 | Plant invertase/pectin methylesterase inhibitor superfamily protein | | 2.0 | | |
| LOC104699600 | Plant invertase/pectin methylesterase inhibitor superfamily protein | | 1.6 | | |
| LOC104788614 | Plant invertase/pectin methylesterase inhibitor superfamily protein | | 1.6 | | |
| LOC104715795 | Invertase/pectin methylesterase inhibitor family protein | | 2.1 | | |
| LOC104779478 | Plant invertase/pectin methylesterase inhibitor | | 1.7 | | |
| LOC104714617 | Pectinesterase inhibitor 10 | | | 0.11 | 0.080 |
| LOC104707529 | Pectin methylesterase inhibitor 1 | | | 2.1 | 1.7 |
| LOC104737245 | Pectin methylesterase inhibitor 1 | | | 1.8 | 1.5 |
| LOC104717621 | Pectin methylesterase inhibitor 1 | | | 1.6 | |
| LOC104790946 | Pectinesterase inhibitor 11 | | | 2.1 | |
| LOC104711196 | Pectinesterase inhibitor 11 | | | 2.1 | |
| LOC104730912 | Pectinesterase inhibitor 4 | | | 2.7 | 2.0 |
| LOC104778832 | Probable pectinesterase/pectinesterase inhibitor 6 | | | 0.66 | |
| LOC104756693 | Plant invertase/pectin methylesterase inhibitor superfamily protein | | | 2.1 | 2.1 |
| LOC104776449 | Plant invertase/pectin methylesterase inhibitor superfamily protein | | | 1.7 | 1.6 |
| LOC104756686 | Plant invertase/pectin methylesterase inhibitor superfamily protein | | | 1.7 | |
| LOC104741040 | Plant invertase/pectin methylesterase inhibitor superfamily protein | | | 1.9 | |
| LOC104745508 | Plant invertase/pectin methylesterase inhibitor superfamily protein | | | | 0.65 |
| LOC104765054 | Plant invertase/pectin methylesterase inhibitor superfamily protein | | | | 0.62 |
| LOC104777086 | Plant invertase/pectin methylesterase inhibitor superfamily protein | | | | 0.50 |
| LOC104765554 | CASP-like protein | | | | 1.7 |
| GO: 0052793 pectin acetylesterase activity | | | | | |
| LOC104704143 | Pectin acetylesterase 6 | 0.64 | | | |
| LOC104714970 | Pectin acetylesterase 3 | | | 2.0 | |
| LOC104723107 | Pectin acetylesterase 7 | | | 1.7 | 1.7 |
| LOC109124411 | Pectin acetylesterase 11 | | | 1.7 | |

*Groups described in TABLE 24.

An alternative filtering of the genes was performed to see if any new genes appeared. In this case, the Tukey test was not used to filter the data, but rather all comparisons for which $\sigma/\mu < 0.75$ for both lines were retained, where is the mean value of the normalized reads for a particular line and a is their standard deviation. The up- and down-regulated genes obtained with the altered filtering method, along with the comparison corresponding to the fold change, are shown in TABLE 26. Only comparisons in which the fold difference between the two lines exceeds 2.0 are included.

TABLE 26

Differentially expressed *Camelina sativa* genes from the
GO categories in TABLE 16 in CCP1+ lines vs. wild type.

GO: 0030570 pectate lyase activity

| | | Fold change* | | | | | |
|---|---|---|---|---|---|---|---|
| *C. sativa* locus | Description | Leaf A/B | Leaf C/E | Leaf D/E | Silique F/G | Silique H/J | Silique I/J |
| LOC104717795 | probable pectate lyase 18 | — | — | — | — | 2.4 | 2.3 |
| LOC104722501 | probable pectate lyase 18 | — | — | — | — | 2.2 | 2.5 |
| LOC104762495 | probable pectate lyase 1 | — | — | — | — | 2.1 | — |
| LOC104754610 | probable pectate lyase 1 | — | — | — | — | 2.0 | — |
| LOC104730966 | probable pectate lyase 18 | — | — | — | — | — | 2.3 |

| | | Fold change | | | | | |
|---|---|---|---|---|---|---|---|
| *C. sativa* locus | Description | Leaf A/B | Leaf C/E | Leaf D/E | Silique F/G | Silique H/J | Silique I/J |

GO: 0030599 pectinesterase activity

| | | | | | | | |
|---|---|---|---|---|---|---|---|
| LOC104781810 | probable pectinesterase/ pectinesterase inhibitor 35 | — | — | — | — | 2.4 | — |
| LOC104769165 | probable pectinesterase/ pectinesterase inhibitor 51 | — | — | — | — | 2.3 | 2.1 |
| LOC104782819 | probable pectinesterase/ pectinesterase inhibitor 16 | — | — | — | — | 2.3 | — |
| LOC104779154 | pectinesterase/ pectinesterase inhibitor 3 | — | — | — | — | 2.2 | — |
| LOC104780230 | probable pectinesterase/ pectinesterase inhibitor 32 | — | — | — | — | 2.1 | — |
| LOC104788138 | probable pectinesterase/ pectinesterase inhibitor 35 | — | — | — | — | 2.1 | — |
| LOC104728462 | probable pectinesterase/ pectinesterase inhibitor 61 | — | — | — | — | 2.1 | — |
| LOC104699225 | probable pectinesterase/ pectinesterase inhibitor 35 | — | — | — | — | 2.1 | — |
| LOC104709803 | probable pectinesterase/ pectinesterase inhibitor 39 | — | — | — | — | 2.1 | 3.4 |

GO: 0046910 pectinesterase inhibitor activity

| | | | | | | | |
|---|---|---|---|---|---|---|---|
| LOC104783356 | 21 kDa protein-like | — | — | — | 3.0 | — | — |
| LOC104730912 | 21 kDa protein-like | — | — | — | — | 2.7 | — |
| LOC104780536 | 21 kDa protein-like | — | — | — | — | 2.5 | — |
| LOC104781810 | probable pectinesterase/ pectinesterase inhibitor 35 | — | — | — | — | 2.4 | — |
| LOC104782819 | probable pectinesterase/ pectinesterase inhibitor 16 | — | — | — | — | 2.3 | — |
| LOC104703885 | 21 kDa protein-like | — | — | — | — | 2.3 | — |
| LOC104779154 | pectinesterase/ pectinesterase inhibitor 3 | — | — | — | — | 2.2 | — |
| LOC104790946 | 21 kDa protein-like | — | — | — | — | 2.1 | — |
| LOC104756693 | 21 kDa protein-like | — | — | — | — | 2.1 | — |
| LOC104707529 | 21 kDa protein | — | — | — | — | 2.1 | — |
| LOC104788138 | probable pectinesterase/ pectinesterase inhibitor 35 | | | | | 2.1 | |
| LOC104711196 | 21 kDa protein-like | — | — | — | — | 2.1 | — |
| LOC104728462 | probable pectinesterase/ pectinesterase inhibitor 61 | — | — | — | — | 2.1 | — |
| LOC104699225 | probable pectinesterase/ pectinesterase inhibitor 35 | — | — | — | — | 2.1 | — |
| LOC104709803 | probable pectinesterase/ pectinesterase inhibitor 39 | — | — | — | — | — | 3.4 |
| LOC104777086 | uncharacterized LOC104777086 | — | — | — | — | — | 0.50 |
| LOC104714617 | 21 kDa protein-like | — | — | — | — | — | 0.08 |

*Groups described in TABLE 24.

Example 20. Genetically Engineered Land Plants that Express the Genes Identified in TABLES 17, 18, 19, 20, 22, 23, 25, and 26

The results described in Examples 15, 18, and 19 and the genes identified in TABLES 17, 18, 19, 20, 22, 23, 25, and 26 validate the use of constitutive and seed specific expression of the mitochondrial transporter encoded by the algal gene CCP1 in soybean, canola, and *Camelina sativa* for identification of gene targets that regulate sugar metabolism in plants. The results reveal new genes that, following expression of CCP1, are upregulated or downregulated. By analogy with the ISY gene, it is believed that the upregulation or downregulation of the new genes, with or without the expression of the algal CCP1 gene, potentially may result in an increase in branching, seed yield, and, in some plants, an increase in the average size of individual seeds too. Upregulation can be achieved by insertion of an expression cassette with a promoter operably linked to the gene of interest followed by an appropriate termination sequence. Upregulation of gene expression or the pattern of gene expression can also be achieved using the promoter replacement strategy with the CRISPR system similar to the one described in FIG. 22 and Example 11. Downregulation can be achieved using the promoter replacement strategy by choosing a weaker promoter or by using CRISPR to delete nucleotides to remove amino acids, or to delete or insert nucleotides to achieve a frameshift mutation.

Given the results obtained with the truncated version of the *Camelina* ISY gene, it is also possible that the expression of N-terminal truncated versions of the genes in TABLES 17, 18, 19, 20, 22, 23, 25, and 26 may result in an increase in branching, seed yield, and, in some plants, an increase in the average size of individual seeds too.

Additional Genetically Engineered Land Plants Modified to Express the Gene Targets Identified in Soybean Considering the gene targets identified in soybean in particular, a genetically engineered land plant that comprises a modified gene for a protein identified in TABLES 17, 18, 19, and 20 is disclosed. The protein comprises one or more of SEQ ID NOS: 141-192. The modified gene comprises (i) a promoter and (ii) a nucleic acid sequence encoding the protein. The promoter is non-cognate with respect to the nucleic acid sequence encoding the protein. The modified gene is configured such that transcription of the nucleic acid sequence is initiated from the promoter and results in expression of the protein.

In some examples, the protein is heterologous with respect to the genetically engineered land plant. In some examples, the protein is homologous with respect to the genetically engineered land plant.

In some examples, the genetically engineered land plant exhibits increased expression of the protein in comparison to a reference land plant that does not include the modified gene. In some of these examples, the increased expression of the protein can be in one or more tissues of the genetically engineered land plant, e.g. in leaf tissue and/or mature seed tissue. Also in some of these examples, the protein comprises one or more of SEQ ID NOS: 141, 142, 143, 144, 146, 150, 151, 152, 153, 154, 155, 156, 157, 158, 159, 160, 161, 162, 163, 164, 165, 166, 167, 168, 169, 170, 172, 173, 175, 177, 182, 183, 184, 185, 189, 190, or 191.

In some examples, the genetically engineered land plant exhibits decreased expression of the protein in comparison to a reference land plant that does not include the modified gene. In some of these examples, the decreased expression of the protein can be in one or more tissues of the genetically engineered land plant, e.g. in leaf tissue and/or mature seed tissue. Also in some of these examples, the protein comprises one or more of SEQ ID NOS: 145, 147, 148, 149, 171, 179, 180, 186, 187, 188, or 192.

In some examples, the genetically engineered land plant exhibits both increased expression and decreased expression of the protein in comparison to a reference land plant that does not include the modified gene. In some of these examples, the increased expression of the protein can be in one or more tissues of the genetically engineered land plant, e.g. in mature seed tissue, and the decreased expression of the protein can be in one or more other tissues of the genetically engineered land plant, e.g. in leaf tissue. Also in some of these examples, the protein comprises one or more of SEQ ID NOS: 174, 176, or 178.

Additional Genetically Engineered Soybean Plants

Considering the gene targets identified in soybean further, a genetically engineered soybean plant that comprises a modified gene for a protein identified in TABLES 17, 18, 19, and 20 also is disclosed. The protein comprises one or more of SEQ ID NOS: 141-192. The modified gene comprises (i) a promoter and (ii) a nucleic acid sequence encoding the protein. The modified gene is configured such that transcription of the nucleic acid sequence is initiated from the promoter and results in a difference in expression of the protein in comparison to a reference soybean plant that does not include the modified gene.

In some examples, the difference in expression is an increase in expression. In some of these examples, the increase in expression can be in one or more tissues of the genetically engineered soybean plant, e.g. in leaf tissue and/or mature seed tissue. Also in some of these examples, the protein comprises one or more of SEQ ID NOS: 141, 142, 143, 144, 146, 150, 151, 152, 153, 154, 155, 156, 157, 158, 159, 160, 161, 162, 163, 164, 165, 166, 167, 168, 169, 170, 172, 173, 175, 177, 182, 183, 184, 185, 189, 190, or 191.

In some examples, the difference in expression is a decrease in expression. In some of these examples, the decrease in expression can be in one or more tissues of the genetically engineered soybean plant, e.g. in leaf tissue and/or mature seed tissue. Also in some of these examples, the protein comprises one or more of SEQ ID NOS: 145, 147, 148, 149, 171, 179, 180, 186, 187, 188, or 192.

In some examples, the difference in expression is both an increase in expression and a decrease in expression. In some of these examples, the increase in expression can be in one or more tissues of the genetically engineered soybean plant, e.g. in mature seed tissue, and the decrease in expression can be in one or more other tissues of the genetically engineered soybean plant, e.g. in leaf tissue. Also in some of these examples, the protein comprises one or more of SEQ ID NOS: 174, 176, or 178.

In some examples, the protein comprises two or more of SEQ ID NOS: 141-192, e.g. two, three, four, five, or more of SEQ ID NOS: 141-192. In some of these examples, the protein comprises at least one of SEQ ID NOS: 141, 142, 143, 144, 146, 150, 151, 152, 153, 154, 155, 156, 157, 158, 159, 160, 161, 162, 163, 164, 165, 166, 167, 168, 169, 170, 172, 173, 175, 177, 182, 183, 184, 185, 189, 190, or 191 with increased expression. In some of these examples, the protein comprises at least one of SEQ ID NOS: 145, 147, 148, 149, 171, 179, 180, 186, 187, 188, or 192 with decreased expression. In some of these examples, the protein comprises at least one of SEQ ID NOS: 174, 176, or 178 with both increased expression and decreased expression. In some of these examples, the protein comprises a combination of at least one of SEQ ID NOS: 141, 142, 143, 144, 146, 150, 151, 152, 153, 154, 155, 156, 157, 158, 159, 160, 161, 162, 163, 164, 165, 166, 167, 168, 169, 170, 172, 173, 175, 177, 182, 183, 184, 185, 189, 190, or 191 with increased expression, and at least one of SEQ ID NOS: 145, 147, 148, 149, 171, 179, 180, 186, 187, 188, or 192 with decreased expression, and optionally also at least one of SEQ ID NOS: 174, 176, or 178 with both increased expression and decreased expression.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "YTEN-59704WO-Sequences_ST25.txt", created Sep. 3, 2019, file size of 577,536 bytes, is hereby incorporated by reference.

What is claimed is:

1. A genetically engineered land plant that expresses a protein that increases seed yield with increased expression ("an ISY protein"), the genetically engineered land plant comprising a modified gene for the ISY protein, wherein:
   the ISY protein comprises SEQ ID NO: 2;
   the ISY protein has homology to a plant invertase inhibitor and/or a pectin methylesterase inhibitor;
   the modified gene comprises (i) a promoter and (ii) a nucleic acid sequence encoding the ISY protein;
   the promoter is non-cognate with respect to the nucleic acid sequence encoding the ISY protein;
   the modified gene is configured such that transcription of the nucleic acid sequence is initiated from the promoter and results in expression of the ISY protein; and
   the genetically engineered land plant is *Camelina sativa*, canola, or soybean.

2. The genetically engineered land plant of claim 1, wherein the ISY protein is one or more of ISY protein of *Camelina sativa* of SEQ ID NO: 2, ISY protein of *Camelina sativa* of SEQ ID NO: 5, modified ISY protein of *Camelina sativa* of SEQ ID NO: 138, or modified ISY protein of *Camelina sativa* of SEQ ID NO: 140.

3. The genetically engineered land plant of claim 1, wherein the ISY protein further comprises only five amino acid residues N-terminal to the cysteine residue at position 6, with numbering of positions relative to SEQ ID NO: 2.

4. The genetically engineered land plant of claim 1, wherein the promoter is a constitutive promoter.

5. The genetically engineered land plant of claim 1, wherein the promoter is a seed-specific promoter.

6. The genetically engineered land plant of claim 1, wherein the genetically engineered land plant exhibits increased expression of the ISY protein in comparison to a reference land plant that does not include the modified gene.

7. The genetically engineered land plant of claim 1, wherein the genetically engineered land plant exhibits increased seed yield, fruit yield, and/or tuber yield in comparison to a reference land plant that does not include the modified gene.

8. The genetically engineered land plant of claim 1, wherein the genetically engineered land plant is *Camelina sativa*.

* * * * *

SEQUENCE LISTING

```
<160> NUMBER OF SEQ ID NOS: 198

<210> SEQ ID NO 1
<211> LENGTH: 405
<212> TYPE: DNA
<213> ORGANISM: Camelina sativa

<400> SEQUENCE: 1
atgaaatatg atttctgcgt caattctctt acacaagatc cacaaagcaa aacggcgacc      60
acccrcgaag gtttagtcct agcatcgacg aagaatgctg cggcggaaac actgaacgta     120
aaaggactcg ctgaacagat cctcaagggg aagggatatg ggccaggtat ggaggcaggg     180
ctacacaagt gcgtcaagat ttatggaggt gcttatgatt ttttaaacac tgctttagcg     240
aacgttcaat cacaccatta tagtactgct gtagaggaat ttctttatgc ttcatttgca     300
ccgttcgact gcgtgaaata ttattggatt tctcccttcg ctaaggagag ctatattatc     360
tttgagaaga ttttgattcc tatgacttta actaaaatgt tgtga                     405

<210> SEQ ID NO 2
<211> LENGTH: 134
<212> TYPE: PRT
<213> ORGANISM: Camelina sativa

<400> SEQUENCE: 2

Met Lys Tyr Asp Phe Cys Val Asn Ser Leu Thr Gln Asp Pro Gln Ser
1               5                   10                  15

Lys Thr Ala Thr Thr Leu Glu Gly Leu Val Leu Ala Ser Thr Lys Asn
            20                  25                  30

Ala Ala Ala Glu Thr Leu Asn Val Lys Gly Leu Ala Glu Gln Ile Leu
        35                  40                  45

Lys Gly Lys Gly Tyr Gly Pro Gly Met Glu Ala Gly Leu His Lys Cys
    50                  55                  60

Val Lys Ile Tyr Gly Gly Ala Tyr Asp Phe Leu Asn Thr Ala Leu Ala
65                  70                  75                  80

Asn Val Gln Ser His His Tyr Ser Thr Ala Val Glu Glu Phe Leu Tyr
                85                  90                  95

Ala Ser Phe Ala Pro Phe Asp Cys Val Lys Tyr Tyr Trp Ile Ser Pro
            100                 105                 110

Phe Ala Lys Glu Ser Tyr Ile Ile Phe Glu Lys Ile Leu Ile Pro Met
        115                 120                 125

Thr Leu Thr Lys Met Leu
    130

<210> SEQ ID NO 3
<211> LENGTH: 3376
```

<212> TYPE: DNA
<213> ORGANISM: Camelina sativa

<400> SEQUENCE: 3

```
tttaaaaaaa tttgatgtat ttagaaatta ggtgttattc aattgtatat tttaaataat      60
ctattaaaat atgtgttatt taatatttac tggattttgt gtgattttgg atttcaacgt     120
actttgcttc taatatacga acaaacacaa tatcacactt tctcaaacat ttcattttc     180
tctcctctct ctctctagat agatctctag cctttaacat attattgttt gattttttt     240
ctaaatcctt aaatataacc atgcttattc ataagatctg tgttattttt gagaattttt     300
ttttttgtgt tctttaattt tttttctgg gttcaagatc tgtaactttt ttttttctgg     360
gtttataata taatctcact tttttttctt ctaggttcaa tgtctgtttt ttcttccaca     420
aagtctatgt ctataatcac acatattcat cagatctttg tttttttttt agattttttt     480
ttgtgttctt taacttttt ttctgggttc ttgatttaaa actttttttt tctgggttca     540
tgatataatc acaccatttt cttcttgatt caatgtaaaa gtctggatgt tgttaattta     600
atatggtttt ggtgtataat acagtttatg aatattttt ttcttttttt tcttctataa     660
ataactttaa aaaatccat aacaatcacc aaaaacagat tataaatgac tttcaaatcc     720
accttatatg cattataaaa tccacataaa tacattagac ttttaaatcc actaatgtcc     780
tgcgtcaatt aaaatccatt aaaatcctta atgcaataac acctctttgg atttatgtat     840
ttttaactaa acaaatcctc tagaatccct aaaacttaat aaaatctaaa tccacaaact     900
ttttgaata acaataaatt ttaaagtaga ttttaaaatg atcaattcaa taacagtgga     960
ttttaatgga ctttttataa tccatgattg aataacatag gatttgtaaa ttttacacaa    1020
ataatttaaa atgttatgtt gaatacatcc ccctaagttt taataattta cactttaggg    1080
tttatgcctt tatccctaaa atatacaaaa caagtctcaa attataaagc atgaaaataa    1140
taaagtttga tgtaaagtaa aatattttc tttttgatta gtatgaaata attgatgtca    1200
aatagttaga atgtgattaa aaaaagaac ttttccaacc aataataatg caccatgtat    1260
cttagtggtc ccaggtttaa tccacattca agatggttta atccacataa attttaata     1320
ttattcaact cccttattgt ataaattcaa ctgttgcatt aatgagtcaa cacctctatt    1380
gtagatagac taagagtctt accataaaat tctatgttct cttatactat aaattgaaaa    1440
acaaagtgaa catgttcttc atcaatcaat tcttatttta tatactttcc ccaaaagaaa    1500
aacaaaataa agttattggt tccttggtt gtgttctctc ttctcttgat cggttttgca    1560
tctgcgcaaa ctctcatagt agattcttgc aagaaagcag ccgcaaaaga gccgtttatg    1620
aaatatgatt tctgcgtcaa ttctcttaca caagatccac aaagcaaaac ggcgaccacc    1680
ctcgaaggtt tagtcctagc atcgacgaag aatgctgcgg cggaaacact gaacgtaaaa    1740
ggactcgctg aacagatcct caaggggaag ggatatgggc caggtatgga ggcagggcta    1800
cacaagtgcg tcaagattta tggaggtgct tatgattttt taaacactgc tttagcgaac    1860
gttcaatcac accattatag tactgctgta gaggaatttc tttatgcttc atttgcaccg    1920
ttcgactgcg tgaaatatta ttggatttct cccttcgcta aggagagcta tattatcttt    1980
gagaagattt tgattcctat gactttaact aaaatgttgt gatgaatttg tcaaagtatt    2040
ttactaatca aaacaacaat taatgtttac catgtaaaat tgagagcaaa gagactgtat    2100
cttaatggaa ataaaaattt tctttacatg tctaggtttt tttttgccag caacattgac    2160
atattggctt tctattaaaa tttataattc tttttttttg gaaagataaa taccaaggta    2220
```

-continued

```
ttagagtttg aagaggctat actacaactg tggatttgaa acaatcatca aatatcttag  2280
tccaaaaaaa cactgataga aatggttcac atacagctaa acaaaagaat atggttaaag  2340
gcttacgatg attttctgta taagaagaac aatcaatata ttttactaaa gaactaatga  2400
aattacaaat ggtaaagttt agaaatttt tttgatatgc atgtgttctc ctactttatt  2460
atataagatt gattaaaaga ggcaattttt ttcaagatat tattctttag tatttaaaaa  2520
tcaatatagt ttaatttagt aattattaga tatggacctg cctgatgtgc agggttaaag  2580
ttttgtatat caaataaaat ttaataaaaa tatattaaat ttattgtaag ttatttataa  2640
atttaatttt gctataatac ctgattttat atctattcac aaattttta tgtatgttac  2700 cattaaaagt gtatttttta cacctaaata tattgtatgt tacaaatata gtatttacct  2760
agaaaatgtc tatataaaga cattaagcca actattatgt ttctttattt tcactttgt  2820 atagttttt taattactaa aattgtttgc tcaaaaaaca tttcgaataa aaatatatt  2880 acataagact actaatcaat gatgtattat cacaatagtg tatggccaac catggagaga  2940
atctcgactc tgccctcttc ctttatagag agaaccttgt atccaacctc ctccacgatg  3000
gagagaacct tggctccgtc ttcctccctt gaggagataa ccttgcatcc aacctcctcc  3060
acctttctcc tttggaaaga taaacttgtg tccaacctcc tccattatag agagaacatc  3120
ggctctgccc ttctcctgtg tggagagaat atgttcacgt attttagcta tctcaaattg  3180
gcttgctctg caaccaatg aaactaatta agaccaatt tctaatgtca caaatcttt  3240 tgataataac caatgttaaa atttttaatg tattcgtaga agtgtctttg acacaccatg  3300
atgtagcctc tgtctctgta acgccctgac cgccaccttg cttagttacc ccatgttcac  3360
tcccagtcca tggtcc                                                  3376
```

<210> SEQ ID NO 4
<211> LENGTH: 190
<212> TYPE: PRT
<213> ORGANISM: Camelina sativa

<400> SEQUENCE: 4

```
Thr Cys Ser Ser Ser Ile Asn Ser Tyr Phe Ile Tyr Phe Pro Gln Lys
1               5                   10                  15

Lys Asn Lys Ile Lys Leu Leu Val Ser Leu Val Phe Ser Leu Leu
            20                  25                  30

Leu Ile Gly Phe Ala Ser Ala Gln Thr Leu Ile Val Asp Ser Cys Lys
        35                  40                  45

Lys Ala Ala Ala Lys Glu Pro Phe Met Lys Tyr Asp Phe Cys Val Asn
    50                  55                  60

Ser Leu Thr Gln Asp Pro Gln Ser Lys Thr Ala Thr Leu Glu Gly
65                  70                  75                  80

Leu Val Leu Ala Ser Thr Lys Asn Ala Ala Ala Glu Thr Leu Asn Val
                85                  90                  95

Lys Gly Leu Ala Glu Gln Ile Leu Lys Gly Lys Gly Tyr Gly Pro Gly
            100                 105                 110

Met Glu Ala Gly Leu His Lys Cys Val Lys Ile Tyr Gly Gly Ala Tyr
        115                 120                 125

Asp Phe Leu Asn Thr Ala Leu Ala Asn Val Gln Ser His His Tyr Ser
    130                 135                 140

Thr Ala Val Glu Glu Phe Leu Tyr Ala Ser Phe Ala Pro Phe Asp Cys
145                 150                 155                 160

Val Lys Tyr Tyr Trp Ile Ser Pro Phe Ala Lys Glu Ser Tyr Ile Ile
```

165                 170                 175
Phe Glu Lys Ile Leu Ile Pro Met Thr Leu Thr Lys Met Leu
            180                 185                 190

<210> SEQ ID NO 5
<211> LENGTH: 168
<212> TYPE: PRT
<213> ORGANISM: Camelina sativa

<400> SEQUENCE: 5

Leu Val Ser Leu Val Val Phe Ser Leu Leu Ile Gly Phe Ala Ser
1               5                   10                  15

Ala Gln Thr Leu Ile Val Asp Ser Cys Lys Lys Ala Ala Lys Glu
            20                  25                  30

Pro Phe Met Lys Tyr Asp Phe Cys Val Asn Ser Leu Thr Gln Asp Pro
            35                  40                  45

Gln Ser Lys Thr Ala Thr Thr Leu Glu Gly Leu Val Leu Ala Ser Thr
50                  55                  60

Lys Asn Ala Ala Ala Glu Thr Leu Asn Val Lys Gly Leu Ala Glu Gln
65                  70                  75                  80

Ile Leu Lys Gly Lys Gly Tyr Gly Pro Gly Met Glu Ala Gly Leu His
                85                  90                  95

Lys Cys Val Lys Ile Tyr Gly Gly Ala Tyr Asp Phe Leu Asn Thr Ala
                100                 105                 110

Leu Ala Asn Val Gln Ser His His Tyr Ser Thr Ala Val Glu Glu Phe
            115                 120                 125

Leu Tyr Ala Ser Phe Ala Pro Phe Asp Cys Val Lys Tyr Tyr Trp Ile
130                 135                 140

Ser Pro Phe Ala Lys Glu Ser Tyr Ile Ile Phe Glu Lys Ile Leu Ile
145                 150                 155                 160

Pro Met Thr Leu Thr Lys Met Leu
                165

<210> SEQ ID NO 6
<211> LENGTH: 507
<212> TYPE: DNA
<213> ORGANISM: Camelina sativa

<400> SEQUENCE: 6
ttggtttcct tggttgtgtt ctctcttctc ttgatcggtt ttgcatctgc gcaaactctc    60
atagtagatt cttgcaagaa agcagccgca aaagagccgt ttatgaaata tgatttctgc   120
gtcaattctc ttacacaaga tccacaaagc aaaacggcga ccaccctcga aggtttagtc   180
ctagcatcga cgaagaatgc tgcggcggaa acactgaacg taaaaggact cgctgaacag   240
atcctcaagg ggaagggata tgggccaggt atggaggcag gctacacaa gtgcgtcaag    300 atttatggag gtgcttatga ttttttaaac actgctttag cgaacgttca atcacaccat   360
tatagtactg ctgtagagga atttctttat gcttcatttg caccgttcga ctgcgtgaaa   420
tattattgga tttctcccct cgctaaggag agctatatta tctttgagaa gattttgatt   480
cctatgactt taactaaaat gttgtga                                      507

<210> SEQ ID NO 7
<211> LENGTH: 576
<212> TYPE: DNA
<213> ORGANISM: Camelina sativa

<400> SEQUENCE: 7

```
tgaacatgtt cttcatcaat caattcttat tttatatact ttccccaaaa gaaaaacaaa      60
ataaagttat tggtttcctt ggttgtgttc tctcttctct tgatcggttt tgcatctgcg     120
caaactctca tagtagattc ttgcaagaaa gcagccgcaa aagagccgtt tatgaaatat     180
gatttctgcg tcaattctct tacacaagat ccacaaagca aaacggcgac caccctcgaa     240
ggtttagtcc tagcatcgac gaagaatgct gcggcggaaa cactgaacgt aaaaggactc     300
gctgaacaga tcctcaaggg gaagggtat gggccaggta tggaggcagg gctacacaag      360
tgcgtcaaga tttatggagg tgcttatgat tttttaaaca ctgctttagc gaacgttcaa     420
tcacaccatt atagtactgc tgtagaggaa tttctttatg cttcatttgc accgttcgac     480
tgcgtgaaat attattggat ttctcccttc gctaaggaga gctatattat ctttgagaag     540
attttgattc ctatgacttt aactaaaatg ttgtga                              576
```

<210> SEQ ID NO 8
<211> LENGTH: 176
<212> TYPE: PRT
<213> ORGANISM: Zea mays

<400> SEQUENCE: 8

```
Met Lys Leu Leu Gln Ala Leu Cys Pro Leu Val Ile Leu Leu Ala Cys
1               5                   10                  15

Ser Thr Ser Asn Ala Ser Val Leu Gln Asp Ala Cys Lys Ser Phe Ala
            20                  25                  30

Ala Lys Ile Pro Asp Thr Gly Tyr Ala Tyr Cys Ile Lys Phe Phe Gln
        35                  40                  45

Ala Asp Arg Gly Ser Ala Gly Ala Asp Lys Arg Gly Leu Ala Ala Ile
    50                  55                  60

Ala Val Arg Ile Met Gly Ala Ala Ala Lys Ser Thr Ala Ser His Ile
65                  70                  75                  80

Ala Ala Leu Arg Ala Ser Glu Lys Asp Lys Glu Arg Leu Ala Cys Leu
                85                  90                  95

Ser Asp Cys Ser Glu Val Tyr Ala Gln Ala Val Asp Gln Thr Gly Val
            100                 105                 110

Ala Ala Lys Gly Ile Ala Ser Gly Thr Pro Arg Gly Arg Ala Asp Ala
        115                 120                 125

Val Met Ala Leu Ser Thr Val Glu Asp Ala Pro Gly Thr Cys Glu Gln
    130                 135                 140

Gly Phe Gln Asp Leu Gly Val Arg Ser Pro Leu Ala Ser Glu Asp Ala
145                 150                 155                 160

Gly Phe Arg Lys Asp Ala Ser Ile Ala Leu Ser Val Thr Ala Ala Leu
                165                 170                 175
```

<210> SEQ ID NO 9
<211> LENGTH: 180
<212> TYPE: PRT
<213> ORGANISM: Arabidopsis thaliana

<400> SEQUENCE: 9

```
Met Ala Ser Ser Leu Ile Phe Leu Leu Leu Val Thr Leu Thr Phe Ser
1               5                   10                  15

Ala Ser Thr Leu Ile Ser Ala Lys Ser Asn Thr Thr Ile Ile Glu
            20                  25                  30

Ser Thr Cys Lys Thr Thr Asn Tyr Tyr Lys Phe Cys Val Ser Ala Leu
        35                  40                  45
```

```
Lys Ser Asp Pro Arg Ser Pro Thr Ala Asp Thr Lys Gly Leu Ala Ser
    50                  55                  60

Ile Met Val Gly Val Gly Met Thr Asn Ala Thr Ser Thr Ala Asn Tyr
65                  70                  75                  80

Ile Ala Gly Asn Leu Ser Ala Thr Val Lys Asp Thr Val Leu Lys Lys
                85                  90                  95

Val Leu Gln Asp Cys Ser Glu Lys Tyr Ala Leu Ala Ala Asp Ser Leu
                100                 105                 110

Arg Leu Thr Ile Gln Asp Leu Asp Asp Glu Ala Tyr Asp Tyr Ala Ser
            115                 120                 125

Met His Val Leu Ala Ala Gln Asp Tyr Pro Asn Val Cys Arg Asn Ile
    130                 135                 140

Phe Arg Arg Val Lys Gly Leu Ala Tyr Pro Val Glu Ile Arg Arg Arg
145                 150                 155                 160

Glu Ala Ser Leu Arg Arg Ile Cys Gly Val Val Ser Gly Ile Leu Asp
                165                 170                 175

Arg Leu Val Glu
            180

<210> SEQ ID NO 10
<211> LENGTH: 205
<212> TYPE: PRT
<213> ORGANISM: Arabidopsis thaliana

<400> SEQUENCE: 10

Met Lys Met Met Lys Val Met Met Leu Ile Val Met Met Met Met Val
1               5                   10                  15

Met Val Met Val Ser Glu Gly Ser Ile Ile Glu Pro Thr Cys Lys Glu
                20                  25                  30

Thr Pro Asp Phe Asn Leu Cys Val Ser Leu Leu Asn Ser Asp Pro Arg
            35                  40                  45

Gly Ser Ser Ala Asp Thr Ser Gly Leu Ala Leu Ile Leu Ile Asp Lys
    50                  55                  60

Ile Lys Gly Leu Ala Thr Lys Thr Leu Asn Glu Ile Asn Gly Leu Tyr
65                  70                  75                  80

Lys Lys Arg Pro Glu Leu Lys Arg Ala Leu Asp Glu Cys Ser Arg Arg
                85                  90                  95

Tyr Lys Thr Ile Leu Asn Ala Asp Val Pro Glu Ala Ile Glu Ala Ile
            100                 105                 110

Ser Lys Gly Val Pro Lys Phe Gly Glu Asp Gly Val Ile Asp Ala Gly
        115                 120                 125

Val Glu Ala Ser Val Cys Gln Gly Gly Phe Asn Gly Ser Ser Pro Leu
    130                 135                 140

Thr Ser Leu Thr Lys Ser Met Gln Lys Ile Ser Asn Val Thr Arg Ala
145                 150                 155                 160

Ile Phe Tyr Ser Asn Ser Ile Val Lys Glu Glu Ala Cys Gly Ser Ser
                165                 170                 175

Trp Pro Ser Leu Ala Leu Asn Ile Asp Ser Lys Ala Cys Val Val Ser
            180                 185                 190

Leu Gln Asn Ile Gln Phe Asn Arg Gly Arg Thr Cys Trp
        195                 200                 205

<210> SEQ ID NO 11
<211> LENGTH: 175
<212> TYPE: PRT
<213> ORGANISM: Solanum lycopersicum
```

<400> SEQUENCE: 11

```
Met Arg Asn Leu Phe Pro Ile Leu Met Leu Leu Thr Asn Leu Ser Leu
1               5                   10                  15

Asn Ile Asp Asn Asn Asn Asn Asn Ile Ile Arg Ala Thr Cys Arg
            20                  25                  30

Glu Thr Pro Tyr Tyr Ser Leu Cys Leu Ser Val Leu Glu Ser Asp Pro
                35                  40                  45

Arg Ser Tyr Lys Ala Glu Gly Ser Asp Ile Thr Thr Leu Gly Leu
    50                  55                  60

Ile Met Val Asp Ala Val Lys Ser Lys Ser Ile Glu Ile Met Lys Lys
65                  70                  75                  80

Leu Lys Glu Leu Glu Lys Ser Asn Pro Glu Trp Arg Val Pro Leu Asn
                85                  90                  95

Gln Cys Tyr Met Val Tyr Asn Thr Val Leu Arg Ala Asp Val Thr Val
                100                 105                 110

Ala Val Glu Ala Leu Lys Arg Gly Val Pro Lys Phe Ala Glu Asp Gly
            115                 120                 125

Met Asp Asp Val Val Val Glu Ala Gln Thr Cys Glu Phe Ser Phe Asn
130                 135                 140

Tyr Tyr Asn Lys Ser Asp Phe Pro Ile Ser Asn Met Ser Lys Asp Ile
145                 150                 155                 160

Val Glu Leu Ser Lys Val Ala Lys Ser Ile Ile Arg Met Leu Leu
                165                 170                 175
```

<210> SEQ ID NO 12
<211> LENGTH: 171
<212> TYPE: PRT
<213> ORGANISM: Solanum lycopersicum

<400> SEQUENCE: 12

```
Met Lys Ile Leu Ile Phe Leu Ile Met Phe Leu Ala Met Leu Leu Val
1               5                   10                  15

Thr Ser Gly Asn Asn Asn Leu Val Glu Thr Thr Cys Lys Asn Thr Pro
                20                  25                  30

Asn Tyr Asn Leu Cys Val Lys Thr Leu Ser Leu Asp Lys Arg Ser Glu
            35                  40                  45

Lys Ala Gly Asp Ile Thr Thr Leu Ala Leu Ile Met Val Asp Ala Ile
    50                  55                  60

Lys Ser Lys Ala Asn Gln Ala Ala Asn Thr Ile Ser Lys Leu Arg His
65                  70                  75                  80

Ser Asn Pro Pro Gln Ala Trp Lys Asp Pro Leu Lys Asn Cys Ala Phe
                85                  90                  95

Ser Tyr Lys Val Ile Leu Thr Ala Ser Met Pro Glu Ala Ile Glu Ala
                100                 105                 110

Leu Thr Lys Gly Asp Pro Lys Phe Ala Glu Asp Gly Met Val Gly Ser
            115                 120                 125

Ser Gly Asp Ala Gln Glu Cys Glu Glu Tyr Phe Lys Ala Thr Thr Ile
130                 135                 140

Lys Tyr Ser Pro Leu Ser Lys Leu Asn Ile Asp Val His Glu Leu Ser
145                 150                 155                 160

Asp Val Gly Arg Ala Ile Val Arg Asn Leu Leu
                165                 170
```

<210> SEQ ID NO 13

```
<211> LENGTH: 184
<212> TYPE: PRT
<213> ORGANISM: Beta vulgaris

<400> SEQUENCE: 13

Met Thr Thr Leu Asn Thr Ser Leu Pro His Leu His Leu Leu Phe Ile
1               5                   10                  15

Thr Leu Leu Thr Leu Phe Thr Thr Ser Thr Leu Ala Tyr Ser Arg Lys
            20                  25                  30

Thr Thr Asn Asp Leu Val Thr Thr Cys Lys Gln Thr Pro Asp Pro
        35                  40                  45

Ile Leu Cys Glu Ala Ser Leu Arg Ser Asp Ser Arg Ser Ser Lys Ala
50                  55                  60

Ala Asp Ser Glu Gly Leu Ile Leu Ile Met Ile Asp Val Val Lys Thr
65                  70                  75                  80

Arg Phe Ser Asp Ser Phe Arg Tyr Val Glu Asp Leu Thr Arg Lys Thr
                85                  90                  95

His Asp Pro Asp Val Ile Arg Ala Leu Gln Glu Cys Lys Gln Leu Tyr
            100                 105                 110

Arg Val Val Leu Asp Val Ser Val Gly Leu Ala Val Arg Ala Val Lys
        115                 120                 125

Gln Gly Asp Pro Lys Phe Gly Glu Gln Ala Met Val Asp Ala Gly Asn
130                 135                 140

Glu Ala Glu Gly Cys Arg Met Ala Phe Pro Glu Gly Lys Val Pro Gly
145                 150                 155                 160

Arg Ile Val Gly Arg Thr Arg Met Leu His Gly Val Ser Asn Val Ala
                165                 170                 175

Ala Ser Met Ile Lys Ser Leu Glu
            180

<210> SEQ ID NO 14
<211> LENGTH: 172
<212> TYPE: PRT
<213> ORGANISM: Nicotiana tabacum

<400> SEQUENCE: 14

Met Arg Asn Leu Phe Pro Ile Phe Met Leu Ile Thr Asn Leu Ala Phe
1               5                   10                  15

Asn Asp Asn Asn Asn Ser Asn Asn Ile Ile Asn Thr Thr Cys Arg Ala
            20                  25                  30

Thr Thr Asn Tyr Pro Leu Cys Leu Thr Thr Leu His Ser Asp Pro Arg
        35                  40                  45

Thr Ser Glu Ala Glu Gly Ala Asp Leu Thr Thr Leu Gly Leu Val Met
50                  55                  60

Val Asp Ala Val Lys Leu Lys Ser Ile Glu Ile Met Lys Ser Ile Lys
65                  70                  75                  80

Lys Leu Glu Lys Ser Asn Pro Glu Leu Arg Leu Pro Leu Ser Gln Cys
                85                  90                  95

Tyr Ile Val Tyr Tyr Ala Val Leu His Ala Asp Val Thr Val Ala Val
            100                 105                 110

Glu Ala Leu Lys Arg Gly Val Pro Lys Phe Ala Glu Asn Gly Met Val
        115                 120                 125

Asp Val Ala Val Glu Ala Glu Thr Cys Glu Phe Ser Phe Lys Tyr Asn
130                 135                 140

Gly Leu Val Ser Pro Val Ser Asp Met Asn Lys Glu Ile Ile Glu Leu
145                 150                 155                 160
```

```
Ser Ser Val Ala Lys Ser Ile Ile Arg Met Leu Leu
            165                 170
```

<210> SEQ ID NO 15
<211> LENGTH: 166
<212> TYPE: PRT
<213> ORGANISM: Nicotiana tabacum

<400> SEQUENCE: 15

```
Met Lys Asn Leu Ile Phe Leu Thr Met Phe Leu Thr Ile Leu Leu Gln
1               5                   10                  15

Thr Asn Ala Asn Asn Leu Val Glu Thr Thr Cys Lys Asn Thr Pro Asn
            20                  25                  30

Tyr Gln Leu Cys Leu Lys Thr Leu Leu Ser Asp Lys Arg Ser Ala Thr
        35                  40                  45

Gly Asp Ile Thr Thr Leu Ala Leu Ile Met Val Asp Ala Ile Lys Ala
    50                  55                  60

Lys Ala Asn Gln Ala Ala Val Thr Ile Ser Lys Leu Arg His Ser Asn
65                  70                  75                  80

Pro Pro Ala Ala Trp Lys Gly Pro Leu Lys Asn Cys Ala Phe Ser Tyr
                85                  90                  95

Lys Val Ile Leu Thr Ala Ser Leu Pro Glu Ala Ile Glu Ala Leu Thr
            100                 105                 110

Lys Gly Asp Pro Lys Phe Ala Glu Asp Gly Met Val Gly Ser Ser Gly
        115                 120                 125

Asp Ala Gln Glu Cys Glu Glu Tyr Phe Lys Gly Ser Lys Ser Pro Phe
    130                 135                 140

Ser Ala Leu Asn Ile Ala Val His Glu Leu Ser Asp Val Gly Arg Ala
145                 150                 155                 160

Ile Val Arg Asn Leu Leu
                165
```

<210> SEQ ID NO 16
<211> LENGTH: 181
<212> TYPE: PRT
<213> ORGANISM: Solanum tuberosum

<400> SEQUENCE: 16

```
Met Arg Asn Leu Phe Pro Ile Leu Met Leu Ile Thr Asn Leu Ala Leu
1               5                   10                  15

Asn Asn Asp Asn Asn Asn Asn Asn Asn Asn Asn Asn Tyr Asn Leu
            20                  25                  30

Ile His Ala Thr Cys Arg Glu Thr Pro Tyr Tyr Ser Leu Cys Leu Thr
        35                  40                  45

Thr Leu Gln Ser Asp Pro Arg Ser Asn Glu Val Glu Gly Asp Asp Ala
    50                  55                  60

Ile Thr Thr Leu Gly Leu Ile Met Val Asp Val Val Lys Ser Lys Ser
65                  70                  75                  80

Ile Glu Ile Met Glu Lys Ile Lys Glu Leu Glu Lys Ser Asn Pro Glu
                85                  90                  95

Trp Arg Ala Pro Leu Ser Gln Cys Tyr Val Ala Tyr Asn Ala Val Leu
            100                 105                 110

Arg Ala Asp Val Thr Val Ala Val Glu Ala Leu Lys Lys Gly Val Pro
        115                 120                 125

Lys Phe Ala Glu Asp Gly Met Asp Asp Val Val Val Glu Ala Gln Thr
    130                 135                 140
```

```
Cys Glu Tyr Ser Phe Asn Tyr Asn Lys Leu Asp Phe Pro Ile Ser
145                 150                 155                 160

Asn Leu Ser Arg Glu Ile Ile Glu Leu Ser Lys Val Ala Lys Ser Ile
            165                 170                 175

Ile Arg Met Leu Leu
            180

<210> SEQ ID NO 17
<211> LENGTH: 10042
<212> TYPE: DNA
<213> ORGANISM: Artificial Sequence
<220> FEATURE:
<223> OTHER INFORMATION: Synthetic construct vector pMBXS1168

<400> SEQUENCE: 17
ggccagtgcc aagcttggcg cgcccctagg cctcagctta attaagcgta ttggctagag      60
cagcttgcca acatggtgga gcacgacact ctcgtctact ccaagaatat caaagataca     120
gtctcagaag accaaaggac tattgagact tttcaacaaa gggtaatatc gggaaacctc     180
ctcggattcc attgcccagc tatctgtcac ttcatcaaaa ggacagtaga aaaggaaggt     240
ggcacctaca atgccatca ttgcgataaa ggaaaggcta tcgttcaaga tgcctctgcc      300
gacagtggtc ccaaagatgg acccccaccc acgaggagca tcgtggaaaa agaagacgtt     360
ccaaccacgt cttcaaagca gtggattga tgtgataaca tggtggagca cgacactctc      420
gtctactcca gaatatcaa agatacagtc tcagaagacc aaagggctat tgagactttt      480
caacaaaggg taatatcggg aaacctcctc ggattccatt gcccagctat ctgtcacttc     540
atcaaaagga cagtagaaaa ggaaggtggc acctacaaat gccatcattg cgataaagga     600
aaggctatcg ttcaagatgc ctctgccgac agtggtccca agatggaccc ccacccacg     660
aggagcatcg tggaaaaaga agacgttcca accacgtctt caaagcaagt ggattgatgt     720
gatatctcca ctgacgtaag ggatgacgca caatcccact atccttcgca agaccttcct     780
ctatataagg aagttcattt catttggaga ggacacgctg aaatcaccag tctctctcta     840
caaatctatc tctctcgagt ctaccagatc taaaatgaaa tatgatttct gcgtcaattc     900
tcttacacaa gatccacaaa gcaaaacggc gaccaccctc gaaggtttag tcctagcatc     960
gacgaagaat gctgcggcgg aaacactgaa cgtaaaagga ctcgctgaac agatcctcaa    1020
ggggaaggga tatgggccag gtatggaggc agggctacac aagtgcgtca agatttatgg    1080
aggtgcttat gattttttaa acactgcttt agcgaacgtt caatcacacc attatagtac    1140
tgctgtagag gaatttcttt atgcttcatt tgcaccgttc gactgcgtga atattattg     1200
gatttctccc ttcgctaagg agagctatat tatctttgag aagattttga ttcctatgac    1260
tttaactaaa atgttgtgac ctcaggctcg agtttctcca taataatgtg tgagtagttc    1320
ccagataagg gaattagggt tcctataggg tttcgctcat gtgttgagca tataagaaac    1380
ccttagtatg tatttgtatt tgtaaaatac ttctatcaat aaaatttcta attcctaaaa    1440
ccaaaatcca gtactaaaat ccagatcccc cgaattaatt cggcgttaat tcagcggacc    1500
gctcgagcaa ttgtacgtag aattcgtaat catgtcatag ctgtttcctg tgtgaaattg    1560
ttatccgctc acaattccac acaacatacg agccggaagc ataaagtgta aagcctgggg    1620
tgcctaatga gtgagctaac tcacattaat tgcgttgcgc tcactgcccg ctttccagtc    1680
gggaaacctg tcgtgccagc tgcattaatg aatcggccaa cgcgcgggga gaggcggttt    1740
gcgtattggc tagagcagct tgccaacatg gtggagcacg acactctcgt ctactccaag    1800
```

```
aatatcaaag atacagtctc agaagaccaa agggctattg agacttttca acaaagggta    1860
atatcgggaa acctcctcgg attccattgc ccagctatct gtcacttcat caaaaggaca    1920
gtagaaaagg aaggtggcac ctacaaatgc catcattgcg ataaaggaaa ggctatcgtt    1980
caagatgcct ctgccgacag tggtcccaaa gatggacccc cacccacgag gagcatcgtg    2040 gaaaagaag acgttccaac cacgtcttca agcaagtgg attgatgtga acatggtgga     2100
gcacgacact ctcgtctact ccaagaatat caaagataca gtctcagaag accaaagggc    2160
tattgagact tttcaacaaa gggtaatatc gggaaacctc ctcggattcc attgcccagc    2220
tatctgtcac ttcatcaaaa ggacagtaga aaggaaggt ggcacctaca aatgccatca     2280
ttgcgataaa ggaaaggcta tcgttcaaga tgcctctgcc gacagtggtc ccaaagatgg    2340
accccacccc acgaggagca tcgtggaaaa agaagacgtt ccaaccacgt cttcaaagca    2400
agtggattga tgtgatatct ccactgacgt aagggatgac gcacaatccc actatccttc    2460
gcaagaccct tcctctatat aaggaagttc atttcatttg gagaggacac gctgaaatca    2520
ccagtctctc tctacaaatc tatctctctc gagaaaatgg cctcctccga aacgtcatc     2580 accgagttca tgcgcttcaa ggtgcgcatg gagggcaccg tgaacggcca cgagttcgag    2640
atcgagggcg agggcgaggg ccgcccctac gagggccaca acaccgtgaa gctgaaggtg    2700
accaagggcg gccccctgcc cttcgcctgg gacatcctgt cccccagtt ccagtacggc     2760 tccaaggtgt acgtgaagca cccgccgac atccccgact acaagaagct gtccttcccc     2820
gagggcttca gtgggagcg cgtgatgaac ttcgaggacg gcggcgtggc gaccgtgacc     2880
caggactcct ccctgcagga cggctgcttc atctacaagg tgaagttcat cggcgtgaac    2940 ttccctccg acggcccgt gatgcagaag aagaccatgg gctgggaggc ctccaccgag     3000
cgcctgtacc cccgcgacgg cgtgctgaag ggcgaaaccc acaaggccct gaagctgaag    3060
gacggcggcc actacctggt ggagttcaag tccatctaca tggccaagaa gcccgtgcag    3120
ctgcccggct actactacgt ggacgccaag ctggacatca cctcccacaa cgaggactac    3180
accatcgtgg agcagtacga gcgcaccgag ggccgccacc acctgttcct ggtaccaatg    3240
agctctgtcc aacagtctca gggttaactc gagtttctcc ataataatgt gtgagtagtt    3300
cccagataag ggaattaggg ttcctatagg gtttcgctca tgtgttgagc atataagaaa    3360 ccccttagtat gtatttgtat ttgtaaaata cttctatcaa taaaatttct aattcctaaa   3420
accaaaatcc agtactaaaa tccagatccc ccgaattaat tcggcgttaa ttcagtacat    3480
taaaaacgtc cgcaatgtgt tattaagttg tctaagcgtc aatttgttta caccacaata    3540
tatcctgcca ccagccagcc aacagctccc cgaccggcag ctcggcacaa aatcaccact    3600
cgatacaggc agcccatcag tccgggacgg cgtcagcggg agagccgttg taaggcggca    3660
gactttgctc atgttaccga tgctattcgg aagaacggca actaagctgc cgggtttgaa    3720
acacggatga tctcgcggag ggtagcatgt tgattgtaac gatgacagag cgttgctgcc    3780
tgtgatcacc gcggtttcaa aatcggctcc gtcgatacta tgttatacgc aactttgaa    3840 aacaactttg aaaagctgt tttctggtat ttaaggtttt agaatgcaag gaacagtgaa    3900
ttggagttcg tcttgttata attagcttct tggggtatct ttaaatactg tagaaaagag    3960
gaaggaaata ataaatggct aaaatgagaa tatcaccgga attgaaaaaa ctgatcgaaa    4020
aataccgctg cgtaaaagat acggaaggaa tgtctcctgc taaggtatat aagctggtgg    4080
gagaaaatga aaacctatat ttaaaaatga cggacagccg gtataaaggg accacctatg    4140
```

-continued

```
atgtggaacg ggaaaaggac atgatgctat ggctggaagg aaagctgcct gttccaaagg    4200
tcctgcactt tgaacggcat gatggctgga gcaatctgct catgagtgag gccgatggcg    4260
tcctttgctc ggaagagtat gaagatgaac aaagccctga aaagattatc gagctgtatg    4320
cggagtgcat caggctcttt cactccatcg acatatcgga ttgtccctat acgaatagct    4380
tagacagccg cttagccgaa ttggattact tactgaataa cgatctggcc gatgtggatt    4440
gcgaaaactg gaagaagac actccattta aagatccgcg cgagctgtat gatttttaa     4500 agacggaaaa gcccgaagag gaacttgtct tttcccacgg cgacctggga gacagcaaca    4560
tctttgtgaa agatggcaaa gtaagtggct ttattgatct tgggagaagc ggcagggcgg    4620
acaagtggta tgacattgcc ttctgcgtcc ggtcgatcag ggaggatatc ggggaagaac    4680
agtatgtcga gctattttt gacttactgg ggatcaagcc tgattgggag aaaataaaat    4740
attatatttt actggatgaa ttgttttagt acctagaatg catgaccaaa atcccttaac    4800
gtgagttttc gttccactga gcgtcagacc ccgtagaaaa gatcaaagga tcttcttgag    4860 atccttttt tctgcgcgta atctgctgct tgcaaacaaa aaaaccaccg ctaccagcgg    4920
tggtttgttt gccggatcaa gagctaccaa ctctttttcc gaaggtaact ggcttcagca    4980
gagcgcagat accaaatact gtccttctag tgtagccgta gttaggccac cacttcaaga    5040
actctgtagc accgcctaca tacctcgctc tgctaatcct gttaccagtg gctgctgcca    5100
gtggcgataa gtcgtgtctt accgggttgg actcaagacg atagttaccg gataaggcgc    5160
agcggtcggg ctgaacgggg ggttcgtgca cacagcccag cttggagcga acgacctaca    5220
ccgaactgag atacctacag cgtgagctat gagaaagcgc cacgcttccc gaagggagaa    5280
aggcggacag gtatccggta agcggcaggg tcggaacagg agagcgcacg agggagcttc    5340 caggggaaa cgcctggtat ctttatagtc ctgtcgggtt tcgccacctc tgacttgagc    5400 gtcgatttt gtgatgctcg tcaggggggc ggagcctatg gaaaaacgcc agcaacgcgg    5460
cctttttacg gttcctggcc ttttgctggc cttttgctca catgttcttt cctgcgttat    5520
cccctgattc tgtggataac cgtattaccg cctttgagtg agctgatacc gctcgccgca    5580
gccgaacgac cgagcgcagc gagtcagtga gcgaggaagc ggaagagcgc ctgatgcggt    5640
attttctcct tacgcatctg tgcggtattt cacaccgcat atggtgcact ctcagtacaa    5700
tctgctctga tgccgcatag ttaagccagt atacactccg ctatcgctac gtgactgggt    5760
catggctgcg ccccgacacc cgccaacacc cgctgacgcg ccctgacggg cttgtctgct    5820
cccggcatcc gcttacagac aagctgtgac cgtctccggg agctgcatgt gtcagaggtt    5880
ttcaccgtca tcaccgaaac gcgcgaggca gggtgccttg atgtgggcgc cggcggtcga    5940
gtggcgacgg cgcggcttgt ccgcgccctg gtagattgcc tggccgtagg ccagccattt    6000
ttgagcggcc agcggccgcg ataggccgac gcgaagcggc gggcgtagg gagcgcagcg    6060 accgaagggt aggcgctttt tgcagctctt cggctgtgcg ctggccagac agttatgcac    6120
aggccaggcg ggttttaaga gttttaataa gttttaaaga gttttaggcg gaaaaatcgc    6180
cttttttctc ttttatatca gtcacttaca tgtgtgaccg gttcccaatg tacggctttg    6240
ggttcccaat gtacgggttc cggttcccaa tgtacggctt tgggttccca atgtacgtgc    6300
tatccacagg aaacagacct tttcgacctt tttcccctgc tagggcaatt tgccctagca    6360
tctgctccgt acattaggaa ccggcggatg cttcgccctc gatcaggttg cggtagcgca    6420
tgactaggat cgggccagcc tgccccgcct cctccttcaa atcgtactcc ggcaggtcat    6480
ttgacccgat cagcttgcgc acggtgaaac agaacttctt gaactctccg gcgctgccac    6540
```

```
tgcgttcgta gatcgtcttg aacaaccatc tggcttctgc cttgcctgcg gcgcggcgtg   6600
ccaggcggta gagaaaacgg ccgatgccgg gatcgatcaa aaagtaatcg gggtgaaccg   6660
tcagcacgtc cgggttcttg ccttctgtga tctcgcggta catccaatca gctagctcga   6720
tctcgatgta ctccgccgc ccggtttcgc tctttacgat cttgtagcgg ctaatcaagg    6780
cttcaccctc ggataccgtc accaggcggc cgttcttggc cttcttcgta cgctgcatgg   6840
caacgtgcgt ggtgtttaac cgaatgcagg tttctaccag gtcgtctttc tgctttccgc   6900
catcggctcg ccggcagaac ttgagtacgt ccgcaacgtg tggacggaac acgcggccgg   6960
gcttgtctcc cttcccttcc cggtatcggt tcatggattc ggttagatgg gaaaccgcca   7020
tcagtaccag gtcgtaatcc cacacactgg ccatgccggc cggccctgcg gaaacctcta   7080
cgtgcccgtc tggaagctcg tagcggatca cctcgccagc tcgtcggtca cgcttcgaca   7140
gacggaaaac ggccacgtcc atgatgctgc gactatcgcg ggtgcccacg tcatagagca   7200
tcggaacgaa aaatctggt tgctcgtcgc ccttgggcgg cttcctaatc gacggcgcac    7260
cggctgccgg cggttgccgg gattctttgc ggattcgatc agcggccgct tgccacgatt   7320
caccggggcg tgcttctgcc tcgatgcgtt gccgctgggc ggcctgcgcg gccttcaact   7380
tctccaccag gtcatcaccc agcgccgcgc cgatttgtac cgggccggat ggtttgcgac   7440
cgctcacgcc gattcctcgg gcttgggggt tccagtgcca ttgcagggcc ggcaggcaac   7500
ccagccgctt acgcctggcc aaccgcccgt tcctccacac atgggggcatt ccacggcgtc  7560
ggtgcctggt tgttcttgat tttccatgcc gcctccttta gccgctaaaa ttcatctact   7620
catttattca tttgctcatt tactctggta gctgcgcgat gtattcagat agcagctcgg   7680
taatggtctt gccttggcgt accgcgtaca tcttcagctt ggtgtgatcc tccgccggca   7740
actgaaagtt gacccgcttc atggctggcg tgtctgccag gctggccaac gttgcagcct   7800
tgctgctgcg tgcgctcgga cggccggcac ttagcgtgtt tgtgcttttg ctcattttct   7860
ctttacctca ttaactcaaa tgagttttga tttaatttca gcggccagcg cctggaccctc  7920
gcggcagcg tcgccctcgg gttctgattc aagaacggtt gtgccggcgg cggcagtgcc   7980
tgggtagctc acgcgctgcg tgatacggga ctcaagaatg ggcagctcgt acccggccag   8040
cgcctcggca acctcaccgc cgatgcgcgt gcctttgatc gcccgcgaca cgacaaaggc   8100
cgcttgtagc cttccatccg tgacctcaat gcgctgctta accagctcca ccaggtcggc   8160
ggtggcccat atgtcgtaag ggcttggctg caccggaatc agcacgaagt cggctgcctt   8220
gatcgcggac acagccaagt ccgccgcctg gggcgctccg tcgatcacta cgaagtcgcg   8280
ccggccgatg gccttcacgt cgcggtcaat cgtcgggcgg tcgatgccga caacggttag   8340
cggttgatct tcccgcacgg ccgcccaatc gcgggcactg ccctggggat cggaatcgac   8400
taacagaaca tcggccccgg cgagttgcag ggcgcgggct agatgggttg cgatggtcgt   8460
cttgcctgac ccgcctttct ggttaagtac agcgataacc ttcatgcgtt cccccttgcgt  8520
atttgtttat ttactcatcg catcatatac gcagcgaccg catgacgcaa gctgttttac   8580
tcaaatacac atcacctttt tagacggcgg cgctcggttt cttcagcggc caagctggcc   8640
ggccaggccg ccagcttggc atcagacaaa ccggccagga tttcatgcag ccgcacggtt   8700
gagacgtgcg cgggcggctc gaacacgtac ccggccgcga tcatctccgc ctcgatctct   8760
tcggtaatga aaaacggttc gtcctggccg tcctggtgcg gtttcatgct tgttcctctt   8820
ggcgttcatt ctcggcggcc gccagggcgt cggcctcggt caatgcgtcc tcacggaagg   8880
```

```
caccgcgccg cctggcctcg gtgggcgtca cttcctcgct gcgctcaagt gcgcggtaca    8940
gggtcgagcg atgcacgcca agcagtgcag ccgcctcttt cacggtgcgg ccttcctggt    9000
cgatcagctc gcgggcgtgc gcgatctgtg ccggggtgag ggtagggcgg gggccaaact    9060
tcacgcctcg ggccttggcg gcctcgcgcc cgctccgggt gcggtcgatg attagggaac    9120
gctcgaactc ggcaatgccg gcgaacacgg tcaacaccat gcggccggcc ggcgtggtgg    9180
tgtcggccca cggctctgcc aggctacgca ggcccgcgcc ggcctcctgg atgcgctcgg    9240
caatgtccag taggtcgcgg gtgctgcggg ccaggcggtc tagcctggtc actgtcacaa    9300
cgtcgccagg gcgtaggtgg tcaagcatcc tggccagctc cgggcggtcg cgcctggtgc    9360
cggtgatctt ctcggaaaac agcttggtgc agccggccgc gtgcagttcg cccgttggt     9420
tggtcaagtc ctggtcgtcg gtgctgacgc gggcatagcc cagcaggcca gcggcggcgc    9480
tcttgttcat ggcgtaatgt ctccggttct agtcgcaagt attctacttt atgcgactaa    9540
aacacgcgac aagaaaacgc caggaaaagg gcagggcggc agcctgtcgc gtaacttagg    9600
acttgtgcga catgtcgttt tcagaagacg gctgcactga acgtcagaag ccgactgcac    9660
tatagcagcg gaggggttgg atcaaagtac tttgatcccg aggggaaccc tgtggttggc    9720
atgcacatac aaatggacga acggataaac cttttcacgc ccttttaaat atccgattat    9780
tctaataaac gctcttttct cttaggttta cccgccaata tcctgtca aacactgata     9840
gtttaaactg aaggcgggaa acgacaatct gatccaagct caagctgctc tagcattcgc    9900
cattcaggct gcgcaactgt tgggaagggc gatcggtgcg ggcctcttcg ctattacgcc    9960
agctggcgaa aggggg
atgt gctgcaaggc gattaagttg ggtaacgcca gggttttccc 10020
agtcacgacg ttgtaaaacg ac                                           10042
```

<210> SEQ ID NO 18
<211> LENGTH: 10144
<212> TYPE: DNA
<213> ORGANISM: Artificial Sequence
<220> FEATURE:
<223> OTHER INFORMATION: Synthetic construct vector pMBXS1169

<400> SEQUENCE: 18

```
ggccagtgcc aagcttggcg cgcccctagg cctcagctta attaagcgta ttggctagag     60
cagcttgcca acatggtgga gcacgacact ctcgtctact ccaagaatat caaagataca    120
gtctcagaag accaaagggc tattgagact tttcaacaaa gggtaatatc gggaaacctc    180
ctcggattcc attgcccagc tatctgtcac ttcatcaaaa ggacagtaga aaaggaaggt    240
ggcacctaca aatgccatca ttgcgataaa ggaaaggcta tcgttcaaga tgcctctgcc    300
gacagtggtc ccaaagatgg acccccaccc acgaggagca tcgtggaaaa agaagacgtt    360
ccaaccacgt cttcaaagca agtggattga tgtgataaca tggtggagca cgacactctc    420
gtctactcca gaatatcaa agatacagtc tcagaagacc aaagggctat tgagactttt    480
caacaaaggg taatatcggg aaacctcctc ggattccatt gcccagctat ctgtcacttc    540
atcaaaagga cagtagaaaa ggaaggtggc acctacaaat gccatcattg cgataaagga    600
aaggctatcg ttcaagatgc ctctgccgac agtggtccca agatggaccc cacccacg     660
aggagcatcg tggaaaaaga agacgttcca accacgtctt caaagcaagt ggattgatgt    720
gatatctcca ctgacgtaag ggatgacgca caatcccact atccttcgca agaccttcct    780
ctatataagg aagttcattt catttggaga ggacacgctg aaatcaccag tctctctcta    840
caaatctatc tctctcgagt ctaccagatc taaattggtt ccttggttg tgttctctct    900
```

```
tctcttgatc ggttttgcat ctgcgcaaac tctcatagta gattcttgca agaaagcagc    960
cgcaaaagag ccgtttatga aatatgattt ctgcgtcaat tctcttacac aagatccaca   1020
aagcaaaacg gcgaccaccc tcgaaggttt agtcctagca tcgacgaaga atgctgcggc   1080
ggaaacactg aacgtaaaag gactcgctga acagatcctc aaggggaagg gatatgggcc   1140
aggtatggag gcagggctac acaagtgcgt caagatttat ggaggtgctt atgatttttt   1200
aaacactgct ttagcgaacg ttcaatcaca ccattatagt actgctgtag aggaatttct   1260
ttatgcttca tttgcaccgt tcgactgcgt gaaatattat tggatttctc ccttcgctaa   1320
ggagagctat attatctttg agaagatttt gattcctatg actttaacta aaatgttgtg   1380
acctcaggct cgagtttctc cataataatg tgtgagtagt tcccagataa gggaattagg   1440
gttcctatag ggtttcgctc atgtgttgag catataagaa acccttagta tgtatttgta   1500
tttgtaaaat acttctatca ataaaatttc taattcctaa aaccaaaatc cagtactaaa   1560
atccagatcc cccgaattaa ttcggcgtta attcagcgga ccgctcgagc aattgtacgt   1620
agaattcgta atcatgtcat agctgtttcc tgtgtgaaat tgttatccgc tcacaattcc   1680
acacaacata cgagccggaa gcataaagtg taaagcctgg ggtgcctaat gagtgagcta   1740
actcacatta attgcgttgc gctcactgcc cgctttccag tcgggaaacc tgtcgtgcca   1800
gctgcattaa tgaatcggcc aacgcgcggg gagaggcggt ttgcgtattg gctagagcag   1860
cttgccaaca tggtggagca cgacactctc gtctactcca agaatatcaa agatacagtc   1920
tcagaagacc aaagggctat tgagactttt caacaaaggg taatatcggg aaacctcctc   1980
ggattccatt gcccagctat ctgtcacttc atcaaaagga cagtagaaaa ggaaggtggc   2040
acctacaaat gccatcattg cgataaagga aaggctatcg ttcaagatgc ctctgccgac   2100
agtggtccca agatggaccc cccacccacg aggagcatcg tggaaaaaga agacgttcca   2160
accacgtctt caaagcaagt ggattgatgt gaacatggtg gagcacgaca ctctcgtcta   2220
ctccaagaat atcaaagata cagtctcaga agaccaaagg ctattgagac ttttcaaca   2280
aagggtaata tcgggaaacc tcctcggatt ccattgccca gctatctgtc acttcatcaa   2340
aaggacagta gaaaggaag gtggcaccta caaatgccat cattgcgata aggaaaggc   2400
tatcgttcaa gatgcctctg ccgacagtgg tcccaaagat ggaccccac ccacgaggag   2460
catcgtggaa aaagaagacg ttccaaccac gtcttcaaag caagtggatt gatgtgatat   2520
ctccactgac gtaagggatg acgcacaatc ccactatcct tcgcaagacc cttcctctat   2580
ataaggaagt tcatttcatt tggagaggac acgctgaaat caccagtctc tctctacaaa   2640
tctatctctc tcgagaaaat ggcctcctcc gagaacgtca tcaccgagtt catgcgcttc   2700
aaggtgcgca tggagggcac cgtgaacggc cacgagttcg agatcgaggg cgagggcgag   2760
ggccgcccct acgagggcca caacaccgtg aagctgaagg tgaccaaggg cggccccctg   2820
cccttcgcct gggacatcct gtccccccag ttccagtacg gctccaaggt gtacgtgaag   2880
caccccgccg acatccccga ctacaagaag ctgtccttcc ccgagggctt caagtgggag   2940
cgcgtgatga acttcgagga cggcggcgtg gcgaccgtga cccaggactc ctccctgcag   3000
gacggctgct tcatctacaa ggtgaagttc atcggcgtga acttccctc cgacggcccc   3060
gtgatgcaga agaagaccat gggctgggag gcctccaccg agcgcctgta ccccgcgac   3120
ggcgtgctga agggcgaaac ccacaaggcc ctgaagctga aggacggcgg ccactacctg   3180
gtggagttca gtccatcta catggccaag aagcccgtgc agctgccgg ctactactac   3240
```

```
gtggacgcca agctggacat cacctcccac aacgaggact acaccatcgt ggagcagtac    3300
gagcgcaccg agggccgcca ccacctgttc ctggtaccaa tgagctctgt ccaacagtct    3360
cagggttaac tcgagtttct ccataataat gtgtgagtag ttcccagata agggaattag    3420
ggttcctata gggtttcgct catgtgttga gcatataaga aacccttagt atgtatttgt    3480
atttgtaaaa tacttctatc aataaaattt ctaattccta aaaccaaaat ccagtactaa    3540
aatccagatc ccccgaatta attcggcgtt aattcagtac attaaaaacg tccgcaatgt    3600
gttattaagt tgtctaagcg tcaatttgtt tacaccacaa tatatcctgc caccagccag    3660
ccaacagctc cccgaccggc agctcggcac aaaatcacca ctcgatacag gcagcccatc    3720
agtccgggac ggcgtcagcg ggagagccgt tgtaaggcgg cagactttgc tcatgttacc    3780
gatgctattc ggaagaacgg caactaagct gccgggtttg aaacacggat gatctcgcgg    3840
agggtagcat gttgattgta acgatgacag agcgttgctg cctgtgatca ccgcggtttc    3900
aaaatcggct ccgtcgatac tatgttatac gccaactttg aaaacaactt tgaaaaagct    3960
gttttctggt atttaaggtt ttagaatgca aggaacagtg aattggagtt cgtcttgtta    4020
taattagctt cttggggtat cttt aaatac tgtagaaaag aggaaggaaa taataaatgg    4080
ctaaaatgag aatatcaccg gaattgaaaa aactgatcga aaaataccgc tgcgtaaaag    4140
atacggaagg aatgtctcct gctaaggtat ataagctggt gggagaaaat gaaaacctat    4200
atttaaaaat gacggacagc cggtataaag ggaccaccta tgatgtggaa cgggaaaagg    4260
acatgatgct atggctggaa ggaaagctgc ctgttccaaa ggtcctgcac tttgaacggc    4320
atgatggctg gagcaatctg ctcatgagtg aggccgatgg cgtcctttgc tcggaagagt    4380
atgaagatga acaaagccct gaaaagatta tcgagctgta tgcggagtgc atcaggctct    4440
ttcactccat cgacatatcg gattgtccct atacgaatag cttagacagc cgcttagccg    4500
aattggatta cttactgaat aacgatctgg ccgatgtgga ttgcgaaaac tgggaagaag    4560
acactccatt taaagatccg cgcgagctgt atgatttttt aaagacggaa aagcccgaag    4620
aggaacttgt cttttcccac ggcgacctgg gagacagcaa catctttgtg aaagatggca    4680
aagtaagtgg ctttattgat cttgggagaa gcggcagggc ggacaagtgg tatgacattg    4740
ccttctgcgt ccggtcgatc agggaggata tcggggaaga acagtatgtc gagctatttt    4800
ttgacttact ggggatcaag cctgattggg agaaaataaa atattatatt ttactggatg    4860 aattgttta gtacctagaa tgcatgacca aaatccctta acgtgagttt tcgttccact    4920
gagcgtcaga ccccgtagaa aagatcaaag gatcttcttg agatcctttt tttctgcgcg    4980
taatctgctg cttgcaaaca aaaaaaccac cgctaccagc ggtggtttgt ttgccggatc    5040
aagagctacc aactcttttt ccgaaggtaa ctggcttcag cagagcgcag ataccaaata    5100
ctgtccttct agtgtagccg tagttaggcc accacttcaa gaactctgta gcaccgccta    5160
catacctcgc tctgctaatc ctgttaccag tggctgctgc cagtggcgat aagtcgtgtc    5220
ttaccgggtt ggactcaaga cgatagttac cggataaggc gcagcggtcg ggctgaacgg    5280
ggggttcgtg cacacagccc agcttggagc gaacgaccta caccgaactg agatacctac    5340
agcgtgagct atgagaaagc gccacgcttc ccgaagggag aaaggcggac aggtatccgg    5400
taagcggcag ggtcggaaca ggagagcgca cgagggagct tccaggggga aacgcctggt    5460
atctttatag tcctgtcggg tttcgccacc tctgacttga gcgtcgattt ttgtgatgct    5520
cgtcaggggg gcggagccta tggaaaaacg ccagcaacgc ggccttttta cggttcctgg    5580
ccttttgctg gccttttgct cacatgttct ttcctgcgtt atcccctgat tctgtggata    5640
```

```
accgtattac cgcctttgag tgagctgata ccgctcgccg cagccgaacg accgagcgca   5700
gcgagtcagt gagcgaggaa gcggaagagc gcctgatgcg gtattttctc cttacgcatc   5760
tgtgcggtat ttcacaccgc atatggtgca ctctcagtac aatctgctct gatgccgcat   5820
agttaagcca gtatacactc cgctatcgct acgtgactgg gtcatggctg cgccccgaca   5880
cccgccaaca cccgctgacg cgccctgacg ggcttgtctg ctcccggcat ccgcttacag   5940
acaagctgtg accgtctccg ggagctgcat gtgtcagagg ttttcaccgt catcaccgaa   6000
acgcgcgagg cagggtgcct tgatgtgggc gccggcggtc gagtggcgac ggcgcggctt   6060
gtccgcgccc tggtagattg cctggccgta ggccagccat ttttgagcgg ccagcggccg   6120
cgataggccg acgcgaagcg gcggggcgta gggagcgcag cgaccgaagg gtaggcgctt   6180
tttgcagctc ttcggctgtg cgctggccag acagttatgc acaggccagg cgggttttaa   6240 gagtttaat aagttttaaa gagtttagg cggaaaaatc gcctttttc tcttttatat       6300 cagtcactta catgtgtgac cggttcccaa tgtacggctt tgggttccca atgtacgggt   6360
tccggttccc aatgtacggc tttgggttcc caatgtacgt gctatccaca ggaaacagac   6420
cttttcgacc ttttttcccct gctagggcaa tttgccctag catctgctcc gtacattagg   6480
aaccggcgga tgcttcgccc tcgatcaggt tgcggtagcg catgactagg atcgggccag   6540
cctgccccgc ctcctccttc aaatcgtact ccggcaggtc atttgacccg atcagcttgc   6600
gcacggtgaa acagaacttc ttgaactctc cggcgctgcc actgcgttcg tagatcgtct   6660
tgaacaacca tctggcttct gccttgcctg cggcgcggcg tgccaggcgg tagagaaaac   6720
ggccgatgcc gggatcgatc aaaaagtaat cggggtgaac cgtcagcacg tccgggttct   6780
tgccttctgt gatctcgcgg tacatccaat cagctagctc gatctcgatg tactccggcc   6840
gcccggtttc gctctttacg atcttgtagc ggctaatcaa ggcttcaccc tcggataccg   6900
tcaccaggcg gccgttcttg gccttcttcg tacgctgcat ggcaacgtgc gtggtgttta   6960
accgaatgca ggtttctacc aggtcgtctt tctgctttcc gccatcggct cgccggcaga   7020
acttgagtac gtccgcaacg tgtggacgga acacgcggcc gggcttgtct cccttccctt   7080
cccggtatcg gttcatggat tcggttagat gggaaaccgc catcagtacc aggtcgtaat   7140
cccacacact ggccatgccg gccggccctg cggaaacctc tacgtgcccg tctggaagct   7200
cgtagcggat cacctcgcca gctcgtcggt cacgcttcga cagacggaaa acggccacgt   7260
ccatgatgct gcgactatcg cgggtgccca cgtcatagag catcggaacg aaaaaatctg   7320
gttgctcgtc gcccttgggc ggcttcctaa tcgacgcgc accggctgcc ggcggttgcc   7380
gggattcttt gcggattcga tcagcggccg cttgccacga ttcaccgggg cgtgcttctg   7440
cctcgatgcg ttgccgctgg gcggcctgcg cggccttcaa cttctccacc aggtcatcac   7500
ccagcgccgc gccgatttgt accgggccgg atggtttgcg accgctcacg ccgattcctc   7560
gggcttgggg gttccagtgc cattgcaggg ccggcaggca acccagccgc ttacgcctgg   7620
ccaaccgccc gttcctccac acatggggca ttccacggcg tcggtgcctg gttgttcttg   7680
attttccatg ccgcctcctt tagccgctaa aattcatcta ctcatttatt catttgctca   7740
tttactctgg tagctgcgcg atgtattcag atagcagctc ggtaatggtc ttgccttggc   7800
gtaccgcgta catcttcagc ttggtgtgat cctccgccgg caactgaaag ttgacccgct   7860
tcatggctgg cgtgtctgcc aggctggcca acgttgcagc cttgctgctg cgtgcgctcg   7920
gacggccggc acttagcgtg tttgtgcttt tgctcatttt ctctttacct cattaactca   7980
```

```
aatgagtttt gatttaattt cagcggccag cgcctggacc tcgcgggcag cgtcgccctc    8040
gggttctgat tcaagaacgg ttgtgccggc ggcggcagtg cctgggtagc tcacgcgctg    8100
cgtgatacgg gactcaagaa tgggcagctc gtacccggcc agcgcctcgg caacctcacc    8160
gccgatgcgc gtgcctttga tcgcccgcga cacgacaaag gccgcttgta gccttccatc    8220
cgtgacctca atgcgctgct taaccagctc caccaggtcg gcggtggccc atatgtcgta    8280
agggcttggc tgcaccggaa tcagcacgaa gtcggctgcc ttgatcgcgg acacagccaa    8340
gtccgccgcc tggggcgctc cgtcgatcac tacgaagtcg cgccggccga tggccttcac    8400
gtcgcggtca atcgtcgggc ggtcgatgcc gacaacggtt agcggttgat cttcccgcac    8460
ggccgcccaa tcgcgggcac tgccctgggg atcggaatcg actaacagaa catcggcccc    8520
ggcgagttgc agggcgcggg ctagatgggt tgcgatggtc gtcttgcctg acccgccttt    8580
ctggttaagt acagcgataa ccttcatgcg ttccccttgc gtatttgttt atttactcat    8640
cgcatcatat acgcagcgac cgcatgacgc aagctgtttt actcaaatac acatcacctt    8700
tttagacggc ggcgctcggt ttcttcagcg gccaagctgg ccggccaggc cgccagcttg    8760
gcatcagaca aaccggccag gatttcatgc agccgcacgg ttgagacgtg cgcgggcggc    8820
tcgaacacgt acccggccgc gatcatctcc gcctcgatct cttcggtaat gaaaaacggt    8880
tcgtcctggc cgtcctggtg cggtttcatg cttgttcctc ttggcgttca ttctcggcgg    8940
ccgccagggc gtcggcctcg gtcaatgcgt cctcacggaa ggcaccgcgc cgcctggcct    9000
cggtgggcgt cacttcctcg ctgcgctcaa gtgcgcggta cagggtcgag cgatgcacgc    9060
caagcagtgc agccgcctct ttcacggtgc ggccttcctg gtcgatcagc tcgcgggcgt    9120
gcgcgatctg tgccggggtg agggtagggc ggggccaaa cttcacgcct cgggccttgg    9180
cggcctcgcg cccgctccgg gtgcggtcga tgattaggga acgctcgaac tcggcaatgc    9240
cggcgaacac ggtcaacacc atgcggccgg ccggcgtggt ggtgtcggcc cacggctctg    9300
ccaggctacg caggcccgcg ccggcctcct ggatgcgctc ggcaatgtcc agtaggtcgc    9360
gggtgctgcg ggccaggcgg tctagcctgg tcactgtcac aacgtcgcca ggcgtaggt    9420 ggtcaagcat cctggccagc tccgggcggt cgcgcctggt gccggtgatc ttctcggaaa    9480
acagcttggt gcagccggcc gcgtgcagtt cggcccgttg gttggtcaag tcctggtcgt    9540
cggtgctgac gcgggcatag cccagcaggc cagcggcggc gctcttgttc atggcgtaat    9600
gtctccggtt ctagtcgcaa gtattctact ttatgcgact aaaacacgcg acaagaaaac    9660
gccaggaaaa gggcagggcg gcagcctgtc gcgtaactta ggacttgtgc gacatgtcgt    9720
tttcagaaga cggctgcact gaacgtcaga agccgactgc actatagcag cggaggggtt    9780
ggatcaaagt actttgatcc cgaggggaac cctgtggttg gcatgcacat acaaatggac    9840
gaacggataa accttttcac gcccttttaa atatccgatt attctaataa acgctctttt    9900
ctcttaggtt tacccgccaa tatatcctgt caaacactga tagtttaaac tgaaggcggg    9960
aaacgacaat ctgatccaag ctcaagctgc tctagcattc gccattcagg ctgcgcaact   10020
gttgggaagg gcgatcggtg cgggcctctt cgctattacg ccagctggcg aaaggggat   10080 gtgctgcaag gcgattaagt tgggtaacgc cagggttttc ccagtcacga cgttgtaaaa   10140
cgac                                                               10144
```

<210> SEQ ID NO 19
<211> LENGTH: 11136
<212> TYPE: DNA
<213> ORGANISM: Artificial Sequence
<220> FEATURE:
<223> OTHER INFORMATION: Synthetic construct vector pMBX058

<400> SEQUENCE: 19

| | | | | | |
|---|---|---|---|---|---|
| tggcaggata | tattgtggtg | taaacaaatt | gacgcttaga | caacttaata | acacattgcg | 60 |
| gacgttttta | atgtactgaa | ttaacgccga | attaattcga | gctcggatct | gataatttat | 120 |
| ttgaaaattc | ataagaaaag | caaacgttac | atgaattgat | gaaacaatac | aaagacagat | 180 |
| aaagccacgc | acatttagga | tattggccga | gattactgaa | tattgagtaa | gatcacggaa | 240 |
| tttctgacag | gagcatgtct | tcaattcagc | ccaaatggca | gttgaaatac | tcaaaccgcc | 300 |
| ccatatgcag | gagcggatca | ttcattgttt | gtttggttgc | ctttgccaac | atgggagtcc | 360 |
| aagattctgc | agtcaaatct | cggtgacggg | caggaccgga | cggggcggta | ccggcaggct | 420 |
| gaagtccagc | tgccagaaac | ccacgtcatg | ccagttcccg | tgcttgaagc | cggccgcccg | 480 |
| cagcatgccg | cgggggggcat | atccgagcgc | ctcgtgcatg | cgcacgctcg | ggtcgttggg | 540 |
| cagcccgatg | acagcgacca | cgctcttgaa | gccctgtgcc | tccagggact | tcagcaggtg | 600 |
| ggtgtagagc | gtggagccca | gtcccgtccg | ctggtggcgg | ggggagacgt | acacggtcga | 660 |
| ctcggccgtc | cagtcgtagg | cgttgcgtgc | cttccagggg | cccgcgtagg | cgatgccggc | 720 |
| gacctcgccg | tccacctcgg | cgacgagcca | gggatagcgc | tcccgcagac | ggacgaggtc | 780 |
| gtccgtccac | tcctgcggtt | cctgcggctc | ggtacgaag | ttgaccgtgc | ttgtctcgat | 840 |
| gtagtggttg | acgatggtgc | agaccgccgg | catgtccgcc | tcggtggcac | ggcggatgtc | 900 |
| ggccgggcgt | cgttctgggc | tcatcgattc | gatttggtgt | atcgagattg | gttatgaaat | 960 |
| tcagatgcta | gtgtaatgta | ttggtaattt | gggaagatat | aataggaagc | aaggctattt | 1020 |
| atccatttct | gaaaggcga | aatggcgtca | ccgcgagcgt | cacgcgcatt | ccgttcttgc | 1080 |
| tgtaaagcgt | tgtttggtac | acttttgact | agcgaggctt | ggcgtgtcag | cgtatctatt | 1140 |
| caaaagtcgt | taatgctgc | ggatcaagaa | aaagttggaa | tagaaacaga | atacccgcga | 1200 |
| aattcaggcc | cggttgccat | gtcctacacg | ccgaaataaa | cgaccaaatt | agtagaaaaa | 1260 |
| taaaaactga | ctcggatact | tacgtcacgt | cttgcgcact | gatttgaaaa | atctcagaat | 1320 |
| tccaatccca | caaaaatctg | agcttaacag | cacagttgct | cctctcagag | cagaatcggg | 1380 |
| tattcaacac | cctcatatca | actactacgt | tgtgtataac | ggtccacatg | ccggtatata | 1440 |
| cgatgactgg | ggttgtacaa | aggcggcaac | aaacggcgtt | cccggagttg | cacacaagaa | 1500 |
| atttgccact | attacagagg | caagagcagc | agctgacgcg | tacacaacaa | gtcagcaaac | 1560 |
| agacaggttg | aacttcatcc | ccaaaggaga | agctcaactc | aagcccaaga | gctttgctaa | 1620 |
| ggccctaaca | agcccaccaa | agcaaaaagc | ccactggctc | acgctaggaa | ccaaaaggcc | 1680 |
| cagcagtgat | ccagccccaa | aagagatctc | ctttgccccg | gagattacaa | tggacgattt | 1740 |
| cctctatctt | tacgatctag | gaaggaagtt | cgaaggtgaa | ggtgacgaca | ctatgttcac | 1800 |
| cactgataat | gagaaggtta | gcctcttcaa | tttcagaaag | aatgctgacc | cacagatggt | 1860 |
| tagagaggcc | tacgcagcag | gtctcatcaa | gacgatctac | ccgagtaaca | atctccagga | 1920 |
| gatcaaatac | cttcccaaga | aggttaaaga | tgcagtcaaa | agattcagga | ctaattgcat | 1980 |
| caagaacaca | gagaaagaca | tatttctcaa | gatcagaagt | actattccag | tatggacgat | 2040 |
| tcaaggcttg | cttcataaac | caaggcaagt | aatagagatt | ggagtctcta | aaaaggtagt | 2100 |
| tcctactgaa | tctaaggcca | tgcatggagt | ctaagattca | aatcgaggat | ctaacagaac | 2160 |
| tcgccgtgaa | gactggcgaa | cagttcatac | agagtctttt | acgactcaat | gacaagaaga | 2220 |

```
aaatcttcgt caacatggtg gagcacgaca ctctggtcta ctccaaaaat gtcaaagata    2280
cagtctcaga agaccaaagg gctattgaga cttttcaaca aaggataatt tcgggaaacc    2340
tcctcggatt ccattgccca gctatctgtc acttcatcga aaggacagta gaaaaggaag    2400
gtggctccta caaatgccat cattgcgata aaggaaaggc tatcattcaa gatctctctg    2460
ccgacagtgg tcccaaagat ggaccccac ccacgaggag catcgtggaa aaagaagacg    2520
ttccaaccac gtcttcaaag caagtggatt gatgtgacat ctccactgac gtaagggatg    2580
acgcacaatc ccactatcct tcgcaagacc cttcctctat ataaggaagt tcatttcatt    2640
tggagaggac acgctcgaga tcacaagttt gtacaaaaaa gcaggctccg cggccgcccc    2700
cttcaccatg tctagtgatg ccatgaccat caatgagtct cttatggaag tcgaacatac    2760
tccagctgtg cataaaagga ttcttgacat tttaccgggt atcagtggcg gggttgccag    2820
agttatgata ggtcagccct tcgacacaat caaagtgcgt ctacaagtgt tggggcaggg    2880
tacggctctc gctgccaaac ttcctcctag tgaagtttac aaggacagca tggattgcat    2940
tcgtaagatg attaagtcgg agggtccact aagcttttac aagggaacag ttgccccact    3000
cgtcggaaac atggtattgc ttggcatcca ttttccggtc ttttccgcgg ttagaaagca    3060
gttggagggt gatgatcatt actctaactt ttcacacgcc aatgtactgc ttagcggcgc    3120
tgcggcagga gctgcgggat cactcatttc ggctcctgtt gaactggtta gaacgaaaat    3180
gcaaatgcaa aggcgagccg cacttgcggg tacagtggct gctggtgcag ctgcatctgc    3240
tggagctgag gagttctata agggaagtct tgattgtttc aaacaagtta tgtctaagca    3300
tgggattaaa ggattgtata gggttttac ttcaactata ctacgagata tgcagggtta    3360
tgcttggttc ttcctcggat atgaggcgac tgtcaatcac ttcttgcaaa atgcgggacc    3420
aggtgttcat accaaggctg acttgaatta ccttcaagtg atggccgctg gggttgttgc    3480
tggatttgga ttatggggct ccatgttccc aatcgatacc atcaaatcta aactccaagc    3540
cgatagcttt gccaaacctc aatattcatc cacaatggat tgtcttaaga aagtattagc    3600
aagtgaggga caggccggct tgtggagagg gttcagcgca gcaatgtata gagcaatacc    3660
ggtgaacgct ggcatttttcc tcgctgttga agggacacgt cagggtataa agtggtacga    3720
ggaaaacgtg gaacacatct acggaggtgt cattggtccc gctacgccta ctgcagcaca    3780
agaacagaaa ctgatctctg aagaagatct gtgaaagggt gggcgcgccg acccagcttt    3840
cttgtacaaa gtggtgccta ggtgagtcta gagagttaat taagacccgg gactagtccc    3900
tagagtcctg ctttaatgag atatgcgaga cgcctatgat cgcatgatat ttgctttcaa    3960
ttctgttgtg cacgttgtaa aaaacctgag catgtgtagc tcagatcctt accgccggtt    4020
tcggttcatt ctaatgaata tatcacccgt tactatcgta tttttatgaa taatattctc    4080
cgttcaattt actgattgta ccctactact tatatgtaca atattaaaat gaaaacaata    4140
tattgtgctg aataggttta tagcgacatc tatgatagag cgccacaata acaaacaatt    4200
gcgttttatt attacaaatc caattttaaa aaaagcggca gaaccggtca aacctaaaag    4260
actgattaca taaatcttat tcaaatttca aaagtgcccc aggggctagt atctacgaca    4320
caccgagcgg cgaactaata acgctcactg aagggaactc cggttcccg ccggcgcgca    4380 tgggtgagat tccttgaagt tgagtattgg ccgtccgctc taccgaaagt tacgggcacc    4440
attcaacccg gtccagcacg gcggccgggt aaccgacttg ctgccccgag aattatgcag    4500
catttttttg gtgtatgtgg gccccaaatg aagtgcaggt caaaccttga cagtgacgac    4560
aaatcgttgg gcgggtccag ggcgaatttt gcgacaacat gtcgaggctc agcaggacct    4620
```

```
gcaggcatgc aagcttggca ctggccgtcg ttttacaacg tcgtgactgg gaaaaccctg    4680
gcgttaccca acttaatcgc cttgcagcac atcccccttt cgccagctgg cgtaatagcg    4740
aagaggcccg caccgatcgc ccttcccaac agttgcgcag cctgaatggc gaatgctaga    4800
gcagcttgag cttggatcag attgtcgttt cccgccttca gtttaaacta tcagtgtttg    4860
acaggatata ttggcgggta aacctaagag aaaagagcgt ttattagaat aacggatatt    4920 taaagggcg tgaaaaggtt tatccgttcg tccatttgta tgtgcatgcc aaccacaggg     4980
ttcccctcgg gatcaaagta ctttgatcca acccctccgc tgctatagtg cagtcggctt    5040
ctgacgttca gtgcagccgt cttctgaaaa cgacatgtcg cacaagtcct aagttacgcg    5100
acaggctgcc gccctgccct tttcctggcg ttttcttgtc gcgtgtttta gtcgcataaa    5160
gtagaatact tgcgactaga accggagaca ttacgccatg aacaagagcg ccgccgctgg    5220
cctgctgggc tatgcccgcg tcagcaccga cgaccaggac ttgaccaacc aacgggccga    5280
actgcacgcg gccggctgca ccaagctgtt ttccgagaag atcaccggca ccaggcgcga    5340
ccgcccggag ctggccagga tgcttgacca cctacgccct ggcgacgttg tgacagtgac    5400
caggctagac cgcctggccc gcagcacccg cgacctactg gacattgccg agcgcatcca    5460
ggaggccggc gcgggcctgc gtagcctggc agagccgtgg gccgacacca ccacgccggc    5520
cggccgcatg gtgttgaccg tgttcgccgg cattgccgag ttcgagcgtt ccctaatcat    5580
cgaccgcacc cggagcgggc gcgaggccgc caaggcccga ggcgtgaagt ttggccccg     5640 ccctacccctc accccggcac agatcgcgca cgcccgcgag ctgatcgacc aggaaggccg    5700
caccgtgaaa gaggcggctg cactgcttgg cgtgcatcgc tcgaccctgt accgcgcact    5760
tgagcgcagc gaggaagtga cgcccaccga ggccaggcgg cgcggtgcct tccgtgagga    5820
cgcattgacc gaggccgacg ccctggcggc cgccgagaat gaacgccaag aggaacaagc    5880
atgaaaccgc accaggacgg ccaggacgaa ccgttttttca ttaccgaaga gatcgaggcg    5940
gagatgatcg cggccgggta cgtgttcgag ccgcccgcgc acgtctcaac cgtgcggctg    6000
catgaaatcc tggccggttt gtctgatgcc aagctggcgg cctggccggc cagcttggcc    6060
gctgaagaaa ccgagcgccg ccgtctaaaa aggtgatgtg tatttgagta aaacagcttg    6120
cgtcatgcgg tcgctgcgta tatgatgcga tgagtaaata aacaaatacg caaggggaac    6180
gcatgaaggt tatcgctgta cttaaccaga aaggcgggtc aggcaagacg accatcgcaa    6240
cccatctagc ccgcgccctg caactcgccg gggccgatgt tctgttagtc gattccgatc    6300
cccagggcag tgcccgcgat tgggcggccg tgcgggaaga tcaaccgcta accgttgtcg    6360
gcatcgaccg cccgacgatt gaccgcgacg tgaaggccat cggccggcgc gacttcgtag    6420
tgatcgacga gcgccccag gcggcggact tggctgtgtc cgcgatcaag gcagccgact    6480
tcgtgctgat tccggtgcag ccaagcccctt acgacatatg ggccaccgcc gacctggtgg    6540
agctggttaa gcagcgcatt gaggtcacgg atggaaggct acaagcggcc tttgtcgtgt    6600
cgcgggcgat caaaggcacg cgcatcggcg gtgaggttgc cgaggcgctg gccgggtacg    6660
agctgcccat tcttgagtcc cgtatcacgc agcgcgtgag ctaccaggc actgccgccg    6720 ccggcacaac cgttcttgaa tcagaacccg agggcgacgt gcccgcgag gtccaggcgc     6780 tggccgctga aattaaatca aaactcattt gagttaatga ggtaaagaga aaatgagcaa    6840
aagcacaaac acgctaagtg ccggccgtcc gagcgcacgc agcagcaagg ctgcaacgtt    6900
ggccagcctg gcagacacgc cagccatgaa gcgggtcaac tttcagttgc cggcggagga    6960
```

-continued

```
tcacaccaag ctgaagatgt acgcggtacg ccaaggcaag accattaccg agctgctatc    7020
tgaatacatc gcgcagctac cagagtaaat gagcaaatga ataaatgagt agatgaattt    7080
tagcggctaa aggaggcggc atggaaaatc aagaacaacc aggcaccgac gccgtggaat    7140
gccccatgtg tggaggaacg ggcggttggc caggcgtaag cggctgggtt gtctgccggc    7200
cctgcaatgg cactggaacc cccaagcccg aggaatcggc gtgacggtcg caaaccatcc    7260
ggcccggtac aaatcggcgc ggcgctgggt gatgacctgg tggagaagtt gaaggccgcg    7320
caggccgccc agcggcaacg catcgaggca gaagcacgcc ccggtgaatc gtggcaagcg    7380
gccgctgatc gaatccgcaa agaatcccgg caaccgccgg cagccggtgc gccgtcgatt    7440
aggaagccgc ccaagggcga cgagcaacca gatttttttcg ttccgatgct ctatgacgtg    7500
ggcacccgcg atagtcgcag catcatggac gtggccgttt ccgtctgtc gaagcgtgac    7560
cgacgagctg gcgaggtgat ccgctacgag cttccagacg ggcacgtaga ggtttccgca    7620
gggccggccg gcatggccag tgtgtgggat tacgacctgg tactgatggc ggtttcccat    7680
ctaaccgaat ccatgaaccg ataccggaa gggaagggag acaagcccgg ccgcgtgttc    7740
cgtccacacg ttgcggacgt actcaagttc tgccggcgag ccgatggcgg aaagcagaaa    7800
gacgacctgg tagaaacctg cattcggtta aacaccacgc acgttgccat gcagcgtacg    7860
aagaaggcca agaacggccg cctggtgacg gtatccgagg gtgaagcctt gattagccgc    7920
tacaagatcg taaagagcga aaccggggcgg ccggagtaca tcgagatcga gctagctgat    7980
tggatgtacc gcgagatcac agaaggcaag aacccggacg tgctgacggt tcaccccgat    8040
tacttttttga tcgatcccgg catcggccgt tttctctacc gcctggcacg ccgcgccgca    8100
ggcaaggcag aagccagatg gttgttcaag acgatctacg aacgcagtgg cagcgccgga    8160
gagttcaaga agttctgttt caccgtcgcg aagctgatcg ggtcaaatga cctgccggag    8220
tacgatttga aggaggaggc ggggcaggct ggcccgatcc tagtcatgcg ctaccgcaac    8280
ctgatcgagg gcgaagcatc cgccggttcc taatgtacgg agcagatgct agggcaaatt    8340
gccctagcag gggaaaaagg tcgaaaaggt ctctttcctg tggatagcac gtacattggg    8400
aacccaaagc cgtacattgg gaaccggaac ccgtacattg gaacccaaa gccgtacatt    8460
gggaaccggt cacacatgta agtgactgat ataaagaga aaaaggcga ttttccgcc    8520
taaaactctt taaacttat taaaactctt aaaacccgcc tggcctgtgc ataactgtct    8580
ggccagcgca cagccgaaga gctgcaaaaa gcgcctaccc ttcggtcgct gcgctcccta    8640
cgccccgccg cttcgcgtcg gcctatcgcg gccgctggcc gctcaaaaat ggctggccta    8700
cggccaggca atctaccagg gcgcggacaa gccgcgccgt cgccactcga ccgccggcgc    8760
ccacatcaag gcaccctgcc tcgcgcgttt cggtgatgac ggtgaaaacc tctgacacat    8820
gcagctcccg gagacggtca cagcttgtct gtaagcggat gccgggagca gacaagcccg    8880
tcagggcgcg tcagcgggtg ttggcggggtg tcgggggcgca gccatgaccc agtcacgtag    8940
cgatagcgga gtgtatactg gcttaactat gcggcatcag agcagattgt actgagagtg    9000
caccatatgc ggtgtgaaat accgcacaga tgcgtaagga gaaaataccg catcaggcgc    9060
tcttccgctt cctcgctcac tgactcgctg cgctcggtcg ttcggctgcg gcgagcggta    9120
tcagctcact caaaggcggt aatacggtta tccacagaat caggggataa cgcaggaaag    9180
aacatgtgag caaaaggcca gcaaaaggcc aggaaccgta aaaaggccgc gttgctggcg    9240
tttttccata ggctccgccc ccctgacgag catcacaaaa atcgacgctc aagtcagagg    9300
tggcgaaacc cgacaggact ataaagatac caggcgtttc ccctggaag ctccctcgtg    9360
```

-continued

```
cgctctcctg ttccgaccct gccgcttacc ggatacctgt ccgcctttct cccttcggga    9420
agcgtggcgc tttctcatag ctcacgctgt aggtatctca gttcggtgta ggtcgttcgc    9480
tccaagctgg gctgtgtgca cgaaccccc gttcagcccg accgctgcgc cttatccggt     9540
aactatcgtc ttgagtccaa cccggtaaga cacgactat cgccactggc agcagccact    9600
ggtaacagga ttagcagagc gaggtatgta ggcggtgcta cagagttctt gaagtggtgg    9660
cctaactacg gctacactag aaggacagta tttggtatct cgctctgct gaagccagtt     9720
accttcggaa aaagagttgg tagctcttga tccggcaaac aaaccaccgc tggtagcggt    9780
ggtttttttg tttgcaagca gcagattacg cgcagaaaaa aaggatctca agaagatcct   9840
ttgatctttt ctacggggtc tgacgctcag tggaacgaaa actcacgtta agggattttg    9900
gtcatgcatt ctaggtacta aaacaattca tccagtaaaa tataatattt tattttctcc    9960
caatcaggct tgatccccag taagtcaaaa atagctcga catactgttc ttccccgata    10020
tcctccctga tcgaccggac gcagaaggca atgtcatacc acttgtccgc cctgccgctt    10080
ctcccaagat caataaagcc acttactttg ccatctttca caaagatgtt gctgtctccc    10140
aggtcgccgt gggaaaagac aagttcctct cgggctttt ccgtctttaa aaatcatac     10200
agctcgcgcg gatctttaaa tggagtgtct tcttcccagt tttcgcaatc cacatcggcc   10260
agatcgttat tcagtaagta atccaattcg gctaagcggc tgtctaagct attcgtatag   10320
ggacaatccg atatgtcgat ggagtgaaag agcctgatgc actccgcata cagctcgata   10380
atcttttcag ggctttgttc atcttcatac tcttccgagc aaaggacgcc atcggcctca   10440
ctcatgagca gattgctcca gccatcatgc cgttcaaagt gcaggacctt tggaacaggc   10500
agctttcctt ccagccatag catcatgtcc ttttcccgtt ccacatcata ggtggtccct   10560
ttataccggc tgtccgtcat ttttaaatat aggttttcat tttctcccac cagcttatat   10620
accttagcag gagacattcc ttccgtatct tttacgcagc ggtatttttc gatcagtttt   10680
ttcaattccg gtgatattct cattttagcc atttattatt tccttcctct tttctacagt   10740
atttaaagat accccaagaa gctaattata acaagacgaa ctccaattca ctgttccttg   10800
cattctaaaa cctaaatac cagaaaacag ctttttcaaa gttgttttca aagttggcgt    10860
ataacatagt atcgacggag ccgattttga aaccgcggtg atcacaggca gcaacgctct   10920
gtcatcgtta caatcaacat gctacctcc gcgagatcat ccgtgtttca aacccggcag    10980
cttagttgcc gttcttccga atagcatcgg taacatgagc aaagtctgcc gccttacaac   11040
ggctctcccg ctgacgccgt cccggactga tgggctgcct gtatcgagtg gtgattttgt   11100
gccgagctgc cggtcgggga gctgttggct ggctgg                              11136
```

```
<210> SEQ ID NO 20
<211> LENGTH: 179
<212> TYPE: PRT
<213> ORGANISM: Camelina sativa

<400> SEQUENCE: 20

Tyr Phe Pro Gln Lys Lys Asn Lys Ile Lys Leu Leu Val Ser Leu Val
1               5                   10                  15

Val Phe Ser Leu Leu Leu Ile Gly Phe Ala Ser Ala Gln Thr Leu Ile
            20                  25                  30

Val Asp Ser Cys Lys Lys Ala Ala Ala Lys Glu Pro Phe Met Lys Tyr
        35                  40                  45

Asp Phe Cys Val Asn Ser Leu Thr Gln Asp Pro Gln Ser Lys Thr Ala
```

```
                     50                   55                  60
Thr Thr Leu Glu Gly Leu Val Leu Ala Ser Thr Lys Asn Ala Ala Ala
 65                  70                  75                  80

Glu Thr Leu Asn Val Lys Gly Leu Ala Glu Gln Ile Leu Lys Gly Lys
                     85                  90                  95

Gly Tyr Gly Pro Gly Met Glu Ala Gly Leu His Lys Cys Val Lys Ile
                100                 105                 110

Tyr Gly Gly Ala Tyr Asp Phe Leu Asn Thr Ala Leu Ala Asn Val Gln
            115                 120                 125

Ser His His Tyr Ser Thr Ala Val Glu Glu Phe Leu Tyr Ala Ser Phe
        130                 135                 140

Ala Pro Phe Asp Cys Val Lys Tyr Tyr Trp Ile Ser Pro Phe Ala Lys
145                 150                 155                 160

Glu Ser Tyr Ile Ile Phe Glu Lys Ile Leu Ile Pro Met Thr Leu Thr
                165                 170                 175

Lys Met Leu

<210> SEQ ID NO 21
<211> LENGTH: 176
<212> TYPE: PRT
<213> ORGANISM: Camelina sativa

<400> SEQUENCE: 21

Met Lys Phe Leu Val Ser Leu Val Met Cys Ser Leu Leu Leu Asn Gly
 1               5                  10                  15

Leu Ala Ser Ala Gln Thr Leu Ile Gln Asp Ser Cys Lys Lys Ala Ala
             20                  25                  30

Ala Lys Asp Pro Gln Met Lys Tyr Asp Phe Cys Val Asn Ser Leu Thr
         35                  40                  45

Gln Asp Pro Gln Ser Lys Thr Ala Thr Thr Leu Glu Gly Leu Val Ile
     50                  55                  60

Ala Ser Thr Lys Asn Ala Ala Lys Thr Thr Asn Val Lys Gly Ile
 65                  70                  75                  80

Val Glu Gln Ile Leu Lys Gly Lys Arg Tyr Gly Pro Gly Ile Glu Thr
                 85                  90                  95

Val Leu His Asp Cys Ile Glu His Tyr Asp Ala Asn Gly Ser Leu
                100                 105                 110

Asn Thr Ala Leu Ala Ser Val Gln Ser His Asp Tyr Ser Thr Ala Thr
            115                 120                 125

Val Asn Leu Gly Ala Ala Leu Asp Ala Pro Gly Asn Cys Glu Asp Gly
        130                 135                 140

Phe Lys Glu Arg Lys Gln Gln Lys Ser Pro Val Thr Asn Glu Asn Asn
145                 150                 155                 160

Ile Leu Phe Gln Lys Ile Leu Ile Pro Leu Ala Phe Thr Asn Met Leu
                165                 170                 175

<210> SEQ ID NO 22
<211> LENGTH: 174
<212> TYPE: PRT
<213> ORGANISM: Camelina sativa

<400> SEQUENCE: 22

Met Lys Phe Leu Val Ser Leu Val Met Cys Ser Leu Leu Leu Asn Gly
 1               5                  10                  15

Phe Ala Ser Ala Gln Thr Leu Ile Gln Asp Ser Cys Lys Lys Ala Ala
             20                  25                  30
```

```
Ala Lys Asp Arg Gln Met Lys Tyr Asp Phe Cys Val Asp Ser Leu Thr
            35                  40                  45

Gln Asp Pro Gln Ser Lys Thr Ala Thr Thr Leu Glu Gly Leu Val Leu
    50                  55                  60

Ala Ser Thr Lys Asn Ala Ala Val Lys Thr Met Asn Val Lys Gly Ile
65                  70                  75                  80

Val Glu Gln Ile Leu Lys Gly Lys Gly Tyr Gly Gly Ile Glu Ala Glu
                85                  90                  95

Leu Arg Gln Cys Ala Glu Phe Tyr Asp Asp Ala Asn Asp Asn Leu Asn
            100                 105                 110

Thr Ala Leu Ala Ser Val Lys Ser His Asp Tyr Glu Thr Ala Asn Val
        115                 120                 125

Asp Phe Ser Ala Ala Leu Asp Val Pro Val Asn Cys Glu Asp Gly Ile
    130                 135                 140

Lys Glu Arg Lys Arg Gln Lys Ser Pro Val Thr Asn Glu Asn Asn Ile
145                 150                 155                 160

Leu Phe Gln Lys Ile Leu Ile Pro Leu Ala Phe Thr Asn Met
                165                 170
```

<210> SEQ ID NO 23
<211> LENGTH: 168
<212> TYPE: PRT
<213> ORGANISM: Camelina sativa

<400> SEQUENCE: 23

```
Met Cys Ser Leu Leu Asn Gly Phe Ala Ser Ala Gln Thr Leu Ile
1                5                  10                  15

Gln Asp Ser Cys Lys Lys Ala Ala Ala Lys Asp Pro Gln Met Lys Tyr
            20                  25                  30

Asp Phe Cys Val Asn Ser Leu Thr Gln Asp Pro Gln Ser Lys Thr Ala
        35                  40                  45

Thr Thr Leu Glu Gly Leu Val Ile Ala Ser Thr Lys Asn Ala Ala Ala
    50                  55                  60

Lys Thr Thr Asn Val Lys Gly Ile Val Glu Gln Ile Leu Lys Gly Lys
65                  70                  75                  80

Arg Tyr Gly Pro Gly Ile Glu Thr Val Leu His Asp Cys Val Glu Leu
                85                  90                  95

Tyr Asp Tyr Ala Asn Gly Ser Leu Asn Thr Ala Leu Ala Ser Val Gln
            100                 105                 110

Ser His Asp Tyr Ser Ser Ala Thr Val Asn Leu Gly Ala Ala Leu Asp
        115                 120                 125

Ala Pro Gly Asn Cys Glu Asp Gly Phe Lys Glu Arg Lys Gln Gln Lys
    130                 135                 140

Ser Pro Val Thr Asn Glu Asn Asn Ile Leu Phe Gln Ile Ile Leu Ile
145                 150                 155                 160

Pro Leu Ala Phe Thr Asn Met Leu
                165
```

<210> SEQ ID NO 24
<211> LENGTH: 175
<212> TYPE: PRT
<213> ORGANISM: Camelina sativa

<400> SEQUENCE: 24

```
Met Lys Phe Leu Val Ser Leu Val Met Cys Ser Leu Leu Leu Asn Gly
1                5                  10                  15
```

Phe Ala Ser Ala Gln Thr Leu Ile Gln Asp Ser Cys Lys Lys Ala Ala
            20                  25                  30

Ala Lys Asp Arg Gln Met Lys Tyr Asp Phe Cys Val Asn Ser Leu Thr
        35                  40                  45

Gln Asp Pro Gln Ser Lys Thr Ala Thr Thr Leu Glu Gly Leu Val Leu
    50                  55                  60

Ala Ser Thr Lys Asn Ala Ala Val Lys Thr Met Asn Val Lys Gly Ile
65                  70                  75                  80

Val Glu Gln Ile Ile Lys Gly Lys Gly Tyr Glu Gly Ile Glu Ala Glu
                85                  90                  95

Leu Arg Asp Cys Ala Glu Phe Tyr Asp Asp Ala Asn Asp Asn Leu Asn
            100                 105                 110

Thr Ala Leu Ala Ser Val Lys Ser His Asp Tyr Glu Thr Ala Asn Val
        115                 120                 125

Asp Phe Ser Ala Ala Leu Asp Val Pro Val Asn Cys Glu Asp Gly Ile
    130                 135                 140

Lys Glu Arg Lys Lys Gln Lys Ser Pro Val Thr Asn Glu Asn Asn Ile
145                 150                 155                 160

Leu Phe Gln Lys Ile Leu Ile Pro Leu Ala Phe Thr Thr Met Leu
                165                 170                 175

<210> SEQ ID NO 25
<211> LENGTH: 175
<212> TYPE: PRT
<213> ORGANISM: Camelina sativa

<400> SEQUENCE: 25

Met Lys Phe Leu Val Ser Leu Val Met Cys Ser Leu Leu Leu Asn Gly
1               5                   10                  15

Phe Ala Ser Ala Gln Thr Leu Ile Gln Asp Ser Cys Lys Lys Ala Ala
            20                  25                  30

Ala Lys Asp Arg Gln Met Lys Tyr His Phe Cys Val Asp Ser Leu Thr
        35                  40                  45

Gln Asp Pro Gln Ser Lys Thr Ala Thr Thr Leu Glu Gly Leu Val Leu
    50                  55                  60

Ala Ser Thr Lys Asn Ala Ala Val Lys Thr Val Asn Val Lys Gly Ile
65                  70                  75                  80

Val Glu Gln Ile Leu Lys Gly Lys Arg Tyr Gly Gly Ile Glu Ala Glu
                85                  90                  95

Leu Arg Glu Cys Ala Glu Phe Tyr Asp Asp Ala Asn Asp Asn Leu Asn
            100                 105                 110

Thr Ala Leu Ala Ser Val Lys Ser His Asp Tyr Glu Thr Ala Asn Val
        115                 120                 125

Asp Phe Ser Ala Ala Leu Asp Val Pro Val Asn Cys Glu Asp Gly Ile
    130                 135                 140

Lys Glu Arg Lys Lys Glu Lys Ser Pro Val Thr Asn Glu Asn Asn Ile
145                 150                 155                 160

Leu Phe Gln Lys Ile Leu Ile Pro Leu Ala Phe Thr Asn Met Leu
                165                 170                 175

<210> SEQ ID NO 26
<211> LENGTH: 176
<212> TYPE: PRT
<213> ORGANISM: Camelina sativa

<400> SEQUENCE: 26

Met Lys Phe Leu Val Ser Leu Val Met Phe Ser Leu Leu Val Asn Gly
1               5                   10                  15

Phe Ala Phe Ala Gln Thr Leu Ile Gln Asp Ser Cys Lys Lys Ala Ala
                20                  25                  30

Val Lys Glu Pro Ala Leu Ile Tyr Asn Phe Cys Val Asp Ser Leu Thr
            35                  40                  45

Gln Asp Pro Gln Ser Lys Thr Ala Thr Thr Leu Glu Gly Leu Ile Leu
50                  55                  60

Ala Ser Thr Lys Asn Ala Ala Val Lys Thr Met Asn Val Lys Gly Ile
65                  70                  75                  80

Ala Glu Gln Ile Phe Lys Gly Lys Gly Tyr Gly Gly Ile Glu Ala Glu
                85                  90                  95

Leu His Asp Cys Val Glu Phe Tyr Asp Asp Ala Asn Asp Leu Leu Asn
                100                 105                 110

Thr Ala Leu Ala Ser Val Gln Ser Gln Asp Tyr Lys Thr Ala Asn Glu
            115                 120                 125

Asp Phe Ser Ile Ala Leu Asp Val Leu Gly Asn Cys Lys Asp Gly Ile
130                 135                 140

Gln Glu Ile Asn Lys Gln Lys Ser Pro Val Ser Asn Glu Asn Asn Ile
145                 150                 155                 160

Leu Leu Gln Lys Ile Leu Ile Pro Phe Val Phe Asn Asn Met Leu Arg
                165                 170                 175

<210> SEQ ID NO 27
<211> LENGTH: 176
<212> TYPE: PRT
<213> ORGANISM: Camelina sativa

<400> SEQUENCE: 27

Met Asn Phe Leu Val Ser Leu Val Met Phe Ser Leu Leu Leu Asn Asp
1               5                   10                  15

Phe Thr Ser Ala Gln Thr Leu Ile Gln Asp Ser Cys Lys Lys Ala Ala
                20                  25                  30

Ala Thr Asn Met Gln Leu Lys Tyr Asp Phe Cys Val Asn Ser Leu Thr
            35                  40                  45

Gln Asp Pro Glu Ser Lys Thr Ala Thr Thr Leu Glu Gly Leu Val Phe
50                  55                  60

Ala Ser Thr Lys Asn Ala Ala Lys Ile Met Asp Val Lys Arg Phe
65                  70                  75                  80

Val Glu Gln Ile Leu Lys Ala Lys Lys Tyr Gly Pro Gly Met Glu Ala
                85                  90                  95

Val Leu Arg Thr Cys Val Glu Leu Tyr Asp Glu Ala Asn Gly Ala Leu
            100                 105                 110

Asn Thr Ala Phe Ser Ser Val Gln Ser His Asp Tyr Asn Thr Ala Asn
            115                 120                 125

Val Phe Met Ser Ala Ala Leu Asp Ala Pro Asp Asn Cys Glu Asp Gly
130                 135                 140

Phe Lys Glu Gly Lys Leu Glu Lys Ser Pro Val Thr Asn Glu Asn Asn
145                 150                 155                 160

Ile Leu Leu Gln Lys Ile Leu Ile Pro Leu Ala Phe Thr Asn Met Leu
                165                 170                 175

<210> SEQ ID NO 28
<211> LENGTH: 175
<212> TYPE: PRT

<213> ORGANISM: Camelina sativa

<400> SEQUENCE: 28

```
Met Lys Phe Leu Val Ser Leu Ile Met Phe Ser Leu Leu Leu Asn Gly
1               5                   10                  15

Phe Ala Phe Ala Gln Thr Leu Ile Gln Asp Ser Cys Lys Lys Ala Thr
            20                  25                  30

Val Ile Glu Pro Gly Leu Thr Tyr Asn Phe Cys Val Asp Ser Leu Thr
        35                  40                  45

Gln Asp Pro Gln Ser Lys Thr Ala Thr Thr Leu Glu Gly Leu Ile Ile
    50                  55                  60

Ala Ser Thr Lys Asn Ala Glu Ala Glu Ala Met Asn Val Lys Gly Ile
65                  70                  75                  80

Val Glu His Ile Leu Lys Gly Lys Gly Tyr Ala Ser Ile Glu Ala Glu
                85                  90                  95

Leu Arg Leu Cys Val Glu Phe Tyr Gly Asp Ala Lys Asp Ser Leu His
            100                 105                 110

Thr Ala Leu Ala Ser Val Arg Ser His Asp Tyr Lys Glu Ala Asn Val
        115                 120                 125

Asn Phe Ser Ile Ala Glu Asp Val Pro Arg Asn Cys Glu Asp Ala Ile
    130                 135                 140

Lys Asp Arg Ile Pro Lys Ser Pro Ile Ser Asn Glu Asn Tyr Ile Leu
145                 150                 155                 160

Phe Gln Lys Ile Ala Ile Pro Ser Val Phe Asp Tyr Met Leu Ile
                165                 170                 175
```

<210> SEQ ID NO 29
<211> LENGTH: 176
<212> TYPE: PRT
<213> ORGANISM: Camelina sativa

<400> SEQUENCE: 29

```
Met Lys Phe Leu Val Ser Leu Val Met Phe Ser Leu Leu Leu Asn Asp
1               5                   10                  15

Phe Thr Ser Ala Gln Thr Leu Ile Gln Asp Ser Cys Lys Lys Ala Ala
            20                  25                  30

Ala Thr Asn Leu Gln Leu Lys Tyr Asp Phe Cys Val Asn Ser Leu Thr
        35                  40                  45

Gln Asp Pro Glu Ser Lys Thr Ala Thr Thr Leu Glu Gly Leu Val Phe
    50                  55                  60

Ala Ser Thr Lys Asn Ala Ala Lys Ile Met Lys Val Lys Arg Phe
65                  70                  75                  80

Val Glu Gln Ile Leu Lys Ala Lys Lys Tyr Gly Pro Gly Met Glu Ala
                85                  90                  95

Val Leu Ser Thr Cys Val Glu Leu Tyr Asp Glu Ala Asn Gly Ser Leu
            100                 105                 110

Asn Thr Ala Phe Ser Ser Val Gln Ser His Asp Tyr Asn Thr Ala Asn
        115                 120                 125

Leu Tyr Met Ser Ala Ala Leu Asp Ala Pro Asp Asn Cys Glu Asp Gly
    130                 135                 140

Phe Lys Glu Gly Lys Leu Lys Lys Ser Pro Val Thr Lys Glu Asn Asn
145                 150                 155                 160

Ile Leu Leu Gln Thr Ile Leu Ile Pro Leu Ala Phe Thr Asn Met Leu
                165                 170                 175
```

```
<210> SEQ ID NO 30
<211> LENGTH: 175
<212> TYPE: PRT
<213> ORGANISM: Camelina sativa

<400> SEQUENCE: 30

Met Asn Phe Leu Val Ser Leu Val Met Tyr Ser Leu Leu Asn Asp
1               5                   10                  15

Phe Thr Ser Ala Gln Thr Leu Ile Gln Asp Ser Cys Lys Lys Ala Ala
                20                  25                  30

Ala Ile Asn Leu Gln Leu Lys Tyr Asp Phe Cys Val Asn Ser Leu Thr
            35                  40                  45

Gln Asp Pro Glu Ser Lys Thr Ala Thr Thr Leu Glu Gly Leu Val Phe
50                  55                  60

Ala Ser Thr Lys Asn Ala Ala Ala Lys Ile Met Asp Val Lys Arg Phe
65                  70                  75                  80

Val Glu Gln Ile Leu Lys Ala Lys Lys Tyr Gly Pro Gly Met Glu Ala
                85                  90                  95

Ala Leu Ser Thr Cys Val Glu Leu Tyr Asp Glu Ala Asn Gly Ser Leu
                100                 105                 110

Asn Thr Ala Phe Ser Ser Val Gln Ser His Asp Tyr Asn Thr Ala Asn
            115                 120                 125

Val Tyr Ile Ser Ala Ala Leu Asp Ala Pro Asp Asn Cys Glu Asp Gly
130                 135                 140

Phe Lys Glu Gly Lys Leu Glu Lys Ser Pro Val Thr Asn Lys Asn Asn
145                 150                 155                 160

Ile Leu Leu Gln Thr Ile Leu Ile Pro Leu Ala Phe Thr Asn Met
                165                 170                 175

<210> SEQ ID NO 31
<211> LENGTH: 176
<212> TYPE: PRT
<213> ORGANISM: Camelina sativa

<400> SEQUENCE: 31

Met Lys Phe Leu Val Ser Leu Val Met Phe Ser Leu Leu Asn Gly
1               5                   10                  15

Phe Thr Phe Ala Gln Thr Leu Ile Gln Asp Ser Cys Lys Lys Ala Ala
                20                  25                  30

Val Lys Val Pro Asp Leu Asp Tyr Asn Phe Cys Val Asp Ser Leu Thr
            35                  40                  45

Gln Asp Pro Gln Ser Lys Thr Ala Thr Thr Leu Glu Gly Leu Ile Leu
50                  55                  60

Ser Ser Thr Lys Asn Ala Glu Ala Lys Ala Met Asn Val Lys Gly Ile
65                  70                  75                  80

Val Glu Gln Ile Leu Lys Gly Lys Lys Tyr Glu Ser Ile Glu Ala Glu
                85                  90                  95

Leu Arg Asp Cys Val Glu Phe Tyr Asp Asp Ala Asn Asp Ser Leu Asn
                100                 105                 110

Thr Ala Leu Ala Ser Val Arg Ser Gln Asp Tyr Ile Thr Ala Asn Glu
            115                 120                 125

Asn Phe Ser Ile Ala Leu Asp Val Pro Gly Asn Cys Glu Glu Glu Ile
            130                 135                 140

Lys Glu Arg Asn Lys Gln His Ser Pro Val Ser Asp Glu Asn Asn Ile
145                 150                 155                 160

Leu Leu Gln Lys Ile Ser Ile Pro Cys Ala Leu Asn Tyr Met Leu Ile
```

```
                165                 170                 175

<210> SEQ ID NO 32
<211> LENGTH: 176
<212> TYPE: PRT
<213> ORGANISM: Camelina sativa

<400> SEQUENCE: 32

Met Lys Phe Leu Val Ser Leu Val Met Phe Ser Leu Leu Asn Gly
1               5                   10                  15

Phe Ala Phe Ala Gln Thr Leu Leu Gln Asp Ser Cys Lys Lys Ala Thr
                20                  25                  30

Val Ile Glu Pro Gly Leu Ile Tyr Asn Phe Cys Val Asp Ser Leu Thr
            35                  40                  45

Gln Asp Pro Gln Ser Lys Thr Ala Thr Thr Leu Glu Gly Leu Ile Leu
    50                  55                  60

Pro Ser Thr Lys Asn Ala Glu Ala Lys Ala Met Asn Val Lys Glu Ile
65                  70                  75                  80

Val Glu His Ile Leu Lys Gly Lys Lys Tyr Glu Ser Ile Glu Ala Glu
                85                  90                  95

Leu Arg Asp Cys Val Glu Phe Tyr Asp Asp Ala Asn Asp Ser Leu Asn
            100                 105                 110

Thr Ala Leu Ala Ser Val Arg Ser His Asp Tyr Lys Thr Ala Asn Glu
        115                 120                 125

Asn Phe Ser Ile Ala Leu Asp Val Pro Gly Asn Cys Glu Asp Gly Ile
    130                 135                 140

Lys Glu Arg Asn Lys Gln His Ser Pro Val Ser Asn Glu Asn Asn Asp
145                 150                 155                 160

Leu Phe Gln Lys Ile Leu Ile Pro Leu Val Phe Asn Tyr Met Leu Ile
                165                 170                 175

<210> SEQ ID NO 33
<211> LENGTH: 176
<212> TYPE: PRT
<213> ORGANISM: Camelina sativa

<400> SEQUENCE: 33

Met Lys Phe Leu Val Ser Leu Val Met Phe Ser Leu Leu Asn Gly
1               5                   10                  15

Phe Ala Phe Ala Gln Thr Leu Ile Gln Asp Ser Cys Lys Lys Ala Ala
                20                  25                  30

Met Lys Asp Ser Asn Leu Ile Tyr Lys Phe Cys Val Asp Ser Leu Thr
            35                  40                  45

Gln Asp Pro Gln Ser Lys Thr Ala Thr Thr Leu Glu Gly Leu Ile Leu
    50                  55                  60

Ala Ser Thr Lys Asn Ala Glu Ala Gln Ala Ile Asn Val Lys Arg Ile
65                  70                  75                  80

Val Glu His Ile Leu Lys Gly Lys Gly Tyr Arg Ser Ile Glu Ala Glu
                85                  90                  95

Leu Arg Asp Cys Val Glu Phe Tyr Gly Asp Ala Asn Asp Ser Leu His
            100                 105                 110

Thr Ala Leu Ala Ser Phe Arg Ser Lys Asp Tyr Glu Ser Ala Asn Ser
        115                 120                 125

Asp Phe Gly Ile Ala Leu Asp Val Pro Gly Asn Cys Glu Glu Gly Ile
    130                 135                 140

Lys Glu Arg Asn Lys Gln Asn Ser Pro Val Ser Asn Glu Asn Asn Ile
```

```
145                 150                 155                 160
Leu Phe Gln Lys Ile Leu Ile Pro Phe Ala Phe Asn Asn Met Leu Ile
                165                 170                 175

<210> SEQ ID NO 34
<211> LENGTH: 176
<212> TYPE: PRT
<213> ORGANISM: Camelina sativa

<400> SEQUENCE: 34

Met Lys Phe Leu Val Ser Leu Val Met Phe Ser Leu Leu Asn Gly
1               5                   10                  15

Phe Ala Phe Ala Gln Thr Leu Ile Gln Asp Ser Cys Lys Lys Ala Ala
                20                  25                  30

Met Lys Asp Ser Ala Met Ile Tyr Asn Phe Cys Val Asp Ser Leu Thr
            35                  40                  45

Gln Asp Pro Gln Ser Lys Thr Ala Thr Thr Leu Glu Asp Leu Ile Leu
        50                  55                  60

Ala Ser Thr Lys Asn Ala Glu Ala Lys Ala Ile Asn Val Lys Arg Ile
65                  70                  75                  80

Val Glu Gln Ile Leu Lys Gly Lys Gly Tyr Arg Ser Ile Glu Ala Glu
                85                  90                  95

Leu Arg Leu Cys Val Glu Phe Tyr Gly Asp Ala Asn Asp Ser Leu His
            100                 105                 110

Thr Ala Leu Ala Ser Phe Arg Ser Lys Asp Tyr Ala Ser Ala Asn Ser
        115                 120                 125

Asp Phe Gly Ile Ala Leu Asp Val Pro Gly Asn Cys Glu Asp Ala Ile
    130                 135                 140

Lys Glu Arg Asn Lys Gln Lys Ser Pro Val Ser Asn Glu Asn Asn Asp
145                 150                 155                 160

Leu Phe Gln Lys Ile Leu Ile Pro Phe Ala Phe Asn Asn Met Leu Ser
                165                 170                 175

<210> SEQ ID NO 35
<211> LENGTH: 147
<212> TYPE: PRT
<213> ORGANISM: Camelina sativa

<400> SEQUENCE: 35

Met Phe Ser Leu Leu Leu Asn Gly Phe Ala Phe Ser Gln Thr Leu Ile
1               5                   10                  15

Gln Asp Ser Cys Lys Lys Ala Thr Val Lys Glu Pro Ala Leu Ile Tyr
                20                  25                  30

Asn Leu Cys Val Asp Ser Leu Thr Gln Asp Pro Gln Ser Arg Thr Ala
            35                  40                  45

Thr Thr Leu Glu Gly Leu Ile Ile Ala Ser Thr Lys Asn Ala Glu Ala
        50                  55                  60

Lys Ala Met Asn Val Lys Gly Ile Ile Glu His Ile Leu Lys Gly Lys
65                  70                  75                  80

Gly Tyr Ala Ser Ile Glu Ala Glu Leu Arg Asp Cys Val Gly Phe Tyr
                85                  90                  95

Asp Asp Ala Asn Asp Leu Leu Asn Thr Ala Leu Ala Ser Val Gln Ser
            100                 105                 110

His Asp Tyr Lys Thr Ala Asn Gly Asp Phe Ser Ile Ala Leu Asp Val
        115                 120                 125

Pro Glu Asn Cys Glu Asp Gly Ile Lys Glu Arg Asn Lys Gln Asn Ser
```

```
                130                 135                 140
Pro Leu Leu
145

<210> SEQ ID NO 36
<211> LENGTH: 175
<212> TYPE: PRT
<213> ORGANISM: Camelina sativa

<400> SEQUENCE: 36

Met Lys Phe Leu Val Ser Leu Val Met Phe Ser Leu Leu Asn Cys
1               5                   10                  15

Phe Thr Phe Ala Gln Thr Leu Ile Gln Asp Ser Cys Lys Lys Ala Ala
                20                  25                  30

Met Lys Ile Pro Asp Phe Tyr Tyr Asn Phe Cys Val Asp Ser Leu Thr
            35                  40                  45

Gln Asp Pro Gln Ser Lys Asn Ala Thr Thr Leu Lys Gly Leu Ile Leu
        50                  55                  60

Ser Ser Thr Lys Asn Ala Glu Ala Asn Ala Met Lys Val Lys Gly Ile
65                  70                  75                  80

Val Glu His Ile Leu Lys Gly Lys Lys Tyr Glu Ser Ile Glu Ala Glu
                85                  90                  95

Leu Arg Asp Cys Val Glu Phe Tyr Asp Asp Ala Asn Asp Ser Leu Asn
            100                 105                 110

Thr Ala Leu Ala Ser Val Arg Ser Gln Asp Tyr Lys Thr Ala Asn Glu
        115                 120                 125

Asn Phe Gly Ile Ala Leu Asp Val Pro Arg Asp Cys Glu Asp Gly Ile
    130                 135                 140

Lys Glu Arg Thr Gln His Ser Pro Ile Thr Asp Glu Asn Asn Thr Leu
145                 150                 155                 160

Leu Gln Lys Ile Ser Val Pro Cys Gly Leu Asn Tyr Ile Leu Ile
                165                 170                 175

<210> SEQ ID NO 37
<211> LENGTH: 183
<212> TYPE: PRT
<213> ORGANISM: Camelina sativa

<400> SEQUENCE: 37

Met Lys Phe Leu Leu Tyr Leu Val Met Phe Ile Leu Leu Asn Val
1               5                   10                  15

Phe Ala Thr Ala Gln Ser Leu Ile Arg Asp Ser Cys Lys Lys Ala Ala
                20                  25                  30

Ala Lys Tyr Pro Lys Leu Lys Tyr Glu Phe Cys Val Lys Ser Leu Glu
            35                  40                  45

Glu His Pro Gln Ser Lys Thr Ala Lys Ser Leu Glu Gly Leu Val Phe
        50                  55                  60

Ala Ser Thr Lys Asn Ala Val Ser Lys Thr Thr Ser Leu Lys Gly Leu
65                  70                  75                  80

Ala Asn Lys Ile Leu Lys Glu Asn Lys Tyr Asp Val Glu Arg Pro Leu
                85                  90                  95

Arg Asp Cys Leu Glu Leu Tyr Thr Gly Ala Ile Asp Ser Leu Asn Gln
            100                 105                 110

Ser Leu Asp Thr Ile Lys Ser Arg Asp Tyr Lys Ile Ala Thr Met Leu
        115                 120                 125

Met Ser Ala Ala Met Asp Ala Thr Gly Asn Cys Glu Thr Gly Phe Thr
```

```
                130                 135                 140
Lys Arg Lys Lys Pro Val Lys Ser Pro Phe Thr Lys Glu Asn Asp Val
145                 150                 155                 160

Leu Phe His Met Val Leu Ile Pro Leu Ala Phe Thr Asn Met Leu Asp
                165                 170                 175

Met Asn Leu Pro Lys Val Leu
            180

<210> SEQ ID NO 38
<211> LENGTH: 175
<212> TYPE: PRT
<213> ORGANISM: Camelina sativa

<400> SEQUENCE: 38

Met Phe Ile Leu Leu Leu Asn Val Phe Ala Thr Ala Gln Ser Leu Ile
1               5                   10                  15

Arg Asp Ser Cys Lys Lys Ala Ala Lys Asp Pro Lys Leu Lys Tyr
            20                  25                  30

Asp Phe Cys Ile Lys Ser Leu Glu Glu His Pro Gln Ser Lys Thr Ala
            35                  40                  45

Lys Ser Leu Glu Gly Leu Val Phe Ala Ser Thr Lys Asn Ala Val Ser
50                  55                  60

Lys Thr Thr Ser Leu Lys Gly Met Ala Asn Lys Ile Leu Lys Glu Asn
65                  70                  75                  80

Lys Tyr Asp Val Glu Arg Pro Leu Arg Asp Cys Ile Glu Leu Tyr Thr
                85                  90                  95

Gly Ala Ile Asp Ser Leu Asn Gln Ser Leu Asp Thr Ile Lys Ser Arg
            100                 105                 110

Asp Tyr Asn Ile Ala Thr Met Leu Met Ser Ala Ala Met Asp Ala Thr
            115                 120                 125

Gly Asn Cys Glu Thr Gly Phe Thr Lys Arg Lys Lys Pro Val Lys Ser
130                 135                 140

Pro Phe Thr Lys Glu Asn Asp Val Leu Phe His Met Val Leu Ile Pro
145                 150                 155                 160

Leu Ala Phe Thr Asn Met Leu Asp Met Lys Leu Pro Lys Met Leu
                165                 170                 175

<210> SEQ ID NO 39
<211> LENGTH: 179
<212> TYPE: PRT
<213> ORGANISM: Camelina sativa

<400> SEQUENCE: 39

Met Lys Tyr Leu Leu Tyr Leu Ile Val Thr Phe Phe Leu Leu Leu Asn
1               5                   10                  15

Gly Phe Ser Thr Ala Gln Thr Leu Ile Arg Asp Ser Cys Lys Lys Ala
            20                  25                  30

Ala Ala Lys Asn Pro Lys Phe Lys Asn Asp Ile Cys Val Lys Ser Leu
            35                  40                  45

Glu Thr Asn Pro Gln Ser Lys Ala Ala Lys Asp Leu Ala Gly Leu Val
50                  55                  60

Val Ala Ser Thr Lys Asn Ala Ala Ser Lys Ala Thr Ser Leu Lys Gly
65                  70                  75                  80

Thr Val Asp Lys Ile Leu Lys Gly Lys Lys Met Asn Lys Met Ser Glu
                85                  90                  95

Met Ala Leu Arg Asp Cys Leu Gln Leu Tyr Thr Asp Ala Ile Asp Ser
```

```
                  100                 105                 110
Leu Asn Gln Ala Leu Ala Ser Val Lys Ser Arg Asp Tyr Asn Thr Val
            115                 120                 125

Ala Thr Val Leu Ser Ala Ala Met Asp Ala Pro Ser Thr Cys Glu Thr
130                 135                 140

Gly Phe Lys Glu Ile Lys Thr Pro Gln Lys Ser Pro Val Thr Lys Asp
145                 150                 155                 160

Asn Asp Thr Leu Tyr Gln Met Ile Leu Ile Pro Leu Ser Phe Thr Asn
                165                 170                 175

Met Leu Lys

<210> SEQ ID NO 40
<211> LENGTH: 178
<212> TYPE: PRT
<213> ORGANISM: Camelina sativa

<400> SEQUENCE: 40

Met Lys Phe Leu Leu Tyr Leu Ile Val Thr Phe Phe Leu Leu Leu Asn
1               5                   10                  15

Ala Phe Ser Thr Ala Gln Thr Leu Ile Arg Asp Ser Cys Lys Lys Ala
            20                  25                  30

Ala Ala Lys Asn Pro Lys Phe Lys Asn Asp Ile Cys Val Lys Ser Leu
        35                  40                  45

Glu Thr Asn Pro Gln Ser Lys Ala Ala Lys Asp Leu Ala Gly Leu Val
    50                  55                  60

Val Ala Ser Thr Lys Asn Ala Ala Ser Lys Ala Thr Ser Leu Lys Gly
65                  70                  75                  80

Thr Val Asn Lys Ile Leu Lys Gly Lys Lys Met Asn Lys Ile Ser Glu
                85                  90                  95

Met Pro Leu Arg Asp Cys Leu Gln Leu Tyr Thr Asp Ala Ile Asp Ser
            100                 105                 110

Leu Asn Gln Ala Leu Ala Ser Met Lys Ser Arg Asp Tyr Asn Thr Val
        115                 120                 125

Val Thr Val Leu Ser Ala Ala Met Asp Ala Pro Ser Thr Cys Glu Thr
130                 135                 140

Gly Phe Lys Glu Arg Lys Thr Pro Gln Lys Ser Pro Val Thr Lys Asp
145                 150                 155                 160

Asn Asp Thr Leu Tyr Gln Met Ile Leu Ile Pro Leu Ser Phe Thr Asn
                165                 170                 175

Met Leu

<210> SEQ ID NO 41
<211> LENGTH: 1148
<212> TYPE: DNA
<213> ORGANISM: Artificial Sequence
<220> FEATURE:
<223> OTHER INFORMATION: Synthetic construct Glycine max Hsp70 promoter

<400> SEQUENCE: 41
gcaacagaag acccaaaact caaaaaagtt agtttcgggc caacatttcc tcttgaggga    60
tgacacgtga cctgctactc tggcccttat ctggcatgtc catccttctt ggcgcgacat   120
ttaattcgtc gtcagaaata actgaaggac accttgcttg tttctctttt ggccgccacc   180
ggtcttgtca tcgtcgaagg cgcccttgcg cttgtcggca gaacctttt cggcgacctc    240 cttgcctttt cctttggcct tgttcgtcat ttctacagag aatgcaatga gaccaacgcc   300
```

```
aattgcatgg ttagagttag agaaatggag agaggaagaa gtgcgtgact agagtgtgtg    360
taactgtgaa gaacgacgag tccaaaatga attttactgt aaataatttg aggaaaaaag    420
tgatcaatac atatcatgcg gtgcatacaa gaatcggcca ttggtcaact tgtgagagga    480
aaaaatcatt taactaatac caaataatct taaaattaat aaaataattt aactaattaa    540
cccacggaag aaccttcttc cgttgactct ggcggaagaa gttcttccgc atagttccat    600
ggaagatggt tcttccgcag ttcttctttc gttgacactc gcggaagaaa tgttccacgg    660
gcgtccgcgg aagaactttc ttccgcaaag ctaaagagca ttttgccat gtcgaaatca     720 tcgccaatga ccagggtaac agaaccacgc cctcttatgt tggtttcacc gattcagagc    780
gtttgatcgg tgatgccgcc aagaatcagg tcgccatgaa ccccgtcaac accgtcttcg    840
gtaagatccc tagccgacac ttcgcctttt caggatttgc attgttccta gattttggga    900
tctgttgttt gaaactccac ttttctattt tggtaatttt tagttttatt ttgtaatcct    960
gctgtttata tgtcttattg ttattattaa tcgttgcatg gtctgaactg gtttagaact   1020
ctacttgtat tgtttgttaa aatcttattt gaaatcgaat agtaatataa ttttaatcga   1080
atggtgatat gcataaacat cgtatttgtt cgtcgaattc tggttttgaa ttgaataata   1140
ttgttatg                                                            1148

<210> SEQ ID NO 42
<211> LENGTH: 1378
<212> TYPE: DNA
<213> ORGANISM: Artificial Sequence
<220> FEATURE:
<223> OTHER INFORMATION: Synthetic construct Glycine max Cab5 promoter

<400> SEQUENCE: 42
ctagaaatta aatgttttta acaggtaatt tgagaaaaat gtacttcaaa ataattagtt     60
ttaccagttt atgtcttctt tttctctttt ttatctttat tctatgtttc aaattctaat    120
aatacatcat ttaaatattt ttaatttaaa agtgcttact aaattttaaa aaaatcatat    180
ttatcaaata acttctactt taaatttaaa cttcattatt tttaacttaa aaataacttt    240
taaattaaaa aaatgaaaac aaacactacc taaaccctaa acactatcta tctaagtcac    300
attacttaat gattcttaat ttatgttctt tgtaaacttt catttcttcc tccttttggc    360
tatacatgtt catttctgtg tacttttacta tattattagt aaaagccttt tataggta    420 tatcaaatca ataattaat ataatatata attctcttaa tttcatttct tcatataaat     480
gtatttcaaa agtatttctt ctagaataaa ctaaagctat tacagatgaa aaattcttaa    540
aaaattattt gaccttcata tatgggtcct tttctaatta ataattaact atataggtgc    600
attctaaatg ctcctatatt atctgctttc tcctcttctt tcctttttc ctagtcgctc     660 acgaaaatct cctataatcc tctgcagttt tcgaaatcaa taaccgactc ctagaacctg    720
tccatgtcta acttaataaa tcgtgagggt gtgattgtga ttactttgaa tctttaattt    780
ttgacattaa aacaagacca aacaaaaacc ttcaggttac gtgagactcc aacctaccca    840
agttatgtat tagtttttcc tggtccagaa gaaagagcc atgcattagt ttattacaac     900
taactatatt tcaatttcat gtaagtgtgc cccctcatta aaatcgacct gtgtaaccat    960
caacctgtag ttcgctcttt tcaccatttg tctctctgtc tttatcttcc ctcccccatt   1020
gccaatattt gttgcaatac aacatctctc cgttgcaatc actcatttca aattttgtgg   1080
ttctcatttg ccctagtaca acattagatg tggacccaaa aatatctcac attgaaagca   1140
tatcagtcac acaattcaat caatttttc cacatcacct cctaaattga ataacatgag    1200
```

| | | | |
|---|---|---|---|
| aaaaaaatag | ctaagtgcac | atacatatct | actggaatcc catagtccta cgtggaagac | 1260 |
| ccacattggc | cacaaaacca | tacgaagaat | ctaaccccatt tagtggatta tgggggtgcc | 1320 |
| aagtgtacca | aacaaaatct | caaaccccca | atgagattgt agcaatagat agcccaag | 1378 |

<210> SEQ ID NO 43
<211> LENGTH: 1500
<212> TYPE: DNA
<213> ORGANISM: Artificial Sequence
<220> FEATURE:
<223> OTHER INFORMATION: Synthetic construct Glycine max PPDK promoter

<400> SEQUENCE: 43

| | | | |
|---|---|---|---|
| gatcctcaca | aacctcactt | ggagacatag | gtgtgagggt aacctttttc cctttatgta | 60 |
| caaatgaaaa | tttgtttgtg | acaccattat | ggacaacatc cttacactac taaaaaagct | 120 |
| ttttttttacg | acatcatatt | tacgacagtc | atacaaaaac gtcttagtat gtataaggat | 180 |
| ggcaatttcg | taaatatttc | aaacatttca | aaggcagttt cagaaaaccg tctttgaatg | 240 |
| cggccatttt | aattttttaac | gcgcccctcg | catccgttcc tcttctttcc gcaaatgtgg | 300 |
| tgctcgttcc | ttttctttcc | cagctggcat | ctgttcctct ccccactcgc tagctatctt | 360 |
| ctgcttctcc | tcttctctcc | tcttcccatt | acatttctcc accttctccc tggtaccacc | 420 |
| accgcccccc | actccacatt | cgtcctccgc | ccccattccc ctatcctcca gtaaaattac | 480 |
| aaaaaaccct | aacaccaaaa | aaacccaaac | ccctgtcgca atgaaatctc cacccccaaa | 540 |
| tagctctttg | gaatagaatc | aaggaactta | ccaaatccat tatatgctat tggggttttg | 600 |
| gcatgtttcc | ggtgtgaaag | aaggaaaaag | aaatgcgtat gcgatggtga tgtacgtagg | 660 |
| tacgccgaag | gactacgaat | tctacatagc | catactcgtg cttctcaaat cgctggctac | 720 |
| gctcgacgtt | gaaattgatc | ttgctgtgat | tgcttcccctt gatgttcctc ctcgatggat | 780 |
| tcgagctctg | taagtctcac | tccttcacca | tcatttgcca ctttattttt atgtactttt | 840 |
| actttattat | tatttgtaac | ctgtatttttt | atttggtttc ggatatctgt tgctttatta | 900 |
| ttcaccctgg | aatttggttg | attttattat | ttttgaaaaa taaggaaaga gatttatttg | 960 |
| ttagcttaat | tgtttttaatt | ggcgaatatg | ttttttctttt cccttttttg cacagagtga | 1020 |
| agctttgttc | ttagggtaat | ggattccctt | ttttgtgatg ctagtggatg atttgactga | 1080 |
| ttagtgttta | gtggaatgaa | gaaccagaac | tagtagtagg tagagggaat cactttttggt | 1140 |
| tttggatgta | aacttagaaa | tgtgcagcac | tgcacagaat tgatatttga tcgtgggtca | 1200 |
| aattgtcaaa | atgtgcaaag | aatacaaagg | cacaggtgat atcattccat tttacgtttt | 1260 |
| ttaacgaagc | tgttagtttc | aattcaatta | tttacatata taataaatat attgatactt | 1320 |
| gctttagttt | catgaattaa | aagaatttga | ttttgtaaat ttcatttgaa tttgttttttg | 1380 |
| tacaagctct | caacttttat | tatatgaacg | agaagtttct ttttttcctttt tgagtttat | 1440 |
| ttgaacttgt | ggtgttctaa | ttgtatatat | ttttgtgcag gtgtcaatcg gtactactac | 1500 |

<210> SEQ ID NO 44
<211> LENGTH: 1261
<212> TYPE: DNA
<213> ORGANISM: Artificial Sequence
<220> FEATURE:
<223> OTHER INFORMATION: Synthetic construct Glycine max actin promoter

<400> SEQUENCE: 44

| | | | |
|---|---|---|---|
| atctctcgac | agttgcgaac | tgaacgctga | gttggtaatg ctatgcccta tcgcttttttg | 60 |

```
caccgtccca tgatcatttc ccccacacca ccccatcaac ctctaaaaag ttaagagtga    120
aaattacaca cacccgagga gaagaaaagc tgcttcttct aagcatcaca acctagttac    180
tttacttgta gggccttttc catttcccct aaattacccc tcttttcatc atatgataat    240
aatatccagc tcagactata gtatgatatt atgatgtcag cataataggt tggcactaaa    300
gtcttaaagg gcattgtaca tgttgcacct ggcattcaaa ttcataaata ctaacactgt    360
gaaatagatt ataaatcctc aaataaatgt cacacggttg gggttcgaat ccactcaaaa    420
aggctaatgg gatgggattt aagtgccaag gaatatacca tggactttaa cagcaacaca    480
atttacaatc taaatgtat tactttttt tttcaaaaaa gatatacaaa ataaggtacc    540
aagaataaaa ggagtattta gaaacagtgg caccaattta ataaattatt tatataaaat    600
gacacttatt taatttatca atgataaaag taatattgat ttattctctg attaactgtt    660
caattaatag tgttattatc ataatctgtc gcaaaagtta tttttatcaa caacaataat    720
tgatacaagt agtataaaat taagcctctt agttaatata gactacttga tactaaaacc    780
atgttacacc aaaaagtaat ttttatgtca cttgtctata taattaattac gactaaatta    840 ataatttta aaaatattac tgaatccatt aaccgaactt ttataatgaa agtattttta    900
tgctttaaaa tcacaaacat tgaataaact aaaaatgata ccacggaatt ggaacaagag    960
acgttccaca caaagaaaaa aatatgttga ataattgaa acggtgacaa gaaaagtgga    1020
ataataatac aaagatggca gatggggtta ttgttattgg aggagatgag tgaaataatg    1080
agtgaggggg gtgtaactgg aaagcaagaa aaagcgcaag agtgccagct atttccaaca    1140
acaaacgtgg cccgtgggat gcgatattcg taacgaacgg cgaggatgga aggacgtgca    1200
atttgcgctt catttgaggc gaatttcatt tggccagacc ttcctttttt aaaccacagg    1260
g                                                                    1261

<210> SEQ ID NO 45
<211> LENGTH: 1094
<212> TYPE: DNA
<213> ORGANISM: Artificial Sequence
<220> FEATURE:
<223> OTHER INFORMATION: Synthetic construct Glycine max AGPase promoter

<400> SEQUENCE: 45
tgtgtcaatg ttgtttctgg tgaattgaca taatgaattc tacctgtacg gagtagagaa     60
taactattta cccaacaaga atgattatct cattaatttt tgaagtagac gcaataacga    120
atatattata cattcagaaa aatttcacca tattattctc aaatcacaac aataatttgt    180 ttttttttg cttgatataa aaccaatact ctatactttt taaggttaat ttaaacttaa    240
agagtatttt taagatgcat gtactttaag gaataataga acatgacaa catcataaaa    300 gaatgaagaa actgaatcat aacgtagttt gttacgcctt ccatttggtg gttgatttgg    360
atacaatcta gattggtttg ctaaatggtt tataagttat gtagacgttt ttattactac    420
tattttagac aaatcaaata cacaccttca ctttattcta ttcaaataac atgatttttc    480
ctaacatttt ttaaaaaaat tacttttttaa atataaacta attattttag aaatagttttt    540 ataaaaatcc acgccaaaaa aattaagttg ttttttataaa tataaacatc gggcttcaat    600
cttaaattta taaatgtacg aaataatttg acagttaaat ggaaattgct agcatggaag    660 tgttttatc atttatcaaa ctcaaccaaa ctgaacatca gaataattat tagtgacaaa    720
ttttgcagca tatgaagtgg cttgcatagc tccaaggctg gcgatcatat gtcagattag    780
agcaggctct cttttggtact atgatacatt tcaagcaaat aacaaccgta aaaattcacg    840
```

```
ccaaaatttt tggaacgaat ctatatatta ttattttatt tcttttgatt tcatgtacgt    900
acagtgcccg taattgacat gtctttgttc cttaatgcct ttcccacgtg aacaggcac    960 ctagaaactt ggactaagta gggaattgag ggccatggac tatagtgcca aaccaacatc   1020
attttatata tatatatata tatatatata tatatgctat tgttttctat agttttgga    1080 aattaatact tatc                                                    1094
```

<210> SEQ ID NO 46
<211> LENGTH: 1449
<212> TYPE: DNA
<213> ORGANISM: Artificial Sequence
<220> FEATURE:
<223> OTHER INFORMATION: Synthetic construct Glycine max GluC promoter

<400> SEQUENCE: 46

```
atttgtacta aaaaaaaata tgtagattaa attaaactcc aattttaatt ggagaacaat     60
acaaacaaca cttaaaacct gtaattaatt tttcttcttt ttaaaagtgg ttcaacaaca    120
caagcttcaa gttttaaaag gaaaaatgtc agccaaaaac tttaaataaa atggtaacaa    180
ggaaattatt caaaaattac aaacctcgtc aaaataggaa agaaaaaaag tttagggatt    240
tagaaaaaac atcaatctag ttccaccttta ttttatagag agaagaaact aatatataag    300
aactaaaaaa cagaagaata gaaaaaaaaa gtattgacag gaaagaaaaa gtagctgtat    360
gcttataagt actttgagga tttgaattct ctcttataaa acacaaacac aattttttaga    420 ttttatttaa ataatcatca atccgattat aattatttat atatttttct attttcaaag    480
aagtaaatca tgagcttttc caactcaaca tctatttttt ttctctcaac cttttttcaca   540 tcttaagtag tctcaccctt tatatatata acttatttct tacctttac attatgtaac    600 ttttatcacc aaaaccaaca acttttaaaat tttattaaat agactccaca agtaacttga    660
cactcttaca ttcatcgaca ttaactttta tctgttttat aaatattatt gtgatataat    720
ttaatcaaaa taaccacaaa ctttcataaa aggttcttat taagcatggc atttaataag    780
caaaacaaac tcaatcactt tcatatagga ggtagcctaa gtacgtactc aaaatgccaa    840
caaataaaaa aaaagttgct ttaataatgc caaaacaaat taataaaaca cttacaacac    900 cggattttt ttaattaaaa tgtgccattt aggataaata gttaatattt ttaataatta    960
tttaaaaagc cgtatctact aaaatgattt ttatttggtt gaaatatta atatgtttaa    1020 atcaacacaa tctatcaaaa ttaaactaaa aaaaaaataa gtgtacgtgg ttaacattag    1080
tacagtaata taagaggaaa atgagaaatt aagaaattga aagcgagtct aattttttaaa    1140 ttatgaacct gcatatataa aaggaaagaa agaatccagg aagaaaagaa atgaaaccat    1200
gcatggtccc ctcgtcatca cgagtttctg ccatttgcaa tagaaacact gaaacacctt    1260
tctctttgtc acttaattga gatgccgaag ccacctcaca ccatgaactt catgaggtgt    1320
agcacccaag gcttccatag ccatgcatac tgaagaatgt ctcaagctca gcaccctact    1380
tctgtgacgt gtccctcatt caccttcctc tcttccctat aaataaccac gcctcaggtt    1440
ctccgcttc                                                          1449
```

<210> SEQ ID NO 47
<211> LENGTH: 1321
<212> TYPE: DNA
<213> ORGANISM: Artificial Sequence
<220> FEATURE:
<223> OTHER INFORMATION: Synthetic construct Glycine max CIN1 promoter

<400> SEQUENCE: 47

```
aaaaacacaa aaaaaaatta tacaaaaatg tttctcacaa catgagaagt aaaatccctc    60
aaagaatttc acatcatcat atcagaatca aaggaatcaa aatcataggt caaaaataca   120
aaaacaccaa gaacactcaa tttattaact aatttgcatc atgacatcaa ttggtccatc   180
aaacacaaca atcttgtaat tataatcgta acgaaagaat tacaatgcaa taaacatccc   240
aaaataaacc tcaatttaat cctctaagga tccctataca tgttcattct aaccccaatt   300
gtgataaatt catcccttac ctctaagcag gctcacgtgt gtagtctggc agtgatagag   360
gcatctctag tggttttcta atagtcctca agcttgtttt tcctctagtt gttctgttag   420
gattttcaag cgttagagag aagaagaaga gattggagcc tctatttcac tgttaccgta   480
caagggatat ttttctcacc ataaacatta ttttgcaaat cccaacgaag gagatgtccg   540
tacataagtt cgaaacctgg tgctcgaatt tcacgacgat tcaatggtta acaagtccaa   600
gattgtattt ttactgtgac agatttgagt gtatacaaga aaaagagagc tccatgcgag   660
gaatatttct ctcacagtag acattatttc ataaatccca atggtaaaaa tatgcaaaaa   720
tgagtttcaa acctgctttt aaaatttcat gacgactcaa cggttaacgt gtccgggatt   780
atattttcac tggaacaagt tgagtgcat gcgggaaaaa agagggtttt gggagaggaa   840
aaaaggaaaa caaatttaag aggaagagag agcgtaaaaa tttatcgtaa atgtaaaaaa   900
tgacctaata tatctctatt tataactagg gtactctcaa tctattattt actcattttt   960
ttatttatt atttttataa aaagaatttt attttacttc ctatcaaatt aataaataaa  1020
acattcttct tattttctaa gatcacatat ttattttatt taccttaaaa tcatcatttt  1080
aattaataaa attatttctt cttatttatt taattacaaa aatcttatta ttttttttaaa 1140
atttatttta tttttaaata aaatattttt taatttattt tataaaaaat gagatgttac  1200
attgaattat aaaataaata gccaacaata aatagccgac ttgcttttgc attgactaag  1260
gaagtcaagt catcaataaa tataatttcc agttggcaat attctcaaag ttggtctata  1320
t                                                                   1321
```

<210> SEQ ID NO 48
<211> LENGTH: 514
<212> TYPE: DNA
<213> ORGANISM: Artificial Sequence
<220> FEATURE:
<223> OTHER INFORMATION: Synthetic construct Glycine max MADS-Box promoter

<400> SEQUENCE: 48

```
agatttgatc gatacttcat taaattgaca ttttattta acacataata cattattaaa    60
aatataaata aacatttaca gcgaagttat ataattaaaa gcctggtcta tgtaatggta   120
ggaaatttga aaatctaaaa gcaaacaaaa attgttgttt atggtgctaa gttgcacctg   180
gaaagatgca ttgtttagct aaaacattca cgtcgagtac ttggtttggg aaaaaaagcc   240
attcaagctt agctggtcct ctctcctgtc tctctctctc tgtctgtctc tctctgtctg   300
tctctctctc aagcacatac acaaacaaag taagggctat aaataggagg gatgaaagtg   360
gaagaaagtc tatagcgaag tttcattcct ttggattaga aattttccc aaagctgatc   420
gagaagccag ccaggccagg tctgtagttt tcttttttc ttttaatat taattcatta   480
ttgtgttctt catcatataa tataattaag cctt                              514
```

<210> SEQ ID NO 49

<211> LENGTH: 702
<212> TYPE: DNA
<213> ORGANISM: Artificial Sequence
<220> FEATURE:
<223> OTHER INFORMATION: Synthetic construct Glycine max Glycinin
subunit G1 promoter

<400> SEQUENCE: 49

```
cgcgccgtac gtaagtacgt actcaaaatg ccaacaaata aaaaaaaagt tgctttaata      60
atgccaaaac aaattaataa aacacttaca acaccggatt tttttaatt aaaatgtgcc     120
atttaggata aatagttaat attttaata attatttaaa aagccgtatc tactaaaatg     180
atttttattt ggttgaaaat attaatatgt ttaaatcaac acaatctatc aaaattaaac     240
taaaaaaaa ataagtgtac gtggttaaca ttagtacagt aatataagag gaaaatgaga     300
aattaagaaa ttgaaagcga gtctaatttt taaattatga acctgcatat ataaaaggaa     360
agaaagaatc caggaagaaa agaaatgaaa ccatgcatgg tccctcgtc atcacgagtt     420
tctgccattt gcaatagaaa cactgaaaca cctttctctt tgtcacttaa ttgagatgcc     480
gaagccacct cacaccatga acttcatgag gtgtagcacc caaggcttcc atagccatgc     540
atactgaaga atgtctcaag ctcagcaccc tacttctgtg acgtgtccct cattcacctt     600
cctctcttcc ctataaataa ccacgcctca ggttctccgc ttcacaactc aaacattctc     660
tccattggtc cttaaacact catcagtcat caccgcggcc gc                         702
```

<210> SEQ ID NO 50
<211> LENGTH: 579
<212> TYPE: DNA
<213> ORGANISM: Artificial Sequence
<220> FEATURE:
<223> OTHER INFORMATION: Synthetic construct Glycine max oleosin isoform
A promoter

<400> SEQUENCE: 50

```
acgcgccgta cgtagtgttt atctttgttg cttttctgaa caatttattt actatgtaaa      60
tatattatca atgtttaatc tattttaatt tgcacatgaa ttttcattt atttttactt     120
tacaaaacaa ataaatatat atgcaaaaaa atttacaaac gatgcacggg ttacaaacta     180
atttcattaa atgctaatgc agattttgtg aagtaaaact ccaattatga tgaaaaatac     240
caccaacacc acctgcgaaa ctgtatccca actgtcctta ataaaatgt taaaagtat       300
attattctca tttgtctgtc ataatttatg taccccactt taatttttct gatgtactaa     360
accgagggca aactgaaacc tgttcctcat gcaaagcccc tactcaccat gtatcatgta     420
cgtgtcatca cccaacaact ccactttgc tatataacaa cacccccgtc acactctccc      480
tctctaacac acacccact aacaattcct tcacttgcag cactgttgca tcatcatctt      540
cattgcaaaa ccctaaactt caccttcaac cgcggccgc                             579
```

<210> SEQ ID NO 51
<211> LENGTH: 1500
<212> TYPE: DNA
<213> ORGANISM: Artificial Sequence
<220> FEATURE:
<223> OTHER INFORMATION: Synthetic construct Oryza sativa Hsp70 promoter

<400> SEQUENCE: 51

```
gcagctgttt tcgcggtaca gggtgcaaca aaagcccatg acggcccaca cctgcctctc      60
tccgctccaa acaccgaaac aagggggtgg gtgcaatggg ccggcgctcg aagaccgcga    120
actcttttcca acagcccagc gcattagccc ctcctcctac tctctctacc ttctttttaa    180
```

```
catgcgactt tctttctgtg gacgacggca tcaacgacgg gagcaggagc gggggctgaa      240
gcacggtgcg tgggctcctg gagtggcgac ggcctctccg gcgagcttcc tctggcgaac      300
tccctccgct cctcctatgg cgaaatccaa acaagggtca gtttcgactc caaccttctc      360
ccaccaccac ctcctgaccg tgccaccacc cggccttgtc ggcactgaaa ggcgtcaact      420
tgtcagcgcg ggcctgctcg gtcggtctcc tcctccccta tttcgtttag ctttgccccc      480
gccaccaaca ccgcccacg gcccatggcc gaccccgcgg ctttggcgcc gccatcgcta       540
tctcgccgct gtccttttt catgaccttc ggtgccatcc ctctaaattc gatgcacctc       600
cctggctcta tctcccttta cctccgaaat cctaacccta cccataatct ctagtgagtc      660
ttgtctttat ttatggcctc tttgaatcgc aggattgata aaacgtagga ttttgatagg      720
aatgtaagtg taaacacat gattgtaaaa tagaggaaaa ataggaat ggccgtttga        780 ttgaaccgca gaaaaacac aggaattaga tgagagagat agactcaaag ttactaagag       840
attgaagctt ttgctaaatt tcctccaaaa tctctatagg attggccatt ccatagaaat      900
ttcaaaagat ttaataggat tcaatccttt gtttcaaaaa acttcataga aaattttct       960 atagaattaa aatcctctaa aattcctatg tttttctcc aattcaaagg ggcccttagg      1020
ttggaatttg gaaagtgttc gcgagaaatc aagcggtcgc acgttagcga attaggattt     1080
ccggaaacaa aggaccgact ccgcctatcc atcgtcacga gcacagtgta gaacctccca     1140
gacctcaaga gaccgttcaa aaagcgcgcg cccaagcggg gcccaccaac gcgtcccac      1200 cgtgtcgcct cctgattggt tgtcccctct cctttcacg cgaaccggca ccctcccgac     1260
ccttccagaa cccccaatcc gacggccagg atcgcccgcg cgcgaacgtt ctagaccccc    1320
gccacctccg ccacaaaacc tctgcccctc ccctctcccc ccgcttcgtc tcgttcgaga    1380
aatcagaaag agagagaaat tcccacgcag cagcaagcaa tccaatccga gagcgcgcgt    1440
ttgcgattat tcgctttcga ttccgcgagg ttttggaga gggaggagaa ggaggaggag      1500
```

<210> SEQ ID NO 52
<211> LENGTH: 1500
<212> TYPE: DNA
<213> ORGANISM: Artificial Sequence
<220> FEATURE:
<223> OTHER INFORMATION: Synthetic construct Oryza sativa Cab5 promoter

<400> SEQUENCE: 52

```
acagcattta ttgtagtctg gtcaagcgtg tcacgctgca tgcaacgcag tacagcgcgt       60
tcctttaccc ggtctgtgac cagtcacaga ccggtcagat cacgggttag gtggcgactg      120
gcggtctgac gcacgccttg ccccatcccg tcaagacgaa agcctctagg cactcgtctc      180
aagccggagc tagcgtgtta tctcttagag atggcacgtt agccctggtt agatttatac      240
caggcttcat cctaaccatt acaggcaagg tgttacacga agaagggcaa aacatgcacg      300
ttgttaaact gacgcgtggg ggacaagaat gaccggtctg acactggtcg catcagcaac      360
gggcagccac gatcccgcgt catctccgtc tccgccggga gtggaggtag gtgtgggctg      420
tcccatcaga agggctcccg gatggaaacc gtaccgatct ccgcccatta aagagaaaaa      480
gaacagtcca gtttggaaag agaagggtgc atgtggtatc cccttgaagt ataaaaggag      540
gaccttgccc atagagaagg gggttgattc tttccagatt cagagcctag aacgagggag      600
aggtgggctc acactttgta acttgtccat acacaaatcc acaaaaacac aggagtaggg      660
tattacgctt ccgagcggcc cgaacctgta tagatcgtcc gtgtctcgcg tttcttgctg      720
```

```
gctgacgatc cttccacata cagagagaga gagagcttgg gatctcaccc taagccccg     780
gccgaaccgg caaaggggg cctgcgcggt ctcccggtga ggagcctcga gctccgtcag     840
acatgttcag tttcattata ttatgaaatg tcacgtactg tttgttctag ttagtgaatt    900
gtcatatggt aagaatatat aaaaattagg ttttctggac tctatcttcc aatgtatttt    960
tggatcctat aacaaaatat tttcataaat atatttttta agaatctaaa cttttttgaa   1020
ataaaagagc aacaagaaa ataaaaacgc tctctcgtaa gtaactcgtg aagatccatc   1080
gagagccact cgtttgaatc gtcgacacaa aagaacactt cattgattgc ttttcgtcaa   1140
ttagccgcac agcacagtac tctccaatct gctaaaccaa aaccaatctc atccatccat   1200
acccttcttg acaccaagtg gcaactcctg attggacgcg ccctatccta catggcaccc   1260
ccaagattct ctcgataggc tacaggggcc acaccgaccc tccacgtcat cgtccacgtc   1320
accctcatcc cggcccatcc agccaatccc agccagcaa aaaatcttcc caagtggcca   1380
ccagataagc ctctccacgt attaatacgc caagtgttcg tcgccatgac acagcacgca   1440
cacacacccc accagcagca gcagcagtag ctgagcttga agcagcagag cgaggtagac   1500
```

<210> SEQ ID NO 53
<211> LENGTH: 1500
<212> TYPE: DNA
<213> ORGANISM: Artificial Sequence
<220> FEATURE:
<223> OTHER INFORMATION: Synthetic construct Oryza sativa PPDK promoter

<400> SEQUENCE: 53

```
tccacctctg ttggttgcat cgacgtcgct tccctagctc ccgtctctag tccggatcct     60
attcctcctt ggagaccgaa gctaccgcaa ccattgctcg gtggttagcg agcgtggagc    120
tgtcctcccc actttcgcgt cctcgttcgc caccacagcc atacttcgca tggtgatgtc    180
ttctccttca ctcaccgcta aactcagtgc aaccgtttct accctagccc cggccgccgc    240
tctcatagag gtgaaagttc atttacatgt aggtcccaca tgttttatgt tttttatttt    300
tcttttactg attagcatgc cacgtaaatc aaaacaacaa tccatagtgt tttaagtatt    360
tttatttaat acgtgagatg gagtacaaaa acgagagatg caaagtgaac ttgctaaaac    420
acattttctg gttgattaca gtcgcttgtt gagccattgg atcggtcata ggattcgtgc    480
tagcatactt aattacgcgt aactagttgt gctttatagg ttacaggtcg ctaattagcg    540
gtctactgga gaactttgct actatttttt tcttcactgc atgcactcga tcaagtatga    600
gtatttgtac cgaccagcga aacacatatg taattaaagt ataaatatgt aattagtata    660
tattagtagt atatttagac agtagttaca ccctacatac acaccactta catatataat    720
tagtatgtaa ttttgtaact tacatatgta attttagtac ttacatatgt aattttgaga    780
cttacattgt aaatacacta aaattacata tgtaatttag taacctacaa tgtaaataca    840
tgccgactaa cttttgatga aaatatggt gttataaata tagctactcc cgaactttat    900
tccttctctg tgagatatca gtggaaacgc tcggtggaat cggggagta tttgggagca    960
cgcgccgacg cgcgcgtcgt gcgtgccgtc gtctttgtcg cggtggagcg gagcgcgccc   1020
acttgcgcgc ctgggccgga ggcggcgcg cggggggttc gggaatcccc tggagccaca   1080
cgtaaaggcg cgggcgggag ggagggaggg gccagctagg ataaggcacg cgcggccgct   1140
gcgattgggg cgcttgtgaa caccggggc ccacgtggag aggacgttac actccagccg   1200
ccaaatttcc actcccacac ccgcgctccc ctccctctc ttttccgtga tcgcacctcg   1260
cccacgcgcc cccgccaca cacaatctct gcagctctcc agcttcgttg gaactcgcga   1320
```

```
atctctctcc gatcccaggt aaagcagcga acgacgtcac gcacgacgct gctcggtgga   1380
tttcgttcct tgctggggaa aaccatgcag agacgaaggt gaatgatctg cttttgtgta   1440
cttgcgttta ccaggtgaag cgcgagcttg gagttggagg ggagatcgat cagggccagg   1500

<210> SEQ ID NO 54
<211> LENGTH: 1500
<212> TYPE: DNA
<213> ORGANISM: Artificial Sequence
<220> FEATURE:
<223> OTHER INFORMATION: Synthetic construct Oryza sativa actin promoter

<400> SEQUENCE: 54
ataattaatt aattaatcaa tcactttcg tgctgtaaaa aatctcaccc gatttgctga     60
aacgaactga gccgggcgac tgtgatattc tttcacgatt tctgtttgtg gcagtgggac   120
attgctgttt attcgaaaca atttcaagt aaaaaaaaat actcaatggt aaggttgcta   180
gtaatagttt aacagtttgt ttgcagctca gcaaatttcg tttcctcaca gatgacacat   240
aactgaaagc actcaatgta atgttgtgct tagctgctaa agcatgtcac gtcttagaaa   300
acaactactc caccatggag aatttttcct cctacttact cctcacatac ttaccatctc   360
catataagtt cccttgtcgt atcatatgtc ttattcttct tgagcacagt tattacagca   420
gattttgtag aatagttatc gcatcaaaat tttcctatgt caccttttgat catgtgttat   480 gtgtgcctct tgagtcttag ggttaatgtg ttgtaatgt gtttaaaaaa ctatatgaaa   540
gctcgtgtgt tgctacggga gagagatacc tcgaatgaat gtgagagatc tccatttgag   600
ttgtgtacct tgagagagtg aaagatcaca ctatttatag acggttaata atggttactg   660
aggtcgattc accacatcgt cttaaacatt taatgagcat cctccacgtg aaaagtagag   720
atgatagcgt gtaagagtgg ttcggccgat atccctcagc cgcctttcac tatctttttt   780
gcccgagtca ttgtcatgtg aaccttggca tgtataatcg gtgaattgcg tcgattttcc   840
tcttataggt gggccaatga atccgtgtga tcgcgtctga ttggctagag atatgtttct   900
tccttgttgg atgtattttc atacataatc atatgcatac aaatatttca ttacacttta   960
tagaaatggt cagtaataaa ccctatcact atgtctggtg tttcatttta tttgctttta  1020
aacgaaaatt gacttcctga ttcaatattt aaggatcgtc aacggtgtgc agttactaaa  1080
ttctggtttg taggaactat agtaaactat tcaagtcttc acttattgtg cactcacctc  1140
tcgccacatc accacagatg ttattcacgt cttaaatttg aactacacat catattgaca  1200
caatattttt tttaaataag cgattaaaac ctagcctcta tgtcaacaat ggtgtacata  1260
accagcgaag tttagggagt aaaaaacatc gccttacaca aagttcgctt taaaaaataa  1320
agagtaaatt ttactttgga ccaccccttca accaatgttt cactttagaa cgagtaattt  1380
tattattgtc actttggacc accctcaaat cttttttcca tctacatcca atttatcatg  1440
tcaaagaaat ggtctacata cagctaagga gattatcga cgaatagtag ctagcataag   1500

<210> SEQ ID NO 55
<211> LENGTH: 1945
<212> TYPE: DNA
<213> ORGANISM: Artificial Sequence
<220> FEATURE:
<223> OTHER INFORMATION: Synthetic construct Oryza sativa AGPase
        promoter

<400> SEQUENCE: 55
aaggtttcat gcgtatcgtg acagatgtta cataatgaca aattccccag ctggagcacc    60
```

```
tttatccctg ctgtttgcat gaaattagct tgtcttgtag ttccctccag caaaagaag     120 tctgaaacaa aacaacattt cgaaaaaaag gcatccatga gttagcattt ctacagttgt    180
ctatagaggg gaaggctgca cgacaaagtt tccaggcttg gaaacaacct cttatgtaaa    240 attttcgta tgtatcagat gatttgtttg cgttacggca tctccaccta acatcacctt    300
catcatgcgc ctatggtctt tctcttgcct gttttatacg taaaattgga aacgacagaa    360
acttttgcca tctttattaa aggaaggcaa atatgcaaat ataggcatca agatcacagt    420
tagtggatta tcatctttgt aggttaacat gtcctacccc aggggagctt atactcaagt    480
actccatgca ttttcatgaa atgagaaaaa acgattttta agagaaatgt actttcttgt    540
atttatgcca aatggcaagg actgaaaggg aaaaactaag aaagggaacg ttacagtaag    600
gctctgtggg gactggggac ttcagagaaa cgtgaaccct gcttccttcc tctgcatgaa    660
cataacacca gaggtttcca gcctttcaca cagttgttga tggcttcaca caattcatct    720
ctacctcctg actcttttata aggaccccca gcatcaccac aattgcacaa gtacaggcat    780
tagatccaca agaacacttg ggcaggcaag cacctctttg atctttaagc cgttgttatg    840 ttctattttct gagcatatgg tttctagtta tattctttttt cttcattcgt ttcatatctt    900
tgaagtgttg atgcaaatgc ggtgaacaac tatcaactgt gtactctcca agtgaatgcg    960
aataatcatt tcctgtgaga attgtgggct agataaacga atgaaatgct gttttatcta   1020
tgtcatgtgt ggaaatttag ttaatttttcc ggtcttttta tgcattgaga tgggtatgct   1080
gtttttttag ttgggtccca tcatcttgag aattctttca aatttccttt tcttatcct   1140 atataaagga tagagaaggc gtatgcctag gtgcaccaac cctgaaagtt ttattctaat   1200
tgcgggaatg gtttgtaatt tttgcttgtt caggttcttt ttcgtggcct ttcttttttt   1260
tccccttatt ttgcttagtc tttcacagtc caattttttgg gaagtagtat atcttagttt   1320
ggtcctaagg caccatgttg tactgcagga aaaaaagag taattgtatt ctgttttttc   1380
cttgattact atatccctgt tttaattaat tttgtgcctt tgttgtttga tgttggaact   1440
tcaatgccca taattagtca tttgacttgt tttgggtttt gacgctatct tgagtgccat   1500
aggaaactgg tagaatttag taataatttt atatagactg aatgttgagc ccaccacaaa   1560
tggtttcctt ctgtacaagt atttaataac tcaagcacag gaaacatcag atctctaatc   1620
taaaggttaa caatgggctc aagcaggagc agtagttcag ctctatctgt atatttagaa   1680
gggctggatc tacctgtcca ccagctttta atttacccct ggcagctgga taacttcttg   1740
tctgttaatt tcatttagtg ctgtgttatt ttcttcttgt tgttcaggat ggatgctttt   1800
gaatttctgg aatttcgtat tttgttctat ctctttatga aatgacgtta tggcacactt   1860
tttctgcata ttcttgatga aaataattac ctagtcattt ttttagttgc aggtttgtct   1920
gggactttga gtacccatgc aattc                                         1945
```

<210> SEQ ID NO 56
<211> LENGTH: 2315
<212> TYPE: DNA
<213> ORGANISM: Artificial Sequence
<220> FEATURE:
<223> OTHER INFORMATION: Synthetic construct Oryza sativa GluC promoter

<400> SEQUENCE: 56

```
gttcaagatt tattttttggt atttaattta cttgcttaag tcagatatat tcccatcgtt     60
gcaggtttgt cacttagtat tattattaag cgctctagca ctaggactct ggataaataa    120
```

| | | |
|---|---|---|
| gaaagtttat tcacgaggct agagtagtaa tcaataacat aagcgtggtg tctaggtcag | 180 |
| cggttatctt catatgtagt gtgctccatg gaaagtgagg taggaggaag gtggtgacag | 240 |
| tcccgtccgt cctttgtatc cctccatgtt cgggtatatc atagagctac aggctagact | 300 |
| tagcttggca gactagggga gagccggtgc tcgaagcaat ccatgaggct ttacatttaa | 360 |
| cataagttag taaattaacc cataggaatc atctctagac tgaacctacc agtagttgtg | 420 |
| cttggatata attatattcc tacatataca tacacgttcc ctgcgattag atacccttgg | 480 |
| aatactctaa ggtgaagtgc tacagcggta tccgtgcgct tgcggattta tctgtgaccg | 540 |
| tatcaaatac caacaggtag atacaaggaa tcatctctcc tatccattgg tttatcatct | 600 |
| tttaaaatta tctcttgctc tcctattgcc tctgcaactg cggataggtg tttctcaaca | 660 |
| atgaaggttg tgaagaatgc tttgtgcaac aagatggatg acaagtatct cagccatagc | 720 |
| ctcatttgct ttgtagaaaa ggatatgtcg gacacaatca ctaagtatca ccgtggaaag | 780 |
| gatgcactgt atgccctatc tatatttacc atttagtaat atttatatgg cttgtgctaa | 840 |
| ctttatgttg tctttacagg caataacatt atttggaagg catatctata tattactatt | 900 |
| taagataatg taatatctca aagttttttat aagctgcaat gaggtgagtt tcacttagct | 960 |
| ttctaacttg ttatgagtta tagatgcatg ccaccagtca ttttttatct tgcatcagcc | 1020 |
| cctgcctgtt agaatatgtt tcttgtctg ggagtccatg tcaactagcc aatttccaaa | 1080 |
| tatatgaaca aaactatgtg gcctttgtaa cccaaatgag ataaagacta ctctccatag | 1140 |
| aaatttagca aacatggcac tcaaagaaaa tgtgttggat agtttcatca tgcatacaaa | 1200 |
| agcaacactt ttgaactacc attccaaatc cttttgtaa attatctttg cttaacacta | 1260 |
| cccctttgag caaatgtggc tttgtgcgga aaaaactcaa acttggtagg gtagacatcc | 1320 |
| atttatataa ttggatccat gtacataagt tgttgagtac ttcaagtact taccttgtg | 1380 |
| atatacatct caaatatatt gaagaagaga agttcttttt tgagagagg ttgaagaaga | 1440 |
| gaagtttgtc catagctgaa gaggagtttt atagtgtcta gcttaccttg ctgctgattg | 1500 |
| catgtctaaa atgtcgttta atttgggcta taatgaaata ttcaccaata tttctgctgg | 1560 |
| tctattaaag tttaatagtt actcgtaact cattttatttt gggctataat ttaatattca | 1620 |
| cctatgtttt tgttagtcta tttttatttcc ctagtgtgca ctagcttaac cccaaattag | 1680 |
| ttttgaacac ttaacctaaa tgtgtctatt atggtcagac actctctcac ggcactctaa | 1740 |
| caaaaagtga atttttgttgt tatgttttttg tcatgatctc acaagcaatg tacatgtacg | 1800 |
| tttctagagt gcaatcttat gctagcctga ttgtgaattt agtgtagttt gtttttctctt | 1860 |
| tttgtagcta cactaccaat aacctattgt cctctagtca taccacgtaa tcacaaggca | 1920 |
| aatccctaac tctcaccttt aaaagcatgt ctttattttc ttgggtggca ctaatacaaa | 1980 |
| atcttttcta gcattcctat gtgcgatagc aagaaaacat ggcataactc ttgcttcact | 2040 |
| ctaacaaaaa aaacactttt ccaactttaa acaatggta tctatgtgtt taatgatcaa | 2100 |
| tcaagcatat aatgacttac aagtttttac ctatgccctt tttgcatcat cttgtttgca | 2160 |
| acagacaaac tagatattcc tttaggctat aaacacatca gcatgataaa gagattaggt | 2220 |
| aagtttgtta tccctttttg catatattct cgtctactcc gtgtatataa gcccctctcc | 2280 |
| tccaactcgt ccatccatca ccaagagcag tggga | 2315 |

<210> SEQ ID NO 57
<211> LENGTH: 1194
<212> TYPE: DNA
<213> ORGANISM: Artificial Sequence

```
<220> FEATURE:
<223> OTHER INFORMATION: Synthetic construct Oryza sativa CIN1 promoter

<400> SEQUENCE: 57
ttgcatgccg tcgtcttaag cgtccgcgtg tgaaaatcgg attttcgcat acggttgaac      60
cggtcgcatg caaagatcgc gatcttcgca gacgatttgg cacatgcggt tgcaccaacc     120
gtatgcgaaa acccttctcg cccgtatgca aaaccatct tgttgtagt gtacggttca       180
caatggtttg gatgggaaat cattgtgaac caaaagtgat agactgattt cgacgagtgt     240
ttttttttaa gtagtgccac aattttggtc atcatacgtc gtgtctaaaa ttgtaacttt     300
tgaaaaccaa tttacattaa attaaattta taagactaaa taagacgat ggtcattgaa      360
caattgttga gaaaaatcta cacacatgtg tgtccaacac aaatgtttac acatatacta     420
ctatgttcat agtcgaagtt agatttttt tttccttaaa gggaaagtct gttttcaaat      480
tttagacctc actccttccg tttcaaatat atcgtgtatt tttttttcta gggcaagctt     540
ttgaccaatg attactctat tatgacacaa tgttaaaggg atagattcat attcaaaatt     600
actattataa ttataattt gtcatataaa taatattta agcaattgtt agccaaaatc       660
tcgtcctaac gaaacaaaat acgccttatt tttaaaaaca cggagtatat ccttaaatat     720
ttctctatcc aatataaaag gtcaatcttt taaaattccg atcatcaata atttctcaaa     780
taattacttt gaaataaaaa aacatatgca aatttgtgtc gtcataatat ccaatgaact     840
tattcaaatt tataaactta ttttaattca aatttgatc attaattttt tttttaaaaa      900
aaaaccaaat cttatcataa acgtcaaata tattttgat agtgggggcg ataataccat      960
aaaactaaca acagaagaga catgatacta ctactgtaat cctaatacgt acgtacgtat    1020
acttctacgc cggatgcata acttcagcct tgtgagacac aacagttgct gcctagctcg    1080
tggtcgttgg ttttttcgct cgagaaacca ctacgcgtaa accgtgaagt atattatata    1140
tagccaactg gtcttctcgc aaatccgcac atcccttct gccccctcgtc ttct          1194

<210> SEQ ID NO 58
<211> LENGTH: 1500
<212> TYPE: DNA
<213> ORGANISM: Artificial Sequence
<220> FEATURE:
<223> OTHER INFORMATION: Synthetic construct Oryza sativa MADS-Box
      promoter

<400> SEQUENCE: 58
gcaaagaagg ccagtggcct ttgcagctaa gctagctagc tagcccttct tcctctcttt      60
cctgctttcc ctttgccttc tcctattaat cctctgcacc tcacacagca gcagaaaacc     120
caccaactgg agctctcctt tcctactcca agaaacgaag gtagagaaag aaagatcaga     180
tcagcttcag gaccaatttt agctaggtta tatatctctt tgcgtgctaa tgtgttttag     240
ttatctgggt gtgtgtagag ttctttgtta aggcactgat tcagctgcag tttagattca     300
agtttgtatg ttctctcttt gaggaaaaga aacccttttc ctgtgcttcg agttcttgca     360
aagagaaact gtgatgcttg gcttccagtt tgatgcttct ttgttcagat tggaaattct     420
tcctagcttc tttctctatt tatgtagcaa ggattcttc cggcccagtg atcctggttt       480
cttttggaag gtttcagttt tttcgttctt tcttgaaatt tctcttcttg ccttaggcag     540
atctttgatc ttgtgaggag acaggagaaa aggaagaagc tagtttcctg cggccgacct     600
cttgcttctc actttgtgat gagttttctt tggtcaattc ttagctagat atgttaagat     660
agttagttaa gcaaatcgaa attgctagct tttccatgct ttcttaaaca tgattcttca     720
```

```
gatttggttg gttcttttt   ttccttttg  tggagacgtg  ctgttcttgc  atcttatcct    780
tcttgattca tctacccatc  tggttctttg  agctttcttt  ttcgcttctt  cccttcatta    840
tttcgagcaa tctctgcaca  tctgaaagtt  ttgtttcttg  agactacttt  tgctagatct    900
tgtttactcg atcactctat  acttgcatct  aggctccttt  ctaaataggc  gatgattgag    960
ctttgcttat gtcaaatgat  gggatagata  ttgtcccagt  ctccaaattt  gatccatatc   1020
cgccaagtct ttcatcatct  ttttctttct  tttttatgag  caaaaatcat  cttttctttt   1080
caaagttcag ctttttctc   ttgttttacc  cctctttagc  tatagctggt  ttcttattcc   1140
ttttggattt acatgtataa  aacatgcttg  aatttgttag  atcgatcact  ttatacacat   1200
actatgtgaa tcacgatctc  agatctctca  gtatagttga  attcattaat  ttcttagatc   1260
gatcagcgtg tgatgtagta  ctgtaaatca  ctactagatc  tttcatcagt  ctcttttctg   1320
catctatcaa tttctcatgc  aagttttagt  tgtttcttta  atccggtctc  tctctctttt   1380
ttaatcagct gagagtttgt  gctgttcttt  aatcattacc  agatctttca  tcagtactct   1440
ctcttctgca tctatcaaac  ttctcatgca  atgtttttgc  tgttctttga  tctgatctct   1500
```

<210> SEQ ID NO 59
<211> LENGTH: 1500
<212> TYPE: DNA
<213> ORGANISM: Artificial Sequence
<220> FEATURE:
<223> OTHER INFORMATION: Synthetic construct Zea mays Hsp70 promoter

<400> SEQUENCE: 59

```
agttttcgct tgtctattca  ccctctatag  gcaactttca  attatgtaat  cactttttt     60 ttcttttttc tgtttaaaat  ctcagtttca  aacttccaat  tgattttgaa  tacgaggttt    120
gggtttaaat tcatattgga  ggcaaaaatc  gaaagttcca  cgtgatgcta  ggttttattt    180
cggttttcta tctcctattg  tttttcacgt  ttcaacttga  ttcaaattct  agttttttt    240 aacttaagca caattaaata  caacataaaa  acaacatgga  ttcaagttct  atttcaattt    300
ttattaacta ttatgttgtc  tagtctgttc  aagcacataa  tacttataaa  tataaaatta    360
aacgaaatca catatttcca  caaatcttgg  gtactacact  cggagacgac  gatggattcc    420
atctcaattt ggatgttgat  tatagctcta  tttcagttgt  cactgttgtc  ctaacacgcc    480
ctattgtgca tgatagtgca  cgtgctcaac  gtaaagaaa   agagatcagt  aacaagtagc    540
agcactgtac aaggtaagcc  gtgattcaat  taaaactgtt  tgagcaattc  agttgctaga    600
tcgttccacc atcgataatt  cgatatgtac  gatgatataa  aaagagccca  taagtttgtc    660
ttgaaaaggt tgatcaaata  atttaaatta  gatgataaaa  aacatggaag  atgtgggagt    720
ggacgacggc tatgaagaat  agtactatat  caggtttata  cgtaaaattt  atttttgaaa    780 tgttttata  atctgtttga  attgtatttt  ttgcttaatt  atgtgattgg  atgttttttc    840
atgaaatgtc gagttttatt  ttaaataaaa  ttctgtaaag  agaagttgct  gcgctgagaa    900
aactataaat cgatagtaaa  ggctgtacgc  aacgtttaag  tccttgtttg  aatgcgtatg    960
aatctgagaa agttcagaat  gattaaatct  tttttattta  attttaattt  gagagagatt   1020
aagttctctc caattctctt  taatttagac  gtaatcgaac  aagctggttg  ccaaactaga   1080
tgagtacatt ttgtccactg  ccatagagcc  atcgactaca  aagtctaga   acacagtgga   1140 aagcaccaga caacgcgcga  ccaaaagggc  ccaggcccca  gcgccccagt  ccggggggttg   1200 tgttcgccga cctgtgcgtg  cctgctcgtc  acgtcacgtc  cctatttgcc  cgtcttcctc   1260
```

```
ccctccagac ccttctcgaa cgcccttccg ttctggatcc aacggtcggt ctctgccggg    1320
ctcgaacgtt ctcgaaacca cgtcaccccc gataaaaccc cacgcacagc ctcctcccct    1380
cctcaaccat cattgcaaaa gcgaagcaag caatccgaat tctctgcgat ttctctagat    1440
ctcgaccacc cctactagtt ttggttcctc ctttcgttcg agagagcgtt tctagtggca    1500

<210> SEQ ID NO 60
<211> LENGTH: 1500
<212> TYPE: DNA
<213> ORGANISM: Artificial Sequence
<220> FEATURE:
<223> OTHER INFORMATION: Synthetic construct Zea mays Cab5 promoter

<400> SEQUENCE: 60
caacttacaa gcgatgaggc caagacgatt agacgaatag ctacagaaca agacaatgag      60
agttcagcac tcactttttg ccagttcctt ctccttggca gcagccaggc gcttgagttt     120
agcagcttgt gcaaatgtgg acggcctaca gcagacatac aggcaaagaa gcgaggagta     180
atttgcagtt ggaaatcatt cttcgatcaa tagggaaact ctgagtcaca gcgaaaggaa     240
ggttaattgc ctacgttgac aactgatcag cctccttgag aagttgcttg atttcaagcc     300
gcactttgat ctgctcatca ctaagtcctc cgctctggat gacaaaagca cagaacgcat     360
gagtggcaag tggaaacact agagcgaaat aaatacaaaa ccgcagacta caggctaaca     420
gatagggaga ccgggaagac aaagactcga gcctgcattc aacagttaca gtcgcctcgg     480
ccaaaggttg agaaatttgc atcaaaatcc aaactgtcta gggccatggg aaatagttcc     540
tcggaatcag agttcaattc atggacgaaa tagatggaac tgatggtagg ctactcttcc     600
gcccaatcag aattcacgga agatccaggt ctcgagacta ggagacggat gggaggcgca     660
acgcgcgatg gggaggggg cggcgctgac ctttctggcg aggtcgaggt agcggtagag     720
cagctgcagc gcggacacga tgaggaagac gaagatagcc gccagggaca tggtcgccgg     780
cggcggcgga gcgaggctga gccggtctct ccggcctccg atcggcgtta agttggggat     840
cgtaacgtga cgtgtctcct ctccacagat cgacacaacc ggcctactcg ggtgcacgac     900
gccgcgacaa gggtgagatg tccgtgcacg cagcccgttt ggagtcctcg ttgcccacga     960 accgaccect tacagaacaa ggcctagccc aaaactattc tgagttgagc ttttgagcct    1020
agcccaccta agccgagcgt catgaactga tgaacccact accactagtc aaggcaaacc    1080
acaaccacaa atggatcaat tgatctagaa caatccgaag gaggggaggc cacgtcacac    1140
tcacaccaac cgaaatatct gccagtatca gatcaaccgg ccaataggac gccagcgagc    1200
ccaacaccta gcgacgccgc aaaattcacc gcgaggggca ccgggcacgg caaaaacaaa    1260
agcccggcgc ggtgagaata tctggcgact ggcggagacc tggtggccag cgcgcggcca    1320
catcagccac cccatccgcc cacctcacct ccggcgagcc aatggcaact cgtcttaaga    1380
ttccacgaga taaggacccg atcgccggcg acgctattta gccaggtgcg cccccacgg    1440 tacactccac cagcggcatc tatagcaacc ggtccaacac tttcacgctc agcttcagca    1500

<210> SEQ ID NO 61
<211> LENGTH: 1500
<212> TYPE: DNA
<213> ORGANISM: Artificial Sequence
<220> FEATURE:
<223> OTHER INFORMATION: Synthetic construct Zea mays Cab5 promoter

<400> SEQUENCE: 61
tctcataaaa gcaataaaac aatatctcac aaaatacaag tggcaaacat tatacaaaca      60
```

```
tacacatagt cagaaagtca caactcagga ccttaaaaaa tgaaactatc cgattgaaaa      120
tacattgata acaattgaac actagaaaat aatatcacaa atcaaactat ggagcatata      180
actagccata taactcttat aatacaataa taaaatcatc atatatttaa ataaaacact      240
agcaagtcta ataacatatg actatagaat caagatgtgt atgatgacat gacacttgca      300
attttatcat ctcctactac tcgacatagt caatataatt gatgtcctcc ttatctttaa      360 agttccatg cgaattataa atatatgtat gaagagtaat gattgataag aaactataaa       420
taagagtcac aatagttcaa acaactctaa actatatatc attagataga tcttgatttt      480
agaaaaataa cgaaatcagt ttcataattt tctaagttaa gatgaattta caagattag       540 tttagattta atattttttc tgaaaaaata ccgatttcgg aaacgggcaa agagatcca       600 aactatttct gttttttttt accgatttca tttccgtatt ttcggtaacg gtttccggtt      660
tcgtatgacc ctaaattttg gtaaagtttc gaaaaaaaat attttaagaa ctgaaaatta     720
acgttcctgt tttcatccat actaatggct ctttaccgct aaaatgttgc ccacaatcat      780
tgagtaggtt tagacgtgag agcaaacagt acaacattac gattcgccct tgcccaaatt     840
tacatgcctt ttccctacgg aaacaacata gaatcaagtt gacggggtta cttacattga      900
agtggccaaa ctgatggtag ctgtagattt ggatgtatgt tttctataaa ttagtcaaaa      960
ttgagacaaa ataaactgca atttaaaact gaggaaatag taaaaaaaag gtgaagaagg     1020
gaggaagagg aaatcagaag caaaaaatgg gcaactttag gcccattatc tcgatggtct    1080
cgtcggagtc cagatatgtg attgacggat tggattgggc cgtacatctt gcatgagagt     1140
tcgccaagat ttcattgttt aacaagaagc gcgtgacaac aaaaccaagc ctatctcatc     1200
cactcttttt ttcccttccc acaatggcaa gtggcagctc ctgattcgct ctggccattc     1260
ctacgtggca cacaccagga ttcttgtgtg ataggccact gggtcccacc caccaggtgc    1320
cacatcagac gccaagccat cccggcagaa ccaatcccag cccagcaaca gatggtctgc    1380
tatccagttc caactgtata aaagcagctg ctgtgttctg ttaatggcac agccatcaca    1440
cgcacgcata cacagcacag agtgaggtaa gcatccgaaa aaagctgtga tctgatcgac    1500
```

<210> SEQ ID NO 62
<211> LENGTH: 1500
<212> TYPE: DNA
<213> ORGANISM: Artificial Sequence
<220> FEATURE:
<223> OTHER INFORMATION: Synthetic construct Zea mays PPDK promoter

<400> SEQUENCE: 62

```
cgagaatata tgttatcttc gtcgttagag aaatctagac agtatacaac aagatccacg      60
tactacaggt aaacttttag gggtattgtg aacaagagga tgagtaaact ctaaaagaac      120
aaagctccaa tgaaaattta ggttttttatg tggttagtca tagggcaagt tgcaaacagg    180
tgttgatcta aaaggaagt agtagggaaa tgtgaagtgt ctttgcgagg aattggaaaa      240
tgaagatcac attttctttg ggtgcatcat gggaagaacc atttgggact cttttaagga    300
ggcctaagaa tgccataaag tttgcaagat cttttttgaag agtgtctacc tataaacaat    360
agtaaatatc atgtcaaaat tttcatcttc gccattattc tttaggagaa tttagaatgt    420
tccgaataaa atatggatag aaaagaagtt cccaaagtca tccaatttc tacaaaatct     480 tcaactttaa gattgagagt gggtgttgta aagttcttgg aagatgagtt gaaccccatg    540
gaggcgttgg ctaaagtact gaaagcaatc taaagacatg gaggtggaag gcctgacgta    600
```

```
gatagagaag atgctcttag ctttcattgt ctttcttttg tagtcatctg atttacctct    660
ctcgtttata caactggttt tttaaacact ccttaacttt tcaaattgtc tctttcttta    720
ccctagacta gataatttta atggtgattt tgctaatgtg gcgccatgtt agatagaggt    780
aaaatgaact agttaaaagc tcagagtgat aaatcaggct ctcaaaaatt cataaactgt    840
tttttaaata tccaaatatt tttacatgga aaataataaa atttagttta gtattaaaaa    900
attcagttga atatagtttt gtcttcaaaa attatgaaac tgatcttaat tattttttcct   960 taaaaccgtg ctctatcttt gatgtctagt ttgagacgat tatataattt ttttgtgct    1020 taactacgac gagctgaagt acgtagaaat actagtggag tcgtgccgcg tgtgcctgta   1080
gccactcgta cgctacagcc caagcgctag agcccaagag gccggaggtg aaggcgtcg    1140 cggcactata gccactcgcc gcaagagccc aagaggccgg agctggaagg atgagggtct   1200
gggtgttcac gaattgcctg gaggcaggag gctcgtcgtc cggagccaca ggcgtggaga   1260
cgtccgggat aaggtgagca gccgctgcga taggggcgcg tgtgaacccc gtcgcgcccc   1320
acggatggta taagaataaa ggcattccgc gtgcaggatt cacccgttcg cctctcacct   1380
tttcgctgta ctcactcgcc acacacaccc cctctccagc tccgttggag ctccggacag   1440
cagcaggcgc ggggcggtca cgtagtaagc agctctcggc tccctctccc cttgctccat   1500
```

<210> SEQ ID NO 63
<211> LENGTH: 1500
<212> TYPE: DNA
<213> ORGANISM: Artificial Sequence
<220> FEATURE:
<223> OTHER INFORMATION: Synthetic construct Zea mays actin promoter
<400> SEQUENCE: 63

```
cgataagaac aatgttggac acaacttaag tctgttttac aacaatgtct ctcaaaacta     60
tagttttaca atattatact ttgcaattat catgacaata atgtagtttc ggtagctcca    120
aaaatacagt agttttgaga acattgttt agatacaata ttataaatca tgtattagac    180
aaaagatagc catgccatta aaactttgaa ttggactgta gttttttcaa tactccaaaa   240
atattatggt acctagaata cgatgtctag aaaacatatt tttaaaatg caaccaaaca    300 tcatatgaca taaataatat agtatttttt tgaaaaccat ggtattacct aaaaaactaca   360 gaatacttca ttctgaaata ggtcctaaca agttgcagca gctaggtcgt acatcagcaa    420
atagctactt catcaatctc agaataaaca tattttatag atgagttaaa ctaaaaatat    480
agaagaacaa cgtacacgcg ttgaatcaca acgtagcgcg atatccattc aactttttgg    540
aagtttttac tgagcacaaa ttcgaaaatg ggaagcgcca cgtaacacga gcgctgggcc    600
aatttctgcc agtgccagtt atcccggccc acatccaatc ctggggaaga cgcgaacccg    660
gctccgcggc acgagttgtc cgcacgtacg gcacgtcggg gctggctcgt ccgcccgcga    720
gtgggaggcc actgtttcct ctgcctcacc gggtcgtgtg gcggagggggc gtggggccat    780 ggttcgcagc gcggggcgac gagcgcgctc ctcctctcgc gcagcgccag cgccaccccg    840
caccgtggct ttatatacac ccctcctccc aaccctaccg aatcatcact accaccgctc    900
tctcttcctc tcctccatct ctcaacgcct gaagctcacc gcacctcccc tcctcgccgc    960
ggatccccca ctactccggt aaccgtctct ccattcaccc tgcctgctgt ctcgctagaa   1020
tcgcctgcct ctgccagcgc cgtgacgcgg gggcgcggta tggctctccc agatccgcct   1080
ggcattgctc gctcgggtcg tgccaggccg atctgatctc gcatttgctg cgcgctcctc   1140
ctgctgcgga tcccaccgga tctcgctgga atcggagcgc gcgtctcttt gaaatgccgc   1200
```

```
agatctgcgt gcttgcgcgc gtgatctaag tccgggcctt tcgttaacga aatggtccga    1260
tctgtggttt ggtggaggca atgccatggt ttttccccgt gaattttttt tgctgatttt    1320
aggagctttt ttctactgtc ctatgttagt aggacaaaaa aaaagaaaca tagattagct    1380
tcaataggcg cctttagaa cagattctgt acagcaactc gtggaaacaa atctgcttcc    1440
ttaatgatgt tgcttgtttt aacaaatgcg catcgggcg agcttttctg taggtagaaa      1500
```

<210> SEQ ID NO 64
<211> LENGTH: 1694
<212> TYPE: DNA
<213> ORGANISM: Artificial Sequence
<220> FEATURE:
<223> OTHER INFORMATION: Synthetic construct Zea mays hybrid cab5/hsp70
      intron promoter

<400> SEQUENCE: 64

```
cacggaagat ccaggtctcg agactaggag acgatgggga ggcgcaacgc gcgatgggga      60 gggggcggc gctgaccttt ctggcgaggt cgaggtagca atcgagcagc tgcagcgcgg     120
acacgatgag gaagacgaag atagccgcca tggacatgtt cgccagcggc ggcggagcga     180
ggctgagccg gtctctccgg cctccggtcg gcgttaagtt ggggatcgta acgtgacgtg     240
tctcgtctcc acggatcgac acaaccggcc tactcgggtg cacgacgccg cgataagggc     300
gagatgtccg tgcacgcagc ccgtttggag tcctcgttgc ccacgaaccg accccttaca     360
gaacaaggcc tagcccaaaa ctattctgag ttgagctttt gagcctagcc cacctaagcc     420
gagcgtcatg aactgatgaa cccactacca ctagtcaagg caaaccacaa ccacaaatgg     480
atcaattgat ctagaacaat ccgaaggagg ggaggccacg tcacactcac accaaccgaa     540
atatctgcca gaatcagatc aaccggccaa taggacgcca gcgagcccaa cacctggcga     600
cgccgcaaaa ttcaccgcga ggggcaccgg gcacggcaaa aacaaaagcc cggcgcggtg     660
agaatatctg gcgactggcg gagacctggt ggccagcgcg cggccacatc agccacccca     720
tccgcccacc tcacctccgg cgagccaatg gcaactcgtc ttaagattcc acgagataag     780
gacccgatcg ccggcgacgc tatttagcca ggtgcgcccc ccacggtaca ctccaccagc     840
ggcatctata gcaaccggtc cagcacttc acgctcagct tcagcaagat ctaccgtctt     900
cggtacgcgc tcactccgcc ctctgccttt gttactgcca cgtttctctg aatgctctct     960
tgtatggtga ttgctgagag tggtttagct ggatctagaa ttacactctg aaatcgtgtt    1020
ctgcctgtgc tgattacttg ccgtcctttg tagcagcaaa atatagggac atggtagtac    1080
gaaacgaaga tagaacctac acagcaatac gagaaatgtg taatttggtg catacggtat    1140
ttatttaagc acctgttgct gctatagggc acttgtattc agaagtttgc tgttaattta    1200
ggcacaggct tcatactaca tgggtcaata gtatagggat tcatattata ggcgatacta    1260
taataatttg ttcgtctgca gagcttatta tttgccaaaa ttagatattc ctattctgtt    1320
tttgtttgtg tgctgttaaa ttgttaacgc ctgaaggaat aaatataaat gacgaaattt    1380
tgatgtttat ctctgctcct ttattgtgac gataagtcaa gatcagatgc acttgtttta    1440
aatattgttg tctgaagaaa taagtactga cagttttttg atgcattgat ctgcttgttt    1500
gttgtaacaa aattttaaaa taaagagttc cctttttgtt gctctcctta cctcctgatg    1560
gtatctagta tctaccaact gatactatat tgcttctctt tacatacgta tcttgctcga    1620
tgccttctcc tagtgttgac cagtgttact cacatagtct ttgctcattt cattgtaatg    1680
cagataccaa gcgg                                                       1694
```

<210> SEQ ID NO 65
<211> LENGTH: 1500
<212> TYPE: DNA
<213> ORGANISM: Artificial Sequence
<220> FEATURE:
<223> OTHER INFORMATION: Synthetic construct Zea mays AGPase promoter

<400> SEQUENCE: 65

| | | | | | |
|---|---|---|---|---|---|
| tttaaatttg | gaacgtcgat | ccaacatcta | acagaagcac | caattttaca | aagaacccct | 60 |
| ttcaccttcc | tcacttggtg | ggacggttct | taatcaaatt | aactgcagcc | gctggtatac | 120 |
| atgtacatgt | gggcccgcct | agcccggcac | ggcacaggcc | cacaaaaaca | cggtccacaa | 180 |
| aagcacgacc | cacaaaagca | catatctaat | tatgggccgt | gccgtgccag | cacgtgtgcc | 240 |
| cagtcatcgg | cccacaatta | gttatgtgtg | ccaggccgac | ccaaatagcc | caaaatacct | 300 |
| taatatgcca | gaccggctca | tatacataca | acagtaatac | atcaacaaaa | cgtataaaat | 360 |
| atatatatga | ccaaaataaa | actaagatgt | tttgtggatg | cacattataa | acctttggtc | 420 |
| agaaagaaaa | aaatattaca | actagctcac | aaaaaatatc | cagttctctg | tttagtgttt | 480 |
| aattgagtac | tatacatcca | tacagaataa | atatacaatg | atcatcatca | ctattcacta | 540 |
| tccatatcta | ggtattggtt | ctcgatggct | tattaaagct | ctagattctc | caagttatgc | 600 |
| tagtcatgtg | ggcttttgaca | gaccttagtt | aaatactgag | tctatatttt | gtgggcctta | 660 |
| gttaaatggg | tcgtggcagg | ccggcccgtg | ggcttgactt | gaggcccagg | cacggcccac | 720 |
| aatgtgggcc | gtgccggccc | atgcccacaa | ttaggttggg | cagtgccaga | tatgggccgt | 780 |
| gccagaaatt | gtgtgctttg | gccggccta | ttaggcacaa | cataaatgta | cacctatagc | 840 |
| cgcatagccg | ctggatgtga | gatgaatgtc | tcagatttaa | aatgtgcact | tgagcaccgt | 900 |
| acctctttga | caacagata | tgttcctta | agattgatgg | tggaaaaaaa | ttagtcagta | 960 |
| cctcactgta | tggcggcatt | gtttgattat | ttcagttcgc | acccgttgga | ccttgctcat | 1020 |
| taaaaaagtt | tataccatgg | agtctttgca | tgtagttgtg | tagtagggga | agagtggcat | 1080 |
| aggaggaatc | acaacttcag | ctagcttctc | tagccttagg | gtattttgt | cttttgcag | 1140 |
| ttcggtcttt | tcgcagccct | gcgctgcccc | ccctgtccgc | ctgtcctag | acctgttttg | 1200 |
| cgtcggcggg | gaagacagtt | gacaggaagg | acacgatctt | cgtgtccgat | gccgatcttc | 1260 |
| atgcgagcag | cgagccacta | cgttgcgctg | ccagtgtcgg | ctatggtatc | caggcattcg | 1320 |
| ttgtgcacgt | tgacgatgag | ctcgaagccg | gtccgggtga | acgcgagcag | cacggtgagg | 1380 |
| tcaacgtcgt | acatccgcac | gtcgatgctg | aggccagcca | gcagcggcat | gacagattgc | 1440 |
| ggcgtcagga | gattgtgcca | gtaggtggcg | gggctggggg | cagaccggca | ggcgaggcct | 1500 |

<210> SEQ ID NO 66
<211> LENGTH: 1500
<212> TYPE: DNA
<213> ORGANISM: Artificial Sequence
<220> FEATURE:
<223> OTHER INFORMATION: Synthetic construct Zea mays CIN1 promoter

<400> SEQUENCE: 66

| | | | | | |
|---|---|---|---|---|---|
| caaaattttc | tatttttaa | aaaatatgaa | ttctagattt | gggattgaac | acatctaggc | 60 |
| tacaacgttg | aattgatgaa | caatagtgct | tgttaataaa | ttgctcacat | tcacattgtc | 120 |
| gctcttactt | caaccatcat | acatccatct | acagtggtca | cccatattta | atcctatgga | 180 |
| ctaaagatga | cagatgaact | tctctcgtta | tatatatcac | tgtcctacat | atatgagaaa | 240 |

```
tgatatgtcc taaactcacc taaaaacaac aacatagttt aaatttaatc atagatgagc    300
ctacagaggt cgaacgtgat ttggaaacat agctctattg ttctctatct catgcataaa    360
tatggtgcaa tgaagaatat tagggttatg atgtcgaaat ctcactcgaa ctcgtgcctc    420
atcataaata gcacactatc aattgttcta tggctgttca aatagggaca atcttgaaac    480
aacatttctc acatgtaaaa cgttgtgaag tatgccaact gaaacggatg acacatacac    540
ttcgtgaacc aatcgatatt ttacttgctt ctatgttaaa taatgttata atacaatatt    600
ttattcaaat gctaaaactt attactagat aaaaataaaa tttaattatc ttcaaaaact    660
aaccaataga tattccatca taactacatt taccaaacta atatactaaa aaatatagga    720
taattactaa attaatcgtg caataatcag tatttatgag attgataatt ttaaattttg    780
tgggctacaa acaaaaatta aaacttactt ttcaagttgg agataagaac aatggtagac    840
gtagctcggg atggtatggc gtcggtgcag acggttaccc tttgtgcgaa gtggcgcggg    900
cacgagggtg gggacttggt acatgcatga gagagaggaa gaacgaaaca acttctcaaa    960
ttaaagcata tgaaaatcac ctaattttg tctgtcggtg gaaactaata actagttttt   1020
attatctttt ttaataagga tccacgaaaa ttattttga ccgatgaaaa tcctggatct   1080
tcgtattatg tttcgccttt tcccgactct ttgcatgcta gatttccatg cttggactaa   1140
aacgaagata ataaaaccaa tctatcattt tcacacgatg tattcatact tgcaatagat   1200
aaaccactac tccgacggga tttgctttct gacctctgaa atcttggaag gattatgtgt   1260
ctacacttct cgatcgaggg gaaaaagtcg tagtaccaag ttgtagttaa atttgtttct   1320
tcgatgacaa aacaaaggag aggggcccgc gcggcgcagc gcagcgcagt tggctggttc   1380
cggaacacga aaaccaagca cactccacca gctgccatcc accgggttgg atggagatta   1440
caatactcga atagtcagcc agccagccgg cttgaacgtg cagttttccc ctataaaacg   1500
```

<210> SEQ ID NO 67
<211> LENGTH: 1500
<212> TYPE: DNA
<213> ORGANISM: Artificial Sequence
<220> FEATURE:
<223> OTHER INFORMATION: Synthetic construct Zea mays MADS-Box promoter

<400> SEQUENCE: 67

```
acacttgctc tcttcgcgtg gtcatttagc ccccgaacat tccaagaaaa aatagcacat     60
ttttgattca taaggtaaag actgccactc cacttaacac agcacgctgc caccacacat    120
ggattagcag gagagcctgc tgtaaaatcc taacaggagg gagaacctcc aaacaagggt    180
tcgccgagca aaaacacagc ccgaccacaa ccgacaacct gaaagaacaa cagagataca    240
caggcatgct gggggaccta gaccagcgcc cagaagtaat aacgccagcg gagatacaac    300
cgctccgaga gagcctgacc atctgagaac acattggtca ccaaaagcac caccaaccgg    360
cctagacaaa gcagctcagt tgaccccgc ctcgacatct tcgatggccg gcatcacctt    420
tctccccttc tttttattct tcgctgtctt caccttgtct tgatttaaca gctccatgat    480
tgcatccatt tgcttcttgg agagaggctt tgtgagaagg cttgtcatct gctcaaatga    540
ctcatcaaag ttagtacatt ttgaagaact aattattatt atatagaatg cactgcacat    600
atattactat taccagtttt cttgggcaca gcagaaaaca tgcacacgca gatagaaaaa    660
ggagaggcca taaccaaaa ggctttaaga atatatgtaa agatatgtct aaatatatgg    720
ctatatctgg ttaagcaaga taacagggct ctggtcatca gtagtagtgg ccttttgccc    780
ttgcccctct ctctcaccctc tcttttctca gccttgcttc cgatggatcc catcccactg    840
```

```
ccatcctttc tttcccttgc gcgcattgcc tagccggccg gccggcctgc tattaaacca      900
ctttacccgc ccctctcgc tcacgctcga cgcagctccc ttttccttgt ttgcttattg      960
caagtctctg caagaacctg ctagagagga acaaggtaga gtagtatcgc ttttttccat     1020
ctaggttatc tcttttaca tgaaaaattt cagccgtatt tcgttctcca tcagtcctgc      1080
gataatatat acgcgcgtct tgtgtgatcc ggcatatgta tagttcctgc taactgatcg     1140
agatcgctct cgtttgtact ttctcccttt gaggaaagag tttccccttt tctgtgcttc     1200
aagttcttgt aaggaaaacc atgcctgcca gcttcttctg ctacttgtat gatgattctt     1260
atttgcttat tacttgattt ccgttttttt tcttgctttc tatatgtatg tatctgggct     1320
gtcttcccct gcgtctcgtt actgctaagc tttggaaggt ttcaactctt tgtatacgat     1380
gaggtttctg ctcctagtag cagatccgcg catatgacta gatgtttgag gaaaagaaaa     1440
gggcaagacg ctatatatat atgcagcacg cagtcgcaca tatattcagt tttccaatct     1500
```

<210> SEQ ID NO 68
<211> LENGTH: 528
<212> TYPE: DNA
<213> ORGANISM: Brassica napus

<400> SEQUENCE: 68

```
atgaagttct tcgtttcagt tgtaatgttt tttctcctct taaactgttt cgcagccgcg       60
caaactttga ttcgagattc ttgcaaaaca gctgcagcaa aagatcctaa tctcaaatat      120
gattttgcg tccaatcact tgaacaagat ccgcaaagca aaactgcaac tagtctatca       180
ggattagtcc tagcgtcaac gaataacgct gcgtccaaaa caattaacgt gaaagggata      240
gttgagacta ttctcaaaag caaaagtat gcaccgagta ctgaacccgc gttacgcact       300
tgcgtaaagc tttatgacaa tgcatatggt tctttaaaag aagctttgat gaacgttaaa      360
tccgatgatt acagaagtgc taatgtgcat ctgagtgctg ctttggatga accgaacact      420
tgtgaggatg gtttcaaaga gaagcacacg aaatctcccg ttacaaacga gaacaatatt      480
ttgtttcaga agattttgat tcctttagct tttacaaata tgctctga                  528
```

<210> SEQ ID NO 69
<211> LENGTH: 175
<212> TYPE: PRT
<213> ORGANISM: Brassica napus

<400> SEQUENCE: 69

```
Met Lys Phe Phe Val Ser Val Val Met Phe Phe Leu Leu Leu Asn Cys
1               5                   10                  15

Phe Ala Ala Ala Gln Thr Leu Ile Arg Asp Ser Cys Lys Thr Ala Ala
            20                  25                  30

Ala Lys Asp Pro Asn Leu Lys Tyr Asp Phe Cys Val Gln Ser Leu Glu
        35                  40                  45

Gln Asp Pro Gln Ser Lys Thr Ala Thr Ser Leu Ser Gly Leu Val Leu
    50                  55                  60

Ala Ser Thr Asn Asn Ala Ala Ser Lys Thr Ile Asn Val Lys Gly Ile
65                  70                  75                  80

Val Glu Thr Ile Leu Lys Ser Lys Lys Tyr Ala Pro Ser Thr Glu Pro
                85                  90                  95

Ala Leu Arg Thr Cys Val Lys Leu Tyr Asp Asn Ala Tyr Gly Ser Leu
            100                 105                 110

Lys Glu Ala Leu Met Asn Val Lys Ser Asp Asp Tyr Arg Ser Ala Asn
```

Val His Leu Ser Ala Ala Leu Asp Glu Pro Asn Thr Cys Glu Asp Gly
              115                 120                 125
                130                 135                 140

Phe Lys Glu Lys His Thr Lys Ser Pro Val Thr Asn Glu Asn Asn Ile
145                 150                 155                 160

Leu Phe Gln Lys Ile Leu Ile Pro Leu Ala Phe Thr Asn Met Leu
                165                 170                 175

<210> SEQ ID NO 70
<211> LENGTH: 528
<212> TYPE: DNA
<213> ORGANISM: Brassica napus

<400> SEQUENCE: 70

| | | | | | |
|---|---|---|---|---|---|
| atgaagttct | tcgtttcagt | tgtaatgttc | tttctcctcc | taaactgttt | cgcagccgcg | 60 |
| caaaccttga | ttcgagattc | ctgcaaaaca | gctgcagcaa | agaccctaa | tctcaagtat | 120 |
| gattttgca | tccaatcact | tgaacaagat | ccgcaaagca | aaactgcaac | tagtctatca | 180 |
| ggattggtcc | tagcggcaac | gaataatgct | gcatccaaaa | caattaacgt | gaaagggata | 240 |
| gttgagacta | ttctcaagag | caaaaagtat | gcaccgagta | ctgaacccgc | gttacgcact | 300 |
| tgcgtaaagc | tttatgacga | tgcttatggt | tctttaaaag | aagctttgat | gaacgttaaa | 360 |
| tccagtgatt | acaaaagtgc | taatatgcat | ctgagtgctg | ctttggatga | acctgtcact | 420 |
| tgtgaagatg | gtttcaaaga | gaagcacgct | aaatctcccg | ttacaaacga | gaacaatgtt | 480 |
| ttgtttcaga | agattttgat | tcctttagct | tttaccaata | tgctctga | | 528 |

<210> SEQ ID NO 71
<211> LENGTH: 175
<212> TYPE: PRT
<213> ORGANISM: Brassica napus

<400> SEQUENCE: 71

Met Lys Phe Phe Val Ser Val Val Met Phe Leu Leu Leu Asn Cys
1               5                   10                  15

Phe Ala Ala Ala Gln Thr Leu Ile Arg Asp Ser Cys Lys Thr Ala Ala
                20                  25                  30

Ala Lys Asp Pro Asn Leu Lys Tyr Asp Phe Cys Ile Gln Ser Leu Glu
            35                  40                  45

Gln Asp Pro Gln Ser Lys Thr Ala Thr Ser Leu Ser Gly Leu Val Leu
    50                  55                  60

Ala Ala Thr Asn Asn Ala Ala Ser Lys Thr Ile Asn Val Lys Gly Ile
65                  70                  75                  80

Val Glu Thr Ile Leu Lys Ser Lys Lys Tyr Ala Pro Ser Thr Glu Pro
                85                  90                  95

Ala Leu Arg Thr Cys Val Lys Leu Tyr Asp Asp Ala Tyr Gly Ser Leu
                100                 105                 110

Lys Glu Ala Leu Met Asn Val Lys Ser Ser Asp Tyr Lys Ser Ala Asn
            115                 120                 125

Met His Leu Ser Ala Ala Leu Asp Glu Pro Val Thr Cys Glu Asp Gly
    130                 135                 140

Phe Lys Glu Lys His Ala Lys Ser Pro Val Thr Asn Glu Asn Asn Val
145                 150                 155                 160

Leu Phe Gln Lys Ile Leu Ile Pro Leu Ala Phe Thr Asn Met Leu
                165                 170                 175

-continued

<210> SEQ ID NO 72
<211> LENGTH: 528
<212> TYPE: DNA
<213> ORGANISM: Brassica napus

<400> SEQUENCE: 72

```
atgaagttct tcgtttcagt tgtaatgttt tttctcctct taaactgttt cgcagccgcg        60
caaactttga ttcgagattc ttgcaaaaca gctgcagcaa agatcctaa tctcaaatat       120 gattttgcg tccaatcact tgaacaagat ccgcaaagca aaactgcaac tagtctatca       180
ggattagtcc tagcgtcaac gaataacgct gcgtccaaaa taattaacgt gaaagggata      240
gttgagatta ttctcaagag caaaaagtat caaccgggta ctgaacccgc gttacgcact      300
tgcgtagaac tttatgacga tgctaatgat tctttaaaag aagctttgat gaacgttaaa      360
tccgatgatt acagaagtgc taatgtgcat ctgagtgctg ctttggatga accgaacact      420
tgtgaggatg gtttcaaaga gaagcacacg aaatctcccg ttacaaacga gaacaatatt      480
ttgtttcaga agattttgat tcctttagct tttacaaata tgctctga                   528
```

<210> SEQ ID NO 73
<211> LENGTH: 175
<212> TYPE: PRT
<213> ORGANISM: Brassica napus

<400> SEQUENCE: 73

```
Met Lys Phe Phe Val Ser Val Val Met Phe Phe Leu Leu Leu Asn Cys
1               5                   10                  15

Phe Ala Ala Ala Gln Thr Leu Ile Arg Asp Ser Cys Lys Thr Ala Ala
            20                  25                  30

Ala Lys Asp Pro Asn Leu Lys Tyr Asp Phe Cys Val Gln Ser Leu Glu
        35                  40                  45

Gln Asp Pro Gln Ser Lys Thr Ala Thr Ser Leu Ser Gly Leu Val Leu
    50                  55                  60

Ala Ser Thr Asn Asn Ala Ala Ser Lys Ile Ile Asn Val Lys Gly Ile
65                  70                  75                  80

Val Glu Ile Ile Leu Lys Ser Lys Lys Tyr Gln Pro Gly Thr Glu Pro
                85                  90                  95

Ala Leu Arg Thr Cys Val Glu Leu Tyr Asp Asp Ala Asn Asp Ser Leu
            100                 105                 110

Lys Glu Ala Leu Met Asn Val Lys Ser Asp Asp Tyr Arg Ser Ala Asn
        115                 120                 125

Val His Leu Ser Ala Ala Leu Asp Glu Pro Asn Thr Cys Glu Asp Gly
    130                 135                 140

Phe Lys Glu Lys His Thr Lys Ser Pro Val Thr Asn Glu Asn Asn Ile
145                 150                 155                 160

Leu Phe Gln Lys Ile Leu Ile Pro Leu Ala Phe Thr Asn Met Leu
                165                 170                 175
```

<210> SEQ ID NO 74
<211> LENGTH: 528
<212> TYPE: DNA
<213> ORGANISM: Brassica napus

<400> SEQUENCE: 74

```
atgaagttct tcgtttcagt tgcattgttc tttctcttct taaactgttt cgctaccgcg        60
caaactctta ttcgagattc ttgcaaaaca gctgcagcaa agatcctac tctcaaatat       120 gattttgcg tccaatctct tgaacaagat ccacagagca aaaccgcaac tagtctaaaa       180
```

```
ggattggtct tagcatcaac tactaacgct gagtccaaaa caactaacgt gaaagggata      240
gttgagacta ttctcaagag caaaacgtat ccaccgggta ctgaacctgc gttaagcact      300
tgcgtagagc tttatgacga tgctaataat tctttaaatg aagctttgat gaacgttaaa      360
tccggcgatt acaaaagtgc taatgtggat ctgagtgctg ctttggatga accgggcact      420
tgtgaagatg gtttcaaaga gaagcacgcg aaatctcccg ttacaaacga gaacaatgtt      480
ttgtttcaga agattttgat tcctttagct tttacaaata tgctctga                  528
```

<210> SEQ ID NO 75
<211> LENGTH: 175
<212> TYPE: PRT
<213> ORGANISM: Brassica napus

<400> SEQUENCE: 75

```
Met Lys Phe Phe Val Ser Val Ala Leu Phe Phe Leu Phe Leu Asn Cys
1               5                   10                  15

Phe Ala Thr Ala Gln Thr Leu Ile Arg Asp Ser Cys Lys Thr Ala Ala
            20                  25                  30

Ala Lys Asp Pro Thr Leu Lys Tyr Asp Phe Cys Val Gln Ser Leu Glu
        35                  40                  45

Gln Asp Pro Gln Ser Lys Thr Ala Thr Ser Leu Lys Gly Leu Val Leu
    50                  55                  60

Ala Ser Thr Thr Asn Ala Glu Ser Lys Thr Thr Asn Val Lys Gly Ile
65                  70                  75                  80

Val Glu Thr Ile Leu Lys Ser Lys Thr Tyr Pro Pro Gly Thr Glu Pro
                85                  90                  95

Ala Leu Ser Thr Cys Val Glu Leu Tyr Asp Asp Ala Asn Asn Ser Leu
            100                 105                 110

Asn Glu Ala Leu Met Asn Val Lys Ser Gly Asp Tyr Lys Ser Ala Asn
        115                 120                 125

Val Asp Leu Ser Ala Ala Leu Asp Glu Pro Gly Thr Cys Glu Asp Gly
    130                 135                 140

Phe Lys Glu Lys His Ala Lys Ser Pro Val Thr Asn Glu Asn Asn Val
145                 150                 155                 160

Leu Phe Gln Lys Ile Leu Ile Pro Leu Ala Phe Thr Asn Met Leu
                165                 170                 175
```

<210> SEQ ID NO 76
<211> LENGTH: 480
<212> TYPE: DNA
<213> ORGANISM: Camelina sativa

<400> SEQUENCE: 76

```
atgaagctga tcgtgatggt gatgacgatg atgatgataa gtgaaggaag tatgatagat       60
cagacatgta acagacacc agacttcaaa ctttgtgtct ctctactcaa ctccgaccca      120
cgtggctcct ctgccgacat ctctggcctc gctctcatcc tcatcgataa aatcaaggtg      180
ctggcgacaa agaccttaac cgagatcaac ggtctatata aaagagacc ggaactaaaa      240 caggctttgg accaatgtag tcgaagatac aaaacgattt taaatgctga tgttcccgaa      300
gccatcgaag ctatctctaa aggagtccct aaattcggcg aagacggcgt gattgacgcc      360
ggggtagaag cttctgtttg tgaagaaggg tttcaaggga atctccgtt gactagttta      420 accaaatcaa tgcaaaacat ctctagtgtg actagagccg ttgtgagaat gttgctttga      480
```

<210> SEQ ID NO 77
<211> LENGTH: 159
<212> TYPE: PRT
<213> ORGANISM: Camelina sativa

<400> SEQUENCE: 77

Met Lys Leu Ile Val Met Val Met Thr Met Met Ile Ser Glu Gly
1               5                   10                  15

Ser Met Ile Asp Gln Thr Cys Lys Gln Thr Pro Asp Phe Lys Leu Cys
            20                  25                  30

Val Ser Leu Leu Asn Ser Asp Pro Arg Gly Ser Ser Ala Asp Ile Ser
        35                  40                  45

Gly Leu Ala Leu Ile Leu Ile Asp Lys Ile Lys Val Leu Ala Thr Lys
    50                  55                  60

Thr Leu Thr Glu Ile Asn Gly Leu Tyr Lys Lys Arg Pro Glu Leu Lys
65                  70                  75                  80

Gln Ala Leu Asp Gln Cys Ser Arg Arg Tyr Lys Thr Ile Leu Asn Ala
                85                  90                  95

Asp Val Pro Glu Ala Ile Glu Ala Ile Ser Lys Gly Val Pro Lys Phe
            100                 105                 110

Gly Glu Asp Gly Val Ile Asp Ala Gly Val Glu Ala Ser Val Cys Glu
        115                 120                 125

Glu Gly Phe Gln Gly Lys Ser Pro Leu Thr Ser Leu Thr Lys Ser Met
    130                 135                 140

Gln Asn Ile Ser Ser Val Thr Arg Ala Val Val Arg Met Leu Leu
145                 150                 155

<210> SEQ ID NO 78
<211> LENGTH: 465
<212> TYPE: DNA
<213> ORGANISM: Camelina sativa

<400> SEQUENCE: 78
atgaagctga tcgtgatggt gatgacgatg atgatgataa gtgaaggaag tatgatagat    60
cagacatgta acagacacc agacttcaaa ctttgtgtct ctctactcaa ctccgaccca    120
cgtggctcct ctgccgacac tctggcctc gctctcatcc tcatcgataa aatcaaggtg    180
ctggcgacaa agaccttaac cgagatcaac ggtctatata aaagagacc ggaactaaaa    240 caggctttgg accaatgtag tcgaagatac aaaacgattt taaacgctga tgttcccgaa    300
gccattgaag ctatctctaa aggagtccct aaattcggcg aagatggtgt gatggacgcc    360
ggggtagaag cttctgcttg tgaagaaggg tttcaaggga atctccgtt gactagttta    420 accaaatcaa tgcaaaacat ctctagtgtg actagagccg ttgtg              465

<210> SEQ ID NO 79
<211> LENGTH: 155
<212> TYPE: PRT
<213> ORGANISM: Camelina sativa

<400> SEQUENCE: 79

Met Lys Leu Ile Val Met Val Met Thr Met Met Ile Ser Glu Gly
1               5                   10                  15

Ser Met Ile Asp Gln Thr Cys Lys Gln Thr Pro Asp Phe Lys Leu Cys
            20                  25                  30

Val Ser Leu Leu Asn Ser Asp Pro Arg Gly Ser Ser Ala Asp Thr Ser
        35                  40                  45

Gly Leu Ala Leu Ile Leu Ile Asp Lys Ile Lys Val Leu Ala Thr Lys

Thr Leu Thr Glu Ile Asn Gly Leu Tyr Lys Lys Arg Pro Glu Leu Lys
65                  70                  75                  80

Gln Ala Leu Asp Gln Cys Ser Arg Arg Tyr Lys Thr Ile Leu Asn Ala
                85                  90                  95

Asp Val Pro Glu Ala Ile Glu Ala Ile Ser Lys Gly Val Pro Lys Phe
            100                 105                 110

Gly Glu Asp Gly Val Met Asp Ala Gly Val Glu Ala Ser Ala Cys Glu
        115                 120                 125

Glu Gly Phe Gln Gly Lys Ser Pro Leu Thr Ser Leu Thr Lys Ser Met
    130                 135                 140

Gln Asn Ile Ser Ser Val Thr Arg Ala Val Val
145                 150                 155

<210> SEQ ID NO 80
<211> LENGTH: 480
<212> TYPE: DNA
<213> ORGANISM: Camelina sativa

<400> SEQUENCE: 80
atgaagatga tcgtgatggt tatgatgatg atgatgatga gtgaaggaag tatgatagat      60
caaacatgta acagacacc agacttcaat ctctgtgtct ctctactcaa ctccgaccca     120
cgtggctctt ctgccgacat ctctggcctc gctctcatcc tcatcgataa aatcaaggtt     180
ctggcgacaa agaccttaaa cgaaatcaac ggtctatata aaagagacc ggaactaaaa      240 caggctttag accaatgtag tcgaagatac aaaacgatct aaatgctga tgttcccgaa      300 gccatcgaag ctatctctaa aggagtccct aaatttggcg aagatggtgt gatcgacgcc     360
ggggtagaag cttctgtttg tgaagaaggg tttcaaggga atctccgtt gactagttta      420 accaaatcaa tgcaaaacat ctctagtgtg actagagccg ttgtgagaat gttgctttga     480

<210> SEQ ID NO 81
<211> LENGTH: 159
<212> TYPE: PRT
<213> ORGANISM: Camelina sativa

<400> SEQUENCE: 81

Met Lys Met Ile Val Met Val Met Met Met Met Met Met Ser Glu Gly
1               5                   10                  15

Ser Met Ile Asp Gln Thr Cys Lys Gln Thr Pro Asp Phe Asn Leu Cys
            20                  25                  30

Val Ser Leu Leu Asn Ser Asp Pro Arg Gly Ser Ser Ala Asp Ile Ser
        35                  40                  45

Gly Leu Ala Leu Ile Leu Ile Asp Lys Ile Lys Val Leu Ala Thr Lys
    50                  55                  60

Thr Leu Asn Glu Ile Asn Gly Leu Tyr Lys Lys Arg Pro Glu Leu Lys
65                  70                  75                  80

Gln Ala Leu Asp Gln Cys Ser Arg Arg Tyr Lys Thr Ile Leu Asn Ala
                85                  90                  95

Asp Val Pro Glu Ala Ile Glu Ala Ile Ser Lys Gly Val Pro Lys Phe
            100                 105                 110

Gly Glu Asp Gly Val Ile Asp Ala Gly Val Glu Ala Ser Val Cys Glu
        115                 120                 125

Glu Gly Phe Gln Gly Lys Ser Pro Leu Thr Ser Leu Thr Lys Ser Met
    130                 135                 140

```
Gln Asn Ile Ser Ser Val Thr Arg Ala Val Val Arg Met Leu Leu
145                 150                 155
```

<210> SEQ ID NO 82
<211> LENGTH: 543
<212> TYPE: DNA
<213> ORGANISM: Camelina sativa

<400> SEQUENCE: 82

```
atggcttctt ctcttatctt cctcctcctc atctttaccc tatcctttcc atcctcaacc    60
ctaatctcag ccaaatccaa cgcgacaata atcgaatcaa cttgcaaaac cacgaacaac   120
tacaaattct gtgtctcggc tctcaaatcc gacccaagaa gtcccacagc cgacacaaaa   180
ggtctcgcag ccattatgat cggcgttggt atgacaaacg ccacttccac cgcaacttac   240
atcgccggaa acctaacatc cgctgcaaac gacgtcgtcc ttaaaaaggt gttacaagat   300
tgctccgaga gtatgctctc gccgctgat tctctccgtc aaacaattca agatcttgat    360
gatgaagctt atgactatgc ttccatgcat gtgctggcgg cggaggatta tcctaatgtt   420
tgccgcaata ttttccgccg agctaagggg ctgtcttatc cggtggggat tcgtcggcgt   480
gaacagagtc tgagacgtat ctgtggtgtt gtctctggga ttcttgatcg tcttgttgaa   540
tga                                                                 543
```

<210> SEQ ID NO 83
<211> LENGTH: 180
<212> TYPE: PRT
<213> ORGANISM: Camelina sativa

<400> SEQUENCE: 83

```
Met Ala Ser Ser Leu Ile Phe Leu Leu Leu Ile Phe Thr Leu Ser Phe
1               5                   10                  15
Pro Ser Ser Thr Leu Ile Ser Ala Lys Ser Asn Ala Thr Ile Ile Glu
                20                  25                  30
Ser Thr Cys Lys Thr Thr Asn Asn Tyr Lys Phe Cys Val Ser Ala Leu
            35                  40                  45
Lys Ser Asp Pro Arg Ser Pro Thr Ala Asp Thr Lys Gly Leu Ala Ala
        50                  55                  60
Ile Met Ile Gly Val Gly Met Thr Asn Ala Thr Ser Thr Ala Thr Tyr
65                  70                  75                  80
Ile Ala Gly Asn Leu Thr Ser Ala Ala Asn Asp Val Val Leu Lys Lys
                85                  90                  95
Val Leu Gln Asp Cys Ser Glu Lys Tyr Ala Leu Ala Ala Asp Ser Leu
            100                 105                 110
Arg Gln Thr Ile Gln Asp Leu Asp Asp Glu Ala Tyr Asp Tyr Ala Ser
        115                 120                 125
Met His Val Leu Ala Ala Glu Asp Tyr Pro Asn Val Cys Arg Asn Ile
    130                 135                 140
Phe Arg Arg Ala Lys Gly Leu Ser Tyr Pro Val Gly Ile Arg Arg Arg
145                 150                 155                 160
Glu Gln Ser Leu Arg Arg Ile Cys Gly Val Val Ser Gly Ile Leu Asp
                165                 170                 175
Arg Leu Val Glu
            180
```

<210> SEQ ID NO 84
<211> LENGTH: 546
<212> TYPE: DNA

<213> ORGANISM: Camelina sativa

<400> SEQUENCE: 84

```
atggcttctt ctcttatctt cctcctcttc ctcatcttta ccctatcctt ttcatcacca    60
accctaatct cagccaaatc caacgcgaca ataatcgaat caacttgcaa aaccacgaac   120
aactacaaat tctgtgtctc ggctctcaaa tccgacccaa gaagtcccac agccgacaca   180
aaaggtctcg cagccattat gattggcgtt ggtatgacaa cgccaccctc cactgcaact   240
tacatcgccg ggaacctaac atccgccgcg aacgacgtcg tccttaaaaa ggtgttacaa   300
gattgctccg agaagtatgc tctcgccgtt gattctctcc gccaaacaat tcaagatctt   360
gatagtgaag cttatgacta tgcttccatg catgtgctgg cggcggagga ttatcctaat   420
gtttgccgca atattttccg ccgagctaag gggctgtctt atccggtgga gattcgtcgg   480
cgtgaacaga gtctgagacg tatctgtggt gttgtctccg ggattcttga tcgccttgtt   540
gaataa                                                              546
```

<210> SEQ ID NO 85
<211> LENGTH: 181
<212> TYPE: PRT
<213> ORGANISM: Camelina sativa

<400> SEQUENCE: 85

```
Met Ala Ser Ser Leu Ile Phe Leu Leu Phe Leu Ile Phe Thr Leu Ser
1               5                   10                  15

Phe Ser Ser Pro Thr Leu Ile Ser Ala Lys Ser Asn Ala Thr Ile Ile
            20                  25                  30

Glu Ser Thr Cys Lys Thr Thr Asn Asn Tyr Lys Phe Cys Val Ser Ala
        35                  40                  45

Leu Lys Ser Asp Pro Arg Ser Pro Thr Ala Asp Thr Lys Gly Leu Ala
    50                  55                  60

Ala Ile Met Ile Gly Val Gly Met Thr Asn Ala Thr Ser Thr Ala Thr
65                  70                  75                  80

Tyr Ile Ala Gly Asn Leu Thr Ser Ala Ala Asn Asp Val Val Leu Lys
                85                  90                  95

Lys Val Leu Gln Asp Cys Ser Glu Lys Tyr Ala Leu Ala Val Asp Ser
            100                 105                 110

Leu Arg Gln Thr Ile Gln Asp Leu Asp Ser Glu Ala Tyr Asp Tyr Ala
        115                 120                 125

Ser Met His Val Leu Ala Ala Glu Asp Tyr Pro Asn Val Cys Arg Asn
    130                 135                 140

Ile Phe Arg Arg Ala Lys Gly Leu Ser Tyr Pro Val Glu Ile Arg Arg
145                 150                 155                 160

Arg Glu Gln Ser Leu Arg Arg Ile Cys Gly Val Val Ser Gly Ile Leu
                165                 170                 175

Asp Arg Leu Val Glu
            180
```

<210> SEQ ID NO 86
<211> LENGTH: 546
<212> TYPE: DNA
<213> ORGANISM: Camelina sativa

<400> SEQUENCE: 86

```
atggcttctt ctcttatctt cctcctgttc ctcatcttca ccctatcctt ttcatcctca    60
accctagtct cagccaaatc caacgcgaca ataatcgaat caacttgcaa aaccacgaac   120
```

```
aactacaaat tctgtgtctc ggctctcaaa tccgacccaa gaagtcccac agccgacaca    180
aaaggtctcg cagccattat gatcggcgtt ggtatgacaa acgccacctc caccgcaact    240
tacatcgccg gaaacctaac atccgccgcg aacgacgtcg tccttaaaaa ggtgttaaaa    300
gattgctccg agaagtatgc tctcgccgcc gattctctcc gtcagacaat tcaagatctt    360
gatgatgaag cttatgacta tgcttccatg catgtgttgg cggcggagga ttatcctaat    420
gtttgccgca atattttccg ccgagctaag gggctgtctt atccggtgga gattcaccgg    480
cgtgaacaga gtctgagacg tatctgtggt gttgtctccg ggattcttga tcgccttgtt    540
gaatga                                                              546

<210> SEQ ID NO 87
<211> LENGTH: 181
<212> TYPE: PRT
<213> ORGANISM: Camelina sativa

<400> SEQUENCE: 87

Met Ala Ser Ser Leu Ile Phe Leu Leu Phe Leu Ile Phe Thr Leu Ser
1               5                   10                  15

Phe Ser Ser Ser Thr Leu Val Ser Ala Lys Ser Asn Ala Thr Ile Ile
            20                  25                  30

Glu Ser Thr Cys Lys Thr Thr Asn Asn Tyr Lys Phe Cys Val Ser Ala
        35                  40                  45

Leu Lys Ser Asp Pro Arg Ser Pro Thr Ala Asp Thr Lys Gly Leu Ala
    50                  55                  60

Ala Ile Met Ile Gly Val Gly Met Thr Asn Ala Thr Ser Thr Ala Thr
65                  70                  75                  80

Tyr Ile Ala Gly Asn Leu Thr Ser Ala Ala Asn Asp Val Val Leu Lys
                85                  90                  95

Lys Val Leu Lys Asp Cys Ser Glu Lys Tyr Ala Leu Ala Ala Asp Ser
            100                 105                 110

Leu Arg Gln Thr Ile Gln Asp Leu Asp Asp Glu Ala Tyr Asp Tyr Ala
        115                 120                 125

Ser Met His Val Leu Ala Ala Glu Asp Tyr Pro Asn Val Cys Arg Asn
    130                 135                 140

Ile Phe Arg Arg Ala Lys Gly Leu Ser Tyr Pro Val Glu Ile His Arg
145                 150                 155                 160

Arg Glu Gln Ser Leu Arg Arg Ile Cys Gly Val Val Ser Gly Ile Leu
                165                 170                 175

Asp Arg Leu Val Glu
            180

<210> SEQ ID NO 88
<211> LENGTH: 552
<212> TYPE: DNA
<213> ORGANISM: Glycine max

<400> SEQUENCE: 88
atgaaattcg cttataacct agtgatgatt ttctttatct ttctctttca atactcaaac     60
ggctccaacc ttatccttca atcatgcaaa gaggcctcaa agaatgatcc aaatttgagc    120
tatgatttct gtgttgcatc ccttgaagaa gccttatcca agtgtcaccc accacccacc    180
aaccttgaag accttgtggg catgtcaatt aatctatcca aatccaacgt aaccaacatg    240
gtttccatca tttcaaacct attgaagaac aaaactttg atcaatacac taaggcttgc    300
```

-continued

| | |
|---|---|
| ctaaaagatt gcttcgatct ttactcggat tcgcttccgg ctttagatga tgctgtggtt | 360 |
| gctttcaagt ccaaggattt ggacacggct ggtataaact tgagtgcttc cttggataat | 420 |
| tctgttacat gtgaagatca attcaaggat aagaaggtg aaacttctcc tataacaaag | 480 |
| gagaacaacg tgtacttcca actcaatgta atatctctag ccttcatcca aatgtttcgt | 540 |
| caacattatt ga | 552 |

<210> SEQ ID NO 89
<211> LENGTH: 183
<212> TYPE: PRT
<213> ORGANISM: Glycine max

<400> SEQUENCE: 89

Met Lys Phe Ala Tyr Asn Leu Val Met Ile Phe Phe Ile Phe Leu Phe
1               5                   10                  15

Gln Tyr Ser Asn Gly Ser Asn Leu Ile Leu Gln Ser Cys Lys Glu Ala
            20                  25                  30

Ser Lys Asn Asp Pro Asn Leu Ser Tyr Asp Phe Cys Val Ala Ser Leu
        35                  40                  45

Glu Glu Ala Leu Ser Lys Cys His Pro Pro Thr Asn Leu Glu Asp
    50                  55                  60

Leu Val Gly Met Ser Ile Asn Leu Ser Lys Ser Asn Val Thr Asn Met
65                  70                  75                  80

Val Ser Ile Ile Ser Asn Leu Leu Lys Asn Lys Thr Phe Asp Gln Tyr
                85                  90                  95

Thr Lys Ala Cys Leu Lys Asp Cys Phe Asp Leu Tyr Ser Asp Ser Leu
            100                 105                 110

Ser Ala Leu Asp Asp Ala Val Val Ala Phe Lys Ser Lys Asp Leu Asp
        115                 120                 125

Thr Ala Gly Ile Asn Leu Ser Ala Ser Leu Asp Asn Ser Val Thr Cys
    130                 135                 140

Glu Asp Gln Phe Lys Asp Lys Lys Gly Glu Thr Ser Pro Ile Thr Lys
145                 150                 155                 160

Glu Asn Asn Val Tyr Phe Gln Leu Asn Val Ile Ser Leu Ala Phe Ile
                165                 170                 175

Gln Met Phe Arg Gln His Tyr
            180

<210> SEQ ID NO 90
<211> LENGTH: 552
<212> TYPE: DNA
<213> ORGANISM: Glycine max

<400> SEQUENCE: 90

| | |
|---|---|
| atgaaattcg cttcatacct agtgattttc ttgatctttc tctttcattg ctcaaatggt | 60 |
| tccaatctta tccctcaatc atgcaaagag gcctccaagc atgacccaaa tttgagctat | 120 |
| gatttctgtg ttgcatccct tgaagaagcc tcctccaagt gtcacccacc acccaccaac | 180 |
| tttgaagacc ttgtgggcat gtcaattcag ctaacagaat ccaacgtaac caacatggtt | 240 |
| tccatcattt caaaccttt ggagaacaaa agttttgatc aatacacaaa agcttgccta | 300 |
| aaagattgct tgatctttta ctcggattcg ctttcggctt tagatgatgc tgtggttgct | 360 |
| ttcaagtcca aggatttgga cacggctgct ataaacttga gcgctacctt cgataattct | 420 |
| gttacatgtg aagatcaatt caaggataag aaaggtgaaa cttcttctcc tttaacaatg | 480 |
| gagaaccgcg tgtacttcca actcaatgta atatctctgg ccttcatcca aatgtttcgt | 540 | caacattatt ga 552

<210> SEQ ID NO 91
<211> LENGTH: 183
<212> TYPE: PRT
<213> ORGANISM: Glycine max

<400> SEQUENCE: 91

```
Met Lys Phe Ala Ser Tyr Leu Val Ile Phe Leu Ile Phe Leu Phe His
  1               5                  10                  15

Cys Ser Asn Gly Ser Asn Leu Ile Pro Gln Ser Cys Lys Glu Ala Ser
             20                  25                  30

Lys His Asp Pro Asn Leu Ser Tyr Asp Phe Cys Val Ala Ser Leu Glu
         35                  40                  45

Glu Ala Ser Ser Lys Cys His Pro Pro Thr Asn Phe Glu Asp Leu
     50                  55                  60

Val Gly Met Ser Ile Gln Leu Thr Glu Ser Asn Val Thr Asn Met Val
 65                  70                  75                  80

Ser Ile Ile Ser Asn Leu Leu Glu Asn Lys Ser Phe Asp Gln Tyr Thr
                 85                  90                  95

Lys Ala Cys Leu Lys Asp Cys Phe Asp Leu Tyr Ser Asp Ser Leu Ser
            100                 105                 110

Ala Leu Asp Asp Ala Val Val Ala Phe Lys Ser Lys Asp Leu Asp Thr
        115                 120                 125

Ala Ala Ile Asn Leu Ser Ala Thr Phe Asp Asn Ser Val Thr Cys Glu
    130                 135                 140

Asp Gln Phe Lys Asp Lys Lys Gly Glu Thr Ser Ser Pro Leu Thr Met
145                 150                 155                 160

Glu Asn Arg Val Tyr Phe Gln Leu Asn Val Ile Ser Leu Ala Phe Ile
                165                 170                 175

Gln Met Phe Arg Gln His Tyr
            180
```

<210> SEQ ID NO 92
<211> LENGTH: 564
<212> TYPE: DNA
<213> ORGANISM: Glycine max

<400> SEQUENCE: 92
atgatccttc cctcttcttc ccttttattc actctcacaa tcctcttgtg ttctttcctt     60
tcttttgttt gtgccaaccg tctcatccaa caaacatgca agaattgctc aaaaaatgac    120
cccaacataa gctacaaatt ttgcgttaca tcattccaat cagaccatag gagccactac    180
gccaaaaacc tccaagaact aggactaatc tccatcaaga taacaaggca caacgtgacg    240
gatactaatg ctcatatcaa tgagcttttg aagaaaaaca agagcttgga cccatttatc    300
aaagaatgct tagatgattg cgttgaagtc tattccgaca ccatttccac atttagagaa    360
gccattagag attacaaggc aaaacgttat gccgattgta atgtcaagct aagctcaata    420
attgatgcct ctacgacatg tgaagatgga ttcaagcaaa agaatgatgc catttcgcca    480
ctaacgaaaa gaaacaagga tacctttcag ctttccgcta tagcactttc cattgttaac    540
atgctcatca atacggataa ataa                                           564

<210> SEQ ID NO 93
<211> LENGTH: 187
<212> TYPE: PRT

<213> ORGANISM: Glycine max

<400> SEQUENCE: 93

Met Ile Leu Pro Ser Ser Leu Leu Phe Thr Leu Thr Ile Leu Leu
1               5                   10                  15

Cys Ser Phe Leu Ser Phe Val Cys Ala Asn Arg Leu Ile Gln Gln Thr
            20                  25                  30

Cys Lys Asn Cys Ser Lys Asn Asp Pro Asn Ile Ser Tyr Lys Phe Cys
        35                  40                  45

Val Thr Ser Phe Gln Ser Asp His Arg Ser His Tyr Ala Lys Asn Leu
    50                  55                  60

Gln Glu Leu Gly Leu Ile Ser Ile Lys Ile Thr Arg His Asn Val Thr
65                  70                  75                  80

Asp Thr Asn Ala His Ile Asn Glu Leu Leu Lys Lys Asn Lys Ser Leu
                85                  90                  95

Asp Pro Phe Ile Lys Glu Cys Leu Asp Asp Cys Val Glu Val Tyr Ser
            100                 105                 110

Asp Thr Ile Ser Thr Phe Arg Glu Ala Ile Arg Asp Tyr Lys Ala Lys
        115                 120                 125

Arg Tyr Ala Asp Cys Asn Val Lys Leu Ser Ser Ile Ile Asp Ala Ser
    130                 135                 140

Thr Thr Cys Glu Asp Gly Phe Lys Gln Lys Asn Asp Ala Ile Ser Pro
145                 150                 155                 160

Leu Thr Lys Arg Asn Lys Asp Thr Phe Gln Leu Ser Ala Ile Ala Leu
                165                 170                 175

Ser Ile Val Asn Met Leu Ile Asn Thr Asp Lys
            180                 185

<210> SEQ ID NO 94
<211> LENGTH: 552
<212> TYPE: DNA
<213> ORGANISM: Glycine max

<400> SEQUENCE: 94
atggaacgct ctacaaaact cttctcggcg gcgttggttc tctgcgtggt tgtgatggca      60
caccagacag cagcacagga actaaaagga agaacctaa tcaacaaggt ttgcacaatc     120
accccgagca gagacctctg cgttgggatc ctctcatcgg acccaatcag aagccctgac     180
gcagacctca aggacttggc agttatctcc cttagggttg ctgccagaaa cgcctccggc     240
atcctcagcg aagccaaaat gttgatcgat gacgacaacc tagaccccga cgtccaacaa     300
ggtttgtctg attgcaagga caatcttg dacgccgaga gccagctcga ggacaccatt     360
gcatccttgt tggtggattc cgacaccgac acacagattt ggctcaaggc tgccttggcc     420
gccatcgaca cctgcgacgc ttccattccc ggagacgacg acgttctctc cgtcaagagt     480
gccatgttcc gcaggctgtg caacattgcc attgccatca ccaagcgctt gaacaaacct     540
cttaaattct aa                                                         552

<210> SEQ ID NO 95
<211> LENGTH: 183
<212> TYPE: PRT
<213> ORGANISM: Glycine max

<400> SEQUENCE: 95

Met Glu Arg Ser Thr Lys Leu Phe Ser Ala Ala Leu Val Leu Cys Val
1               5                   10                  15

Val Val Met Ala His Gln Thr Ala Ala Gln Glu Leu Lys Gly Lys Asn
            20                  25                  30

Leu Ile Asn Lys Val Cys Thr Ile Thr Pro Ser Arg Asp Leu Cys Val
        35                  40                  45

Gly Ile Leu Ser Ser Asp Pro Ile Arg Ser Pro Asp Ala Asp Leu Lys
    50                  55                  60

Asp Leu Ala Val Ile Ser Leu Arg Val Ala Arg Asn Ala Ser Gly
65                  70                  75                  80

Ile Leu Ser Glu Ala Lys Met Leu Ile Asp Asp Asn Leu Asp Pro
                85                  90                  95

Asp Val Gln Gln Gly Leu Ser Asp Cys Lys Glu Thr Ile Leu Asp Ala
            100                 105                 110

Glu Ser Gln Leu Glu Asp Thr Ile Ala Ser Leu Leu Val Asp Ser Asp
        115                 120                 125

Thr Asp Thr Gln Ile Trp Leu Lys Ala Ala Leu Ala Ala Ile Asp Thr
    130                 135                 140

Cys Asp Ala Ser Ile Pro Gly Asp Asp Val Leu Ser Val Lys Ser
145                 150                 155                 160

Ala Met Phe Arg Arg Leu Cys Asn Ile Ala Ile Ala Ile Thr Lys Arg
                165                 170                 175

Leu Asn Lys Pro Leu Lys Phe
            180

<210> SEQ ID NO 96
<211> LENGTH: 11380
<212> TYPE: DNA
<213> ORGANISM: Artificial Sequence
<220> FEATURE:
<223> OTHER INFORMATION: Synthetic construct vector pMBX084

<400> SEQUENCE: 96
tcgagtttct ccataataat gtgtgagtag ttcccagata agggaattag ggttcctata      60
gggtttcgct catgtgttga gcatataaga aacccttagt atgtatttgt atttgtaaaa     120
tacttctatc aataaaattt ctaattccta aaaccaaaat ccagtactaa atccagatc      180 ccccgaatta attcggcgtt aattcagtac attaaaaacg tccgcaatgt gttattaagt     240
tgtctaagcg tcaatttgtt tacaccacaa tatatcctgc caccagccag ccaacagctc     300
cccgaccggc agctcggcac aaaatcacca ctcgatacag cagcccatc agtccggac      360 ggcgtcagcg ggagagccgt tgtaaggcgg cagactttgc tcatgttacc gatgctattc     420
ggaagaacgg caactaagct gccgggtttg aaacacggat gatctcgcgg agggtagcat     480
gttgattgta acgatgacag agcgttgctg cctgtgatca ccgcggtttc aaaatcggct     540
ccgtcgatac tatgttatac gccaactttg aaaacaactt tgaaaaagct gttttctggt     600
atttaaggtt ttagaatgca aggaacagtg aattggagtt cgtcttgtta taattagctt     660 cttgggtat ctttaaatac tgtagaaaag aggggtaatg actccaactt attgatagtg     720
ttttatgttc agataatgcc cgatgacttt gtcatgcagc tccaccgatt ttgagaacga     780
cagcgacttc cgtcccagcc gtgccaggtg ctgcctcaga ttcaggttat gccgctcaat     840
tcgctgcgta tatcgcttgc tgattacgtg cagctttccc ttcaggcggg attcatacag     900
cggccagcca tccgtcatcc atatcaccac gtcaaagggt gacagcaggc tcataagacg     960
ccccagcgtc gccatagtgc gttcaccgaa tacgtgcgca acaaccgtct tccggagact    1020
gtcatacgcg taaaacagcc agcgctggcg cgatttagcc ccgacatagc cccactgttc    1080

```
gtccatttcc gcgcagacga tgacgtcact gcccggctgt atgcgcgagg ttaccgactg      1140
cggcctgagt ttttaagtg acgtaaaatc gtgttgaggc caacgcccat aatgcgggct       1200
gttgcccggc atccaacgcc attcatggcc atatcaatga ttttctggtg cgtaccgggt     1260
tgagaagcgg tgtaagtgaa ctgcagttgc catgttttac ggcagtgaga gcagagatag      1320
cgctgatgtc cggcggtgct tttgccgtta cgcaccaccc cgtcagtagc tgaacaggag     1380
ggacagctga tagaaacaga agccactgga gcacctcaaa aacaccatca tacactaaat      1440
cagtaagttg gcagcatcac cgaagaagga aataataaat ggctaaaatg agaatatcac     1500
cggaattgaa aaaactgatc gaaaaatacc gctgcgtaaa agatacggaa ggaatgtctc     1560
ctgctaaggt atataagctg gtgggagaaa atgaaaacct atatttaaaa atgacggaca     1620
gccggtataa agggaccacc tatgatgtgg aacgggaaaa ggacatgatg ctatggctgg     1680
aaggaaagct gcctgttcca aaggtcctgc actttgaacg gcatgatggc tggagcaatc     1740
tgctcatgag tgaggccgat ggcgtccttt gctcggaaga gtatgaagat gaacaaagcc     1800
ctgaaaagat tatcgagctg tatgcggagt gcatcaggct ctttcactcc atcgacatat     1860
cggattgtcc ctatacgaat agcttagaca gccgcttagc cgaattggat tacttactga     1920
ataacgatct ggccgatgtg gattgcgaaa actgggaaga agacactcca tttaaagatc      1980
cgcgcgagct gtatgatttt ttaaagacgg aaaagcccga gaggaacttg tcttttccc      2040 acggcgacct gggagacagc aacatctttg tgaaagatgg caaagtaagt ggctttattg     2100
atcttgggag aagcggcagg gcggacaagt ggtatgacat tgccttctgc gtccggtcga     2160
tcagggagga tatcggggaa gaacagtatg tcgagctatt ttttgactta ctggggatca     2220
agcctgattg ggagaaaata aaatattata ttttactgga tgaattgttt tagtacctag     2280
aatgcatgac caaaatccct taacgtgagt tttcgttcca ctgagcgtca gaccccgtag     2340
aaaagatcaa aggatcttct tgagatcctt ttttctgcg cgtaatctgc tgcttgcaaa      2400
caaaaaaacc accgctacca gcggtggttt gtttgccgga tcaagagcta ccaactcttt      2460
ttccgaaggt aactggcttc agcagagcgc agataccaaa tactgtcctt ctagtgtagc     2520
cgtagttagg ccaccacttc aagaactctg tagcaccgcc tacataccct gctctgctaa     2580
tcctgttacc agtggctgct gccagtggcg ataagtcgtg tcttaccggg ttggactcaa     2640
gacgatagtt accggataag gcgcagcggt cgggctgaac ggggggttcg tgcacacagc     2700
ccagcttgga gcgaacgacc tacaccgaac tgagatacct acagcgtgag ctatgagaaa     2760
gcgccacgct tcccgaaggg agaaaggcgg acaggtatcc ggtaagcggc agggtcggaa     2820
caggagagcg cacgagggag cttccagggg gaaacgcctg gtatctttat agtcctgtcg     2880
ggtttcgcca cctctgactt gagcgtcgat ttttgtgatg ctcgtcaggg gggcggagcc     2940
tatggaaaaa cgccagcaac gcggcctttt tacggttcct ggccttttgc tggccttttg     3000
ctcacatgtt ctttcctgcg ttatcccctg attctgtgga taaccgtatt accgcctttg     3060
agtgagctga taccgctcgc cgcagccgaa cgaccgagcg cagcgagtca gtgagcgagg     3120
aagcggaaga gcgcctgatg cggtattttc tccttacgca tctgtgcggt atttcacacc     3180
gcatatggtg cactctcagt acaatctgct ctgatgccgc atagttaagc cagtatacac     3240
tccgctatcg ctacgtgact gggtcatggc tgcgccccga cacccgccaa cacccgctga     3300
cgcgccctga cgggcttgtc tgctcccggc atccgcttac agacaagctg tgaccgtctc     3360
cgggagctgc atgtgtcaga ggttttcacc gtcatcaccg aaacgcgcga ggcagggtgc     3420
cttgatgtgg gcgccggcgg tcgagtggcg acggcgcggc ttgtccgcgc cctggtagat     3480
```

-continued

```
tgcctggccg taggccagcc attttttgagc ggccagcggc cgcgataggc cgacgcgaag    3540
cggcggggcg tagggagcgc agcgaccgaa gggtaggcgc ttttttgcagc tcttcggctg    3600
tgcgctggcc agacagttat gcacaggcca ggcgggtttt aagagtttta ataagtttta    3660
aagagtttta ggcggaaaaa tcgccttttt tctcttttat atcagtcact tacatgtgtg    3720
accggttccc aatgtacggc tttgggttcc caatgtacgg gttccggttc ccaatgtacg    3780
gctttgggtt cccaatgtac gtgctatcca caggaaagag acctttttcga cctttttccc   3840
ctgctagggc aatttgccct agcatctgct ccgtacatta ggaaccggcg gatgcttcgc    3900
cctcgatcag gttgcggtag cgcatgacta ggatcgggcc agcctgcccc gcctcctcct    3960
tcaaatcgta ctccggcagg tcatttgacc cgatcagctt gcgcacggtg aaacagaact    4020
tcttgaactc tccggcgctg ccactgcgtt cgtagatcgt cttgaacaac catctggctt    4080
ctgccttgcc tgcggcgcgg cgtgccaggc ggtagagaaa acggccgatg ccgggatcga    4140
tcaaaaagta atcggggtga accgtcagca cgtccgggtt cttgccttct gtgatctcgc    4200
ggtacatcca atcagctagc tcgatctcga tgtactccgg ccgcccggtt tcgctcttta    4260
cgatcttgta gcggctaatc aaggcttcac cctcggatac cgtcaccagg cggccgttct    4320
tggccttctt cgtacgctgc atggcaacgt gcgtggtgtt taaccgaatg caggtttcta    4380
ccaggtcgtc tttctgcttt ccgccatcgg ctcgccggca gaacttgagt acgtccgcaa    4440
cgtgtggacg gaacacgcgg ccgggcttgt ctcccttccc ttcccggtat cggttcatgg    4500
attcggttag atgggaaacc gccatcagta ccaggtcgta atcccacaca ctggccatgc    4560
cggccggccc tgcggaaacc tctacgtgcc cgtctggaag ctcgtagcgg aacacctcgc    4620
cagctcgtcg gtcacgcttc gacagacgga aaacggccac gtccatgatg ctgcgactat    4680
cgcgggtgcc cacgtcatag agcatcggaa cgaaaaaatc tggttgctcg tcgcccttgg    4740
gcggcttcct aatcgacggc gcaccggctg ccggcgttg ccgggattct ttgcggattc     4800
gatcagcggc cgcttgccac gattcaccgg ggcgtgcttc tgcctcgatg cgttgccgct    4860
gggcggcctg cgcggccttc aacttctcca ccaggtcatc acccagcgcc gcgccgattt    4920
gtaccgggcc ggatggtttg cgaccgctca cgccgattcc tcgggcttgg gggttccagt    4980
gccattgcag ggccggcagg caacccagcc gcttacgcct ggccaaccgc ccgttcctcc    5040
acacatgggg cattccacgg cgtcggtgcc tggttgttct tgattttcca tgccgcctcc    5100
tttagccgct aaaattcatc tactcattta ttcatttgct catttactct ggtagctgcg    5160
cgatgtattc agatagcagc tcggtaatgg tcttgccttg gcgtaccgcg tacatcttca    5220
gcttggtgtg atcctccgcc ggcaactgaa agttgacccg cttcatggct ggcgtgtctg    5280
ccaggctggc caacgttgca gccttgctgc tgcgtgcgct cggacggccg gcacttagcg    5340
tgtttgtgct tttgctcatt ttctcttttac ctcattaact caaatgagtt tgatttaat    5400
ttcagcggcc agcgcctgga cctcgcgggc agcgtcgccc tcgggttctg attcaagaac    5460
ggttgtgccg gcggcggcag tgcctgggta gctcacgcgc tgcgtgatac gggactcaag    5520
aatgggcagc tcgtacccgg ccagcgcctc ggcaacctca ccgccgatgc gcgtgccttt    5580
gatcgcccgc gacacgacaa aggccgcttg tagccttcca tccgtgacct caatgcgctg    5640
cttaaccagc tccaccaggt cggcggtggc ccatatgtcg taagggcttg gctgcaccgg    5700
aatcagcacg aagtcggctg ccttgatcgc ggacacagcc aagtccgccg cctggggcgc    5760
tccgtcgatc actacgaagt cgcgccggcc gatggccttc acgtcgcggt caatcgtcgg    5820
```

```
gcggtcgatg ccgacaacgg ttagcggttg atcttcccgc acggccgccc aatcgcgggc    5880
actgccctgg ggatcggaat cgactaacag aacatcggcc ccggcgagtt gcagggcgcg    5940
ggctagatgg gttgcgatgg tcgtcttgcc tgacccgcct ttctggttaa gtacagcgat    6000
aaccttcatg cgttcccctt gcgtatttgt ttatttactc atcgcatcat atacgcagcg    6060
accgcatgac gcaagctgtt ttactcaaat acacatcacc ttttagacg gcggcgctcg     6120 gtttcttcag cggccaagct ggccggccag gccgccagct tggcatcaga caaaccggcc    6180
aggatttcat gcagccgcac ggttgagacg tgcgcgggcg gctcgaacac gtacccggcc    6240
gcgatcatct ccgcctcgat ctcttcggta atgaaaaacg gttcgtcctg ccgtcctgg     6300 tgcggtttca tgcttgttcc tcttggcgtt cattctcggc ggccgccagg gcgtcggcct    6360
cggtcaatgc gtcctcacgg aaggcaccgc gccgcctggc ctcggtgggc gtcacttcct    6420
cgctgcgctc aagtgcgcgg tacagggtcg agcgatgcac gccaagcagt gcagccgcct    6480 cttcacggt gcggccttcc tggtcgatca gctcgcgggc gtgcgcgatc tgtgccgggg     6540
tgagggtagg gcggggggcca aacttcacgc ctcgggcctt ggcggcctcg cgcccgctcc    6600
gggtgcggtc gatgattagg gaacgctcga actcggcaat gccggcgaac acggtcaaca    6660
ccatgcggcc ggccggcgtg gtggtgtcgg cccacggctc tgccaggcta cgcaggcccg    6720
cgccggcctc ctggatgcgc tcggcaatgt ccagtaggtc gcgggtgctg cgggccaggc    6780
ggtctagcct ggtcactgtc acaacgtcgc cagggcgtag gtggtcaagc atcctggcca    6840
gctccgggcg gtcgcgcctg gtgccggtga tcttctcgga aaacagcttg gtgcagccgg    6900
ccgcgtgcag ttcggcccgt tggttggtca agtcctggtc gtcggtgctg acgcgggcat    6960
agcccagcag gccagcggcg gcgctcttgt tcatggcgta atgtctccgg ttctagtcgc    7020
aagtattcta ctttatgcga ctaaaacacg cgacaagaaa acgccaggaa aagggcaggg    7080
cggcagcctg tcgcgtaact taggacttgt gcgacatgtc gttttcagaa gacggctgca    7140
ctgaacgtca gaagccgact gcactatagc agcggagggg ttggatcaaa gtactttgat    7200
cccgagggga accctgtggt tggcatgcac atacaaatgg acgaacggat aaaccttttc    7260
acgccctttt aaatatccgt tattctaata aacgctcttt tctcttaggt ttacccgcca    7320
atatatcctg tcaaacactg atagtttaaa ctgaaggcgg gaaacgacaa tctgatccaa    7380
gctcaagctg ctctagcatt cgccattcag gctgcgcaac tgttgggaag ggcgatcggt    7440
gcgggcctct tcgctattac gccagctggc gaaagggggga tgtgctgcaa ggcgattaag    7500
ttgggtaacg ccagggtttt cccagtcacg acgttgtaaa acgacggcca gtgccaagct    7560
tgtacgtagt gtttatcttt gttgcttttc tgaacaattt atttactatg taaatatatt    7620
atcaatgttt aatctatttt aatttgcaca tgaattttca ttttattttt actttacaaa    7680
acaaataaat atatatgcaa aaaaatttac aaacgatgca cgggttacaa actaatttca    7740
ttaaatgcta atgcagattt tgtgaagtaa aactccaatt atgatgaaaa ataccaccaa    7800
caccacctgc gaaactgtat cccaactgtc cttaataaaa atgttaaaaa gtatattatt    7860
ctcatttgtc tgtcataatt tatgtacccc actttaattt ttctgatgta ctaaaccgag    7920
ggcaaactga aacctgttcc tcatgcaaag cccctactca ccatgtatca tgtacgtgtc    7980
atcacccaac aactccactt ttgctatata acaacacccc cgtcacactc tccctctcta    8040
acacacaccc cactaacaat tccttcactt gcagcactgt tgcatcatca tcttcattgc    8100
aaaaccctaa acttcacctt caaccgcggc cgcttcgaaa aaatgtctag tgatgccatg    8160
accatcaatg agtctcttat ggaagtcgaa catactccag ctgtgcataa aaggattctt    8220
```

```
gacattttac cgggtatcag tggcggggtt gccagagtta tgataggtca gcccttcgac   8280
acaatcaaag tgcgtctaca agtgttgggg cagggtacgg ctctcgctgc caaacttcct   8340
cctagtgaag tttacaagga cagcatggat tgcattcgta agatgattaa gtcggagggt   8400
ccactaagct tttacaaggg aacagttgcc ccactcgtcg gaaacatggt attgcttggc   8460
atccattttc cggtcttttc cgcggttaga aagcagttgg agggtgatga tcattactct   8520
aacttttcac acgccaatgt actgcttagc ggcgctgcgg caggagctgc gggatcactc   8580
atttcggctc ctgttgaact ggttagaacg aaaatgcaaa tgcaaaggcg agccgcactt   8640
gcgggtacag tggctgctgg tgcagctgca tctgctggag ctgaggagtt ctataaggga   8700
agtcttgatt gtttcaaaca agttatgtct aagcatggga ttaaaggatt gtataggggt   8760
tttacttcaa ctatactacg agatatgcag ggttatgctt ggttcttcct cggatatgag   8820
gcgactgtca atcacttctt gcaaaatgcg ggaccaggtg ttcataccaa ggctgacttg   8880 aattccttc aagtgatggc cgctgggtt gttgctggat ttggattatg gggctccatg   8940
tttccaatcg ataccatcaa atctaaactc aagccgata gctttgccaa acctcaatat   9000 tcatcccacaa tggattgtct taagaaagta ttagcaagtg agggacaggc cggcttgtgg   9060
agagggttca gcgcagcaat gtatagagca ataccggtga acgctggcat tttcctcgct   9120
gttgaaggga cacgtcaggg tataaagtgg tacgaggaaa acgtgaaca catctacgga   9180 ggtgtcattg gtcccgctac gcctactgca gcacaatgac gaaatttaaa tgcggccgct   9240
gagtaattct gatattagag ggagcattaa tgtgttgttg tgatgtggtt tatatgggga   9300
aattaaataa atgatgtatg tacctcttgc ctatgtaggt ttgtgtgttt tgttttgttg   9360
tctagctttg gttattaagt agtagggacg ttcgttcgtg tctcaaaaaa agggtacta   9420 ccactctgta gtgtatatgg atgctggaaa tcaatgtgtt ttgtatttgt tcacctccat   9480
tgttgaattc aatgtcaaat gtgttttgcg ttggttatgt gtaaaattac tatctttctc   9540
gtccgatgat caaagtttta agcaacaaaa ccaagggtga aatttaaact gtgctttgtt   9600
gaagattctt ttatcatatt gaaaatcaaa ttactagcag cagattttac ctagcatgaa   9660
attttatcaa cagtacagca ctcactaacc aagttccaaa ctaagatgcg ccattaacat   9720
cagccaatag gcattttcag caacctcagc actagtcgtc aaagggcgac accccctaat   9780
tagcccaatt cgtaatcatg gtcatagctg tttcctgtgt gaaattgtta tccgctcaca   9840
attccacaca acatacgagc cggaagcata agtgtaaag cctggggtgc ctaatgagtg   9900
agctaactca cattaattgc gttgcgctca ctgcccgctt tccagtcggg aaacctgtcg   9960
tgccagctgc attaatgaat cggccaacgc gcggggagag gcggtttgcg tattggctag  10020
agcagcttgc caacatggtg gagcacgaca ctctcgtcta ctccaagaat atcaaagata  10080
cagtctcaga agaccaaagg gctattgaga cttttcaaca agggtaata tcgggaaacc  10140 tcctcggatt ccattgccca gctatctgtc acttcatcaa aggacagta gaaaggaag   10200 gtggcaccta caaatgccat cattgcgata aaggaaaggc tatcgttcaa gatgcctctg  10260
ccgacagtgg tcccaaagat ggaccccac ccacgaggag catcgtggaa aagaagacg   10320 ttccaaccac gtcttcaaag caagtggatt gatgtgataa catggtggag cacgacactc  10380
tcgtctactc caagaatatc aaagatacag tctcagaaga ccaaagggct attgagactt  10440
ttcaacaaag gtaatatcg ggaaacctcc tcggattcca ttgcccagct atctgtcact  10500
tcatcaaaag gacagtagaa aaggaaggtg gcacctacaa atgccatcat tgcgataaag  10560
```

```
gaaaggctat cgttcaagat gcctctgccg acagtggtcc caaagatgga cccccaccca    10620
cgaggagcat cgtggaaaaa gaagacgttc caaccacgtc ttcaaagcaa gtggattgat    10680
gtgatatctc cactgacgta agggatgacg cacaatccca ctatccttcg caagaccttc    10740
ctctatataa ggaagttcat ttcatttgga gaggacacgc tgaaatcacc agtctctctc    10800
tacaaatcta tctctctcga gtctaccatg agcccagaac gacgcccggc cgacatccgc    10860
cgtgccaccg aggcggacat gccggcggtc tgcaccatcg tcaaccacta catcgagaca    10920
agcacggtca acttccgtac cgagccgcag gaaccgcagg agtggacgga cgacctcgtc    10980
cgtctgcggg agcgctatcc ctggctcgtc gccgaggtgg acggcgaggt cgccggcatc    11040
gcctacgcgg cccctggaa ggcacgcaac gcctacgact ggacggccga gtcgaccgtg    11100
tacgtctccc cccgccacca gcggacggga ctgggctcca cgctctacac ccacctgctg    11160
aagtccctgg aggcacaggg cttcaagagc gtggtcgctg tcatcgggct gcccaacgac    11220
ccgagcgtgc gcatgcacga ggcgctcgga tatgccccc gcggcatgct gcgggcggcc    11280
ggcttcaagc acgggaactg gcatgacgtg ggtttctggc agctggactt cagcctgccg    11340
gtaccgcccc gtccggtcct gcccgtcacc gagatttgac                          11380
```

<210> SEQ ID NO 97
<211> LENGTH: 12494
<212> TYPE: DNA
<213> ORGANISM: Artificial Sequence
<220> FEATURE:
<223> OTHER INFORMATION: Synthetic construct vector pMXS1091

<400> SEQUENCE: 97

```
catgccaacc acagggttcc cctcgggatc aaagtacttt gatccaaccc ctccgctgct      60
atagtgcagt cggcttctga cgttcagtgc agccgtcttc tgaaaacgac atgtcgcaca     120
agtcctaagt tacgcgacag gctgccgccc tgccctttc ctggcgtttt cttgtcgcgt     180
gttttagtcg cataaagtag aatacttgcg actagaaccg gagacattac gccatgaaca     240
agagcgccgc cgctggcctg ctgggctatg cccgcgtcag caccgacgac caggacttga     300
ccaaccaacg gccgaactg cacgcggccg gctgcaccaa gctgttttcc gagaagatca     360
ccggcaccag gcgcgaccgc ccggagctgg ccaggatgct tgaccaccta cgccctggcg     420
acgttgtgac agtgaccagg ctagaccgcc tggcccgcag cacccgcgac ctactgaca     480 ttgccgagcg catccaggag gccggcgcgg gcctgcgtag cctggcagag ccgtgggccg     540
acaccaccac gccggccggc cgcatggtgt tgaccgtgtt cgccggcatt gccgagttcg     600
agcgttccct aatcatcgac cgcacccgga gcgggcgcga ggccgccaag gcccgaggcg     660
tgaagtttgg cccccgccct acccctcaccc cggcacagat cgcgcacgcc cgcgagctga     720
tcgaccagga aggccgcacc gtgaaagagg cggctgcact gcttggcgtg catcgctcga     780
ccctgtaccg cgcacttgag cgcagcgagg aagtgacgcc caccgaggcc aggcggcgcg     840
gtgccttccg tgaggacgca ttgaccgagg ccgacgccct ggcggccgcc gagaatgaac     900
gccaagagga caagcatga aaccgcacca ggacggccag gacgaaccgt ttttcattac     960
cgaagagatc gaggcggaga tgatcgcggc cgggtacgtg ttcgagccgc ccgcgcacgt    1020
ctcaaccgtg cggctgcatg aaatcctggc cggtttgtct gatgccaagc tggcggcctg    1080
gccggccagc ttggccgctg aagaaaccga gcgccgccgt ctaaaaggt gatgtgtatt    1140 tgagtaaaac agcttgcgtc atgcggtcgc tgcgtatatg atgcgatgag taaataaaca    1200
aatacgcaag gggaacgcat gaaggttatc gctgtactta accagaaagg cgggtcaggc    1260
```

-continued

```
aagacgacca tcgcaaccca tctagcccgc gccctgcaac tcgccggggc cgatgttctg    1320
ttagtcgatt ccgatcccca gggcagtgcc cgcgattggg cggccgtgcg ggaagatcaa    1380
ccgctaaccg ttgtcggcat cgaccgcccg acgattgacc gcgacgtgaa ggccatcggc    1440
cggcgcgact tcgtagtgat cgacggagcg ccccaggcgg cggacttggc tgtgtccgcg    1500
atcaaggcag ccgacttcgt gctgattccg gtgcagccaa gcccttacga catatgggcc    1560
accgccgacc tggtggagct ggttaagcag cgcattgagg tcacggatgg aaggctacaa    1620
gcggcctttg tcgtgtcgcg ggcgatcaaa ggcacgcgca tcggcggtga ggttgccgag    1680
gcgctggccg ggtacgagct gcccattctt gagtcccgta tcacgcagcg cgtgagctac    1740
ccaggcactg ccgccgccgg cacaaccgtt cttgaatcag aacccgaggg cgacgctgcc    1800
cgcgaggtcc aggcgctggc cgctgaaatt aaatcaaaac tcatttgagt taatgaggta    1860
aagagaaaat gagcaaaagc acaaacacgc taagtgccgg ccgtccgagc gcacgcagca    1920
gcaaggctgc aacgttggcc agcctggcag acacgccagc catgaagcgg gtcaactttc    1980
agttgccggc ggaggatcac accaagctga agatgtacgc ggtacgccaa ggcaagacca    2040
ttaccgagct gctatctgaa tacatcgcgc agctaccaga gtaaatgagc aaatgaataa    2100
atgagtagat gaattttagc ggctaaagga ggcggcatgg aaaatcaaga caaccaggc     2160 accgacgccg tggaatgccc catgtgtgga ggaacgggcg gttggccagg cgtaagcggc    2220
tgggttgtct gccggccctg caatggcact ggaaccccca gcccgagga atcggcgtga    2280 cggtcgcaaa ccatccggcc cggtacaaat cggcgcggcg ctgggtgatg acctggtgga    2340
gaagttgaag gccgcgcagg ccgcccagcg gcaacgcatc gaggcagaag cacgccccgg    2400
tgaatcgtgg caagcggccg ctgatcgaat ccgcaaagaa tcccggcaac cgccggcagc    2460
cggtgcgccg tcgattagga agccgcccaa gggcgacgag caaccagatt ttttcgttcc    2520
gatgctctat gacgtgggca cccgcgatag tcgcagcatc atggacgtgg ccgttttccg    2580
tctgtcgaag cgtgaccgac gagctggcga ggtgatccgc tacgagcttc cagacgggca    2640
cgtagaggtt ccgcagggc cggccggcat ggccagtgtg tgggattacg acctggtact    2700
gatggcggtt tcccatctaa ccgaatccat gaaccgatac cgggaaggga agggagacaa    2760
gcccggccgc gtgttccgtc cacacgttgc ggacgtactc aagttctgcc ggcgagccga    2820
tggcggaaag cagaaagacg acctggtaga aacctgcatt cggttaaaca ccacgcacgt    2880
tgccatgcag cgtacgaaga aggccaagaa cggccgcctg gtgacggtat ccgagggtga    2940
agccttgatt agccgctaca agatcgtaaa gagcgaaacc gggcggccgg agtacatcga    3000
gatcgagcta gctgattgga tgtaccgcga gatcacagaa ggcaagaacc cggacgtgct    3060
gacggttcac cccgattact ttttgatcga tccggcatc ggccgttttc tctaccgcct    3120
ggcacgccgc gccgcaggca aggcagaagc cagatggttg ttcaagacga tctacgaacg    3180
cagtggcagc gccggagagt tcaagaagtt ctgtttcacc gtgcgcaagc tgatcgggtc    3240 aaaatgacctg ccggagtacg atttgaagga ggaggcgggg caggctggcc cgatcctagt    3300
catgcgctac cgcaacctga tcgagggcga agcatccgcc ggttcctaat gtacggagca    3360
gatgctaggg caaattgccc tagcagggga aaaaggtcga aaaggtctct ttcctgtgga    3420
tagcacgtac attgggaacc caaagccgta cattgggaac cggaacccgt acattgggaa    3480
cccaaagccg tacattggga accggtcaca catgtaagtg actgatataa aagagaaaaa    3540
aggcgatttt tccgcctaaa actctttaaa acttattaaa actcttaaaa cccgcctggc    3600
```

-continued

```
ctgtgcataa ctgtctggcc agcgcacagc cgaagagctg caaaaagcgc ctacccttcg    3660
gtcgctgcgc tccctacgcc ccgccgcttc gcgtcggcct atcgcggccg ctggccgctc    3720
aaaaatggct ggcctacggc caggcaatct accagggcgc ggacaagccg cgccgtcgcc    3780
actcgaccgc cggcgcccac atcaaggcac cctgcctcgc gcgtttcggt gatgacggtg    3840
aaaacctctg acacatgcag ctcccggaga cggtcacagc ttgtctgtaa gcggatgccg    3900
ggagcagaca gcccgtcag ggcgcgtcag cgggtgttgg cgggtgtcgg ggcgcagcca    3960
tgacccagtc acgtagcgat agcggagtgt atactggctt aactatgcgg catcagagca    4020
gattgtactg agagtgcacc atatgcggtg tgaaataccg cacagatgcg taaggagaaa    4080
ataccgcatc aggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440
ctttctccct tcgggaagcg tggcgctttc tcatagctca cgctgtaggt atctcagttc    4500
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
caccgctggt agcggtggtt tttttgtttg caagcagcag attacgcgca gaaaaaaagg    4860
atctcaagaa gatcctttga tcttttctac ggggtctgac gctcagtgga acgaaaactc    4920
acgttaaggg attttggtca tgcattctag gtactaaaac aattcatcca gtaaaatata    4980 atatttatt ttctcccaat caggcttgat ccccagtaag tcaaaaaata gctcgacata    5040
ctgttcttcc ccgatatcct ccctgatcga ccggacgcag aaggcaatgt cataccactt    5100
gtccgccctg ccgcttctcc caagatcaat aaagccactt actttgccat cttttcacaaa    5160 gatgttgctg tctcccaggt cgccgtggga aagacaagt tcctcttcgg cttttccgt    5220 ctttaaaaaa tcatacagct cgcgcggatc tttaaatgga gtgtcttctt cccagttttc    5280
gcaatccaca tcggccagat cgttattcag taagtaatcc aattcggcta agcggctgtc    5340
taagctattc gtatagggac aatccgatat gtcgatggag tgaaagagcc tgatgcactc    5400
cgcatacagc tcgataatct tttcagggct ttgttcatct tcatactctt ccgagcaaag    5460
gacgccatcg gcctcactca tgagcagatt gctccagcca tcatgccgtt caaagtgcag    5520
gacctttgga acaggcagct ttccttccag ccatagcatc atgtcctttt cccgttccac    5580
atcataggtg gtcccttttat accggctgtc cgtcattttt aaatataggt ttcattttc    5640 tcccaccagc ttatataccct tagcaggaga cattccttcc gtatctttta cgcagcggta    5700
tttttcgatc agttttttca attccggtga tattctcatt ttagccattt attatttcct    5760
tcctcttttc tacagtattt aaagatacccc caagaagcta attataacaa gacgaactcc    5820
aattcactgt tccttgcatt ctaaaacctt aaataccaga aaacagcttt tcaaagttg    5880 ttttcaaagt tggcgtataa catagtatcg acggagccga ttttgaaacc gcggtgatca    5940
caggcagcaa cgctctgtca tcgttacaat caacatgcta ccctccgcga gatcatccgt    6000
```

```
gtttcaaacc cggcagctta gttgccgttc ttccgaatag catcggtaac atgagcaaag   6060
tctgccgcct tacaacggct ctcccgctga cgccgtcccg gactgatggg ctgcctgtat   6120
cgagtggtga ttttgtgccg agctgccggt cggggagctg ttggctggct ggtggcagga   6180
tatattgtgg tgtaaacaaa ttgacgctta gacaacttaa taacacattg cggacgtttt   6240
taatgtactg aattaacgcc gaattaattc ggggatctg atttttagta ctggattttg    6300
gttttaggaa ttagaaattt tattgataga agtattttac aaatacaaat acatactaag   6360
ggtttcttat atgctcaaca catgagcgaa accctatagg aaccctaatt cccttatctg   6420
ggaactactc acacattatt atggagaaac tcgagggatc ccggtcggca tctactctat   6480
tcctttgccc tcggacgagt gctggggcgt cggtttccac tatcggcgag tacttctaca   6540
cagccatcgg tccagacggc cgcgcttctg cgggcgattt tgtacgccc gacagtcccg    6600 gctccggatc ggacgattgc gtcgcatcga ccctgcgccc aagctgcatc atcgaaattg   6660
ccgtcaacca agctctgata gagttggtca agaccaatgc ggagcatata cgcccggagc   6720
cgcggcgatc ctgcaagctc cggatgcctc cgctcgaagt agcgcgtctg ctgctccata   6780
caagccaacc acggcctcca gaagaagatg ttggcgacct cgtattggga atccccgaac   6840
atcgcctcgc tccagtcaat gaccgctgtt atgcggccat tgtccgtcag acattgttg    6900 gagccgaaat ccgcgtgcac gaggtgccgg acttcggggc agtcctcggc ccaaagcatc   6960
agctcatcga gagcctgcgc gacggacgca ctgacggtgt cgtccatcac agtttgccag   7020
tgatacacat ggggatcagc aatcgcgcat atgaaatcac gccatgtagt gtattgaccg   7080
attccttgcg gtccgaatgg gccgaacccg ctcgtctggc taagatcggc cgcagcgatc   7140
gcatccatgg cctccgcgac cggctgcagt tatcatcatc atcatagaca cacgaaataa   7200
agtaatcaga ttatcagtta aagctatgta atatttacac cataaccaat caattaaaaa   7260
atagatcagt ttaagaaag atcaaagctc aaaaaaataa aaagagaaaa gggtcctaac    7320
caagaaaatg aaggagaaaa actagaaatt tacctgcaga acagcgggca gttcggtttc   7380
aggcaggtct tgcaacgtga caccctgtgc acgcgggag atgcaatagg tcaggctctc    7440
gctgaattcc ccaatgtcaa gcacttccgg aatcgggagc gcggccgatg caaagtgccg   7500
ataaacataa cgatctttgt agaaaccatc ggcgcagcta tttacccgca ggacatatcc   7560
acgccctcct acatcgaagc tgaaagcacg agattcttcg ccctccgaga gctgcatcag   7620
gtcggagacg ctgtcgaact tttcgatcag aaacttctcg acagacgtcg cggtgagttc   7680 aggcttttc atggtagagg agctcgccgc ttggtatctg cattacaatg aaatgagcaa    7740
agactatgtg agtaacactg gtcaacacta gggagaaggc atcgagcaag atacgtatgt   7800
aaagagaagc aatatagtgt cagttggtag atactagata ccatcaggag gtaaggagag   7860
caacaaaaag gaaactcttt attttttaaat tttgttacaa caaacaagca gatcaatgca   7920
tcaaaatact gtcagtactt attttcttcag acaacaatat ttaaaacaag tgcatctgat  7980
cttgacttat ggtcacaata aaggagcaga gataaacatc aaaatttcgt catttatatt   8040
tattccttca ggcgttaaca atttaacagc acacaaacaa aaacagaata ggaatatcta   8100
attttggcaa ataataagct ctgcagacga acaaattatt atagtatcgc ctataatatg   8160
aatccctata ctattgaccc atgtagtatg aagcctgtgc ctaaattaac agcaaacttc   8220
tgaatccaag tgcccaataa caccaacatg tgcttaaata aataccgcta agcaccaaat   8280
tacacatttc tcgtattgct gtgtaggttc tatcttcgtt tcgtactacc atgtccctat   8340
```

```
attttgctgc tacaaaggac ggcaagtaat cagcacaggc agaacacgat ttcagagtgt    8400
aattctagat ccagctaaac cactctcagc aatcaccaca caagagagca ttcagagaaa    8460
cgtggcagta acaaaggcag agggcggagt gagcgcgtac cgaagacggt agatctctcg    8520
agagagatag atttgtagag agagactggt gatttcagcg tgtcctctcc aaatgaaatg    8580
aacttcctta tatagaggaa ggtcttgcga aggatagtgg gattgtgcgt catcccttac    8640
gtcagtggag atatcacatc aatccacttg ctttgaagac gtggttggaa cgtcttcttt    8700
ttccacgatg ctcctcgtgg gtggggtcc atctttggga ccactgtcgg cagaggcatc    8760
ttgaacgata gcctttcctt tatcgcaatg atggcatttg taggtgccac cttccttttc    8820
tactgtcctt ttgatgaagt gacagatagc tgggcaatgg aatccgagga ggtttcccga    8880 tattacccctt tgttgaaaag tctcaatagc cctttggtct tctgagactg tatctttgat    8940
attcttggag tagacgagag tgtcgtgctc caccatgtta tcacatcaat ccacttgctt    9000
tgaagacgtg gttggaacgt cttcttttc cacgatgctc ctcgtgggtg ggggtccatc    9060
tttgggacca ctgtcggcag aggcatcttg aacgatagcc tttcctttat cgcaatgatg    9120
gcatttgtag gtgccacctt ccttttctac tgtccttttg atgaagtgac agatagctgg    9180
gcaatggaat ccgaggaggt ttcccgatat tacccctttgt tgaaaagtct caatagccct    9240
ttggtcttct gagactgtat ctttgatatt cttggagtag acgagagtgt cgtgctccac    9300
catgttggca agctgctcta gccaatacgc aaaccgcctc tccccgcgcg ttggccgatt    9360
cattaatgca gctggcacga caggtttccc gactggaaag cgggcagtga gcgcaacgca    9420
attaatgtga gttagctcac tcattaggca ccccaggctt tacactttat gcttccggct    9480
cgtatgttgt gtggaattgt gagcggataa caatttcaca caggaaacag ctatgaccat    9540
gattacgaat tcgagctcgg taccttgcat gccgtcgtct taagcgtccg cgtgtgaaaa    9600
tcggattttc gcatacggtt gaaccggtcg catgcaaaga tcgcgatctt cgcagacgat    9660
ttggcacatg cggttgcacc aaccgtatgc gaaaacccctt ctcgcccgta tgcaaaaacc    9720
atctttgttg tagtgtacgg ttcacaatgg tttggatggg aaatcattgt gaaccaaaag    9780
tgatagactg atttcgacga gtgttttttt ttaagtagtg ccacaatttt ggtcatcata    9840
cgtcgtgtct aaaattgtaa cttttgaaaa ccaatttaca ttaaattaaa tttataagac    9900
taaataaaga cgatggtcat tgaacaattg ttgagaaaaa tctacacaca tgtgtgtcca    9960
acacaaatgt ttacacatat actactatgt tcatagtcga agttagattt tttttttcct    10020
taaagggaaa gtctgttttc aaattttaga cctcactcct tccgtttcaa atatatcgtg    10080
tatttttttt tctagggcaa gctttgacc aatgattact ctattatgac acaatgttaa    10140
agggatagat tcatattcaa aattactatt ataattataa ttttgtcata taataatat    10200 tttaagcaat tgttagccaa aatctcgtcc taacgaaaca aaatacgcct tatttttaaa    10260
aacacggagt atatccttaa atatttctct atccaatata aaaggtcaat cttttaaaat    10320
tccgatcatc aataatttct caaataatta ctttgaaata aaaaaacata tgcaaatttg    10380
tgtcgtcata atatccaatg aacttattca aatttataaa cttattttaa ttcaaaattt    10440
gatcattaat tttttttta aaaaaaacc aaatcttatc ataaacgtca atatatttt    10500 tgatagtggg ggcgataata ccataaaact aacaacagaa gagacatgat actactactg    10560
taatcctaat acgtacgtac gtatacttct acgccggatg cataacttca gccttgtgag    10620
acacaacagt tgctgcctag ctcgtggtcg ttggtttttt cgctcgagaa accactacgc    10680
gtaaaccgtg aagtatatta tatatagcca actggtcttc tcgcaaatcc gcacatccct    10740
```

| | | | | | |
|---|---|---|---|---|---|
| ttctgcccct | cgtcttctgg | taccatgtcc | tctgatgcaa | tgacgattaa | cgaaagcctg | 10800
| atggaggttg | agcacacccc | agctgttcac | aagaggatcc | tggatatact | gccgggtatt | 10860
| agcggcggtg | tcgcgcgtgt | catgattggg | cagccattcg | acacgatcaa | agtccgcctc | 10920
| caagtattgg | gccagggaac | cgctctggcc | gcaaaattac | ctccgagtga | agtgtacaag | 10980
| gactctatgg | actgtatcag | aaaaatgatc | aagtccgagg | gtcctctttc | attctataag | 11040
| ggcacagtgg | ctccactcgt | gggcaacatg | gtgctactgg | ggatccattt | tcccgtgttt | 11100
| tccgccgtgc | ggaagcagct | cgaggggggat | gatcattatt | caaacttctc | gcacgccaac | 11160
| gtgctcttgt | ccggcgctgc | tgccggagcg | gcgggcagcc | tgatctcggc | accggttgaa | 11220
| ctcgtccgca | caaagatgca | gatgcagagg | agggcagcat | tggccggcac | tgtcgccgcc | 11280
| ggcgcggccg | cctcggcggg | agcggaggag | ttctacaagg | gctctctcga | ctgcttcaaa | 11340
| caagtcatga | gcaaacatgg | cattaagggc | ctatacaggg | gtttcaccag | cactatcctt | 11400
| cgggacatgc | agggttacgc | ttggttcttc | ctcggttacg | aggccactgt | caatcacttt | 11460
| ctccaaaatg | ccggaccagg | cgttcataca | aaggcggatt | tgaactacct | tcaagttatg | 11520
| gcggctggcg | tagttgccgg | gttcggacta | tgggggtcaa | tgtttcctat | cgataccatt | 11580
| aagtctaaac | ttcaagctga | cagtttcgcg | aagccccagt | actcatccac | gatggactgc | 11640
| ctgaagaagg | tcctggcttc | cgagggccaa | gccggtcttt | ggagagggtt | cagcgcagcg | 11700
| atgtatcgag | ctatacctgt | aaacgcagga | attttcctgg | cggtggaggg | cacccgccag | 11760
| ggcataaagt | ggtacgaaga | gaatgtcgaa | cacatctacg | ggggcgtgat | cgggcccgcc | 11820
| acgccgacag | cagcccagga | acagaagtta | atctcggagg | aggacctctg | acccgggggc | 11880
| gcgccatcgt | tcaaacattt | ggcaataaag | tttcttaaga | ttgaatcctg | ttgccggtct | 11940
| tgcgatgatt | atcatataat | ttctgttgaa | ttacgttaag | catgtaataa | ttaacatgta | 12000
| atgcatgacg | ttatttatga | gatgggtttt | tatgattaga | gtcccgcaat | tatacattta | 12060
| atacgcgata | gaaaacaaaa | tatagcgcgc | aaactaggat | aaattatcgc | gcgcggtgtc | 12120
| atctatgtta | ctagatccga | tgataagctg | tcaaacatga | aagcttggca | ctggccgtcg | 12180
| ttttacaacg | tcgtgactgg | gaaaaccctg | gcgttaccca | acttaatcgc | cttgcagcac | 12240
| atccccctttt | cgccagctgg | cgtaatagcg | aagaggcccg | caccgatcgc | ccttcccaac | 12300
| agttgcgcag | cctgaatggc | gaatgctaga | gcagcttgag | cttggatcag | attgtcgttt | 12360
| cccgccttca | gtttaaacta | tcagtgtttg | acaggatata | ttggcgggta | aacctaagag | 12420
| aaaagagcgt | ttattagaat | aacggatatt | taaaagggcg | tgaaaaggtt | tatccgttcg | 12480
| tccatttgta | tgtg | | | | | 12494

<210> SEQ ID NO 98
<211> LENGTH: 654
<212> TYPE: DNA
<213> ORGANISM: Zea mays

<400> SEQUENCE: 98

| | | | | | |
|---|---|---|---|---|---|
| atgctagctg | caacaatgta | ctatcacaat | aagacgaaga | tgccaccacc | accttgctct | 60
| tgcttctctg | ctgtctctgt | tcccttctcc | tccttcaaaa | ccataacaat | gctcctcctc | 120
| ctcctcctca | tccttcagca | actgtctgcg | gctgcggttg | cagggatggc | caccaccaag | 180
| cttgggttgt | ctgacgtggt | aaccgacacc | tgcgacagat | gcagcaagag | caatccacag | 240
| gtgaactaca | ccctctgcgt | ctcgtctctg | tgtcggacc | ccgagagcag | gcaggcggac | 300

```
ctccacggtc tcgccatcat ctcggccaag ctgctgaggt caggcgcggt ggccatggag    360
gccaagatgg cggacctcag caggaaggag cgcccatggt ccccccggag gtcctgcctg    420
gacgcctgcg tcggggtgta ccgcaactcc ctctacgacc tcggcagctc catcgtagcc    480
atccaggaga ggaggtacgc ggacgccaag acgtccatga gcgccgcggt ggatgcgccc    540
gtcacctgcg aggatgagtt caaggagcag ggcttggagc cacccatgag agcggagacc    600
aaacgcctgt tcaacaggc ggtcatctcc ctcgcaatca tctccctgct atga           654
```

<210> SEQ ID NO 99
<211> LENGTH: 217
<212> TYPE: PRT
<213> ORGANISM: Zea mays

<400> SEQUENCE: 99

Met Leu Ala Ala Thr Met Tyr Tyr His Asn Lys Thr Lys Met Pro Pro
1               5                   10                  15

Pro Pro Cys Ser Cys Phe Ser Ala Val Ser Val Pro Phe Ser Ser Phe
            20                  25                  30

Lys Thr Ile Thr Met Leu Leu Leu Leu Leu Ile Leu Gln Gln Leu
        35                  40                  45

Ser Ala Ala Val Ala Gly Met Ala Thr Thr Lys Leu Gly Leu Ser
    50                  55                  60

Asp Val Val Thr Asp Thr Cys Asp Arg Cys Ser Lys Ser Asn Pro Gln
65                  70                  75                  80

Val Asn Tyr Thr Leu Cys Val Ser Ser Leu Ser Ser Asp Pro Glu Ser
                85                  90                  95

Arg Gln Ala Asp Leu His Gly Leu Ala Ile Ile Ser Ala Lys Leu Leu
            100                 105                 110

Arg Ser Gly Ala Val Ala Met Glu Ala Lys Met Ala Asp Leu Ser Arg
        115                 120                 125

Lys Glu Arg Pro Trp Ser Pro Arg Arg Ser Cys Leu Asp Ala Cys Val
    130                 135                 140

Gly Val Tyr Arg Asn Ser Leu Tyr Asp Leu Gly Ser Ser Ile Val Ala
145                 150                 155                 160

Ile Gln Glu Arg Arg Tyr Ala Asp Ala Lys Thr Ser Met Ser Ala Ala
                165                 170                 175

Val Asp Ala Pro Val Thr Cys Glu Asp Glu Phe Lys Glu Gln Gly Leu
            180                 185                 190

Glu Pro Pro Met Arg Ala Glu Thr Lys Arg Leu Phe Gln Gln Ala Val
        195                 200                 205

Ile Ser Leu Ala Ile Ile Ser Leu Leu
    210                 215

<210> SEQ ID NO 100
<211> LENGTH: 687
<212> TYPE: DNA
<213> ORGANISM: Zea mays

<400> SEQUENCE: 100

```
atgacccgtg ccagcagcag tagcagcagc cggcgtgtga cgctggtact gctcggtctc    60
cgcctgctgc ttctggttgg tgttgcgcag gcggtagtgg agttggtgcc tgctgatgat   120
aatatcgccg ccgccgctgc tggcacggcg gtggacgatg cgagccgcc tcagcagtgc    180 gcgaccccgg tgagcgtgga ggaggcgtgc cgcggcgcgt ccgagacgca cgccggcgtg    240
gcctacgacc actgcatggc gtcgctgggc gccgacccgc gcagcaagga ggccggcaac    300
```

```
aagaacatgc acgggctggc ggtgctggcc accaggatgg ccatcgacca cgccgccagc        360
accgagtcca agatcgacga cctcgcggag ctggaggcgg cgtcgtcgga tccgcaggcg        420
cgcgcccgct tcaaccactg cctggagcag tacggcggcg ccgccgacct cctccgcgac        480
gcgctggaca acctcaaggc gaagatctac ggcaaggcca tggagcagct gaccgccgca        540
atgggcgcct ccgagagctg cgaggacgcg tggaagggcg aggaggagga tgtccccgtc        600
gccgcgcacg acaggagta cggtcggatg gcgcacatcg ccttcggatt cacacaccac        660
gccgccgtcg ccgccgccgc cgcatga                                            687
```

<210> SEQ ID NO 101
<211> LENGTH: 228
<212> TYPE: PRT
<213> ORGANISM: Zea mays

<400> SEQUENCE: 101

```
Met Thr Arg Ala Ser Ser Ser Ser Ser Arg Arg Val Thr Leu Val
1               5                   10                  15

Leu Leu Gly Leu Arg Leu Leu Leu Val Gly Val Ala Gln Ala Val
            20                  25                  30

Val Glu Leu Val Pro Ala Asp Asp Asn Ile Ala Ala Ala Ala Gly
        35                  40                  45

Thr Ala Val Asp Asp Gly Glu Pro Pro Gln Gln Cys Ala Thr Pro Val
50                  55                  60

Ser Val Glu Glu Ala Cys Arg Gly Ala Ser Glu Thr His Ala Gly Val
65                  70                  75                  80

Ala Tyr Asp His Cys Met Ala Ser Leu Gly Ala Asp Pro Arg Ser Lys
                85                  90                  95

Glu Ala Gly Asn Lys Asn Met His Gly Leu Ala Val Leu Ala Thr Arg
            100                 105                 110

Met Ala Ile Asp His Ala Ala Ser Thr Glu Ser Lys Ile Asp Asp Leu
        115                 120                 125

Ala Glu Leu Glu Ala Ala Ser Ser Asp Pro Gln Ala Arg Ala Arg Phe
    130                 135                 140

Asn His Cys Leu Glu Gln Tyr Gly Gly Ala Ala Asp Leu Leu Arg Asp
145                 150                 155                 160

Ala Leu Asp Asn Leu Lys Ala Lys Ile Tyr Gly Lys Ala Met Glu Gln
                165                 170                 175

Leu Thr Ala Ala Met Gly Ala Ser Glu Ser Cys Glu Asp Ala Trp Lys
            180                 185                 190

Gly Glu Glu Glu Asp Val Pro Val Ala Ala His Asp Arg Glu Tyr Gly
        195                 200                 205

Arg Met Ala His Ile Ala Phe Gly Phe Thr His His Ala Ala Val Ala
    210                 215                 220

Ala Ala Ala Ala
225
```

<210> SEQ ID NO 102
<211> LENGTH: 636
<212> TYPE: DNA
<213> ORGANISM: Zea mays

<400> SEQUENCE: 102

```
atggcgatga ggtcgctagc gctactggtc ctcctcagcc tgctggttgt tggtgtggcg        60
caggcggtgg agttggagat ggagttggtg cctgctgatg caattgcgat gactatggat       120
```

```
cgtgagccgc cgcaggagtg cgcgaccccg gtgagcgtgg aggaggcgtg ccgcagcgcg      180
tcggagacgc acgccggcgt ggcctacgac cactgcatgg cgtcgctggg cgccgacccg      240
cgcagcaagg aggccggcaa caagaacatg cacgcgctgg cggtgctggc caccaggatg      300
gccatcgacc acgccgccag caccgagtcc aagatcgacg acctcgcgga gctggaggcg      360
gcgtcgtcgg atccgcaggc gcgcgcacgc ttcaaccact gcctggagca gtacggcggc      420
gccgccgacc tcctccgcga cgcgctggac aacctcaagg ccaagatcta cggcaaggcc      480
atggagcagc tgaccgcggc gatgggcgcc tccgagagct gcgaggacgc gtggaagggc      540
gaggaggatg tccccgtcgc cgcgcacgac agggagtacg gcggatggc gcacatcgcc      600 ttcggattca cacaccacgc cgccgccgcc gcatga                                636
```

```
<210> SEQ ID NO 103
<211> LENGTH: 211
<212> TYPE: PRT
<213> ORGANISM: Zea mays

<400> SEQUENCE: 103

Met Ala Met Arg Ser Leu Ala Leu Leu Val Leu Leu Ser Leu Leu Val
1               5                   10                  15

Val Gly Val Ala Gln Ala Val Glu Leu Glu Met Glu Leu Val Pro Ala
                20                  25                  30

Asp Ala Ile Ala Met Thr Met Asp Arg Glu Pro Gln Glu Cys Ala
            35                  40                  45

Thr Pro Val Ser Val Glu Glu Ala Cys Arg Ser Ala Ser Glu Thr His
    50                  55                  60

Ala Gly Val Ala Tyr Asp His Cys Met Ala Ser Leu Gly Ala Asp Pro
65                  70                  75                  80

Arg Ser Lys Glu Ala Gly Asn Lys Asn Met His Ala Leu Ala Val Leu
                85                  90                  95

Ala Thr Arg Met Ala Ile Asp His Ala Ala Ser Thr Glu Ser Lys Ile
            100                 105                 110

Asp Asp Leu Ala Glu Leu Glu Ala Ala Ser Ser Asp Pro Gln Ala Arg
        115                 120                 125

Ala Arg Phe Asn His Cys Leu Glu Gln Tyr Gly Gly Ala Ala Asp Leu
    130                 135                 140

Leu Arg Asp Ala Leu Asp Asn Leu Lys Ala Lys Ile Tyr Gly Lys Ala
145                 150                 155                 160

Met Glu Gln Leu Thr Ala Ala Met Gly Ala Ser Glu Ser Cys Glu Asp
                165                 170                 175

Ala Trp Lys Gly Glu Glu Asp Val Pro Val Ala Ala His Asp Arg Glu
            180                 185                 190

Tyr Gly Arg Met Ala His Ile Ala Phe Gly Phe Thr His His Ala Ala
        195                 200                 205

Ala Ala Ala
    210

<210> SEQ ID NO 104
<211> LENGTH: 588
<212> TYPE: DNA
<213> ORGANISM: Zea mays

<400> SEQUENCE: 104
atggcttccg gaacgcccta cactgccgtc ggcgtcatct tcctctccgt cttcctcgtc      60
```

| | |
|---|---|
| gccgcggcat ccgcaggccg caccgcggca cctgcggccg cgccgtcgag caagtactcg | 120 |
| ctcgaggaag cgtgcgagca gaccgcgggg cacgaggacc tgtgcgtgga gacgctgtcc | 180 |
| gcggacccgt cgtccaagac tgccgacact acggggctcg cacggttggc catccaggcg | 240 |
| gcacagcgga acgcgtcgga gacggcgacc tacctctcca gcatctacga cgacgacagc | 300 |
| cttgagaaca agacggcgca gctgcagcag tgccttgaaa actgcggcga gaggtacgag | 360 |
| tcggcggtgg agcagctgtc ggacgcgacg tcggcgctgg acacgggcgc gtacagcgag | 420 |
| tcggaggagc tggtggtggc gagccaggct gaggtgaggc tgtgtcagcg tggctgccaa | 480 |
| gccgtgccga accaccgcaa catcctctcg gcgcgcaacc gcaacgtcga ccagctctgc | 540 |
| agcatcgcgc tcgccatcac caagctcatc cacggaccgc catcttga | 588 |

<210> SEQ ID NO 105
<211> LENGTH: 195
<212> TYPE: PRT
<213> ORGANISM: Zea mays

<400> SEQUENCE: 105

```
Met Ala Ser Gly Thr Pro Tyr Thr Ala Val Gly Val Ile Phe Leu Ser
1               5                   10                  15

Val Phe Leu Val Ala Ala Ala Ser Ala Gly Arg Thr Ala Ala Pro Ala
            20                  25                  30

Ala Ala Pro Ser Ser Lys Tyr Ser Leu Glu Glu Ala Cys Glu Gln Thr
        35                  40                  45

Ala Gly His Glu Asp Leu Cys Val Glu Thr Leu Ser Ala Asp Pro Ser
    50                  55                  60

Ser Lys Thr Ala Asp Thr Thr Gly Leu Ala Arg Leu Ala Ile Gln Ala
65                  70                  75                  80

Ala Gln Arg Asn Ala Ser Glu Thr Ala Thr Tyr Leu Ser Ser Ile Tyr
                85                  90                  95

Asp Asp Asp Ser Leu Glu Asn Lys Thr Ala Gln Leu Gln Gln Cys Leu
            100                 105                 110

Glu Asn Cys Gly Glu Arg Tyr Glu Ser Ala Val Glu Gln Leu Ser Asp
        115                 120                 125

Ala Thr Ser Ala Leu Asp Thr Gly Ala Tyr Ser Glu Ser Glu Glu Leu
    130                 135                 140

Val Val Ala Ser Gln Ala Glu Val Arg Leu Cys Gln Arg Gly Cys Gln
145                 150                 155                 160

Ala Val Pro Asn His Arg Asn Ile Leu Ser Ala Arg Asn Arg Asn Val
                165                 170                 175

Asp Gln Leu Cys Ser Ile Ala Leu Ala Ile Thr Lys Leu Ile His Gly
            180                 185                 190

Pro Pro Ser
        195
```

<210> SEQ ID NO 106
<211> LENGTH: 531
<212> TYPE: DNA
<213> ORGANISM: Zea mays

<400> SEQUENCE: 106

| | |
|---|---|
| atgaagcttc tgcaagctct gtgccctctc gtcatcctcc tcgcctgctc cacgtccaac | 60 |
| gcttccgtcc tacaagacgc gtgcaagtcc ttcgccgcta agatcccgga caccggctac | 120 |
| gcctactgca tcaagttctt ccaggccgac aggggaagcg ccggcgcgga caagcgtggc | 180 |

```
ctcgccgcca tcgccgtgag gatcatgggg gcagccgcca agagcaccgc cagtcacatc    240
gccgccctgc gggcctccga gaaggacaag gagcggctgg cgtgcctcag cgattgctcc    300
gaggtgtacg cgcaggccgt ggaccagacc ggcgtggcgg cgaagggcat cgcctcgggc    360
acgccccggg gccgcgcgga cgcggtgatg gcgctcagca cggtggagga tgccccggc    420 acctgtgagc agggggttcca ggacctgggc gtgcgttcgc cgctggcctc ggaggacgcc    480
gggttccgga aggatgcgtc catcgcgctg tctgtaacgg ccgcgttgta a              531
```

```
<210> SEQ ID NO 107
<211> LENGTH: 176
<212> TYPE: PRT
<213> ORGANISM: Zea mays

<400> SEQUENCE: 107

Met Lys Leu Leu Gln Ala Leu Cys Pro Leu Val Ile Leu Leu Ala Cys
1               5                   10                  15

Ser Thr Ser Asn Ala Ser Val Leu Gln Asp Ala Cys Lys Ser Phe Ala
            20                  25                  30

Ala Lys Ile Pro Asp Thr Gly Tyr Ala Tyr Cys Ile Lys Phe Phe Gln
        35                  40                  45

Ala Asp Arg Gly Ser Ala Gly Ala Asp Lys Arg Gly Leu Ala Ala Ile
    50                  55                  60

Ala Val Arg Ile Met Gly Ala Ala Lys Ser Thr Ala Ser His Ile
65                  70                  75                  80

Ala Ala Leu Arg Ala Ser Glu Lys Asp Lys Glu Arg Leu Ala Cys Leu
                85                  90                  95

Ser Asp Cys Ser Glu Val Tyr Ala Gln Ala Val Asp Gln Thr Gly Val
            100                 105                 110

Ala Ala Lys Gly Ile Ala Ser Gly Thr Pro Arg Gly Arg Ala Asp Ala
        115                 120                 125

Val Met Ala Leu Ser Thr Val Glu Asp Ala Pro Gly Thr Cys Glu Gln
    130                 135                 140

Gly Phe Gln Asp Leu Gly Val Arg Ser Pro Leu Ala Ser Glu Asp Ala
145                 150                 155                 160

Gly Phe Arg Lys Asp Ala Ser Ile Ala Leu Ser Val Thr Ala Ala Leu
                165                 170                 175
```

```
<210> SEQ ID NO 108
<211> LENGTH: 770
<212> TYPE: DNA
<213> ORGANISM: Artificial Sequence
<220> FEATURE:
<223> OTHER INFORMATION: Synthetic construct CaMV35S promoter

<400> SEQUENCE: 108
agagatagat tgtagagag agactggtga tttcagcgtg tcctctccaa atgaaatgaa     60
cttccttata tagaggaagg tcttgcgaag gatagtggga ttgtgcgtca tcccttacgt    120
cagtggagat atcacatcaa tccacttgct ttgaagacgt ggttggaacg tcttcttttt    180
ccacgatgct cctcgtgggt gggggtccat ctttgggacc actgtcggca gaggcatctt    240
gaacgatagc ctttccttta tcgcaatgat ggcatttgta ggtgccacct tcctttttcta    300 ctgtcctttt gatgaagtga cagatagctg ggcaatggaa tccgaggagg tttcccgata    360
ttaccctttg ttgaaaagtc tcaatagccc tttggtcttc tgagactgta tctttgatat    420
tcttggagta gacgagagtg tcgtgctcca ccatgttatc acatcaatcc acttgctttg    480
```

| | | |
|---|---|---|
| aagacgtggt tggaacgtct tcttttccca cgatgctcct cgtgggtggg ggtccatctt | 540 | |
| tgggaccact gtcggcagag gcatcttgaa cgatagcctt tcctttatcg caatgatggc | 600 | |
| atttgtaggt gccaccttcc ttttctactg tccttttgat gaagtgacag atagctgggc | 660 | |
| aatggaatcc gaggaggttt cccgatatta ccctttgttg aaaagtctca atagcccttt | 720 | |
| ggtcttctga gactgtatct tgatattct tggagtagac gagagtgtcg | 770 | |

<210> SEQ ID NO 109
<211> LENGTH: 1507
<212> TYPE: DNA
<213> ORGANISM: Artificial Sequence
<220> FEATURE:
<223> OTHER INFORMATION: Synthetic construct Zea mays hybrid promoter

<400> SEQUENCE: 109

| | | |
|---|---|---|
| ctgcagtgca gcgtgacccg gtcgtgcccc tctctagaga taatgagcat tgcatgtcta | 60 | |
| agttataaaa aattaccaca tattttttt gtcacacttg tttgaagtgc agtttatcta | 120 | |
| tctttataca tatatttaaa ctttactcta cgaataatat aatctatagt actacaataa | 180 | |
| tatcagtgtt ttagagaatc atataaatga acagttagac atggtctaaa ggacaattga | 240 | |
| gtattttgac aacaggactc tacagtttta tctttttagt gtgcatgtgt tctcctttt | 300 | |
| ttttgcaaat agcttcacct atataatact tcatccattt tattagtaca tccatttagg | 360 | |
| gtttagggtt aatggttttt atagactaat ttttttagta catctatttt attctatttt | 420 | |
| agcctctaaa ttaagaaaac taaaactcta tttagtttt tttatttaat aatttagata | 480 | |
| taaaatagaa taaaataaag tgactaaaaa ttaaacaaat accctttaag aaattaaaaa | 540 | |
| aactaaggaa acatttttct tgtttcgagt agataatgcc agcctgttaa acgccgtcga | 600 | |
| tcgacgagtc taacgacac caaccagcga accagcagcg tcgcgtcggg ccaagcgaag | 660 | |
| cagacggcac ggcatctctg tcgctgcctc tggacccctc tcgagagttc cgctccaccg | 720 | |
| ttggacttgc tccgctgtcg gcatccagaa attgcgtggc ggagcggcag acgtgagccg | 780 | |
| gcacggcagg cggcctcctc ctcctctcac ggcaccggca gctacggggg attccttttcc | 840 | |
| caccgctcct tcgcttttccc ttcctcgccc gccgtaataa atagacaccc cctccacacc | 900 | |
| ctcttttcccc aacctcgtgt tgttcggagc gcacacacac acaaccagat ctcccccaaa | 960 | |
| tccacccgtc ggcacctccg cttcaaggta cgccgctcgt cctcccccc cccccctctc | 1020 | |
| taccttctct agatcggcgt tccggtccat ggttagggcc cggtagttct acttctgttc | 1080 | |
| atgtttgtgt tagatccgtg tttgtgttag atccgtgctg ctagcgttcg tacacggatg | 1140 | |
| cgacctgtac gtcagacacg ttctgattgc taacttgcca gtgtttctct ttggggaatc | 1200 | |
| ctgggatggc tctagccgtt ccgcagacgg gatcgatcta ggataggtat acatgttgat | 1260 | |
| gtgggtttta ctgatgcata tacatgatgg catatgcagc atctattcat atgctctaac | 1320 | |
| cttgagtacc tatctattat aataaacaag tatgttttat aattattttg atcttgatat | 1380 | |
| acttggatga tggcatatgc agcagctata tgtggatttt tttagccctg ccttcatacg | 1440 | |
| ctatttattt gcttggtact gtttcttttg tcgatgctca ccctgttgtt tggtgttact | 1500 | |
| tctgcag | 1507 | |

<210> SEQ ID NO 110
<211> LENGTH: 1996
<212> TYPE: DNA
<213> ORGANISM: Artificial Sequence
<220> FEATURE:
<223> OTHER INFORMATION: Synthetic construct Maize ubiquitin promoter/intron

<400> SEQUENCE: 110

```
ctgcagtgca gcgtgacccg gtcgtgcccc tctctagaga taatgagcat tgcatgtcta      60
agttataaaa aattaccaca tattttttt gtcacacttg tttgaagtgc agtttatcta     120
tctttataca tatatttaaa ctttactcta cgaataatat aatctataaa gtactacaat     180
aatatcagtg ttttagagaa tcatataaat gaacagttag acatggtcta aaggacaatt     240
gagtattttg acaacaggac tctacagttt tatcttttta gtgtgcatgt gttctccttt     300
ttttttgcaa atagcttcac ctatataata cttcatccat tttattagta catccattta     360
gggtttaggg ttaatggttt ttatagacta atttttttag tacatctatt ttattctatt     420
ttagcctcta aattaagaaa actaaaactc tattttagtt tttttattta ataatttaga     480
tataaaatag aataaaataa agtgactaaa aattaaacaa ataccctttta agaaattaaa    540
aaaactaagg aaacattttt cttgtttcga gtagataatg ccagcctgtt aaacgccgtc     600
gacgagtcta acggacacca accagcgaac cagcagcgtc gcgtcgggcc aagcgaagca     660
gacggcacgg catctctgtc gctgcctctg accctctc gagagttccg ctccaccgtt      720
ggacttgctc cgctgtcggc atccagaaat tgcgtggcgg agcggcagac gtgagccggc     780
acggcaggcg gcctcctcct cctctcacgg caccggcagc tacgggggat tcctttccca    840
ccgctccttc gctttccctt cctcgcccgc cgtaataaat agacaccccc tccacaccct     900
cttccccaa cctcgtgttg ttcggagcgc acacacacac aaccagatct cccccaaatc      960
cacccgtcgg cacctccgct tcaaggtacg ccgctcgtcc tcccccccc cccctctcta    1020
ccttctctag atcggcgttc cggtccatgg ttagggcccg gtagttctac ttctgttcat    1080
gtttgtgtta gatccgtgtt tgtgttagat ccgtgctgct agcgttcgta cacggatgcg    1140
acctgtacgt cagacacgtt ctgattgcta acttgccagt gtttctcttt ggggaatcct    1200
gggatggctc tagccgttcc gcagacggga tcgatttcat gattttttt gtttcgttgc     1260
atagggtttg gtttgcccctt ttcctttatt tcaatatatg ccgtgcactt gtttgtcggg    1320
tcatctttc atgctttttt ttgtcttggt tgtgatgatg tggtctggtt gggcggtcgt    1380
tctagatcgg agtagaaatc tgtttcaaac tacctggtgg atttattaat tttggatctg    1440
tatgtgtgtg ccatacatat tcatagttac gaattgaaga tgatggatgg aaatatcgat    1500
ctaggatagg tatacatgtt gatgcgggtt ttactgatgc atatacagag atgcttttg     1560
ttcgcttggt tgtgatgatg tggtgtggtt gggcggtcgt tcattcgttc tagatcggag    1620
tagaatactg tttcaaacta cctggtgtat ttattaattt tggaactgta tgtgtgtgtc    1680
atacatcttc atagttacga gtttaagatg gatggaaata tcgatctagg ataggtatac    1740
atgttgatgt gggttttact gatgcatata catgatggca tatgcagcat ctattcatat    1800
gctctaacct tgagtaccta tctattataa taaacaagta tgtttataa ttatttgat     1860
cttgatatac ttggatgatg gcatatgcag cagctatatg tggatttttt tagccctgcc    1920
ttcatacgct atttatttgc ttggtactgt ttcttttgtc gatgctcacc ctgttgtttg    1980
gtgttacttc tgcagg                                                    1996
```

<210> SEQ ID NO 111
<211> LENGTH: 1500
<212> TYPE: DNA
<213> ORGANISM: Artificial Sequence
<220> FEATURE:
<223> OTHER INFORMATION: Synthetic construct Maize trpA promoter

<400> SEQUENCE: 111

```
gattcgcgcg tgctggaact cgggattgga ttcatgcgtg ctggaacttg gaagtctgga      60
gtggactttg gaagcctgga ttccagaaca agaactcaag aagtctagga gccgccgagc     120
aggtagggaa ttagggaaat aaagagaaga ggcggctggc gttcgacgtt ccatcttcag     180
tagaggcggc tggcgtttca actccctgta gtcgggccgc ctgccaaaaa agcccacgaa     240
ggcaggaaat caaaaaatct aggtcctaaa cctagtcgcg cagaaccggc taatcgagcg     300
actaatcgac cctaatcgtc gactagtcgg acggccaggg cgattaggta ctctaatcga     360
gtcggttgtg ctaatcgagc tctgctaacc gactagcccg accgcgatta gtcagatgac     420
ttgaaaacaa agatagagac atactttttt atattctttg cattgttttg tttctatcca     480
aaactgctat ttagaaattg gaaaatctgc acattgaaaa atctaatgga ttagatatgt     540
tgatttgttt ttattcacga gcataatcaa ataaattaga tttagaattg gactgcacgc     600
agtgaactac tgaactgaac tgtgttcaat aatttaaata ctcacggctg agccgtgagc     660
tgtaggctgg agcacaagca cgagccagca ccgagcggcg gagcactgga gcagcaggcg     720
agcagggagg cggccaggcg ggagcagcca gccagcaagc aggcagcagc ggagcagccc     780
acagccgagc gcccaagctg gagctgctgc agagcctgca gcgtgccgct gcgcgccggc     840
aggacaggag cggccgagcg ggagtgcagg actgtggcct gcgggacgcg gggatgggcg     900
gacggcgtag cgcttacagt ccgcggacag cggactcacg gtggcggcta agatagtgag     960
accgatgacc taatctctat ttggaccggt tcaaggtttt gcccagttaa tattggacca    1020
tattgggcct tccgcccctg ctcgcaagac acactgaaca aagaatccac acggctctcc    1080
aaaagataga gagataattc acatgcttct ctctctctga aaaaaggaa cttgcatggt     1140
tgacacggaa aacgtcatta aacgcgcacg tggctgcaaa tgcaacgtaa cagatccatc    1200
atctatccat ccatagaatc agacggccac agaaggcaac gaccgtgtgc ctgtccaccg    1260
gcgcaggtgg cccacagacg cccgtgcgat tcatccgtct cggcccacca accacgggag    1320
gggcccagg gccctcctta gtccttacaa ataccggcag cagcatcacc cggccaccac    1380
cacccacccg ttttatccac gcacggcgtc gaacaccccg cggtcgctca cgtgaggcgc    1440
caccccgcgc acccagtcag cgcccgcctc caccacccac ccacacgaca aaaatccgcc    1500
```

<210> SEQ ID NO 112
<211> LENGTH: 358
<212> TYPE: PRT
<213> ORGANISM: Chlamydomonas reinhardtii

<400> SEQUENCE: 112

```
Met Ser Ser Asp Ala Met Thr Ile Asn Glu Ser Leu Met Glu Val Glu
  1               5                  10                  15

His Thr Pro Ala Val His Lys Arg Ile Leu Asp Ile Leu Pro Gly Ile
             20                  25                  30

Ser Gly Gly Val Ala Arg Val Met Ile Gly Gln Pro Phe Asp Thr Ile
         35                  40                  45

Lys Val Arg Leu Gln Val Leu Gly Gln Gly Thr Ala Leu Ala Ala Lys
     50                  55                  60

Leu Pro Pro Ser Glu Val Tyr Lys Asp Ser Met Asp Cys Ile Arg Lys
 65                  70                  75                  80

Met Ile Lys Ser Glu Gly Pro Leu Ser Phe Tyr Lys Gly Thr Val Ala
                 85                  90                  95
```

```
Pro Leu Val Gly Asn Met Val Leu Leu Gly Ile His Phe Pro Val Phe
                100                 105                 110

Ser Ala Val Arg Lys Gln Leu Glu Gly Asp Asp His Tyr Ser Asn Phe
            115                 120                 125

Ser His Ala Asn Val Leu Leu Ser Gly Ala Ala Gly Ala Ala Gly
        130                 135                 140

Ser Leu Ile Ser Ala Pro Val Glu Leu Val Arg Thr Lys Met Gln Met
145                 150                 155                 160

Gln Arg Arg Ala Ala Leu Ala Gly Thr Val Ala Gly Ala Ala Ala
                165                 170                 175

Ser Ala Gly Ala Glu Glu Phe Tyr Lys Gly Ser Leu Asp Cys Phe Lys
            180                 185                 190

Gln Val Met Ser Lys His Gly Ile Lys Gly Leu Tyr Arg Gly Phe Thr
            195                 200                 205

Ser Thr Ile Leu Arg Asp Met Gln Gly Tyr Ala Trp Phe Phe Leu Gly
        210                 215                 220

Tyr Glu Ala Thr Val Asn His Phe Leu Gln Asn Ala Gly Pro Gly Val
225                 230                 235                 240

His Thr Lys Ala Asp Leu Asn Tyr Leu Gln Val Met Ala Ala Gly Val
                245                 250                 255

Val Ala Gly Phe Gly Leu Trp Gly Ser Met Phe Pro Ile Asp Thr Ile
            260                 265                 270

Lys Ser Lys Leu Gln Ala Asp Ser Phe Ala Lys Pro Gln Tyr Ser Ser
            275                 280                 285

Thr Met Asp Cys Leu Lys Lys Val Leu Ala Ser Glu Gly Gln Ala Gly
            290                 295                 300

Leu Trp Arg Gly Phe Ser Ala Ala Met Tyr Arg Ala Ile Pro Val Asn
305                 310                 315                 320

Ala Gly Ile Phe Leu Ala Val Glu Gly Thr Arg Gln Gly Ile Lys Trp
                325                 330                 335

Tyr Glu Glu Asn Val Glu His Ile Tyr Gly Gly Val Ile Gly Pro Ala
            340                 345                 350

Thr Pro Thr Ala Ala Gln
        355

<210> SEQ ID NO 113
<211> LENGTH: 356
<212> TYPE: PRT
<213> ORGANISM: Gonium pectorale

<400> SEQUENCE: 113

Met Val Ser Met Thr Met Asn Asp Thr Leu Asn Gln Val Glu His Thr
1               5                   10                  15

Pro Val Asn Pro Pro His Lys Lys Val Leu Glu Leu Pro Gly Ile
            20                  25                  30

Ser Gly Gly Val Ala Arg Val Met Ile Gly Gln Pro Phe Asp Thr Ile
        35                  40                  45

Lys Val Arg Leu Gln Val Leu Gly Ala Gly Thr Ala Leu Ala Ala Lys
50                  55                  60

Leu Pro Pro Ser Glu Val Tyr Lys Asp Ser Met Asp Cys Val Arg Lys
65                  70                  75                  80

Met Ile Arg Thr Glu Gly Pro Leu Ser Phe Tyr Lys Gly Thr Val Ala
                85                  90                  95

Pro Leu Ile Gly Asn Met Ile Leu Leu Gly Ile His Phe Pro Thr Phe
                100                 105                 110
```

```
Ser Ser Val Arg Lys Gln Leu Glu Gly Asp Asp His Tyr Ser Asn Phe
        115                 120                 125

Ser Tyr Thr Asn Thr Leu Ile Ala Gly Ala Ala Gly Ala Ala Gly
    130                 135                 140

Ser Leu Val Ser Thr Pro Val Glu Leu Val Arg Thr Lys Met Gln Met
145                 150                 155                 160

Gln Arg Arg Ala Ala Leu Ala Gly Ser Val Gly Ser Ala Ala Ser
                165                 170                 175

Ser Gly Ala Glu Glu Phe Tyr Lys Gly Ser Val Asp Cys Phe Lys Gln
                180                 185                 190

Val Leu Ser Lys His Gly Ile Lys Gly Leu Tyr Arg Gly Phe Thr Ser
                195                 200                 205

Thr Val Leu Arg Asp Met Gln Gly Tyr Ala Trp Phe Phe Leu Gly Tyr
    210                 215                 220

Glu Ala Thr Val Asn Tyr Phe Leu Gln Asn Ala Gly Pro Gly Val His
225                 230                 235                 240

Ser Lys Ala Asp Leu Asn Tyr Leu Gln Val Met Ala Ala Gly Val Val
                245                 250                 255

Ala Gly Phe Gly Leu Trp Gly Ser Met Phe Pro Ile Asp Thr Ile Lys
                260                 265                 270

Ser Lys Met Gln Ala Asp Ser Leu Ala Lys Pro Gln Tyr Thr Thr Thr
                275                 280                 285

Met Asp Cys Leu Arg Lys Val Leu Lys Thr Glu Gly Gln Val Gly Leu
    290                 295                 300

Trp Arg Gly Phe Ser Ala Ala Met Tyr Arg Ala Ile Pro Val Asn Ala
305                 310                 315                 320

Gly Ile Phe Leu Ala Val Glu Gly Ser Arg Gln Gly Ile Lys Trp Tyr
                325                 330                 335

Glu Glu Asn Val Glu His Ile Tyr Gly Gly Val Val Gly Ala Ala Pro
                340                 345                 350

Gly Ala Ala Ser
        355

<210> SEQ ID NO 114
<211> LENGTH: 354
<212> TYPE: PRT
<213> ORGANISM: Gonium pectorale

<400> SEQUENCE: 114

Met Ser Ser Met Thr Val Asn Asp Thr Leu Asn Glu Val Glu His Thr
1               5                   10                  15

Pro Lys Asp Pro Pro His Lys Arg Val Leu Glu Leu Pro Gly Ile
            20                  25                  30

Ser Gly Gly Val Ala Arg Val Met Ile Gly Gln Pro Phe Asp Thr Ile
        35                  40                  45

Lys Thr Arg Leu Gln Val Leu Gly Ala Gly Thr Ala Leu Ala Ala Lys
        50                  55                  60

Leu Pro Pro Ser Glu Val Tyr Lys Asp Ser Met Asp Cys Val Arg Lys
65                  70                  75                  80

Met Val Arg Ser Glu Gly Pro Leu Ser Phe Tyr Lys Gly Thr Val Ala
                85                  90                  95

Pro Leu Phe Gly Asn Met Ile Leu Leu Gly Ile His Phe Pro Val Phe
            100                 105                 110

Ser His Val Arg Lys Gln Leu Glu Gly Asp Asp His Tyr Ser Asn Phe
```

```
            115                 120                 125
Ser Tyr Thr Asn Ala Leu Ile Ser Gly Ala Ala Gly Ala Ala Gly
        130                 135                 140

Ser Leu Val Ser Thr Pro Val Glu Leu Val Arg Thr Lys Met Gln Met
145                 150                 155                 160

Gln Arg Arg Ala Ala Leu Ala Gly Ser Ala Gly Ser Ala Ala Ala Ser
                165                 170                 175

Ser Gly Ala Glu Val Phe Tyr Lys Gly Ser Val Asp Cys Phe Lys Gln
            180                 185                 190

Val Leu Ser Lys His Gly Val Lys Gly Leu Tyr Arg Gly Val Thr Ser
        195                 200                 205

Thr Val Leu Arg Asp Met Gln Gly Tyr Ala Trp Phe Phe Leu Gly Tyr
    210                 215                 220

Glu Ala Thr Val Asn Tyr Phe Leu Gln Asn Ala Gly Pro Gly Val His
225                 230                 235                 240

Ser Lys Ala Asp Leu Asn Tyr Leu Gln Val Met Ala Ala Gly Val Val
                245                 250                 255

Ala Gly Phe Gly Leu Trp Gly Ser Met Phe Pro Ile Asp Thr Ile Lys
            260                 265                 270

Ser Lys Met Gln Ala Asp Ser Leu Val Lys Pro Gln Tyr Ser Thr Thr
        275                 280                 285

Tyr Asp Cys Val Arg Lys Val Leu Lys Thr Glu Gly Asn Asn Gly Leu
    290                 295                 300

Trp Arg Gly Phe Ser Ala Ala Met Tyr Arg Ala Ile Pro Val Asn Ala
305                 310                 315                 320

Gly Ile Phe Leu Ala Val Glu Ala Thr Arg Gln Gly Ile Lys Leu Tyr
                325                 330                 335

Glu Glu Asn Val Glu His Ile Tyr Gly Gly Val Val Gly Thr Thr Thr
            340                 345                 350

Ala Ala

<210> SEQ ID NO 115
<211> LENGTH: 339
<212> TYPE: PRT
<213> ORGANISM: Volvox carteri

<400> SEQUENCE: 115

Met Asn Asp Thr Leu Asn Gln Val Glu His Thr Pro Pro Val His Lys
1               5                   10                  15

Arg Ile Leu Asp Ile Leu Pro Gly Ile Ser Gly Gly Val Ala Arg Val
                20                  25                  30

Met Ile Gly Gln Pro Phe Asp Thr Ile Lys Val Arg Leu Gln Val Leu
            35                  40                  45

Gly Gln Gly Thr Ala Leu Ala Ala Gln Leu Pro Pro Ser Glu Val Tyr
        50                  55                  60

Lys Asp Ser Leu Asp Cys Val Arg Lys Met Val Arg Asn Glu Gly Pro
65                  70                  75                  80

Leu Ser Phe Tyr Lys Gly Thr Val Ala Pro Leu Val Gly Asn Met Val
                85                  90                  95

Leu Leu Gly Ile His Phe Pro Thr Phe Ser Tyr Val Arg Lys Gln Leu
            100                 105                 110

Glu Gly Asp Asp His Tyr Thr Asn Phe Ser Tyr Thr Asn Thr Leu Leu
        115                 120                 125

Ser Gly Ala Ala Ala Gly Ala Ala Gly Ser Leu Val Ser Thr Pro Val
```

```
            130                 135                 140
Glu Leu Val Arg Thr Lys Met Gln Leu Gln Ser Ala Ala Ser Ser Ala
145                 150                 155                 160

Ser Asp Glu Phe Tyr Lys Gly Ser Val Asp Cys Phe Lys Gln Val Leu
                165                 170                 175

Ser Lys Tyr Gly Ile Lys Gly Leu Tyr Arg Gly Phe Thr Ala Thr Val
            180                 185                 190

Leu Arg Asp Met Gln Gly Tyr Ala Trp Phe Phe Leu Gly Tyr Glu Ser
        195                 200                 205

Thr Val Asn Tyr Phe Leu Gln Lys Ala Gly Pro Gly Leu His Ser Lys
    210                 215                 220

Ala Asp Leu Asn Tyr Met Gln Val Met Ser Ala Gly Val Val Ala Gly
225                 230                 235                 240

Phe Gly Leu Trp Gly Ser Met Phe Pro Ile Asp Thr Val Lys Ser Lys
                245                 250                 255

Leu Gln Ala Asp Thr Leu Ala Thr Pro Gln Tyr Arg Ser Thr Tyr Asp
            260                 265                 270

Cys Leu Ser Lys Val Leu Lys Ser Glu Gly Gln Ala Gly Leu Trp Arg
        275                 280                 285

Gly Phe Ser Ala Ala Met Tyr Arg Ala Ile Pro Val Asn Ala Gly Ile
    290                 295                 300

Phe Leu Ala Val Glu Gly Thr Arg Gln Gly Ile Lys Trp Tyr Glu Glu
305                 310                 315                 320

Asn Val Glu His Leu Tyr Gly Gly Val Val Gly Pro Ala Thr Pro Ala
                325                 330                 335

Ala Thr Ser

<210> SEQ ID NO 116
<211> LENGTH: 353
<212> TYPE: PRT
<213> ORGANISM: Ettlia oleoabundans

<400> SEQUENCE: 116

Met Pro Ala Thr Ala Gln Val Met Asn Asp Thr Leu Met Glu Val Glu
1               5                   10                  15

His Thr Pro Pro Val His Lys Arg Ile Leu Asp Ile Leu Pro Gly Val
                20                  25                  30

Ser Gly Gly Val Ala Arg Ile Met Val Gly Gln Pro Phe Asp Thr Ile
            35                  40                  45

Lys Thr Arg Leu Gln Val Leu Gly Lys Gly Thr Ile Gly Ala Ala Gly
        50                  55                  60

Met Pro Pro Glu Met Val Tyr Asn Ser Gly Met Asp Cys Val Arg Lys
65                  70                  75                  80

Met Met Lys Ser Glu Gly Pro Met Ser Leu Tyr Lys Gly Thr Val Ala
                85                  90                  95

Pro Leu Leu Gly Asn Met Val Leu Leu Gly Ile His Phe Pro Thr Phe
            100                 105                 110

Thr Lys Thr Arg Ala Tyr Leu Glu Ala Gly Asp Ala Pro Gly Ser Phe
        115                 120                 125

Ser Pro Trp Lys Ile Leu Ala Ala Gly Ala Ala Gly Ala Ala Gly
    130                 135                 140

Ser Val Val Ser Ser Pro Thr Glu Leu Ile Arg Thr Lys Met Gln Met
145                 150                 155                 160

Val Arg Lys Asn Asn Ile Leu Ala Gln Ile Lys Gly Ser Ala Ala Gly
```

```
                    165                 170                 175
Gly Leu Asn Pro Glu Glu Asn Tyr Lys Gly Asn Trp Asp Cys Ala Lys
                180                 185                 190

Lys Ile Phe Arg Asn His Gly Leu Arg Gly Met Tyr Ser Gly Tyr Leu
            195                 200                 205

Ser Thr Leu Leu Arg Asp Met Gln Gly Tyr Ala Trp Phe Phe Phe Gly
        210                 215                 220

Tyr Glu Ala Thr Ile His Tyr Leu Ala Gly Pro Gly Lys Thr Lys Ala
225                 230                 235                 240

Asp Leu Asp Tyr Ser Gln Val Met Leu Ala Gly Val Met Ala Gly Phe
                245                 250                 255

Gly Leu Trp Gly Ser Met Phe Pro Ile Asp Thr Ile Lys Ser Lys Ile
            260                 265                 270

Gln Ala Asp Ser Leu Ser Lys Pro Glu Phe Lys Gly Thr Leu Asp Cys
        275                 280                 285

Val Arg Arg Ser Val Gln Ile Glu Gly Tyr Gly Gly Leu Trp Arg Gly
290                 295                 300

Val Thr Ala Ala Leu Trp Arg Ala Ile Pro Val Asn Ala Ala Ile Phe
305                 310                 315                 320

Leu Ala Val Glu Gly Thr Arg Gln Leu Ile Ala Asp Thr Glu Glu Ser
                325                 330                 335

Ile Asp Ala Phe Val Asp Gln Val Ser Gly Lys Thr Ser Glu Ala Ala
            340                 345                 350

Leu

<210> SEQ ID NO 117
<211> LENGTH: 353
<212> TYPE: PRT
<213> ORGANISM: Chlorella sorokiniana

<400> SEQUENCE: 117

Met Val Ala Arg Thr Ile Asn Glu Thr Leu Met Glu Val Glu His Thr
1               5                   10                  15

Pro Pro Val His Lys Arg Val Leu Asp Val Leu Pro Gly Val Ser Gly
                20                  25                  30

Gly Val Thr Arg Val Leu Val Gly Gln Pro Phe Asp Thr Ile Lys Thr
            35                  40                  45

Arg Leu Gln Val Met Gly Gln Gly Thr Ala Leu Ala Lys Met Leu Pro
        50                  55                  60

Pro Ser Asp Val Tyr Ile Asn Ser Ser Asp Cys Leu Lys Lys Met Val
65                  70                  75                  80

Arg Asn Glu Gly Ala Leu Ser Leu Tyr Arg Gly Val Val Ala Pro Leu
                85                  90                  95

Leu Gly Asn Met Val Leu Gly Ile His Phe Pro Thr Phe Ser Asn
            100                 105                 110

Thr Arg Lys Tyr Leu Glu Ser Val Asp Ala Thr Pro Ala Gly Glu Phe
        115                 120                 125

Pro Tyr Trp Lys Val Leu Ala Ala Gly Gly Ala Ala Gly Leu Ala Gly
    130                 135                 140

Ser Phe Ile Ser Cys Pro Ser Glu His Ile Arg Thr Lys Met Gln Leu
145                 150                 155                 160

Gln Arg Arg Ala Ala Leu Ala Ala Gln Met Gly Leu Lys Ala Gln Gly
                165                 170                 175

Leu Glu Thr Tyr Lys Gly Ser Trp Asp Cys Ala Val Gln Ile Leu Arg
```

```
                180                 185                 190
Asn His Gly Ile Lys Gly Leu Tyr Arg Gly Met Thr Ser Thr Val Leu
            195                 200                 205

Arg Asp Ile Gln Gly Tyr Ala Trp Phe Phe Leu Cys Tyr Glu Ala Thr
210                 215                 220

Leu His Ala Leu Ala Gly Pro Ala His Thr Arg Ser Glu Leu Asp Tyr
225                 230                 235                 240

Lys His Val Leu Gly Ala Gly Val Met Ala Gly Phe Gly Leu Trp Gly
                245                 250                 255

Ser Met Phe Pro Ile Asp Thr Ile Lys Ser Lys Met Gln Gly Asp Ser
            260                 265                 270

Leu Ser Asn Pro Gln Tyr Arg Asn Thr Leu Asp Cys Leu Arg Gln Ser
        275                 280                 285

Val Ala Val Glu Gly Phe Gly Gly Leu Phe Arg Gly Phe Gly Ala Ala
    290                 295                 300

Met Tyr Arg Ala Ile Pro Val Asn Ala Gly Ile Phe Leu Ala Val Glu
305                 310                 315                 320

Gly Thr Arg Gln Leu Leu Asn Lys Tyr Glu Gly Tyr Ile Asp Glu Lys
                325                 330                 335

Leu Gly Ile Ser Val Pro Ala Ser Ala Thr Val Pro Ala Pro Ala
            340                 345                 350

Gln

<210> SEQ ID NO 118
<211> LENGTH: 352
<212> TYPE: PRT
<213> ORGANISM: Erigeron breviscapus

<400> SEQUENCE: 118

Met Pro Ala Thr Pro Gln Leu Met Asn Glu Thr Leu Met Glu Val Glu
1               5                   10                  15

His Thr Pro Ala Val His Lys Arg Ile Leu Asp Ile Leu Pro Gly Val
                20                  25                  30

Ser Gly Gly Val Ala Arg Ile Met Val Gly Gln Pro Phe Asp Thr Ile
            35                  40                  45

Lys Thr Arg Leu Gln Val Leu Gly Lys Gly Thr Ile Gly Ala Ala Gly
        50                  55                  60

Met Pro Pro Glu Met Val Tyr Thr Ser Gly Met Asp Cys Val Arg Lys
65                  70                  75                  80

Met Ile Lys Ser Glu Gly Pro Leu Ser Leu Tyr Lys Gly Thr Ile Ala
                85                  90                  95

Pro Leu Leu Gly Asn Met Val Leu Leu Gly Ile His Phe Pro Thr Phe
            100                 105                 110

His Lys Thr Arg Ala Tyr Leu Glu Arg Glu Asp Ala Pro Gly Thr His
        115                 120                 125

Thr Pro Trp Lys Ile Leu Ala Ala Gly Ala Thr Ala Gly Ala Ala Gly
    130                 135                 140

Ser Ile Val Ser Thr Pro Thr Glu Leu Ile Arg Thr Lys Met Gln Met
145                 150                 155                 160

Val Arg Lys Asn Asn Ile Leu Gln Gln Ile Lys Gly Ala Gly Ala Gly
                165                 170                 175

Gly Leu Asn Pro Glu Glu Asn Tyr Lys Gly Asn Trp Asp Cys Ala Lys
            180                 185                 190

Lys Ile Phe Arg Asn His Gly Val Arg Gly Leu Tyr Ser Gly Tyr Leu
```

```
              195                 200                 205
Ser Thr Leu Leu Arg Asp Met Gln Gly Tyr Ala Trp Phe Phe Gly
    210                 215                 220

Tyr Glu Ala Thr Ile His Tyr Leu Ala Gly Pro Gly Lys Thr Lys Ala
225                 230                 235                 240

Asp Leu Asp Tyr Thr Gln Val Met Leu Ala Gly Val Ile Ala Gly Phe
                245                 250                 255

Gly Leu Trp Gly Ser Met Phe Pro Ile Asp Thr Ile Lys Ser Lys Ile
            260                 265                 270

Gln Ala Asp Ser Leu Ser Lys Pro Glu Phe Lys Gly Thr Leu Asp Cys
        275                 280                 285

Leu Lys Arg Ser Leu Ala Val Glu Gly Gln Arg Gly Leu Trp Arg Gly
    290                 295                 300

Val Thr Ala Ala Leu Trp Arg Ala Ile Pro Val Asn Ala Ala Ile Phe
305                 310                 315                 320

Leu Ala Val Glu Gly Thr Arg Gln Leu Ile Ala Asp Thr Glu Glu Ser
                325                 330                 335

Val Asp Lys Phe Val Asn Asn Leu Thr Gly Lys Glu Thr Ala Ala Val
            340                 345                 350

<210> SEQ ID NO 119
<211> LENGTH: 354
<212> TYPE: PRT
<213> ORGANISM: Zea nicaraguensis

<400> SEQUENCE: 119

Met Pro Ile Ala Thr Gly Gln Val Met Asn Asp Thr Leu Met Glu Val
1               5                   10                  15

Glu His Thr Pro Pro Val His Lys Arg Ile Leu Asp Ile Leu Pro Gly
                20                  25                  30

Val Ser Gly Gly Val Ala Arg Ile Met Val Gly Gln Pro Phe Asp Thr
            35                  40                  45

Ile Lys Thr Arg Leu Gln Val Leu Gly Ala Gly Thr Ile Gly Ala Gln
        50                  55                  60

Gly Met Pro Ala Asp Met Val Tyr Asn Asn Gly Met Asp Cys Val Arg
65                  70                  75                  80

Lys Met Ile Lys Ser Glu Gly Pro Gly Ser Leu Tyr Lys Gly Thr Val
                85                  90                  95

Ala Pro Leu Leu Gly Asn Met Val Leu Gly Ile His Phe Pro Thr
            100                 105                 110

Phe Thr Lys Thr Arg Ala Tyr Leu Glu Gln Gly Asp Ala Pro Gly Thr
        115                 120                 125

Phe Ser Pro Trp Lys Ile Leu Ala Ala Gly Ala Ala Gly Ala Ala
    130                 135                 140

Gly Ser Val Val Ser Thr Pro Thr Glu Leu Ile Arg Thr Lys Met Gln
145                 150                 155                 160

Met Val Arg Lys Asn Asn Leu Met Ala Gln Met Lys Gly Ala Ala Ala
                165                 170                 175

Thr Leu Asn Pro Glu Glu Asn Tyr Lys Gly Asn Trp Asp Cys Ala Lys
            180                 185                 190

Lys Ile Leu Arg Asn His Gly Leu Arg Gly Ile Tyr Ser Gly Tyr Val
        195                 200                 205

Ser Thr Leu Leu Arg Asp Met Gln Gly Tyr Ala Trp Phe Phe Gly
    210                 215                 220
```

```
Tyr Glu Ala Thr Ile His Met Met Cys Thr Glu Gly Lys Thr Lys Ala
225                 230                 235                 240

Asp Leu Asn Phe Leu Gln Val Met Gly Ala Gly Val Ile Ala Gly Phe
            245                 250                 255

Gly Leu Trp Gly Ser Met Phe Pro Ile Asp Thr Ile Lys Ser Lys Ile
            260                 265                 270

Gln Ala Asp Ser Leu Ser Lys Pro Glu Phe Lys Gly Thr Met Asp Cys
            275                 280                 285

Leu Lys Arg Ser Leu Ala Val Glu Gly His Ala Gly Leu Trp Arg Gly
            290                 295                 300

Val Thr Ala Ala Leu Trp Arg Ala Ile Pro Val Asn Ala Ala Ile Phe
305                 310                 315                 320

Val Ala Val Glu Gly Thr Arg Gln Leu Ile Ala Asp Thr Glu Glu Ser
                325                 330                 335

Val Asp Ala Phe Val Asn Asn Leu Thr Gly Ser Gly Ser Thr Ala Ala
                340                 345                 350

Ala Val

<210> SEQ ID NO 120
<211> LENGTH: 141
<212> TYPE: PRT
<213> ORGANISM: Poa pratensis

<400> SEQUENCE: 120

Tyr Lys Gly Asn Trp Asp Cys Ala Lys Lys Ile Leu Arg Asn His Gly
1               5                   10                  15

Leu Arg Gly Ile Tyr Ser Gly Tyr Val Ser Thr Leu Leu Arg Asp Met
            20                  25                  30

Gln Gly Tyr Ala Trp Phe Phe Gly Tyr Glu Ala Thr Ile His Tyr
        35                  40                  45

Leu Ala Gly Gln His Gly Lys Thr Lys Ala Asp Leu Glu Tyr Trp Gln
    50                  55                  60

Val Met Gly Ala Gly Val Met Ala Gly Phe Gly Leu Trp Gly Ser Met
65                  70                  75                  80

Phe Pro Ile Asp Thr Ile Lys Ser Lys Ile Gln Ala Asp Ser Leu Ser
                85                  90                  95

Lys Pro Glu Phe Lys Gly Thr Ile Asp Cys Leu Lys Arg Ser Leu Ala
            100                 105                 110

Val Glu Gly Tyr Ala Gly Met Trp Arg Gly Val Thr Ala Ala Leu Trp
            115                 120                 125

Arg Ala Ile Pro Val Asn Ala Ala Ile Phe Leu Ala Val
        130                 135                 140

<210> SEQ ID NO 121
<211> LENGTH: 354
<212> TYPE: PRT
<213> ORGANISM: Cosmos bipinnatus

<400> SEQUENCE: 121

Met Pro Ser Ala Thr Pro Gln Val Ile Asn Asp Thr Leu Met Glu Val
1               5                   10                  15

Glu His Thr Pro Ala Val His Lys Arg Ile Leu Asp Ile Leu Pro Gly
            20                  25                  30

Val Ser Gly Gly Val Ala Arg Ile Met Val Gly Gln Pro Phe Asp Thr
        35                  40                  45

Ile Lys Thr Arg Leu Gln Val Leu Gly Lys Gly Thr Ile Gly Ala Lys
```

```
                    50                  55                  60
Gly Met Pro Ala Asp Met Val Tyr Asn Asn Gly Met Asp Cys Val Arg
 65                  70                  75                  80

Lys Met Ile Lys Ser Glu Gly Ala Gly Ser Leu Tyr Lys Gly Thr Val
                 85                  90                  95

Ala Pro Leu Leu Gly Asn Met Val Leu Leu Gly Ile His Phe Pro Thr
            100                 105                 110

Phe Thr Lys Thr Arg Ala Tyr Leu Glu Gln Gly Asp Ala Pro Gly Thr
        115                 120                 125

Phe Ser Pro Ala Lys Ile Leu Ala Ala Gly Ala Ala Gly Ala Ala
        130                 135                 140

Gly Ser Val Val Ser Thr Pro Thr Glu Leu Ile Arg Thr Lys Met Gln
145                 150                 155                 160

Met Val Arg Lys Asn Asn Ile Leu Ala Gln Met Lys Gly Ala Ala Ala
                165                 170                 175

Thr Leu Asn Pro Glu Glu Asn Tyr Lys Gly Asn Trp Asp Cys Ala Lys
            180                 185                 190

Lys Ile Leu Arg Asn His Gly Leu Arg Gly Ile Tyr Ser Gly Tyr Val
        195                 200                 205

Ser Thr Leu Leu Arg Asp Met Gln Gly Tyr Ala Trp Phe Phe Phe Gly
    210                 215                 220

Tyr Glu Ala Thr Ile His Met Met Cys Thr Asp Gly Lys Thr Lys Ala
225                 230                 235                 240

Asp Leu Asn Phe Leu Gln Val Met Gly Ala Gly Val Ile Ala Gly Phe
                245                 250                 255

Gly Leu Trp Gly Ser Met Phe Pro Ile Asp Thr Ile Lys Ser Lys Ile
            260                 265                 270

Gln Ala Asp Ser Leu Ser Lys Pro Glu Phe Lys Gly Thr Met Asp Cys
        275                 280                 285

Leu Lys Arg Ser Leu Ala Val Glu Gly His Ala Gly Leu Trp Arg Gly
    290                 295                 300

Val Thr Ala Ala Leu Trp Arg Ala Ile Pro Val Asn Ala Ala Ile Phe
305                 310                 315                 320

Val Ala Val Glu Gly Thr Arg Gln Leu Ile Ala Asp Thr Glu Glu Ser
                325                 330                 335

Val Asp Ala Phe Val Asn Asn Leu Thr Gly Ser Ser Thr Thr Ala
            340                 345                 350

Ala Val

<210> SEQ ID NO 122
<211> LENGTH: 297
<212> TYPE: PRT
<213> ORGANISM: Glycine max

<400> SEQUENCE: 122

Met Gly Asp Val Ala Lys Asp Leu Thr Ala Gly Thr Val Gly Gly Ala
 1               5                  10                  15

Ala Gln Leu Ile Val Gly His Pro Phe Asp Thr Ile Lys Val Lys Leu
                20                  25                  30

Gln Ser Gln Pro Thr Pro Leu Pro Gly Gln Leu Pro Lys Tyr Ser Gly
            35                  40                  45

Ala Ile Asp Ala Val Lys Gln Thr Val Ala Ala Glu Gly Pro Arg Gly
        50                  55                  60

Leu Tyr Lys Gly Met Gly Ala Pro Leu Ala Thr Val Ala Ala Phe Asn
```

```
            65                  70                  75                  80
    Ala Val Leu Phe Thr Val Arg Gly Gln Met Glu Ala Leu Leu Arg Ser
                    85                  90                  95

His Pro Gly Ala Thr Leu Thr Ile Asn Gln Gln Val Val Cys Gly Ala
                    100                 105                 110

Gly Ala Gly Val Ala Val Ser Phe Leu Ala Cys Pro Thr Glu Leu Ile
                    115                 120                 125

Lys Cys Arg Leu Gln Ala Gln Ser Val Leu Ala Gly Thr Gly Thr Ala
                    130                 135                 140

Ala Val Ala Val Lys Tyr Gly Pro Met Asp Val Ala Arg Gln Val
    145                 150                 155                 160

Leu Arg Ser Glu Gly Val Lys Gly Leu Phe Lys Gly Leu Val Pro
                    165                 170                 175

Thr Met Ala Arg Glu Val Pro Gly Asn Ala Ala Met Phe Gly Val Tyr
                    180                 185                 190

Glu Ala Leu Lys Arg Leu Leu Ala Gly Gly Thr Asp Thr Ser Gly Leu
                    195                 200                 205

Gly Arg Gly Ser Leu Met Leu Ala Gly Val Ala Gly Ala Ala Phe
                    210                 215                 220

Trp Leu Met Val Tyr Pro Thr Asp Val Val Lys Ser Val Ile Gln Val
    225                 230                 235                 240

Asp Asp Tyr Lys Asn Pro Lys Phe Ser Gly Ser Ile Asp Ala Phe Arg
                    245                 250                 255

Arg Ile Ser Ala Ser Glu Gly Ile Lys Gly Leu Tyr Lys Gly Phe Gly
                    260                 265                 270

Pro Ala Met Ala Arg Ser Val Pro Ala Asn Ala Ala Cys Phe Leu Ala
                    275                 280                 285

Tyr Glu Met Thr Arg Ser Ala Leu Gly
                    290                 295

<210> SEQ ID NO 123
<211> LENGTH: 296
<212> TYPE: PRT
<213> ORGANISM: Zea mays

<400> SEQUENCE: 123

Met Gly Asp Val Ala Lys Asp Leu Thr Ala Gly Thr Val Gly Gly Ala
    1               5                   10                  15

Ala Asn Leu Ile Val Gly His Pro Phe Asp Thr Ile Lys Val Lys Leu
                    20                  25                  30

Gln Ser Gln Pro Thr Pro Ala Pro Gly Gln Leu Pro Lys Tyr Ala Gly
                    35                  40                  45

Ala Ile Asp Ala Val Lys Gln Thr Val Ala Ala Glu Gly Pro Arg Gly
                    50                  55                  60

Leu Tyr Lys Gly Met Gly Ala Pro Leu Ala Thr Val Ala Ala Phe Asn
    65                  70                  75                  80

Ala Val Leu Phe Ser Val Arg Gly Gln Met Glu Ala Phe Leu Arg Ser
                    85                  90                  95

Glu Pro Gly Val Pro Leu Thr Val Lys Gln Gln Val Val Ala Gly Ala
                    100                 105                 110

Gly Ala Gly Ile Ala Val Ser Phe Leu Ala Cys Pro Thr Glu Leu Ile
                    115                 120                 125

Lys Cys Arg Leu Gln Ala Gln Ser Ser Leu Ala Glu Ala Ala Thr Ala
                    130                 135                 140
```

Ser Gly Val Ala Leu Pro Lys Gly Pro Ile Asp Val Ala Lys His Val
145                 150                 155                 160

Val Arg Asp Ala Gly Ala Lys Gly Leu Phe Lys Gly Leu Val Pro Thr
                165                 170                 175

Met Gly Arg Glu Val Pro Gly Asn Ala Leu Met Phe Gly Val Tyr Glu
            180                 185                 190

Ala Thr Lys Gln Tyr Leu Ala Gly Gly Pro Asp Thr Ser Gly Leu Gly
        195                 200                 205

Arg Gly Ser Gln Val Leu Ala Gly Leu Ala Gly Ala Ala Phe Trp
        210                 215                 220

Leu Ser Val Tyr Pro Thr Asp Val Val Lys Ser Val Ile Gln Val Asp
225                 230                 235                 240

Asp Tyr Lys Lys Pro Lys Tyr Ser Gly Ser Leu Asp Ala Leu Arg Lys
                245                 250                 255

Ile Val Ala Ala Asp Gly Val Lys Gly Leu Tyr Lys Gly Phe Gly Pro
                260                 265                 270

Ala Met Ala Arg Ser Val Pro Ala Asn Ala Ala Thr Phe Val Ala Tyr
            275                 280                 285

Glu Ile Thr Arg Ser Ala Leu Gly
        290                 295

<210> SEQ ID NO 124
<211> LENGTH: 296
<212> TYPE: PRT
<213> ORGANISM: Oryza sativa

<400> SEQUENCE: 124

Met Gly Asp Val Val Lys Asp Leu Val Ala Gly Thr Val Gly Gly Ala
1               5                   10                  15

Ala Asn Leu Ile Val Gly His Pro Phe Asp Thr Ile Lys Val Lys Leu
                20                  25                  30

Gln Ser Gln Pro Thr Pro Ala Pro Gly Gln Phe Pro Lys Tyr Ala Gly
            35                  40                  45

Ala Val Asp Ala Val Lys Gln Thr Ile Ala Thr Glu Gly Pro Arg Gly
        50                  55                  60

Leu Tyr Lys Gly Met Gly Ala Pro Leu Ala Thr Val Ala Ala Phe Asn
65                  70                  75                  80

Ala Leu Leu Phe Thr Val Arg Gly Gln Met Glu Ala Leu Leu Arg Ser
                85                  90                  95

Glu Pro Gly Gln Pro Leu Thr Val Asn Gln Gln Val Val Ala Gly Ala
            100                 105                 110

Gly Ala Gly Val Ala Val Ser Phe Leu Ala Cys Pro Thr Glu Leu Ile
        115                 120                 125

Lys Cys Arg Leu Gln Ala Gln Ser Ala Leu Ala Glu Ala Ala Ala Ala
    130                 135                 140

Ser Gly Val Ala Leu Pro Lys Gly Pro Ile Asp Val Ala Lys His Val
145                 150                 155                 160

Val Arg Glu Ala Gly Met Lys Gly Leu Phe Lys Gly Leu Val Pro Thr
                165                 170                 175

Met Gly Arg Glu Val Pro Gly Asn Ala Val Met Phe Gly Val Tyr Glu
            180                 185                 190

Gly Thr Lys Gln Tyr Leu Ala Gly Gly Gln Asp Thr Ser Asn Leu Gly
        195                 200                 205

Arg Gly Ser Leu Ile Leu Ser Gly Gly Leu Ala Gly Ala Val Phe Trp
    210                 215                 220

```
Leu Ser Val Tyr Pro Thr Asp Val Val Lys Ser Val Ile Gln Val Asp
225                 230                 235                 240

Asp Tyr Lys Lys Pro Arg Tyr Ser Gly Ser Val Asp Ala Phe Lys Lys
            245                 250                 255

Ile Leu Ala Ala Asp Gly Val Lys Gly Leu Tyr Lys Gly Phe Gly Pro
            260                 265                 270

Ala Met Ala Arg Ser Val Pro Ala Asn Ala Ala Thr Phe Leu Ala Tyr
            275                 280                 285

Glu Ile Thr Arg Ser Ala Leu Gly
            290                 295
```

<210> SEQ ID NO 125
<211> LENGTH: 324
<212> TYPE: PRT
<213> ORGANISM: Triticum aestivum

<400> SEQUENCE: 125

```
Met Glu Phe Trp Pro Glu Phe Leu Ala Ser Ser Gly Gly His Glu Phe
1               5                   10                  15

Val Ala Gly Gly Val Gly Gly Met Ala Gly Val Leu Ala Gly His Pro
            20                  25                  30

Leu Asp Thr Leu Arg Ile Arg Leu Gln Gln Pro Pro Arg Pro Val Ser
        35                  40                  45

Pro Gly Ile Thr Ala Ala Arg Val Thr Arg Pro Pro Ser Ala Val Ala
    50                  55                  60

Leu Leu Arg Gly Ile Leu Arg Ala Glu Gly Pro Ser Ala Leu Tyr Arg
65                  70                  75                  80

Gly Met Gly Ala Pro Leu Ala Ser Val Ala Phe Gln Asn Ala Met Val
                85                  90                  95

Phe Gln Val Tyr Ala Ile Leu Ser Arg Ser Leu Asp Arg Arg Met Ser
            100                 105                 110

Thr Ser Glu Pro Pro Ser Tyr Thr Ser Val Ala Leu Ala Gly Val Gly
        115                 120                 125

Thr Gly Ala Leu Gln Thr Leu Ile Leu Ser Pro Val Glu Leu Val Lys
    130                 135                 140

Ile Arg Leu Gln Leu Glu Ala Ala Gly Arg Lys Arg Gln Gly Pro Val
145                 150                 155                 160

Asp Met Ala Arg Asp Ile Met Arg Arg Glu Gly Leu Arg Gly Ile Tyr
                165                 170                 175

Arg Gly Leu Thr Val Thr Ala Leu Arg Asp Ala Pro Ser His Gly Val
            180                 185                 190

Tyr Phe Trp Thr Tyr Glu Tyr Ala Arg Glu Arg Leu His Pro Gly Cys
        195                 200                 205

Arg Arg Thr Gly Gln Glu Ser Leu Ala Thr Met Leu Val Ser Gly Gly
    210                 215                 220

Leu Ala Gly Val Ala Ser Trp Val Cys Cys Tyr Pro Leu Asp Val Val
225                 230                 235                 240

Lys Ser Arg Leu Gln Ala Gln Thr Gln Thr His Pro Ser Pro Arg
                245                 250                 255

Tyr Arg Gly Val Val Asp Cys Phe Arg Lys Ser Val Arg Glu Glu Gly
            260                 265                 270

Leu Pro Val Leu Trp Arg Gly Leu Gly Thr Ala Val Ala Arg Ala Phe
        275                 280                 285

Val Val Asn Gly Ala Ile Phe Ser Ala Tyr Glu Leu Ala Leu Arg Phe
```

```
                290                 295                 300
Leu Val Arg Asn Asn Gly Arg Gln Thr Leu Val Met Glu Glu Met Lys
305                 310                 315                 320

Cys His Asp His

<210> SEQ ID NO 126
<211> LENGTH: 296
<212> TYPE: PRT
<213> ORGANISM: Sorghum bicolor

<400> SEQUENCE: 126

Met Gly Asp Val Ala Arg Asp Leu Thr Ala Gly Thr Val Gly Gly Val
1               5                   10                  15

Ala Asn Leu Val Val Gly His Pro Phe Asp Thr Ile Lys Val Lys Leu
            20                  25                  30

Gln Ser Gln Pro Thr Pro Ala Pro Gly Gln Leu Pro Lys Tyr Ala Gly
        35                  40                  45

Ala Ile Asp Ala Val Lys Gln Thr Ile Ala Ala Glu Gly Pro Arg Gly
    50                  55                  60

Leu Tyr Lys Gly Met Gly Ala Pro Leu Ala Thr Val Ala Ala Phe Asn
65                  70                  75                  80

Ala Leu Leu Phe Ser Val Arg Gly Gln Met Glu Ala Leu Leu Arg Ser
                85                  90                  95

Glu Pro Gly Val Pro Leu Thr Val Lys Gln Val Val Ala Gly Ala
            100                 105                 110

Gly Ala Gly Ile Ala Val Ser Phe Leu Ala Cys Pro Thr Glu Leu Ile
        115                 120                 125

Lys Cys Arg Leu Gln Ala Gln Ser Ser Leu Ala Glu Ala Ala Ala
    130                 135                 140

Ser Gly Val Ala Leu Pro Lys Gly Pro Ile Asp Val Ala Lys His Val
145                 150                 155                 160

Val Arg Asp Ala Gly Ala Lys Gly Leu Phe Lys Gly Leu Val Pro Thr
                165                 170                 175

Met Gly Arg Glu Val Pro Gly Asn Ala Met Met Phe Gly Val Tyr Glu
            180                 185                 190

Ala Thr Lys Gln Tyr Leu Ala Gly Gly Pro Asp Thr Ser Asn Leu Gly
        195                 200                 205

Arg Gly Ser Gln Ile Leu Ala Gly Leu Ala Gly Ala Ala Phe Trp
    210                 215                 220

Leu Ser Val Tyr Pro Thr Asp Val Val Lys Ser Val Ile Gln Val Asp
225                 230                 235                 240

Asp Tyr Lys Lys Pro Arg Tyr Ser Gly Ser Leu Asp Ala Leu Arg Lys
                245                 250                 255

Ile Val Ala Ala Asp Gly Val Lys Gly Leu Tyr Lys Gly Phe Gly Pro
            260                 265                 270

Ala Met Ala Arg Ser Val Pro Ala Asn Ala Ala Thr Phe Val Ala Tyr
        275                 280                 285

Glu Ile Thr Arg Ser Ala Leu Gly
    290                 295

<210> SEQ ID NO 127
<211> LENGTH: 323
<212> TYPE: PRT
<213> ORGANISM: Solanum tuberosum

<400> SEQUENCE: 127
```

Met Cys Asp Glu Leu Ser Arg Cys Leu Ile Trp Cys Cys Leu Arg Ser
1               5                   10                  15

Ala Ser Ile Ser Pro Ile Ser Val Phe Ser Gln Met Asp Ile Met Lys
            20                  25                  30

Asp Leu Thr Ala Gly Thr Val Gly Ala Ala Gln Leu Ile Val Gly
        35                  40                  45

His Pro Phe Asp Thr Ile Lys Val Lys Leu Gln Ser Gln Pro Thr Pro
    50                  55                  60

Leu Pro Gly Gln Pro Pro Lys Tyr Ala Gly Ala Ile Asp Ala Val Arg
65              70                  75                  80

Lys Thr Val Ala Ser Glu Gly Pro Arg Gly Leu Tyr Lys Gly Met Gly
                85                  90                  95

Ala Pro Leu Ala Thr Val Ala Ala Phe Asn Ala Leu Leu Phe Thr Val
            100                 105                 110

Arg Gly Gln Thr Glu Ala Leu Leu Arg Ser Glu Pro Gly Ala Pro Leu
        115                 120                 125

Thr Val Lys Gln Gln Ile Leu Cys Gly Ala Val Ala Gly Thr Ala Ala
    130                 135                 140

Ser Phe Leu Ala Cys Pro Thr Glu Leu Ile Lys Cys Arg Leu Gln Ala
145                 150                 155                 160

His Ser Ala Leu Ala Ser Val Gly Ser Ala Ser Val Ala Ile Lys Tyr
                165                 170                 175

Thr Gly Pro Met Asp Val Ala Arg His Val Leu Arg Ser Glu Gly Gly
            180                 185                 190

Val Arg Gly Leu Phe Lys Gly Met Cys Pro Thr Leu Ala Arg Glu Val
        195                 200                 205

Pro Gly Asn Ala Val Met Phe Gly Val Tyr Glu Ala Leu Lys Gln Tyr
    210                 215                 220

Phe Ala Gly Gly Met Asp Thr Ser Gly Leu Gly Arg Gly Ser Leu Ile
225                 230                 235                 240

Val Ala Gly Gly Leu Ala Gly Gly Ser Val Trp Phe Ala Val Tyr Pro
                245                 250                 255

Thr Asp Val Ile Lys Ser Val Ile Gln Val Asp Asp Tyr Arg Ser Pro
            260                 265                 270

Lys Tyr Ser Gly Ser Phe Asp Ala Leu Lys Lys Ile Leu Ala Ser Glu
        275                 280                 285

Gly Val Lys Gly Leu Tyr Lys Gly Phe Gly Pro Ala Ile Thr Arg Ser
    290                 295                 300

Ile Pro Ala Asn Ala Ala Cys Phe Leu Ala Tyr Glu Met Thr Arg Ser
305                 310                 315                 320

Ser Leu Gly

<210> SEQ ID NO 128
<211> LENGTH: 15178
<212> TYPE: DNA
<213> ORGANISM: Artificial Sequence
<220> FEATURE:
<223> OTHER INFORMATION: Synthetic construct vector pMBX074

<400> SEQUENCE: 128
gcgtataatg gactattgtg tgctgataag gagaacataa gcgcagaaca atatgtatct    60
attccggtgt tgtgttcctt tgttattctg ctattatgtt ctcttatagt gtgacgaaag   120
cagcataatt aatcgtcact tgttctttga ttgtgttacg atatccagag acttagaaac   180

```
gggggaaccg ggatgagcaa ggtaaaaatc ggtgagttga tcaacacgct tgtgaatgag    240
gtagaggcaa ttgatgcctc agaccgccca caaggcgaca aaacgaagag aattaaagcc    300
gcagccgcac ggtataagaa cgcgttattt aatgataaaa gaaagttccg tgggaaagga    360
ttgcagaaaa gaataaccgc gaatactttt aacgcctata tgagcagggc aagaaagcgg    420
tttgatgata aattacatca tagctttgat aaaaatatta ataaattatc ggaaaagtat    480
cctctttaca gcgaagaatt atcttcatgg ctttctatgc ctacggctaa tattcgccag    540
cacatgtcat cgttacaatc taaattgaaa gaataatgc cgcttgccga agagttatca    600
aatgtaagaa taggctctaa aggcagtgat gcaaaaatag caagactaat aaaaaaatat    660
ccagattgga gttttgctct tagtgattta acagtgatg attggaagga gcgccgtgac    720
tatctttata agttattcca acaaggctct gcgttgttag aagaactaca ccagctcaag    780
gtcaaccatg aggttctgta ccatctgcag ctaagccctg cggagcgtac atctatacag    840
caacgatggg ccgatgttct cgcgagaag aagcgtaatg ttgtggttat tgactaccca    900
acatacatgc agtctatcta tgatattttg aataatcctg cgactttatt tagtttaaac    960
actcgttctg gaatggcacc tttggccttt gctctggctg cggtatcagg gcgaagaatg   1020
attgagataa tgtttcaggg tgaatttgcc gtttcaggaa agtatacggt taatttctca   1080
gggcaagcta aaaacgctc tgaagataaa agcgtaacca gaacgattta actttatgc   1140
gaagcaaaat tattcgttga attattaaca gaattgcgtt cttgctctgc tgcatctgat   1200
ttcgatgagg ttgttaaagg atatggaaag gatgatacaa ggtctgagaa cggcaggata   1260
aatgctattt tagcaaaagc atttaaccct tgggttaaat catttttcgg cgatgaccgt   1320
cgtgtttata agatagccg cgctatttac gctcgcatcg cttatgagat gttcttccgc   1380
gtcgatccac ggtggaaaaa cgtcgacgag gatgtgttct tcatggagat tctcggacac   1440
gacgatgaga acacccagct gcactataag cagttcaagc tggccaactt ctccagaacc   1500
tggcgacctg aagttgggga tgaaaacacc aggctggtgg ctctgcagaa actggacgat   1560
gaaatgccag gctttgccag aggtgacgct ggcgtccgtc tccatgaaac cgttaagcag   1620
ctggtgggagc aggacccatc agcaaaaata accaacagca ctctccgggc ctttaaattt   1680
agcccgacga tgattagccg gtacctggag tttgccgctg atgcattggg gcagttcgtt   1740
ggcgagaacg ggcagtggca gctgaagata gagacacctg caatcgtcct gcctgatgaa   1800
gaatccgttg agaccatcga cgaaccggat gatgagtccc aagacgacga gctggatgaa   1860
gatgaaattg agctcgacga gggtggcggc gatgaaccaa ccgaagagga agggccagaa   1920
gaacatcagc caactgctct aaaacccgtc ttcaagcctg caaaaaataa cggggacgga   1980
acgtacaaga tagagtttga atacgatgga aagcattatg cctggtccgg ccccgccgat   2040
agccctatgg ccgcaatgcg atccgcatgg gaaacgtact acagctaaaa gaaaagccac   2100
cggtgttaat cggtggcttt tttattgagg cctgtcccta cccatcccct gcaagggacg   2160
gaaggattag gcggaaactg cagctgcaac tacggacatc gccgtcccga ctgcagggac   2220
ttccccgcgt aaagcggggc ttaaattcgg gctggccaac cctattttc tgcaatcgct   2280
ggcgatgtta gttcgtggaa tagcgtttcc agcttttcaa tggccagctc aaaatgtgct   2340
ggcagcacct tctccagttc cgtatcaata tcggtgatcg gcagctctcc acaagacata   2400
ctccggcgac cgccacgaac tacatcgcgc agcagctccc gttcgtagac acgcatgttg   2460
cccagagccg tttctgcagc cgttaatatc cggcgcagct cggcgatgat tgccgggaga   2520
tcatccacgg ttattgggtt cggtgatggg ttcctgcagg cgcggcggag agccatccag   2580
```

```
acgccgctaa cccatgcgtt acggtactga aaactttgtg ctatgtcgtt tatcaggccc    2640
cgaagttctt ctttctgccg ccagtccagt ggttcaccgg cgttcttagg ctcaggctcg    2700
acaaaagcat actcgccgtt tttccggata gctggcagaa cctcgttcgt cacccacttg    2760
cggaaccgcc aggctgtcgt ccctgtttc accgcgtcgc ggcagcggag gattatggtg    2820
tagagaccag attccgatac cacatttact tccctggcca tccgatcaag tttttgtgcc    2880
tcggttaaac cgagggtcaa ttttcatca tgatccagct tacgcaatgc atcagaaggg    2940
ttggctatat tcaatgcagc acagatatcc agcgccacaa accacgggtc accaccgaca    3000
agaaccaccc gtatagggtg gctttcctga aatgaaaaga cggagagagc cttcattgcg    3060
cctccccgga tttcagctgc tcagaaaggg acagggagca gccgcgagct tcctgcgtga    3120
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcggtg gatatgggat tttttgtccg tgcggacgac    3420
agctgcaaat ttgaatttga acatggtatg cattcctatc ttgtataggg tgctaccacc    3480
agagttgaga atctctatag gggtggtagc ccagacaggg ttctcaacac cggtacaaga    3540
agaaaccggc ccaaccgaag ttggccccat ctgagccacc ataattcagg tatgcgcaga    3600
tttaacacac aaaaaaacac gctggcgcgt gttgtgcgct tcttgtcatt cggggttgag    3660
aggcccggct gcagattttg ctgcagcggg gtaactctac cgccaaagca gaacgcacgt    3720
caataattta ggtggatatt ttaccccgtg accagtcacg tgcacaggtg tttttatagt    3780
ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc cagaacgtcg    3960
catcacgacg ttccatccat tcggtattgt cgacgacctg gtaagcgtat tgtcctggcg    4020
tttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat cattttttgt agatcatgcg ccactattca    4500
cccccactgg ccatcagcaa ataaagcttc tactcggac accggcaggc ggcttccacg    4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttttctctt cggcctcaat    4740 agcccggatg cggttatcgc acagctcgcg acagtactttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
```

```
tcactatctg agaacccgtt catccgaatg atcgtgaatg gaagttcccg gccagtttta    4980
taatcgctat agcttgtcgc gtcgtggctg accttgacca cataagggtc gtagccctcc    5040
acgatgacaa ggcattcccg ttgttttccc attaccccct cggttatatc gccacggctt    5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtggggc gtccggaacg tgctctgttt    5340
tggatcgagg gttaccatgt atatctatat ttagatccaa atcgcgatcc acttcgatgg    5400
tggttttttc caccttacgt gcgtgaattg ataaaccggc ctcgcggcgc ttctccacga    5460
tattcatgag gaactcgacc gagtccgggt caatggaacg catcgtgggg cgtgcatcgc    5520
cgtctctggc gcgtctggtc ttactggata gccccataga ctccaggatg cctatgcaga    5580
ggtctgcagg cgcttcttc ttgcctttct ctgtgttgaa gccgccgatg cgtaaaacgt    5640
tgtttagcag atcgcgccgt tccggcgtga gcaggttatc tctggcgcgt ttgagggcgt    5700
ccatgtctgc ttcaccttcc agggttttg gatcgatacc gcagtcgcgg aagtactgct    5760
gcagcgtcgc cgatttgagg gtgtagaaac cacgcatgcc tatctcaaca gcaggggtcg    5820
atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact tttttcaggc cgccgtcgaa atagaatttt aacgccacct    6060
cgtcgacatc cagctgcagc tccttttcga tgtcccagcg gaccagctgg gcctgctcat    6120
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgattttt tccggatcgg tttcacgttt accgcgaagc ttgtcgaaac    6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900
gattttctc ggtataaaat acgcggatag gcttgttggt ttcgcggttg cgaacgtcga    6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
```

```
cggctttcgc gcctttccct tcggtcatca tttcatgcag gccgcctatc agggatacgc    7380
ggtgcgcgac ggaaacgcca cgcgtggact gcagcatcag tggacgcagg aggcctgtcg    7440
atttacccga ccccatcccg gcgcggacaa taacgatgcc ctgcagctgt gcggcgtatg    7500
tcatcacctc atcggtcatc ctggaggttt caaaccgttt gtaagtgatg tgtgacgggc    7560
gaaggttcgg gttggtgatg cgttcactga acgaacgtga tgtttgcgcg gcacggcatt    7620
tgcgattcaa ccggcgcgta atgtgatctt taacggtacc gttataaatt tctgcgatac    7680
ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacagatcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat ttgcgcagcc gggtacatgt    8100
tcaccagctc ctcgacaacg tgaatcatgt tgttagcgga aaccgcaatg actaccgcgt    8160
caaagcgttt tttcgggtcg tttctggtcg ccagccagat ggatgccccg gtggcgaaac    8220
cctctgcagt cgcaattttt tgcgccccct gcaggtcgcc aataacaaag catgcaccga    8280
cgaaatcacc gttagtgatg gcgctggtct ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attccctttt ttaccgcata aggccaggag ccatcttcag    8520
ctggcgaatg ttcccaggcg cgatggaaag ccaaccatcc aagcaggcgt tcctgctcca    8580
tctgattgtt ttttaaatca ttaacgcgtt gttgttcagc tcggaggcgg cgtgcttcag    8640
cctggcgctc catgcgtgca cgttcttctt ccggctgagc gaccacggtc gcaccattcc    8700
gttgctgttc acggcgatac tccgaaaaca ggaatgaaaa gccactccag gagccagcgt    8760
catgcgcttt ttcaacgaag ttaacgaaag gataactgat gccatccttg ctctgctcaa    8820
ggcgtgaata gatttccaca cggcctttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcattt    9060
tttagccttt ccatgcgaat tagcattttt tcggttgaa aaaatccgca ggagcagcca    9120
caataaacgc actatctttc tgaaggacgt atctgcgtta tcgtggctac ttcctgaaaa    9180
aggcccgagt ttgccgactc gggtttttt tcgtcttttt tcggctgcta cggtctggtt    9240
caaccccgac aaagtataga tcggattaaa ccagaattat agtcagcaat aaaccctgtt    9300
attgtatcat ctaccctcaa ccatgaacga tttgatcgta ccgactactt ggtgcacaaa    9360
ttgaagatca ctttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
```

```
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttggacgcc cggaagagag attcctacag cttctgccac    9840
ttgcttcagc gtcagtttca gctctaaacg gcgtgctttc agtcgttcgc ctcgtgtttt    9900
cataccctta atcataaatg atctctttat agctggctat aatttttata aattatacct    9960
agctttaatt ttcacttatt gattataata atccccatga aacccgaaga acttgtgcgc   10020
catttcggcg atgtggaaaa agcagcggtt ggcgtgggcg tgacacccgg cgcagtctat   10080
caatggctgc aagctgggga gattccacct ctacgacaaa gcgatataga ggtccgtacc   10140
gcgtacaaat taagagtga tttcacctct cagcgcatgg gtaaggaagg gcataacagg   10200
ggatcctcta gacgcagaaa ggcccacccg aaggtgagcc agtgtgatta catttgcggc   10260
ctaactgtgg ccagtccagt tacgctggag tcactagtgc ggccgcgaca acttgtctag   10320
ggcccatggc aatcccacaa aaatctgagc ttaacagcac agttgctcct ctcagagcag   10380
aatcgggtat tcaacaccct catatcaact actacgttgt gtataacggt ccacatgccg   10440
gtatatacga tgactggggt tgtacaaagg cggcaacaaa cggcgttccc ggagttgcac   10500
acaagaaatt tgccactatt acagaggcaa gagcagcagc tgacgcgtac acaacaagtc   10560
agcaaacaga caggttgaac ttcatcccca aaggagaagc tcaactcaag cccaagagct   10620
ttgctaaggc cctaacaagc ccaccaaagc aaaaagccca ctggctcacg ctaggaacca   10680
aaaggcccag cagtgatcca gccccaaaag agatctcctt tgccccggag attacaatgg   10740
acgatttcct ctatctttac gatctaggaa ggaagttcga aggtgaaggt gacgacacta   10800
tgttcaccac tgataatgag aaggttagcc tcttcaattt cagaaagaat gctgacccac   10860
agatggttag agaggcctac gcagcaggtc tcatcaagac gatctaccog agtaacaatc   10920 tccaggagat caaatacctt cccaagaagg ttaaagatgc agtcaaaaga ttcaggacta   10980
attgcatcaa gaacacagag aaagacatat ttctcaagat cagaagtact attccagtat   11040
ggacgattca aggcttgctt cataaaccaa ggcaagtaat agagattgga gtctctaaaa   11100
aggtagttcc tactgaatct aaggccatgc atggagtcta agattcaaat cgaggatcta   11160
acagaactcg ccgtgaagac tggcgaacag ttcatacaga gtcttttacg actcaatgac   11220
aagaagaaaa tcttcgtcaa catggtggag cacgacactc tggtctactc caaaaatgtc   11280
aaagatacag tctcagaaga ccaaagggct attgagactt ttcaacaaag gataaatttcg   11340 ggaaacctcc tcggattcca ttgcccagct atctgtcact tcatcgaaag gacagtagaa   11400
aaggaaggtg gctcctacaa atgccatcat tgcgataaag gaaaggctat cattcaagat   11460
ctctctgccg acagtggtcc caaagatgga cccccaccca cgaggagcat cgtggaaaaa   11520
gaagacgttc caaccacgtc ttcaaagcaa gtggattgat gtgacatctc cactgacgta   11580
agggatgacg cacaatccca ctatccttcg caagacccct tcctctatata aggaagttca   11640 tttcatttgg agaggacacg cccgggaaaa tgtctagtga tgccatgacc atcaatgagt   11700
ctcttatgga agtcgaacat actccagctg tgcataaaag gattcttgac attttaccgg   11760
gtatcagtgg cggggttgcc agagttatga taggtcagcc cttcgacaca atcaaagtgc   11820
gtctacaagt gttggggcag ggtacggctc tcgctgccaa acttcctcct agtgaagttt   11880
acaaggacag catggattgc attcgtaaga tgattaagtc ggagggtcca ctaagctttt   11940
acaagggaac agttgcccca ctcgtcggaa acatggtatt gctggcatc cattttccgg   12000 tcttttccgc ggttagaaag cagttggagg gtgatgatca ttactctaac ttttcacacg   12060
```

```
ccaatgtact gcttagcggc gctgcggcag gagctgcggg atcactcatt tcggctcctg    12120
ttgaactggt tagaacgaaa atgcaaatgc aaggcgagc cgcacttgcg ggtacagtgg     12180
ctgctggtgc agctgcatct gctggagctg aggagttcta aagggaagt cttgattgtt    12240 tcaaacaagt tatgtctaag catgggatta aaggattgta tagggtttt acttcaacta    12300 tactacgaga tatgcagggt tatgcttggt tcttcctcgg atatgaggcg actgtcaatc    12360
acttcttgca aaatgcggga ccaggtgttc ataccaaggc tgacttgaat taccttcaag    12420
tgatggccgc tggggttgtt gctggatttg gattatgggg ctccatgttt ccaatcgata    12480
ccatcaaatc taaactccaa gccgatagct ttgccaaacc tcaatattca tccacaatgg    12540
attgtcttaa gaaagtatta gcaagtgagg acaggccgg cttgtggaga gggttcagcg     12600
cagcaatgta tagagcaata ccggtgaacg ctggcatttt cctcgctgtt gaagggacac    12660
gtcagggtat aaagtggtac gaggaaaacg tggaacacat ctacggaggt gtcattggtc    12720
ccgctacgcc tactgcagca caatgagcgg ccgcgtttct ccataataat gtgtgagtag    12780
ttcccagata agggaattag ggttcctata gggtttcgct catgtgttga gcatataaga    12840
aacccttagt atgtatttgt atttgtaaaa tacttctatc aataaaattt ctaattccta    12900
aaaccaaaat ccagtactaa aatccagatc ccccgaatta attcggcgtt aattcagggg    12960
ccattagact tgaagtcaag cggccgctta caactggacc ttgctggtac atagaactga    13020
ttaactgacc atttaaatca taccaacatg gtcaaataaa acgaaaggct cagtcgaaag    13080
actgggcctt tcgttttaat ctgatcggca cgtaagaggt tccaactttc accataatga    13140
aataagatca ctaccgggcg tatttttgag ttatcgagat tttcaggagc taaggaagct    13200
aaaatgagcc atattcaacg ggaaacgtct tgctcgaggc cgcgattaaa ttccaacatg    13260
gatgctgatt tatatgggta taaatgggct cgcgataatg tcgggcaatc aggtgcgaca    13320
atctatcgat tgtatgggaa gcccgatgcg ccagagttgt ttctgaaaca tggcaaaggt    13380
agcgttgcca atgatgttac agatgagatg gtcaggctaa actggctgac ggaatttatg    13440
cctcttccga ccatcaagca tttttatccgt actcctgatg atgcatggtt actcaccact    13500
gcgatcccag ggaaaacagc attccaggta ttagaagaat atcctgattc aggtgaaaat    13560
attgttgatg cgctggcagt gttcctgcgc cggttgcatt cgattcctgt ttgtaattgt    13620
ccttttaacg cgatcgcgt atttcgtctc gctcaggcgc aatcacgaat gaataacggt    13680
ttggttggtg cgagtgattt tgatgacgag cgtaatggct ggcctgttga caagtctgg    13740 aaagaaatgc ataaacttt gccattctca ccggattcag tcgtcactca tggtgatttc    13800
tcacttgata accttatttt tgacgagggg aaattaatag gttgtattga tgttggacga    13860
gtcggaatcg cagaccgata ccaggatctt gccatcctat ggaactgcct cggtgagttt    13920
tctccttcat tacagaaacg ctttttcaa aaatatggta ttgataatcc tgatatgaat    13980
aaattgcagt ttcacttgat gctcgatgag ttttctaac ctaggtgaca gaagtcaaaa    14040
gcctccggtc ggaggctttt gactttctgc tagatctgtt tcaatgcggt gaagggccag    14100
gcagctgggg attatgtcga gacccggcca gcatgttggt tttatcgcat attcagcgtt    14160
gtcgcgttta cccaggtaaa atggaagcag tgtatcgtct gcgtgaatgt gcaaatcagg    14220
aacgtaaccg tggtacatag atgcagtccc ttgcgggtcg ttcccttcaa cgagtatgac    14280
gcggtgccct tgcaaggcta accattgcgc ctggtgtact gcagatgagg ttttataaac    14340
ccctcccttg tgtgacataa cggaaagtac aaccgggttt ttatcgtcag gtcttggtt    14400
```

| | |
|---|---|
| tgggttacca aacacactcc gcatatggct aatttggtca attgtgtagc cagcgcgacg | 14460 |
| ttctactcgg cccctcatct caaaatcagg agccggtaga cgaccagctt tttccgcgtc | 14520 |
| tctgatagcc tgcggtgtta cgccgatcag gtctgcaact tctgttatac cccagcggcg | 14580 |
| agtaatacga cgcgcttccg ggctgtcatc gccgaactgt gcgatggcaa tagcgcgcgt | 14640 |
| catttcctga ccgcgattga tacagtcttt cagcaaatta attaacgaca tcctgtttcc | 14700 |
| tctcaaacat gccctatct ttgtgtttttt catcatactt tacgtttttta aagcaaagca | 14760 |
| acataaaaaa agcaaagtga cttagaaaac gcaaagttaa ggttcaaatc aatttttga | 14820 |
| tgcgctacag aagctattta gcttcatcta agcgcaacgg tattacttac gttggtatat | 14880 |
| ttaaaaccta acttaatgat tttaaatgat aataaatcat accaattgct atcaaaagtt | 14940 |
| aagcgaacat gctgattttc acgctgttta tacactttga gcatctcta tctcttccgt | 15000 |
| ctctatattg aaacacaatc aaagaacatc aatccatgtg acatccccca ctatctaaga | 15060 |
| acaccataac agaacacaac ataggaatgc aacattaatg tatcaataat tcggaacata | 15120 |
| tgcactatat catatctcaa ttacggaaca tatcagcaca caattgccca ttatacgc | 15178 |

<210> SEQ ID NO 129
<211> LENGTH: 2269
<212> TYPE: DNA
<213> ORGANISM: Artificial Sequence
<220> FEATURE:
<223> OTHER INFORMATION: Synthetic construct vector pMBXO92

<400> SEQUENCE: 129

| | |
|---|---|
| aagcttgcca acatggtgga gcacgacact ctcgtctact ccaagaatat caaagataca | 60 |
| gtctcagaag accaaagggc tattgagact tttcaacaaa gggtaatatc gggaaacctc | 120 |
| ctcggattcc attgcccagc tatctgtcac ttcatcaaaa ggacagtaga aaaggaaggt | 180 |
| ggcacctaca aatgccatca ttgcgataaa ggaaaggcta tcgttcaaga tgcctctgcc | 240 |
| gacagtggtc ccaaagatgg accccacacc acgaggagca tcgtgaaaaa agaagacgtt | 300 |
| ccaaccacgt cttcaaagca agtggattga tgtgaacatg gtggagcacg acactctcgt | 360 |
| ctactccaag aatatcaaag atacagtctc agaagaccaa agggctattg agacttttca | 420 |
| acaaagggta atatcgggaa acctcctcgg attccattgc ccagctatct gtcacttcat | 480 |
| caaaaggacc aagtggattg atgtgaacat ggtggagcac gacactctcg tctactccaa | 540 |
| gaatatcaaa gatacagtct cagaagacca aagggctatt gagacttttc aacaaagggt | 600 |
| aatatcggga aacctcctcg gattccattg cccagctatc tgtcacttca tcaaaaggac | 660 |
| agtagaaaag gaaggtggca cctacaaatg ccatcattgc gataaaggaa aggctatcgt | 720 |
| tcaagatgcc tctgccgaca gtggtcccaa agatggaccc ccaccacga ggagcatcgt | 780 |
| ggaaaaagaa gacgttccaa ccacgtcttc aaagcaagtg gattgatgtg atatctccac | 840 |
| tgacgtaagg gatgacgcac aatcccacta ccttgcgcaa gacccttcct ctatataagg | 900 |
| aagttcattt catttggaga ggacacgctg aaatcaccag tctctctcta caaatctatc | 960 |
| tctctcgagc tttcgcgagc tcggtaccaa aatgtcctca gacgctatga ccattaatga | 1020 |
| gagcttgatg gaggttgaac acacacctgc cgtgcataaa aggatcctcg atattttgcc | 1080 |
| tggaatatca gggggagttg ctagagttat gatagggcaa ccttttgata caattaaggt | 1140 |
| cagactgcag gttttgggcc aaggtacagc cttggcagct aagttgcccc catctgaagt | 1200 |
| gtataaagac tctatggact gcatcagaaa aatgattaaa tctgagggc cattgtcatt | 1260 |
| ctataaggga accgtggctc ccttggttgg caatatggtc cttttgggaa tccatttccc | 1320 |

```
tgtgttttcc gcagtcagaa agcaactgga aggagatgat cattatagta acttttccca    1380
tgctaatgtt ttgctgtccg gggctgccgc tggggctgct ggctcactca tctccgctcc    1440
cgttgaactg gttagaacca agatgcagat gcagaggcgc gcagccctcg ccggaactgt    1500
tgccgctggt gctgctgcat ctgctggcgc cgaagagttt tacaaaggga gtctcgactg    1560
tttcaaacag gtaatgtcaa agcatgggat taaaggtctt tatagggat ttacttccac     1620
aatactcaga gacatgcaag gttatgcttg gttttttttg gggtatgagg ctactgtcaa    1680
ccacttcctt caaaatgctg gccctggtgt tcataccaaa gcagacctca attaccttca    1740
agtcatggct gccggcgtgg tcgccggttt gggctttgg ggtagtatgt tcccaatcga     1800
taccattaag agcaaactcc aagctgattc tttcgccaag cctcaataca gttccactat    1860
ggattgtttg aaaaaagtgc ttgcctcaga gggacaagca ggtttgtgga ggggttttag    1920
tgccgctatg tatagggcta ttcctgttaa cgcagggatt ttttggcag tggagggaac     1980
caggcaagga attaagtggt acgaggaaaa cgtggagcat atctacggag gcgtgattgg    2040
acctgctacc cctactgccg ctcagtaagg catgcaagct cgagtttctc cataataatg    2100
tgtgagtagt tcccagataa gggaattagg gttcctatag ggtttcgctc atgtgttgag    2160
catataagaa acccttagta tgtatttgta tttgtaaaat acttctatca ataaaatttc    2220
taattcctaa aaccaaaatc cagtactaaa atccagatcc cccgaattc                2269
```

<210> SEQ ID NO 130
<211> LENGTH: 14758
<212> TYPE: DNA
<213> ORGANISM: Artificial Sequence
<220> FEATURE:
<223> OTHER INFORMATION: Synthetic construct vector pMBX075

<400> SEQUENCE: 130

```
gcgtataatg gactattgtg tgctgataag gagaacataa gcgcagaaca atatgtatct      60
attccggtgt tgtgttcctt tgttattctg ctattatgtt ctcttatagt gtgacgaaag     120
cagcataatt aatcgtcact tgttctttga ttgtgttacg atatccagag acttagaaac     180
gggggaaccg ggatgagcaa ggtaaaaatc ggtgagttga tcaacacgct tgtgaatgag     240
gtagaggcaa ttgatgcctc agaccgccca caaggcgaca aaacgaagag aattaaagcc     300
gcagccgcac ggtataagaa cgcgttattt aatgataaaa gaagttccg tgggaagga      360
ttgcagaaaa gaataaccgc gaatactttt aacgcctata tgagcagggc aagaaagcgg     420
tttgatgata aattacatca tagctttgat aaaaatatta taaattatc ggaaaagtat      480
cctctttaca gcgaagaatt atcttcatgg ctttctatgc ctacggctaa tattcgccag     540
cacatgtcat cgttacaatc taaattgaaa gaataatgc cgcttgccga agagttatca      600
aatgtaagaa taggctctaa aggcagtgat gcaaaaatag caagactaat aaaaaaatat     660
ccagattgga gttttgctct tagtgattta acagtgatg attggaagga gcgccgtgac      720
tatctttata agttattcca acaaggctct gcgttgttag aagaactaca ccagctcaag     780
gtcaaccatg aggttctgta ccatctgcag ctaagccctg cggagcgtac atctatacag     840
caacgatggg ccgatgttct gcgcgagaag aagcgtaatg ttgtggttat tgactaccca    900
acatacatgc agtctatcta tgatatttg aataatcctg cgactttatt tagtttaaac      960
actcgttctg gaatggcacc tttggccttt gctctggctg cggtatcagg gcgaagaatg    1020
attgagataa tgtttcaggg tgaatttgcc gtttcaggaa agtatacggt taatttctca    1080
```

-continued

```
gggcaagcta aaaaacgctc tgaagataaa agcgtaacca gaacgattta tactttatgc      1140
gaagcaaaat tattcgttga attattaaca gaattgcgtt cttgctctgc tgcatctgat      1200
ttcgatgagg ttgttaaagg atatggaaag gatgatacaa ggtctgagaa cggcaggata      1260
aatgctattt tagcaaaagc atttaaccct tgggttaaat cattttttcgg cgatgaccgt     1320 cgtgttata aagatagccg cgctatttac gctcgcatcg cttatgagat gttcttccgc      1380
gtcgatccac ggtggaaaaa cgtcgacgag gatgtgttct tcatggagat tctcggacac      1440
gacgatgaga acacccagct gcactataag cagttcaagc tggccaactt ctccagaacc      1500
tggcgacctg aagttgggga tgaaaacacc aggctggtgg ctctgcagaa actggacgat      1560
gaaatgccag gctttgccag aggtgacgct ggcgtccgtc tccatgaaac cgttaagcag      1620
ctggtggagc aggacccatc agcaaaaata accaacagca ctctccgggc ctttaaattt      1680
agcccgacga tgattagccg gtacctggag tttgccgctg atgcattggg gcagttcgtt      1740
ggcgagaacg ggcagtggca gctgaagata gagacacctg caatcgtcct gcctgatgaa      1800
gaatccgttg agaccatcga cgaaccggat gatgagtccc aagacgacga gctggatgaa      1860
gatgaaattg agctcgacga gggtggcggc gatgaaccaa ccgaagagga agggccagaa      1920
gaacatcagc caactgctct aaaacccgtc ttcaagcctg caaaaaataa cggggacgga      1980
acgtacaaga tagagtttga atacgatgga aagcattatg cctggtccgg ccccgccgat      2040
agccctatgg ccgcaatgcg atccgcatgg gaaacgtact acagctaaaa gaaaagccac      2100
cggtgttaat cggtggcttt tttattgagg cctgtcccta cccatcccct gcaagggacg      2160
gaaggattag gcgaaaactg cagctgcaac tacgacatcc gccgtcccga ctgcagggac      2220
ttccccgcgt aaagcggggc ttaaattcgg gctggccaac cctattttc tgcaatcgct      2280 ggcgatgtta gttcgtggaa tagcgttccc agcttttcaa tggccagctc aaaatgtgct      2340
ggcagcacct tctccagttc cgtatcaata tcggtgatcg gcagctctcc acaagacata      2400
ctccggcgac cgccacgaac tacatcgcgc agcagctccc gttcgtagac acgcatgttg      2460
cccagagccg tttctgcagc cgttaatatc cggcgcagct cggcgatgat tgccgggaga      2520
tcatccacgg ttattgggtt cggtgatggg ttcctgcagg cgcggcggag agccatccag      2580
acgccgctaa cccatgcgtt acggtactga aaactttgtg ctatgtcgtt tatcaggccc      2640
cgaagttctt ctttctgccg ccagtccagt ggttcaccgg cgttcttagg ctcaggctcg      2700
acaaaagcat actcgccgtt tttccggata gctggcagaa cctcgttcgt cacccacttg      2760
cggaaccgcc aggctgtcgt cccctgtttc accgcgtcgc ggcagcggag gattatggtg      2820
tagagaccag attccgatac cacatttact tccctggcca tccgatcaag ttttttgtgcc      2880 tcggttaaac cgagggtcaa ttttttcatca tgatccagct tacgcaatgc atcagaaggg      2940
ttggctatat tcaatgcagc acagatatcc agcgccacaa accacgggtc accaccgaca      3000
agaaccaccc gtatagggtg gctttcctga aatgaaaaga cggagagagc cttcattgcg      3060
cctccccgga tttcagctgc tcagaaaggg acagggagca gccgcgagct tcctgcgtga      3120
gttcgcgcgc gacctgcaga agttccgcag cttcctgcaa atacagcgtg gcctcataac      3180
tggagatagt gcggtgagca gagcccacaa gcgcttcaac ctgcagcagg cgttcctcaa      3240
tcgtctccag caggccctgg gcgtttaact gaatctggtt catgcgatca cctcgctgac      3300
cgggatacgg gctgacagaa cgaggacaaa acggctggcg aactggcgac gagcttctcg      3360 ctcgatgat gcaatggtgg aaaggcggtg gatatgggat ttttttgtccg tgcggacgac       3420 agctgcaaat ttgaatttga acatggtatg cattcctatc ttgtataggg tgctaccacc      3480
```

```
agagttgaga atctctatag gggtggtagc ccagacaggg ttctcaacac cggtacaaga   3540
agaaaccggc ccaaccgaag ttggccccat ctgagccacc ataattcagg tatgcgcaga   3600
tttaacacac aaaaaaacac gctggcgcgt gttgtgcgct tcttgtcatt cggggttgag   3660
aggcccggct gcagattttg ctgcagcggg gtaactctac cgccaaagca gaacgcacgt   3720
caataattta ggtggatatt ttaccccgtg accagtcacg tgcacaggtg tttttatagt   3780
ttgctttact gactgatcag aacctgatca gttattggag tccggtaatc ttattgatga   3840
ccgcagccac cttagatgtt gtctcaaacc ccatacggcc acgaatgagc cactggaacg   3900
gaatagtcag caggtacagc ggaacgaacc acaaacggtt cagacgctgc agaacgtcg    3960 catcacgacg ttccatccat tcggtattgt cgacgacctg gtaagcgtat tgtcctggcg   4020
tttttgctgc ttccgagtag caatcctctt caccacaaag aaagttactt atctgcttcc   4080
agttttcgaa cccttcttct ttgagccgct tttccagctc attcctccac aaaacaggca   4140
cccatcctct gcgataaatc atgattattt gtcctttaaa taaggctgta gaactgcaaa   4200
atcgctctcg ttcacatgct gtacgtagat gcgtagcaaa ttgccgttcc atccctgtaa   4260
tccaccttct ttggaaagat cgtccttgac ctcacgaaga accttatcca atagccctgc   4320
ggcacaagaa attgcctgct ctggatcagc aaattcatat tgattaatag gtgattgcca   4380
cacaccaaaa acaggaatca tctttttcggc taaacgcctc tcctgttctt tcttaatctc   4440
aagttgtaag cggaccagct caccatccat catttttgt agatcatgcg ccactattca    4500
cccccactgg ccatcagcaa ataaagcttc atactcggac accggcaggc ggcttccacg   4560
gattgaaagg tcaagccaac cacgtccaga tgggtcagcc ttatccgatt cttcccaccg   4620
ttctgcagct gtagcaacca ggcattctac cgccttcatg tagtcttctg tacggaacca   4680
gccgtagtta atgccaccat cagtaactgc ccaggccatc ttttctctt cggcctcaat    4740 agcccggatg cggttatcgc acagctcgcg acagtacttc agctgttcgt aatccagttg   4800
cttcaggaac tctggtgtcg acgtcatagt ggcttcacct tataggcttt tagaagcgcc   4860
ctggcttcgt ctgtgtggtc ttccatgctc ttatcgctgg caatgcagca ataaactccc   4920
tcactatctg agaacccgtt catccgaatg atcgtgaatg gaagttcccg gccagttta    4980 taatcgctat agcttgtcgc gtcgtggctg accttgacca cataagggtc gtagccctcc   5040
acgatgacaa ggcattcccg ttgttttccc attacccctc cggttatatc gccacggctt   5100
gccgctggct tagaaacgct ttcagcagcc ttatttcgcg tactgatagc aggtccataa   5160
attcggtcat gtacagcgag gcgaacgttc tcgcgatgct ggccactggc cacaggcgta   5220
ccgcctccat ttcggttgct ggcaacgcgt tctccgccca cgcctccggt accgccaccg   5280
ggatagcctc cagtgcctgg ataattactg attgtgggc gtccggaacg tgctctgttt    5340
tggatcgagg gttaccatgt atatctatat ttagatccaa atcgcgatcc acttcgatgg   5400 tggtttttc cacccttacgt gcgtgaattg ataaaccggc ctcgcggcgc ttctccacga   5460
tattcatgag gaactcgacc gagtccgggt caatggaacg catcgtgggg cgtgcatcgc   5520
cgtctctggc gcgtctggtc ttactggata gccccataga ctccaggatg cctatgcaga   5580
ggtctgcagg cgctttcttc ttgcctttct ctgtgttgaa gccgccgatg cgtaaaacgt   5640
tgtttagcag atcgcgccgt tccggcgtga gcaggttatc tctggcgcgt ttgagggcgt   5700
ccatgtctgc ttccaccttcc agggttttg gatcgatacc gcagtcgcgg aagtactgct   5760
gcagcgtcgc cgatttgagg gtgtagaaac cacgcatgcc tatctcaaca gcaggggtcg   5820
```

```
atttcactcg gtaatcggtt atggccggga atttagcctg gaactctgcg tcggcctgtt    5880
cccgcgtcat ggccgtagtg acgaactgct gccatcttcc ggcaacgcga taagcgtagg    5940
taaagtgaat caacgcttct tcacggtcaa ggcgacgggc ggttatctca tccagctgca    6000
tggtttcaaa caggcgcact ttttcaggc cgccgtcgaa atagaatttt aacgccacct     6060
cgtcgacatc cagctgcagc tccttttcga tgtcccagcg gaccagctgg gcctgctcat    6120
ccagggacag ggtgcgtttt tttatcaact catcgtgttc ggcctggtca ggagtatcga    6180
cactcaggtg gcgctccata agctgctcaa agaccagttc acgggcttct ttacgtaaat    6240
ccttaccgat gctgtttgca agcgcgtcgg tggcccatagg cgcgacctga tagccatcat    6300
catgcatgat gcaaatcatg ttgctggcat aatcatttct ggccgatgcc tcgagcgcgg    6360
cggctttaat tttgagctgc atgaatgaag agttagccac gccgagtgaa attcggtcac    6420
cgtcaaagac aacgtctgtc agcagcccgg agtggccagc cgtttcgagc aaggcctgcg    6480
cgtaggcgcg tttgattttt tccgatcgg tttcacgttt accgcgaagc ttgtcgaaac      6540
cgataatgta ttcctgagct gtacggtcgc ggcgcagcat ctggatggcg tcgctgggga    6600
ccacttcgcc gcagaacatg ccgaaatggc ggtggaagtg tttctcctca atcgatacac    6660
ctgaagatat cgacgggctg tagatgaggc cgtcatattt tttcaccatc actttaggct    6720
ggttggtgaa atcgtcgact tccttctcct gtttgttttt ctggttaacg cagagaaact    6780
ttttgtcagg gaactgtagt ctcagctgca tggtaacgtc ttcggcgaac gtcgaactgt    6840
cggtggccag catgattcgt tcgccgcgtt gcactgcagc gataacctcg gtcatgatcc    6900
gatttttctc ggtataaaat acgcggatag gcttgttggt ttcgcggttg cgaacgtcga    6960
ccgggagttc aatcacgtga atttgcagcc aggcaggtag gcccagctcc tcgcgtcgct    7020
tcatcgccag ttcagccagg tcaacaagca gatcgttggc atcggcatcc accataatgg    7080
catgctcttc agtacgcgcc agcgcgtcga taagcgtgtt gaatacgcct accgggtttt    7140
ccatcgcacg cccggccaga atggcacgca ggccctgtgt tgcttcatcg aagccgaaga    7200
agtcatgctg gcgcatcagc ggttgccagc agcctttaag tatggagttg atgcaaatag    7260
tcagcttgtt ggcatatggc gccatttcct gatagccggg atcctgataa tgcagaatgt    7320
cggctttcgc gccttccct tcggtcatca tttcatgcag gccgcctatc agggatacgc      7380
ggtgcgcgac ggaaacgcca cgcgtggact gcagcatcag tggacgcagg aggcctgtcg    7440
atttacccga ccccatcccg cgcggacaa taacgatgcc ctgcagctgt gcggcgtatg      7500
tcatcacctc atcggtcatc ctggaggttt caaaccgttt gtaagtgatg tgtgacgggc    7560
gaaggttcgg gttggtgatg cgttcactga acgaacgtga tgtttgcgcg gcacggcatt    7620
tgcgattcaa ccggcgcgta atgtgatctt taacggtacc gttataaatt ctgcgatac     7680
ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacagatcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat ttgcgcagcc gggtacatgt    8100
tcaccagctg ctcgacaacg tgaatcatgt tgttagcgga aaccgcaatg actaccgcgt    8160
caaagcgttt tttcgggtcg tttctggtcg ccagccagat ggatgccccg gtggcgaaac    8220
```

```
cctctgcagt cgcaattttt tgcgcccct gcaggtcgcc aataacaaag catgcaccga   8280
cgaaatcacc gttagtgatg gcgctggtct ggaacttgcc accattcaga tcgatacgtt   8340
gccagccaac aatccgcccg tcttttcttc cgtccaggtg ggacagaggt atcgccatgt   8400
aagttgttgg tccacggctc catttcgcac tgtcgtgact ggtcacgcga cgtatatcac   8460
aagcgccaaa tacgtcacga attccctttt ttaccgcata aggccaggag ccatcttcag   8520
ctggcgaatg ttcccaggcg cgatggaaag ccaaccatcc aagcaggcgt tcctgctcca   8580
tctgattgtt ttttaaatca ttaacgcgtt gttgttcagc tcggaggcgg cgtgcttcag   8640
cctggcgctc catgcgtgca cgttcttctt ccggctgagc gaccacggtc gcaccattcc   8700
gttgctgttc acggcgatac tccgaaaaca ggaatgaaaa gccactccag gagccagcgt   8760
catgcgcttt tcaacgaag ttaacgaaag gataactgat gccatccttg ctctgctcaa    8820
ggcgtgaata gatttccaca cggcctttaa ggctcttctg cagagcttcc ggggaggaat   8880
tattgtaggt ggtatagcgc tctacaccac cgcgcggatt gagctgaatc ttatcagcac   8940
acgcaggcca gttgataccg ccatcttcg ccagctcagt cagctcatca cgtgccgcgt    9000
caagcagtga aaacggatcg ctgccaaagc gctccgcgta gaattcttgt aaggtcattt   9060
tttagccttt ccatgcgaat tagcattttt tcggttgaa aaatccgca ggagcagcca     9120 caataaacgc actatctttc tgaaggacgt atctgcgtta tcgtggctac ttcctgaaaa   9180
aggcccgagt ttgccgactc gggttttttt tcgtcttttt tcggctgcta cggtctggtt   9240
caaccccgac aaagtataga tcggattaaa ccagaattat agtcagcaat aaaccctgtt   9300
attgtatcat ctaccctcaa ccatgaacga tttgatcgta ccgactactt ggtgcacaaa   9360
ttgaagatca cttttatcat ggataacccg ttgagagtta gcactatcaa ggtagtaatg   9420
ctgctcgtca taacgggcta atcgttgaat tgtgatctcg ccgttattat cacaaaccag   9480
tacatcctca cccggtacaa gcgtaagtga agaatcgacc aggataacgt ctcccggctg   9540
gtagtttcgc tgaatctggt tcccgaccgt cagtgcgtaa acggtgttcc gttgactcac   9600
gaacggcagg aatcgctctg tgttggcagg ttctccaggc tgccagtctc tatccggtcc   9660
ggtctctgtc gtaccaataa caggaacgcg gtctggatca gattcagtgc catacagtat   9720
ccattgcacg ggcttacgca ggcattttgc cagcgatagc ccgatctcca gcgacggcat   9780
cacgtcgcca cgttctaagt tttggacgcc cggaagagag attcctacag cttctgccac   9840
ttgcttcagc gtcagtttca gctctaaacg gcgtgctttc agtcgttcgc ctcgtgtttt   9900 catacccttaa tcataaatg atctctttat agctggctat aattttttata aattatacct   9960 agctttaatt ttcacttatt gattataata tccccatga acccgaaga acttgtgcgc    10020 catttcggcg atgtggaaaa agcagcggtt ggcgtgggcg tgacacccgg cgcagtctat   10080
caatggctgc aagctgggga gattccacct ctacgacaaa gcgatataga ggtccgtacc   10140
gcgtacaaat taaagagtga tttcacctct cagcgcatgg gtaaggaagg gcataacagg   10200
ggatcctcta gacgcagaaa ggcccacccg aaggtgagcc agtgtgatta catttgcggc   10260
ctaactgtgg ccagtccagt tacgctggag tcactagtgc ggccgcgaca acttgtctag   10320
ggcccaatgg cccgggactg gcgcgccgta cgtagtgttt atctttgttg cttttctgaa   10380
caatttattt actatgtaaa tatattatca atgtttaatc tattttaatt tgcacatgaa   10440
ttttcatttt atttttactt tacaaaacaa ataaatatat atgcaaaaaa atttacaaac   10500
gatgcacggg ttacaaacta atttcattaa atgctaatgc agattttgtg aagtaaaact   10560
```

```
ccaattatga tgaaaaatac caccaacacc acctgcgaaa ctgtatccca actgtcctta   10620
ataaaaatgt taaaaagtat attattctca tttgtctgtc ataatttatg taccccactt   10680
taattttcct gatgtactaa accgagggca aactgaaacc tgttcctcat gcaaagcccc   10740
tactcaccat gtatcatgta cgtgtcatca cccaacaact ccacttttgc tatataacaa   10800
cacccccgtc acactctccc tctctaacac acccccact  aacaattcct tcacttgcag   10860
cactgttgca tcatcatctt cattgcaaaa ccctaaactt caccttcaac cgcggccgcg   10920
gtaccaaaat gtcctcagat gcaatgacta tcaatgagag tctgatggaa gtcgagcaca   10980
cacctgccgt acataaaaga atccttgata ttctccccgg aatttctggc ggagtagcta   11040
gagttatgat tggacagcca ttcgatacaa ttaaagttag gctccaagtg cttggtcagg   11100
ggactgcact tgccgctaag cttcctcctt ctgaggtgta taaggattca atggattgca   11160
ttcgcaaaat gattaagtcc gaaggaccac tttcatttta caagggaaca gttgccccc    11220 ttgttggaaa tatggttctt cttggtatcc acttcccagt tttttctgcc gttaggaaac   11280
aacttgaggg agatgaccat tactctaatt tcagtcatgc aaatgttctt ctcagtgggg   11340
ccgcagctgg cgctgcaggt agtttgatta gtgcacctgt ggagttggtc aggacaaaga   11400
tgcaaatgca acgcagagca gctttggccg ggactgtggc agccggtgcc gctgcttctg   11460
caggagccga agagttttat aagggctccc ttgactgctt caaacaagta atgtccaaac   11520
atggtattaa gggtctttac cgtggtttta catccactat cctccgcgat atgcagggtt   11580
acgcttggtt ttttcttggc tacgaggcaa ctgtcaatca ttttcttcag aatgctggcc   11640
ctggagttca taccaaagca gatcttaact accttcaagt catggcagct ggagttgttg   11700
caggcttggg attgtgggga tctatgtttc ctatagatac aatcaagagt aagctccaag   11760
ccgatagctt cgcaaagcca cagtacagta gtaccatgga ctgcctgaaa aaggttttgg   11820
caagcgaagg tcaagcaggg ttgtggaggg gcttctctgc tgcaatgtat cgtgccatac   11880
ctgtgaacgc tggtatattt ctcgcagttg aaggaactag acagggaatc aagtggtacg   11940
aagaaaacgt cgaacacatt tatggcggtg ttattggacc tgctactcct accgctgcac   12000
agtaatctag agcggccgct gagtaattct gatattagag ggagcattaa tgtgttgttg   12060
tgatgtggtt tatatgggga aattaaataa atgatgtatg tacctcttgc ctatgtaggt   12120
ttgtgtgttt tgttttgttg tctagctttg gttattaagt agtagggacg ttcgttcgtg   12180
tctcaaaaaa aggggtacta ccactctgta gtgtatatgg atgctggaaa tcaatgtgtt   12240
ttgtatttgt tcacctccat tgttgaattc aatgtcaaat gtgttttgcg ttggttatgt   12300
gtaaaattac tatctttctc gtccgatgat caaagtttta agcaacaaaa ccaagggtga   12360
aatttaaact gtgctttgtt gaagattctt ttatcatatt gaaatcaaa ttactagcag    12420 cagattttac ctagcatgaa attttatcaa cagtacagca ctcactaacc aagttccaaa   12480
ctaagatgcg ccattaacat cagccaatag gcattttcag caaggcgcgc cagtcccggg   12540
ccattagact tgaagtcaag cggccgctta caactgacc ttgctggtac atagaactga    12600
ttaactgacc atttaaatca taccaacatg gtcaaataaa acgaaaggct cagtcgaaag   12660
actgggcctt tcgttttaat ctgatcggca cgtaagaggt tccaactttc accataatga   12720
aataagatca ctaccgggcg tatttttgag ttatcgagat tttcaggagc taaggaagct   12780
aaaatgagcc atattcaacg ggaaacgtct tgctcgaggc cgcgattaaa ttccaacatg   12840
gatgctgatt tatatgggta taaatgggct cgcgataatg tcgggcaatc aggtgcgaca   12900
atctatcgat tgtatgggaa gcccgatgcg ccagagttgt ttctgaaaca tggcaaaggt   12960
```

-continued

```
agcgttgcca atgatgttac agatgagatg gtcaggctaa actggctgac ggaatttatg    13020
cctcttccga ccatcaagca ttttatccgt actcctgatg atgcatggtt actcaccact    13080
gcgatcccag ggaaaacagc attccaggta ttagaagaat atcctgattc aggtgaaaat    13140
attgttgatg cgctggcagt gttcctgcgc cggttgcatt cgattcctgt ttgtaattgt    13200
ccttttaacg gcgatcgcgt atttcgtctc gctcaggcgc aatcacgaat gaataacggt    13260
ttggttggtg cgagtgattt tgatgacgag cgtaatggct ggcctgttga acaagtctgg    13320
aaagaaatgc ataaactttt gccattctca ccggattcag tcgtcactca tggtgatttc    13380
tcacttgata accttatttt tgacgagggg aaattaatag gttgtattga tgttggacga    13440
gtcggaatcg cagaccgata ccaggatctt gccatcctat ggaactgcct cggtgagttt    13500
tctccttcat tacagaaacg gcttttcaa aaatatggta ttgataatcc tgatatgaat    13560
aaattgcagt ttcacttgat gctcgatgag ttttctaac ctaggtgaca gaagtcaaaa    13620
gcctccggtc ggaggctttt gactttctgc tagatctgtt tcaatgcggt gaagggccag    13680
gcagctgggg attatgtcga gacccggcca gcatgttggt tttatcgcat attcagcgtt    13740
gtcgcgttta cccaggtaaa atggaagcag tgtatcgtct gcgtgaatgt gcaaatcagg    13800
aacgtaaccg tggtacatag atgcagtccc ttgcgggtcg ttcccttcaa cgagtatgac    13860
gcggtgccct tgcaaggcta accattgcgc tggtgtact gcagatgagg ttttataaac    13920
ccctcccttg tgtgacataa cggaaagtac aaccgggttt ttatcgtcag gtctttggtt    13980
tgggttacca acacactcc gcatatggct aatttggtca attgtgtagc cagcgcgacg    14040
ttctactcgg cccctcatct caaaatcagg agccggtaga cgaccagctt tttccgcgtc    14100
tctgatagcc tgcggtgtta cgccgatcag gtctgcaact tctgttatac cccagcggcg    14160
agtaatacga cgcgcttccg ggctgtcatc gccgaactgt gcgatggcaa tagcgcgcgt    14220
catttcctga ccgcgattga tacagtcttt cagcaaatta ttaacgaca tcctgtttcc    14280 tctcaaacat gcccttatct ttgtgttttt catcatactt tacgttttta aagcaaagca    14340
acataaaaaa agcaaagtga cttagaaaac gcaaagttaa ggttcaaatc aattttttga    14400
tgcgctacag aagctattta gcttcatcta agcgcaacgg tattacttac gttggtatat    14460
ttaaaaccta acttaatgat tttaaatgat aataaatcat accaattgct atcaaaagtt    14520
aagcgaacat gctgattttc acgctgttta tacactttga ggcatctcta tctcttccgt    14580
ctctatattg aaacacaatc aaagaacatc aatccatgtg acatccccca ctatctaaga    14640
acaccataac agaacacaac ataggaatgc aacattaatg tatcaataat tcggaacata    14700
tgcactatat catatctcaa ttacggaaca tatcagcaca caattgccca ttatacgc      14758
```

<210> SEQ ID NO 131
<211> LENGTH: 22
<212> TYPE: DNA
<213> ORGANISM: Artificial Sequence
<220> FEATURE:
<223> OTHER INFORMATION: Synthetic construct primer P675

<400> SEQUENCE: 131
ccttggttgt gttctctctt ct                                               22

<210> SEQ ID NO 132
<211> LENGTH: 21
<212> TYPE: DNA
<213> ORGANISM: Artificial Sequence
<220> FEATURE:

<223> OTHER INFORMATION: Synthetic construct primer P676

<400> SEQUENCE: 132
gatctgttca gcgagtcctt t                                        21

<210> SEQ ID NO 133
<211> LENGTH: 21
<212> TYPE: DNA
<213> ORGANISM: Artificial Sequence
<220> FEATURE:
<223> OTHER INFORMATION: Synthetic construct primer P677

<400> SEQUENCE: 133
tagtcctagc atcgacgaag a                                        21

<210> SEQ ID NO 134
<211> LENGTH: 22
<212> TYPE: DNA
<213> ORGANISM: Artificial Sequence
<220> FEATURE:
<223> OTHER INFORMATION: Synthetic construct primer P678

<400> SEQUENCE: 134
agcgaaggga gaaatccaat aa                                       22

<210> SEQ ID NO 135
<211> LENGTH: 20
<212> TYPE: DNA
<213> ORGANISM: Artificial Sequence
<220> FEATURE:
<223> OTHER INFORMATION: Synthetic construct primer P602

<400> SEQUENCE: 135
cggccgattc tgtttatctc                                          20

<210> SEQ ID NO 136
<211> LENGTH: 20
<212> TYPE: DNA
<213> ORGANISM: Artificial Sequence
<220> FEATURE:
<223> OTHER INFORMATION: Synthetic construct primer P603

<400> SEQUENCE: 136
tccttctggt tcatcccaac                                          20

<210> SEQ ID NO 137
<211> LENGTH: 507
<212> TYPE: DNA
<213> ORGANISM: Artificial Sequence
<220> FEATURE:
<223> OTHER INFORMATION: Synthetic construct L1M variant gene

<400> SEQUENCE: 137
atggtttcct tggttgtgtt ctctcttctc ttgatcggtt ttgcatctgc gcaaactctc    60
atagtagatt cttgcaagaa agcagccgca aaagagccgt ttatgaaata tgatttctgc   120
gtcaattctc ttacacaaga tccacaaagc aaaacggcga ccaccctcga aggtttagtc   180
ctagcatcga cgaagaatgc tgcggcggaa acactgaacg taaaaggact cgctgaacag   240
atcctcaagg ggaagggata tgggccaggt atggaggcag ggctacacaa gtgcgtcaag   300
atttatggag gtgcttatga tttttttaaac actgctttag cgaacgttca atcacaccat   360
tatagtactg ctgtagagga atttctttat gcttcatttg caccgttcga ctgcgtgaaa   420
tattattgga tttctcccct tcgctaagga gagctatatta tctttgagaa gatttttgatt   480 cctatgactt taactaaaat gttgtga                                        507

<210> SEQ ID NO 138
<211> LENGTH: 168
<212> TYPE: PRT
<213> ORGANISM: Artificial Sequence
<220> FEATURE:
<223> OTHER INFORMATION: Synthetic construct L1M variant protein

<400> SEQUENCE: 138

Met Val Ser Leu Val Val Phe Ser Leu Leu Ile Gly Phe Ala Ser
1               5                   10                  15

Ala Gln Thr Leu Ile Val Asp Ser Cys Lys Lys Ala Ala Ala Lys Glu
            20                  25                  30

Pro Phe Met Lys Tyr Asp Phe Cys Val Asn Ser Leu Thr Gln Asp Pro
        35                  40                      45

Gln Ser Lys Thr Ala Thr Thr Leu Glu Gly Leu Val Leu Ala Ser Thr
    50                  55                      60

Lys Asn Ala Ala Ala Glu Thr Leu Asn Val Lys Gly Leu Ala Glu Gln
65              70                  75                  80

Ile Leu Lys Gly Lys Gly Tyr Gly Pro Gly Met Glu Ala Gly Leu His
            85                  90                  95

Lys Cys Val Lys Ile Tyr Gly Gly Ala Tyr Asp Phe Leu Asn Thr Ala
        100                 105                 110

Leu Ala Asn Val Gln Ser His His Tyr Ser Thr Ala Val Glu Glu Phe
    115                 120                     125

Leu Tyr Ala Ser Phe Ala Pro Phe Asp Cys Val Lys Tyr Tyr Trp Ile
130                 135                     140

Ser Pro Phe Ala Lys Glu Ser Tyr Ile Ile Phe Glu Lys Ile Leu Ile
145             150                 155                 160

Pro Met Thr Leu Thr Lys Met Leu
                165

<210> SEQ ID NO 139
<211> LENGTH: 510
<212> TYPE: DNA
<213> ORGANISM: Artificial Sequence
<220> FEATURE:
<223> OTHER INFORMATION: Synthetic construct L1ML variant gene

<400> SEQUENCE: 139
atgttggttt ccttggttgt gttctctctt ctcttgatcg ttttgcatc tgcgcaaact       60 ctcatagtag attcttgcaa gaaagcagcc gcaaagagc cgtttatgaa atatgatttc      120
tgcgtcaatt ctcttacaca agatccacaa agcaaaacgg cgaccaccct cgaaggttta    180
gtcctagcat cgacgaagaa tgctgcggcg gaaacactga acgtaaaagg actcgctgaa    240
cagatcctca aggggaaggg atatgggcca ggtatggagg cagggctaca caagtgcgtc    300
aagatttatg gaggtgctta tgattttta aacactgctt tagcgaacgt tcaatcacac    360
cattatagta ctgctgtaga ggaatttctt tatgcttcat ttgcaccgtt cgactgcgtg    420
aaatattatt ggatttctcc cttcgctaag gagagctata ttatctttga gaagattttg    480
attcctatga ctttaactaa aatgttgtga                                     510

<210> SEQ ID NO 140
<211> LENGTH: 169
<212> TYPE: PRT
<213> ORGANISM: Artificial Sequence
<220> FEATURE:
<223> OTHER INFORMATION: Synthetic construct L1ML variant protein

<400> SEQUENCE: 140

Met Leu Val Ser Leu Val Val Phe Ser Leu Leu Ile Gly Phe Ala
1               5                   10                  15

Ser Ala Gln Thr Leu Ile Val Asp Ser Cys Lys Lys Ala Ala Lys
                20                  25                  30

Glu Pro Phe Met Lys Tyr Asp Phe Cys Val Asn Ser Leu Thr Gln Asp
                35                  40                  45

Pro Gln Ser Lys Thr Ala Thr Thr Leu Glu Gly Leu Val Leu Ala Ser
            50                  55                  60

Thr Lys Asn Ala Ala Ala Glu Thr Leu Asn Val Lys Gly Leu Ala Glu
65                  70                  75                  80

Gln Ile Leu Lys Gly Lys Gly Tyr Gly Pro Gly Met Glu Ala Gly Leu
                85                  90                  95

His Lys Cys Val Lys Ile Tyr Gly Gly Ala Tyr Asp Phe Leu Asn Thr
            100                 105                 110

Ala Leu Ala Asn Val Gln Ser His His Tyr Ser Thr Ala Val Glu Glu
        115                 120                 125

Phe Leu Tyr Ala Ser Phe Ala Pro Phe Asp Cys Val Lys Tyr Tyr Trp
130                 135                 140

Ile Ser Pro Phe Ala Lys Glu Ser Tyr Ile Ile Phe Glu Lys Ile Leu
145                 150                 155                 160

Ile Pro Met Thr Leu Thr Lys Met Leu
                165

<210> SEQ ID NO 141
<211> LENGTH: 408
<212> TYPE: PRT
<213> ORGANISM: Glycine max

<400> SEQUENCE: 141

Met Thr Ser Thr Leu Leu Ser Leu Leu Phe Leu Leu Phe Ser Leu Leu
1               5                   10                  15

Ile Pro Ser Phe Ile Ser Ser Pro Val Arg Asn Pro Glu Glu Val
                20                  25                  30

Val Gln Glu Val Asn Arg Lys Ile Asn Gly Ser Ile Ala Arg Pro Arg
            35                  40                  45

Arg Asn Leu Gly Tyr Leu Trp Cys Gly Ser Gly Asn Pro Ile Asp Asp
        50                  55                  60

Cys Trp Arg Cys Asp Pro Asn Trp Glu Gln Asn Arg Gln Arg Leu Ala
65                  70                  75                  80

Asp Cys Ala Ile Gly Phe Gly Lys Asn Ala Ile Gly Gly Arg Asp Gly
                85                  90                  95

Lys Ile Tyr Val Val Asp Asp Asp Gly Asp Asp Ala Val Asn Pro
            100                 105                 110

Lys Pro Gly Ser Leu Arg His Ala Val Ile Gln Asp Glu Pro Leu Trp
        115                 120                 125

Ile Ile Phe Ala Arg Asp Met Val Ile Gln Leu Lys Glu Glu Leu Leu
130                 135                 140

Met Asn Ser Phe Lys Thr Ile Asp Gly Arg Gly Ala Ser Val His Val
145                 150                 155                 160

Ala Gly Gly Pro Cys Ile Thr Ile Gln Tyr Val Thr Asn Val Ile Ile
                165                 170                 175

His Gly Ile His Ile His Asp Cys Lys Gln Gly Gly Asn Ala Met Val
            180                 185                 190

Arg Asp Ser Pro Arg His Tyr Gly Trp Arg Thr Val Ser Asp Gly Asp
        195                 200                 205

Gly Val Ser Ile Phe Gly Gly Ser His Val Trp Ile Asp His Cys Ser
    210                 215                 220

Leu Ser Asn Cys Asn Asp Gly Leu Ile Asp Ala Ile His Gly Ser Thr
225                 230                 235                 240

Ala Ile Thr Ile Ser Asn Asn Tyr Met Thr His His Asp Lys Val Met
            245                 250                 255

Leu Leu Gly His Ser Asp Ala Tyr Thr Gln Asp Lys Ala Met Gln Val
        260                 265                 270

Thr Ile Ala Phe Asn His Phe Gly Glu Gly Leu Val Gln Arg Met Pro
    275                 280                 285

Arg Cys Arg Leu Gly Tyr Phe His Val Val Asn Asn Asp Tyr Thr His
290                 295                 300

Trp Glu Met Tyr Ala Ile Gly Gly Ser Ala Asn Pro Thr Ile Asn Cys
305                 310                 315                 320

Gln Gly Asn Arg Phe Val Ala Pro Asp Arg Phe Ser Lys Glu Val
            325                 330                 335

Thr Lys Arg Glu Asp Ala Pro Glu Ser Glu Trp Gln Asp Trp Asn Trp
        340                 345                 350

Arg Ser Glu Gly Asp Leu Leu Val Asn Gly Ala Phe Phe Thr Ser Ser
            355                 360                 365

Gly Ala Gly Ala Ser Ser Tyr Ala Arg Ala Ser Ser Leu Ser Ala
370                 375                 380

Arg Pro Ser Ser Leu Val Gly Ser Ile Thr Thr Gly Ala Gly Ala Leu
385                 390                 395                 400

Ser Cys Lys Lys Gly Ser Pro Cys
            405

<210> SEQ ID NO 142
<211> LENGTH: 504
<212> TYPE: PRT
<213> ORGANISM: Glycine max

<400> SEQUENCE: 142

Met Leu Pro Ile Thr Cys Ile Leu Phe Met Cys Leu Leu Ser Ser Phe
1               5                   10                  15

Ser Pro Pro Ile Asn Ala Leu Leu Asn Leu Asn Leu Thr Leu Pro His
            20                  25                  30

Gln Tyr Pro His Pro Glu Ser Val Val Gln Asp Ile Gln Arg Lys Val
        35                  40                  45

Asn Ala Ser Leu Arg Arg Arg Glu Met Leu Ser Lys Asp Glu Gln Gln
    50                  55                  60

Gly Met Ser Ser Cys Leu Thr Gly Asn Pro Ile Asp Asp Cys Trp Arg
65                  70                  75                  80

Cys Glu Pro Asn Trp Ala Ala Glu Arg Gln Lys Leu Ala Glu Cys Gly
                85                  90                  95

Leu Gly Phe Gly Lys Tyr Ala Met Gly Gly Lys Gly Gln Ile Tyr
            100                 105                 110

Ile Val Thr Asp Ser Ser Asp Arg Asp Pro Ala Asn Pro Ile Pro Gly
        115                 120                 125

Thr Leu Arg His Ala Val Ile Gln Asp Glu Ala Leu Trp Ile Val Phe
    130                 135                 140

Ala Ala Asp Met Thr Ile Asn Leu Lys His Glu Leu Ile Phe Asn Ser
145                 150                 155                 160

Tyr Lys Thr Leu Asp Gly Arg Gly Ala Asn Val His Val Thr Gly His
                165                 170                 175

Gly Cys Ile Thr Leu Gln Tyr Val Ser Asn Ile Ile His Asn Ile
            180                 185                 190

His Ile His His Cys Thr Pro Ser Gly Asn Thr Asn Ile Arg Ala Ser
            195                 200                 205

Pro Thr His Val Gly Trp Arg Gly Lys Ser Asp Gly Asp Gly Ile Ser
210                 215                 220

Ile Phe Gly Ser Arg Lys Ile Trp Ile Asp His Cys Ser Leu Ser Tyr
225                 230                 235                 240

Cys Thr Asp Gly Leu Ile Asp Ala Ile Met Gly Ser Thr Gly Ile Thr
                245                 250                 255

Ile Ser Asn Ser His Phe Ala His His Asp Glu Val Met Leu Leu Gly
                260                 265                 270

His Asp Asp Lys Tyr Leu Val Asp Arg Gly Met Gln Val Thr Ile Ala
            275                 280                 285

Phe Asn His Phe Gly Glu Gly Leu Val Gln Arg Met Pro Arg Cys Arg
290                 295                 300

Leu Gly Tyr Ile His Val Val Asn Asn Asp Phe Thr Gln Trp Arg Met
305                 310                 315                 320

Tyr Ala Ile Gly Gly Ser Ala Asn Pro Thr Ile Asn Ser Gln Gly Asn
                325                 330                 335

Arg Tyr Thr Ala Pro Gly Asp Pro Asp Ala Lys Glu Val Thr Lys Arg
            340                 345                 350

Val Asp Thr Asp Arg Glu Trp Ser Gly Trp Asn Trp Arg Thr Glu
            355                 360                 365

Gly Asp Ile Met Val Asn Gly Ala Phe Phe Val Pro Ser Gly Ala Ala
370                 375                 380

Gly Gln Ser Gly Gln Tyr Gln Glu Ala Thr Ser Val Gln Ala Lys Ser
385                 390                 395                 400

Ala Val Gln Ile Asp Gln Leu Thr Met Tyr Ser Gly Val Leu Gly Asp
                405                 410                 415

Pro Arg Asp Asn Gly Asp Leu Tyr Pro Gly Phe Asn Gly Gly Thr
            420                 425                 430

Val Thr Gly Ala Thr Ser Lys Gly Asn Thr Asp Gly Ser Ser Ser Asp
            435                 440                 445

Asp Gly Asp Phe Phe Gly Met Ile Phe Arg Gly Ser Ser Ser
            450                 455                 460

Ser Ser Ser Ser Gln Ala Ala Pro Pro Ser Ser Val Leu Phe Val Ser
465                 470                 475                 480

Ile Phe Leu Ser Leu Leu Ile Ile Phe Val Leu Asp Thr Thr Asn
                485                 490                 495

His Ala Phe Leu Leu Ser Leu Leu
            500

<210> SEQ ID NO 143
<211> LENGTH: 450
<212> TYPE: PRT
<213> ORGANISM: Glycine max

<400> SEQUENCE: 143

Met Ala Val Ser Ser Ser Ala Thr Lys Trp Val Leu Phe Leu Leu Leu

-continued

```
1               5                    10                   15
Ala Leu Leu Ile Arg Glu Glu Ala Met Ala Met Ala Thr Thr Pro Gln
                20                  25                  30
Ile Ser Asp Leu Arg Asn Val Glu Val Glu Arg His Arg Leu Pro Ser
                35                  40                  45
Leu Thr Asn Ser Ser Met Val Glu Arg Ala Lys Glu Ala Asp Lys Leu
 50                  55                  60
Asn Glu Gln Ala Ala Val Ala Asn Pro Glu Glu Val Val Ser Met Val
 65                  70                  75                  80
Glu Met Ser Ile Gln Asn Ser Thr Glu Arg Arg Lys Leu Gly Tyr Phe
                 85                  90                  95
Ser Cys Gly Thr Gly Asn Pro Ile Asp Asp Cys Trp Arg Cys Asp Pro
                100                 105                 110
Asn Trp Gln Arg Asn Arg Lys Arg Leu Ala Asp Cys Gly Ile Gly Phe
                115                 120                 125
Gly Arg Asn Ala Ile Gly Gly Arg Asp Gly Lys Phe Tyr Val Val Thr
                130                 135                 140
Asp Pro Arg Asp Asp Pro Val Asn Pro Lys Pro Gly Thr Leu Arg
145                 150                 155                 160
His Ala Val Ile Gln Asp Arg Pro Leu Trp Ile Val Phe Lys Arg Asp
                165                 170                 175
Met Val Ile Gln Leu Lys Gln Glu Leu Ile Met Asn Ser Phe Lys Thr
                180                 185                 190
Ile Asp Ala Arg Gly Val Asn Val His Ile Ala Asn Gly Ala Cys Ile
                195                 200                 205
Thr Ile Gln Phe Val Thr Asn Val Ile Ile His Gly Leu His Ile His
                210                 215                 220
Asp Cys Lys Pro Thr Gly Asn Ala Met Val Arg Ser Ser Pro Thr His
225                 230                 235                 240
Phe Gly Trp Arg Thr Met Ala Asp Gly Asp Ala Ile Ser Ile Phe Gly
                245                 250                 255
Ser Ser His Ile Trp Val Asp His Asn Ser Leu Ser His Cys Ala Asp
                260                 265                 270
Gly Leu Val Asp Ala Val Met Gly Ser Thr Ala Ile Thr Ile Ser Asn
                275                 280                 285
Asn His Phe Thr His His Asn Glu Val Ile Leu Leu Gly His Ser Asp
                290                 295                 300
Ser Tyr Thr Arg Asp Lys Leu Met Gln Val Thr Ile Ala Tyr Asn His
305                 310                 315                 320
Phe Gly Glu Gly Leu Ile Gln Arg Met Pro Arg Cys Arg His Gly Tyr
                325                 330                 335
Phe His Val Val Asn Asn Asp Tyr Thr His Trp Glu Met Tyr Ala Ile
                340                 345                 350
Gly Gly Ser Ala Asn Pro Thr Ile Asn Ser Gln Gly Asn Arg Tyr Asn
                355                 360                 365
Ala Pro Thr Asn Pro Phe Ala Lys Glu Val Thr Lys Arg Val Glu Thr
                370                 375                 380
Ala Glu Thr Gln Trp Lys Gly Trp Asn Trp Arg Ser Glu Gly Asp Leu
385                 390                 395                 400
Leu Leu Asn Gly Ala Tyr Phe Thr Pro Ser Gly Ala Gly Ala Ser Ala
                405                 410                 415
Ser Tyr Ala Arg Ala Ser Ser Leu Gly Ala Lys Ser Ser Met Val
                420                 425                 430
```

```
Asp Ser Met Thr Ser Asn Ala Gly Ala Leu Gly Cys Lys Arg Gly Arg
        435                 440                 445

Gln Cys
    450

<210> SEQ ID NO 144
<211> LENGTH: 489
<212> TYPE: PRT
<213> ORGANISM: Glycine max

<400> SEQUENCE: 144

Met Leu Glu Pro Ser Glu Ser Thr Pro Pro Asn Ser Leu Ser Leu Leu
1               5                   10                  15

Phe Leu Ser Ser Thr Phe Ser Leu Thr Lys Ala Thr Thr His Thr Leu
            20                  25                  30

Arg Ala Arg Gly Ile Gln Leu Ser Ala Met Ala Val Ser Ser Ser Ser
        35                  40                  45

Ala Thr Lys Trp Val Val Phe Leu Leu Leu Ala Leu Leu Ile Arg Glu
    50                  55                  60

Glu Ala Met Ala Thr Pro Gln Ile Ser Asp Leu Arg Asn Leu Glu Val
65                  70                  75                  80

Glu Arg His Arg Leu Pro Ser Leu Thr Asn Ser Ser Met Ala Glu Arg
                85                  90                  95

Ala Lys Glu Ala Glu Lys Leu Asn Glu Gln Ala Ala Val Ala Asn Pro
            100                 105                 110

Glu Glu Val Val Ser Met Val Glu Met Ser Ile Gln Asn Ser Thr Glu
        115                 120                 125

Arg Arg Lys Leu Gly Phe Phe Ser Cys Gly Thr Gly Asn Pro Ile Asp
    130                 135                 140

Asp Cys Trp Arg Cys Asp Pro Asn Trp Gln Arg Asn Arg Lys Arg Leu
145                 150                 155                 160

Ala Asp Cys Gly Ile Gly Phe Gly Arg Asn Ala Ile Gly Gly Arg Asp
                165                 170                 175

Gly Lys Phe Tyr Val Val Thr Asp Pro Arg Asp Asp Pro Val Asn
            180                 185                 190

Pro Lys Pro Gly Thr Leu Arg His Ala Val Ile Gln Asp Lys Pro Leu
        195                 200                 205

Trp Ile Val Phe Lys Arg Asp Met Val Ile Gln Leu Lys Gln Glu Leu
    210                 215                 220

Ile Met Asn Ser Phe Lys Thr Ile Asp Gly Arg Gly Val Asn Val His
225                 230                 235                 240

Ile Ala Asn Gly Ala Cys Ile Thr Ile Gln Phe Val Thr Asn Val Ile
                245                 250                 255

Ile His Gly Leu His Ile His Asp Cys Lys Pro Thr Gly Asn Ala Met
            260                 265                 270

Val Arg Ser Ser Pro Thr His Phe Gly Trp Arg Thr Met Ala Asp Gly
        275                 280                 285

Asp Ala Ile Ser Ile Phe Gly Ser Ser His Ile Trp Val Asp His Asn
    290                 295                 300

Ser Leu Ser His Cys Ala Asp Gly Leu Val Asp Ala Val Leu Gly Ser
305                 310                 315                 320

Thr Ala Ile Thr Ile Ser Asn Asn His Phe Thr His His Asn Glu Val
                325                 330                 335

Ile Leu Leu Gly His Ser Asp Ser Tyr Thr Arg Asp Lys Gln Met Gln
```

```
             340                 345                 350
Val Thr Ile Ala Tyr Asn His Phe Gly Glu Gly Leu Ile Gln Arg Met
             355                 360                 365

Pro Arg Cys Arg His Gly Tyr Phe His Val Val Asn Asn Asp Tyr Thr
        370                 375                 380

His Trp Glu Met Tyr Ala Ile Gly Gly Ser Ala Asn Pro Thr Ile Asn
385                 390                 395                 400

Ser Gln Gly Asn Arg Tyr Asn Ala Pro Thr Asn Arg Phe Ala Lys Glu
                405                 410                 415

Val Thr Lys Arg Val Glu Thr Ala Glu Ser Gln Trp Lys Gly Trp Asn
            420                 425                 430

Trp Arg Ser Glu Gly Asp Leu Leu Leu Asn Gly Ala Tyr Phe Thr Pro
        435                 440                 445

Ser Gly Ala Gly Ala Ser Ala Ser Tyr Ala Arg Ala Ser Ser Leu Gly
            450                 455                 460

Ala Lys Ser Ser Met Val Gly Ser Met Thr Ser Asn Ala Gly Ala
465                 470                 475                 480

Leu Gly Cys Lys Arg Gly Ser Gln Cys
                485

<210> SEQ ID NO 145
<211> LENGTH: 316
<212> TYPE: PRT
<213> ORGANISM: Glycine max

<400> SEQUENCE: 145

Met Ala Ala Leu Val Ile Thr Val Ser Gln Asp Gly Thr Gly Gln Tyr
1               5                   10                  15

Arg Thr Val Gln Glu Ala Ile Asp Ala Val Pro Leu Gly Asn Thr Arg
            20                  25                  30

Arg Thr Val Ile Arg Val Ser Pro Gly Thr Tyr Arg Gln Pro Leu Tyr
        35                  40                  45

Val Ala Lys Thr Lys Asn Phe Ile Thr Leu Val Gly Leu Arg Pro Glu
    50                  55                  60

Asp Thr Val Leu Thr Trp Asn Asn Thr Ala Thr Ser Ile His His His
65                  70                  75                  80

Gln Asp Ala Arg Val Ile Gly Thr Gly Thr Phe Gly Cys Gly Thr Ile
                85                  90                  95

Ile Val Glu Gly Gly Asp Phe Ile Ala Glu Asn Ile Thr Phe Glu Asn
            100                 105                 110

Ser Ser Pro Gln Gly Ala Gly Gln Ala Val Ala Val Arg Val Thr Val
        115                 120                 125

Asp Arg Cys Ala Phe Tyr Asn Cys Arg Phe Leu Gly Trp Gln Asp Thr
    130                 135                 140

Leu Tyr Leu His Tyr Gly Ile Gln Tyr Leu Lys Asp Cys Tyr Ile Glu
145                 150                 155                 160

Gly Ser Val Asp Phe Ile Phe Gly Asn Ser Thr Ala Leu Leu Glu His
                165                 170                 175

Cys His Ile His Cys Lys Ser Ala Gly Phe Ile Thr Ala Gln Ser Arg
            180                 185                 190

Asn Ser Pro Gln Glu Lys Thr Gly Tyr Val Phe Leu Arg Cys Val Val
        195                 200                 205

Thr Gly Asn Gly Gly Thr Ser Tyr Ala Tyr Leu Gly Arg Pro Trp Arg
    210                 215                 220
```

```
Pro Phe Ala Arg Val Val Phe Ala Phe Thr Tyr Met Asp Gln Cys Ile
225                 230                 235                 240

Lys Pro Ala Gly Trp Asn Asn Trp Gly Lys Ile Glu Asn Glu Lys Thr
            245                 250                 255

Ala Cys Phe Tyr Glu Tyr Arg Cys Phe Gly Pro Gly Trp Cys Pro Ser
        260                 265                 270

Gln Arg Val Lys Trp Ala Arg Glu Leu Gln Ala Glu Ala Glu Gln
    275                 280                 285

Phe Leu Met His Ser Phe Ile Asp Pro Glu Ser Glu Arg Pro Trp Leu
290                 295                 300

Ala Gln Arg Met Ala Leu Lys Ile Pro Tyr Ser Ala
305                 310                 315

<210> SEQ ID NO 146
<211> LENGTH: 316
<212> TYPE: PRT
<213> ORGANISM: Glycine max

<400> SEQUENCE: 146

Met Ala Ala Cys Ile Phe Thr Val Ala Gln Asp Gly Thr Ala Asp Phe
1               5                   10                  15

Gln Thr Val Gln Glu Ala Ile Asp Ala Val Pro Leu Gly Asn Ile Arg
                20                  25                  30

Arg Thr Val Ile Arg Val Ser Pro Gly Ile Tyr Arg Gln Pro Val Tyr
            35                  40                  45

Val Pro Lys Thr Lys Asn Phe Ile Thr Leu Ala Ala Leu Ser Pro Glu
    50                  55                  60

Asp Thr Val Leu Thr Trp Asn Asn Thr Ala Thr Gly Ile Asp His His
65                  70                  75                  80

Gln Pro Ala Arg Val Ile Gly Thr Gly Thr Phe Gly Cys Gly Ser Thr
                85                  90                  95

Ile Val Glu Gly Glu Asp Phe Ile Ala Glu Asn Ile Thr Phe Glu Asn
            100                 105                 110

Ser Ala Pro Glu Gly Ser Gly Gln Ala Val Ala Ile Arg Val Thr Ala
        115                 120                 125

Asp Arg Cys Ala Phe Tyr Asn Cys Arg Phe Leu Gly Trp Gln Asp Thr
    130                 135                 140

Leu Tyr Leu His Tyr Gly Lys Gln Tyr Leu Lys Asp Cys Tyr Ile Glu
145                 150                 155                 160

Gly Ser Val Asp Phe Ile Phe Gly Asn Ser Thr Ala Leu Leu Glu His
                165                 170                 175

Cys His Ile His Cys Lys Ser Ala Gly Phe Ile Thr Ala Gln Ser Arg
            180                 185                 190

Lys Ser Ser Gln Glu Thr Thr Gly Tyr Val Phe Leu Arg Cys Val Ile
        195                 200                 205

Thr Gly Asn Gly Gly Asn Ser Tyr Ala Tyr Leu Gly Arg Pro Trp Gly
    210                 215                 220

Pro Phe Gly Arg Val Val Phe Ala Tyr Thr Tyr Met Asp Gln Cys Ile
225                 230                 235                 240

Arg His Val Gly Trp Asp Asn Trp Gly Lys Met Glu Asn Glu Arg Ser
                245                 250                 255

Ala Cys Phe Tyr Glu Tyr Arg Cys Phe Gly Pro Gly Cys Cys Pro Ser
            260                 265                 270

Lys Arg Val Thr Trp Cys Arg Glu Leu Leu Asp Glu Glu Ala Glu Gln
        275                 280                 285
```

```
Phe Leu Thr His Pro Phe Ile Asp Pro Glu Leu Glu Lys Pro Trp Leu
    290                 295                 300

Ala Gln Arg Met Ala Leu Arg Ile Pro Tyr Ser Ala
305                 310                 315

<210> SEQ ID NO 147
<211> LENGTH: 184
<212> TYPE: PRT
<213> ORGANISM: Glycine max

<400> SEQUENCE: 147

Met Thr Asn Leu Lys Pro Leu Ile Leu Phe Phe Tyr Leu Leu Ala Ile
1               5                   10                  15

Val Val Met Ile Ser Ile Pro Ser Ser His Cys Ser Arg Thr Leu Leu
            20                  25                  30

Pro Glu Asn Glu Lys Leu Ile Glu Asn Thr Cys Lys Lys Thr Pro Asn
        35                  40                  45

Tyr Asn Val Cys Leu Glu Ser Leu Lys Ala Ser Pro Gly Ser Ser Ser
    50                  55                  60

Ala Asp Val Thr Gly Leu Ala Gln Ile Met Val Lys Glu Met Lys Ala
65                  70                  75                  80

Lys Ala Asn Asp Ala Leu Lys Arg Ile Gln Glu Leu Gln Arg Val Gly
                85                  90                  95

Ala Ser Gly Pro Lys Gln Arg Arg Ala Leu Ser Ser Cys Ala Asp Lys
            100                 105                 110

Tyr Lys Ala Val Leu Ile Ala Asp Val Pro Gln Ala Thr Glu Ala Leu
        115                 120                 125

Gln Lys Gly Asp Pro Lys Phe Ala Glu Asp Gly Ala Asn Asp Ala Ala
    130                 135                 140

Asn Glu Ala Thr Tyr Cys Glu Thr Asp Phe Ser Ala Ala Gly Asn Ser
145                 150                 155                 160

Pro Leu Thr Lys Gln Asn Asn Ala Met His Asp Val Ala Ala Val Thr
                165                 170                 175

Ala Ala Ile Val Arg Leu Leu Leu
            180

<210> SEQ ID NO 148
<211> LENGTH: 182
<212> TYPE: PRT
<213> ORGANISM: Glycine max

<400> SEQUENCE: 148

Met Lys Ile Met Glu Ser Leu Ala Leu Ile Phe Tyr Ser Thr Leu Val
1               5                   10                  15

Leu Ala Thr Ile Ser Val Pro Ala Thr Asn Ser Arg Ile Ile His Gln
            20                  25                  30

Lys Asn Asn Ala Asn Leu Ile Glu Glu Thr Cys Lys Gln Thr Pro His
        35                  40                  45

His Asp Leu Cys Ile Gln Tyr Leu Ser Ser Asp Pro Arg Ser Thr Glu
    50                  55                  60

Ala Asp Val Thr Gly Leu Ala Leu Ile Met Val Asn Val Ile Lys Ile
65                  70                  75                  80

Lys Ala Asn Asn Ala Leu Asp Lys Ile His Gln Leu Leu Gln Lys Asn
                85                  90                  95

Pro Glu Pro Ser Gln Lys Glu Pro Leu Ser Ser Cys Ala Ala Arg Tyr
            100                 105                 110
```

```
Lys Ala Ile Val Glu Ala Asp Val Ala Gln Ala Val Ala Ser Leu Gln
            115                 120                 125

Lys Gly Asp Pro Lys Phe Ala Glu Asp Gly Ala Asn Asp Ala Ala Ile
        130                 135                 140

Glu Ala Thr Thr Cys Glu Asn Ser Phe Ser Ala Gly Lys Ser Pro Leu
145                 150                 155                 160

Thr Asn His Asn Asn Ala Met His Asp Val Ala Thr Ile Thr Ala Ala
                165                 170                 175

Ile Val Arg Gln Leu Leu
            180
```

<210> SEQ ID NO 149
<211> LENGTH: 203
<212> TYPE: PRT
<213> ORGANISM: Glycine max

<400> SEQUENCE: 149

```
Met Ala Thr Thr Thr Leu Met Lys Leu Ala Phe Met Leu Leu Met Asn
1               5                   10                  15

Leu Val Ile Cys Ser Ala Glu Ser Ser Ile Gly Arg Lys Ser Asn Pro
            20                  25                  30

Asn Pro Glu Glu Phe Val Lys Ser Ser Cys Arg Ala Thr Arg Tyr Pro
        35                  40                  45

Val Leu Cys Val Lys Ser Leu Leu Ala Tyr Ala Ser Val Ile Arg Arg
    50                  55                  60

Ser Asp Arg Gln Leu Ala Thr Thr Ala Leu Ser Val Ser Ile Ser Arg
65                  70                  75                  80

Ser Arg Ser Ser Ala Trp Leu Val Lys Lys Met Leu Lys Ala Arg Gly
                85                  90                  95

Met Lys Pro Arg Glu Tyr Arg Ala Val Gln Asp Cys Val Glu Asn Ile
            100                 105                 110

Gly Asp Ser Val Asp Arg Leu Arg Gln Ser Val Thr Glu Leu Gly Arg
        115                 120                 125

Thr Gly Glu Asp Phe Val Trp His Met Ser Asn Val Gln Thr Trp Val
    130                 135                 140

Ser Ala Ala Leu Thr Asp Asp Ser Thr Cys Leu Asp Gly Phe Ala Gly
145                 150                 155                 160

Ser Ala Met Asn Gly Asn Val Lys Ala Leu Ile Lys Asp Arg Ile Val
                165                 170                 175

His Val Ala Gln Val Thr Ser Asn Ala Leu Ala Leu Val Asn Arg Phe
            180                 185                 190

Ala Ser Arg His Pro Ser Ala Thr Gln Thr Pro
        195                 200
```

<210> SEQ ID NO 150
<211> LENGTH: 214
<212> TYPE: PRT
<213> ORGANISM: Glycine max

<400> SEQUENCE: 150

```
Met Arg Thr Gln Arg Leu Asn His Leu Leu Leu Ser Leu Phe Leu Phe
1               5                   10                  15

Ala Ala Ala Phe Ser Ser Leu His Pro Thr Ala Thr Ala Gly Asp Glu
            20                  25                  30

Gly Ala Pro Ser Pro Gly Asp Gly Asp Gly Asp Ala Asp Phe Ile Arg
        35                  40                  45
```

```
Thr Ser Cys Asn Thr Thr Leu Tyr Pro Asp Val Cys Phe Thr Ser Leu
    50                  55                  60

Ser Arg Tyr Ala Ser Ala Val Gln Gln Asn Pro Gly Gln Leu Ala Arg
65                  70                  75                  80

Val Ala Ile Ser Val Ser Leu Ser Lys Val His Arg Ala Ala Ser Tyr
                85                  90                  95

Val Ser Asn Leu Thr Arg Asp Ala Asp Tyr Asp Gly Thr Thr Arg Ala
            100                 105                 110

Ala Leu Ala Leu His Asp Cys Phe Ser Asn Leu Gly Asp Ala Val Asp
            115                 120                 125

Glu Ile Arg Gly Ser Leu Lys Gln Met Arg Gln Ile Gly Ala Ala Gly
        130                 135                 140

Ala Gly Ala Ser Ser Phe Leu Phe Gln Met Ser Asn Val Gln Thr Trp
145                 150                 155                 160

Met Ser Ala Ala Leu Thr Asp Glu Glu Thr Cys Thr Asp Gly Phe Gln
                165                 170                 175

Asp Val Ala Asp Cys Pro Val Lys Thr Asp Val Cys Asp Arg Val Thr
            180                 185                 190

Asn Val Lys Lys Phe Thr Ser Asn Ala Leu Ala Leu Val Asn Ser Tyr
        195                 200                 205

Ala Asn Lys Gly Met Pro
    210
```

<210> SEQ ID NO 151
<211> LENGTH: 214
<212> TYPE: PRT
<213> ORGANISM: Glycine max

<400> SEQUENCE: 151

```
Met Arg Thr Gln Arg Leu Asn His Leu Leu Ser Leu Phe Leu Phe
1                   5                   10                  15

Ala Ala Ala Phe Ser Ser Leu His Pro Thr Ala Thr Ala Gly Asp Glu
                20                  25                  30

Gly Ala Pro Ser Ala Gly Asp Gly Asp Arg Asp Ala Asp Phe Ile Arg
            35                  40                  45

Thr Ser Cys Asn Thr Thr Leu Tyr Pro Glu Val Cys Phe Thr Ser Leu
    50                  55                  60

Ser Arg Tyr Ala Asn Ala Val Gln Gln Asn Pro Gly His Leu Ala Arg
65                  70                  75                  80

Val Ala Ile Ala Val Ser Leu Ser Lys Val His Arg Ala Ala Ser Tyr
                85                  90                  95

Val Ser Asn Leu Thr Arg Asp Ala Asp Tyr Gly Gly Ser Thr Arg Ala
            100                 105                 110

Ala Leu Ala Leu His Asp Cys Phe Ser Asn Leu Gly Asp Ala Val Asp
            115                 120                 125

Glu Ile Arg Gly Ser Leu Lys Gln Met Arg Gln Ile Gly Ser Ala Gly
        130                 135                 140

Ala Gly Ala Ser Ser Phe Leu Phe Gln Met Ser Asn Val Gln Thr Trp
145                 150                 155                 160

Leu Ser Ala Ala Leu Thr Asp Glu Glu Thr Cys Thr Asp Gly Phe Gln
                165                 170                 175

Asp Val Ala Asp Cys Pro Met Lys Thr Gly Val Cys Asp Arg Val Ser
            180                 185                 190

Asn Val Lys Lys Phe Thr Ser Asn Ala Leu Ala Leu Val Asn Ser Tyr
```

Ala Asn Lys Gly Met Pro
    210

<210> SEQ ID NO 152
<211> LENGTH: 555
<212> TYPE: PRT
<213> ORGANISM: Glycine max

<400> SEQUENCE: 152

Met Met Ala Ser Ser Ser Leu Phe Tyr Leu Ser Leu Ser Leu Ile Leu
1               5                   10                  15

Thr Leu Thr Ser Ala Ala Arg His Lys Pro His Pro Ser Pro Ala Lys
            20                  25                  30

Pro Pro Ala Lys Pro Ala Val Thr Thr Ala Thr Ser Pro Ala Ile Gln
        35                  40                  45

Gln Ala Cys Ala Ala Thr Arg Phe Pro Gln Gln Cys Glu Ala Ser Leu
    50                  55                  60

Ser Gln Ser Gln Asn Leu Pro Pro Asn Pro Asn Pro Thr Pro Leu Gln
65                  70                  75                  80

Leu Leu Gln Ser Ala Ile Ala Leu Ser Ser Asp Asn Leu Ala Thr Ala
                85                  90                  95

Gln Thr Met Val Lys Ser Leu His Asp Ala Ser Ala Asp Ser Arg Asn
            100                 105                 110

Arg Thr Val Ala Ala Ala Thr Cys Ile Glu Ile Leu Ala Asn Ser His
        115                 120                 125

Tyr Arg Ile Ser Leu Ala Ser Asp Ala Leu Pro Arg Gly Arg Thr Lys
    130                 135                 140

Asp Ala Arg Ala Trp Leu Gly Ala Ala Leu Ala Tyr Gln Tyr Asp Cys
145                 150                 155                 160

Trp Asn Ser Leu Lys Tyr Ala Asn Asp Thr Glu Met Val Gly Lys Thr
                165                 170                 175

Met Leu Phe Ile Asp Asn Leu Glu Thr Leu Ser Ser Asn Ala Leu Ser
            180                 185                 190

Met Ala Phe Ser Phe Asp Ala Phe Gly Asn Asp Thr Ala Ser Trp Lys
        195                 200                 205

Pro Pro Val Thr Glu Arg Asp Gly Phe Trp Glu Ala Val Gly Ser Gly
    210                 215                 220

Gly Pro Ala Ser Ala Gly Gly Val Pro Pro Asn Leu Thr Pro Asp Val
225                 230                 235                 240

Thr Val Cys Asn Asn Gly Gly Asp Gly Cys Tyr Lys Thr Val Gln Glu
                245                 250                 255

Ala Val Asn Ala Ala Pro Ala Asn Gly Thr Lys Arg Phe Val Ile Tyr
            260                 265                 270

Ile Lys Glu Gly Val Tyr Glu Glu Thr Val Arg Ile Pro Leu Glu Lys
        275                 280                 285

Arg Asn Val Val Phe Leu Gly Asp Gly Ile Gly Lys Thr Val Ile Thr
    290                 295                 300

Gly Asn Gly Asn Val Gly Gln Gln Gly Met Thr Thr Tyr Asn Ser Ala
305                 310                 315                 320

Thr Val Ala Val Leu Gly Asp Gly Phe Met Ala Lys Glu Leu Thr Val
                325                 330                 335

Glu Asn Thr Ala Gly Pro Asp Ala His Gln Ala Val Ala Phe Arg Leu
            340                 345                 350

```
Asp Ser Asp Leu Ser Val Ile Glu Asn Cys Glu Phe Leu Gly Asn Gln
            355                 360                 365

Asp Thr Leu Tyr Ala His Ser Leu Arg Gln Phe Tyr Lys Ser Cys Arg
        370                 375                 380

Ile Glu Gly Ser Val Asp Phe Ile Phe Gly Asn Ala Ala Ala Val Phe
385                 390                 395                 400

Gln Asp Cys Gln Ile Leu Val Arg Pro Arg Gln Val Lys Pro Glu Lys
                405                 410                 415

Gly Glu Asn Asn Ala Ile Thr Ala His Gly Arg Thr Asp Pro Ala Glu
                420                 425                 430

Pro Thr Gly Phe Val Phe Gln Asn Cys Leu Ile Asn Gly Thr Glu Glu
            435                 440                 445

Tyr Ile Ala Leu Tyr Leu Ser Lys Pro Gln Val His Lys Asn Tyr Leu
        450                 455                 460

Gly Arg Pro Trp Lys Glu Tyr Ser Arg Thr Val Phe Ile Asn Ser Ile
465                 470                 475                 480

Leu Glu Ala Leu Val Thr Pro Gln Gly Trp Met Pro Trp Ser Gly Asp
                485                 490                 495

Phe Ala Leu Lys Thr Leu Tyr Tyr Gly Glu Phe Glu Asn Lys Gly Thr
            500                 505                 510

Gly Ser Asp Leu Ser Gln Arg Val Pro Trp Ser Ser Lys Ile Pro Ala
        515                 520                 525

Glu His Val Leu Thr Tyr Ser Val Gln Asn Phe Ile Gln Gly Asn Asp
        530                 535                 540

Trp Ile Pro Ser Ser Val Gly Ser Pro Ser Ser
545                 550                 555

<210> SEQ ID NO 153
<211> LENGTH: 584
<212> TYPE: PRT
<213> ORGANISM: Glycine max

<400> SEQUENCE: 153

Met Glu Tyr Gly Arg Leu Gly Pro Ser Asp Pro Gly Gly Ser Ser Arg
1               5                   10                  15

Leu Asn Asn Val Pro Pro Thr Ser Ser Gly Arg Lys Lys Ile Val Leu
                20                  25                  30

Leu Ser Leu Phe Ser Val Leu Leu Ile Ala Ala Ser Ala Val Thr Ala
            35                  40                  45

Val Val Val Arg Ser Arg Ile Gln Gln Asn Thr Arg Ala His Glu Thr
        50                  55                  60

Arg Leu Gly Lys Pro Thr Gln Ala Ile Ser Arg Thr Cys Ser Lys Thr
65                  70                  75                  80

Arg Phe Lys Thr Leu Cys Val Lys Ser Leu Leu Asp Phe Pro Gly Ser
                85                  90                  95

Glu Glu Ala Ser Glu Lys Asp Leu Val His Ile Ser Phe Asn Val Thr
                100                 105                 110

Leu Gln His Phe Ser Lys Ala Leu Tyr Ser Ser Ala Ala Met Ser Tyr
            115                 120                 125

Thr Ala Met Asp Pro Arg Val Arg Ala Ala Tyr Asp Asp Cys Leu Glu
        130                 135                 140

Leu Leu Asp Asp Ser Val Asp Ala Leu Ala Arg Ser Leu Asn Thr Val
145                 150                 155                 160

Ser Val Gly Ala Val Gly Ser Ala Asn Asp Asp Val Leu Thr Trp Leu
                165                 170                 175
```

```
Ser Ala Ala Leu Thr Asn Gln Asp Thr Cys Ala Glu Gly Phe Thr Asp
            180                 185                 190

Ala Val Gly Thr Val Lys Asp His Met Ser Ser Asn Leu Arg Asp Leu
            195                 200                 205

Ser Glu Leu Val Ser Asn Cys Leu Ala Ile Phe Ser Gly Ala Gly Ala
210                 215                 220

Gly Asp Asp Phe Ala Gly Val Pro Ile Gln Asn Arg Arg Leu Met
225                 230                 235                 240

Glu Met Arg Glu Asp Asn Phe Pro Thr Trp Leu Ser Arg Arg Asp Arg
                245                 250                 255

Lys Leu Leu Ile Leu Pro Leu Ser Gln Ile Gln Ala Asp Ile Val Val
            260                 265                 270

Ser Lys Asp Gly Asn Gly Thr Val Lys Thr Ile Ala Glu Ala Ile Lys
            275                 280                 285

Lys Val Pro Glu Tyr Ser Ser Arg Ile Ile Ile Tyr Val Arg Ala
290                 295                 300

Gly Arg Tyr Glu Glu Glu Asn Leu Lys Leu Gly Arg Lys Lys Thr Asn
305                 310                 315                 320

Val Met Phe Ile Gly Asp Gly Lys Gly Lys Thr Val Ile Thr Gly Gly
                325                 330                 335

Arg Asn Tyr Tyr Gln Asn Leu Thr Thr Phe His Thr Ala Ser Phe Ala
            340                 345                 350

Ala Ser Gly Ser Gly Phe Ile Ala Lys Asp Met Thr Phe Glu Asn Tyr
            355                 360                 365

Ala Gly Pro Gly Arg His Gln Ala Val Ala Leu Arg Val Gly Ala Asp
            370                 375                 380

His Ala Val Val Tyr Arg Cys Asn Ile Ile Gly Tyr Gln Asp Thr Met
385                 390                 395                 400

Tyr Val His Ser Asn Arg Gln Phe Tyr Arg Glu Cys Asp Ile Tyr Gly
                405                 410                 415

Thr Val Asp Phe Ile Phe Gly Asn Ala Ala Val Val Phe Gln Asn Cys
            420                 425                 430

Thr Leu Trp Ala Arg Lys Pro Met Ala Gln Gln Lys Asn Thr Ile Thr
            435                 440                 445

Ala Gln Asn Arg Lys Asp Pro Asn Gln Asn Thr Gly Ile Ser Ile His
450                 455                 460

Asn Cys Arg Ile Met Ala Thr Pro Asp Leu Glu Ala Ser Lys Gly Ser
465                 470                 475                 480

Tyr Pro Thr Tyr Leu Gly Arg Pro Trp Lys Leu Tyr Ala Arg Thr Val
                485                 490                 495

Tyr Met Leu Ser Tyr Ile Gly Asp His Val His Pro Arg Gly Trp Leu
            500                 505                 510

Glu Trp Asn Thr Ser Ser Phe Ala Leu Asp Thr Cys Tyr Tyr Gly Glu
            515                 520                 525

Tyr Met Asn Tyr Gly Pro Gly Ser Gly Leu Gly Gln Arg Val Asn Trp
            530                 535                 540

Ala Gly Tyr Arg Val Ile Asn Ser Thr Val Glu Ala Ser Arg Phe Thr
545                 550                 555                 560

Val Gly Gln Phe Ile Ser Gly Ser Ser Trp Leu Pro Ser Thr Gly Val
                565                 570                 575

Ala Phe Ile Ala Gly Leu Ser Thr
            580
```

```
<210> SEQ ID NO 154
<211> LENGTH: 615
<212> TYPE: PRT
<213> ORGANISM: Glycine max

<400> SEQUENCE: 154

Met Pro Ala Thr Asn His Pro Ile Tyr Pro Leu Gln Thr Ser His Ser
1               5                   10                  15

Thr Lys Ser Gln Tyr His Leu Pro Ser Ser Ser Ser Ser Ser Ser Ser
            20                  25                  30

Ser Ser Ser Ser Ser Ser Ser Ser Ser Ser Ile Tyr Ile Tyr
        35                  40                  45

Ile Tyr Thr Met Tyr Ser Pro Ile Ser Arg Lys Lys Pro Pro Met Glu
    50                  55                  60

Ser His Val Asp Thr Ile Leu Ser Ala Ile Phe Val Leu Leu Leu Ser
65                  70                  75                  80

Ser Leu Thr His Phe Ser Ile Thr Ala Asn Ala Thr Arg Thr Pro Gln
                85                  90                  95

Glu Asn Ser Leu His Phe Gln Val Ala Asn Ser Thr Cys Glu Gly Thr
            100                 105                 110

Leu Tyr Ser Asp Leu Cys Val Ser Thr Leu Ala Ser Phe Pro Asp Leu
        115                 120                 125

Thr Ser Lys Thr Leu Pro Gln Met Ile Arg Ser Val Val Asn His Thr
    130                 135                 140

Ile Tyr Glu Val Thr Leu Ser Ala Ser Asn Cys Ser Gly Leu Arg Arg
145                 150                 155                 160

Asn Leu Pro Lys Leu Asp Lys Leu Glu Gln Arg Ala Leu Asp Asp Cys
                165                 170                 175

Leu Asn Leu Phe Asp Asp Thr Val Ser Glu Leu Glu Thr Thr Ile Ala
            180                 185                 190

Asp Leu Ser Gln Ser Thr Ile Gly Pro Lys Arg Tyr His Asp Ala Gln
        195                 200                 205

Thr Leu Leu Ser Gly Ala Met Thr Asn Leu Tyr Thr Cys Leu Asp Gly
    210                 215                 220

Phe Ala Tyr Ser Lys Gly His Val Arg Asp Arg Phe Glu Glu Gly Leu
225                 230                 235                 240

Leu Glu Ile Ser His His Val Ser Asn Ser Leu Ala Met Leu Lys Lys
                245                 250                 255

Leu Pro Ala Gly Val Lys Lys Leu Ala Ser Lys Asn Glu Val Phe Pro
            260                 265                 270

Gly Tyr Gly Lys Ile Lys Asp Gly Phe Pro Thr Trp Leu Ser Thr Lys
        275                 280                 285

Asp Arg Lys Leu Leu Gln Ala Val Asn Glu Thr Asn Phe Asn Leu
    290                 295                 300

Leu Val Ala Lys Asp Gly Thr Gly Asn Phe Thr Thr Ile Ala Glu Ala
305                 310                 315                 320

Val Ala Val Ala Pro Asn Ser Ser Ala Thr Arg Phe Val Ile His Ile
                325                 330                 335

Lys Ala Gly Ala Tyr Phe Glu Asn Val Glu Val Ile Arg Lys Lys Thr
            340                 345                 350

Asn Leu Met Phe Val Gly Asp Gly Ile Gly Lys Thr Val Lys Ala
        355                 360                 365

Ser Arg Asn Val Val Asp Gly Trp Thr Thr Phe Gln Ser Ala Thr Val
    370                 375                 380
```

```
Ala Val Val Gly Asp Gly Phe Ile Ala Lys Gly Ile Thr Phe Glu Asn
385                 390                 395                 400

Ser Ala Gly Pro Ser Lys His Gln Ala Val Ala Leu Arg Ser Gly Ser
            405                 410                 415

Asp Phe Ser Ala Phe Tyr Lys Cys Ser Phe Val Ala Tyr Gln Asp Thr
        420                 425                 430

Leu Tyr Val His Ser Leu Arg Gln Phe Tyr Arg Asp Cys Asp Val Tyr
            435                 440                 445

Gly Thr Val Asp Phe Ile Phe Gly Asn Ala Ala Thr Val Leu Gln Asn
        450                 455                 460

Cys Asn Leu Tyr Ala Arg Lys Pro Asn Glu Asn Gln Arg Asn Leu Phe
465                 470                 475                 480

Thr Ala Gln Gly Arg Glu Asp Pro Asn Gln Asn Thr Gly Ile Ser Ile
            485                 490                 495

Leu Asn Cys Lys Val Ala Ala Ala Asp Leu Ile Pro Val Lys Ser
        500                 505                 510

Gln Phe Lys Asn Tyr Leu Gly Arg Pro Trp Lys Lys Tyr Ser Arg Thr
            515                 520                 525

Val Tyr Leu Asn Ser Tyr Met Glu Asp Leu Ile Asp Pro Lys Gly Trp
530                 535                 540

Leu Glu Trp Asn Gly Thr Phe Ala Leu Asp Thr Leu Tyr Tyr Gly Glu
545                 550                 555                 560

Tyr Asn Asn Arg Gly Pro Gly Ser Asn Thr Ser Ala Arg Val Thr Trp
            565                 570                 575

Pro Gly Tyr Arg Val Ile Lys Asn Ala Thr Glu Ala Asn Gln Phe Thr
            580                 585                 590

Val Arg Asn Phe Ile Gln Gly Asn Glu Trp Leu Ser Ser Thr Asp Ile
            595                 600                 605

Pro Phe Phe Ser Asp Phe Ser
    610                 615

<210> SEQ ID NO 155
<211> LENGTH: 600
<212> TYPE: PRT
<213> ORGANISM: Glycine max
<220> FEATURE:
<221> NAME/KEY: misc_feature
<222> LOCATION: (69)..(101)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid

<400> SEQUENCE: 155

Met Thr Asn Pro Lys Leu Gly Tyr Ala Gly Ile Ser Asp Ser Glu Glu
1               5                   10                  15

His Ile Pro Ser Ser Lys Lys Asn His Lys Lys Leu Leu Leu Ser Leu
            20                  25                  30

Leu Ala Thr Leu Leu Val Ala Ala Ser Val Val Ala Ile Val Ala Gly
        35                  40                  45

Val Lys Asn Lys Thr Lys Asn Ser Asp Asn Ser Asp Thr Asn Ser Thr
    50                  55                  60

Ser Leu Ser Leu Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95
```

```
Xaa Xaa Xaa Xaa Xaa Asn Gln Arg Xaa Val Leu Thr Met Thr Arg Asp
                100             105                 110

Val Ile Gln Leu Ser Leu Ser Ile Thr Phe Arg Ala Val Glu Arg Asn
            115                 120                 125

Tyr Phe Thr Val Lys Lys Leu Leu Thr Lys His Asp Leu Thr Lys Arg
        130                 135                 140

Glu Thr Thr Ala Leu His Asp Cys Leu Glu Thr Ile Asp Glu Thr Leu
145                 150                 155                 160

Asp Glu Leu Arg Glu Ala Gln His Asp Leu Glu Leu Tyr Pro Asn Lys
                165                 170                 175

Lys Thr Leu Tyr Gln His Ala Asp Asp Leu Lys Thr Leu Ile Ser Ala
            180                 185                 190

Ala Ile Thr Asn Gln Val Thr Cys Leu Asp Gly Phe Ser His Asp Asp
        195                 200                 205

Ala Asp Lys His Val Arg Lys Glu Leu Glu Lys Gly Gln Val His Val
    210                 215                 220

Glu His Met Cys Ser Asn Ala Leu Ala Met Thr Lys Asn Met Thr Asp
225                 230                 235                 240

Gly Asp Ile Ala Asn Tyr Glu Tyr Lys Met Lys Val Glu Asn Thr Asn
                245                 250                 255

Ser Asn Arg Lys Leu Leu Val Glu Asn Gly Val Glu Trp Pro Glu Trp
            260                 265                 270

Ile Ser Ala Ala Asp Arg Arg Leu Leu Gln Ala Ala Thr Val Lys Ala
        275                 280                 285

Asp Val Thr Val Ala Ala Asp Gly Ser Gly Asp Phe Lys Thr Val Thr
    290                 295                 300

Glu Ala Val Lys Ala Ala Pro Leu Lys Ser Ser Lys Arg Tyr Val Ile
305                 310                 315                 320

Arg Ile Lys Gly Gly Val Tyr Arg Glu Asn Val Glu Val Asp Lys Lys
                325                 330                 335

Lys Thr Asn Ile Met Phe Leu Gly Asp Gly Arg Thr Asn Thr Ile Ile
            340                 345                 350

Thr Ala Ser Arg Asn Val Val Asp Gly Ser Thr Thr Phe His Ser Ala
        355                 360                 365

Thr Val Ala Val Val Gly Ala Asn Phe Leu Ala Arg Asp Ile Thr Phe
    370                 375                 380

Gln Asn Thr Ala Gly Pro Ser Lys His Gln Ala Val Ala Leu Arg Val
385                 390                 395                 400

Gly Gly Asp Leu Ser Ala Phe Phe Asn Cys Asp Phe Leu Ala Phe Gln
                405                 410                 415

Asp Thr Leu Tyr Val His Asn Asn Arg Gln Phe Phe Val Lys Cys Leu
            420                 425                 430

Ile Thr Gly Thr Val Asp Phe Ile Phe Gly Asn Ser Ala Val Val Phe
        435                 440                 445

Gln Asp Cys Asp Ile His Ala Arg Leu Pro Asp Ser Gly Gln Lys Asn
    450                 455                 460

Met Val Thr Ala Gln Gly Arg Val Asp Pro Asn Gln Asn Thr Gly Ile
465                 470                 475                 480

Val Ile Gln Lys Cys Arg Ile Gly Ala Thr Lys Asp Leu Glu Ser Val
                485                 490                 495

Lys Lys Asn Phe Lys Thr Tyr Leu Gly Arg Pro Trp Lys Glu Tyr Ser
            500                 505                 510
```

```
Arg Thr Val Ile Met Gln Ser Ile Ser Asp Val Ile Asp Pro Ile
            515                 520                 525

Gly Trp His Glu Trp Ser Gly Asn Phe Ala Leu Ser Thr Leu Val Tyr
            530                 535                 540

Arg Glu Tyr Gln Asn Thr Gly Pro Gly Ala Gly Thr Ser Asn Arg Val
545                 550                 555                 560

Thr Trp Lys Gly Tyr Lys Val Ile Thr Asp Ala Ala Glu Ala Arg Asp
                565                 570                 575

Tyr Thr Pro Gly Ser Phe Ile Gly Ser Ser Trp Leu Gly Ser Thr
            580                 585                 590

Gly Phe Pro Phe Ser Leu Gly Leu
            595                 600

<210> SEQ ID NO 156
<211> LENGTH: 598
<212> TYPE: PRT
<213> ORGANISM: Glycine max

<400> SEQUENCE: 156

Met Thr Asn Pro Lys Leu Gly Tyr Ala Gly Ile Ser Asp Ser Gly Asn
1               5                   10                  15

His Ile Pro Ser Ser Lys Lys Asn His Lys Lys Leu Leu Ser Leu
            20                  25                  30

Leu Ala Thr Leu Leu Val Ala Ala Ser Leu Val Ala Ile Val Val Gly
            35                  40                  45

Val Lys Asn Lys Asn Ser Asp Asn Ser Ala Thr Ser Thr Pro Leu Ser
50                  55                  60

Leu Ser His His Ser His Thr Ile Val Lys Ser Ala Cys Ser Ser Thr
65                  70                  75                  80

Phe Tyr Pro Glu Leu Cys Tyr Ser Ala Ile Ala Ser Glu Pro Asn Val
            85                  90                  95

Thr His Lys Ile Thr Thr Asn Arg Asp Val Ile Gln Leu Ser Leu Lys
            100                 105                 110

Ile Thr Phe Arg Ala Val Glu Gln Asn Tyr Phe Thr Val Lys Lys Leu
            115                 120                 125

Phe Thr Glu His Asp Asp Leu Thr Lys Arg Glu Lys Thr Ala Leu His
            130                 135                 140

Asp Cys Leu Glu Thr Ile Asp Glu Thr Leu Asp Glu Leu Arg Glu Ala
145                 150                 155                 160

Gln His Asn Leu Glu Leu Tyr Pro Asn Lys Lys Thr Leu Tyr Gln His
            165                 170                 175

Ala Asp Asp Leu Lys Thr Leu Ile Ser Ala Ala Ile Thr Asn Gln Val
            180                 185                 190

Thr Cys Leu Asp Gly Phe Ser His Asp Ala Asp Lys His Val Arg
            195                 200                 205

Lys Ala Leu Glu Lys Gly Gln Val His Val Glu His Met Cys Ser Asn
            210                 215                 220

Ala Leu Ala Met Thr Lys Asn Met Thr Asp Ser Asp Ile Ala Asn Tyr
225                 230                 235                 240

Glu Tyr Asn Met Arg Val Glu Asn Asn Gly Gln Asn Gly Asn Ser Asn
            245                 250                 255

Arg Lys Leu Leu Val Glu Asn Asp Val Glu Trp Pro Glu Trp Ile Ser
            260                 265                 270

Ala Ala Asp Arg Arg Leu Leu Gln Ala Ser Thr Val Lys Ala Asp Val
            275                 280                 285
```

-continued

```
Thr Val Ala Ala Asp Gly Ser Gly Asp Phe Lys Thr Val Thr Glu Ala
    290                 295                 300

Val Asp Ala Ala Pro Leu Lys Ser Ser Lys Arg Phe Val Ile Arg Ile
305                 310                 315                 320

Lys Ala Gly Val Tyr Arg Glu Asn Val Glu Val Pro Lys Lys Lys Asn
                325                 330                 335

Asn Ile Met Phe Leu Gly Asp Gly Arg Thr Asn Thr Ile Ile Thr Ala
            340                 345                 350

Ser Arg Asn Val Val Asp Gly Ser Thr Thr Phe His Ser Ala Thr Val
        355                 360                 365

Ala Val Val Gly Ser Asn Phe Leu Ala Arg Asp Leu Thr Phe Gln Asn
    370                 375                 380

Thr Ala Gly Pro Ser Lys His Gln Ala Val Ala Leu Arg Val Gly Gly
385                 390                 395                 400

Asp Leu Ser Ala Phe Phe Asn Cys Asp Ile Leu Ala Phe Gln Asp Thr
                405                 410                 415

Leu Tyr Val His Asn Asn Arg Gln Phe Phe Val Lys Cys Leu Ile Ala
            420                 425                 430

Gly Thr Val Asp Phe Ile Phe Gly Asn Ser Ala Val Val Phe Gln Asp
        435                 440                 445

Cys Asp Ile His Ala Arg Leu Pro Ser Ser Gly Gln Lys Asn Met Val
    450                 455                 460

Thr Ala Gln Gly Arg Val Asp Pro Asn Gln Asn Thr Gly Ile Val Ile
465                 470                 475                 480

Gln Lys Cys Arg Ile Gly Ala Thr Asn Asp Leu Glu Ser Val Lys Lys
                485                 490                 495

Asn Phe Lys Thr Tyr Leu Gly Arg Pro Trp Lys Glu Tyr Ser Arg Thr
            500                 505                 510

Val Ile Met Gln Ser Ser Ile Ser Asp Val Ile Asp Pro Ile Gly Trp
        515                 520                 525

His Glu Trp Ser Gly Asn Phe Gly Leu Ser Thr Leu Val Tyr Arg Glu
    530                 535                 540

Tyr Gln Asn Thr Gly Pro Gly Ala Gly Thr Ser Asn Arg Val Thr Trp
545                 550                 555                 560

Lys Gly Tyr Lys Val Ile Thr Asp Thr Ala Glu Ala Arg Glu Tyr Thr
                565                 570                 575

Pro Gly Ser Phe Ile Gly Gly Ser Ser Trp Leu Gly Ser Thr Gly Phe
            580                 585                 590

Pro Phe Ser Leu Gly Leu
        595

<210> SEQ ID NO 157
<211> LENGTH: 405
<212> TYPE: PRT
<213> ORGANISM: Glycine max

<400> SEQUENCE: 157

Met Glu Ile Pro Ile Pro Ile Pro Leu Ser Ser Met Leu Leu Phe Leu
1               5                   10                  15

Leu Leu Val Pro Cys Cys Ile Cys Ser Ser Pro Leu Gln Asp Pro Glu
                20                  25                  30

Leu Val Val Glu Asp Val Gln Lys Ser Ile Asn Ala Ser Arg Arg Asn
            35                  40                  45

Leu Ala Phe Leu Ser Cys Gly Thr Gly Asn Pro Ile Asp Asp Cys Trp
```

```
            50                  55                  60
Arg Cys Asp Pro Asn Trp Glu Lys Asn Arg Lys Arg Leu Ala Asp Cys
 65                  70                  75                  80

Ser Ile Gly Phe Gly Lys His Ala Val Gly Gly Arg Asp Gly Lys Leu
                 85                  90                  95

Tyr Val Val Thr Asp Pro Gly Asp His Pro Val Asn Pro Lys Pro Gly
            100                 105                 110

Thr Leu Arg Tyr Gly Val Ile Gln Glu Glu Pro Leu Trp Ile Ile Phe
        115                 120                 125

Lys Arg Asp Met Val Ile Lys Leu Lys Gln Glu Leu Met Met Asn Ser
    130                 135                 140

Phe Lys Thr Ile Asp Gly Arg Gly Val Ser Val His Ile Ala Gly Gly
145                 150                 155                 160

Pro Cys Ile Thr Ile Gln Tyr Val Thr Asn Ile Ile His Gly Ile
                165                 170                 175

Asn Ile His Asp Cys Lys Gln Gly Gly Asn Ala Tyr Val Arg Asp Ser
            180                 185                 190

Pro Thr His Tyr Gly Trp Arg Thr Leu Ser Asp Gly Asp Gly Val Ser
        195                 200                 205

Ile Phe Gly Gly Ser His Val Trp Val Asp His Cys Ser Leu Ser Asn
210                 215                 220

Cys Arg Asp Gly Leu Ile Asp Ala Ile His Gly Ser Thr Ala Ile Thr
225                 230                 235                 240

Ile Ser Asn Asn Tyr Met Thr His His Asn Lys Val Met Leu Leu Gly
                245                 250                 255

His Ser Asp Thr Phe Thr Arg Asp Lys Asn Met Gln Val Thr Ile Ala
            260                 265                 270

Phe Asn His Phe Gly Glu Gly Leu Val Gln Arg Met Pro Arg Cys Arg
        275                 280                 285

His Gly Tyr Phe His Val Val Asn Asn Asp Tyr Thr His Trp Arg Met
    290                 295                 300

Tyr Ala Ile Gly Gly Ser Ala Ala Pro Thr Ile Asn Ser Gln Gly Asn
305                 310                 315                 320

Arg Phe Leu Ala Pro Asn Asp Asn Thr Phe Lys Glu Val Thr Lys Arg
                325                 330                 335

Glu Asn Ser Pro Gln Ser Lys Trp Lys Asn Trp Asn Trp Arg Ser Asn
            340                 345                 350

Gly Asp Leu Met Leu Asn Gly Ala Phe Phe Thr Ala Ser Gly Ala Gly
        355                 360                 365

Ala Ser Ser Ser Tyr Ala Arg Ala Ser Ser Leu Ala Ala Lys Ser Ser
    370                 375                 380

Ser Leu Val Ser Ser Ile Thr Ala Ser Ala Gly Ser Leu Arg Cys Arg
385                 390                 395                 400

Lys Gly Ser Arg Cys
            405

<210> SEQ ID NO 158
<211> LENGTH: 402
<212> TYPE: PRT
<213> ORGANISM: Glycine max

<400> SEQUENCE: 158

Met Glu Ile Pro Ile Pro Leu Ser Phe Met Leu Leu Leu Leu Leu Val
 1               5                  10                  15
```

Pro Ser Cys Ile Cys Ser Ser Pro Leu Gln Asp Pro Glu Leu Val Val
            20                  25                  30

Glu Asp Val Gln Lys Ser Ile Asn Ala Ser Arg Arg Asn Leu Ala Phe
        35                  40                  45

Leu Ser Cys Gly Thr Gly Asn Pro Ile Asp Asp Cys Trp Arg Cys Asp
    50                  55                  60

Pro Asn Trp Glu Lys Asn Arg Lys Arg Leu Ala Asp Cys Ser Ile Gly
65                  70                  75                  80

Phe Gly Lys His Ala Val Gly Gly Arg Asp Gly Lys Ile Tyr Val Val
                85                  90                  95

Thr Asp Pro Gly Asp His Pro Val Asn Pro Lys Pro Gly Thr Leu Arg
            100                 105                 110

Tyr Gly Val Ile Gln Glu Pro Leu Trp Ile Ile Phe Lys Arg Asp
        115                 120                 125

Met Val Ile Lys Leu Lys Gln Glu Leu Met Met Asn Ser Phe Lys Thr
    130                 135                 140

Ile Asp Gly Arg Gly Ala Ser Val His Ile Ala Gly Gly Pro Cys Ile
145                 150                 155                 160

Thr Ile Gln Tyr Val Thr Asn Ile Ile His Gly Ile Asn Ile His
                165                 170                 175

Asp Cys Lys Gln Gly Gly Asn Ala Tyr Val Arg Asp Ser Pro Thr His
            180                 185                 190

Tyr Gly Trp Arg Thr Leu Ser Asp Gly Asp Val Ser Ile Phe Gly
        195                 200                 205

Gly Ser His Val Trp Val Asp His Cys Ser Leu Ser Asn Cys Arg Asp
    210                 215                 220

Gly Leu Ile Asp Ala Ile His Gly Ser Thr Gly Ile Thr Ile Ser Asn
225                 230                 235                 240

Asn Tyr Leu Thr His His Asn Lys Val Met Leu Gly His Ser Asp
                245                 250                 255

Thr Phe Thr Arg Asp Lys Asn Met Gln Val Thr Ile Ala Phe Asn His
            260                 265                 270

Phe Gly Glu Gly Leu Val Gln Arg Met Pro Arg Cys Arg His Gly Tyr
        275                 280                 285

Phe His Val Val Asn Asn Asp Tyr Thr His Trp Arg Met Tyr Ala Ile
    290                 295                 300

Gly Gly Ser Ala Ala Pro Thr Ile Asn Ser Gln Gly Asn Arg Phe Leu
305                 310                 315                 320

Ala Pro Asn Asp Asn Thr Phe Lys Glu Val Thr Lys Arg Glu Asn Ser
                325                 330                 335

Ala Gln Ser Lys Trp Lys Asn Trp Asn Trp Arg Ser Ser Gly Asp Leu
            340                 345                 350

Met Leu Asn Gly Ala Phe Phe Thr Ala Ser Gly Ala Gly Ala Ser Ser
        355                 360                 365

Ser Tyr Ala Arg Ala Ser Ser Leu Ala Ala Lys Ser Ser Ser Leu Val
    370                 375                 380

Ser Ser Ile Thr Ala Ser Ala Gly Ser Leu Ser Cys Arg Lys Gly Ser
385                 390                 395                 400

Arg Cys

<210> SEQ ID NO 159
<211> LENGTH: 502
<212> TYPE: PRT
<213> ORGANISM: Glycine max

<400> SEQUENCE: 159

```
Met Leu His Ile Thr Cys Ile Leu Leu Met Cys Leu Leu Ser Ser Phe
1               5                   10                  15

Ser Pro Pro Ile Asn Ala Leu Leu Asn Leu Thr Leu Pro His Gln His
            20                  25                  30

Pro His Pro Glu Ser Val Val His Asp Leu Gln Arg Lys Val Asn Ala
        35                  40                  45

Ser Leu Trp Arg Arg Glu Met Leu Ser Lys Glu Asp Gln Gln Glu Gly
    50                  55                  60

Met Ser Ser Ser Cys Leu Thr Gly Asn Pro Ile Asp Asp Cys Trp
65                  70                  75                  80

Arg Cys Asp Pro Asn Trp Ala Ala Asp Arg Gln Lys Leu Ala Glu Cys
                85                  90                  95

Gly Leu Gly Phe Gly Lys Tyr Ala Met Gly Gly Lys Gly Gln Ile
            100                 105                 110

Tyr Ile Val Thr Asp Ser Ser Asp Arg Asp Pro Ala Asn Pro Val Pro
        115                 120                 125

Gly Thr Leu Arg His Ala Val Ile Gln Asp Glu Pro Leu Trp Ile Val
130                 135                 140

Phe Ala Ala Asp Met Thr Ile Asn Leu Lys His Glu Leu Ile Phe Asn
145                 150                 155                 160

Ser Tyr Lys Thr Leu Asp Gly Arg Gly Ala Asn Val His Val Thr Gly
                165                 170                 175

His Gly Cys Ile Thr Leu Gln Tyr Val Ser Asn Ile Ile His Asn
            180                 185                 190

Ile His Val His His Cys Thr Pro Ser Gly Asn Thr Asn Ile Arg Ala
        195                 200                 205

Ser Pro Thr His Val Gly Trp Arg Gly Lys Ser Asp Gly Asp Gly Ile
210                 215                 220

Ser Ile Phe Gly Ser Arg Lys Ile Trp Ile Asp His Cys Ser Leu Ser
225                 230                 235                 240

Tyr Cys Thr Asp Gly Leu Ile Asp Ala Ile Met Gly Ser Thr Gly Ile
                245                 250                 255

Thr Ile Ser Asn Ser His Phe Ala His His Asp Glu Val Met Leu Leu
            260                 265                 270

Gly His Asp Asp Lys Tyr Leu Pro Asp Arg Gly Met Gln Val Thr Ile
        275                 280                 285

Ala Phe Asn His Phe Gly Glu Gly Leu Val Gln Arg Met Pro Arg Cys
290                 295                 300

Arg Leu Gly Tyr Ile His Val Val Asn Asn Asp Phe Thr Gln Trp Lys
305                 310                 315                 320

Met Tyr Ala Ile Gly Gly Ser Ala Asn Pro Thr Ile Asn Ser Gln Gly
                325                 330                 335

Asn Arg Tyr Thr Ala Pro Ala Asp Pro Asp Ala Lys Glu Val Thr Lys
            340                 345                 350

Arg Val Asp Thr Asp Arg Glu Trp Ser Gly Trp Asn Trp Arg Thr
        355                 360                 365

Glu Gly Asp Ile Met Val Asn Gly Ala Phe Phe Val Pro Ser Gly Ala
            370                 375                 380

Gly Gln Ser Ala Gln Tyr Ala Glu Ala Thr Ser Val Gln Ala Lys Ser
385                 390                 395                 400

Ala Val Gln Ile Asp Gln Leu Thr Met Tyr Ser Gly Val Phe Gly Asp
```

```
                        405                 410                 415
Pro Arg Asp Asn Gly Asp Leu Tyr Pro Gly Phe Asn Gly Gly Thr
            420                 425                 430

Val Thr Gly Ala Thr Ser Lys Gly Asn Thr Glu Gly Ser Ser Asp
            435                 440                 445

Asp Gly Asp Phe Phe Gly Met Ile Phe Arg Gly Ser Ser Ser Gln
            450                 455                 460

Ala Ala Pro Pro Ser Pro Ser Ser Ser Ile Val Phe Val Ser Thr Phe
465                 470                 475                 480

Leu Ser Leu Leu Ile Ile Phe Ile Leu Asp Thr Thr Thr Asn His Ala
                485                 490                 495

Ile Leu Leu Ser Leu Leu
                500

<210> SEQ ID NO 160
<211> LENGTH: 477
<212> TYPE: PRT
<213> ORGANISM: Glycine max

<400> SEQUENCE: 160

Met Leu Gln Thr Thr Cys Ile Ile Leu Phe Ser Val Val Ala Ile Phe
1               5                   10                  15

Leu Pro His Gly Thr Ala Met Leu Asn Leu Thr Leu Pro Gly Gln His
                20                  25                  30

Pro Asp Pro Glu Ala Val Ala Arg Glu Val His Arg Lys Val Asn Ala
            35                  40                  45

Ser Met Ala Arg Arg Glu Met Leu Gly Val Ser Glu Lys Glu Val Ala
50                  55                  60

Ser Cys Leu Thr Gly Asn Pro Ile Asp Asp Cys Trp Lys Cys Asp Pro
65                  70                  75                  80

Asp Trp Ala Asn Asn Arg Gln Arg Leu Ala Asp Cys Ala Ile Gly Phe
                85                  90                  95

Gly Gln Asn Ala Lys Gly Gly Lys Gly Gly Gln Phe Tyr Ile Val Thr
                100                 105                 110

Asp Ser Ser Asp Glu Asp Pro Val Asn Pro Lys Pro Gly Thr Leu Arg
            115                 120                 125

Tyr Ala Val Ile Gln Asn Glu Pro Leu Trp Ile Val Phe Pro Ser Asn
130                 135                 140

Met Met Ile Lys Leu Ser Gln Glu Leu Ile Phe Asn Ser Tyr Lys Thr
145                 150                 155                 160

Ile Asp Gly Arg Gly Ala Asp Val His Ile Val Gly Gly Gly Cys Ile
                165                 170                 175

Thr Leu Gln Tyr Ile Ser Asn Val Ile Ile His Asn Ile His Ile His
            180                 185                 190

His Cys His Pro Ser Gly Asn Ala Asn Val Arg Ser Ser Pro Glu His
            195                 200                 205

Tyr Gly Tyr Arg Thr Glu Ser Asp Gly Asp Gly Ile Ser Ile Phe Gly
            210                 215                 220

Ser Arg Asp Ile Trp Ile Asp His Cys Thr Leu Ser Arg Cys Lys Asp
225                 230                 235                 240

Gly Leu Ile Asp Ala Val Met Gly Ser Ser Ala Ile Thr Ile Ser Asn
                245                 250                 255

Asn His Phe Ser His His Asn Asp Val Met Leu Leu Gly His Ser Asp
            260                 265                 270
```

```
His Tyr Leu Pro Asp Ser Gly Met Gln Val Thr Ile Gly Phe Asn His
            275                 280                 285

Phe Gly Glu Gly Leu Val Gln Arg Met Pro Arg Cys Arg Arg Gly Tyr
            290                 295                 300

Ile His Val Val Asn Asn Asp Phe Thr Arg Trp Glu Met Tyr Ala Ile
305                 310                 315                 320

Gly Gly Ser Ala Gly Pro Thr Ile Asn Ser Gln Gly Asn Arg Tyr Thr
            325                 330                 335

Ala Pro Glu Asp Pro Tyr Ala Lys Gln Val Thr Lys Arg Leu Asp Ala
            340                 345                 350

Gly Glu Gly Glu Trp Ser Gly Trp Asn Trp Arg Ser Glu Gly Asp Val
            355                 360                 365

Leu Leu Asn Gly Ala Phe Phe Val Ala Ser Gly Ala Val Ala Glu Pro
            370                 375                 380

Asn Tyr Gln Asn Ala Tyr Ser Thr Gln Pro Lys Asn Val Asp Arg Ile
385                 390                 395                 400

Ser Leu Leu Thr Met Ser Ala Gly Val Leu Gly Val Ala Arg Asp Asn
            405                 410                 415

Asn Leu Gly Met Trp Ile Arg Gly Pro Asn Asp Gly Thr Val Tyr Phe
            420                 425                 430

Ser Asp Ser Gly Pro Glu Tyr Thr Asp Glu Met Ser Arg Ser Thr Met
            435                 440                 445

Pro Leu Leu Pro Ser Arg Ile Leu Ile Leu Val Ser Ala Leu Leu Cys
            450                 455                 460

Phe Leu Gly His Thr Thr Thr Leu Thr Thr Leu Pro Asn
465                 470                 475

<210> SEQ ID NO 161
<211> LENGTH: 379
<212> TYPE: PRT
<213> ORGANISM: Glycine max

<400> SEQUENCE: 161

Met Ser Asn Leu His Tyr Met Phe Ile Leu Phe Ala Val Leu Leu Val
1               5                   10                  15

Gln Asn Pro Ser Arg Ile His Cys His Thr Lys Gly Ile Arg Pro Arg
            20                  25                  30

Leu Ser Ala Gly Lys Gly Leu Ser Thr Asn Ile Thr Arg Val Gln Tyr
            35                  40                  45

Ser Glu Gln Gln Phe Met Lys Trp Val Asn Phe Val Gly Ser Leu Lys
            50                  55                  60

His Ser Val Phe Lys Ser Ala Lys Asn Lys Leu Val Ala Ser Tyr Thr
65                  70                  75                  80

Leu His Val Asp Lys Asp Pro Gly Ala Gly Asp Phe Thr Ser Ile Gln
            85                  90                  95

Glu Ala Ile Asp Ser Leu Pro Phe Ile Asn Leu Val Arg Val Val Ile
            100                 105                 110

Lys Val His Ala Gly Val Tyr Thr Glu Lys Val Asn Ile Pro Pro Leu
            115                 120                 125

Lys Ser Tyr Ile Thr Ile Glu Gly Ala Gly Thr Asp Lys Thr Ile Val
            130                 135                 140

Lys Trp Gly Asp Thr Ala Gln Thr Pro Gly Pro Asn Gly Arg Pro Leu
145                 150                 155                 160

Gly Thr Tyr Gly Ser Ala Thr Phe Ala Val Asn Ser Pro Tyr Phe Leu
            165                 170                 175
```

```
Ala Lys Asn Ile Thr Phe Gln Asn Thr Thr Pro Val Pro Ala Pro Gly
            180                 185                 190

Ala Val Gly Lys Gln Ala Val Ala Leu Arg Ile Ser Ala Asp Thr Ala
            195                 200                 205

Ala Phe Val Gly Cys Lys Phe Leu Gly Ala Gln Asp Thr Leu Tyr Asp
        210                 215                 220

His Leu Gly Arg His Tyr Tyr Lys Asp Cys Tyr Ile Glu Gly Ser Val
225                 230                 235                 240

Asp Phe Ile Phe Gly Asn Ser Leu Ser Leu Phe Glu Gly Cys His Val
                245                 250                 255

His Ala Ile Ala Gln Asn Thr Gly Ala Val Thr Ala Gln Gly Arg Ser
            260                 265                 270

Ser Met Leu Glu Asp Thr Gly Phe Ser Phe Val Asn Cys Lys Val Thr
        275                 280                 285

Gly Ser Gly Ala Leu Tyr Leu Gly Arg Ala Trp Gly Pro Phe Ser Arg
290                 295                 300

Val Val Phe Ala Tyr Thr Phe Met Asp Asn Ile Ile Pro Lys Gly
305                 310                 315                 320

Trp Tyr Asn Trp Gly Asp Pro Asn Arg Glu Met Thr Val Phe Tyr Gly
                325                 330                 335

Gln Tyr Lys Cys Thr Gly Leu Gly Ala Ser Phe Ala Gly Arg Val Pro
            340                 345                 350

Trp Ser Arg Glu Leu Thr Asp Glu Glu Ala Ala Pro Phe Leu Ser Leu
            355                 360                 365

Ser Phe Ile Asp Gly Thr Glu Trp Ile Lys Val
        370                 375

<210> SEQ ID NO 162
<211> LENGTH: 375
<212> TYPE: PRT
<213> ORGANISM: Glycine max

<400> SEQUENCE: 162

Met Ser Asn Leu His Phe Ile Phe Tyr Gly Leu Val Val Ile Leu Leu
1               5                   10                  15

Leu Gln Asn Pro Ser Ala Thr Gln Cys His Thr Lys Gly Ile Gln Pro
            20                  25                  30

Lys Pro Gly Asn Gly Leu Ser Thr Asn Met Thr Arg Val Glu Phe Ser
        35                  40                  45

Glu Gln Gln Phe Met Lys Trp Val Lys Phe Val Gly Gly Leu Lys His
    50                  55                  60

Ser Val Phe Arg Thr Ala Asn Asn Lys Leu Phe Pro Ser His Thr Leu
65                  70                  75                  80

His Val Ser Lys Lys His Gly Lys Gly Gly Phe Ser Ser Ile Gln Ala
                85                  90                  95

Ala Ile Asp Ser Leu Pro Phe Ile Asn Val Val Arg Val Ile Lys
            100                 105                 110

Val His Ala Gly Val Tyr Thr Glu Lys Val Asn Ile Ser Pro Phe Lys
        115                 120                 125

Ser Phe Ile Thr Ile Gln Gly Glu Gly Ala Asp Lys Thr Ile Val Gln
    130                 135                 140

Trp Gly Asp Thr Ala Gln Ser Gln Pro Leu Gly Thr Tyr Gly Ser Ala
145                 150                 155                 160

Thr Phe Ala Val Asn Ser Ala Tyr Phe Ile Ala Lys Asn Ile Thr Phe
```

```
            165                 170                 175
Lys Asn Thr Ala Pro Ile Pro Ala Pro Gly Ala Val Gly Lys Gln Gly
        180                 185                 190

Val Ala Leu Arg Ile Ser Ala Asp Thr Ala Val Phe Gln Gly Cys Lys
        195                 200                 205

Phe Leu Gly Ala Gln Asp Thr Leu Tyr Asp His Ile Gly Arg His Tyr
        210                 215                 220

Tyr Lys Asp Cys Tyr Ile Glu Gly Ser Val Asp Phe Ile Phe Gly Asn
225                 230                 235                 240

Ala Leu Ser Leu Phe Glu Gly Cys His Val His Ala Ile Ala Gln Leu
                245                 250                 255

Thr Gly Ala Leu Thr Ala Gln Gly Arg Ser Ser Leu Leu Glu Asp Thr
            260                 265                 270

Gly Phe Ser Phe Val His Cys Lys Val Thr Gly Ser Gly Ala Leu Tyr
        275                 280                 285

Leu Gly Arg Ala Trp Gly Pro Phe Ser Arg Val Val Phe Ala Tyr Thr
        290                 295                 300

Tyr Met Asp Asn Ile Ile Ile Pro Lys Gly Trp Tyr Asn Trp Gly Asp
305                 310                 315                 320

Pro Asn Arg Glu Met Thr Val Phe Tyr Gly Gln Tyr Lys Cys Thr Gly
                325                 330                 335

Pro Gly Ala Ser Tyr Ala Gly Arg Val Ser Trp Ser Arg Glu Leu Thr
            340                 345                 350

Asp Glu Glu Ala Lys Pro Phe Ile Ser Leu Ser Tyr Ile Asp Gly Ser
        355                 360                 365

Glu Trp Ile Asn Leu Ser Leu
        370                 375

<210> SEQ ID NO 163
<211> LENGTH: 375
<212> TYPE: PRT
<213> ORGANISM: Glycine max

<400> SEQUENCE: 163

Met Ser Asn Leu His Phe Ile Phe Tyr Gly Leu Val Val Ile Leu Phe
1               5                   10                  15

Leu Gln Asn Pro Ser Ala Thr Gln Cys His Thr Lys Gly Ile Arg Pro
            20                  25                  30

Lys Pro Gly Asn Gly Leu Ser Thr Asn Met Thr Arg Val Glu Phe Ser
        35                  40                  45

Glu Gln Gln Phe Met Lys Trp Val Lys Phe Val Gly Gly Leu Lys His
    50                  55                  60

Ser Val Phe Arg Thr Ala Lys Asn Lys Leu Phe Pro Ser His Thr Leu
65                  70                  75                  80

His Val Ser Lys Lys His Gly Lys Gly Gly Phe Ser Ser Ile Gln Ala
                85                  90                  95

Ala Ile Asp Ser Leu Pro Phe Ile Asn Val Val Arg Val Val Ile Lys
            100                 105                 110

Val His Ala Gly Val Tyr Thr Glu Lys Val Asn Ile Ser Pro Phe Lys
        115                 120                 125

Ser Phe Val Thr Ile Gln Gly Glu Gly Ala Asp Lys Thr Ile Val Gln
    130                 135                 140

Trp Gly Asp Thr Ala Gln Ser Gln Pro Leu Gly Thr Tyr Gly Ser Ala
145                 150                 155                 160
```

```
Thr Phe Ala Val Asn Ser Pro Tyr Phe Ile Ala Lys Asn Ile Thr Phe
                165                 170                 175

Lys Asn Thr Ala Pro Ile Pro Ala Pro Gly Ala Val Gly Lys Gln Gly
            180                 185                 190

Val Ala Leu Arg Ile Ser Ala Asp Thr Ala Val Phe Leu Gly Cys Lys
        195                 200                 205

Phe Leu Gly Ala Gln Asp Thr Leu Tyr Asp His Ile Gly Arg His Tyr
    210                 215                 220

Tyr Lys Asp Cys Tyr Ile Glu Gly Ser Val Asp Phe Ile Phe Gly Asn
225                 230                 235                 240

Ala Leu Ser Leu Phe Glu Gly Cys His Val His Ala Ile Ala Gln Leu
                245                 250                 255

Thr Gly Ala Leu Thr Ala Gln Gly Arg Asn Ser Leu Leu Glu Asp Thr
            260                 265                 270

Gly Phe Ser Phe Val His Cys Lys Val Thr Gly Ser Gly Ala Leu Tyr
        275                 280                 285

Leu Gly Arg Ala Trp Gly Pro Phe Ser Arg Val Val Phe Ala Tyr Thr
    290                 295                 300

Tyr Met Asp Asn Ile Ile Ile Pro Lys Gly Trp Tyr Asn Trp Gly Asp
305                 310                 315                 320

Pro Asn Arg Glu Met Thr Val Phe Tyr Gly Gln Tyr Lys Cys Thr Gly
                325                 330                 335

Pro Gly Ala Ser Tyr Ala Gly Arg Val Ser Trp Ser Arg Glu Leu Ser
            340                 345                 350

Asp Glu Glu Ala Lys Pro Phe Ile Ser Leu Ser Tyr Ile Asp Gly Ser
        355                 360                 365

Glu Trp Ile Asn Leu Ser Leu
    370                 375

<210> SEQ ID NO 164
<211> LENGTH: 554
<212> TYPE: PRT
<213> ORGANISM: Glycine max

<400> SEQUENCE: 164

Met Met Val Ala Ser Leu Phe Tyr Leu Ser Leu Ser Leu Ser Leu Ile
1               5                   10                  15

Leu Thr Leu Ser Ser Ala Ala His His Lys Pro Pro His Ser Pro Ser
            20                  25                  30

Lys Pro Pro Ala Asn Pro Ala Val Thr Ala Ala Ser Pro Ala Ile Glu
        35                  40                  45

Gln Ala Cys Ala Ala Thr Leu Phe Pro Gln Gln Cys Glu Ala Ser Leu
    50                  55                  60

Ser Gln Ser Gln Asn Leu Pro Pro Asn Pro Thr Pro Leu Gln Leu Leu
65                  70                  75                  80

Gln Ser Ala Ile Ala Leu Ser Ser Asp Asn Leu Ala Thr Ala Gln Thr
                85                  90                  95

Met Ala Lys Ser Leu Leu Asp Ala Ser Ala Asp Ser Arg Asn Arg Thr
            100                 105                 110

Val Ala Ala Ala Thr Cys Ile Glu Ile Leu Ala Asn Ser His His Arg
        115                 120                 125

Ile Ser Leu Ala Ser Asp Ala Leu Pro Arg Gly Arg Thr Lys Asp Ala
    130                 135                 140

Arg Ala Trp Leu Gly Ala Ala Leu Ala Tyr Gln Tyr Asp Cys Trp Asn
145                 150                 155                 160
```

Ser Leu Lys Tyr Ala Asn Asp Thr Gln Met Val Gly Lys Thr Met Ser
            165                 170                 175

Phe Ile Asp Asn Leu Glu Ile Leu Ser Ser Asn Ala Leu Ser Met Ala
        180                 185                 190

Phe Ser Phe Asp Ala Phe Gly Asn Asp Ile Ala Ser Trp Lys Pro Pro
    195                 200                 205

Ala Thr Glu Arg Val Gly Phe Trp Gly Thr Val Gly Ser Gly Gly Pro
210                 215                 220

Gly Pro Ala Gly Gly Val Pro Leu Asn Leu Thr Pro Asp Val Thr Val
225                 230                 235                 240

Cys Lys Asn Gly Gly Asp Gly Cys Tyr Lys Thr Val Gln Glu Ala Val
                245                 250                 255

Asn Ala Ala Pro Asp Asn Gly Asn Arg Thr Lys Arg Phe Val Ile His
            260                 265                 270

Ile Lys Glu Gly Val Tyr Gln Glu Thr Val Arg Val Pro Leu Ala Lys
        275                 280                 285

Arg Asn Val Val Phe Leu Gly Asp Gly Ile Gly Lys Thr Val Ile Thr
    290                 295                 300

Gly Asp Ala Asn Val Gly Gln Gln Gly Met Thr Thr Tyr Asn Ser Ala
305                 310                 315                 320

Thr Val Ala Val Leu Gly Asp Gly Phe Met Ala Lys Asp Leu Thr Ile
                325                 330                 335

Glu Asn Thr Ala Gly Pro Asp Ala His Gln Ala Val Ala Phe Arg Leu
            340                 345                 350

Asp Ser Asp Leu Ser Val Ile Glu Asn Cys Glu Phe Leu Gly Asn Gln
        355                 360                 365

Asp Thr Leu Tyr Ala His Ser Leu Arg Gln Phe Tyr Lys Ser Cys Arg
    370                 375                 380

Ile Glu Gly Asn Val Asp Phe Ile Phe Gly Asn Ala Ala Ala Ile Phe
385                 390                 395                 400

Gln Asp Cys Gln Ile Leu Val Arg Pro Arg Gln Val Lys Pro Glu Lys
                405                 410                 415

Gly Glu Asn Asn Ala Ile Thr Ala His Gly Arg Thr Asp Pro Ala Gln
            420                 425                 430

Pro Thr Gly Phe Val Phe Gln Asn Cys Leu Ile Asn Gly Thr Glu Glu
        435                 440                 445

Tyr Met Thr Leu Tyr His Ser Lys Pro Gln Val His Lys Asn Tyr Leu
    450                 455                 460

Gly Arg Pro Trp Lys Glu Tyr Ser Arg Thr Val Phe Ile Asn Ser Phe
465                 470                 475                 480

Leu Glu Val Leu Val Thr Pro Gln Gly Trp Met Pro Trp Ser Gly Asp
                485                 490                 495

Phe Ala Leu Lys Thr Leu Tyr Tyr Gly Glu Phe Glu Ser Lys Gly Pro
            500                 505                 510

Gly Ser Tyr Leu Ser Gln Arg Val Pro Trp Ser Ser Lys Ile Pro Ala
        515                 520                 525

Glu His Val Leu Thr Tyr Ser Val Gln Asn Phe Ile Gln Gly Asn Asp
    530                 535                 540

Trp Ile Pro Ser Ile Gly Ser Pro Ser Ser
545                 550

<210> SEQ ID NO 165
<211> LENGTH: 581

```
<212> TYPE: PRT
<213> ORGANISM: Glycine max

<400> SEQUENCE: 165

Met Glu Tyr Gly Arg Leu Gly Pro Ser Asp Pro Gly Gly Ser Ser Arg
1               5                   10                  15

Leu Asn Pro Pro Arg Ser Ser Gly Arg Lys Asn Ile Val Phe Leu Ser
            20                  25                  30

Leu Phe Ala Val Leu Leu Ile Ala Ala Ser Ala Val Thr Ala Val Ala
        35                  40                  45

Val Arg Ser Arg Thr Lys Asn Thr Gly Gly Asp Gly Thr Ser Leu Gly
    50                  55                  60

Lys Phe Thr Gln Ala Ile Ser Arg Thr Cys Ser Lys Thr Arg Phe Lys
65                  70                  75                  80

Met Leu Cys Met Lys Ser Leu Leu Asp Phe Pro Gly Ser Gln Gly Ala
                85                  90                  95

Ser Glu Lys Asp Leu Val His Ile Ser Phe Asn Val Thr Leu Gln His
            100                 105                 110

Phe Ser Lys Ala Leu Tyr Ser Ser Ala Thr Ile Ser Tyr Thr Ala Met
        115                 120                 125

Asp Pro Arg Val Arg Ala Ala Tyr His Asp Cys Leu Glu Leu Leu Asp
130                 135                 140

Asp Ser Val Asp Ala Leu Ala Arg Ser Leu Asn Thr Val Ser Val Gly
145                 150                 155                 160

Ala Val Gly Ser Ala Asn Asp Asp Val Leu Thr Trp Leu Ser Ala Ala
                165                 170                 175

Leu Thr Asn Gln Asp Thr Cys Ala Glu Gly Phe Ala Asp Ala Ala Gly
            180                 185                 190

Thr Val Lys Asp Gln Met Ala Asn Asn Leu Lys Asp Leu Ser Glu Leu
        195                 200                 205

Val Ser Asn Cys Leu Ala Ile Phe Ser Gly Ala Gly Ala Gly Asp Asp
    210                 215                 220

Phe Ala Gly Val Pro Ile Gln Asn Arg Arg Leu Met Ala Met Arg
225                 230                 235                 240

Glu Asp Asn Phe Pro Thr Trp Leu Asn Gly Arg Asp Arg Arg Leu Leu
                245                 250                 255

Ser Leu Pro Leu Ser Gln Ile Gln Ala Asp Ile Val Val Ser Lys Asp
            260                 265                 270

Gly Asn Gly Thr Val Lys Thr Ile Ala Glu Ala Ile Lys Lys Val Pro
        275                 280                 285

Glu Tyr Ser Ser Arg Arg Ile Ile Tyr Ile Arg Ala Gly Arg Tyr
    290                 295                 300

Glu Glu Asp Asn Leu Lys Leu Gly Arg Lys Lys Thr Asn Val Met Phe
305                 310                 315                 320

Ile Gly Asp Gly Lys Gly Lys Thr Val Ile Thr Gly Arg Asn Tyr
                325                 330                 335

Tyr Gln Asn Leu Thr Thr Phe His Thr Ala Ser Phe Ala Ala Ser Gly
            340                 345                 350

Ser Gly Phe Ile Ala Lys Asp Met Thr Phe Glu Asn Tyr Ala Gly Pro
        355                 360                 365

Gly Arg His Gln Ala Val Ala Leu Arg Val Gly Ala Asp His Ala Val
    370                 375                 380

Val Tyr Arg Cys Asn Ile Ile Gly Tyr Gln Asp Thr Met Tyr Val His
385                 390                 395                 400
```

```
Ser Asn Arg Gln Phe Tyr Arg Glu Cys Asp Ile Tyr Gly Thr Val Asp
                405                 410                 415

Phe Ile Phe Gly Asn Ala Ala Val Val Phe Gln Asn Cys Thr Leu Trp
            420                 425                 430

Ala Arg Lys Pro Met Ala Gln Gln Lys Asn Thr Ile Thr Ala Gln Asn
        435                 440                 445

Arg Lys Asp Pro Asn Gln Asn Thr Gly Ile Ser Ile His Asn Cys Arg
    450                 455                 460

Ile Met Ala Thr Pro Asp Leu Glu Ala Ser Lys Gly Ser Tyr Pro Thr
465                 470                 475                 480

Tyr Leu Gly Arg Pro Trp Lys Leu Tyr Ala Arg Thr Val Phe Met Leu
                485                 490                 495

Ser Tyr Ile Gly Asp His Val His Pro Arg Gly Trp Leu Glu Trp Asn
            500                 505                 510

Thr Ser Ser Phe Ala Leu Asp Thr Cys Tyr Tyr Gly Glu Tyr Met Asn
        515                 520                 525

Tyr Gly Pro Gly Ser Ala Leu Gly Gln Arg Val Asn Trp Ala Gly Tyr
    530                 535                 540

Arg Ala Ile Asn Ser Thr Val Glu Ala Ser Arg Phe Thr Val Gly Gln
545                 550                 555                 560

Phe Ile Ser Gly Ser Ser Trp Leu Pro Ser Thr Gly Val Ala Phe Ile
                565                 570                 575

Ala Gly Leu Ser Thr
            580

<210> SEQ ID NO 166
<211> LENGTH: 354
<212> TYPE: PRT
<213> ORGANISM: Glycine max

<400> SEQUENCE: 166

Met Ala Pro Leu Phe Ile Ser Met Gln Met Leu Leu Leu Val Phe Thr
1               5                   10                  15

Cys Ile Leu Leu His Val Thr Cys Thr Thr Tyr His Asp Ser Thr Pro
            20                  25                  30

Lys Thr Val Pro Ser Thr Asn Ser Ser Lys Trp Val Gly Pro Ile Gly
        35                  40                  45

His Arg Val Ile Thr Val Asp Val Asn Gly Gly Ala His Phe Arg Ser
    50                  55                  60

Val Lys Ala Ala Val Asn Ala Val Pro Glu Asn Asn Arg Met Asn Val
65                  70                  75                  80

Leu Ile Gln Ile Ser Ala Gly Tyr Tyr Ile Glu Lys Val Val Val Pro
                85                  90                  95

Val Thr Lys Pro Tyr Ile Thr Phe Gln Gly Ala Gly Arg Asp Val Thr
            100                 105                 110

Val Ile Glu Trp His Asp Arg Ala Ser Asp Pro Gly Pro Asn Gly Gln
        115                 120                 125

Gln Leu Arg Thr Tyr Arg Thr Ala Ser Val Thr Val Phe Ala Asn Tyr
    130                 135                 140

Phe Ser Ala Arg Asn Ile Ser Phe Lys Asn Thr Ala Pro Ala Pro Met
145                 150                 155                 160

Pro Gly Met Glu Gly Trp Gln Ala Ala Ala Phe Arg Ile Ser Gly Asp
                165                 170                 175

Lys Ala Tyr Phe Ser Gly Cys Gly Phe Tyr Gly Ala Gln Asp Thr Leu
```

```
                180                 185                 190
Cys Asp Asp Ala Gly Arg His Tyr Phe Lys Glu Cys Tyr Ile Glu Gly
            195                 200                 205

Ser Ile Asp Phe Ile Phe Gly Asn Gly Arg Ser Met Tyr Lys Asp Cys
            210                 215                 220

Arg Leu His Ser Ile Ala Thr Arg Phe Gly Ser Ile Ala Ala Gln Asp
225                 230                 235                 240

Arg Gln Phe Pro Tyr Glu Lys Thr Gly Phe Ser Phe Val Arg Cys Lys
            245                 250                 255

Val Thr Gly Thr Gly Pro Ile Tyr Val Gly Arg Ala Met Gly Gln Tyr
            260                 265                 270

Ser Arg Ile Val Tyr Ala Tyr Thr Tyr Phe Asp Gly Ile Val Ala His
            275                 280                 285

Gly Gly Trp Asp Asp Ile Asp Trp Asn Thr Ser Asn Asn Asn Lys Thr
            290                 295                 300

Val Phe Phe Gly Val Tyr Lys Cys Trp Gly Pro Gly Ala Ala Ala Ile
305                 310                 315                 320

Arg Gly Val Pro Leu Ala Gln Glu Leu Asp Phe Glu Ser Ala His Pro
            325                 330                 335

Phe Leu Val Lys Ser Phe Val Asn Gly Arg His Trp Ile Ala Pro Ser
            340                 345                 350

Asp Ala

<210> SEQ ID NO 167
<211> LENGTH: 358
<212> TYPE: PRT
<213> ORGANISM: Glycine max

<400> SEQUENCE: 167

Met Ala Ser Ser Leu Leu Val Ser Leu Gln Val Ala Leu Val Val
1               5                   10                  15

Phe Thr Cys Ile Phe His Ala Ala Thr Val Thr Cys Asp Arg Ser Phe
            20                  25                  30

Lys Ile Phe Ser Ser Met Asn Asn Ser Ser Lys Ser Ser His His Trp
            35                  40                  45

Ile Gly Pro Ile Gly His Arg Lys Ile Thr Val Asp Val Asn Gly Gly
            50                  55                  60

Gly His Tyr Arg Ser Val Gln Asp Ala Val Asn Ala Val Pro Asp Asn
65                  70                  75                  80

Asn Arg Lys Asn Val Leu Val Gln Ile Asn Ala Gly Cys Tyr Lys Glu
            85                  90                  95

Lys Val Val Val Pro Val Thr Lys Pro Tyr Ile Thr Phe Gln Gly Ala
            100                 105                 110

Gly Lys Glu Val Thr Val Ile Glu Trp His Asp Arg Ala Ser Asp Pro
            115                 120                 125

Gly Pro Ser Gly Gln Gln Leu Arg Thr Tyr Arg Thr Ala Ser Val Thr
            130                 135                 140

Val Phe Ala Thr Tyr Phe Ser Ala Arg Asn Ile Ser Phe Lys Asn Thr
145                 150                 155                 160

Ala Pro Ala Pro Met Pro Gly Met Gln Gly Arg Gln Ala Val Ala Phe
            165                 170                 175

Arg Ile Ser Gly Asp Lys Ala Tyr Phe Ser Gly Cys Gly Phe Tyr Gly
            180                 185                 190

Ala Gln Asp Thr Leu Cys Asp Asp Ala Gly Arg His Tyr Phe Lys Glu
```

```
            195                 200                 205
Cys Tyr Ile Glu Gly Ser Ile Asp Phe Ile Phe Gly Asn Gly Arg Ser
210                 215                 220

Met Tyr Lys Asp Cys Glu Leu His Ser Ile Ala Thr Arg Phe Gly Ser
225                 230                 235                 240

Ile Ala Ala His Asp Arg Lys Glu Ala Glu Glu Lys Thr Gly Phe Ala
                245                 250                 255

Phe Val Gly Cys Lys Val Thr Gly Thr Gly Pro Leu Tyr Val Gly Arg
                260                 265                 270

Ala Met Gly Gln Tyr Ser Arg Ile Val Tyr Ser Tyr Thr Tyr Phe Asp
                275                 280                 285

Asp Ile Val Ala His Gly Gly Trp Asp Trp Asp His Ala Asp Asn
290                 295                 300

Lys Asn Lys Thr Val Phe Phe Gly Val Tyr Lys Cys Trp Gly Pro Gly
305                 310                 315                 320

Ala Glu Ala Val Arg Gly Val Ser Trp Ala Arg Asp Leu Asn Phe Glu
                325                 330                 335

Ser Ala His Pro Phe Ile Arg Lys Ser Phe Val Asn Gly Arg His Trp
                340                 345                 350

Ile Ala Pro Ser Asp Ala
                355

<210> SEQ ID NO 168
<211> LENGTH: 363
<212> TYPE: PRT
<213> ORGANISM: Glycine max

<400> SEQUENCE: 168

Met Thr Ser Ser Leu Leu Val Ser Leu Gln Val Ala Leu Ala Ile
1               5                   10                  15

Phe Ala Cys Ile Phe His Ala Ala Thr Val Thr Cys Lys Pro His His
                20                  25                  30

Arg Asp Arg Thr Leu Lys Ile Phe Ser Ser Thr Ser Asn Ser Ser Lys
                35                  40                  45

Ser Ser His His Trp Ile Gly Pro Ile Gly His Arg Lys Ile Thr Val
50                  55                  60

Asp Ile Asn Gly Gly His Tyr Arg Ser Val Gln Asp Ala Val Asn
65                  70                  75                  80

Ala Val Pro Asp Asn Asn Arg Arg Asn Val Leu Ile Gln Ile Asn Ala
                85                  90                  95

Gly Cys Tyr Lys Glu Lys Val Val Pro Val Thr Lys Pro Tyr Ile
                100                 105                 110

Thr Phe Glu Gly Ala Gly Lys Glu Val Thr Val Ile Glu Trp His Asp
                115                 120                 125

Arg Ala Ser Asp Pro Gly Pro Ser Gly Gln Gln Leu Arg Thr Tyr Arg
130                 135                 140

Thr Ala Ser Val Thr Val Phe Ala Ser Tyr Phe Ser Ala Arg Asn Ile
145                 150                 155                 160

Ser Phe Lys Asn Thr Ala Pro Ala Pro Met Pro Gly Met Gln Gly Trp
                165                 170                 175

Gln Ala Val Ala Phe Arg Ile Ser Gly Asp Lys Ala Tyr Phe Ser Gly
                180                 185                 190

Cys Gly Phe Tyr Gly Ala Gln Asp Thr Leu Cys Asp Asp Ala Gly Arg
                195                 200                 205
```

```
His Tyr Phe Lys Glu Cys Tyr Ile Glu Gly Ser Ile Asp Phe Ile Phe
    210                 215                 220

Gly Asn Gly Arg Ser Met Tyr Lys Asp Cys Glu Leu His Ser Ile Ala
225                 230                 235                 240

Thr Arg Phe Gly Ser Ile Ala Ala His Asp Arg Lys Gln Pro Glu Glu
                245                 250                 255

Lys Thr Gly Phe Ala Phe Val Arg Cys Lys Val Thr Gly Thr Gly Pro
                260                 265                 270

Leu Tyr Val Gly Arg Ala Met Gly Gln Tyr Ser Arg Ile Val Tyr Ser
            275                 280                 285

Tyr Thr Tyr Phe Asp Asp Ile Val Ala His Gly Gly Trp Asp Asp Trp
290                 295                 300

Asp His Ala His Asn Lys Asn Lys Thr Val Phe Phe Gly Val Tyr Lys
305                 310                 315                 320

Cys Trp Gly Pro Gly Ala Glu Ala Val Arg Gly Val Ser Trp Ala Arg
                325                 330                 335

Asp Leu Asp Phe Glu Ala Ala His Pro Phe Ile Arg Lys Ser Phe Val
                340                 345                 350

Asn Gly Arg His Trp Ile Ala Pro Ser Asp Ala
            355                 360

<210> SEQ ID NO 169
<211> LENGTH: 216
<212> TYPE: PRT
<213> ORGANISM: Glycine max

<400> SEQUENCE: 169

Met Gln Leu Gln Pro Thr Leu Ser Thr Leu Tyr Leu Ser Leu Leu Leu
1               5                   10                  15

Thr Ile Thr Leu Thr Ser Pro Thr Leu Ala Ala Gln Ser Lys Pro Gln
                20                  25                  30

Asp Leu Val Arg Ser Ser Cys Val His Ala Arg Tyr Pro Arg Leu Cys
            35                  40                  45

Leu Arg Thr Leu Ser Asn Tyr Pro Gly Pro Ala Asn Thr Pro Leu Asp
50                  55                  60

Val Ala Arg Ala Ala Leu Arg Val Ser Leu Ala His Thr Arg Arg Ala
65                  70                  75                  80

Ser Lys Phe Leu His Ala Leu Ser His Gly Gly Ala Ala Ala Met Ser
                85                  90                  95

Lys Arg Gln Arg Ser Ala Leu Arg Asp Cys Asn Glu Gln Ile Ser Asp
            100                 105                 110

Ser Val Asp Gln Leu Arg Arg Ser Leu Asp Glu Leu Gln His Leu Arg
            115                 120                 125

Ser Glu Thr Phe Lys Trp Gln Met Ser Asn Ala Leu Thr Trp Val Ser
130                 135                 140

Ala Ala Leu Thr Asn Gly Asp Thr Cys Leu Asp Gly Phe Gly Gly Asn
145                 150                 155                 160

Ala Arg Pro Asp Val Lys Arg Val Thr Asp Val Ala Arg Val Thr
                165                 170                 175

Ser Asn Ala Leu Tyr Met Ile Asn Arg Leu Gly Gln Ser Arg Thr Gly
            180                 185                 190

Lys Pro Lys Pro Lys Pro Arg Ser Arg Pro Gln Pro Arg Ser
            195                 200                 205

Ala Ser Ser Thr Glu Lys Leu Asn
            210                 215
```

<210> SEQ ID NO 170
<211> LENGTH: 406
<212> TYPE: PRT
<213> ORGANISM: Glycine max

<400> SEQUENCE: 170

```
Met Ala Thr Thr Phe Leu Ser Leu Leu Phe Leu Ile Phe Ser Leu Leu
1               5                   10                  15

Thr Pro Ala Leu Ile Ser Ser Ser Pro Val Gln Asp Pro Glu Phe Val
            20                  25                  30

Ala Gln Glu Val Asn Arg Lys Ile Asn Ala Ser Val Ala Arg Arg Asn
        35                  40                  45

Leu Gly Tyr Leu Ser Cys Ala Thr Gly Asn Pro Ile Asp Asp Cys Trp
    50                  55                  60

Arg Cys Asp Pro Asn Trp Glu Lys Asn Arg Gln Arg Leu Ala Asp Cys
65                  70                  75                  80

Ala Ile Gly Phe Gly Lys Asn Ala Ile Gly Gly Lys Asn Gly Lys Ile
                85                  90                  95

Tyr Val Val Thr Asp Ser Gly Asp Asp Pro Val Thr Pro Lys Pro
            100                 105                 110

Gly Thr Leu Arg Tyr Ala Val Ile Gln Asp Glu Pro Leu Trp Ile Ile
        115                 120                 125

Phe Ala Arg Asp Met Val Ile Lys Leu Lys Glu Glu Arg Ile Met Asn
    130                 135                 140

Ser Phe Lys Thr Ile Asp Gly Arg Gly Ala Ser Val His Ile Ala Gly
145                 150                 155                 160

Gly Pro Cys Ile Thr Ile Gln Tyr Val Thr Asn Val Ile Ile His Gly
                165                 170                 175

Ile Asn Ile His Asp Cys Lys Gln Gly Gly Asn Ala Met Val Arg Asp
            180                 185                 190

Ser Pro Arg His Tyr Gly Trp Arg Thr Val Ser Asp Gly Asp Gly Val
        195                 200                 205

Ser Ile Phe Gly Gly Ser His Val Trp Val Asp His Cys Ser Leu Ser
    210                 215                 220

Asn Cys Asn Asp Gly Leu Ile Asp Ala Ile His Gly Ser Thr Ala Ile
225                 230                 235                 240

Thr Ile Ser Asn Asn Tyr Met Thr His His Asp Lys Val Met Leu Leu
                245                 250                 255

Gly His Ser Asp Ser Tyr Thr Gln Asp Lys Asn Met Gln Val Thr Ile
            260                 265                 270

Ala Phe Asn His Phe Gly Glu Gly Leu Val Gln Arg Met Pro Arg Cys
        275                 280                 285

Arg His Gly Tyr Phe His Val Val Asn Asn Asp Tyr Thr His Trp Glu
    290                 295                 300

Met Tyr Ala Ile Gly Gly Ser Ala Asn Pro Thr Ile Asn Ser Arg Gly
305                 310                 315                 320

Asn Arg Phe Val Ala Pro Asp Asp Arg Phe Ser Lys Glu Val Thr Lys
                325                 330                 335

His Glu Asp Ala Ala Glu Ser Glu Trp Lys Gly Trp Asn Trp Arg Ser
            340                 345                 350

Glu Gly Asp Leu Leu Val Asn Gly Ala Phe Phe Thr Ala Ser Gly Ala
        355                 360                 365

Gly Ala Ser Ser Ser Tyr Ala Arg Ala Ser Ser Leu Ser Ala Arg Pro
```

```
                    370                 375                 380
Ser Ser Leu Val Gly Ser Ile Thr Thr Gly Ala Gly Ala Leu Thr Cys
385                 390                 395                 400

Arg Lys Gly Ser Arg Cys
                405
```

<210> SEQ ID NO 171
<211> LENGTH: 334
<212> TYPE: PRT
<213> ORGANISM: Glycine max

<400> SEQUENCE: 171

```
Met Ala Gly Met Gln Lys Leu Pro Tyr Gly Asp Val Asp Ser Ser Leu
1               5                   10                  15

Arg Ala Leu Ala Gly Arg Ala Glu Gly Phe Gly Arg Leu Ala Ile Gly
                20                  25                  30

Gly Leu His Gly Pro Leu Tyr Phe Val Thr Thr Leu Ser Asp Asp Gly
                35                  40                  45

Pro Gly Ser Leu Arg Glu Gly Cys Arg Arg Lys Glu Pro Leu Trp Ile
        50                  55                  60

Val Phe Glu Val Ser Gly Thr Ile His Leu Ser Ser Tyr Leu Ser Val
65                  70                  75                  80

Ser Ser Tyr Lys Thr Ile Asp Gly Arg Gly Gln Arg Val Lys Leu Thr
                85                  90                  95

Gly Lys Gly Leu Arg Leu Lys Glu Cys Glu His Ile Ile Cys Asn
                100                 105                 110

Leu Glu Phe Glu Gly Gly Arg Gly His Asp Val Asp Gly Ile Gln Ile
                115                 120                 125

Lys Pro Asn Ser Arg His Ile Trp Ile Asp Arg Cys Thr Leu Arg Asp
            130                 135                 140

Tyr Asp Asp Gly Leu Ile Asp Ile Thr Arg Gln Ser Thr Asp Ile Thr
145                 150                 155                 160

Val Ser Arg Cys Cys Phe Gly Gln His Asp Lys Thr Met Leu Ile Gly
                165                 170                 175

Ala Asp Pro Thr His Ile Gly Asp Arg Cys Ile Arg Val Thr Ile His
                180                 185                 190

His Cys Phe Phe Asp Gly Thr Arg Gln Arg Gln Pro Arg Val Arg Phe
            195                 200                 205

Gly Lys Val His Leu Tyr Asn Asn Tyr Thr Arg Asn Trp Gly Ile Tyr
        210                 215                 220

Ala Val Cys Ala Ser Val Glu Ser Gln Ile Tyr Ser Gln Cys Asn Val
225                 230                 235                 240

Tyr Glu Ala Gly Thr Lys Lys Lys Thr Phe Glu Phe Tyr Thr Glu Lys
                245                 250                 255

Ala Val Asp Lys Glu Glu Gln Lys Ser Gly Phe Ile Ile Ser Glu Gly
                260                 265                 270

Asp Met Phe Leu Asn Gly Ala Glu Pro Ser Leu Leu Thr Glu Asn Arg
            275                 280                 285

Glu Glu Ser Met Phe His Pro Ser Glu Tyr Tyr Pro Thr Trp Thr Met
290                 295                 300

Glu Ala Ala Gly His Ser Leu Arg Glu Val Leu Leu Cys Thr Gly
305                 310                 315                 320

Trp Gln Ser Ile Cys Arg Pro Val Asp Asn Met Val Leu Gln
                325                 330
```

<210> SEQ ID NO 172
<211> LENGTH: 587
<212> TYPE: PRT
<213> ORGANISM: Glycine max

<400> SEQUENCE: 172

| | | | | | | | | | | | | | | |
|---|---|---|---|---|---|---|---|---|---|---|---|---|---|---|
| Met | Asp | Thr | Ile | Lys | Ser | Phe | Lys | Gly | Tyr | Gly | Lys | Val | Asp | Glu | Leu |
| 1 | | | | 5 | | | | | 10 | | | | | 15 | |
| Glu | Gln | Gln | Ala | Tyr | Gln | Lys | Lys | Thr | Arg | Lys | Arg | Leu | Ile | Ile | Ile |
| | | | 20 | | | | | 25 | | | | | 30 | | |
| Ala | Val | Ser | Ser | Ile | Val | Leu | Phe | Ala | Val | Ile | Ile | Ala | Ala | Val | Ala |
| | | 35 | | | | | 40 | | | | | 45 | | | |
| Gly | Val | Val | Ile | His | Lys | Arg | Asn | Thr | Ser | Ser | Ser | Pro | Ser | Ser | Asp |
| | 50 | | | | | 55 | | | | | 60 | | | | |
| Ser | Pro | Pro | Gln | Thr | Glu | Leu | Thr | Pro | Ala | Ala | Ser | Leu | Lys | Ala | Val |
| 65 | | | | | 70 | | | | | 75 | | | | | 80 |
| Cys | His | Val | Thr | Gln | Tyr | Pro | Asn | Ser | Cys | Phe | Ser | Ala | Ile | Ser | Ser |
| | | | | 85 | | | | | 90 | | | | | 95 | |
| Leu | Pro | Glu | Ser | Asn | Thr | Thr | Asp | Pro | Glu | Leu | Leu | Phe | Lys | Leu | Ser |
| | | | 100 | | | | | 105 | | | | | 110 | | |
| Leu | Arg | Val | Ala | Ile | Asp | Glu | Leu | Ser | Lys | Leu | Ser | Ser | Phe | Pro | Ser |
| | | 115 | | | | | 120 | | | | | 125 | | | |
| Lys | Leu | Arg | Ala | Asn | Ala | Glu | His | Asp | Ala | Arg | Leu | Gln | Lys | Ala | Ile |
| | 130 | | | | | 135 | | | | | 140 | | | | |
| Asp | Val | Cys | Gly | Asn | Val | Phe | Gly | Asp | Ala | Leu | Glu | Gln | Leu | Asn | Asp |
| 145 | | | | | 150 | | | | | 155 | | | | | 160 |
| Ser | Ile | Ser | Ala | Leu | Gly | Ser | Gly | Ala | Ala | Glu | Ala | Gly | Lys | Ile | Ile |
| | | | | 165 | | | | | 170 | | | | | 175 | |
| Ser | Pro | Ala | Ser | Val | Gly | Asp | Val | Glu | Thr | Trp | Ile | Ser | Ala | Ala | Leu |
| | | | 180 | | | | | 185 | | | | | 190 | | |
| Thr | Asp | Gln | Asp | Thr | Cys | Leu | Asp | Ala | Leu | Ala | Glu | Leu | Asn | Ser | Thr |
| | | 195 | | | | | 200 | | | | | 205 | | | |
| Ala | Ser | Arg | Gly | Ala | Leu | Arg | Glu | Ile | Glu | Thr | Ala | Met | Arg | Asn | Ser |
| | 210 | | | | | 215 | | | | | 220 | | | | |
| Thr | Glu | Phe | Ala | Ser | Asn | Ser | Leu | Ala | Ile | Val | Thr | Lys | Ile | Leu | Gly |
| 225 | | | | | 230 | | | | | 235 | | | | | 240 |
| Leu | Leu | Ser | Lys | Phe | Asp | Ser | Pro | Ile | His | His | Arg | Arg | Leu | Leu | Gly |
| | | | | 245 | | | | | 250 | | | | | 255 | |
| Phe | Pro | Glu | Trp | Leu | Gly | Ala | Ala | Glu | Arg | Arg | Leu | Leu | Gln | Val | Asn |
| | | | 260 | | | | | 265 | | | | | 270 | | |
| Ser | Ser | Glu | Thr | Thr | Pro | Asp | Ala | Val | Val | Ala | Ser | Asp | Gly | Ser | Gly |
| | | 275 | | | | | 280 | | | | | 285 | | | |
| Gln | Phe | Arg | Thr | Ile | Gly | Glu | Ala | Leu | Arg | Leu | Val | Lys | Lys | Lys | Ser |
| | 290 | | | | | 295 | | | | | 300 | | | | |
| Glu | Lys | Arg | Phe | Val | Val | His | Val | Lys | Glu | Gly | Arg | Tyr | Val | Glu | Asn |
| 305 | | | | | 310 | | | | | 315 | | | | | 320 |
| Ile | Asp | Leu | Asp | Lys | Asn | Thr | Trp | Asn | Val | Phe | Ile | Phe | Gly | Asp | Gly |
| | | | | 325 | | | | | 330 | | | | | 335 | |
| Lys | Glu | Lys | Thr | Val | Val | Gly | Ser | Arg | Asn | Phe | Met | Asp | Gly | Thr | |
| | | | 340 | | | | | 345 | | | | | 350 | | |
| Pro | Thr | Phe | Glu | Thr | Ala | Thr | Phe | Ala | Val | Lys | Gly | Lys | Gly | Phe | Ile |
| | | 355 | | | | | 360 | | | | | 365 | | | |
| Ala | Lys | Asp | Ile | Gly | Phe | Val | Asn | Asn | Ala | Gly | Ala | Ser | Lys | His | Gln |
| | 370 | | | | | 375 | | | | | 380 | | | | |

```
Ala Val Ala Leu Arg Ser Gly Ser Asp Arg Ser Val Phe Phe Arg Cys
385                 390                 395                 400

Ser Phe Asp Gly Phe Gln Asp Thr Leu Tyr Ala His Ser Asn Arg Gln
            405                 410                 415

Phe Tyr Arg Asp Cys Asp Ile Thr Gly Thr Ile Asp Phe Ile Phe Gly
        420                 425                 430

Asn Ala Ala Val Phe Gln Asn Cys Lys Ile Met Pro Arg Gln Pro
    435                 440                 445

Leu Pro Asn Gln Phe Asn Thr Ile Thr Ala Gln Gly Lys Lys Asp Pro
    450                 455                 460

Asn Gln Asn Thr Gly Ile Ile Ile Gln Lys Ser Lys Phe Ile Pro Leu
465                 470                 475                 480

Gly Asn Asn Leu Thr Ala Pro Thr Tyr Leu Gly Arg Pro Trp Lys Asp
                485                 490                 495

Phe Ser Thr Thr Val Ile Met Gln Ser Asp Ile Gly Ser Phe Leu Lys
                500                 505                 510

Pro Val Gly Trp Ile Ser Trp Val Ser Asn Val Glu Pro Val Ser Thr
            515                 520                 525

Ile Phe Tyr Ala Glu Tyr Gln Asn Thr Gly Pro Gly Ala Asp Val Ser
    530                 535                 540

Gln Arg Val Lys Trp Ala Gly Tyr Lys Pro Thr Leu Thr Asp Val Glu
545                 550                 555                 560

Ala Asp Lys Phe Thr Val Gln Ser Phe Ile Gln Gly Pro Glu Trp Leu
                565                 570                 575

Pro Asn Ala Ala Val Glu Phe Asp Ser Thr Leu
                580                 585

<210> SEQ ID NO 173
<211> LENGTH: 518
<212> TYPE: PRT
<213> ORGANISM: Glycine max

<400> SEQUENCE: 173

Met Ala Ile Pro Ser Leu Ile Asn Gln Pro Gln Arg Thr Pro Ser Leu
1               5                   10                  15

Thr Phe Ser Phe Leu Leu Phe Leu Ala Ile Cys Thr Pro Leu Asp Ala
            20                  25                  30

Ala His Thr Asp Phe Ala Gly Ser Ala Cys Leu Lys Val Ser Pro Ser
        35                  40                  45

His Phe Ala Gly Ser Val Thr Glu Val Ile Ala Ala Ile Arg Gln Leu
    50                  55                  60

Ala Ser Ile Leu Ser Arg Phe Gly Ser Pro Leu Ala Asn Phe Arg Leu
65                  70                  75                  80

Ser Thr Ala Ile Ala Asp Cys Leu Asp Leu Leu Asp Leu Ser Ser Asp
                85                  90                  95

Val Leu Ser Trp Ala Leu Ser Ala Ser Gln Asn Pro Lys Gly Lys His
            100                 105                 110

Asn Ser Thr Gly Asn Leu Ser Ser Asp Leu Arg Thr Trp Leu Ser Ala
        115                 120                 125

Ala Leu Ala His Pro Glu Thr Cys Met Glu Gly Phe Glu Gly Thr Asn
    130                 135                 140

Ser Ile Val Lys Gly Leu Val Ser Ala Ile Gly Gln Val Val Ser
145                 150                 155                 160

Leu Val Glu Gln Leu Leu Ala Gln Val Leu Pro Ala Gln Asp Gln Phe
```

```
            165                 170                 175
Asp Ala Ser Ser Lys Gly Gln Phe Pro Ser Trp Ile Lys Pro Lys
        180                 185                 190

Glu Arg Lys Leu Leu Gln Ala Ile Ala Val Thr Pro Asp Val Thr Val
            195                 200                 205

Ala Leu Asp Gly Ser Gly Asn Tyr Ala Lys Ile Met Asp Ala Val Leu
        210                 215                 220

Ala Ala Pro Asp Tyr Ser Met Lys Arg Phe Val Ile Leu Val Lys Lys
225                 230                 235                 240

Gly Val Tyr Val Glu Asn Val Glu Ile Lys Lys Lys Trp Asn Ile
            245                 250                 255

Met Ile Leu Gly Gln Gly Met Asp Ala Thr Val Ile Ser Gly Asn Arg
        260                 265                 270

Ser Val Val Asp Gly Trp Thr Thr Phe Arg Ser Ala Thr Phe Ala Val
            275                 280                 285

Ser Gly Arg Gly Phe Ile Ala Arg Asp Ile Ser Phe Gln Asn Thr Ala
        290                 295                 300

Gly Pro Glu Lys His Gln Ala Val Ala Leu Arg Ser Asp Ser Asp Leu
305                 310                 315                 320

Ser Val Phe Phe Arg Cys Gly Ile Phe Gly Tyr Gln Asp Ser Leu Tyr
            325                 330                 335

Thr His Thr Met Arg Gln Phe Phe Arg Asp Cys Thr Ile Ser Gly Thr
        340                 345                 350

Val Asp Tyr Ile Phe Gly Asp Ala Thr Ala Val Phe Gln Asn Cys Phe
            355                 360                 365

Leu Arg Val Lys Lys Gly Leu Pro Asn Gln Lys Asn Thr Ile Thr Ala
        370                 375                 380

His Gly Arg Lys Asp Pro Asn Glu Pro Thr Gly Phe Ser Phe Gln Phe
385                 390                 395                 400

Cys Asn Ile Thr Ala Asp Ser Asp Leu Ile Pro Ser Val Gly Thr Ala
            405                 410                 415

Gln Thr Tyr Leu Gly Arg Pro Trp Lys Ser Tyr Ser Arg Thr Val Phe
        420                 425                 430

Met Gln Ser Tyr Met Ser Glu Val Ile Gly Ala Glu Gly Trp Leu Glu
            435                 440                 445

Trp Asn Gly Asn Phe Ala Leu Asp Thr Leu Tyr Tyr Ala Glu Tyr Met
        450                 455                 460

Asn Thr Gly Ala Gly Ala Gly Val Ala Asn Arg Val Lys Trp Pro Gly
465                 470                 475                 480

Tyr His Ala Leu Asn Asp Ser Ser Gln Ala Ser Asn Phe Thr Val Ser
            485                 490                 495

Gln Phe Ile Glu Gly Asn Leu Trp Leu Pro Ser Thr Gly Val Thr Phe
        500                 505                 510

Thr Ala Gly Leu Thr Val
        515

<210> SEQ ID NO 174
<211> LENGTH: 528
<212> TYPE: PRT
<213> ORGANISM: Glycine max

<400> SEQUENCE: 174

Met Glu Leu Ser Ser Lys Lys Glu Leu Leu Ser Arg Ile Val Ser Thr
1               5                   10                  15
```

-continued

```
Leu Thr Pro Thr Ile Thr Leu Ile Phe Phe Leu Val Leu Ser Pro
             20              25              30
Ser Leu Cys Thr Ser Leu Gly Ser Thr Asn Thr Val Gly Ser Glu Leu
         35              40              45
Leu Lys Val Ala Pro Ser Glu Phe Glu Gly Thr Val Arg Thr Val Val
     50              55              60
Asp Val Leu Gln Glu Val Thr Ser Ile Leu Ser Glu Phe Gly Ser Gly
65              70              75              80
Phe Gly Asp Ser Arg Leu Ser Asn Ala Val Ser Asp Cys Leu Asp Leu
             85              90              95
Leu Asp Met Ser Ser Asp Glu Leu Asp Trp Ser Val Ser Ala Thr Gln
         100             105             110
Ser Pro Lys Gly Lys His Asn Ser Thr Gly Asn Thr Ser Ser Asp Leu
     115             120             125
Arg Thr Trp Leu Ser Ala Ala Leu Ala Asn Gln Asp Thr Cys Ile Asp
130             135             140
Gly Phe Asp Gly Thr Asn Gly Met Val Lys Gly Leu Val Ser Thr Gly
145             150             155             160
Ile Gly Gln Val Met Ser Leu Leu Gln Gln Leu Leu Thr Gln Val Lys
                 165             170             175
Pro Val Ser Asp His Phe Ser Phe Ser Ser Pro Gln Gly Gln Tyr Pro
             180             185             190
Ser Trp Val Lys Thr Gly Glu Arg Lys Leu Leu Gln Ala Asn Val Val
         195             200             205
Ser Phe Asp Ala Val Val Ala Ala Asp Gly Thr Gly Asn Tyr Thr Lys
     210             215             220
Val Met Asp Ala Val Leu Ala Ala Pro Asn Tyr Ser Met Gln Arg Tyr
225             230             235             240
Val Ile His Ile Lys Arg Gly Val Tyr Tyr Glu Asn Val Glu Ile Lys
                 245             250             255
Lys Lys Lys Trp Asn Leu Met Met Val Gly Asp Gly Met Asp Ala Thr
             260             265             270
Ile Ile Ser Gly Asn Arg Ser Phe Ile Asp Gly Trp Thr Thr Phe Arg
         275             280             285
Ser Ala Thr Phe Ala Val Ser Gly Arg Gly Phe Ile Ala Arg Asp Ile
     290             295             300
Thr Phe Gln Asn Thr Ala Gly Pro Glu Lys His Gln Ala Val Ala Leu
305             310             315             320
Arg Ser Asp Ser Asp Leu Ser Val Phe Phe Arg Cys Gly Ile Phe Gly
                 325             330             335
Tyr Gln Asp Ser Leu Tyr Thr His Thr Met Arg Gln Phe Tyr Arg Glu
             340             345             350
Cys Lys Ile Ser Gly Thr Val Asp Phe Ile Phe Gly Asp Ala Thr Ala
         355             360             365
Ile Phe Gln Asn Cys His Ile Ser Ala Lys Gly Leu Pro Asn Gln
     370             375             380
Lys Asn Thr Ile Thr Ala His Gly Arg Lys Asn Pro Asp Glu Pro Thr
385             390             395             400
Gly Phe Ser Ile Gln Phe Cys Asn Ile Ser Ala Asp Tyr Asp Leu Val
                 405             410             415
Asn Ser Val Asn Ser Phe Asn Ser Thr His Thr Tyr Leu Gly Arg Pro
             420             425             430
Trp Lys Pro Tyr Ser Arg Thr Ile Phe Met Gln Ser Tyr Ile Ser Asp
```

```
                   435                 440                 445
Val Leu Arg Pro Glu Gly Trp Leu Glu Trp Asn Gly Asp Phe Ala Leu
    450                 455                 460

Asp Thr Leu Tyr Tyr Ala Glu Tyr Met Asn Tyr Gly Pro Gly Ala Gly
465                 470                 475                 480

Val Ala Asn Arg Val Lys Trp Gln Gly Tyr His Val Met Asn Asp Ser
                485                 490                 495

Ser Gln Ala Ser Asn Phe Thr Val Ser Gln Phe Ile Glu Gly Asn Leu
                500                 505                 510

Trp Leu Pro Ser Thr Gly Val Thr Phe Thr Ala Gly Leu Gly Val Val
                515                 520                 525

<210> SEQ ID NO 175
<211> LENGTH: 547
<212> TYPE: PRT
<213> ORGANISM: Glycine max

<400> SEQUENCE: 175

Met Pro Leu Lys Leu Ala Gly Val Ala Thr Val Gly Ser Leu Leu Leu
1               5                   10                  15

Cys Val Ala Ile Ser Leu Phe His Ile Ala Gly Ala Glu Asp Pro Tyr
                20                  25                  30

Arg Phe Phe Asn Trp Asn Ile Thr Tyr Gly Asp Ile Tyr Pro Leu Gly
            35                  40                  45

Val Arg Gln Thr Gly Ile Leu Ile Asn Gly Gln Phe Pro Gly Pro Asp
    50                  55                  60

Ile His Ser Val Thr Asn Asp Asn Leu Ile Ile Asn Val Phe Asn Ser
65                  70                  75                  80

Leu Asp Glu Pro Phe Leu Leu Ser Trp Asn Gly Ile Gln Gln Arg Arg
                85                  90                  95

Asn Ser Phe Glu Asp Gly Val Phe Gly Thr Thr Cys Pro Ile Pro Ala
                100                 105                 110

Gly Lys Asn Phe Thr Tyr Ile Leu Gln Val Lys Asp Gln Ile Gly Thr
            115                 120                 125

Phe Tyr Tyr Phe Pro Ser Leu Ala Phe His Lys Ala Ala Gly Gly Phe
    130                 135                 140

Gly Gly Ile Arg Ile Leu Ser Arg Pro Arg Ile Pro Val Pro Phe Pro
145                 150                 155                 160

Asp Pro Ala Gly Asp Tyr Thr Val Leu Ile Gly Asp Trp Tyr Lys Ser
                165                 170                 175

Asn His Thr Thr Leu Lys Ala Arg Leu Asp Arg Gly Lys Lys Leu Pro
                180                 185                 190

Phe Pro Asp Gly Ile Leu Ile Asn Gly Arg Gly Pro Asn Gly Val Ser
            195                 200                 205

Phe Asn Val Glu Gln Gly Lys Thr Tyr Arg Leu Arg Ile Ser Asn Val
    210                 215                 220

Gly Leu Gln His Ser Leu Asn Phe Arg Ile Gln Asn His Lys Met Lys
225                 230                 235                 240

Leu Val Glu Val Glu Gly Thr His Thr Leu Gln Thr Met Tyr Ser Ser
                245                 250                 255

Leu Asp Val His Val Gly Gln Ser Tyr Ser Val Leu Val Thr Ala Asp
                260                 265                 270

Gln Pro Ala Gln Asp Tyr Tyr Ile Val Val Ser Thr Arg Phe Ser Tyr
            275                 280                 285
```

```
Lys Val Leu Thr Thr Thr Gly Val Leu Arg Tyr Ser Asn Ser Ala Gly
            290                 295                 300

Pro Val Ser Gly Pro Pro Gly Gly Pro Thr Ile Gln Ile Asp Trp
305                 310                 315                 320

Ser Leu Asn Gln Ala Arg Ser Ile Arg Thr Asn Leu Thr Ala Ser Gly
                325                 330                 335

Pro Arg Pro Asn Pro Gln Gly Ser Tyr His Tyr Gly Met Ile Asn Thr
            340                 345                 350

Thr Lys Thr Ile Ile Leu Ala Ser Ala Gly Gln Val Asn Gly Lys
        355                 360                 365

Gln Arg Tyr Ala Ile Asn Ser Val Ser Tyr Val Val Pro Asp Thr Pro
370                 375                 380

Leu Lys Leu Ala Asp Tyr Phe Lys Ile Ser Gly Val Phe Arg Pro Gly
385                 390                 395                 400

Ser Ile Ser Asp Arg Pro Thr Gly Gly Gly Ile Tyr Leu Asp Thr Ser
                405                 410                 415

Val Leu Gln Ala Asp Tyr Arg Asn Phe Val Glu Ile Val Phe Gln Asn
            420                 425                 430

Asn Glu Asn Ile Val Gln Ser Tyr His Leu Asp Gly Tyr Ser Phe Phe
        435                 440                 445

Val Val Gly Met Asp Gly Gln Trp Thr Thr Ala Ser Arg Asn Gln
450                 455                 460

Tyr Asn Leu Arg Asp Ala Val Ala Arg Cys Thr Thr Gln Val Tyr Pro
465                 470                 475                 480

Phe Ser Trp Thr Ala Ile Tyr Ile Ala Leu Asp Asn Val Gly Met Trp
                485                 490                 495

Asn Leu Arg Ser Glu Phe Trp Ala Arg Gln Tyr Leu Gly Gln Gln Leu
            500                 505                 510

Tyr Leu Arg Val Tyr Thr Thr Ser Thr Ser Ile Arg Asp Glu Phe Pro
        515                 520                 525

Val Pro Lys Asn Ala Ile Leu Cys Gly Arg Ala Ser Gly Arg His Thr
530                 535                 540

Arg Pro Leu
545

<210> SEQ ID NO 176
<211> LENGTH: 226
<212> TYPE: PRT
<213> ORGANISM: Glycine max

<400> SEQUENCE: 176

Met Asp Ser Leu Lys Met Leu Lys Gly Tyr Gly Lys Val Glu His His
1               5                   10                  15

Leu Glu Asp His Arg Asn Pro Lys Pro Lys Pro Lys Phe Ser Lys Pro
            20                  25                  30

Phe Ile Ala Ala Ile Ser Val Phe Ala Ile Leu Phe Leu Thr Leu Thr
        35                  40                  45

Phe Ala Phe Ala Leu Ala Ser Met Leu His His Ser His His Thr Glu
    50                  55                  60

Ser Gln Gln Gln Leu Leu Asn Ser Ala Glu Ser Ile Arg Val Val Cys
65                  70                  75                  80

Asn Val Thr Arg Phe Pro Gly Ala Cys Leu Ala Ala Ile Pro Pro Ser
                85                  90                  95

Ala Asn Ala Thr Asn Pro Gln Ala Ile Leu Ser Leu Ser Leu Arg Ala
            100                 105                 110
```

Ser Leu His Ala Leu Gln Ser Leu Asn Ser Ser Leu Gly Thr Lys Asn
            115                 120                 125

Ser Arg Leu Ala Asp Cys Arg Asp Gln Leu Asp Ala Leu Gly Arg
        130                 135                 140

Leu Asn Asp Ala Leu Ser Ala Ala Ala Leu Thr Glu Ala Lys Ile
145                 150                 155                 160

Ser Asp Val Gln Thr Trp Val Ser Ala Ala Ile Thr Asp Gln Thr
                165                 170                 175

Cys Leu Asp Gly Leu Glu Glu Val Gly Asp Val Ala Ala Met Glu Glu
            180                 185                 190

Met Lys Lys Met Met Lys Arg Ser Asn Glu Tyr Thr Ser Asn Ser Leu
        195                 200                 205

Ala Ile Val Ala Asn Ile Arg Asn Leu Leu Gln Arg Phe His Met Ala
    210                 215                 220

Leu His
225

<210> SEQ ID NO 177
<211> LENGTH: 193
<212> TYPE: PRT
<213> ORGANISM: Glycine max

<400> SEQUENCE: 177

Met Thr Thr Ile Ser Asn Cys Ser Leu Leu Phe Leu Phe Leu Phe Leu
1               5                   10                  15

Ser Thr Leu His Ile Ala Ser Thr Leu Ser Thr Pro Thr Asn Phe Ile
            20                  25                  30

Lys Ser Ser Cys Ser Thr Thr Gln Tyr Pro Ala Leu Cys Ile Gln Ser
        35                  40                  45

Leu Ser Val Tyr Ala Ser Thr Ile Gln Gln Asp Pro His Glu Leu Val
    50                  55                  60

Gln Thr Ala Leu Ser Leu Ser Leu Asn His Thr Glu Ala Thr Lys Thr
65                  70                  75                  80

Phe Val Ala Lys Cys Asn Lys Phe Arg Gly Leu Lys Pro Arg Glu Tyr
                85                  90                  95

Ala Ala Leu Lys Asp Cys Ala Glu Glu Ile Ser Asp Ser Val Asp Arg
            100                 105                 110

Leu Ser Arg Ser Leu Lys Glu Leu Lys Leu Cys Lys Val Lys Gly Glu
        115                 120                 125

Asp Phe Thr Trp His Ile Ser Asn Val Glu Thr Trp Val Ser Ser Ala
    130                 135                 140

Leu Thr Asp Glu Ser Thr Cys Gly Asp Gly Phe Ala Gly Lys Ala Leu
145                 150                 155                 160

Asn Gly Lys Ile Lys Glu Ala Ile Arg Ala Arg Met Val Asn Val Ala
                165                 170                 175

Gln Val Thr Ser Asn Ala Leu Ser Leu Ile Asn Gln Tyr Ala Ala Gln
            180                 185                 190

His

<210> SEQ ID NO 178
<211> LENGTH: 450
<212> TYPE: PRT
<213> ORGANISM: Glycine max

<400> SEQUENCE: 178

```
Met Glu Asn Ala Arg Ile Ser Gln Trp Leu Ile Leu Val Cys Ala
  1               5                  10                  15
Leu Leu Leu Leu Ile Ser Glu Ala Ser Tyr Val Pro Ile Thr Ile Val
                20                  25                  30
Gln Asn Ala Val Ala Lys Gly Ala Val Cys Leu Asp Gly Ser Pro Pro
            35                  40                  45
Ala Tyr His Phe Asp Arg Gly Phe Gly Ser Gly Ile Asn Asn Trp Leu
        50                  55                  60
Val Ala Phe Glu Gly Gly Trp Cys Asn Asn Val Thr Thr Cys Leu
 65                  70                  75                  80
Ala Arg Lys Thr Asn Arg Leu Gly Ser Ser Lys Gln Met Ala Lys Leu
                85                  90                  95
Ile Ala Phe Ser Gly Ile Leu Asn Asn Arg Glu Met Phe Asn Pro Asp
               100                 105                 110
Phe Tyr Asn Trp Asn Arg Ile Lys Val Arg Tyr Cys Asp Gly Ser Ser
               115                 120                 125
Phe Thr Gly Asp Val Glu Ala Val Asn Pro Val Thr Lys Leu His Phe
               130                 135                 140
Arg Gly Gly Arg Ile Phe Asn Ala Val Met Glu Asp Leu Leu Ala Lys
145                 150                 155                 160
Gly Met Lys Asn Ala Arg Asn Ala Ile Ile Ser Gly Cys Ser Ala Gly
                165                 170                 175
Gly Leu Thr Ser Val Leu His Cys Asp Arg Phe Arg Ala Leu Leu Pro
                180                 185                 190
Arg Gly Ala Arg Val Lys Cys Leu Ser Asp Ala Gly Tyr Phe Ile Asn
                195                 200                 205
Gly Lys Asp Val Leu Gly Glu Gln His Ile Glu Gln Tyr Phe Ser Gln
                210                 215                 220
Val Val Ala Thr His Gly Ser Ala Arg Asn Leu Pro Gln Ser Cys Thr
225                 230                 235                 240
Ser Arg Leu Ser Pro Arg Leu Cys Phe Phe Pro Gln Tyr Leu Val Ser
                245                 250                 255
Arg Ile Thr Thr Pro Ile Phe Phe Val Asn Ala Ala Tyr Asp Ser Trp
                260                 265                 270
Gln Ile Lys Asn Ile Leu Ala Pro Gly Val Ala Asp Pro Glu Gly His
                275                 280                 285
Trp His Ser Cys Lys Leu Asp Ile Asn Asn Cys Ser Pro Asp Gln Leu
                290                 295                 300
Asp Leu Met Gln Gly Phe Arg Thr Glu Phe Leu Arg Ala Ile Thr Val
305                 310                 315                 320
Leu Gly Asn Ser Ser Lys Gly Met Phe Ile Asp Ser Cys Tyr Ala
                325                 330                 335
His Cys Gln Thr Glu Met Gln Glu Thr Trp Leu Arg Ser Asp Ser Pro
                340                 345                 350
Glu Leu Lys Lys Thr Thr Ile Ala Lys Ala Val Ala Asp Trp Phe Tyr
                355                 360                 365
Glu Arg Arg Pro Phe His Gln Ile Asp Cys Pro Tyr Pro Cys Asn Pro
                370                 375                 380
Thr Cys His Asn Arg Val Phe Asp Pro Gln Asp Asp His Pro Gly Lys
385                 390                 395                 400
Asn Val Thr Ala Lys Gly Thr Ser Asp Ala Ser Ala Thr Lys Pro Asn
                405                 410                 415
Phe Pro Lys Leu Thr Asn Lys Ala Gln Trp Ile Glu Leu Val Cys Ile
```

-continued

```
                420             425             430
Ser Arg Gly Ile Ser Gly Leu Leu Leu Thr Leu Val Leu Leu Asn Lys
            435             440             445
Met Lys
    450

<210> SEQ ID NO 179
<211> LENGTH: 399
<212> TYPE: PRT
<213> ORGANISM: Glycine max

<400> SEQUENCE: 179

Met Glu Ile Thr Arg Ile Gly Gln Trp Leu Ser Leu Ile Cys Val
1               5                   10                  15

Leu Leu Leu Gln Thr Glu Gly Val Pro Val Gly Ile Thr Phe Val
                20                  25                  30

Glu Asn Ala Val Ala Lys Gly Ala Val Cys Leu Asp Gly Ser Pro Pro
                35                  40                  45

Ala Tyr His Phe His Lys Gly Ser Gly Ala Gly Ile Asn Asn Trp Ile
            50                  55                  60

Val His Phe Glu Gly Gly Gly Trp Cys Asn Asn Val Thr Thr Cys Leu
65                  70                  75                  80

Ser Arg Arg Asp Thr Arg Leu Gly Ser Ser Lys Lys Met Asp Thr Ser
                85                  90                  95

Leu Ser Phe Ser Gly Phe Phe Ser Asn Ser Lys Lys Phe Asn Pro Asp
                100                 105                 110

Phe Tyr Asp Trp Asn Arg Ile Lys Val Arg Tyr Cys Asp Gly Ser Ser
                115                 120                 125

Phe Thr Gly Asp Val Glu Ala Val Asp Pro Lys Thr Asn Leu His Phe
            130                 135                 140

Arg Gly Ala Arg Val Phe Ala Val Val Glu Asp Leu Leu Ala Lys
145                 150                 155                 160

Gly Met Lys Asn Ala Gln Asn Ala Ile Ile Ser Gly Cys Ser Ala Gly
                165                 170                 175

Gly Leu Ala Ser Ile Leu Asn Cys Asp Arg Phe Lys Ser Leu Leu Pro
            180                 185                 190

Ala Thr Thr Lys Val Lys Cys Leu Ala Asp Ala Gly Phe Phe Ile Asn
            195                 200                 205

Val Lys Asp Val Ser Gly Ala Gln Arg Ile Glu Glu Phe Tyr Ser Gln
            210                 215                 220

Val Val Gln Thr His Gly Ser Ala Lys Asn Leu Pro Thr Ser Cys Thr
225                 230                 235                 240

Ser Arg Leu Arg Pro Gly Leu Cys Phe Phe Pro Gln Asn Val Val Ser
                245                 250                 255

Gln Ile Ser Thr Pro Ile Phe Phe Val Asn Ala Ala Tyr Asp Ser Trp
            260                 265                 270

Gln Ile Lys Asn Ile Leu Ala Pro Gly Ala Ala Asp Pro Arg Gly Gln
            275                 280                 285

Trp Arg Glu Cys Lys Leu Asp Ile Lys Asn Cys Ser Pro Asn Gln Leu
290                 295                 300

Ser Val Met Gln Gly Phe Arg Thr Asp Phe Leu Arg Ala Phe Ser Val
305                 310                 315                 320

Val Gly Asn Ala Ala Ser Lys Gly His Phe Ile Asp Gly Cys Tyr Ala
                325                 330                 335
```

His Cys Gln Thr Gly Ile Gln Glu Thr Trp Leu Arg Asn Asp Ser Pro
                340                 345                 350

Val Val Ala Lys Thr Ser Ile Ala Lys Ala Val Gly Asp Trp Phe Tyr
            355                 360                 365

Asp Arg Arg Pro Phe Arg Glu Ile Asp Cys Ala Tyr Pro Cys Asn Pro
        370                 375                 380

Thr Cys His Asn Arg Ile Phe Asp Gln Asn Glu Arg Pro Asp Val
385                 390                 395

<210> SEQ ID NO 180
<211> LENGTH: 408
<212> TYPE: PRT
<213> ORGANISM: Glycine max

<400> SEQUENCE: 180

Met Thr Ser Thr Leu Leu Ser Leu Leu Phe Leu Leu Phe Ser Leu Leu
1               5                   10                  15

Thr Pro Thr Leu Ile Ser Ser Ser Pro Val Leu Asn Pro Gln Glu Val
            20                  25                  30

Val Gln Glu Val Asn Lys Lys Ile Asn Gly Ser Ile Ala Arg Pro Arg
        35                  40                  45

Arg Asn Leu Gly Tyr Leu Ser Cys Gly Ser Gly Asn Pro Ile Asp Asp
    50                  55                  60

Cys Trp Arg Cys Asp Pro Asn Trp Glu Gln Asn Arg Gln Arg Leu Ala
65                  70                  75                  80

Asp Cys Ala Ile Gly Phe Gly Lys Asn Ala Ile Gly Gly Arg Asp Gly
                85                  90                  95

Lys Ile Tyr Val Val Glu Asp Gly Asp Asp Ala Val Asn Pro
            100                 105                 110

Lys Pro Gly Thr Leu Arg His Ala Val Ile Gln Asp Glu Pro Leu Trp
        115                 120                 125

Ile Ile Phe Ala Arg Asp Met Val Ile Gln Leu Lys Glu Glu Leu Leu
    130                 135                 140

Met Asn Ser Phe Lys Thr Ile Asp Gly Arg Gly Ala Ser Val His Val
145                 150                 155                 160

Ala Gly Gly Pro Cys Ile Thr Ile Gln Tyr Val Thr Asn Val Ile Ile
                165                 170                 175

His Gly Ile His Ile His Asp Cys Lys Gln Gly Gly Asn Ala Met Val
            180                 185                 190

Arg Asp Ser Pro Arg His Tyr Gly Trp Arg Thr Val Ser Asp Gly Asp
        195                 200                 205

Gly Val Ser Ile Phe Gly Gly Ser His Val Trp Val Asp His Cys Ser
    210                 215                 220

Leu Ser Asn Cys Asn Asp Gly Leu Ile Asp Ala Ile His Gly Ser Thr
225                 230                 235                 240

Ala Ile Thr Ile Ser Asn Asn Tyr Met Thr His His Asp Lys Val Met
                245                 250                 255

Leu Leu Gly His Ser Asp Ser Tyr Thr Gln Asp Lys Asp Met Gln Val
            260                 265                 270

Thr Ile Ala Phe Asn His Phe Gly Glu Gly Leu Val Gln Arg Met Pro
        275                 280                 285

Arg Cys Arg Leu Gly Tyr Phe His Val Val Asn Asn Asp Tyr Thr His
    290                 295                 300

Trp Glu Met Tyr Ala Ile Gly Gly Ser Ala Asn Pro Thr Ile Asn Cys
305                 310                 315                 320

-continued

```
Gln Gly Asn Arg Phe Val Ala Pro Asp Asp Arg Phe Ser Lys Glu Val
            325                 330                 335

Thr Lys Arg Glu Asp Thr Pro Glu Ser Glu Trp Gln Asp Trp Asn Trp
            340                 345                 350

Arg Ser Glu Gly Asp Leu Leu Val Asn Gly Ala Phe Phe Thr Ala Ser
            355                 360                 365

Gly Ala Gly Ala Ser Ser Tyr Ala Arg Ala Ser Ser Leu Ser Ala
            370                 375                 380

Arg Pro Ser Ser Leu Val Gly Ser Ile Thr Thr Gly Ala Gly Ala Leu
385                 390                 395                 400

Ser Cys Lys Lys Gly Ser Pro Cys
            405
```

<210> SEQ ID NO 181
<211> LENGTH: 406
<212> TYPE: PRT
<213> ORGANISM: Glycine max

<400> SEQUENCE: 181

```
Met Ala Thr Thr Phe Leu Ser Leu Leu Phe Leu Leu Phe Ser Leu Leu
1               5                   10                  15

Thr Pro Thr Leu Ile Ser Ser Pro Val Gln Asp Pro Glu Phe Val
            20                  25                  30

Ala Gln Glu Val His Arg Lys Ile Asn Ala Ser Val Ala Arg Arg Asn
            35                  40                  45

Leu Gly Tyr Leu Ser Cys Ala Thr Gly Asn Pro Ile Asp Asp Cys Trp
50                  55                  60

Arg Cys Asp Pro Asn Trp Glu Lys Asn Arg Gln Arg Leu Ala Asp Cys
65                  70                  75                  80

Ala Ile Gly Phe Gly Lys Asn Ala Ile Gly Gly Lys Asn Gly Lys Ile
                85                  90                  95

Tyr Val Val Thr Asp Ser Gly Asp Asp Pro Val Thr Pro Lys Pro
            100                 105                 110

Gly Thr Leu Arg Tyr Ala Val Ile Gln Asp Glu Pro Leu Trp Ile Ile
            115                 120                 125

Phe Ala Arg Asp Met Val Ile Lys Leu Lys Glu Glu Leu Ile Met Asn
            130                 135                 140

Ser Phe Lys Thr Ile Asp Gly Arg Gly Ala Ser Val His Ile Ala Gly
145                 150                 155                 160

Gly Pro Cys Ile Thr Ile Gln Tyr Val Thr Asn Val Ile Ile His Gly
                165                 170                 175

Ile Asn Ile His Asp Cys Lys Gln Gly Gly Asn Ala Met Val Arg Asp
            180                 185                 190

Ser Pro Arg His Tyr Gly Trp Arg Thr Ile Ser Asp Gly Asp Gly Val
            195                 200                 205

Ser Ile Phe Gly Gly Ser His Val Trp Val Asp His Cys Ser Leu Ser
            210                 215                 220

Asn Cys Asn Asp Gly Leu Ile Asp Ala Ile His Gly Ser Thr Gly Ile
225                 230                 235                 240

Thr Ile Ser Asn Asn Tyr Met Thr His His Asp Lys Val Met Leu Leu
                245                 250                 255

Gly His Ser Asp Ser Tyr Thr Gln Asp Lys Ser Met Gln Val Thr Ile
            260                 265                 270

Ala Phe Asn His Phe Gly Glu Gly Leu Val Gln Arg Met Pro Arg Cys
```

```
            275                 280                 285
Arg His Gly Tyr Phe His Val Val Asn Asn Asp Tyr Thr His Trp Glu
290                 295                 300

Met Tyr Ala Ile Gly Gly Ser Ala Asn Pro Thr Ile Asn Ser Gln Gly
305                 310                 315                 320

Asn Arg Phe Val Ala Pro Asp Asp Arg Phe Ser Lys Glu Val Thr Lys
                325                 330                 335

His Glu Asp Ala Pro Glu Ser Glu Trp Lys Gly Trp Asn Trp Arg Ser
            340                 345                 350

Glu Gly Asp Leu Leu Val Asn Gly Ala Phe Phe Thr Ala Ser Gly Ala
        355                 360                 365

Gly Ala Ser Ser Tyr Ala Arg Ala Ser Ser Leu Ser Ala Arg Pro
    370                 375                 380

Ser Ser Leu Val Gly Ser Ile Thr Thr Gly Ala Gly Ala Leu Ser Cys
385                 390                 395                 400

Arg Lys Gly Ser Arg Cys
                405

<210> SEQ ID NO 182
<211> LENGTH: 379
<212> TYPE: PRT
<213> ORGANISM: Glycine max

<400> SEQUENCE: 182

Met Gly Asn Ala His His Ser Gln Trp His Arg Lys His Gly Asn Ser
1               5                   10                  15

Val Leu Pro Pro His Lys Tyr Asn Pro Gln Pro Pro Thr Thr Ser
            20                  25                  30

Asn Ser Asn Met Leu Ser Leu Pro Tyr Thr His Val Asp Thr Thr Leu
        35                  40                  45

Arg Ser Leu Ala Ala Gln Ala Glu Gly Phe Gly Arg Phe Ala Ile Gly
    50                  55                  60

Gly Leu His Gly Pro Leu His His Val Thr Ser Leu Ala Asp Asp Gly
65                  70                  75                  80

Pro Gly Ser Leu Arg Asn Ala Cys Arg Arg Lys Glu Pro Leu Trp Ile
                85                  90                  95

Val Phe Glu Val Ser Gly Thr Ile Gln Leu Ser Ser Tyr Leu Asn Val
            100                 105                 110

Ser Ser His Lys Thr Ile Asp Gly Arg Gly Gln Arg Ile Lys Leu Ser
        115                 120                 125

Gly Lys Gly Leu Arg Leu Lys Glu Cys Glu His Val Ile Ile Cys Asn
130                 135                 140

Leu Glu Phe Glu Gly Gly Arg Gly His Asp Val Asp Ala Ile Gln Ile
145                 150                 155                 160

Lys Pro Asn Ser Lys His Ile Trp Ile Asp Arg Cys Thr Leu Ser Asp
                165                 170                 175

Phe Asp Asp Gly Leu Ile Asp Ile Thr Arg Glu Ser Thr Asp Ile Thr
            180                 185                 190

Ile Ser Arg Cys His Phe Ser Gln His Asp Lys Ala Met Leu Ile Gly
        195                 200                 205

Ala Asp Pro Ser His Val Gly Asp Arg Cys Met Arg Val Thr Ile His
    210                 215                 220

His Cys Phe Phe Asn Gly Thr Arg Gln Arg Gln Pro Arg Val Arg Phe
225                 230                 235                 240
```

-continued

```
Ala Lys Val His Leu Tyr Asn Asn Tyr Ile Arg Asn Trp Gly Ile Tyr
            245                 250                 255

Ala Val Cys Ala Ser Val Glu Ser Gln Ile Phe Ser Gln His Asn Ile
        260                 265                 270

Tyr Glu Ala Gly Gln Lys Lys Val Ala Phe Lys Tyr Leu Thr Glu Gln
    275                 280                 285

Ala Ala Asp Lys Glu Val Gly Ala Thr Gly Thr Ile Met Ser Glu Gly
290                 295                 300

Asp Ile Phe Leu Asn Gly Ala Lys Ala Gly Leu Met Ala Val Asp Val
305                 310                 315                 320

Ser Cys Asn Met Phe His Pro Ser Glu His Tyr Pro Ser Trp Thr Val
                325                 330                 335

Glu Ala Pro Thr Asp Asp Leu Lys Pro Ile Leu Leu His Cys Thr Gly
            340                 345                 350

Gly His Phe Phe Val Gly Pro Ala Val Gly Pro Phe Gly Ala Leu Gly
        355                 360                 365

His Asn Arg Leu Leu Glu Val Arg Val Leu Leu
    370                 375

<210> SEQ ID NO 183
<211> LENGTH: 528
<212> TYPE: PRT
<213> ORGANISM: Glycine max

<400> SEQUENCE: 183

Met Ala Leu Ser Ser Lys Lys Glu Leu Ser Gln Ile Ala Ala Thr Pro
1               5                   10                  15

Lys Leu Thr Ile Thr Leu Ile Phe Phe Val Leu Phe Leu Thr Ala
            20                  25                  30

Leu Gly Asn Thr Asn Thr Asn Thr Val Gly Ser Glu Leu Leu Lys Val
        35                  40                  45

Ala Pro Ser Glu Phe Ala Gly Thr Val Arg Thr Val Val Asp Val Leu
    50                  55                  60

Gln Asp Ile Thr Ser Ile Leu Ser Glu Phe Gly Ser Gly Phe Gly Asp
65                  70                  75                  80

Ser Arg Leu Ser Asn Ala Val Ser Asp Cys Leu Glu Leu Leu Asp Met
                85                  90                  95

Ser Ser Asp Glu Leu Asp Trp Ser Val Ser Ala Thr Gln Ser Pro Lys
            100                 105                 110

Gly Lys His Asn Ser Thr Gly Asn Thr Ser Ser Asp Leu Arg Thr Trp
        115                 120                 125

Leu Ser Ala Ala Leu Ala Asn Gln Asp Thr Cys Met Asp Gly Phe Asp
    130                 135                 140

Gly Thr Asn Gly Ile Val Lys Gly Leu Val Ser Thr Gly Leu Gly Gln
145                 150                 155                 160

Val Met Ser Leu Leu Gln Gln Leu Leu Thr Gln Val Asn Pro Val Ser
                165                 170                 175

Asp His Tyr Thr Phe Ser Ser Pro Gln Gly His Phe Pro Pro Trp Val
            180                 185                 190

Lys Pro Gly Glu Arg Lys Leu Leu Gln Ala Ala Asn Gly Val Ser Phe
        195                 200                 205

Asp Ala Val Val Ala Ala Asp Gly Thr Gly Asn Phe Thr Lys Val Met
    210                 215                 220

Asp Ala Val Leu Ala Ala Pro Asn Tyr Ser Met Gln Arg Tyr Val Ile
225                 230                 235                 240
```

-continued

```
His Ile Lys Arg Gly Val Tyr Asn Glu Asn Val Glu Ile Lys Lys Lys
                245                 250                 255

Lys Trp Asn Leu Met Met Val Gly Asp Gly Met Asp Asn Thr Val Ile
            260                 265                 270

Ser Gly Asn Arg Ser Phe Ile Asp Gly Trp Thr Thr Phe Arg Ser Ala
        275                 280                 285

Thr Phe Ala Val Ser Gly Arg Gly Phe Val Ala Arg Asp Ile Thr Phe
    290                 295                 300

Gln Asn Thr Ala Gly Pro Glu Lys His Gln Ala Val Ala Leu Arg Ser
305                 310                 315                 320

Asp Ser Asp Leu Ser Val Phe Phe Arg Cys Gly Ile Phe Gly Tyr Gln
                325                 330                 335

Asp Ser Leu Tyr Thr His Thr Met Arg Gln Phe Tyr Arg Glu Cys Lys
            340                 345                 350

Ile Ser Gly Thr Val Asp Phe Ile Phe Gly Asp Ala Thr Ala Ile Phe
        355                 360                 365

Gln Asn Cys His Ile Ser Ala Lys Lys Gly Leu Pro Asn Gln Lys Asn
    370                 375                 380

Thr Ile Thr Ala His Gly Arg Lys Asn Pro Asp Glu Pro Thr Gly Phe
385                 390                 395                 400

Ser Ile Gln Phe Cys Asn Ile Ser Ala Asp Tyr Asp Leu Val Asn Ser
                405                 410                 415

Ile Asn Asn Asn Ser Asn Asn Ser Ile Gly Thr Tyr Leu Gly Arg Pro
            420                 425                 430

Trp Lys Pro Tyr Ser Arg Thr Val Phe Met Gln Ser Tyr Ile Ser Asp
        435                 440                 445

Val Leu Arg Pro Glu Gly Trp Leu Glu Trp Asn Gly Asp Phe Ala Leu
    450                 455                 460

Asp Thr Leu Tyr Tyr Ala Glu Tyr Met Asn Tyr Gly Pro Gly Ala Gly
465                 470                 475                 480

Val Ala Asn Arg Val Lys Trp Pro Gly Tyr His Val Met Asn Asp Ser
                485                 490                 495

Ser Gln Ala Ser Asn Phe Thr Val Ser Gln Phe Ile Glu Gly Asn Leu
            500                 505                 510

Trp Leu Pro Ser Thr Gly Val Thr Phe Thr Ala Gly Leu Gly Gly Val
        515                 520                 525

<210> SEQ ID NO 184
<211> LENGTH: 586
<212> TYPE: PRT
<213> ORGANISM: Glycine max

<400> SEQUENCE: 184

Met Asp Thr Ile Lys Ser Phe Lys Gly Tyr Gly Lys Val Asp Glu Leu
1               5                   10                  15

Glu Gln Gln Ala Tyr Gln Lys Lys Thr Arg Lys Arg Leu Ile Ile Ile
            20                  25                  30

Thr Val Ser Ser Ile Val Leu Ile Ala Val Ile Ala Ala Ile Ala
        35                  40                  45

Gly Val Val Ile His Lys Arg Asn Thr Ser Ser Pro Ser Ser Asp
    50                  55                  60

Ser Pro Pro Gln Thr Glu Leu Thr Pro Ala Ala Ser Leu Lys Ala Val
65                  70                  75                  80

Cys Asp Val Thr Gln Tyr Pro Asn Ser Cys Phe Ser Ala Ile Ser Ser
```

-continued

```
                85                  90                  95
Leu Pro Asp Ser Asn Thr Thr Asp Pro Glu Leu Leu Phe Lys Leu Ser
            100                 105                 110

Leu Arg Val Ala Ile Asp Glu Leu Ser Lys Leu Ser Ser Phe Pro Ser
            115                 120                 125

Lys Leu Arg Ala Asn Ala Glu His Asp Ala Arg Leu Gln Lys Ala Ile
            130                 135                 140

Asp Val Cys Gly Asn Ile Phe Gly Asp Ala Leu Asp Arg Leu Asn Asp
145                 150                 155                 160

Ser Ile Ser Ala Leu Gly Ser Ser Gly Ala Gly Lys Ile Ile Ser
                165                 170                 175

Pro Ala Ser Val Ser Asp Val Glu Thr Trp Ile Ser Ala Ala Leu Thr
                180                 185                 190

Asp Gln Asp Thr Cys Leu Asp Ala Leu Gly Glu Leu Asn Ser Thr Ala
                195                 200                 205

Ala Ser Gly Ala Leu Arg Glu Ile Glu Thr Ala Met Arg Asn Ser Thr
            210                 215                 220

Glu Phe Ala Ser Asn Ser Leu Ala Ile Val Thr Lys Ile Leu Gly Leu
225                 230                 235                 240

Leu Ser Gln Phe Ala Ala Pro Ile His His Arg Leu Leu Gly Phe
                245                 250                 255

Pro Glu Trp Leu Gly Ala Ala Glu Arg Arg Leu Leu Gln Val Asn Ser
                260                 265                 270

Ser Glu Thr Thr Leu Asp Ala Val Val Ala Gln Asp Gly Ser Gly Gln
            275                 280                 285

Phe Arg Thr Ile Gly Glu Ala Leu Lys Leu Val Lys Lys Ser Glu
290                 295                 300

Lys Arg Phe Val Val His Val Lys Glu Gly Arg Tyr Leu Glu Asn Ile
305                 310                 315                 320

Asp Leu Asp Lys Asn Thr Trp Asn Val Phe Ile Phe Gly Asp Gly Lys
                325                 330                 335

Asp Lys Thr Val Val Val Gly Ser Arg Asn Phe Met Asp Gly Thr Pro
            340                 345                 350

Thr Phe Glu Thr Ala Thr Phe Ala Val Lys Gly Lys Gly Phe Ile Ala
            355                 360                 365

Lys Asp Ile Gly Phe Val Asn Asn Ala Gly Ala Ser Lys His Gln Ala
            370                 375                 380

Val Ala Phe Arg Ser Gly Ser Asp Arg Ser Val Phe Phe Arg Cys Ser
385                 390                 395                 400

Phe Asn Gly Phe Gln Asp Thr Leu Tyr Ala His Ser Asn Arg Gln Phe
                405                 410                 415

Tyr Arg Asp Cys Asp Ile Thr Gly Thr Ile Asp Phe Ile Phe Gly Asn
                420                 425                 430

Ala Ala Val Phe Gln Asn Cys Lys Ile Met Pro Arg Gln Pro Leu
            435                 440                 445

Pro Asn Gln Phe Asn Thr Ile Thr Ala Gln Gly Lys Lys Asp Arg Asn
        450                 455                 460

Gln Asn Thr Gly Ile Ile Ile Gln Lys Ser Lys Phe Thr Pro Leu Glu
465                 470                 475                 480

Asn Asn Leu Thr Ala Pro Thr Tyr Leu Gly Arg Pro Trp Lys Asp Phe
            485                 490                 495

Ser Thr Thr Val Ile Met Gln Ser Asp Ile Gly Ser Phe Leu Lys Pro
            500                 505                 510
```

```
Val Gly Trp Met Ser Trp Val Pro Asn Val Glu Pro Val Ser Thr Ile
            515                 520                 525

Phe Tyr Ala Glu Tyr Gln Asn Thr Gly Pro Gly Ala Asp Val Ser Gln
        530                 535                 540

Arg Val Lys Trp Ala Gly Tyr Lys Pro Thr Leu Thr Asp Gly Glu Ala
545                 550                 555                 560

Gly Lys Phe Thr Val Gln Ser Phe Ile Gln Gly Pro Glu Trp Leu Pro
                565                 570                 575

Asn Ala Ala Val Gln Phe Asp Ser Thr Leu
            580                 585

<210> SEQ ID NO 185
<211> LENGTH: 262
<212> TYPE: PRT
<213> ORGANISM: Glycine max

<400> SEQUENCE: 185

Met Phe Ile Gly Asp Gly Lys Gly Lys Thr Val Ile Thr Gly Lys Lys
1               5                   10                  15

Asn Val Ile Asp Gly Met Thr Thr Phe His Ser Ala Ser Phe Ala Ala
            20                  25                  30

Ser Gly Ala Gly Phe Ile Ala Arg Asp Ile Thr Phe Glu Asn Tyr Ala
        35                  40                  45

Gly Pro Ala Lys His Gln Ala Val Ala Leu Arg Val Gly Ala Asp His
    50                  55                  60

Ala Val Val Tyr Arg Cys Asn Ile Val Gly Tyr Gln Asp Ser Cys Tyr
65                  70                  75                  80

Val His Ser Asn Arg Gln Phe Phe Arg Glu Cys Asn Ile Tyr Gly Thr
                85                  90                  95

Val Asp Phe Ile Phe Gly Asn Ala Ala Val Val Phe Gln Lys Cys Asn
            100                 105                 110

Ile Tyr Ala Arg Lys Pro Met Ala Gln Gln Lys Asn Thr Ile Thr Ala
        115                 120                 125

Gln Asn Arg Lys Asp Pro Asn Gln Asn Thr Gly Ile Ser Leu His Asn
    130                 135                 140

Cys Arg Ile Leu Pro Ala Pro Asp Leu Ala Pro Val Lys Gly Ser Phe
145                 150                 155                 160

Pro Thr Tyr Leu Gly Arg Pro Trp Lys Gln Tyr Ser Arg Thr Val Tyr
                165                 170                 175

Leu Val Ser Tyr Met Gly Asp His Ile His Pro Arg Gly Trp Leu Glu
            180                 185                 190

Trp Asn Gly Asp Phe Ala Leu Asn Thr Leu Tyr Tyr Gly Glu Tyr Met
        195                 200                 205

Asn Tyr Gly Pro Gly Ala Ala Val Gly Gln Arg Val Gln Trp Pro Gly
    210                 215                 220

Tyr Arg Val Ile Lys Ser Thr Met Glu Ala Asn Arg Phe Thr Val Ala
225                 230                 235                 240

Gln Phe Ile Ser Gly Ser Ala Trp Leu Pro Ser Thr Gly Val Ala Phe
                245                 250                 255

Ala Ala Gly Leu Ser Thr
            260

<210> SEQ ID NO 186
<211> LENGTH: 520
<212> TYPE: PRT
```

<213> ORGANISM: Glycine max

<400> SEQUENCE: 186

```
Met Ala Ile Pro Ser Pro Lys Ile Phe Leu Leu Thr Phe Phe Phe
1               5                   10                  15

Ser His Ser Ile Ala Val Lys Ser Ser Asn Val Ser Thr Thr Pro Thr
                20                  25                  30

Leu His Ala Thr Phe Pro Phe Pro Glu Val Ser Ser Phe Asn Ser Ser
            35                  40                  45

Lys Leu Ser Ile Ser Ile Asn Ile Asn Pro Asn Ile Ile Asn Thr Leu
        50                  55                  60

Leu Gln Ser Leu Gln Ala Ala Ile Ser Glu Ala Thr Lys Leu Ser Asp
65                  70                  75                  80

Leu Leu Asn Asn Ala Gly His Asn Ile Ile Glu Asn Lys Ile Gly Ala
                85                  90                  95

Val Gln Asp Cys Arg Glu Leu Gln Gln Ser Thr Leu Ala Ser Leu Lys
            100                 105                 110

Arg Ser Leu Ser Gly Ile Arg Ser Gln Asp Ser Arg Lys Leu Val Asp
        115                 120                 125

Ala Arg Thr Tyr Leu Ser Ala Ala Leu Thr Asn Lys Asp Thr Cys Leu
    130                 135                 140

Glu Ser Leu Asp Ser Ala Ser Gly Thr Leu Lys Pro Val Leu Val Asn
145                 150                 155                 160

Ser Val Ile Asn Ser Tyr Lys Asp Val Ser Asp Ser Leu Ser Met Leu
                165                 170                 175

Pro Lys Pro Glu Arg Lys Ala Ser Lys Gly His Lys Asn Arg Arg Leu
            180                 185                 190

Leu Trp Leu Ser Thr Lys Asn Arg Arg Leu Leu Gln Ser Asn Asp Gly
        195                 200                 205

Gly Glu Leu Val Val Ala Ala Asp Gly Thr Gly Asn Phe Ser Thr Ile
    210                 215                 220

Thr Glu Ala Ile Asn Phe Ala Pro Asn Asn Ser Val Gly Arg Thr Val
225                 230                 235                 240

Ile Tyr Val Lys Glu Gly Thr Tyr Glu Glu Asn Val Glu Ile Pro Ser
                245                 250                 255

Tyr Lys Thr Asn Ile Val Leu Leu Gly Asp Gly Lys Asp Val Thr Phe
            260                 265                 270

Ile Thr Gly Asn Arg Ser Val Ile Asp Gly Trp Thr Thr Phe Arg Ser
        275                 280                 285

Ala Thr Leu Ala Val Ser Gly Glu Gly Phe Leu Ala Arg Asp Ile Ala
    290                 295                 300

Phe Glu Asn Lys Ala Gly Pro Glu Lys His Gln Ala Val Ala Leu Arg
305                 310                 315                 320

Val Asn Ala Asp Phe Thr Ala Phe Tyr Arg Cys Ala Met Tyr Gly Tyr
                325                 330                 335

Gln Asp Thr Leu Tyr Val His Ser Phe Arg Gln Phe Tyr Arg Glu Cys
            340                 345                 350

Glu Ile Phe Gly Thr Ile Asp Tyr Ile Phe Gly Asn Ala Ala Val Val
        355                 360                 365

Leu Gln Ala Ser Asn Ile Ile Thr Arg Met Pro Met Leu Gly Gln Phe
    370                 375                 380

Thr Val Ile Thr Ala Gln Ser Arg Asp Ser Pro Asp Glu Asp Thr Gly
385                 390                 395                 400
```

```
Ile Ser Ile Gln Asn Cys Ser Ile Leu Ala Thr Thr Asp Leu Tyr Ser
                    405                 410                 415

Asn Ser Gly Ser Val Lys Ser Tyr Leu Gly Arg Pro Trp Arg Val Tyr
            420                 425                 430

Ser Arg Thr Val Phe Leu Glu Ser Tyr Ile Asp Gln Phe Ile Asp Pro
            435                 440                 445

Met Gly Trp Lys Glu Trp Ser Gly Asp Gln Gly Leu Asp Thr Leu Tyr
450                 455                 460

Tyr Gly Glu Tyr Ala Asn Tyr Gly Pro Gly Ser Gly Thr Asp Asn Arg
465                 470                 475                 480

Val Asn Trp Ala Gly Phe His Val Met Asp Tyr Asp Ser Ala Tyr Asn
            485                 490                 495

Phe Thr Val Ser Glu Phe Ile Ile Gly Asp Ala Trp Leu Gly Ser Thr
            500                 505                 510

Ser Phe Pro Tyr Asp Asp Gly Ile
            515                 520

<210> SEQ ID NO 187
<211> LENGTH: 553
<212> TYPE: PRT
<213> ORGANISM: Glycine max

<400> SEQUENCE: 187

Met Ala Ile Gln Gln Ser Leu Leu Asp Arg Pro Arg Lys Ser Val Ser
1               5                   10                  15

Lys Thr Ile Cys Leu Ile Phe Ser Ile Ala Ala Val Met Ile Ser Ser
            20                  25                  30

Ala Phe Val Gly Ser Tyr Leu Ile Lys Ser Thr Ser Phe Phe Asn Gln
            35                  40                  45

Ser Ser Pro Gln His Leu Cys Asp His Ala Leu Asp Arg Ala Thr Cys
50                  55                  60

Leu Thr His Val Ser Glu Val Val Gln Gly Pro Ile Leu Thr Pro Thr
65                  70                  75                  80

Lys Asp His Lys Phe Asn Leu Leu Gln Ser Phe Leu Met Lys Tyr Thr
            85                  90                  95

Ser His Ile Lys Arg Val Met Asn Thr Ala Ser Ser Ile Lys Leu Arg
            100                 105                 110

Ile Asn Ser Pro Lys Glu Glu Ala Leu His Asp Cys Val Glu Leu
            115                 120                 125

Met Asp Leu Ser Ile Ser Arg Val Arg Asp Ser Met Val Thr Leu Thr
130                 135                 140

Lys Gln Thr Ile Glu Ser Gln Gln Asp Ala His Thr Trp Leu Ser Ser
145                 150                 155                 160

Val Leu Thr Asn His Ala Thr Cys Leu Asp Gly Leu Glu Gly Ser Ala
            165                 170                 175

Arg Ala Phe Met Lys Asp Glu Leu Glu Asp Leu Ile Ser Arg Ala Arg
            180                 185                 190

Thr Ser Leu Ala Met Phe Val Ala Val Leu Pro Pro Lys Val Glu Gln
            195                 200                 205

Ile Ile Asp Glu Pro Leu Ser Gly Asp Phe Pro Ser Trp Val Ser Ser
210                 215                 220

Lys Asp Arg Arg Leu Leu Glu Ser Thr Val Gly Asp Ile Lys Ala Asn
225                 230                 235                 240

Val Val Val Ala Lys Asp Gly Ser Gly Lys Phe Lys Thr Val Ala Glu
            245                 250                 255
```

Ala Val Ala Ser Ala Pro Asp Asn Gly Lys Thr Arg Tyr Val Ile Tyr
            260                 265                 270

Val Lys Lys Gly Thr Tyr Lys Glu Asn Val Glu Ile Gly Lys Lys Lys
            275                 280                 285

Thr Asn Val Met Leu Val Gly Asp Gly Lys Asp Ala Thr Val Ile Thr
290                 295                 300

Gly Asn Leu Asn Phe Ile Asp Gly Thr Thr Thr Phe Lys Thr Ala Thr
305                 310                 315                 320

Val Ala Ala Val Gly Asp Gly Phe Ile Ala Gln Asp Ile Trp Phe Gln
            325                 330                 335

Asn Thr Ala Gly Pro Gln Lys His Gln Ala Val Ala Leu Arg Val Gly
            340                 345                 350

Ala Asp Gln Ser Val Ile Asn Arg Cys Arg Ile Asp Ala Phe Gln Asp
            355                 360                 365

Thr Leu Tyr Ala His Ser Asn Arg Gln Phe Tyr Arg Asp Ser Phe Ile
    370                 375                 380

Thr Gly Thr Val Asp Phe Ile Phe Gly Asn Ala Ala Val Val Phe Gln
385                 390                 395                 400

Lys Cys Asp Leu Val Ala Arg Lys Pro Met Asp Lys Gln Asn Asn Met
                405                 410                 415

Val Thr Ala Gln Gly Arg Glu Asp Pro Asn Gln Asn Thr Gly Thr Ser
            420                 425                 430

Ile Gln Gln Cys Asn Leu Thr Pro Ser Ser Asp Leu Lys Pro Val Val
            435                 440                 445

Gly Ser Ile Lys Thr Phe Leu Gly Arg Pro Trp Lys Lys Tyr Ser Arg
450                 455                 460

Thr Val Val Met Gln Ser Thr Leu Asp Ser His Ile Asp Pro Thr Gly
465                 470                 475                 480

Trp Ala Glu Trp Asp Ala Gln Ser Lys Asp Phe Leu Gln Thr Leu Tyr
                485                 490                 495

Tyr Gly Glu Tyr Met Asn Asn Gly Pro Gly Ala Gly Thr Ser Lys Arg
            500                 505                 510

Val Asn Trp Pro Gly Tyr His Ile Ile Lys Thr Ala Ala Glu Ala Ser
            515                 520                 525

Lys Phe Thr Val Ala Gln Leu Ile Gln Gly Asn Val Trp Leu Lys Asn
            530                 535                 540

Thr Gly Val Asn Phe Ile Glu Gly Leu
545                 550

<210> SEQ ID NO 188
<211> LENGTH: 197
<212> TYPE: PRT
<213> ORGANISM: Glycine max

<400> SEQUENCE: 188

Met Ile Ile Ile Ala Arg Leu Met Phe Leu Leu Ala Leu Phe Leu Leu
1               5                   10                  15

Leu Val Thr Asn Thr Gly Gln Met Val Phe Ala Gln Asp Asp Asn Asn
            20                  25                  30

Val Arg Asp Ala Cys Ser Val Thr Arg Phe Gln Ser Leu Cys Val Gln
        35                  40                  45

Thr Leu Gly His Phe Ser Arg Thr Ala Gly Thr Ser Pro Ser Lys Trp
    50                  55                  60

Ala Arg Ala Gly Val Ser Val Ser Ile Gly Glu Val Lys Asn Val Glu

```
                65                  70                  75                  80
Ala Tyr Leu Ala Gln Val Lys Arg Gln Gly Gln Leu Lys Gly Arg Asn
                    85                  90                  95

Ser Val Ala Leu Ser Asp Cys Val Glu Thr Phe Gly Tyr Ala Ile Asp
                    100                 105                 110

Glu Leu His Lys Ser Leu Gly Val Leu Arg Ser Leu Lys Ser Lys
                115                 120                 125

Phe Ser Thr Gln Met Gly Asp Leu Asn Thr Trp Ile Ser Ala Ala Leu
            130                 135                 140

Thr Asp Glu Val Thr Cys Leu Asp Gly Phe Glu Gly Ser Lys Gly Thr
145                 150                 155                 160

Asn Val Lys Leu Leu Gln Asn Arg Val Gln Asn Ala Ser Tyr Ile Thr
                165                 170                 175

Ser Asn Ala Leu Ala Leu Ile Asn Lys Leu Ala Thr Glu Gly Leu Gly
                180                 185                 190

Ser Ile Asn Asp Pro
        195
```

<210> SEQ ID NO 189
<211> LENGTH: 208
<212> TYPE: PRT
<213> ORGANISM: Glycine max

<400> SEQUENCE: 189

```
Met Lys Pro Thr Phe Leu Leu Ser Leu Leu Phe Phe Thr Phe Thr Leu
1               5                   10                  15

Ser His Leu Thr Pro Pro Ala Thr Ala Gly Asp Arg Tyr Val Ser Gly
                20                  25                  30

Asp Asn Ser Gly Asp Ala Asp Phe Ile Arg Ala Ser Cys Asn Ala Thr
            35                  40                  45

Leu Tyr Pro Asp Leu Cys Phe Ser Ser Leu Ser Arg Tyr Ala Ala Ala
        50                  55                  60

Val Gln Ser Ser His Ala Ala Leu Ala Arg Val Ala Val Ala Val Ala
65                  70                  75                  80

Leu Ala Lys Ala His Gly Ala Ala Ala Tyr Leu Ser His Gln Thr Ala
                85                  90                  95

Ala Ala Ser Asp Asp Asp Ser Gly Ala Gly Ser Ala Leu His Asp Cys
                100                 105                 110

Phe Ser Asn Leu Glu Asp Ala Val Asp Glu Ile Arg Gly Ser Leu Lys
            115                 120                 125

Gln Met Arg Arg Leu Lys Pro Ala Gly Ala Gly Asn Ser Asp Ser Ser
        130                 135                 140

Ser Val Arg Phe Gly Leu Ser Asn Val Leu Thr Trp Met Ser Ala Ala
145                 150                 155                 160

Leu Thr Asp Glu Glu Thr Cys Thr Asp Gly Phe Glu Gly Val Glu Glu
                165                 170                 175

Gly Pro Val Lys Thr Ser Val Cys Asp Arg Val Thr Arg Val Lys Lys
                180                 185                 190

Phe Thr Ser Asn Ala Leu Ala Leu Val Asn Gly Phe Ala Asn Asn Leu
            195                 200                 205
```

<210> SEQ ID NO 190
<211> LENGTH: 191
<212> TYPE: PRT
<213> ORGANISM: Glycine max

<400> SEQUENCE: 190

Met Arg Leu Leu Pro Ser Ser Leu Ile Ser Leu Ser Thr Met Thr Asn
1               5                   10                  15

Leu Lys Pro Leu Ile Leu Leu Ala Ile Ile Val Met Ile Ser Ile Pro
            20                  25                  30

Ser Ser His Cys Arg Thr Leu Leu Pro Glu Asn Glu Lys Leu Ile Glu
        35                  40                  45

Asn Thr Cys Arg Lys Thr Pro Asn Tyr Asn Val Cys Leu Glu Ser Leu
    50                  55                  60

Lys Ala Ser Pro Gly Ser Ser Ala Asp Val Thr Gly Leu Ala Gln
65                  70                  75                  80

Ile Met Val Lys Glu Met Lys Ala Lys Ala Asn Tyr Ala Leu Lys Arg
                85                  90                  95

Ile Gln Glu Leu Gln Arg Val Gly Ala Gly Pro Asn Lys Gln Arg Arg
            100                 105                 110

Ala Leu Ser Ser Cys Val Asp Lys Tyr Lys Thr Val Leu Ile Ala Asp
        115                 120                 125

Val Pro Gln Ala Thr Glu Ala Leu Gln Lys Gly Asp Pro Lys Phe Ala
130                 135                 140

Glu Asp Gly Ala Asn Asp Ala Ala Asn Glu Ala Thr Phe Cys Glu Ala
145                 150                 155                 160

Asp Phe Ser Ala Gly Asn Ser Pro Leu Thr Lys Gln Asn Asn Ala Met
                165                 170                 175

His Asp Val Ala Ala Val Thr Ala Ala Ile Val Arg Leu Leu Leu
            180                 185                 190

<210> SEQ ID NO 191
<211> LENGTH: 420
<212> TYPE: PRT
<213> ORGANISM: Glycine max

<400> SEQUENCE: 191

Met Glu Met Glu Arg Val Leu Trp Val Gly Ile Ala Ile Gly Leu Val
1               5                   10                  15

Phe Ser Asn Trp Val Val Gly Tyr Glu Gln Tyr His Phe Asn Glu Thr
            20                  25                  30

Glu Leu Ser Leu Leu Glu Ala His Glu Ala Ser Leu Ser Tyr Ala Gly
        35                  40                  45

Thr Glu Arg Asn Asn Leu Leu Leu Val Gly Leu Thr Leu Ile Gln Asn
    50                  55                  60

Ala Ala Ala Lys Gly Ala Val Cys Leu Asp Gly Thr Leu Pro Gly Tyr
65                  70                  75                  80

His Trp His Arg Gly Tyr Gly Ser Gly Ala Asn Ser Trp Leu Ile Asn
                85                  90                  95

Leu Glu Gly Gly Gly Trp Cys Asn Asn Ile Arg Thr Cys Val Tyr Arg
            100                 105                 110

Lys Lys Thr Arg Arg Gly Ser Ser Asp Phe Met Glu Lys Glu Ile Pro
        115                 120                 125

Phe Thr Gly Ile Leu Ser Asn Lys Ala Glu Glu Asn Pro Asp Phe Phe
130                 135                 140

Asn Trp Asn Arg Val Lys Leu Arg Tyr Cys Asp Gly Ala Ser Phe Thr
145                 150                 155                 160

Gly Asp Ser Glu Asp Glu Thr Ala Glu Leu Gln Phe Arg Gly Gln Arg
                165                 170                 175

```
Ile Trp Ala Ala Ala Met Glu Asp Leu Met Ser Lys Gly Met Arg Phe
            180                 185                 190

Ala Asn Gln Ala Leu Leu Ser Gly Cys Ser Ala Gly Gly Leu Ala Thr
        195                 200                 205

Ile Ile His Cys Asp Glu Phe Arg Gly Leu Phe Pro Arg Thr Thr Lys
    210                 215                 220

Val Lys Cys Leu Ser Asp Ala Gly Leu Phe Leu Asp Val Ile Asp Val
225                 230                 235                 240

Ser Gly Gly His Thr Leu Arg Asn Leu Tyr Ser Gly Val Val Gly Leu
                245                 250                 255

Gln Gly Ala Gln Lys Asn Leu Pro Gln Ile Cys Thr Asn His Leu Asp
            260                 265                 270

Pro Ile Ser Cys Phe Phe Pro Gln Asn Leu Ile Ala Ser Val Lys Thr
        275                 280                 285

Pro Leu Phe Ile Leu Asn Ala Ala Tyr Asp Ser Trp Gln Ile Gln Ser
    290                 295                 300

Ser Leu Ala Pro Pro Ser Ala Asp Pro His Gly Tyr Trp Gln Gln Cys
305                 310                 315                 320

Arg Leu Asn His Ala Lys Cys Thr Gly Pro Gln Ile Gln Phe Leu Gln
                325                 330                 335

Gly Phe Arg Asn His Met Leu Asn Ala Ile Lys Tyr Phe Ser Arg Ser
            340                 345                 350

Lys Gln Asn Gly Leu Phe Ile Asn Ser Cys Phe Ser His Cys Gln Thr
        355                 360                 365

Glu Arg Gln Asp Thr Trp Phe Ala Asp Asn Ser Pro Val Ile Arg Asn
    370                 375                 380

Lys Ala Ile Ala Leu Ala Val Gly Asp Trp Tyr Phe Asp Arg Ala Gly
385                 390                 395                 400

Val Lys Ala Ile Asp Cys Pro Tyr Pro Cys Asp Asn Thr Cys His His
                405                 410                 415

Leu Ile Phe Arg
            420

<210> SEQ ID NO 192
<211> LENGTH: 398
<212> TYPE: PRT
<213> ORGANISM: Glycine max

<400> SEQUENCE: 192

Met Glu Ser Ala Arg Ile Ser Gln Trp Leu Asn Leu Leu Val Cys Val
1               5                   10                  15

Leu Leu Leu Leu Lys Ala Glu Gly Ser Leu Val Pro Leu Ile Leu Val
            20                  25                  30

Glu Asn Ala Glu Ser Lys Gly Ala Val Cys Leu Asp Gly Ser Pro Pro
        35                  40                  45

Ala Tyr His Phe Asp Lys Gly Phe Gly Glu Gly Ile Asn Ser Trp Ile
    50                  55                  60

Val His Ile Glu Gly Gly Gly Trp Cys Asn Asn Ile Glu Ser Cys Leu
65                  70                  75                  80

Asp Arg Lys Asp Thr Arg Leu Gly Ser Ser Lys Gln Met Glu Asp Ile
                85                  90                  95

Tyr Phe Ser Gly Ile Leu Ser Asn Glu Gln Gln Phe Asn Pro Asp Phe
            100                 105                 110

Tyr Asn Trp Asn Arg Val Lys Val Arg Tyr Cys Asp Gly Ser Ser Phe
        115                 120                 125
```

Thr Gly Asp Val Glu Val Asp Pro Thr Thr Asn Leu His Phe Arg
    130                 135                 140

Gly Ala Arg Ile Phe Ser Ala Val Ile Glu Leu Leu Ala Lys Gly
145                 150                 155                 160

Leu Glu Arg Ala Glu Asn Ala Ile Leu Ser Gly Cys Ser Ala Gly Gly
                165                 170                 175

Leu Thr Thr Ile Leu His Cys Asp Ser Phe Lys Thr Phe Leu Pro Ser
                180                 185                 190

Arg Ala Asn Val Lys Cys Val Pro Asp Ala Gly Tyr Phe Val Asn Val
                195                 200                 205

Glu Asp Ile Ser Gly Ala His Phe Ile Gln Gln Tyr Tyr Ser Glu Val
    210                 215                 220

Val Ser Thr His Gly Ser Ala Lys Asn Leu Pro Thr Ser Cys Thr Ser
225                 230                 235                 240

Lys Leu Ser Pro Thr Leu Cys Phe Phe Pro Gln Tyr Val Ala Ser His
                245                 250                 255

Ile Ser Thr Pro Ile Phe Val Val Asn Ser Ala Tyr Asp Ser Trp Gln
                260                 265                 270

Ile Arg Tyr Ile Phe Val Pro Gly Ser Ala Asp Pro Ser Asp Ser Trp
                275                 280                 285

Asn Ser Cys Lys Val Asn Met Ser Asn Cys Ser Pro Asp Gln Leu Ser
    290                 295                 300

Lys Leu Gln Gly Phe Lys Ser Glu Phe Glu Arg Ala Leu Ser Glu Val
305                 310                 315                 320

Gly Asp Ser Pro Ser Lys Gly Met Phe Ile Asp Ser Cys Tyr Ala His
                325                 330                 335

Cys Gln Thr Glu Pro Gln Glu Thr Trp Phe Lys Thr Asp Ser Pro Lys
                340                 345                 350

Leu Ala Asn Thr Thr Ile Ala Lys Ala Val Ala Asp Trp Phe Tyr Gly
                355                 360                 365

Arg Ser Ser Phe Arg His Val Asp Cys Asn Tyr Pro Cys Asn Pro Ser
    370                 375                 380

Cys Gln Asn Arg Val Phe Asp Leu Lys Asp Leu Pro Gly Ile
385                 390                 395

<210> SEQ ID NO 193
<211> LENGTH: 11983
<212> TYPE: DNA
<213> ORGANISM: Artificial Sequence
<220> FEATURE:
<223> OTHER INFORMATION: Synthetic construct vector pMBXS1274

<400> SEQUENCE: 193

| | | |
|---|---|---|
| taagcggcag ggtcggaaca ggagagcgca cgagggagct tccaggggga aacgcctggt | 60 |
| atctttatag tcctgtcggg tttcgccacc tctgacttga gcgtcgattt ttgtgatgct | 120 |
| cgtcaggggg gcggagccta tggaaaaacg ccagcaacgc ggccttttta cggttcctgg | 180 |
| cctttgctg gccttttgct cacatgttct ttcctgcgtt atcccctgat tctgtggata | 240 |
| accgtattac cgcctttgag tgagctgata ccgctcgccg cagccgaacg accgagcgca | 300 |
| gcgagtcagt gagcgaggaa gcggaagagc gcctgatgcg gtattttctc cttacgcatc | 360 |
| tgtgcggtat ttcacaccgc atatggtgca ctctcagtac aatctgctct gatgccgcat | 420 |
| agttaagcca gtatacactc cgctatcgct acgtgactgg gtcatggctg cgccccgaca | 480 |
| cccgccaaca cccgctgacg cgccctgacg ggcttgtctg ctcccggcat ccgcttacag | 540 |

-continued

```
acaagctgtg accgtctccg ggagctgcat gtgtcagagg ttttcaccgt catcaccgaa    600
acgcgcgagg cagggtgcct tgatgtgggc gccggcggtc gagtggcgac ggcgcggctt    660
gtccgcgccc tggtagattg cctggccgta ggccagccat ttttgagcgg ccagcggccg    720
cgataggccg acgcgaagcg gcggggcgta gggagcgcag cgaccgaagg gtaggcgctt    780
tttgcagctc ttcggctgtg cgctggccag acagttatgc acaggccagg cgggttttaa    840
gagtttaat aagttttaaa gagtttagg cggaaaaatc gccttttttc tcttttatat      900
cagtcactta catgtgtgac cggttcccaa tgtacggctt tgggttccca atgtacgggt    960
tccggttccc aatgtacggc tttgggttcc caatgtacgt gctatccaca ggaaacagac   1020
cttttcgacc tttttcccct gctagggcaa tttgccctag catctgctcc gtacattagg   1080
aaccggcgga tgcttcgccc tcgatcaggt tgcggtagcg catgactagg atcgggccag   1140
cctgccccgc ctcctccttc aaatcgtact ccggcaggtc atttgacccg atcagcttgc   1200
gcacggtgaa acagaacttc ttgaactctc cggcgctgcc actgcgttcg tagatcgtct   1260
tgaacaacca tctggcttct gccttgcctg cggcgcggcg tgccaggcgg tagagaaaac   1320
ggccgatgcc gggatcgatc aaaaagtaat cggggtgaac cgtcagcacg tccgggttct   1380
tgccttctgt gatctcgcgg tacatccaat cagctagctc gatctcgatg tactccggcc   1440
gcccggtttc gctcttacg atcttgtagc ggctaatcaa ggcttcaccc tcggataccg    1500
tcaccaggcg gccgttcttg gccttcttcg tacgctgcat ggcaacgtgc gtggtgttta   1560
accgaatgca ggtttctacc aggtcgtctt tctgctttcc gccatcggct cgccggcaga   1620
acttgagtac gtccgcaacg tgtggacgga acacgcggcc gggcttgtct cccttcccctt  1680
cccggtatcg gttcatggat tcggttagat gggaaaccgc catcagtacc aggtcgtaat   1740
cccacacact ggccatgccg gccggccctg cggaaacctc tacgtgcccg tctggaagct   1800
cgtagcggat cacctcgcca gctcgtcggt cacgcttcga cagacggaaa acggccacgt   1860
ccatgatgct gcgactatcg cgggtgccca cgtcatagag catcggaacg aaaaaatctg   1920
gttgctcgtc gcccttgggc ggcttcctaa tcgacggcgc accggctgcc ggcggttgcc   1980
gggattcttt gcggattcga tcagcggccg cttgccacga ttcaccgggg cgtgcttctg   2040
cctcgatgcg ttgccgctgg gcggcctgcg cggccttcaa cttctccacc aggtcatcac   2100
ccagcgccgc gccgatttgt accgggccgg atggtttgcg accgctcacg ccgattcctc   2160
gggcttgggg gttccagtgc cattgcaggg ccggcaggca acccagccgc ttacgcctgg   2220
ccaaccgccc gttcctccac acatggggca ttccacggcg tcggtgcctg gttgttcttg   2280
attttccatg ccgcctcctt tagccgctaa aattcatcta ctcatttatt catttgctca   2340
tttactctgg tagctgcgcg atgtattcag atagcagctc ggtaatggtc ttgccttggc   2400
gtaccgcgta catcttcagc ttggtgtgat cctccgccgg caactgaaag ttgacccgct   2460
tcatggctgg cgtgtctgcc aggctggcca acgttcagc cttgctgctg cgtgcgctcg    2520
gacggccggc acttagcgtg tttgtgcttt tgctcatttt ctctttacct cattaactca   2580
aatgagtttt gatttaattt cagcggccag cgcctggacc tcgcgggcag cgtcgccctc   2640
gggttctgat tcaagaacgg ttgtgccggc ggcggcagtg cctgggtagc tcacgcgctg   2700
cgtgatacgg gactcaagaa tgggcagctc gtacccggcc agcgcctcgg caacctcacc   2760
gccgatgcgc gtgcctttga tcgcccgcga cacgacaaag gccgcttgta gccttccatc   2820
cgtgacctca atgcgctgct taaccagctc caccaggtcg gcggtggccc atatgtcgta   2880
```

```
agggcttggc tgcaccggaa tcagcacgaa gtcggctgcc ttgatcgcgg acacagccaa      2940
gtccgccgcc tggggcgctc cgtcgatcac tacgaagtcg cgccggccga tggccttcac      3000
gtcgcggtca atcgtcgggc ggtcgatgcc gacaacggtt agcggttgat cttcccgcac      3060
ggccgcccaa tcgcgggcac tgccctgggg atcggaatcg actaacagaa catcggcccc      3120
ggcgagttgc agggcgcggg ctagatgggt tgcgatggtc gtcttgcctg accgcctttt      3180
ctggttaagt acagcgataa ccttcatgcg ttccccttgc gtatttgttt atttactcat      3240
cgcatcatat acgcagcgac cgcatgacgc aagctgtttt actcaaatac acatcacctt      3300
tttagacggc ggcgctcggt ttcttcagcg gccaagctgg ccggccaggc cgccagcttg      3360
gcatcagaca aaccggccag gatttcatgc agccgcacgg ttgagacgtg cgcgggcggc      3420
tcgaacacgt acccgccgc gatcatctcc gcctcgatct cttcggtaat gaaaaacggt      3480
tcgtcctggc cgtcctggtg cggtttcatg cttgttcctc ttggcgttca ttctcggcgg      3540
ccgccagggc gtcggcctcg gtcaatgcgt cctcacggaa ggcaccgcgc cgcctggcct      3600
cggtgggcgt cacttcctcg ctgcgctcaa gtgcgcggta cagggtcgag cgatgcacgc      3660
caagcagtgc agccgcctct ttcacggtgc ggccttcctg gtcgatcagc tcgcgggcgt      3720
gcgcgatctg tgccggggtg agggtagggc ggggggccaaa cttcacgcct cgggccttgg      3780
cggcctcgcg cccgctccgg gtgcggtcga tgattaggga acgctcgaac tcggcaatgc      3840
cggcgaacac ggtcaacacc atgcggccgg ccggcgtggt ggtgtcggcc cacggctctg      3900
ccaggctacg caggcccgcg ccggcctcct ggatgcgctc ggcaatgtcc agtaggtcgc      3960
gggtgctgcg ggccaggcgg tctagcctgg tcactgtcac aacgtcgcca gggcgtaggt      4020
ggtcaagcat cctggccagc tccgggcggt cgcgcctggt gccggtgatc ttctcggaaa      4080
acagcttggt gcagccggcc gcgtgcagtt cggcccgttg gttggtcaag tcctggtcgt      4140
cggtgctgac gcgggcatag cccagcaggc cagcggcggc gctcttgttc atggcgtaat      4200
gtctccggtt ctagtcgcaa gtattctact ttatgcgact aaaacacgcg acaagaaaac      4260
gccaggaaaa gggcagggcg gcagcctgtc gcgtaactta ggacttgtgc gacatgtcgt      4320
tttcagaaga cggctgcact gaacgtcaga agccgactgc actatagcag cggaggggtt      4380
ggatcaaagt actttgatcc cgaggggaac cctgtggttg gcatgcacat acaaatggac      4440
gaacggataa accttttcac gccctttaa atatccgatt attctaataa acgtctcttt      4500
ctcttaggtt tacccgccaa tatatcctgt caaacactga tagtttaaac tgaaggcggg      4560
aaacgacaat ctgatccaag ctcaagctgc tctagcattc gccattcagg ctgcgcaact      4620
gttgggaagg gcgatcggtg cgggcctctt cgctattacg ccagctggcg aaaggggat      4680 gtgctgcaag gcgattaagt tgggtaacgc cagggttttc ccagtcacga cgttgtaaaa      4740
cgacggccag tgccaagctt ggcgcgcccc taggcctcag cttaattaag cgtattggct      4800
agagcagctt gccaacatgg tggagcacga cactctcgtc tactccaaga atatcaaaga      4860
tacagtctca gaagaccaaa gggctattga acttttcaa caaagggtaa tatcgggaaa      4920
cctcctcgga ttccattgcc cagctatctg tcacttcatc aaaaggacag tagaaaagga      4980
aggtggcacc tacaaatgcc atcattgcga taaggaaag gctatcgttc aagatgcctc      5040
tgccgacagt ggtcccaaag atggaccccc acccacgagg agcatcgtgg aaaagaaga      5100 cgttccaacc acgtcttcaa agcaagtgga ttgatgtgat aacatggtgg agcacgacac      5160
tctcgtctac tccaagaata tcaaagatac agtctcagaa gaccaaaggg ctattgagac      5220
ttttcaacaa agggtaatat cgggaaacct cctcggattc cattgcccag ctatctgtca      5280
```

```
cttcatcaaa aggacagtag aaaaggaagg tggcacctac aaatgccatc attgcgataa    5340
aggaaaggct atcgttcaag atgcctctgc cgacagtggt cccaaagatg gaccccacc    5400 cacgaggagc atcgtggaaa aagaagacgt tccaaccacg tcttcaaagc aagtggattg    5460
atgtgatatc tccactgacg taagggatga cgcacaatcc cactatcctt cgcaagacct    5520
tcctctatat aaggaagttc atttcatttg gagaggacac gctgaaatca ccagtctctc    5580
tctacaaatc tatctctctc gagtctacca gatctaaaat gaagttcttc gtttcagttg    5640
taatgttctt tctcctccta aactgtttcg cagccgcgca aaccttgatt cgagattcct    5700
gcaaaacagc tgcagcaaaa gaccctaatc tcaagtatga tttttgcatc caatcacttg    5760
aacaagatcc gcaaagcaaa actgcaacta gtctatcagg attggtccta gcggcaacga    5820
ataatgctgc atccaaaaca attaacgtga aagggatagt tgagactatt ctcaagagca    5880
aaaagtatgc accgagtact gaacccgcgt tacgcacttg cgtaaagctt tatgacgatg    5940
cttatggttc tttaaaagaa gctttgatga acgttaaatc cagtgattac aaaagtgcta    6000
atatgcatct gagtgctgct ttggatgaac ctgtcacttg tgaagatggt ttcaaagaga    6060
agcacgctaa atcccccgtt acaaacgaga acaatgtttt gtttcagaag attttgattc    6120
ctttagcttt taccaatatg ctctgaattt aaatcctcag gctcgagttt ctccataata    6180
atgtgtgagt agttcccaga taagggaatt agggttccta tagggtttcg ctcatgtgtt    6240
gagcatataa gaaaccctta gtatgtattt gtatttgtaa aatacttcta tcaataaaat    6300
ttctaattcc taaaaccaaa atccagtact aaaatccaga tcccccgaat taattcggcg    6360
ttaattcaga ctagtcgtca aagggcgaca cccctaatt agcccaattc gtaatcatgt    6420
catagctgtt tcctgtgtga aattgttatc cgctcacaat tccacacaac atacgagccg    6480
gaagcataaa gtgtaaagcc tggggtgcct aatgagtgag ctaactcaca ttaattgcgt    6540
tgcgctcact gcccgctttc cagtcgggaa acctgtcgtg ccagctgcat taatgaatcg    6600
gccaacgcgc ggggagaggc ggtttgcgta ttggctagag cagcttgcca acatggtgga    6660
gcacgacact ctcgtctact ccaagaatat caaagataca gtctcagaag accaaagggc    6720
tattgagact tttcaacaaa gggtaatatc gggaaacctc ctcggattcc attgcccagc    6780
tatctgtcac ttcatcaaaa ggacagtaga aaaggaaggt ggcacctaca aatgccatca    6840
ttgcgataaa ggaaaggcta tcgttcaaga tgcctctgcc gacagtggtc ccaaagatgg    6900 accccaccc acgaggagca tcgtggaaaa agaagacgtt ccaaccacgt cttcaaagca    6960
agtggattga tgtgaacatg gtggagcacg acactctcgt ctactccaag aatatcaaag    7020
atacagtctc agaagaccaa agggctattg acttttca acaaagggta atatcgggaa    7080
acctcctcgg attccattgc ccagctatct gtcacttcat caaaggaca gtagaaaagg    7140 aaggtggcac ctacaaatgc catcattgcg ataaaggaaa ggctatcgtt caagatgcct    7200
ctgccgacag tggtcccaaa gatgaccccc acccacgag gagcatcgtg gaaaagaag    7260 acgttccaac cacgtcttca agcaagtgg attgatgtga tatctccact gacgtaaggg    7320
atgacgcaca atcccactat ccttcgcaag accttcctc tatataagga agttcatttc    7380
atttggagag gacacgctga atcaccagt ctctctctac aaatctatct ctctcgagtc    7440
taccatgagc ccagaacgac gcccggccga catccgccgt gccaccgagg cggacatgcc    7500
ggcggtctgc accatcgtca accactacat cgagacaagc acggtcaact tccgtaccga    7560
gccgcaggaa ccgcaggagt ggacggacga cctcgtccgt ctgcgggagc gctatccctg    7620
```

```
gctcgtcgcc gaggtggacg gcgaggtcgc cggcatcgcc tacgcgggcc cctggaaggc    7680
acgcaacgcc tacgactgga cggccgagtc gaccgtgtac gtctcccccc gccaccagcg    7740
gacgggactg ggctccacgc tctacaccca cctgctgaag tccctggagg cacagggctt    7800
caagagcgtg gtcgctgtca tcgggctgcc caacgacccg agcgtgcgca tgcacgaggc    7860
gctcggatat gcccccccgcg gcatgctgcg ggcggccggc ttcaagcacg ggaactggca    7920
tgacgtgggt ttctggcagc tggacttcag cctgccggta ccgccccgtc cggtcctgcc    7980
cgtcaccgag atttgactcg agtttctcca taataatgtg tgagtagttc ccagataagg    8040
gaattagggt tcctataggg tttcgctcat gtgttgagca tataagaaac ccttagtatg    8100
tatttgtatt tgtaaaatac ttctatcaat aaaatttcta attcctaaaa ccaaaatcca    8160
gtactaaaat ccagatcccc cgaattaatt cggcgttaat tcaggaattc gtaatcatgt    8220
catagctgtt tcctgtgtga aattgttatc cgctcacaat tccacacaac atacgagccg    8280
gaagcataaa gtgtaaagcc tggggtgcct aatgagtgag ctaactcaca ttaattgcgt    8340
tgcgctcact gcccgctttc cagtcgggaa acctgtcgtg ccagctgcat taatgaatcg    8400
gccaacgcgc ggggagaggc ggtttgcgta ttggctagag cagcttgcca acatggtgga    8460
gcacgacact ctcgtctact ccaagaatat caaagataca gtctcagaag accaaagggc    8520
tattgagact tttcaacaaa gggtaatatc gggaaacctc ctcggattcc attgcccagc    8580
tatctgtcac ttcatcaaaa ggacagtaga aaaggaaggt ggcacctaca aatgccatca    8640
ttgcgataaa ggaaaggcta tcgttcaaga tgcctctgcc gacagtggtc ccaaagatgg    8700
acccccaccc acgaggagca tcgtggaaaa agaagacgtt ccaaccacgt cttcaaagca    8760
agtggattga tgtgaacatg gtggagcacg acactctcgt ctactccaag aatatcaaag    8820
atacagtctc agaagaccaa agggctattg agacttttca acaaagggta atatcgggaa    8880
acctcctcgg attccattgc ccagctatct gtcacttcat caaaaggaca gtagaaaagg    8940
aaggtggcac ctacaaatgc catcattgcg ataaaggaaa ggctatcgtt caagatgcct    9000
ctgccgacag tggtcccaaa gatggacccc cacccacgag gagcatcgtg gaaaagaag    9060
acgttccaac cacgtcttca agcaagtgg attgatgtga tctccact gacgtaaggg    9120
atgacgcaca atcccactat ccttcgcaag acccttcctc tatataagga agttcatttc    9180
atttggagag gacacgctga atcaccagt ctctctctac aaatctatct ctctcgagaa    9240
aatggcctcc tccgagaacg tcatcaccga gttcatgcgc ttcaaggtgc gcatggaggg    9300
caccgtgaac ggccacgagt tcgagatcga gggcgagggc gagggccgcc ctacgaggg    9360
ccacaacacc gtgaagctga aggtgaccaa gggcggcccc ctgcccttcg cctgggacat    9420
cctgtccccc cagttccagt acggctccaa ggtgtacgtg aagcaccccg ccgacatccc    9480
cgactacaag aagctgtcct tccccgaggg cttcaagtgg gagcgcgtga tgaacttcga    9540
ggacggcggc gtggcgaccg tgacccagga ctcctccctg caggacggct gcttcatcta    9600
caaggtgaag ttcatcggcg tgaacttccc ctccgacggc cccgtgatgc agaagaagac    9660
catgggctgg gaggcctcca ccgagcgcct gtaccccgc gacggcgtgc tgaagggcga    9720
aacccacaag gccctgaagc tgaaggacgg cggccactac ctggtggagt tcaagtccat    9780
ctacatggcc aagaagcccg tgcagctgcc cggctactac tacgtggacg ccaagctgga    9840
catcacctcc cacaacgagg actacaccat cgtggagcag tacgagcgca ccgagggccg    9900
ccaccacctg ttcctggtac caatgagctc tgtccaacag tctcagggtt aactcgagtt    9960
tctccataat aatgtgtgag tagttcccag ataagggaat tagggttcct ataggggtttc    10020
```

```
gctcatgtgt tgagcatata agaaaccctt agtatgtatt tgtatttgta aaatacttct   10080
atcaataaaa tttctaattc ctaaaaccaa aatccagtac taaaatccag atcccccgaa   10140
ttaattcggc gttaattcag tacattaaaa acgtccgcaa tgtgttatta agttgtctaa   10200
gcgtcaattt gtttacacca caatatatcc tgccaccagc cagccaacag ctccccgacc   10260
ggcagctcgg cacaaaatca ccactcgata caggcagccc atcagtccgg acggcgtca    10320 gcgggagagc cgttgtaagg cggcagactt tgctcatgtt accgatgcta ttcggaagaa   10380
cggcaactaa gctgccgggt ttgaaacacg gatgatctcg cggagggtag catgttgatt   10440
gtaacgatga cagagcgttg ctgcctgtga tcaccgcggt ttcaaaatcg ctccgtcga    10500 tactatgtta tacgccaact ttgaaaacaa ctttgaaaaa gctgttttct ggtatttaag   10560
gttttagaat gcaaggaaca gtgaattgga gttcgtcttg ttataattag cttcttgggg   10620
tatctttaaa tactgtagaa aagaggaagg aaataataaa tggctaaaat gagaatatca   10680
ccggaattga aaaaactgat cgaaaaatac cgctgcgtaa aagatacgga aggaatgtct   10740
cctgctaagg tatataagct ggtgggagaa aatgaaaacc tatatttaaa aatgacggac   10800
agccggtata aagggaccac ctatgatgtg aacgggaaaa aggacatgat gctatggctg   10860
gaaggaaagc tgcctgttcc aaaggtcctg cactttgaac ggcatgatgg ctggagcaat   10920
ctgctcatga gtgaggccga tggcgtcctt tgctcggaag agtatgaaga tgaacaaagc   10980
cctgaaaaga ttatcgagct gtatgcggag tgcatcaggc tctttcactc catcgacata   11040
tcggattgtc cctatacgaa tagcttagac agccgcttag ccgaattgga ttacttactg   11100
aataacgatc tggccgatgt ggattgcgaa aactgggaag aagacactcc atttaaagat   11160
ccgcgcgagc tgtatgattt tttaaagacg gaaaagcccg aagaggaact tgtcttttcc   11220
cacggcgacc tgggagacag caacatcttt gtgaaagatg gcaaagtaag tggctttatt   11280
gatcttggga aagcggcag gcggacaag tggtatgaca ttgccttctg cgtccggtcg   11340
atcagggagg atatcgggga agaacagtat gtcgagctat ttttgactt actggggatc    11400 aagcctgatt gggagaaaat aaaatattat attttactgg atgaattgtt ttagtaccta   11460
gaatgcatga ccaaaatccc ttaacgtgag ttttcgttcc actgagcgtc agaccccgta   11520
gaaaagatca aaggatcttc ttgagatcct ttttttctgc gcgtaatctg ctgcttgcaa   11580
acaaaaaaac caccgctacc agcggtggtt tgtttgccgg atcaagagct accaactctt   11640
tttccgaagg taactggctt cagcagagcg cagataccaa atactgtcct tctagtgtag   11700
ccgtagttag gccaccactt caagaactct gtagcaccgc ctacatacct cgctctgcta   11760
atcctgttac cagtggctgc tgccagtggc gataagtcgt gtcttaccgg gttggactca   11820
agacgatagt taccggataa ggcgcagcgg tcgggctgaa cggggggttc gtgcacacag   11880
cccagcttgg agcgaacgac ctacaccgaa ctgagatacc tacagcgtga gctatgagaa   11940
agcgccacgc ttcccgaagg gagaaaggcg gacaggtatc cgg                     11983
```

<210> SEQ ID NO 194
<211> LENGTH: 417
<212> TYPE: DNA
<213> ORGANISM: Artificial Sequence
<220> FEATURE:
<223> OTHER INFORMATION: Synthetic construct open reading frame encoding
      shortened canola ortholog to ISY

<400> SEQUENCE: 194

```
atgaagtatg attttgcat ccaatcactt gaacaagatc cgcaaagcaa aactgcaact     60
```

-continued

```
agtctatcag gattggtcct agcggcaacg aataatgctg catccaaaac aattaacgtg      120
aaagggatag ttgagactat tctcaagagc aaaaagtatg caccgagtac tgaacccgcg      180
ttacgcactt gcgtaaagct ttatgacgat gcttatggtt ctttaaaaga agctttgatg      240
aacgttaaat ccagtgatta caaaagtgct aatatgcatc tgagtgctgc tttggatgaa      300
cctgtcactt gtgaagatgg tttcaaagag aagcacgcta atctcccgt tacaaacgag       360 aacaatgttt tgtttcagaa gattttgatt cctttagctt ttaccaatat gctctga         417

<210> SEQ ID NO 195
<211> LENGTH: 138
<212> TYPE: PRT
<213> ORGANISM: Artificial Sequence
<220> FEATURE:
<223> OTHER INFORMATION: Synthetic construct shortened canola ortholog
      to ISY

<400> SEQUENCE: 195

Met Lys Tyr Asp Phe Cys Ile Gln Ser Leu Glu Gln Asp Pro Gln Ser
1               5                   10                  15

Lys Thr Ala Thr Ser Leu Ser Gly Leu Val Leu Ala Ala Thr Asn Asn
            20                  25                  30

Ala Ala Ser Lys Thr Ile Asn Val Lys Gly Ile Val Glu Thr Ile Leu
        35                  40                  45

Lys Ser Lys Lys Tyr Ala Pro Ser Thr Glu Pro Ala Leu Arg Thr Cys
    50                  55                  60

Val Lys Leu Tyr Asp Asp Ala Tyr Gly Ser Leu Lys Glu Ala Leu Met
65                  70                  75                  80

Asn Val Lys Ser Ser Asp Tyr Lys Ser Ala Asn Met His Leu Ser Ala
                85                  90                  95

Ala Leu Asp Glu Pro Val Thr Cys Glu Asp Gly Phe Lys Glu Lys His
            100                 105                 110

Ala Lys Ser Pro Val Thr Asn Glu Asn Asn Val Leu Phe Gln Lys Ile
        115                 120                 125

Leu Ile Pro Leu Ala Phe Thr Asn Met Leu
    130                 135

<210> SEQ ID NO 196
<211> LENGTH: 11983
<212> TYPE: DNA
<213> ORGANISM: Artificial Sequence
<220> FEATURE:
<223> OTHER INFORMATION: Synthetic construct vector pMBXS1277

<400> SEQUENCE: 196
taagcggcag ggtcggaaca ggagagcgca cgagggagct ccaggggga aacgcctggt        60 atctttatag tcctgtcggg tttcgccacc tctgacttga gcgtcgattt tgtgatgct       120 cgtcaggggg gcggagccta tggaaaaacc ccagcaacgc ggcctttta cggttcctgg       180 ccttttgctg gccttttgct cacatgttct ttcctgcgtt atcccctgat tctgtggata      240
accgtattac cgcctttgag tgagctgata ccgctcgccg cagccgaacg accgagcgca      300
gcgagtcagt gagcgaggaa gcggaagagc gcctgatgcg gtattttctc cttacgcatc     360
tgtgcggtat ttcacaccgc atatggtgca ctctcagtac aatctgctct gatgccgcat     420
agttaagcca gtatacactc cgctatcgct acgtgactgg gtcatggctg cgccccgaca     480
cccgccaaca cccgctgacg cgccctgacg ggcttgtctg ctcccggcat ccgcttacag     540
```

```
acaagctgtg accgtctccg ggagctgcat gtgtcagagg ttttcaccgt catcaccgaa    600
acgcgcgagg cagggtgcct tgatgtgggc gccggcggtc gagtggcgac ggcgcggctt    660
gtccgcgccc tggtagattg cctggccgta ggccagccat ttttgagcgg ccagcggccg    720
cgataggccg acgcgaagcg gcggggcgta gggagcgcag cgaccgaagg gtaggcgctt    780
tttgcagctc ttcggctgtg cgctggccag acagttatgc acaggccagg cgggttttaa    840
gagtttaat aagttttaaa gagttttagg cggaaaaatc gccttttttc tcttttatat     900
cagtcactta catgtgtgac cggttcccaa tgtacggctt tgggttccca atgtacgggt    960
tccggttccc aatgtacggc tttgggttcc aatgtacgt gctatccaca ggaaacagac    1020
cttttcgacc ttttccct gctagggcaa tttgccctag catctgctcc gtacattagg     1080
aaccggcgga tgcttcgccc tcgatcaggt tgcggtagcg catgactagg atcgggccag    1140
cctgccccgc ctcctccttc aaatcgtact ccggcaggtc atttgacccg atcagcttgc    1200
gcacggtgaa acagaacttc ttgaactctc cggcgctgcc actgcgttcg tagatcgtct    1260
tgaacaacca tctggcttct gccttgcctg cggcgcggcg tgccaggcgg tagagaaaac    1320
ggccgatgcc gggatcgatc aaaaagtaat cggggtgaac cgtcagcacg tccgggttct    1380
tgccttctgt gatctcgcgg tacatccaat cagctagctc gatctcgatg tactccggcc    1440
gcccggtttc gctctttacg atcttgtagc ggctaatcaa ggcttcaccc tcggataccg    1500
tcaccaggcg gccgttcttg gccttcttcg tacgctgcat ggcaacgtgc gtggtgttta    1560
accgaatgca ggtttctacc aggtcgtctt tctgcttttcc gccatcggct cgccggcaga    1620
acttgagtac gtccgcaacg tgtggacgga acacgcggcc gggcttgtct cccttcccctt   1680
cccggtatcg gttcatggat tcggttagat gggaaaccgc catcagtacc aggtcgtaat    1740
cccacacact ggccatgccg gccggccctg cggaaacctc tacgtgcccg tctggaagct    1800
cgtagcggat cacctcgcca gctcgtcggt cacgcttcga cagacggaaa acggccacgt    1860
ccatgatgct gcgactatcg cgggtgccca cgtcatagag catcggaacg aaaaaatctg    1920
gttgctcgtc gcccttgggc ggcttcctaa tcgacggcgc accggctgcc ggcggttgcc    1980
gggattcttt gcggattcga tcagcggccg cttgccacga ttcaccgggg cgtgcttctg    2040
cctcgatgcg ttgccgctgg gcggcctgcg cggccttcaa cttctccacc aggtcatcac    2100
ccagcgccgc gccgatttgt accgggccgg atggtttgcg accgctcacg ccgattcctc    2160
gggcttgggg gttccagtgc cattgcaggg ccggcaggca acccagccgc ttacgcctgg    2220
ccaaccgccc gttcctccac acatgggca ttccacggcg tcggtgcctg gttgttcttg     2280
attttccatg ccgcctcctt tagccgctaa aattcatcta ctcatttatt catttgctca    2340
tttactctgg tagctgcgcg atgtattcag atagcagctc ggtaatggtc ttgccttggc    2400
gtaccgcgta catcttcagc ttggtgtgat cctccgccgg caactgaaag ttgacccgct    2460
tcatggctgg cgtgtctgcc aggctggcca acgttgcagc cttgctgctg cgtgcgctcg    2520
gacggccggc acttagcgtg tttgtgcttt tgctcatttt ctctttacct cattaactca    2580
aatgagtttt gatttaattt cagcggccag cgcctggacc tcgcgggcag cgtcgccctc    2640
gggttctgat tcaagaacgg ttgtgccggc ggcggcagtg cctgggtagc tcacgcgctg    2700
cgtgatacgg gactcaagaa tgggcagctc gtacccggcc agcgcctcgg caacctcacc    2760
gccgatgcgc gtgcctttga tcccgcgcga cacgacaaag gccgcttgta gccttccatc    2820
cgtgacctca atgcgctgct taaccagctc caccaggtcg gcggtggccc atatgtcgta    2880
agggcttggc tgcaccggaa tcagcacgaa gtcggctgcc ttgatcgcgg acacagccaa    2940
```

```
gtccgccgcc tggggcgctc cgtcgatcac tacgaagtcg cgccggccga tggccttcac   3000
gtcgcggtca atcgtcgggc ggtcgatgcc gacaacggtt agcggttgat cttcccgcac   3060
ggccgcccaa tcgcgggcac tgccctgggg atcggaatcg actaacagaa catcggcccc   3120
ggcgagttgc agggcgcggg ctagatgggt tgcgatggtc gtcttgcctg acccgccttt   3180
ctggttaagt acagcgataa ccttcatgcg ttccccttgc gtatttgttt atttactcat   3240
cgcatcatat acgcagcgac cgcatgacgc aagctgtttt actcaaatac acatcacctt   3300
tttagacggc ggcgctcggt ttcttcagcg gccaagctgg ccggccaggc cgccagcttg   3360
gcatcagaca aaccggccag gatttcatgc agccgcacgg ttgagacgtg cgcgggcggc   3420
tcgaacacgt acccggccgc gatcatctcc gcctcgatct cttcggtaat gaaaaacggt   3480
tcgtcctggc cgtcctggtg cggtttcatg cttgttcctc ttggcgttca ttctcggcgg   3540
ccgccagggc gtcggcctcg gtcaatgcgt cctcacggaa ggcaccgcgc cgcctggcct   3600
cggtgggcgt cacttcctcg ctgcgctcaa gtgcgcggta cagggtcgag cgatgcacgc   3660
caagcagtgc agccgcctct ttcacggtgc ggccttcctg gtcgatcagc tcgcgggcgt   3720
gcgcgatctg tgccggggtg agggtagggc ggggcgcaaa cttcacgcct cgggccttgg   3780
cggcctcgcg cccgctccgg gtgcggtcga tgattaggga acgctcgaac tcggcaatgc   3840
cggcgaacac ggtcaacacc atgcggccgg ccggcgtggt ggtgtcggcc cacggctctg   3900
ccaggctacg caggcccgcg ccggcctcct ggatgcgctc ggcaatgtcc agtaggtcgc   3960
gggtgctgcg ggccaggcgg tctagcctgg tcactgtcac aacgtcgcca gggcgtaggt   4020
ggtcaagcat cctggccagc tccgggcggt cgcgcctggt gccggtgatc ttctcggaaa   4080
acagcttggt gcagccggcc gcgtgcagtt cggcccgttg gttggtcaag tcctggtcgt   4140
cggtgctgac gcgggcatag cccagcaggc cagcggcggc gctcttgttc atggcgtaat   4200
gtctccggtt ctagtcgcaa gtattctact ttatgcgact aaaacacgcg acaagaaaac   4260
gccaggaaaa gggcagggcg gcagcctgtc gcgtaactta ggacttgtgc gacatgtcgt   4320
tttcagaaga cggctgcact gaacgtcaga agccgactgc actatagcag cggaggggtt   4380
ggatcaaagt actttgatcc cgaggggaac cctgtggttg gcatgcacat acaaatggac   4440
gaacggataa accttttcac gcccttttaa atatccgatt attctaataa cgctcttttt   4500
ctcttaggtt tacccgccaa tatatcctgt caaacactga tagtttaaac tgaaggcggg   4560
aaacgacaat ctgatccaag ctcaagctgc tctagcattc gccattcagg ctgcgcaact   4620
gttgggaagg gcgatcggtg cgggcctctt cgctattacg ccagctggcg aaaggggat   4680
gtgctgcaag gcgattaagt tgggtaacgc cagggttttc ccagtcacga cgttgtaaaa   4740
cgacggccag tgccaagctt ggcgcgcccc taggcctcag cttaattaag cgtattggct   4800
agagcagctt gccaacatgg tggagcacga cactctcgtc tactccaaga atatcaaaga   4860
tacagtctca gaagaccaaa gggctattga acttttcaa caagggtaa tatcgggaaa   4920
cctcctcgga ttccattgcc cagctatctg tcacttcatc aaaaggacag tagaaaagga   4980
aggtggcacc tacaaatgcc atcattgcga taaaggaaag gctatcgttc aagatgcctc   5040
tgccgacagt ggtcccaaag atggacccc acccacgagg agcatcgtgg aaaaagaaga   5100
cgttccaacc acgtcttcaa agcaagtgga ttgatgtgat aacatggtgg agcacgacac   5160
tctcgtctac tccaagaata tcaaagatac agtctcagaa gaccaaaggg ctattgagac   5220
ttttcaacaa agggtaatat cgggaaacct cctcggattc cattgcccag ctatctgtca   5280
```

```
cttcatcaaa aggacagtag aaaaggaagg tggcacctac aaatgccatc attgcgataa    5340
aggaaaggct atcgttcaag atgcctctgc cgacagtggt cccaaagatg acccccacc    5400
cacgaggagc atcgtggaaa aagaagacgt tccaaccacg tcttcaaagc aagtggattg    5460
atgtgatatc tccactgacg taagggatga cgcacaatcc cactatcctt cgcaagacct    5520
tcctctatat aaggaagttc atttcatttg gagaggacac gctgaaatca ccagtctctc    5580
tctacaaatc tatctctctc gagtctacca gatctaaaat gaagttcttc gtttcagttg    5640
taatgttctt tctcctccta aactgtttcg cagccgcgca aaccttgatt cgagattcct    5700
gcaaaacagc tgcagcaaaa gaccctaatc tcaagtatga tttttgcatc caatcacttg    5760
aacaagatcc gcaaagcaaa actgcaacta gtctatcagg attggtccta gcggcaacga    5820
ataatgctgc atccaaaaca attaacgtga aagggatagt tgagactatt ctcaagagca    5880
aaaagtatgc accgagtact gaacccgcgt tacgcacttg cgtaaagctt tatgacgatg    5940
cttatggttc tttaaaagaa gctttgatga acgttaaatc cagtgattac aaaagtgcta    6000
atatgcatct gagtgctgct ttggatgaac ctgtcacttg tgaagatggt ttcaaagaga    6060
agcacgctaa atctcccgtt acaaacgaga acaatgtttt gtttcagaag attttgattc    6120
ctttagcttt taccaatatg ctctgaattt aaatcctcag gctcgagttt ctccataata    6180
atgtgtgagt agttcccaga taagggaatt agggttccta tagggtttcg ctcatgtgtt    6240
gagcatataa gaaacccctta gtatgtattt gtatttgtaa atacttcta tcaataaaat    6300
ttctaattcc taaaaccaaa atccagtact aaaatccaga tcccccgaat taattcggcg    6360
ttaattcaga ctagtcgtca aagggcgaca cccctaatt agcccaattc gtaatcatgt    6420
catagctgtt tcctgtgtga aattgttatc cgctcacaat tccacacaac atacgagccg    6480
gaagcataaa gtgtaaagcc tggggtgcct aatgagtgag ctaactcaca ttaattgcgt    6540
tgcgctcact gcccgctttc cagtcgggaa acctgtcgtg ccagctgcat taatgaatcg    6600
gccaacgcgc ggggagaggc ggtttgcgta ttggctagag cagcttgcca acatggtgga    6660
gcacgacact ctcgtctact ccaagaatat caaagataca gtctcagaag accaaagggc    6720
tattgagact tttcaacaaa gggtaatatc gggaaacctc ctcggattcc attgcccagc    6780
tatctgtcac ttcatcaaaa ggacagtaga aaaggaaggt ggcacctaca aatgccatca    6840
ttgcgataaa ggaaaggcta tcgttcaaga tgcctctgcc gacagtggtc caaagatgg    6900
accccacccc acgaggagca tcgtggaaaa agaagacgtt ccaaccacgt cttcaaagca    6960
agtggattga tgtgaacatg gtggagcacg acactctcgt ctactccaag aatatcaaag    7020
atacagtctc agaagaccaa agggctattg acttttca acaaagggta atatcgggaa    7080
acctcctcgg attccattgc ccagctatct gtcacttcat caaaaggaca gtagaaaagg    7140
aaggtggcac ctacaaatgc catcattgcg ataaaggaaa ggctatcgtt caagatgcct    7200
ctgccgacag tggtcccaaa gatggacccc cacccacgag gagcatcgtg gaaaagaag    7260
acgttccaac cacgtcttca aagcaagtgg attgatgtga tatctccact gacgtaaggg    7320
atgacgcaca atcccactat ccttcgcaag accttcctc tatataagga agttcatttc    7380
atttggagag gacacgctga atcaccagt ctctctctac aaatctatct ctctcgagtc    7440
taccatgagc ccagaacgac gcccggccga catccgccgt gccaccgagg cggacatgcc    7500
ggcggtctgc accatcgtca accactacat cgagacaagc acggtcaact tccgtaccga    7560
gccgcaggaa ccgcaggagt ggacggacga cctcgtccgt ctgcgggagc gctatccctg    7620
gctcgtcgcc gaggtggacg cgcgaggtcgc cggcatcgcc tacgcgggcc cctggaaggc    7680
```

```
acgcaacgcc tacgactgga cggccgagtc gaccgtgtac gtctccccccc gccaccagcg   7740
gacgggactg ggctccacgc tctacaccca cctgctgaag tccctggagg cacagggctt   7800
caagagcgtg gtcgctgtca tcgggctgcc caacgacccg agcgtgcgca tgcacgaggc   7860
gctcggatat gccccccgcg gcatgctgcg ggcggccggc ttcaagcacg gaactggca   7920
tgacgtgggt ttctggcagc tggacttcag cctgccggta ccgccccgtc cggtcctgcc   7980
cgtcaccgag atttgactcg agtttctcca taataatgtg tgagtagttc ccagataagg   8040
gaattagggt tcctataggg tttcgctcat gtgttgagca tataagaaac ccttagtatg   8100
tatttgtatt tgtaaaatac ttctatcaat aaaatttcta attcctaaaa ccaaaatcca   8160
gtactaaaat ccagatcccc cgaattaatt cggcgttaat tcaggaattc gtaatcatgt   8220
catagctgtt tcctgtgtga aattgttatc cgctcacaat tccacacaac atacgagccg   8280
gaagcataaa gtgtaaagcc tggggtgcct aatgagtgag ctaactcaca ttaattgcgt   8340
tgcgctcact gcccgctttc cagtcgggaa acctgtcgtg ccagctgcat taatgaatcg   8400
gccaacgcgc ggggagaggc ggtttgcgta ttggctagag cagcttgcca acatggtgga   8460
gcacgacact ctcgtctact ccaagaatat caaagataca gtctcagaag accaaagggc   8520
tattgagact tttcaacaaa gggtaatatc gggaaacctc ctcggattcc attgcccagc   8580
tatctgtcac ttcatcaaaa ggacagtaga aaggaaggt ggcacctaca aatgccatca   8640
ttgcgataaa ggaaaggcta tcgttcaaga tgcctctgcc gacagtggtc ccaaagatgg   8700
acccccaccc acgaggagca tcgtggaaaa agaagacgtt ccaaccacgt cttcaaagca   8760
agtggattga tgtgaacatg gtggagcacg acactctcgt ctactccaag aatatcaaag   8820
atacagtctc agaagaccaa agggctattg acttttca acaaagggta atatcgggaa   8880
acctcctcgg attccattgc ccagctatct gtcacttcat caaaaggaca gtagaaaagg   8940
aaggtggcac ctacaaatgc catcattgcg ataaaggaaa ggctatcgtt caagatgcct   9000
ctgccgacag tggtcccaaa gatggacccc cacccacgag gagcatcgtg gaaaagaag   9060
acgttccaac cacgtcttca agcaagtgg attgatgtga tctccact gacgtaaggg   9120
atgacgcaca atcccactat ccttcgcaag acccttcctc tatataagga agttcatttc   9180
atttggagag acacgctga atcaccagt ctctctctac aaatctatct ctctcgagaa   9240
aatgcctcc tccgagaacg tcatcaccga gttcatgcgc ttcaaggtgc gcatggaggg   9300
caccgtgaac ggccacgagt tcgagatcga gggcgagggc gagggccgcc cctacgaggg   9360
ccacaacacc gtgaagctga aggtgaccaa gggcggcccc ctgcccttcg cctgggacat   9420
cctgtcccc cagttccagt acggctccaa ggtgtacgtg aagcaccccg ccgacatccc   9480
cgactacaag aagctgtcct tccccgaggg cttcaagtgg gagcgcgtga tgaacttcga   9540
ggacggcggc gtggcgaccg tgacccagga ctcctccctg caggacggct gcttcatcta   9600
caaggtgaag ttcatcggcg tgaacttccc ctccgacggc ccgtgatgc agaagaagac   9660
catgggctgg gaggcctcca ccgagcgcct gtaccccgc gacggcgtgc tgaagggcga   9720
aacccacaag gccctgaagc tgaaggacgg cggccactac ctggtggagt tcaagtccat   9780
ctacatggcc aagaagcccg tgcagctgcc cggctactac tacgtggacg ccaagctgga   9840
catcacctcc cacaacgagg actacaccat cgtggagcag tacgagcgca ccgagggccg   9900
ccaccacctg ttcctggtac caatgagctc tgtccaacag tctcagggtt aactcgagtt   9960
tctccataat aatgtgtgag tagttcccag ataagggaat tagggttcct ataggtttc  10020
```

```
gctcatgtgt tgagcatata agaaacccct tagtatgtatt tgtatttgta aaatacttct   10080
atcaataaaa tttctaattc ctaaaaccaa aatccagtac taaaatccag atcccccgaa   10140
ttaattcggc gttaattcag tacattaaaa acgtccgcaa tgtgttatta agttgtctaa   10200
gcgtcaattt gtttacacca caatatatcc tgccaccagc cagccaacag ctccccgacc   10260
ggcagctcgg cacaaaatca ccactcgata caggcagccc atcagtccgg gacggcgtca   10320
gcgggagagc cgttgtaagg cggcagactt tgctcatgtt accgatgcta ttcggaagaa   10380
cggcaactaa gctgccgggt ttgaaacacg gatgatctcg cggagggtag catgttgatt   10440
gtaacgatga cagagcgttg ctgcctgtga tcaccgcggt ttcaaaatcg ctccgtcga    10500
tactatgtta tacgccaact ttgaaaacaa ctttgaaaaa gctgttttct ggtatttaag   10560
gttttagaat gcaaggaaca gtgaattgga gttcgtcttg ttataattag cttcttgggg   10620
tatcttttaaa tactgtagaa agaggaagg aaataataaa tggctaaaat gagaatatca   10680
ccggaattga aaaaactgat cgaaaaatac cgctgcgtaa agatacgga aggaatgtct   10740
cctgctaagg tatataagct ggtgggagaa aatgaaaacc tatatttaaa aatgacggac   10800
agccggtata aagggaccac ctatgatgtg aacggaaaa aggacatgat gctatggctg   10860
gaaggaaagc tgcctgttcc aaaggtcctg cactttgaac ggcatgatgg ctggagcaat   10920
ctgctcatga gtgaggccga tggcgtcctt tgctcggaag agtatgaaga tgaacaaagc   10980
cctgaaaaga ttatcgagct gtatgcgag tgcatcaggc tctttcactc catcgacata   11040
tcggattgtc cctatacgaa tagcttagac agccgcttag ccgaattgga ttacttactg   11100
aataacgatc tggccgatgt ggattgcgaa actgggaag aagacactcc atttaaagat   11160
ccgcgcgagc tgtatgattt tttaaagacg gaaaagcccg aagaggaact tgtcttttcc   11220
cacggcgacc tgggagacag caacatcttt gtgaaagatg gcaaagtaag tggctttatt   11280
gatcttggga agcggcag gcggacaag tggtatgaca ttgccttctg cgtccggtcg   11340
atcagggagg atatcgggga agaacagtat gtcgagctat ttttgactt actggggatc   11400
aagcctgatt gggagaaaat aaaatattat atttttactgg atgaattgtt ttagtaccta   11460
gaatgcatga ccaaaatccc ttaacgtgag ttttcgttcc actgagcgtc agaccccgta   11520
gaaaagatca aggatcttc ttgagatcct ttttttctgc gcgtaatctg ctgcttgcaa   11580
acaaaaaaac caccgctacc agcggtggtt tgtttgccgg atcaagagct accaactctt   11640
tttccgaagg taactggctt cagcagagcg cagataccaa atactgtcct tctagtgtag   11700
ccgtagttag gccaccactt caagaactct gtagcaccgc ctacatacct cgctctgcta   11760
atcctgttac cagtggctgc tgccagtggc gataagtcgt gtcttaccgg gttggactca   11820
agacgatagt taccggataa ggcgcagcgg tcgggctgaa cggggggttc gtgcacacag   11880
cccagcttgg agcgaacgac ctacaccgaa ctgagatacc tacagcgtga gctatgagaa   11940
agcgccacgc ttcccgaagg gagaaaggcg gacaggtatc cgg                     11983
```

<210> SEQ ID NO 197
<211> LENGTH: 9677
<212> TYPE: DNA
<213> ORGANISM: Artificial Sequence
<220> FEATURE:
<223> OTHER INFORMATION: Synthetic construct vector pMBXS1269

<400> SEQUENCE: 197

```
ctcggtaatg gtcttgcctt ggcgtaccgc gtacatcttc agcttggtgt gatcctccgc     60
cggcaactga aagttgaccc gcttcatggc tggcgtgtct gccaggctgg ccaacgttgc    120
```

```
agccttgctg ctgcgtgcgc tcggacggcc ggcacttagc gtgtttgtgc ttttgctcat    180
tttctcttta cctcattaac tcaaatgagt tttgatttaa tttcagcggc cagcgcctgg    240
acctcgcggg cagcgtcgcc ctcgggttct gattcaagaa cggttgtgcc ggcggcggca    300
gtgcctgggt agctcacgcg ctgcgtgata cgggactcaa gaatgggcag ctcgtacccg    360
gccagcgcct cggcaacctc accgccgatg cgcgtgcctt tgatcgcccg cgacacgaca    420
aaggccgctt gtagccttcc atccgtgacc tcaatgcgct gcttaaccag ctccaccagg    480
tcggcggtgg cccatatgtc gtaagggctt ggctgcaccg gaatcagcac gaagtcggct    540
gccttgatcg cggacacagc caagtccgcc gcctggggcg ctccgtcgat cactacgaag    600
tcgcgccggc cgatggcctt cacgtcgcgg tcaatcgtcg ggcggtcgat gccgacaacg    660
gttagcggtt gatcttcccg cacggccgcc caatcgcggg cactgccctg gggatcggaa    720
tcgactaaca gaacatcggc cccggcgagt tgcagggcgc gggctagatg ggttgcgatg    780
gtcgtcttgc ctgaccccgcc tttctggtta agtacagcga taaccttcat gcgttcccct    840
tgcgtatttg tttatttact catcgcatca tatacgcagc gaccgcatga cgcaagctgt    900
tttactcaaa tacacatcac ctttttagac ggcggcgctc ggtttcttca gcggccaagc    960
tggccggcca ggccgccagc ttggcatcag acaaaccggc caggatttca tgcagccgca   1020
cggttgagac gtgcgcgggc ggctcgaaca cgtaccggc cgcgatcatc tccgcctcga   1080
tctcttcggt aatgaaaaac ggttcgtcct ggccgtcctg gtgcggtttc atgcttgttc   1140
ctcttggcgt tcattctcgg cggccgccag ggcgtcggcc tcggtcaatg cgtcctcacg   1200
gaaggcaccg cgccgcctgg cctcggtggg cgtcacttcc tcgctgcgct caagtgcgcg   1260
gtacagggtc gagcgatgca cgccaagcag tgcagccgcc tctttcacgg tgcggccttc   1320
ctggtcgatc agctcgcggg cgtgcgcgat ctgtgccggg gtgagggtag ggcgggggcc   1380
aaacttcacg cctcgggcct tggcggcctc gcgcccgctc cgggtgcggt cgatgattag   1440
ggaacgctcg aactcggcaa tgccggcgaa cacggtcaac accatgcggc cggccggcgt   1500
ggtggtgtcg gcccacggct ctgccaggct acgcaggccc cgccggcct cctggatgcg   1560 ctcggcaatg tccagtaggt cgcgggtgct gcgggccagg cggtctagcc tggtcactgt   1620
cacaacgtcg ccagggcgta ggtggtcaag catcctggcc agctccgggc ggtcgcgcct   1680
ggtgccggtg atcttctcgg aaaacagctt ggtgcagccg gccgcgtgca gttcggcccg   1740
ttggttggtc aagtcctggt cgtcggtgct gacgcgggca tagcccagca ggccagcggc   1800
ggcgctcttg ttcatggcgt aatgtctccg gttctagtcg caagtattct actttatgcg   1860
actaaaacac gcgacaagaa aacgccagga aaagggcagg gcggcagcct gtcgcgtaac   1920
ttaggacttg tgcgacatgt cgttttcaga agacggctgc actgaacgtc agaagccgac   1980
tgcactatag cagcggaggg gttggatcaa agtactttga tcccgagggg aaccctgtgg   2040
ttggcatgca catacaaatg gacgaacgga taaacctttt cacgccctt taaatatccg   2100 attattctaa taaacgctct tttctcttag gtttacccgc caatatatcc tgtcaaacac   2160
tgatagttta aactgaaggc gggaaacgac aatctgatcc aagctcaagc tgctctagca   2220
ttcgccattc aggctgcgca actgtttggga agggcgatcg gtgcgggcct cttcgctatt   2280
acgccagctg gcgaaagggg gatgtgctgc aaggcgatta agttgggtaa cgccagggtt   2340
ttcccagtca cgacgttgta aaacgacggc cagtgccaag cttggcgcgc cctaggcct   2400 cagcttaatt aagcgtattg ctagagcag cttgccaaca tggtggagca cgacactctc   2460
```

```
gtctactcca agaatatcaa agatacagtc tcagaagacc aaagggctat tgagactttt    2520
caacaaaggg taatatcggg aaacctcctc ggattccatt gcccagctat ctgtcacttc    2580
atcaaaagga cagtagaaaa ggaaggtggc acctacaaat gccatcattg cgataaagga    2640
aaggctatcg ttcaagatgc ctctgccgac agtggtccca agatggaccc ccacccacg    2700 aggagcatcg tggaaaaaga agacgttcca accacgtctt caaagcaagt ggattgatgt    2760
gataacatgg tggagcacga cactctcgtc tactccaaga atatcaaaga tacagtctca    2820
gaagaccaaa gggctattga acttttcaa caaagggtaa tatcgggaaa cctcctcgga    2880
ttccattgcc cagctatctg tcacttcatc aaaaggacag tagaaaagga aggtggcacc    2940
tacaaatgcc atcattgcga taaggaaag gctatcgttc aagatgcctc tgccgacagt    3000
ggtcccaaag atggaccccc acccacgagg agcatcgtgg aaaagaaga cgttccaacc    3060 acgtcttcaa agcaagtgga ttgatgtgat atctccactg acgtaaggga tgacgcacaa    3120
tcccactatc cttcgcaaga ccttcctcta tataaggaag ttcatttcat ttggagagga    3180
cacgctgaaa tcaccagtct ctctctacaa atctatctct ctcgagtcta ccagatctaa    3240
aatgaaatat gatttctgcg tcaattctct tacacaagat ccacaaagca aaacggcgac    3300
caccctcgaa ggtttagtcc tagcatcgac gaagaatgct gcggcggaaa cactgaacgt    3360
aaaaggactc gctgaacaga tcctcaaggg gaagggatat gggccaggta tggaggcagg    3420
gctacacaag tgcgtcaaga tttatggagg tgcttatgat tttttaaaca ctgctttagc    3480
gaacgttcaa tcacaccatt atagtactgc tgtagaggaa tttctttatg cttcatttgc    3540
accgttcgac tgcgtgaaat attattggat ttctcccttc gctaaggaga gctatattat    3600
ctttgagaag attttgattc ctatgacttt aactaaaatg ttgtgacctc aggctcgagt    3660
ttctccataa taatgtgtga gtagttccca gataagggaa ttagggttcc tatagggttt    3720
cgctcatgtg ttgagcatat aagaaaccct tagtatgtat ttgtatttgt aaaatacttc    3780
tatcaataaa atttctaatt cctaaaacca aaatccagta ctaaaatcca gatccccga    3840 attaattcgg cgttaattca gcggaccgct cgagcaattg tacgtagaat tcgcgtattg    3900
gctagagcag cttgccaaca tggtggagca cgacactctc gtctactcca agaatatcaa    3960
agatacagtc tcagaagacc aaagggctat tgagactttt caacaaaggg taatatcggg    4020
aaacctcctc ggattccatt gcccagctat ctgtcacttc atcaaaagga cagtagaaaa    4080
ggaaggtggc acctacaaat gccatcattg cgataaagga aaggctatcg ttcaagatgc    4140
ctctgccgac agtggtccca agatggaccc ccacccacg aggagcatcg tggaaaaaga    4200
agacgttcca accacgtctt caaagcaagt ggattgatgt gaacatggtg gagcacgaca    4260
ctctcgtcta ctccaagaat atcaaagata cagtctcaga agaccaaagg ctattgaga    4320 cttttcaaca aagggtaata tcgggaaacc tcctcggatt ccattgccca gctatctgtc    4380
acttcatcaa aaggacagta gaaaggaag gtggcaccta caaatgccat cattgcgata    4440
aaggaaaggc tatcgttcaa gatgcctctg ccgacagtgg tcccaaagat ggaccccac    4500 ccacgaggag catcgtggaa aaagaagacg ttccaaccac gtcttcaaag caagtggatt    4560
gatgtgatat ctccactgac gtaagggatg acgcacaatc ccactatcct tcgcaagacc    4620
cttcctctat ataaggaagt tcatttcatt tggagaggac acgctgaaat caccagtctc    4680
tctctacaaa tctatctctc tcgagtctac catgagccca gaacgacgcc cggccgacat    4740
ccgccgtgcc accgaggcgg acatgccggc ggtctgcacc atcgtcaacc actacatcga    4800
gacaagcacg gtcaacttcc gtaccgagcc gcaggaaccg caggagtgga cggacgacct    4860
```

```
cgtccgtctg cgggagcgct atccctggct cgtcgccgag gtggacggcg aggtcgccgg    4920
catcgcctac gcgggcccct ggaaggcacg caacgcctac gactggacgg ccgagtcgac    4980
cgtgtacgtc tcccccgcc accagcggac gggactgggc tccacgctct acacccacct     5040
gctgaagtcc ctggaggcac agggcttcaa gagcgtggtc gctgtcatcg ggctgcccaa    5100
cgacccgagc gtgcgcatgc acgaggcgct cggatatgcc cccgcggca tgctgcgggc    5160 ggccggcttc aagcacggga actggcatga cgtgggtttc tggcagctgg acttcagcct    5220
gccggtaccg ccccgtccgg tcctgcccgt caccgagatt tgactcgagt ttctccataa    5280
taatgtgtga gtagttccca gataagggaa ttagggttcc tatagggttt cgctcatgtg    5340
ttgagcatat aagaaaccct tagtatgtat ttgtatttgt aaaatacttc tatcaataaa    5400
atttctaatt cctaaaacca aaatccagta ctaaaatcca gatcccccga attaattcgg    5460
cgttaattca gcacgtgtac attaaaaacg tccgcaatgt gttattaagt tgtctaagcg    5520
tcaatttgtt tacaccacaa tatatcctgc caccagccag ccaacagctc cccgaccggc    5580
agctcggcac aaaatcacca ctcgatacag gcagcccatc agtccgggac ggcgtcagcg    5640
ggagagccgt tgtaaggcgg cagactttgc tcatgttacc gatgctattc ggaagaacgg    5700
caactaagct gccgggtttg aaacacggat gatctcgcgg agggtagcat gttgattgta    5760
acgatgacag agcgttgctg cctgtgatca ccgcggtttc aaaatcggct ccgtcgatac    5820
tatgttatac gccaactttg aaaacaactt tgaaaaagct gttttctggt atttaaggtt    5880
ttagaatgca aggaacagtg aattggagtt cgtcttgtta taattagctt cttggggtat    5940
ctttaaatac tgtagaaaag aggaaggaaa taataaatgg ctaaaatgag aatatcaccg    6000
gaattgaaaa aactgatcga aaaataccgc tgcgtaaaag atacggaagg aatgtctcct    6060
gctaaggtat ataagctggt gggagaaaat gaaaacctat atttaaaaat gacggacagc    6120
cggtataaag ggaccaccta tgatgtggaa cgggaaaagg acatgatgct atggctggaa    6180
ggaaagctgc ctgttccaaa ggtcctgcac tttgaacggc atgatggctg gagcaatctg    6240
ctcatgagtg aggccgatgg cgtcctttgc tcggaagagt atgaagatga acaaagccct    6300
gaaaagatta tcgagctgta tgcggagtgc atcaggctct ttcactccat cgacatatcg    6360
gattgtccct atacgaatag cttagacagc cgcttagccg aattggatta cttactgaat    6420
aacgatctgg ccgatgtgga ttgcgaaaac tgggaagaag acactccatt taaagatccg    6480
cgcgagctgt atgatttttt aaagacggaa aagcccgaag aggaacttgt cttttcccac    6540
ggcgacctgg gagacagcaa catctttgtg aaagatggca agtaagtgg ctttattgat    6600 cttgggagaa gcggcagggc ggacaagtgg tatgacattg ccttctgcgt ccggtcgatc    6660
agggaggata tcgggaaga acagtatgtc gagctatttt ttgacttact ggggatcaag    6720
cctgattggg agaaaataaa atattatatt ttactggatg aattgtttta gtacctagaa    6780
tgcatgacca aaatccctta acgtgagttt tcgttccact gagcgtcaga ccccgtagaa    6840
aagatcaaag gatcttcttg agatcctttt tttctgcgcg taatctgctg cttgcaaaca    6900
aaaaaaccac cgctaccagc ggtggtttgt ttgccggatc aagagctacc aactcttttt    6960
ccgaaggtaa ctggcttcag cagagcgcag ataccaaata ctgtccttct agtgtagccg    7020
tagttaggcc accacttcaa gaactctgta gcaccgccta catacctcgc tctgctaatc    7080
ctgttaccag tggctgctgc cagtggcgat aagtcgtgtc ttaccgggtt ggactcaaga    7140
cgatagttac cggataaggc gcagcggtcg ggctgaacgg ggggttcgtg cacacagccc    7200
```

```
agcttggagc gaacgaccta caccgaactg agatacctac agcgtgagct atgagaaagc   7260
gccacgcttc ccgaagggag aaaggcggac aggtatccgg taagcggcag ggtcggaaca   7320
ggagagcgca cgagggagct tccaggggga aacgcctggt atctttatag tcctgtcggg   7380
tttcgccacc tctgacttga gcgtcgattt ttgtgatgct cgtcaggggg gcggagccta   7440
tggaaaaacg ccagcaacgc ggcctttta cggttcctgg ccttttgctg gccttttgct   7500
cacatgttct ttcctgcgtt atcccctgat tctgtggata accgtattac cgcctttgag   7560
tgagctgata ccgctcgccg cagccgaacg accgagcgca gcgagtcagt gagcgaggaa   7620
gcggaagagc gcctgatgcg gtattttctc cttacgcatc tgtgcggtat ttcacaccgc   7680
atatggtgca ctctcagtac aatctgctct gatgccgcat agttaagcca gtatacactc   7740
cgctatcgct acgtgactgg gtcatggctg cgccccgaca cccgccaaca cccgctgacg   7800
cgccctgacg ggcttgtctg ctcccggcat ccgcttacag acaagctgtg accgtctccg   7860
ggagctgcat gtgtcagagg ttttcaccgt catcaccgaa acgcgcgagg cagggtgcct   7920
tgatgtgggc gccggcggtc gagtggcgac ggcgcggctt gtccgcgccc tggtagattg   7980
cctggccgta ggccagccat ttttgagcgg ccagcggccg cgataggccg acgcgaagcg   8040
gcggggcgta gggagcgcag cgaccgaagg gtaggcgctt tttgcagctc ttcggctgtg   8100
cgctggccag acagttatgc acaggccagg cgggttttaa gagttttaat aagttttaaa   8160
gagttttagg cggaaaaatc gccttttttc tcttttatat cagtcactta catgtgtgac   8220
cggttcccaa tgtacggctt tgggttccca atgtacgggt tccggttccc aatgtacggc   8280
tttgggttcc caatgtacgt gctatccaca ggaaacagac cttttcgacc ttttccct     8340
gctagggcaa tttgccctag catctgctcc gtacattagg aaccggcgga tgcttcgccc   8400
tcgatcaggt tgcggtagcg catgactagg atcgggccag cctgccccgc ctcctccttc   8460
aaatcgtact ccggcaggtc atttgacccg atcagcttgc gcacggtgaa acagaacttc   8520
ttgaactctc cggcgctgcc actgcgttcg tagatcgtct tgaacaacca tctggcttct   8580
gccttgcctg cggcgcggcg tgccaggcgg tagagaaaac ggccgatgcc gggatcgatc   8640
aaaaagtaat cggggtgaac cgtcagcacg tccgggttct tgccttctgt gatctcgcgg   8700
tacatccaat cagctagctc gatctcgatg tactccggcc gcccggtttc gctctttacg   8760
atcttgtagc ggctaatcaa ggcttcaccc tcggataccg tcaccaggcg gccgttcttg   8820
gccttcttcg tacgctgcat ggcaacgtgc gtggtgttta accgaatgca ggtttctacc   8880
aggtcgtctt tctgctttcc gccatcggct cgccggcaga acttgagtac gtccgcaacg   8940
tgtggacgga acacgcggcc gggcttgtct cccttcccct cccggtatcg gttcatggat   9000
tcggttagat gggaaaccgc catcagtacc aggtcgtaat cccacacact ggccatgccg   9060
gccggccctg cggaaacctc tacgtgcccg tctggaagct cgtagcggat cacctcgcca   9120
gctcgtcggt cacgcttcga cagacggaaa acgccacgt ccatgatgct gcgactatcg   9180
cgggtgccca cgtcatagag catcggaacg aaaaaatctg gttgctcgtc gcccttgggc   9240
ggcttcctaa tcgacggcgc accggctgcc ggcggttgcc gggattcttt gcggattcga   9300
tcagcggccg cttgccacga ttcaccgggg cgtgcttctg cctcgatgcg ttgccgctgg   9360
gcggcctgcg cggccttcaa cttctccacc aggtcatcac ccagcgccgc gccgatttgt   9420
accgggccgg atggtttgcg accgctcacg ccgattcctc gggcttgggg gttccagtgc   9480
cattgcaggg ccgcaggca acccagccgc ttacgcctgg ccaaccgccc gttcctccac   9540
acatggggca ttccacggcg tcggtgcctg gttgttcttg attttccatg ccgcctcctt   9600
```

```
tagccgctaa aattcatcta ctcatttatt catttgctca tttactctgg tagctgcgcg    9660
atgtattcag atagcag                                                   9677

<210> SEQ ID NO 198
<211> LENGTH: 9779
<212> TYPE: DNA
<213> ORGANISM: Artificial Sequence
<220> FEATURE:
<223> OTHER INFORMATION: Synthetic construct vector pMBXS1270

<400> SEQUENCE: 198
ctcggtaatg tcttgccctt ggcgtaccgc gtacatcttc agcttggtgt gatcctccgc      60
cggcaactga aagttgaccc gcttcatggc tggcgtgtct gccaggctgg ccaacgttgc     120
agccttgctg ctgcgtgcgc tcggacggcc ggcacttagc gtgtttgtgc ttttgctcat     180
tttctcttta cctcattaac tcaaatgagt tttgatttaa tttcagcggc cagcgcctgg     240
acctcgcggg cagcgtcgcc ctcgggttct gattcaagaa cggttgtgcc ggcggcggca     300
gtgcctgggt agctcacgcg ctgcgtgata cgggactcaa gaatgggcag ctcgtacccg     360
gccagcgcct cggcaacctc accgccgatg cgcgtgcctt tgatcgcccg cgacacgaca     420
aaggccgctt gtagccttcc atccgtgacc tcaatgcgct gcttaaccag ctccaccagg     480
tcggcggtgg cccatatgtc gtaagggctt ggctgcaccg gaatcagcac gaagtcggct     540
gccttgatcg cggacacagc caagtccgcc gcctggggcg ctccgtcgat cactacgaag     600
tcgcgccggc cgatggcctt cacgtcgcgg tcaatcgtcg ggcggtcgat gccgacaacg     660
gttagcggtt gatcttcccg cacggccgcc caatcgcggg cactgccctg gggatcggaa     720
tcgactaaca gaacatcggc cccggcgagt gcaggcgcgc gggctagatg ggttgcgatg     780
gtcgtcttgc ctgacccgcc tttctggtta agtacagcga taaccttcat gcgttcccct     840
tgcgtatttg tttatttact catcgcatca tatacgcagc gaccgcatga cgcaagctgt     900
tttactcaaa tacacatcac cttttttagac ggcggcgctc ggtttcttca gcggccaagc     960
tggccggcca ggccgccagc ttggcatcag acaaaccggc caggatttca tgcagccgca    1020
cggttgagac gtgcgcgggc ggctcgaaca cgtacccggc cgcgatcatc tccgcctcga    1080
tctcttcggt aatgaaaaac ggttcgtcct ggccgtcctg gtgcggtttc atgcttgttc    1140
ctcttggcgt tcattctcgg cggccgccag ggcgtcggcc tcggtcaatg cgtcctcacg    1200
gaaggcaccg cgccgcctgg cctcggtggg cgtcacttcc tcgctgcgct caagtgcgcg    1260
gtacagggtc gagcgatgca cgccaagcag tgcagccgcc tctttcacgg tgcggccttc    1320
ctggtcgatc agctcgcggg cgtgcgcgat ctgtgccggg gtgagggtag ggcgggggcc    1380
aaacttcacg cctcgggcct tggcggcctc gcgcccgctc cgggtgcggt cgatgattag    1440
ggaacgctcg aactcggcaa tgccggcgaa cacggtcaac accatgcggc cggccggcgt    1500
ggtggtgtcg gccacggct ctgccaggct acgcaggccc gcgccggcct cctggatgcg    1560
ctcggcaatg tccagtaggt cgcgggtgct gcgggccagg cggtctagcc tggtcactgt    1620
cacaacgtcg ccagggcgta ggtggtcaag catcctggcc agctccgggc ggtcgcgcct    1680
ggtgccggtg atcttctcgg aaaacagctt ggtgcagccg gccgcgtgca gttcggcccg    1740
ttggttggtc aagtcctggt cgtcggtgct gacgcgggca tagcccagca ggccagcggc    1800
ggcgctcttg ttcatggcgt aatgtctccg gttctagtcg caagtattct actttatgcg    1860
actaaaacac gcgacaagaa aacgccagga aaagggcagg gcggcagcct gtcgcgtaac    1920
```

```
ttaggacttg tgcgacatgt cgttttcaga agacggctgc actgaacgtc agaagccgac    1980
tgcactatag cagcggaggg gttggatcaa agtactttga tcccgagggg aaccctgtgg    2040
ttggcatgca catacaaatg gacgaacgga taaaccttt cacgcccttt taaatatccg     2100
attattctaa taaacgctct tttctcttag gtttacccgc caatatatcc tgtcaaacac    2160
tgatagttta aactgaaggc gggaaacgac aatctgatcc aagctcaagc tgctctagca    2220
ttcgccattc aggctgcgca actgttggga agggcgatcg gtgcgggcct cttcgctatt    2280
acgccagctg gcgaaagggg gatgtgctgc aaggcgatta agttgggtaa cgccagggtt    2340
ttcccagtca cgacgttgta aaacgacggc cagtgccaag cttggcgcgc cctaggcct    2400
cagcttaatt aagcgtattg gctagagcag cttgccaaca tggtggagca cgacactctc    2460
gtctactcca agaatatcaa agatacagtc tcagaagacc aaagggctat tgagactttt    2520
caacaaaggg taatatcggg aaacctcctc ggattccatt gcccagctat ctgtcacttc    2580
atcaaaagga cagtagaaaa ggaaggtggc acctacaaat gccatcattg cgataaagga    2640
aaggctatcg ttcaagatgc ctctgccgac agtggtccca agatggaccc ccacccacg    2700
aggagcatcg tggaaaaaga agacgttcca accacgtctt caaagcaagt ggattgatgt    2760
gataacatgg tggagcacga cactctcgtc tactccaaga atatcaaaga tacagtctca    2820
gaagaccaaa gggctattga cttttcaa caaagggtaa tatcgggaaa cctcctcgga    2880
ttccattgcc cagctatctg tcacttcatc aaaaggacag tagaaaagga aggtggcacc    2940
tacaaatgcc atcattgcga taaaggaaag gctatcgttc aagatgcctc tgccgacagt    3000
ggtcccaaag atggaccccc acccacgagg agcatcgtgg aaaaagaaga cgttccaacc    3060
acgtcttcaa agcaagtgga ttgatgtgat atctccactg acgtaaggga tgacgcacaa    3120
tcccactatc cttcgcaaga ccttcctcta tataaggaag ttcatttcat ttggagagga    3180
cacgctgaaa tcaccagtct ctctctacaa atctatctct ctcgagtcta ccagatctaa    3240
attggtttcc ttggttgtgt tctctcttct cttgatcggt tttgcatctg cgcaaactct    3300
catagtagat tcttgcaaga aagcagccgc aaaagagccg tttatgaaat atgatttctg    3360
cgtcaattct cttacacaag atccacaaag caaaacggcg accacccctcg aaggtttagt    3420
cctagcatcg acgaagaatg ctgcggcgga aacactgaac gtaaaaggac tcgctgaaca    3480
gatcctcaag gggaagggat atgggccagg tatggaggca gggctacaca agtgcgtcaa    3540
gatttatgga ggtgcttatg atttttttaaa cactgcttta gcgaacgttc aatcacacca    3600
ttatagtact gctgtagagg aatttcttta tgcttcattt gcaccgttcg actgcgtgaa    3660
atattattgg atttctccct tcgctaagga gagctatatt atctttgaga agatttgat    3720
tcctatgact ttaactaaaa tgttgtgacc tcaggctcga gtttctccat aataatgtgt    3780
gagtagttcc cagataaggg aattagggtt cctatagggt ttcgctcatg tgttgagcat    3840
ataagaaacc cttagtatgt atttgtattt gtaaaatact tctatcaata aaatttctaa    3900
ttcctaaaac caaaatccag tactaaaatc cagatccccc gaattaattc ggcgttaatt    3960
cagcggaccg ctcgagcaat tgtacgtaga attcgcgtat tggctagagc agcttgccaa    4020
catggtggag cacgacactc tcgtctactc caagaatatc aaagatacag tctcagaaga    4080
ccaaagggct attgagactt ttcaacaaag ggtaatatcg ggaaacctcc tcggattcca    4140
ttgcccagct atctgtcact tcatcaaaag gacagtagaa aaggaaggtg gcacctacaa    4200
atgccatcat tgcgataaag gaaaggctat cgttcaagat gcctctgccg acagtggtcc    4260
caaagatgga ccccacccca cgaggagcat cgtggaaaaa gaagacgttc aaccacgtc    4320
```

```
ttcaaagcaa gtggattgat gtgaacatgg tggagcacga cactctcgtc tactccaaga    4380
atatcaaaga tacagtctca gaagaccaaa gggctattga acttttcaa caaagggtaa    4440
tatcgggaaa cctcctcgga ttccattgcc cagctatctg tcacttcatc aaaaggacag    4500
tagaaaagga aggtggcacc tacaaatgcc atcattgcga taaaggaaag gctatcgttc    4560
aagatgcctc tgccgacagt ggtcccaaag atggaccccc acccacgagg agcatcgtgg    4620
aaaaagaaga cgttccaacc acgtcttcaa agcaagtgga ttgatgtgat atctccactg    4680
acgtaaggga tgacgcacaa tcccactatc cttcgcaaga cccttcctct atataaggaa    4740
gttcatttca tttggagagg acacgctgaa atcaccagtc tctctctaca aatctatctc    4800
tctcgagtct accatgagcc cagaacgacg cccggccgac atccgccgtg ccaccgaggc    4860
ggacatgccg gcggtctgca ccatcgtcaa ccactacatc gagacaagca cggtcaactt    4920
ccgtaccgag ccgcaggaac cgcaggagtg gacggacgac ctcgtccgtc tgcgggagcg    4980
ctatccctgg ctcgtcgccg aggtggacgg cgaggtcgcc ggcatcgcct acgcgggccc    5040
ctggaaggca cgcaacgcct acgactggac ggccgagtcg accgtgtacg tctcccccg    5100
ccaccagcgg acgggactgg gctccacgct ctacacccac ctgctgaagt ccctggaggc    5160
acagggcttc aagagcgtgg tcgctgtcat cgggctgccc aacgacccga gcgtgcgcat    5220
gcacgaggcg ctcggatatg ccccccgcgg catgctgcgg gcggccggct tcaagcacgg    5280
gaactggcat gacgtgggtt tctggcagct ggacttcagc ctgccggtac cgccccgtcc    5340
ggtcctgccc gtcaccgaga tttgactcga gtttctccat aataatgtgt gagtagttcc    5400
cagataaggg aattagggtt cctataggt ttcgctcatg tgttgagcat ataagaaacc    5460
cttagtatgt atttgtattt gtaaaatact tctatcaata aaatttctaa ttcctaaaac    5520
caaaatccag tactaaaatc cagatccccc gaattaattc ggcgttaatt cagcacgtgt    5580
acattaaaaa cgtccgcaat gtgttattaa gttgtctaag cgtcaatttg tttacaccac    5640
aatatatcct gccaccagcc agccaacagc tccccgaccg gcagctcggc acaaaatcac    5700
cactcgatac aggcagccca tcagtccggg acggcgtcag cgggagagcc gttgtaaggc    5760
ggcagacttt gctcatgtta ccgatgctat tcggaagaac ggcaactaag ctgccgggtt    5820
tgaaacacgg atgatctcgc ggagggtagc atgttgattg taacgatgac agagcgttgc    5880
tgcctgtgat caccgcggtt tcaaaatcgg ctccgtcgat actatgttat acgccaactt    5940
tgaaaacaac tttgaaaaag ctgttttctg gtatttaagg ttttagaatg caaggaacag    6000
tgaattggag ttcgtcttgt tataattagc ttcttggggt atctttaaat actgtagaaa    6060
agaggaagga aataataaat ggctaaaatg agaatatcac cggaattgaa aaaactgatc    6120
gaaaaatacc gctgcgtaaa agatacggaa ggaatgtctc ctgctaaggt atataagctg    6180
gtgggagaaa atgaaaacct atatttaaaa atgacggaca gccggtataa agggaccacc    6240
tatgatgtgg aacggaaaaa ggacatgatg ctatggctgg aaggaaagct gcctgttcca    6300
aaggtcctgc actttgaacg gcatgatggc tggagcaatc tgctcatgag tgaggccgat    6360
ggcgtccttt gctcggaaga gtatgaagat gaacaaagcc ctgaaaagat tatcgagctg    6420
tatgcggagt gcatcaggct cttttcactcc atcgacatat cggattgtcc ctatacgaat    6480
agcttagaca gccgcttagc cgaattggat tacttactga ataacgatct ggccgatgtg    6540
gattgcgaaa actgggaaga agacactcca tttaaagatc cgcgcgagct gtatgatttt    6600
ttaaagacgg aaaagcccga agaggaactt gtctttcc acggcgacct gggagacagc    6660
```

```
aacatctttg tgaaagatgg caaagtaagt ggctttattg atcttgggag aagcggcagg    6720
gcggacaagt ggtatgacat tgccttctgc gtccggtcga tcaggagga tatcgggaa      6780
gaacagtatg tcgagctatt ttttgactta ctggggatca agcctgattg ggagaaaata   6840
aaatattata ttttactgga tgaattgttt tagtacctag aatgcatgac caaaatccct   6900
taacgtgagt tttcgttcca ctgagcgtca gaccccgtag aaaagatcaa aggatcttct   6960
tgagatcctt ttttttctgcg cgtaatctgc tgcttgcaaa caaaaaaacc accgctacca   7020
gcggtggttt gtttgccgga tcaagagcta ccaactcttt ttccgaaggt aactggcttc    7080
agcagagcgc agataccaaa tactgtcctt ctagtgtagc cgtagttagg ccaccacttc    7140
aagaactctg tagcaccgcc tacataccte gctctgctaa tcctgttacc agtggctgct    7200
gccagtggcg ataagtcgtg tcttaccggg ttggactcaa gacgatagtt accggataag   7260
gcgcagcggt cgggctgaac ggggggttcg tgcacacagc ccagcttgga gcgaacgacc    7320
tacaccgaac tgagatacct acagcgtgag ctatgagaaa gcgccacgct cccgaaggg    7380
agaaaggcgg acaggtatcc ggtaagcggc agggtcggaa caggagagcg cacgagggag   7440
cttccagggg gaaacgcctg gtatctttat agtcctgtcg gtttcgcca cctctgactt     7500
gagcgtcgat ttttgtgatg ctcgtcaggg gggcggagcc tatggaaaaa cgccagcaac    7560
gcggcctttt tacggttcct ggccttttgc tggccttttg ctcacatgtt ctttcctgcg    7620
ttatcccctg attctgtgga taaccgtatt accgcctttg agtgagctga taccgctcgc    7680
cgcagccgaa cgaccgagcg cagcgagtca gtgagcgagg aagcggaaga gcgcctgatg    7740
cggtattttc tccttacgca tctgtgcggt atttcacacc gcatatggtg cactctcagt    7800
acaatctgct ctgatgccgc atagttaagc cagtatacac tccgctatcg ctacgtgact    7860
gggtcatggc tgcgccccga cacccgccaa caccgctga cgcgcctga cgggcttgtc     7920
tgctcccggc atccgcttac agacaagctg tgaccgtctc cgggagctgc atgtgtcaga    7980
ggttttcacc gtcatcaccg aaacgcgcga ggcagggtgc cttgatgtgg gcgccggcgg    8040
tcgagtggcg acggcgcggc ttgtccgcgc cctggtagat tgcctggccg taggccagcc    8100
atttttgagc ggccagcggc cgcgataggc cgacgcgaag cggcggggcg tagggagcgc    8160
agcgaccgaa gggtaggcgc tttttgcagc tcttcggctg tgcgctggcc agacagttat    8220
gcacaggcca ggcgggtttt aagagtttta ataagtttta aagagtttta ggcggaaaaa   8280
tcgccttttt tctcttttat atcagtcact tacatgtgtg accggttccc aatgtacggc    8340
tttgggttcc caatgtacgg gttccggttc caatgtacg gctttgggtt cccaatgtac    8400
gtgctatcca caggaaacag accttttcga cctttttccc ctgctagggc aatttgccct    8460
agcatctgct ccgtacatta ggaaccggcg gatgcttcgc cctcgatcag gttgcggtag    8520
cgcatgacta ggatcgggcc agcctgcccc gcctcctcct tcaaatcgta ctccggcagg    8580
tcatttgacc cgatcagctt gcgcacggtg aaacagaact tcttgaactc tccggcgctg    8640
ccactgcgtt cgtagatcgt cttgaacaac catctggctt ctgccttgcc tgcggcgcgg    8700
cgtgccaggc ggtagagaaa acggccgatg ccgggatcga tcaaaaagta atcggggtga   8760
accgtcagca cgtccgggtt cttgccttct gtgatctcgc ggtacatcca atcagctagc    8820
tcgatctcga tgtactccgg ccgccggtt tcgctctttta cgatcttgta gcggctaatc    8880
aaggcttcac cctcggatac cgtcaccagg cggccgttct tggccttctt cgtacgctgc    8940
atggcaacgt gcgtggtgtt taaccgaatg caggtttcta ccaggtcgtc tttctgcttt    9000
ccgccatcgg ctcgccggca gaacttgagt acgtccgcaa cgtgtggacg gaacacgcgg    9060
```

-continued

```
ccgggcttgt ctcccttccc ttcccggtat cggttcatgg attcggttag atgggaaacc    9120
gccatcagta ccaggtcgta atcccacaca ctggccatgc cggccggccc tgcggaaacc    9180
tctacgtgcc cgtctggaag ctcgtagcgg atcacctcgc cagctcgtcg gtcacgcttc    9240
gacagacgga aaacgccac gtccatgatg ctgcgactat cgcgggtgcc cacgtcatag     9300
agcatcggaa cgaaaaaatc tggttgctcg tcgcccttgg gcggcttcct aatcgacggc    9360
gcaccggctg ccggcggttg ccgggattct ttgcggattc gatcagcggc cgcttgccac    9420
gattcaccgg ggcgtgcttc tgcctcgatg cgttgccgct gggcggcctg cgcggccttc    9480
aacttctcca ccaggtcatc acccagcgcc gcgccgattt gtaccgggcc ggatggtttg    9540
cgaccgctca cgccgattcc tcgggcttgg gggttccagt gccattgcag ggccggcagg    9600
caacccagcc gcttacgcct ggccaaccgc ccgttcctcc acacatgggg cattccacgg    9660
cgtcggtgcc tggttgttct tgattttcca tgccgcctcc tttagccgct aaaattcatc    9720
tactcattta ttcatttgct catttactct ggtagctgcg cgatgtattc agatagcag    9779
```